(12) United States Patent
Banno et al.

(10) Patent No.: US 8,309,580 B2
(45) Date of Patent: Nov. 13, 2012

(54) HETEROCYCLIC COMPOUND

(75) Inventors: Yoshihiro Banno, Osaka (JP); Ryoma Hara, Osaka (JP); Ryosuke Tokunoh, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 82 days.

(21) Appl. No.: 12/734,427

(22) PCT Filed: Oct. 31, 2008

(86) PCT No.: PCT/JP2008/069967
§ 371 (c)(1),
(2), (4) Date: Apr. 30, 2010

(87) PCT Pub. No.: WO2009/057784
PCT Pub. Date: May 7, 2009

(65) Prior Publication Data
US 2010/0256156 A1 Oct. 7, 2010

(30) Foreign Application Priority Data
Nov. 1, 2007 (JP) ................... 2007-285526

(51) Int. Cl.
*A61K 31/44* (2006.01)
*C07D 401/00* (2006.01)
(52) U.S. Cl. ............... 514/336; 514/438; 546/268.1
(58) Field of Classification Search .............. 514/336, 514/438; 549/29; 546/268.1
See application file for complete search history.

(56) References Cited

U.S. PATENT DOCUMENTS

| | | |
|---|---|---|
| 6,503,949 B1 | 1/2003 | Lau et al. |
| 6,875,760 B2 | 4/2005 | Lau et al. |
| 6,881,746 B2 | 4/2005 | Lau et al. |
| 2003/0220350 A1 | 11/2003 | Lau et al. |
| 2003/0236292 A1 | 12/2003 | Kodra et al. |
| 2004/0014789 A1 | 1/2004 | Lau et al. |
| 2005/0203108 A1 | 9/2005 | Lau et al. |
| 2005/0256175 A1 | 11/2005 | Lau et al. |
| 2006/0084681 A1 | 4/2006 | Parmee et al. |

FOREIGN PATENT DOCUMENTS

| | | |
|---|---|---|
| GB | 2 387 172 | 10/2003 |
| JP | 2002-544254 | 12/2002 |
| JP | 2005-511683 | 4/2005 |
| JP | 2006-500325 | 1/2006 |
| JP | 2006-516622 | 7/2006 |
| WO | 00/69810 | 11/2000 |
| WO | 2004/002480 | 1/2004 |
| WO | 2004/069158 | 8/2004 |
| WO | 2004/098528 | 11/2004 |
| WO | 2006/102067 | 9/2006 |
| WO | 2007/091396 | 8/2007 |
| WO | WO2007091396 | * 8/2007 |
| WO | 2009/110520 | 9/2009 |

OTHER PUBLICATIONS

Walker's CAS: 131:31809, 1999.*
Hasegawa et al. CAS:147:257767, 2007.*

* cited by examiner

*Primary Examiner* — Rei-tsang Shiao
(74) *Attorney, Agent, or Firm* — Wenderoth, Lind & Ponack, L.L.P.

(57) ABSTRACT

The present invention provides a heterocyclic compound represented by the following formula (I), which has a glucagon antagonistic action and is useful for the prophylaxis or treatment of diabetes and the like, a compound represented by

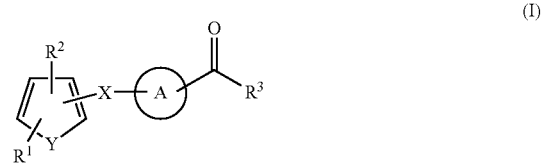

(I)

wherein ring A is an optionally substituted benzene ring and the like; Y is a nitrogen atom and the like; X is —O— and the like; $R^4$ is a hydrogen atom and the like; $R^5$ and $R^6$ are each independently a hydrogen atom and the like; $R^1$ is an optionally substituted hydrocarbon group and the like; $R^2$ is a hydrogen atom and the like; and $R^3$ is —$(CH_2)_3$—COOH and the like, or a salt thereof.

15 Claims, No Drawings

HETEROCYCLIC COMPOUND

This application is a U.S. national stage of International Application No. PCT/JP2008/069967 filed Oct. 31, 2008.

TECHNICAL FIELD

The present invention relates to a heterocyclic compound having a glucagon antagonistic action, which is useful for the prophylaxis.treatment of diabetes and the like.

BACKGROUND OF THE INVENTION

Glucagon is a straight chain peptide hormone having 29 amino acids, which is secreted from pancreatic α cells and promotes glycogenolysis and gluconeogenesis in the liver. Diabetes patients generally show promoted secretion and reactivity of glucagon, which is one cause of hyperglycemia. Therefore, glucagon receptor antagonists can suppress excess sugar production from the liver by shutting off the actions of glucagon, and are expected to be therapeutic drugs for diabetes.

As glucagon antagonists, the following compounds are known.

1) a compound represented by the following formula:

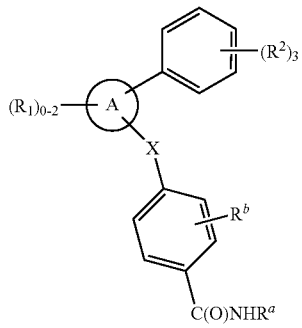

wherein ring A is 6- to 10-membered aryl, 6- to 10-membered heteroaryl, 6-membered aryl condensed with 5- or 6-membered carbocycle; $R_1$ is, when it is present, (a) halogen, OH, $CO_2R^4$, $SO_pR^5$, CN, $NO_2$, $C(O)NR^6R^7$ or $NR^6R^7$, (b) $C_{1-6}$ alkyl, $C(O)C_{1-6}$ alkyl or $C(O)C_{1-6}$ alkyl (substitutable with (a)), (c) 6- to 10-membered aryl, aryloxy or arylthio, or 5- to 10-membered heteroaryl, heteroaryl-oxy or heteroaryl-thio (each substitutable with (a) or (b); these groups are further substitutable with pyrazole, imidazole, tetrazole, pyrrole, triazole, thiazole, furan, thiophene, thiadiazole or oxazole (each substitutable with (a) or (b))); $R^2$ is H, or substituent (a) or (b); X is —O—, —S—, —$(C(R^3)_2)_{1-2}$—, —$OC(R^3)_2$— or —$C(R^3)_2O$—; $R^3$ is H, or $C_{1-10}$ alkyl, $C_{2-4}$ alkenyl, aryl or heteroaryl (substitutable with (a) or (b); one of $R^3$ is other than H or $C_{1-10}$ alkyl); $R^4$ is H or $C_{1-6}$ alkyl; $R^5$ is $C_{1-10}$ alkyl, aryl or aryl-$C_{1-10}$ alkyl; $R^6$ and $R^7$ are each H or $C_{1-3}$ alkyl; p is 0-2; $R^a$ is $CH_2CH_2CO_2R^4$, $CH_2CH(OH)CO_2R^4$ or 5-tetrazole; and $R^b$ is H, or substituent (a) or (b) (patent document 1: WO2006/102067).

2) A compound represented by the following formula:

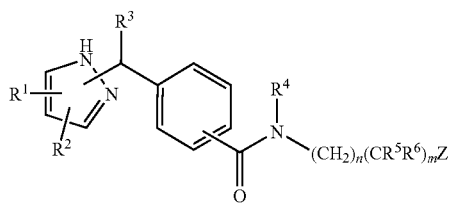

wherein $R^1$ is (a) $C_{1-10}$ alkyl, $C_{2-10}$ alkenyl or $C_{2-10}$ alkynyl (each substitutable), or (b) aryl, heteroaryl or heterocyclyl (each substitutable); $R^2$ is H or $R^1$; $R^3$ and $R^4$ are each H or $C_{1-10}$ alkyl; $R^5$ is H or F; $R^6$ is H, OH, F or $C_{1-3}$ alkyl, or $R^5$ and $R^6$ form oxo; $R^6$ is H, or $C_{1-10}$ alkyl (substitutable with phenyl, OH, $OC_{1-6}$ alkyl, $CO_2H$, $CO_2C_{1-6}$ alkyl, halo); m is 0-2; n is 1-6; when one of m and n is other than 0, Z is $COR^8$, 5-tetrazolyl or 5-(2-oxo-1,3,4-oxadiazolyl), and when m and n are both 0, Z is 5-tetrazolyl or 5-(2-oxo-1,3,4-oxadiazolyl) (patent document 2: WO2004/069158).

3) A compound represented by the following formula:

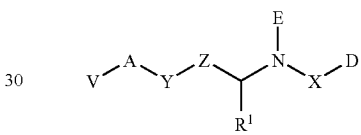

wherein V is —$C(O)OR^2$, —$C(O)NR^2R^3$, —$C(O)NR^2OR^3$, —$S(O)_2OR^2$,

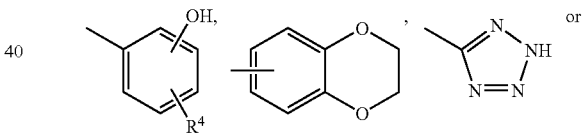

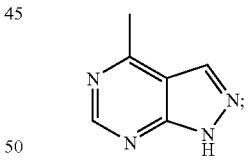

$R^2$ and $R^3$ are each independently H or $C_{1-6}$ alkyl; $R^4$ is H, halogen and the like; A is

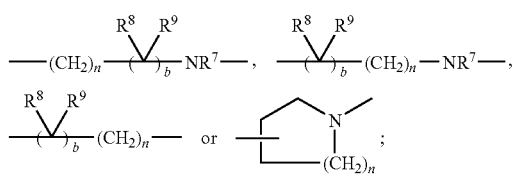

b is 0 or 1; n is 0-3; $R^7$ is H, $C_{1-6}$ alkyl and the like; $R^8$ and $R^9$ are each independently H or $C_{1-6}$ alkyl; Y is —$C(O)$—, —$S(O)_2$—, —O— or a bond; Z is phenyl, 5-6-membered aromatic heterocycle (each substitutable with halo etc.); R¹ is H or $C_{1-6}$ alkyl; X is

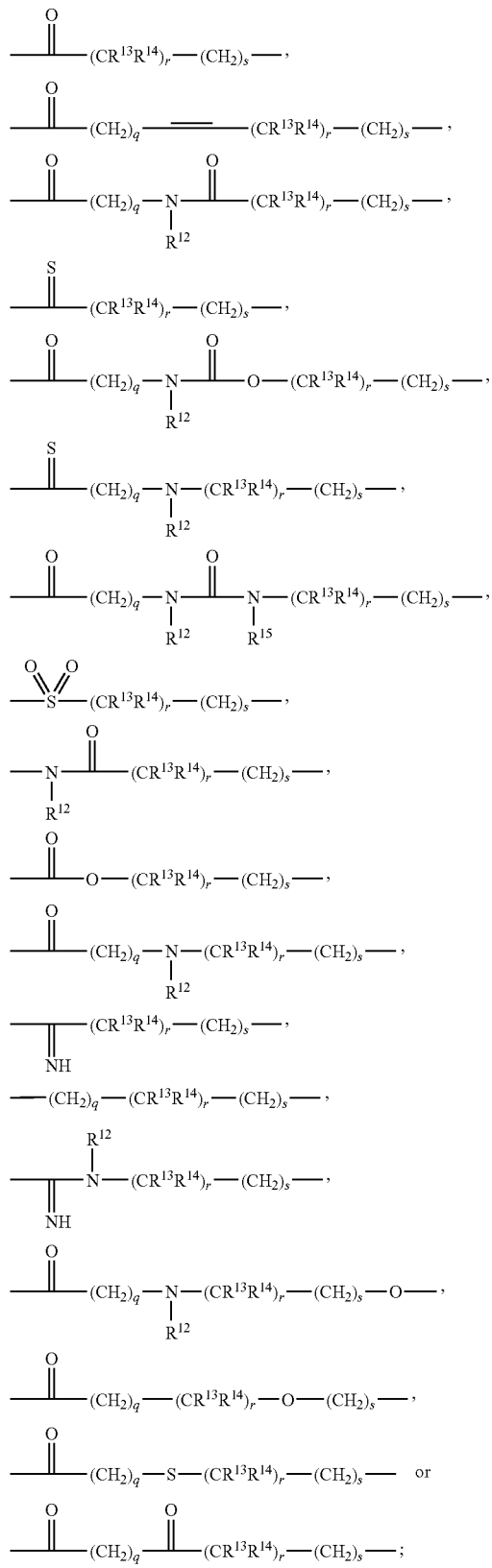

r is 0 or 1; q and s are each 0-3; $R^{12}$, $R^{13}$, $R^{14}$ and $R^{15}$ are each independently H or $C_{1-6}$ alkyl; D is

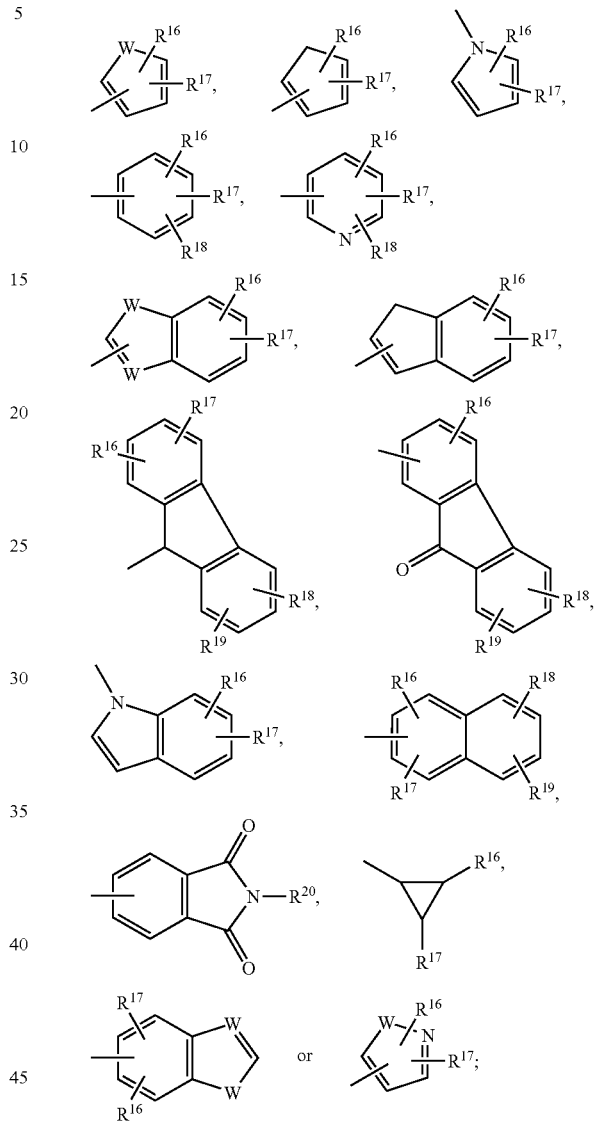

W is —O—, —S—, —S(O)₂— or —NR²⁰—; W' is =CR²⁰'— or —N=; $R^{16}$, $R^{17}$, $R^{18}$ and $R^{19}$ are each independently H, —C(O)NR²¹R²², C(O)R²¹ and the like; $R^{20}$ and $R^{20'}$ are each H, $C_{1-6}$ alkyl, $C_{3-8}$ cycloalkyl or $C_{3-8}$ cycloalkyl-$C_{1-6}$ alkyl; $R^{21}$ and $R^{22}$ are each H, —CF₃, $C_{1-6}$ alkyl, aryl, heteroaryl and the like; and E is an optionally substituted 3- to 9-membered monocyclic or bicyclic ring and the like (patent document 3: WO00/69810).

4) A compound represented by the following formula:

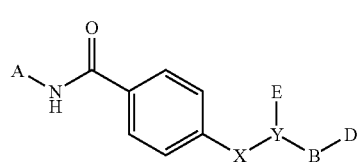

wherein A is

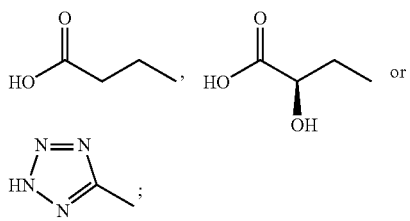

X is a bond, —CR¹R²— or —NR¹—; Y is >CR³— or >N—; R¹, R² and R³ are each independently H or $C_{1-6}$ alkyl, or R¹ and R² optionally form a double bond; E is $C_{1-10}$ alkyl, or $C_{3-10}$ cycloalkyl, $C_{3-10}$ cycloalkyl-$C_{1-6}$ alkyl, aryl, heteroaryl or aryl-$C_{1-6}$ alkyl (these are each substitutable with halogen, $C_{1-6}$ alkyl etc.) and the like; B is

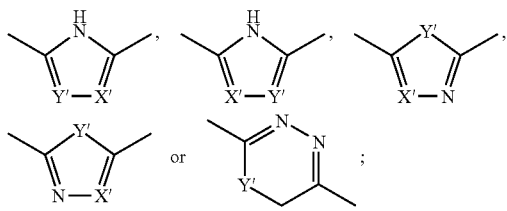

X' is —N= or —CR⁸=; Y' is —S—, —O— or NR⁸—; R⁸ is H, or $C_{1-6}$ alkyl or aryl (these are each substitutable with halogen, $C_{1-6}$ alkyl etc.); R⁹ is H or $C_{1-6}$ alkyl; D is aryl or heteroaryl (each substitutable with halogen, $C_{1-10}$ alkyl, $C_{1-6}$ alkoxy, $C_{3-8}$ cycloalkyl, aryl (these rings are substitutable with halogen, $C_{1-10}$ alkyl etc.) and the like) (patent document 4: WO2004/002480).

In addition, as a compound having a structure similar to that of the compound of the present invention, the following compound is known.

5) A compound useful as a therapeutic agent for inflammatory diseases, which is represented by the following formula

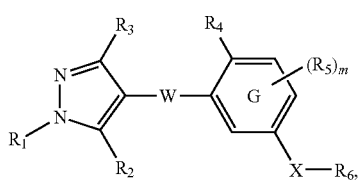

wherein G is phenyl or pyridyl; W is —NH(C=O)(CHR₈)ᵣ—, —CH(R₈)NH—, —NHCH(R₈)—, —CH₂—O— or —(C=O)O—; R₈ is H or alkyl; r is 0, 1 or 2; R₁ is H, optionally substituted alkyl, optionally substituted aryl, optionally substituted heteroaryl, optionally substituted cycloalkyl, optionally substituted heterocyclyl and the like; R₂ is H, optionally substituted alkyl, optionally substituted alkoxy, amino and the like; R₃ is H, —CF₃, —OCF₃, halogen, optionally substituted $C_{1-4}$ alkyl, —OR₁₁ and the like; R₄ is H, optionally substituted $C_{1-4}$ alkyl, halogen, —CF₃, —OCF₃, —OR₁₃ and the like; R₅ is —CF₃, —OCF₃, optionally substituted alkyl, optionally substituted cycloalkyl, optionally substituted heterocyclyl, optionally substituted aryl, optionally substituted heteroaryl, —OR₁₃, —C(=O)R₁₃, —C(=O)NR₁₃R₁₄ and the like; X is —(C=O)NH—, —NH(C=O)—, —NH(C=O)O—, —SO₂NH—, —CO₂— or a bond; R₆ is H, optionally substituted $C_{1-4}$ alkyl, optionally substituted alkoxy, optionally substituted phenoxy, optionally substituted cycloalkyl, optionally substituted heterocyclyl, optionally substituted aryl, optionally substituted heteroaryl and the like; R₆ and R₅ may be bonded to each other to form 5- or 6-membered ring; R₁₁, R₁₃ and R₁₄ are each independently H, optionally substituted alkyl, optionally substituted cycloalkyl, optionally substituted heterocyclyl, optionally substituted aryl or optionally substituted heteroaryl; m is 0, 1, 2 or 3 (patent document 5: WO2004/098528).

patent document 1: WO2006/102067
patent document 2: WO2004/069156
patent document 3: WO00/69610
patent document 4: WO2004/002480
patent document 5: WO2004/098528

DISCLOSURE OF THE INVENTION

Problems to be Solved by the Invention

Development of a compound having a glucagon antagonistic action, which is useful for the prophylaxis or treatment of diabetes and the like, and shows superior efficacy has been desired.

Means of Solving the Problems

The present inventors have found for the first time that a compound represented by the formula (I):

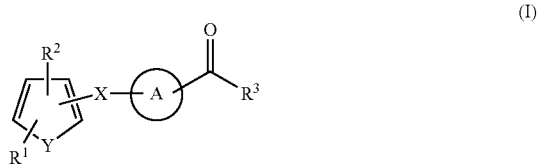

(I)

wherein ring A is a benzene ring or a 5- or 6-membered heterocycle, each of which is optionally further substituted;
Y is an oxygen atom, a sulfur atom or a nitrogen atom;
X is —O—, —S—, —SO—, —SO₂—, —CR⁴R⁵—O—, —O—CR⁴R⁵—, —CO—CR⁴R⁵—, —CR⁴R⁵—CO—, —CR⁴R⁵—NR⁶— or —CO—NR⁶—;
R⁴ is a hydrogen atom or a $C_{1-6}$ alkyl group;
R⁵ and R⁶ are each independently a hydrogen atom, an optionally substituted $C_{1-6}$ alkyl group, an optionally substituted $C_{3-10}$ cycloalkyl group, an optionally substituted $C_{6-14}$ aryl group or an optionally substituted 5- or 6-membered heterocyclic group;
R¹ is an optionally substituted hydrocarbon group, an optionally substituted heterocyclic group, an optionally substituted hydroxy group or an acyl group;
R² is a hydrogen atom, an optionally substituted hydrocarbon group, an optionally substituted heterocyclic group, an optionally substituted hydroxy group or an acyl group;
R³ is —(CH₂)₃—COOH or —NR⁷—CR⁸R⁹—CR¹⁰R¹¹—COOH;
R⁷, R⁸, R⁹ and R¹⁰ are each independently a hydrogen atom or a $C_{1-6}$ alkyl group;
R¹¹ is a hydrogen atom, a $C_{1-6}$ alkyl group or a hydroxy group, provided that when Y is a nitrogen atom, then ring A is not an optionally substituted pyrrole, or a salt thereof [hereinafter to be sometimes referred to as compound (I)] has a superior glucagon antagonistic action, is useful for the prophylaxis or treatment of diabetes and the like, and shows superior efficacy. Based on this finding, the present inventors have conducted intensive studies and completed the present invention.

Accordingly, the present invention relates to (1) compound (I);
(2) the compound of the above-mentioned (1), wherein ring A is an optionally substituted benzene ring or an optionally substituted pyridine ring;
(3) the compound of the above-mentioned (1), wherein X is —$CR^4R^5$—O— or —$CR^4R^5$—$NR^6$—;
(4) the compound of the above-mentioned (1), wherein $R^1$ is an optionally substituted $C_{1-6}$ alkyl group, an optionally substituted $C_{3-10}$ cycloalkyl group, an optionally substituted $C_{6-14}$ aryl group, an optionally substituted heterocyclic group, a $C_{1-6}$ alkyl-carbonyl group or a $C_{3-10}$ cycloalkyl-carbonyl group;
(5) the compound of the above-mentioned (1), wherein $R^2$ is an optionally substituted $C_{1-6}$ alkyl group or an optionally substituted $C_{3-10}$ cycloalkyl group;
(6) the compound of the above-mentioned (1), wherein $R^3$ is —$NR^7$—$CR^8R^9$—$CR^{10}R^{11}$—COOH;
(7) the compound of the above-mentioned (1), wherein ring A is an optionally substituted benzene ring or an optionally substituted pyridine ring;
Y is an oxygen atom, a sulfur atom or a nitrogen atom;
X is —$CR^4R^5$—O— or —$CR^4R^5$—$NR^6$—;
$R^1$ is an optionally substituted $C_{1-6}$ alkyl group, an optionally substituted $C_{3-10}$ cycloalkyl group, an optionally substituted $C_{6-14}$ aryl group, an optionally substituted heterocyclic group, a $C_{1-6}$ alkyl-carbonyl group or a $C_{3-10}$ cycloalkyl-carbonyl group;
$R^2$ is an optionally substituted $C_{1-6}$ alkyl group or an optionally substituted $C_{3-10}$ cycloalkyl group; and
$R^3$ is —$NR^7$—$CR^8R^9$—$CR^{10}R^{11}$—COOH;
(8) 3-[{[4-({1-[5-(6-methoxypyridin-3-yl)-2-methylfuran-3-yl]-3-methylbutyl}amino)phenyl]carbonyl}(methyl)amino]propanoic acid or a salt thereof;
(9) 3-[{[4-({cyclohexyl[5-(4-fluorophenyl)-2-(methoxymethyl)furan-3-yl]methyl}amino)phenyl]carbonyl}(methyl)amino]propanoic acid or a salt thereof;
(10) 3-[{[5-({cyclohexyl[5-(4-fluorophenyl)-2-methylfuran-3-yl]methyl}amino)pyridin-2-yl]carbonyl}(methyl)amino]propanoic acid or a salt thereof;
(11) 3-[{[4-({cyclohexyl[5-(6-methoxypyridin-3-yl)-2-methylfuran-3-yl]methyl}amino)phenyl]carbonyl}(methyl)amino]propanoic acid or a salt thereof;
(12) 3-{[(5-{[cyclohexyl(2-methyl-5-phenylthiophen-3-yl)methyl]amino}pyridin-2-yl)carbonyl](methyl)amino}propanoic acid or a salt thereof;
(13) a prodrug of compound (I);
(14) a medicament comprising compound (I) or a prodrug thereof;
(15) the medicament of the above-mentioned (14), which is a glucagon antagonist;
(16) the medicament of the above-mentioned (14), which is an agent for the prophylaxis or treatment of diabetes;
(17) a method of suppressing sugar production in a mammal, comprising administering compound (I) or a prodrug thereof to the mammal;
(18) a method for the prophylaxis or treatment of diabetes in a mammal, comprising administering compound (I) or a prodrug thereof to the mammal;
(19) use of compound (I) or a prodrug thereof for the production of a glucagon antagonist;
(20) use of compound (I) or a prodrug thereof for the production of an agent for the prophylaxis or treatment of diabetes; and the like.

Effect of the Invention

The compound of the present invention has a glucagon antagonistic action, is useful for the prophylaxis or treatment of diabetes and the like, and shows superior efficacy.

DETAILED DESCRIPTION OF THE INVENTION

The definition of each symbol in the formula (I) is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy, pentoxy, isopentoxy, hexoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

In the present specification, examples of the "$C_{1-10}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Among these, a $C_{1-6}$ alkyl group is preferable.

In the present specification, examples of the "$C_{2-10}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Among these, a $C_{2-6}$ alkenyl group is preferable.

In the present specification, examples of the "$C_{2-10}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Among these, a $C_{2-6}$ alkynyl group is preferable.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

The $C_{3-10}$ cycloalkyl group may form a fused ring group with a benzene ring and examples of such fused ring group include indanyl and the like.

In the present specification, examples of the "C$_{3-10}$ cycloalkenyl group" include 2-cyclopenten-1-yl, 3-cyclopenten-1-yl 2-cyclohexen-1-yl, 3-cyclohexen-1-yl and the like.

The C$_{3-10}$ cycloalkenyl group may form a fused ring group with a benzene ring and examples of such fused ring group include dihydronaphthyl and the like.

In the present specification, examples of the "C$_{4-10}$ cycloalkadienyl group" include 2,4-cyclopentadien-1-yl, 2,4-cyclohexadien-1-yl, 2,5-cyclohexadien-1-yl and the like.

The C$_{4-10}$ cycloalkadienyl group may form a fused ring group with a benzene ring and examples of such fused ring group include fluorenyl and the like.

In the present specification, examples of the "C$_{6-14}$ aryl group" include phenyl, naphthyl, anthryl, phenanthryl, acenaphthyl, biphenylyl and the like.

In the present specification, examples of the "C$_{7-13}$ aralkyl group" include benzyl, phenethyl, naphthylmethyl, biphenylylmethyl and the like.

Examples of the "C$_{8-13}$ arylalkenyl group" include styryl and the like.

In the present specification, examples of the "aromatic heterocyclic group" include a 4- to 12-membered aromatic heterocyclic group, for example, a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom, and a 8- to 12-membered fused aromatic heterocyclic group. Examples of the fused aromatic heterocyclic group include a group derived from a fused ring of 1 or 2 selected from rings corresponding to these 4- to 7-membered monocyclic aromatic heterocyclic groups, a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like;
and the like.

In the present specification, examples of the "nonaromatic heterocyclic group" include a 4- to 12-membered nonaromatic heterocyclic group, for example, a 4- to 7-membered (preferably 5- or 6-membered) monocyclic nonaromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a 8- to 12-membered fused nonaromatic heterocyclic group. Examples of the fused nonaromatic heterocyclic group include a group derived from a fused ring of 1 or 2 rings selected from rings corresponding to these 4- to 7-membered monocyclic nonaromatic heterocyclic groups, a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring, a group obtained by partial saturation of the group, and the like.

Preferable examples of the nonaromatic heterocyclic group include
monocyclic nonaromatic heterocyclic groups such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;
fused nonaromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;
and the like.

$R^1$ is an optionally substituted hydrocarbon group, an optionally substituted heterocyclic group, an optionally substituted hydroxy group or an acyl group.

$R^2$ is a hydrogen atom, an optionally substituted hydrocarbon group, an optionally substituted heterocyclic group, an optionally substituted hydroxy group or an acyl group.

Examples of the "hydrocarbon group" of the "optionally substituted hydrocarbon group" for $R^1$ or $R^2$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

The $C_{1-10}$ alkyl group, $C_{2-10}$ alkenyl group and $C_{2-10}$ alkynyl group, which are exemplified as the "hydrocarbon group", optionally have 1 to 3 substituents at substitutable positions. Examples of such substituents include (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(3) a 4- to 12-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(4) a 4- to 12-membered nonaromatic heterocyclic group (e.g., tetrahydrofuryl, morpholinyl, thiomorpholinyl, piperidinyl, pyrrolidinyl, piperazinyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms,
 (d) a halogen atom, and
 (e) an oxo group;
(5) an amino group optionally mono- or di-substituted by substituent(s) selected from
 (a) a $C_{1-6}$ alkyl group optionally substituted by 1 to 3 halogen atoms,
 (b) a $C_{1-6}$ alkyl-carbonyl group optionally substituted by 1 to 3 halogen atoms,
 (c) a $C_{1-6}$ alkoxy-carbonyl group optionally substituted by 1 to 3 halogen atoms,
 (d) a $C_{1-6}$ alkylsulfonyl group (e.g., methylsulfonyl) optionally substituted by 1 to 3 halogen atoms,
 (e) a carbamoyl group optionally mono- or di-substituted by a $C_{1-6}$ alkyl group optionally substituted by 1 to 3 halogen atoms, and
 (f) a 4- to 12-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3% halogen atoms;
(7) a $C_{1-6}$ alkoxy-carbonyl group optionally substituted by 1 to 3 substituents selected from
 (a) a halogen atom,
 (b) a $C_{1-6}$ alkoxy group, and
 (c) a $C_{6-14}$ aryl group (e.g., phenyl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by a $C_{1-6}$ alkyl group optionally substituted by 1 to 3 halogen atoms;
(10) a thiocarbamoyl group optionally mono- or di-substituted by a $C_{1-6}$ alkyl group optionally substituted by 1 to 3 halogen atoms;
(11) a sulfamoyl group optionally mono- or di-substituted by a $C_{1-6}$ alkyl group optionally substituted by 1 to 3 halogen atoms;
(12) a carboxy group;
(13) a hydroxy group;
(14) a $C_{1-6}$ alkoxy group (e.g., methoxy, ethoxy, propoxy, isopentoxy) optionally substituted by 1 to 3 substituents selected from
 (a) a halogen atom,
 (b) a carboxy group,
 (c) a $C_{1-6}$ alkoxy group (e.g., methoxy),
 (d) a $C_{1-6}$ alkoxy-carbonyl group optionally substituted by 1 to 3 $C_{6-14}$ aryl groups (e.g., phenyl),
 (e) an amino group optionally mono- or di-substituted by substituent(s) selected from a $C_{1-6}$ alkyl group and a $C_{1-6}$ alkoxy-carbonyl group,
 (f) a hydroxy group,
 (g) a 4- to 12-membered nonaromatic heterocyclic group (e.g., pyrrolidinyl) optionally substituted by 1 or 2 oxo groups,
 (h) a $C_{1-6}$ alkylthio group (e.g., methylthio),
 (i) a $C_{1-6}$ alkylsulfinyl group (e.g., methylsulfinyl), and
 (j) a $C_{1-6}$ alkylsulfonyl group (e.g., methylsulfonyl);
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
 (a) a halogen atom, and
 (b) a $C_{1-6}$ alkyl group optionally substituted by 1 to 3 halogen atoms;
(20) a 4- to 12-membered nonaromatic heterocyclylcarbonyl group (e.g., pyrrolidinylcarbonyl, morpholinylcarbonyl) optionally substituted by 1 to 3 $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
 (a) a halogen atom, and
 (b) a $C_{1-6}$ alkoxycarbonyl group;
(23) a $C_{7-13}$ aralkylthio group (e.g., benzylthio);
(24) a $C_{6-14}$ arylthio group (e.g., phenylthio, naphthylthio);
(25) a $C_{1-6}$ alkylsulfinyl group (e.g., methylsulfinyl);
(26) a cyano group;
(27) a nitro group;

(28) a halogen atom;
(29) a $C_{1-3}$ alkylenedioxy group;
(30) a 4- to 12-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms; and the like. When the number of the substituents is not less than 2, the respective substituents may be the same or different.

In addition, the $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, which are exemplified as the "hydrocarbon group", optionally have 1 to 3 substituents at substitutable positions.

Examples of such substituents include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(3) a 4- to 12-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) a 4- to 12-membered nonaromatic heterocyclic group (e.g., tetrahydrofuryl, morpholinyl, thiomorpholinyl, piperidinyl, pyrrolidinyl, piperazinyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms,
(d) a halogen atom, and
(e) an oxo group;
(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by a $C_{1-6}$ alkyl group optionally substituted by 1 to 3 halogen atoms, and
    (f) a 4- to 12-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by a $C_{1-6}$ alkyl group optionally substituted by 1 to 3 halogen atoms;
(10) a thiocarbamoyl group optionally mono- or di-substituted by a $C_{1-6}$ alkyl group optionally substituted by 1 to 3 halogen atoms;
(11) a sulfamoyl group optionally mono- or di-substituted by a $C_{1-6}$ alkyl group optionally substituted by 1 to 3 halogen atoms;
(12) a carboxy group;
(13) a hydroxy group;
(14) a $C_{1-6}$ alkoxy group (e.g., methoxy, ethoxy, propoxy, isopentoxy) optionally substituted by 1 to 3 substituents selected from
    (a) a halogen atom,
    (b) a carboxy group,
    (c) a $C_{1-6}$ alkoxy group (e.g., methoxy),
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a hydroxy group,
    (g) a 4- to 12-membered nonaromatic heterocyclic group (e.g., pyrrolidinyl) optionally substituted by 1 or 2 oxo groups,
    (h) a $C_{1-6}$ alkylthio group (e.g., methylthio),
    (i) a $C_{1-6}$ alkylsulfinyl group (e.g., methylsulfinyl), and
    (j) a $C_{1-6}$ alkylsulfonyl group (e.g., methylsulfonyl);
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(20) a 4- to 12-membered nonaromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
    (a) a halogen atom, and
    (b) $C_{1-6}$ alkoxycarbonyl;
(23) a $C_{7-13}$ aralkylthio group (e.g., benzylthio);
(24) a $C_{6-14}$ arylthio group (e.g., phenylthio, naphthylthio);
(25) a $C_{1-6}$ alkylsulfinyl group (e.g., methylsulfinyl);
(26) a cyano group;
(27) a nitro group;
(28) a halogen atom;
(29) a $C_{1-3}$ alkylenedioxy group;
(30) a 4- to 12-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms;

(31) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;
(32) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{3-6}$ alkoxy group, and
  (f) an amino group optionally mono- or di-substituted by a $C_{1-6}$ alkyl group;
(33) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
and the like. When the number of the substituents is not less than 2, the respective substituents may be the same or different.

Examples of the "heterocyclic group" of the "optionally substituted heterocyclic group" for $R^1$ or $R^2$ include an aromatic heterocyclic group and a nonaromatic heterocyclic group.

The "heterocyclic group" of the "optionally substituted heterocyclic group" optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group" for $R^1$ or $R^2$ optionally has. When the heterocyclic group is a "nonaromatic heterocyclic group", the substituent further includes an oxo group. When the number of the substituents is not less than 2, the respective substituents may be the same or different.

Examples of the "optionally substituted hydroxy group" for $R^1$ or $R^2$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the heterocyclic group exemplified as the substituent of the hydroxy group include those similar to the "heterocyclic group" of the "optionally substituted heterocyclic group" for $R^1$ or $R^2$.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group exemplified as the substituent of the hydroxyl group optionally have 1 to 3 substituents at substitutable positions. When the number of the substituents is not less than 2, the respective substituents may be the same or different.

Examples of the substituent for the $C_{1-10}$ alkyl group, $C_{2-10}$ alkenyl group and $C_{1-6}$ alkyl-carbonyl group include those similar to the substituents that the $C_{1-10}$ alkyl group and the like exemplified as the "hydrocarbon group" of the "optionally substituted hydrocarbon group" for $R^1$ or $R^2$ optionally have.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituents that the $C_{3-10}$ cycloalkyl group and the like exemplified as the "hydrocarbon group" of the "optionally substituted hydrocarbon group" for $R^1$ or $R^2$ optionally have. Examples of the substituent for the heterocyclic group include those similar to the substituents of the "optionally substituted heterocyclic group" for $R^1$ or $R^2$.

Examples of the "acyl group" for $R^1$ or $R^2$ include a group represented by the formula: $-COR^A$, $-CO-OR^A$, $-SO_3R^A$, $-SO_2R^A$, $-SOR^A$, $-CO-NR^{A'}R^{B'}$, $-CS-NR^{A'}R^{B'}$ or $-SO_2NR^{A'}R^{B'}$ wherein $R^A$ is a hydrogen atom, an optionally substituted hydrocarbon group or an optionally substituted heterocyclic group, and $R^{A'}$ and $R^{B'}$ are each independently a hydrogen atom, an optionally substituted hydrocarbon group or an optionally substituted heterocyclic group, or $R^{A'}$ and $R^{B'}$ optionally form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A'}$ or $R^{B'}$ include those similar to the "optionally substituted hydrocarbon group" and "optionally substituted heterocyclic group" exemplified as the "substituent" for $R_1$ or $R_2$.

Examples of the "nitrogen-containing heterocycle" of the "optionally substituted nitrogen-containing heterocycle" formed by $R^{a'}$ and $R^{b'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 3 substituents at substitutable positions. Examples of the substituent include those similar to the substituent of the "optionally substituted heterocyclic group" for $R^1$ or $R^2$. When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group optionally substituted by 1 to 3 substituents selected from
  (i) a halogen atom,
  (ii) a $C_{1-6}$ alkoxy-carbonyl group,
  (iii) a $C_{6-14}$ aryl group (e.g., phenyl), and
  (iv) a $C_{1-6}$ alkoxy group;
(4) a $C_{1-6}$ alkoxy-carbonyl group optionally substituted by 1 to 3 substituents selected from
  (i) a halogen atom,
  (ii) a $C_{6-14}$ aryl group (e.g., phenyl), and
  (iii) a $C_{1-6}$ alkoxy group;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl) optionally substituted by 1 to 3 halogen atoms;

(7) a carbamoyl group optionally mono- or di-substituted by substituent(s) selected from
  (i) a $C_{1-6}$ alkyl group optionally substituted by 1 to 3 substituents selected from
    (a) a halogen atom,
    (b) a $C_{1-6}$ alkoxy-carbonyl group,
    (c) a $C_{6-14}$ aryl group (e.g., phenyl),
    (d) a $C_{1-6}$ alkoxy group, and
    (e) a 4- to 12-membered aromatic heterocyclic group (e.g., furyl),
  (ii) a $C_{3-10}$ cycloalkyl group (e.g., cyclohexyl),
  (iii) a $C_{6-14}$ aryl group (e.g., phenyl) optionally substituted by 1 to 3 substituents selected from
    (a) a halogen atom,
    (b) a $C_{1-6}$ alkyl group optionally substituted by 1 to 3 halogen atoms, and
    (c) a $C_{1-6}$ alkoxy group, and
  (iv) a 4- to 12-membered aromatic heterocyclic group (e.g., pyridyl);
(8) a $C_{1-6}$ alkylsulfonyl group (e.g., methylsulfonyl, ethylsulfonyl, isopropylsulfonyl) optionally substituted by 1 to 3 substituents selected from
  (i) a halogen atom, and
  (ii) a $C_{6-14}$ aryl group (e.g., phenyl);
(9) a $C_{6-14}$ arylsulfonyl group (e.g., benzenesulfonyl) optionally substituted by 1 to 3 halogen atoms;
(10) a sulfamoyl group optionally mono- or di-substituted by substituent(s) selected from
  (i) a $C_{1-6}$ alkyl group optionally substituted by 1 to 3 substituents selected from
    (a) a halogen atom, and
    (b) a 4- to 12-membered nonaromatic heterocyclic group (e.g., pyrrolidinyl) optionally substituted by oxo group(s);
(11) a thiocarbamoyl group optionally mono- or di-substituted by substituent(s) selected from a $C_{1-6}$ alkyl group optionally substituted by 1 to 3 halogen atoms;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a nonaromatic heterocyclylcarbonyl group (e.g., tetrahydrofurylcarbonyl) optionally substituted by 1 to 3 substituents selected from a $C_{1-6}$ alkyl group optionally substituted by 1 to 3 halogen atoms; and the like.

$R^1$ is preferably
(1) an optionally substituted $C_{1-6}$ alkyl group,
(2) an optionally substituted $C_{3-10}$ cycloalkyl group,
(3) an optionally substituted $C_{6-14}$ aryl group,
(4) an optionally substituted heterocyclic group,
(5) a $C_{1-6}$ alkyl-carbonyl group or
(6) a $C_{3-10}$ cycloalkyl-carbonyl group.

$R^1$ is more preferably
(1) a $C_{1-6}$ alkyl group (e.g., methyl, isobutyl, tert-butyl, isopentyl, 2-ethylbutyl) optionally substituted by 1 to 3 hydroxy groups;
(2) a $C_{3-10}$ cycloalkyl group (e.g., cyclohexyl);
(3) a $C_{6-14}$ aryl group (preferably a phenyl group) optionally substituted by 1 to 3 substituents selected from
  (i) a halogen atom (e.g., fluorine, chlorine),
  (ii) a $C_{1-6}$ alkyl group (e.g., methyl) optionally substituted by 1 to 3 halogen atoms (e.g., fluorine, chlorine),
  (iii) a $C_{1-6}$ alkoxy group (e.g., methoxy, ethoxy, propoxy) optionally substituted by 1 to 3 substituents selected from
    (a) a halogen atom (e.g., fluorine; chlorine),
    (b) a $C_{1-6}$ alkylthio group (e.g., methylthio),
    (c) a $C_{1-6}$ alkylsulfinyl group (e.g., methylsulfinyl), and
    (d) a $C_{1-6}$ alkylsulfonyl group (e.g., methylsulfonyl),
  (vi) a $C_{1-6}$ alkylsulfonyl group (e.g., methylsulfonyl), and
  (v) a carbamoyl group;
(4) a 4- to 12-membered heterocyclic group (preferably, a 5- or 6-membered monocyclic nonaromatic heterocyclic group (e.g., dihydrothiopyranyl, tetrahydrothiopyranyl, 1-oxidetetrahydrothiopyranyl, 1,1-dioxidetetrahydrothiopyranyl, tetrahydropyranyl) or a 5- or 6-membered monocyclic aromatic heterocyclic group (e.g., pyrazolyl, oxazolyl, pyridyl, pyridazinyl)) optionally substituted by 1 to 3 substituents selected from
  (i) a halogen atom (e.g., fluorine, chlorine),
  (ii) a $C_{1-6}$ alkyl group (e.g., methyl, tert-butyl), and
  (iii) a $C_{1-6}$ alkoxy group (e.g., methoxy, ethoxy, propoxy, isopentoxy) optionally substituted by 1 to 3 substituents selected from
    (a) a $C_{1-6}$ alkoxy group (e.g., methoxy),
    (b) a hydroxy group, and
    (c) a 5- or 6-membered monocyclic nonaromatic heterocyclic group (e.g., pyrrolidinyl) optionally substituted by 1 or 2 oxo groups;
(5) a $C_{1-6}$ alkyl-carbonyl group (e.g., propylcarbonyl, isopropylcarbonyl); or
(6) a $C_{3-10}$ cycloalkyl-carbonyl group (e.g., cyclohexylcarbonyl).

$R^2$ is preferably
(1) an optionally substituted $C_{1-6}$ alkyl group; or
(2) an optionally substituted $C_{3-10}$ cycloalkyl group.

$R^2$ is more preferably
(1) a $C_{1-6}$ alkyl group (e.g., methyl, ethyl, isopropyl) optionally substituted by 1 to 3 substituents selected from
  (i) a $C_{1-6}$ alkoxy group (e.g., methoxy, ethoxy),
  (ii) a $C_{1-6}$ alkylthio group (e.g., methylthio),
  (iii) a $C_{1-6}$ alkylsulfinyl group (e.g., methylsulfinyl), and
  (iv) a $C_{1-6}$ alkylsulfonyl group (e.g., methylsulfonyl); or
(2) a $C_{3-10}$ cycloalkyl group (e.g., cyclopropyl, cyclohexyl).

Y is an oxygen atom, a sulfur atom or an oxygen atom.

When Y is a nitrogen atom, it is substituted by any of the aforementioned $R^1$ group, $R^2$ group and a group represented by

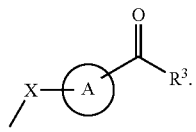

In other words, in this embodiment, the formula (I) is

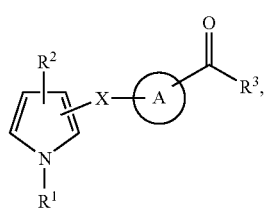

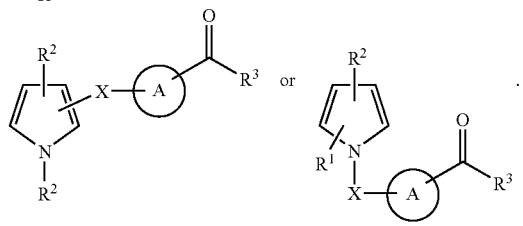

When Y is a nitrogen atom, it is preferably substituted by $R^1$.

$R^1$ group, $R^2$ group and

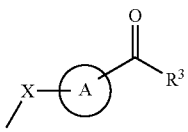

are each present at any substitutable position on the ring represented by

When Y is an oxygen atom, the formula (I) is preferably

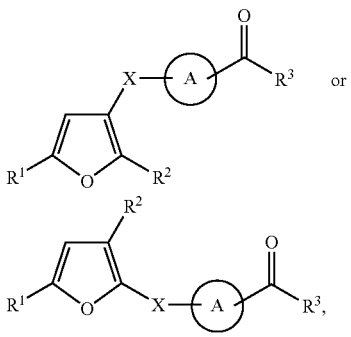

more preferably

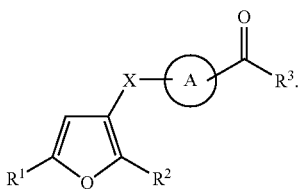

When Y is a sulfur atom, the formula (I) is preferably

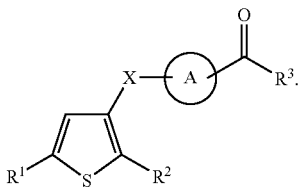

When Y is a nitrogen atom, the formula (I) is preferably

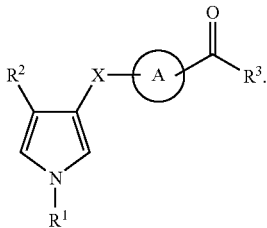

X is —O—, —S—, —SO—, —$CR^4R^5$—O—, —O—$CR^4R^5$—, —CO—$CR^4R^5$—, —$CR^4R^5$—CO—, —$CR^4R^5$—$NR^6$— or —CO—$NR^6$—.

$R^4$ is a hydrogen atom or a $C_{1-6}$ alkyl group.

$R^5$ and $R^6$ are each independently a hydrogen atom, an optionally substituted $C_{1-6}$ alkyl group, an optionally substituted $C_{3-10}$ cycloalkyl group, an optionally substituted $C_{6-14}$ aryl group or an optionally substituted 5- or 6-membered heterocyclic group.

Examples of the "5- or 6-membered heterocyclic group" of the "optionally substituted 5- or 6-membered heterocyclic group" for $R^5$ or $R^6$ include a 5- or 6-membered monocyclic aromatic heterocyclic group and a monocyclic nonaromatic heterocyclic group (e.g., furyl, thienyl, pyridyl, pyrimidinyl, pyridazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl, pyrrolidinyl, piperidinyl, morpholinyl, thiomorpholinyl, piperazinyl, hexamethyleniminyl, oxazolidinyl, dihydrothiopyranyl, imidazolidinyl, oxazolinyl, imidazolinyl, dioxolyl, dioxolanyl, dihydrooxadiazolyl, pyranyl, thiopyranyl, tetrahydrothiopyranyl, tetrahydrofuryl, pyrazolinyl, tetrahydrotriazolyl).

The "$C_{1-6}$ alkyl group" of the "optionally substituted $C_{1-6}$ alkyl group" for $R^5$ or $R^6$ optionally has 1 to 3 substituents at substitutable positions. Examples of such substituent include those similar to the substituents that the $C_{1-10}$ alkyl group and the like exemplified as the "hydrocarbon group" of the "optionally substituted hydrocarbon group" for $R^1$ or $R^2$ optionally have. When the number of the substituents is not less than 2, the respective substituents may be the same or different.

The "$C_{3-10}$ cycloalkyl group", "$C_{6-14}$ aryl group" and "5- or 6-membered heterocyclic group" of the "optionally substituted $C_{3-10}$ cycloalkyl group", "optionally substituted $C_{6-14}$ aryl group" and "optionally substituted 5- or 6-membered heterocyclic group" for $R^5$ or $R^6$ optionally have 1 to 3 substituents at substitutable positions. Examples of such substituent for the "$C_{3-10}$ cycloalkyl group" and "$C_{6-14}$ aryl group" include those similar to the substituents that the $C_{3-10}$ cycloalkyl group and the like exemplified as the "hydrocarbon group" of the "optionally substituted hydrocarbon group" for $R^1$ or $R^2$ optionally have, and examples of such substituent for the "5- or 6-membered heterocyclic group" include those similar to the substituents of the "optionally substituted heterocyclic group" for $R^1$ or $R^2$. When the number of the substituents is not less than 2, the respective substituents may be the same or different.

X is preferably $$—CR^4R^5—O—; \text{ or} \qquad (1)$$

$$—CR^4R^5—NR^6—, \qquad (2)$$

wherein $R^4$, $R^5$ and $R^6$ are each as defined above.

X is more preferably $$—CH(R^5)—O—; \text{ or} \qquad (1)$$

$$—CH(R^5)—NH—, \qquad (2)$$

wherein $R^5$ is
(i) a hydrogen atom,
(ii) a $C_{1-6}$ alkyl group (e.g., methyl, butyl, isobutyl, neopentyl),
(iii) a $C_{3-10}$ cycloalkyl group (e.g., cyclobutyl, cyclopentyl, cyclohexyl) optionally substituted by 1 to 3 substituents selected from
 (a) an oxo group,
 (b) a hydroxy group, and
 (c) a $C_{1-3}$ alkylenedioxy (e.g., ethylenedioxy),
(iv) a $C_{6-14}$ aryl group (e.g., phenyl), or
(v) a 5- or 6-membered monocyclic nonaromatic heterocyclic group (e.g., tetrahydropyranyl).

$R^3$ is a group represented by —$(CH_2)_3$—COOH or a group represented by —$NR^7$—$CR^8R^9$—$CR^{10}R^{11}$—COOH.

$R^7$, $R^8$, $R^9$ and $R^{10}$ are each independently a hydrogen atom or a $C_{1-6}$ alkyl group.

$R^{11}$ is a hydrogen atom, a $C_{1-6}$ alkyl group or a hydroxy group.

$R^3$ is preferably

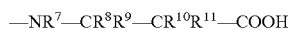

wherein $R^7$, $R^8$, $R^9$, $R^{10}$ and $R^{11}$ are each as defined above.
$R^3$ is more preferably

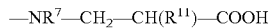

wherein $R^7$ is
(1) a hydrogen atom, or
(2) a $C_{1-6}$ alkyl group (e.g., methyl); and
$R^{11}$ is
(1) a hydrogen atom, or
(2) a hydroxy group.

Ring A is a benzene ring or a 5- or 6-membered heterocycle, each of which is optionally further substituted.

Examples of the "optionally further substituted 5- or 6-membered heterocycle" for ring A include a 5- or 6-membered monocyclic aromatic heterocycle and a 5- or 6-membered monocyclic nonaromatic heterocycle. Preferable examples of the 5- or 6-membered monocyclic aromatic heterocycle include furan, thiophene, pyridine, pyrimidine, pyridazine, pyrrole, imidazole, pyrazole, thiazole, isothiazole, oxazole, isoxazole, oxadiazole, thiadiazole, triazole, tetrazole, triazine and the like.

In addition, preferable examples of the 5- or 6-membered monocyclic nonaromatic heterocycle include pyrrolidine, piperidine, morpholine, thiomorpholine, piperazine, hexamethylenimine, oxazolidine, dihydrothiopyran, imidazolidine, oxazoline, imidazoline, dioxole, dioxolane, dihydrooxadiazoline, pyran, thiopyran, tetrahydrothiopyran, tetrahydrofuran, pyrazoline, tetrahydrotriazoline and the like.

When ring A is a benzene ring or a 6-membered heterocycle, the following binding mode:

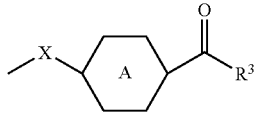

is preferable. Here, when ring A is a 6-membered heterocycle, it is preferably bonded to an —X— group and a —CO—$R^3$ group via a carbon atom of the ring.

When ring A is a 5-membered heterocycle, the following binding mode:

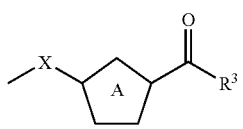

is preferable.

The "benzene ring or 5- or 6-membered heterocycle" of the "optionally further substituted, benzene ring or 5- or 6-membered heterocycle" for ring A each optionally has 1 to 3 substituents in addition to the group:

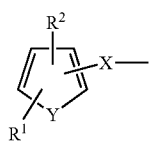

and a group: —CO—$R^3$, at substitutable positions. Examples of such substituent include those similar to the substituent of the "optionally substituted heterocyclic group" for $R^1$ or $R^2$. When the number of the substituents is not less than 2, the respective substituents may be the same or different.

As ring A, an optionally substituted benzene ring or an optionally substituted pyridine ring is preferable.

Ring A is more preferably a benzene ring or a pyridine ring optionally substituted by 1 to 3 substituents selected from
(1) a halogen atom (e.g., fluorine);
(2) a $C_{1-6}$ alkyl group (e.g., methyl); and
(3) a $C_{1-6}$ alkoxy group (e.g., methoxy).

In the formula (I) wherein Y is a nitrogen atom, the compound is novel when ring A is other than optionally substituted pyrrole.

Preferable examples of the compound represented by the formula (I) or a salt thereof include the following.

[Compound A]

A compound of the formula (I), wherein
ring A is a benzene ring;
Y is an oxygen atom or a sulfur atom;
X is —$CR^4R^5$—O— or —$CR^4R^5$—$NR^6$—;
$R^4$ is a hydrogen atom or a $C_{1-6}$ alkyl group;
$R^5$ is a hydrogen atom, a $C_{1-6}$ alkyl group, a $C_{3-10}$ cycloalkyl group or a $C_{6-14}$ aryl group;
$R^6$ is a hydrogen atom;
$R^1$ is
(1) a $C_{1-10}$ alkyl group (preferably, isobutyl, tert-butyl, 1-ethylpropyl),
(2) a $C_{3-10}$ cycloalkyl group (preferably, cyclohexyl), or
(3) a $C_{6-14}$ aryl group (preferably, phenyl), each of which is optionally substituted by 1 to 3 substituents selected from
  (a) a halogen atom (preferably, a fluorine atom, a chlorine atom),
  (b) a $C_{1-6}$ alkyl group (preferably, methyl) optionally substituted by 1 to 3 halogen atoms (preferably, a fluorine atom, a chlorine atom), and
  (c) a $C_{1-6}$ alkoxy group (preferably, methoxy) optionally substituted by 1 to 3 halogen atoms (preferably, a fluorine atom), or
(4) a 5- or 6-membered monocyclic nonaromatic heterocyclic group (preferably, dihydrothiopyranyl (e.g., dihydrothiopyran-4-yl)) optionally substituted by a hydroxyl group;
$R^2$ is a $C_{1-10}$ alkyl group (preferably, methyl, ethyl, isopropyl) or a $C_{3-10}$ cycloalkyl group (preferably, cyclohexyl);
$R^3$ is a group represented by —$NR^7$—$CR^8R^9$—$CR^{10}$COOH;
$R^7$ is a hydrogen atom or a $C_{1-6}$ alkyl group (preferably, methyl); and
$R^8$, $R^9$, $R^{10}$ and $R^{11}$ are each a hydrogen atom; or a salt thereof.

[Compound B]

A compound of the formula (I), wherein
ring A is an optionally substituted benzene ring or an optionally substituted pyridine ring;
Y is an oxygen atom, a sulfur atom or a nitrogen atom;
X is $$—CR^4R^5—O— \quad \text{or} \tag{1}$$

$$—CR^4R^5—NR^6— \tag{2}$$

wherein $R^4$, $R^5$ and $R^6$ are each as defined above;
$R^1$ is
(1) an optionally substituted $C_{1-6}$ alkyl group,
(2) an optionally substituted $C_{3-10}$ cycloalkyl group,
(3) an optionally substituted $C_{6-14}$ aryl group, (4) an optionally substituted heterocyclic group,
(5) a $C_{1-6}$ alkyl-carbonyl group or
(6) a $C_{3-10}$ cycloalkyl-carbonyl group;
$R^2$ is
(1) an optionally substituted $C_{1-6}$ alkyl group or
(2) an optionally substituted $C_{3-10}$ cycloalkyl group; and
$R^3$ is $$-NR^7-CR^8R^9-CR^{10}R^{11}-COOH$$

wherein $R^7$, $R^8$, $R^9$, $R^{10}$ and $R^{11}$ are each as defined above; or a salt thereof.

[Compound C]

A compound of the formula (I), wherein
ring A is a benzene ring or a pyridine ring, each of which is optionally substituted by 1 to 3 substituents selected from
(1) a halogen atom (e.g., fluorine),
(2) a $C_{1-6}$ alkyl group (e.g., methyl), and
(3) a $C_{1-6}$ alkoxy group (e.g., methoxy);
Y is an oxygen atom, a sulfur atom or a nitrogen atom;
X is $$-CH(R^5)-O-\text{ or} \quad (1)$$

$$-CH(R^5)-NH-, \quad (2)$$

wherein $R^5$ is
  (i) a hydrogen atom,
  (ii) a $C_{1-6}$ alkyl group (e.g., methyl, butyl, isobutyl, neopentyl),
  (iii) a $C_{3-10}$ cycloalkyl group (e.g., cyclobutyl, cyclopentyl, cyclohexyl) optionally substituted by 1 to 3 substituents selected from
    (a) an oxo group,
    (b) a hydroxy group, and
    (c) a $C_{1-3}$ alkylenedioxy (e.g., ethylenedioxy),
  (iv) a $C_{6-14}$ aryl group (e.g., phenyl), or
  (v) a 5- or 6-membered monocyclic nonaromatic heterocyclic group (e.g., tetrahydropyranyl);
$R^1$ is
(1) a $C_{1-6}$ alkyl group (e.g., methyl, isobutyl, tert-butyl, isopentyl, 2-ethylbutyl) optionally substituted by 1 to 3 hydroxy groups;
(2) a $C_{3-10}$ cycloalkyl group (e.g., cyclohexyl);
(3) a $C_{6-14}$ aryl group (preferably, a phenyl group) optionally substituted by 1 to 3 substituents selected from
  (i) a halogen atom (e.g., fluorine, chlorine),
  (ii) a $C_{1-6}$ alkyl group (e.g., methyl) optionally substituted by 1 to 3 halogen atoms (e.g., fluorine, chlorine),
  (iii) a $C_{1-6}$ alkoxy group (e.g., methoxy, ethoxy, propoxy) optionally substituted by 1 to 3 substituents selected from
    (a) a halogen atom (e.g., fluorine, chlorine),
    (b) a $C_{1-6}$ alkylthio group (e.g., methylthio),
    (c) a $C_{1-6}$ alkylsulfinyl group (e.g., methylsulfinyl), and
    (d) a $C_{1-6}$ alkylsulfonyl group (e.g., methylsulfonyl),
  (vi) a $C_{1-6}$ alkylsulfonyl group (e.g., methylsulfonyl), and
  (v) a carbamoyl group;
(4) a 4- to 12-membered heterocyclic group (preferably, a 5- or 6-membered monocyclic nonaromatic heterocyclic group (e.g., dihydrothiopyranyl, tetrahydrothiopyranyl, 1-oxidetetrahydrothiopyranyl, 1,1-dioxidetetrahydrothiopyranyl, tetrahydropyranyl) or a 5- or 6-membered monocyclic aromatic heterocyclic group (e.g., pyrazolyl, oxazolyl, pyridyl, pyridazinyl)) optionally substituted by 1 to 3 substituents selected from
  (i) a halogen atom (e.g., fluorine, chlorine),
  (ii) a $C_{1-6}$ alkyl group (e.g., methyl, tert-butyl), and
  (iii) a $C_{1-6}$ alkoxy group (e.g., methoxy, ethoxy, propoxy, isopentoxy) optionally substituted by 1 to 3 substituents selected from
    (a) a $C_{1-6}$ alkoxy group (e.g., methoxy),
    (b) a hydroxy group, and (c) a 5- or 6-membered monocyclic nonaromatic heterocyclic group (e.g., pyrrolidinyl) optionally substituted by 1 or 2 oxo groups;
(5) a $C_{1-6}$ alkyl-carbonyl group (e.g., propylcarbonyl, isopropylcarbonyl); or
(6) a $C_{3-10}$ cycloalkyl-carbonyl group (e.g., cyclohexylcarbonyl);
$R^2$ is
(1) a $C_{1-6}$ alkyl group (e.g., methyl, ethyl, isopropyl) optionally substituted by 1 to 3 substituents selected from
  (i) a $C_{1-6}$ alkoxy group (e.g., methoxy, ethoxy),
  (ii) a $C_{1-6}$ alkylthio group (e.g., methylthio),
  (iii) a $C_{1-6}$ alkylsulfinyl group (e.g., methylsulfinyl), and
  (iv) a $C_{1-6}$ alkylsulfonyl group (e.g., methylsulfonyl), or
(2) a $C_{3-10}$ cycloalkyl group (e.g., cyclopropyl, cyclohexyl);
$R^3$ is $$-NR^7-CH_2-CH(R^{11})-COOH$$

wherein $R^7$ is
(1) a hydrogen atom, or
(2) a $C_{1-6}$ alkyl group (e.g., methyl), and
$R^{11}$ is
(1) a hydrogen atom, or
(2) a hydroxy group; or a salt thereof.

[Compound D]

A compound of the formula (I), which is

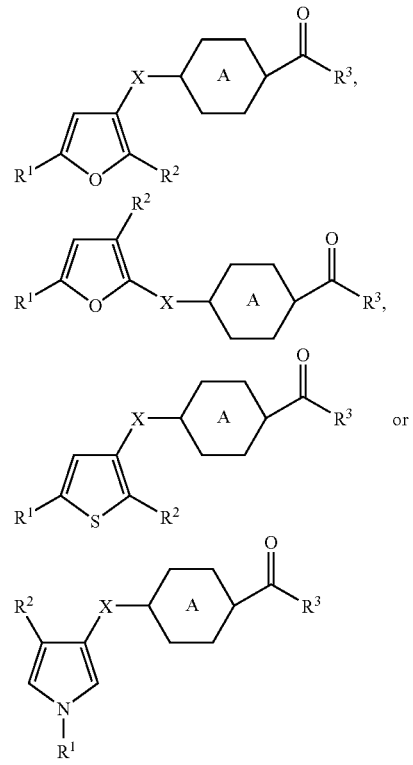

(more preferably

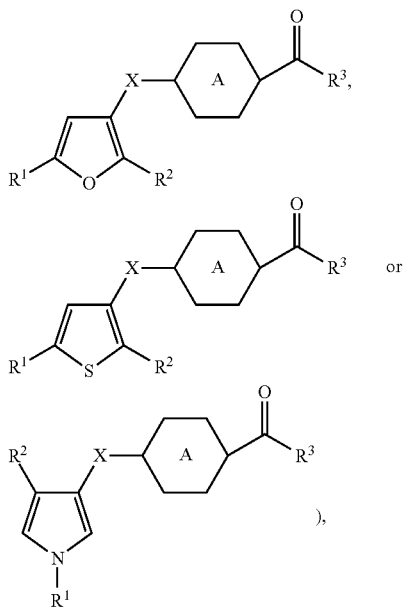

wherein
ring A is a benzene ring or a pyridine ring optionally substituted by 1 to 3 substituents selected from
(1) a halogen atom (e.g., fluorine),
(2) a $C_{1-6}$ alkyl group (e.g., methyl), and
(3) a $C_{1-6}$ alkoxy group (e.g., methoxy);
X is $$—CH(R^5)—O—, \text{ or} \qquad (1)$$

$$—CH(R^5)—NH—, \qquad (2)$$

wherein $R^5$ is
  (i) a hydrogen atom,
  (ii) a $C_{1-6}$ alkyl group (e.g., methyl, butyl, isobutyl, neopentyl),
  (iii) a $C_{3-10}$ cycloalkyl group (e.g., cyclobutyl, cyclopentyl, cyclohexyl) optionally substituted by 1 to 3 substituents selected from
    (a) an oxo group,
    (b) a hydroxy group, and
    (c) $C_{1-3}$ alkylenedioxy (e.g., ethylenedioxy),
  (iv) a $C_{6-14}$ aryl group (e.g., phenyl), or
  (v) a 5- or 6-membered monocyclic nonaromatic heterocyclic group (e.g., tetrahydropyranyl);
$R^1$ is
(1) a $C_{1-6}$ alkyl group (e.g., methyl, isobutyl, tert-butyl, isopentyl, 2-ethylbutyl) optionally substituted by 1 to 3 hydroxy groups;
(2) a $C_{3-10}$ cycloalkyl group (e.g., cyclohexyl);
(3) a $C_{6-14}$ aryl group (preferably, a phenyl group) optionally substituted by 1 to 3 substituents selected from
  (i) a halogen atom (e.g., fluorine, chlorine),
  (ii) a $C_{1-6}$ alkyl group (e.g., methyl) optionally substituted by 1 to 3 halogen atoms (e.g., fluorine, chlorine),
  (iii) a $C_{1-6}$ alkoxy group (e.g., methoxy, ethoxy, propoxy) optionally substituted by 1 to 3 substituents selected from
    (a) a halogen atom (e.g., fluorine, chlorine),
    (b) a $C_{1-6}$ alkylthio group (e.g., methylthio),
    (c) a $C_{1-6}$ alkylsulfinyl group (e.g., methylsulfinyl), and
    (d) a $C_{1-6}$ alkylsulfonyl group (e.g., methylsulfonyl),
  (vi) a $C_{1-6}$ alkylsulfonyl group (e.g., methylsulfonyl), and
  (v) a carbamoyl group;
(4) a 4- to 12-membered heterocyclic group (preferably, 5- or a 6-membered monocyclic nonaromatic heterocyclic group (e.g., dihydrothiopyranyl, tetrahydrothiopyranyl, 1-oxidetetrahydrothiopyranyl, 1,1-dioxidetetrahydrothiopyranyl, tetrahydropyranyl) or a 5- or 6-membered monocyclic aromatic heterocyclic group (e.g., pyrazolyl, oxazolyl, pyridyl, pyridazinyl)) optionally substituted by 1 to 3 substituents selected from
  (i) a halogen atom (e.g., fluorine, chlorine),
  (ii) a $C_{1-6}$ alkyl group (e.g., methyl, tert-butyl), and
  (iii) a $C_{1-6}$ alkoxy group (e.g., methoxy, ethoxy, propoxy, isopentoxy) optionally substituted by 1 to 3 substituents selected from
    (a) a $C_{1-6}$ alkoxy group (e.g., methoxy),
    (b) a hydroxy group, and
    (c) a 5- or 6-membered monocyclic nonaromatic heterocyclic group (e.g., pyrrolidinyl) optionally substituted by 1 or 2 oxo groups;
(5) a $C_{1-6}$ alkyl-carbonyl group (e.g., propylcarbonyl, isopropylcarbonyl); or
(6) a $C_{3-10}$ cycloalkyl-carbonyl group (e.g., cyclohexylcarbonyl);
$R^2$ is
(1) a $C_{1-6}$ alkyl group (e.g., methyl, ethyl, isopropyl) optionally substituted by 1 to 3 substituents selected from
  (i) a $C_{1-6}$ alkoxy group (e.g., methoxy, ethoxy),
  (ii) a $C_{1-6}$ alkylthio group (e.g., methylthio),
  (iii) a $C_{1-6}$ alkylsulfinyl group (e.g., methylsulfinyl), and
  (iv) a $C_{1-6}$ alkylsulfonyl group (e.g., methylsulfonyl), or
(2) a $C_{3-10}$ cycloalkyl group (e.g., cyclopropyl, cyclohexyl);
$R^3$ is $$—NR^7—CH_2—CH(R^{11})—COOH$$

wherein $R^7$ is
(1) a hydrogen atom, or
(2) a $C_{1-6}$ alkyl group (e.g., methyl), and
$R^{11}$ is
(1) a hydrogen atom, or
(2) a hydroxy group; or a salt thereof.
[Compound E]
3-[{[4-({1-[5-(6-methoxypyridin-3-yl)-2-methylfuran-3-yl]-3-methylbutyl}amino)phenyl]carbonyl}(methyl)amino]propanoic acid (Example 319);
3-[{[4-({cyclohexyl[5-(4-fluorophenyl)-2-(methoxymethyl)furan-3-yl]methyl}amino)phenyl]carbonyl}(methyl)amino]propanoic acid (Example 314);
3-[{[5-({cyclohexyl[5-(4-fluorophenyl)-2-methylfuran-3-yl]methyl}amino)pyridin-2-yl]carbonyl}(methyl)amino]propanoic acid (Example 318);
3-[{[4-({cyclohexyl[5-(6-methoxypyridin-3-yl)-2-methylfuran-3-yl]methyl}amino)phenyl]carbonyl}(methyl)amino]propanoic acid (Example 166); or
3-{[(5-{[cyclohexyl(2-methyl-5-phenylthiophen-3-yl)methyl]amino}pyridin-2-yl)carbonyl](methyl)amino}propanoic acid (Example 311);
or a salt thereof.

As a salt of the compound represented by the formula (I), a pharmacologically acceptable salt is preferable. Examples of such salt include salts with inorganic base, salts with organic base, salts with inorganic acid, salts with organic acid, salts with basic or acidic amino acid, and the like.

Preferable examples of a salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of a compound represented by the formula (I) means a compound which is converted to the compound represented by the formula (I) with a reaction due to an enzyme, an gastric acid, etc. under the physiological condition in the living body, that is, a compound which is converted to the compound represented by the formula (I) with oxidation, reduction, hydrolysis, etc. according to an enzyme; a compound which is converted to the compound represented by the formula (I) by hydrolysis etc. due to gastric acid, etc.

A prodrug of a compound represented by the formula (I) may be a compound obtained by subjecting an amino group in the compound represented by the formula (I) to an acylation, alkylation or phosphorylation (e.g., a compound obtained by subjecting an amino group in the compound represented by the formula (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation);
a compound obtained by subjecting a hydroxy group in the compound represented by the formula (I) to an acylation, alkylation, phosphorylation or boration (e.g., a compound obtained by subjecting a hydroxy group in the compound represented by the formula (I) to an acetylation, palmitoylation, propanoylation, pivaloylation, succinylation, fumarylation, alanylation and dimethylaminomethylcarbonylation);
a compound obtained by subjecting a carboxyl group in the compound represented by the formula (I) to an esterification or amidation (e.g., a compound obtained by subjecting a carboxy group in the compound represented by the formula (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation) and the like. Any of these compounds can be produced from the compound represented by the formula (I) by a method known per se.

In addition, the prodrug of the compound represented by the formula (I) may also be one which is converted into a compound represented by the formula (I) under a physiological condition, such as those described in IYAKUHIN no KAIHATSU (Development of Pharmaceuticals), Vol. 7, Design of Molecules, p. 163-198, 1990, published by HIROKAWA SHOTEN.

The compound represented by the formula (I) or a salt thereof, or a prodrug thereof in the present invention also contains, besides stereoisomers such as cis, transisomer and the like, and racemate, an optically active form such as R-form and S-form and the like. In addition, the isomers by conformation are generated depending on the kind of ring such as ring A and the like. Such isomers are also encompassed in the compound represented by the formula (I) or a salt thereof, or a prodrug thereof of the present invention.

In addition, the compound represented by the formula (I) or a salt thereof, or a prodrug thereof may be labeled with isotope (e.g., $^3$H, $^{14}$C, $^{35}$S, $^{125}$I) and the like.

Furthermore, a compound represented by the formula (I) or a prodrug thereof may be a non-solvate (including anhydride) or a solvate (including hydrate).

Furthermore, a deuterium conversion form wherein $^1$H is converted to $^2$H(D) is also encompassed in the compound of the present invention.

The compound represented by the formula (I) or a salt thereof or a prodrug thereof (sometimes to be simply abbreviated as "the compound of the present invention" in the present specification) has low toxicity, and can be used as an agent for the prophylaxis or treatment of various diseases to be mentioned below in mammals (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid preparation; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the dosage form of the above-mentioned pharmaceutical composition include oral preparations such as tablets (inclusive of sugar-coated tablets, film-coated tablets, sublingual tablets, orally disintegrating tablets), capsules (inclusive of soft capsules, microcapsules), granules, powders, troches, syrups, emulsions, suspensions, films (e.g., orally disintegrable films) and the like; and parenteral preparations such as injections (e.g., subcutaneous injections, intravenous injections, intramuscular injections, intraperitoneal injections, drip infusions), external preparations (e.g., dermal preparations, ointments), suppository (e.g., rectal suppositories, vaginal suppositories), pellets, nasal preparations, pulmonary preparations (inhalants), eye drops and the like. These may be safely administered orally or parenterally (e.g., topically, rectally, intravenously administered).

These preparations may be release control preparations such as immediate-release preparation, sustained-release preparation and the like (e.g., sustained-release microcapsule).

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., cytotoxicity, acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior glucagon antagonistic action. The compound of the present invention can suppress excess sugar production by the liver by blocking the action of glucagon. Therefore, the compound of the present invention is useful as an agent for the prophylaxis or treatment of a disease characterized by excess sugar production.

Specifically, the compound of the present invention can be used as a prophylactic or therapeutic agent for obesity, diabetes (e.g., type 1 diabetes, type 2 diabetes, gestational diabetes, obese diabetes), hyperlipidemia (e.g., hypertriglyceridemia, hypercholesterolemia, hypo-HDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], metabolic syndrome (pathology containing three or more selected from hyper-triglycerid(TG)emia, hypo-HDL cholesterol (HDL-C) emia, hypertension, abdomen obesity and impaired glucose tolerance), sarcopenia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood glucose level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is low toxic and safe. Therefore, the compound of the present invention, or a salt thereof, or a prodrug thereof having a superior glucagon antagonistic action can also be used, for example, as a prophylactic or therapeutic agent to a subject of administration for osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal diseases (e.g., diabetic nephropathy, glomerulonephritis, glomerulosclerosis, nephrosissyndrome, hypertensive nephrosclerosis, endstage renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., rheumatoid arthritis, spondylitis deformans, osteoarthritis, lumbago, gout, inflammation after operation or trauma, swelling, neuralgia, pharyngolaryngitis, cystitis, hepatitis (including nonalcoholic steatohepatitis), pneumonia, pancreatitis, enteritis, inflammatory intestine disease (including inflammatory colitis), ulcerative colitis, gastric mucosa injury (including gastric mucosa injury caused by aspirin), small intestinal mucosa injury, malabsorption, testis dysfunction, visceral obesity syndrome, or sarcopenia.

While the administration subject of the pharmaceutical composition of the present invention is not particularly limited, mammals (e.g., mouse, rat, hamster, rabbit, cat, dog, bovine, sheep, monkey, human etc.) are preferable. By administration of the compound of the present invention to the above-mentioned mammals, diabetes in the mammal can also be prevented or treated.

The compound of the present invention can also be used for the secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult diabetic patient, it is generally about 0.01 to 100 mg/kg body weight, preferably 0.05 to 30 mg/kg body weight, more preferably 0.1 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and they may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agent for diabetes include insulin preparations (e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitor (e.g., Vildagliptin, Sitagliptin, Saxagliptin, T-6666, TS-021), β3 agonist (e.g., AJ-9677), GPR40 agonist, GLP-1 receptor agonist [e.g., GLP-1, GLP-1MR, N,N-2211, AC-2993 (exendin-4), BIM-51077, Aib(8,35)hGLP-1(7,37) $NH_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitors, glucagon antagonists), SGLUT (sodium-glucose, cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP(Glucose-dependent insulinotropic peptide) and the like.

Examples of the therapeutic agents for diabetic complications include aldose reductase inhibitors (e.g., tolrestat, epalrestat, zenarestat, zopolrestat, minalrestat, fidarestat, CT-112), neurotrophic factor and an increasing drug thereof (e.g., NGF, NT-3, BDNF, neurotrophin production and secretion promoter described in WO01/14372 (e.g., 4-(4-chlorophenyl)-2-(2-methyl-1-imidazolyl)-5-[3-(2-methylphenoxy)propyl]oxazole)), nerve regeneration promoter (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1 (ASK-1) inhibitor and the like.

Examples of the therapeutic agent for hyperlipidemia include statin compound (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol (γ-oryzanol)) and the like.

Examples of the antihypertensive agent include angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonist (e.g., manidipine, nifedipine, amlodipine, efonidipine, nicardipine), potassium channel opener (e.g., levcromakalim, L-27152, AL 0671, NIP-121), clonidine and the like.

Examples of the antiobesity agent include central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compound described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), feeding deterrent (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide and furosemide and the like.

Examples of the antithrombotic agent include heparin (e.g., heparin sodium, heparin calcium, dalteparin sodium), warfarin (e.g., warfarin potassium), anti-thrombin drug (e.g., aragatroban), thrombolytic agent (e.g., urokinase, tisokinase, alteplase, nateplase, monteplase, pamiteplase), platelet aggregation inhibitor (e.g., ticlopidine hydrochloride, cilostazol), ethyl icosapentate, beraprost sodium, sarpogrelate hydrochloride) and the like can be mentioned.

The production methods of the compound of the present invention are explained in the following.

The compound of the present invention can be produced according to a method known per se, for example, the methods described in detail in the following, or a method analogous thereto. In addition, unless otherwise specified, the starting compound for each of the following reactions can be produced by a method known per se. The compounds (II)-(XIV) of the following formulas also include salts. Examples of such salt include those similar to the salts used for compound (I).

While the compound obtained by each step in the following formulas can be directly used for the next reaction as a reaction mixture or a crude product, it can be easily isolated and purified from the reaction mixture by a known separation and purification means, for example, concentration, concentration under reduced pressure, solvent extraction, crystallization, recrystallization, phase transfer, chromatography and the like. Moreover, when the compounds of the following formulas are commercially available, the commercially available products can also be used directly.

In each of the following reactions, when the starting compound has an amino group, a carboxyl group or a hydroxy group as a substituent, such group may be protected by a protecting group generally used in the peptide chemistry and the like. In this case, the protecting group is removed as necessary after the reaction to give the object compound.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

These groups are optionally substituted by 1 to 3 substituents selected from a halogen atom, a $C_{1-6}$ alkyl group, a $C_{1-6}$ alkoxy group and a nitro group.

The above-mentioned protecting group can be removed according to a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyliodide, trimethylsilyl bromide and the like) and the like, a reduction method and the like are used.

Compound (I) can be produced, for example, by the methods shown in the following reaction schemes 1-9 (in the following reaction schemes, compounds (I) produced by the methods shown in respective reaction schemes are indicated as compounds (I-A)-(I-I), respectively).

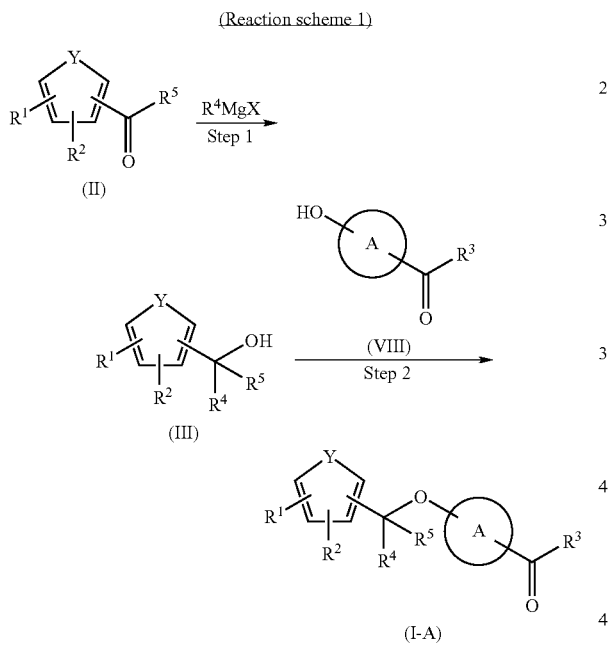

wherein each symbol is as defined above.
Step 1

Compound (III) can be produced by reacting compound (II) with Grignard reagent.

This reaction is performed in a solvent inert to the reaction. Such solvent is not particularly limited as long as the reaction proceeds and, for example, ethers such as diethyl ether, tetrahydrofuran, 1,4-dioxane and the like; aliphatic hydrocarbons such as hexane, heptane and the like; aromatic hydrocarbons such as benzene, toluene, xylene and the like can be mentioned. These solvents may be used in a mixture at an appropriate ratio.

The amount of the Grignard reagent to be used is generally about 1-10 mol, preferably about 1-2 mol, per 1 mol of compound (II).

The reaction temperature is generally −80° C. to 100° C., preferably −20° C. to 50° C.

The reaction time is generally 0.5-20 hr.
Step 2

Compound (I-A) can be produced by subjecting compound (III) and phenol compound (VIII) to a method known per se as Mitsunobu reaction or a method analogous thereto. This reaction is generally performed in the presence of an organic phosphorus compound and an electrophilic reagent in a solvent inert to the reaction.

Examples of the organic phosphorus compound include triphenylphosphine, tributylphosphine and the like.

Examples of the electrophilic reagent include diethyl azodicarboxylate, diisopropyl azodicarboxylate, azodicarbonyldipiperazine, 1,1'-(azodicarbonyl)dipiperidine and the like.

The amount of the organic phosphorus compound and electrophilic reagent to be used is generally about 0.5-10% mol, preferably about 1-2 mol, respectively, per 1 mol of compound (III).

The Mitsunobu reaction is performed in a solvent inert to the reaction. Such solvent is not particularly limited as long as the reaction proceeds and, for example, ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide etc.; and the like can be mentioned. These solvents may be used in a mixture at an appropriate ratio.

The amount of phenol compound (VIII) to be used is generally 1-10 molar equivalents, preferably 1-3 molar equivalents, per 1 mol of compound (III).

The reaction temperature is generally −50° C.-150° C., preferably −10° C.-100° C.

The reaction time is generally 0.5-20 hr.

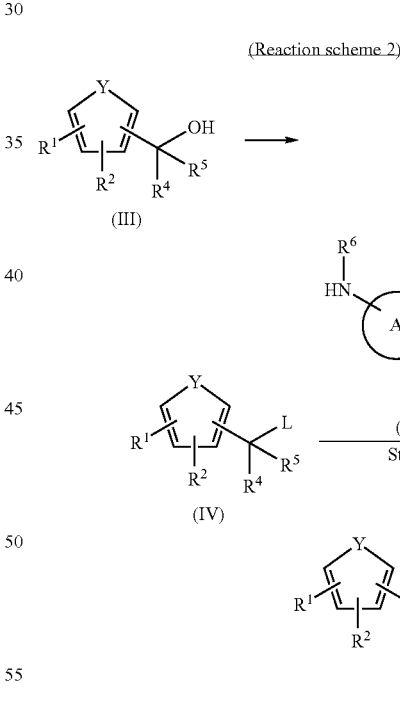

wherein L is a leaving group (e.g., a substituted sulfonyloxy group (e.g., a methanesulfonyloxy group, a p-toluenesulfonyloxy group), a halogen atom (e.g., chlorine, bromine)), and other symbols are as defined above.
Step 3

Compound (IV) can be produced, for example, by converting a hydroxyl group of compound (III) to a leaving group. Such conversion to a leaving group can be performed according to a conventional method, for example, by reaction with methanesulfonyl chloride in the presence of an appropriate base, or reaction with thionyl chloride or the like.

Examples of the appropriate base to be used for the conversion to a leaving group include N,N-diisopropylethylamine (DIEA), triethylamine (TEA), pyridine, N,N-dimethylaniline and the like.

The amount of the base to be used is generally 1-10 molar equivalents, preferably 1-5 molar equivalents, per 1 mol of compound (III).

The amount of the methanesulfonyl chloride to be used is generally 1-10 molar equivalents, preferably 1-5 molar equivalents, per 1 mol of compound (III).

The amount of the thionyl chloride to be used is generally 1-10 molar equivalents, preferably 1-5 Molar equivalents, per 1 mol of compound (III).

This reaction is performed in a solvent inert to the reaction. Such solvent is not particularly limited as long as the reaction proceeds and, for example, ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; and the like can be mentioned. These solvents may be used in a mixture at an appropriate ratio.

The reaction temperature is generally -80-150° C., preferably -10-100° C.

The reaction time is generally 0.5-20 hr.
Step 4

Compound (I-B) can be produced, for example, by reacting compound (IV) with compound (VI) in the presence of a base.

Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate, cesium carbonate and the like; alkali metal hydrogen carbonate such as sodium hydrogen carbonate, potassium hydrogen carbonate and the like; alkali metal alkoxide having 1 to 6 carbon atoms such as sodium methoxide, sodium ethoxide, potassium tert-butoxide and the like; metal hydride such as sodium hydride, potassium hydride and calcium hydride; and the like.

The amount of the base to be used is generally 1-10 molar equivalents, preferably 1-5 molar equivalents, per 1 mol of compound (IV).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; and the like can be mentioned. Two or more kinds of these solvents may be used in a mixture at an appropriate ratio.

In addition, for the reaction, alkali metal iodide such as sodium iodide and the like may be added as a reaction promoter in 1 molar equivalent to a large excess (preferably 1-10 molar equivalents), per 1 mol of compound (IV).

The amount of compound (VI) to be used is generally 1-10 molar equivalents, preferably 1-3 molar equivalents, per 1 mol of compound (IV).

The reaction temperature is generally -80° C.-200° C., preferably 0° C.-150° C.

The reaction time is generally 0.5-20 hr.

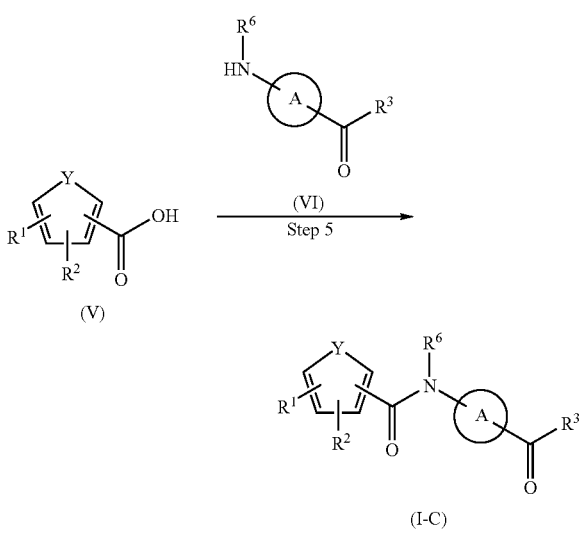

(Reaction scheme 3)

wherein each symbol is as defined above.
Step 5

In this method, compound (I-C) is produced by condensing compound (V) and compound (VI).

The condensation reaction is performed according to a conventional method, for example, according to a general peptide coupling method. Examples of such method include a method comprising directly condensing compound (V) and compound (VI) with a condensing agent, or a method comprising reacting a reactive derivative of compound (V) with compound (VI) and the like.

Examples of the condensing agent include carbodiimide condensation reagents such as dicyclohexylcarbodiimide (DCC), diisopropylcarbodiimide (DIPC), 1-ethyl-3-(3-dimethylaminopropyl)carbodiimide (EDC) and hydrochloride thereof and the like; phosphoric acid condensation reagents such as diethyl cyanophosphate, diphenylphosphoryl azide and the like; carbonyldiimidazole, 2-chloro-1,3-dimethylimidazolium tetrafluoroborate, O-(7-azabenzotriazol-1-yl)-1,1,3,3-tetramethyluronium hexafluorophosphate (HATU) and the like.

Examples of the solvent to be used for direct condensation using a condensing agent include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water; and the like. These solvents may be used in a mixture at an appropriate ratio.

The amount of the condensing agent to be used is generally 0.1-10 mol, preferably 0.3-3 mol, per 1 mol of compound (V).

When carbodiimide condensation reagent is used as the condensing agent, the reaction efficiency can be improved by the use of a suitable condensation promoter (e.g., 1-hydroxy-7-azabenzotriazole, 1-hydroxybenzotriazole, N-hydroxysuccinimide, N-hydroxyphthalimide) as necessary. When HATU or phosphoric acid condensation reagent is used as the condensing agent, the reaction efficiency can be improved by the use of an organic amine base such as triethylamine, N,N-diisopropylethylamine and the like.

The amount of each of the above-mentioned condensation promoter and organic amine base to be used is generally 0.1-10 mol, preferably 0.3-3 mol, per 1 mol of compound (V).

The amount of compound (VI) to be used is generally 1-10 mol, preferably 1-3 mol, per 1 mol of compound (V).

The reaction temperature is generally −30° C.-120° C., preferably −10-100° C.

The reaction time is generally 0.5-60 hr.

Examples of the reactive derivative of compound (V) include acid anhydride, acid halide (e.g., acid chloride, acid bromide), imidazolide, mixed acid anhydride (e.g., anhydride with methyl carbonate, ethyl carbonate, isobutyl carbonate etc.) and the like.

For example, when acid anhydride or acid halide is used as a reactive derivative of compound (V), the reaction is generally performed in the presence of a base in a solvent inert to the reaction.

Examples of the base to be used for this case include amines such as triethylamine, pyridine, N-methylmorpholine, N,N-dimethylaniline, 4-dimethylaminopyridine and the like; alkali metal salts such as lithium hydroxide, sodium hydroxide, potassium hydroxide, sodium hydrogen carbonate, sodium carbonate, potassium carbonate etc.; and the like.

The amount of the base to be used is generally 1-10 mol, preferably 1-5 mol, per 1 mol of compound (V).

Examples of the solvent inert to the reaction to be used in this case include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. These solvents may be used in a mixture at an appropriate ratio.

When the above-mentioned amide is used as a solvent inert to the reaction, the reaction can also be performed in the absence of a base.

The amount of compound (VI) to be used is generally 1-10 mol, preferably 1-5 mol, per 1 mol of compound (V).

The reaction temperature is generally −30° C.-100° C., preferably −10° C.-100° C.

The reaction time is generally 0.5-30 hr.

When mixed acid anhydride is used as a reactive derivative of compound (V), compound (V) is reacted with chlorocarbonate ester (e.g., methyl chlorocarbonate, ethyl chlorocarbonate, isobutyl chlorocarbonate) in the presence of a base, and further reacted with compound (VI).

Examples of the base to be used for this case include, those exemplified above as the base to be used for the reaction of acid anhydride or acid halide of compound (V) with compound (VI), and the like.

The amount of the base to be used is generally 1-10 mol, preferably 1-3 mol, per 1 mol of compound (V).

The amount of compound (VI) to be used is generally 1-10 mol, preferably 1-5 mol, per 1 mol of compound (V).

The reaction temperature is generally −30° C.-120° C., preferably −10° C.-100° C.

The reaction time is generally 0.5-20 hr.

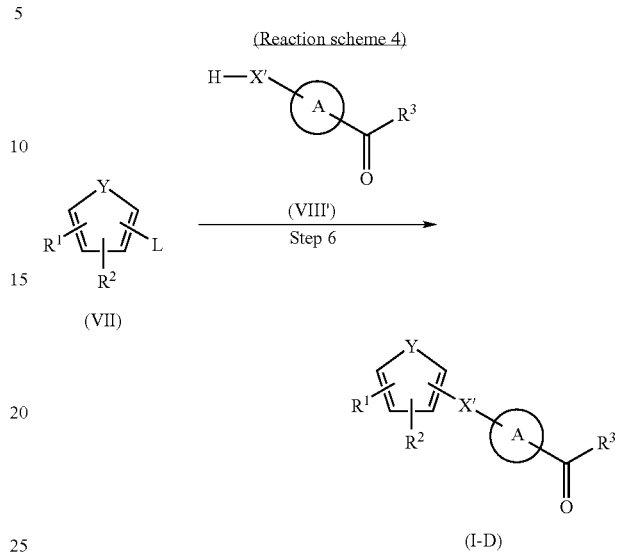

(Reaction scheme 4)

wherein X' is an oxygen atom or a sulfur atom, L is a leaving group (e.g., a halogen atom (e.g., chlorine, bromine)), and other symbols are as defined above.

Step 6

Compound (I-D) can be produced, for example, by reacting compound (VII) with a phenol compound or thiophenol compound (VIII') in the presence of a base.

Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate, cesium carbonate and the like; alkali metal hydrogen carbonate such as sodium hydrogen carbonate, potassium hydrogen carbonate and the like; alkali metal alkoxides having 1 to 6 carbon atoms such as sodium methoxide, sodium ethoxide, potassium tert-butoxide and the like; metal hydrides such as sodium hydroxide, potassium hydride and calcium hydride; and the like.

The amount of the base to be used is generally 1-10 molar equivalents, preferably 1-5 molar equivalents, per 1 mol of compound (VII).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; for example, sulfoxides such as dimethylsulfoxide and the like; sulfolane; hexamethylphosphoramide and the like can be mentioned. Two or more kinds of these solvents may be used in a mixture at an appropriate ratio.

In addition, for the reaction, alkali metal iodide such as sodium iodide and the like may be added as a reaction promoter in 1 molar equivalent to a large excess (preferably 1-10 molar equivalents), per 1 mol of compound (VII).

The amount of compound (VIII) to be used is generally 1-10 molar equivalents, preferably 1-5 molar equivalents, per 1 mol of compound (VII).

The reaction temperature is generally −80° C.-200° C., preferably 0° C.-150° C.

The reaction time is generally 0.5-20 hr.

(Reaction scheme 5)

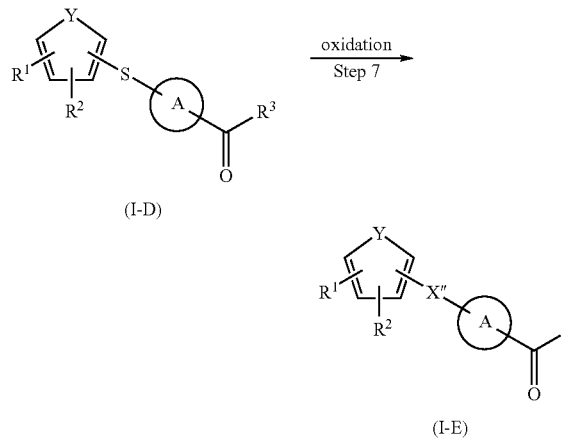

wherein X″ is —SO— or —SO$_2$—, and other symbols are as defined above.

Compound (I-E) can be produced, for example, by oxidizing compound (I-D).

Examples of the oxidant to be used for the oxidation reaction include hydrogen peroxide, m-chloroperbenzoic acid, sulfuryl chloride and the like.

The amount of the oxidant to be used is generally 1-10 molar equivalents, preferably 1-5 molar equivalents, per 1 mol of compound (I-D).

This reaction is preferably performed in a solvent inert to the reaction. Such solvent is not particularly limited as long as the reaction proceeds and, for example, ethers such as 1,4-dioxane, tetrahydrofuran, diethyl ether, dimethoxyethane, tert-butyl methyl ether, diisopropyl ether, ethylene glycol dimethyl ether and the like; halogenated hydrocarbons such as dichloromethane, chloroform, carbon tetrachloride, trichloroethylene and the like; hydrocarbons such as n-hexane, benzene, toluene etc. and the like can be mentioned. Two or more kinds of these solvents may be used in a mixture at an appropriate ratio.

The reaction temperature is generally −80° C.-200° C., preferably −80° C.-100° C.

The reaction time is generally 0.5-20 hr.

(Reaction scheme 6)

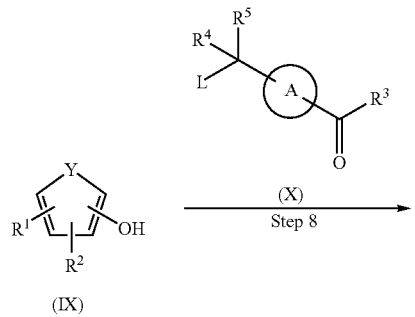

-continued

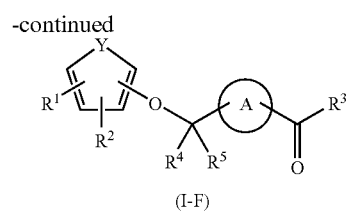

wherein L is a leaving group (e.g., a substituted sulfonyloxy group (e.g., a methanesulfonyloxy group, a p-toluenesulfonyloxy group) or a halogen atom (e.g., chlorine, bromine)), and other symbols are as defined above.

Step 8

Compound (I-F) can be produced, for example, by reacting compound (IX) with compound (X) in the presence of a base.

Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate, cesium carbonate and the like; alkali metal hydrogen carbonate such as sodium hydrogen carbonate, potassium hydrogen carbonate and the like; alkali metal alkoxide having 1 to 6 carbon atoms such as sodium methoxide, sodium ethoxide, potassium tert-butoxide and the like; metal hydrides such as sodium hydride, potassium hydride and calcium hydride; and the like.

The amount of the base to be used is generally 1-10 molar equivalents, preferably 1-5 molar equivalents, per 1 mol of compound (IX).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; and the like can be mentioned. Two or more kinds of these solvents may be used in a mixture at an appropriate ratio.

In addition, for the reaction, alkali metal iodide such as sodium iodide and the like may be added as a reaction promoter in 1 molar equivalent to a large excess (preferably 1-10 molar equivalents).

The amount of compound (X) to be used is generally 1-10 molar equivalents, preferably 1-5 molar equivalents, per 1 mol of compound (IX).

The reaction temperature is generally −80° C.-200° C., preferably 0° C.-150° C.

The reaction time is generally 0.5-20 hr.

(Reaction scheme 7)

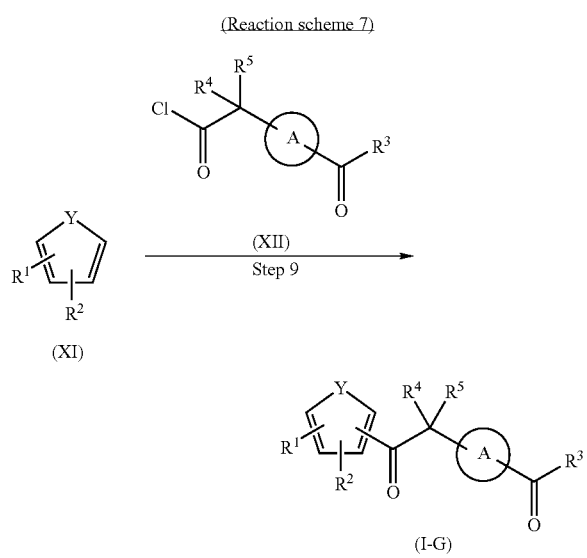

wherein each symbol is as defined above.

Step 9

Compound (I-G) can be produced by reacting compound (XI) with compound (XII) in the presence of a Lewis acid.

Examples of the Lewis acid include aluminum trichloride, diethyl aluminum and the like.

The amount of the Lewis acid to be used is 1-10 molar equivalents, preferably 1-5 molar equivalents, per 1 mol of compound (X).

This reaction is performed in a solvent inert to the reaction. Such solvent is not particularly limited as long as the reaction proceeds and, for example, ethers such as diethyl ether, tetrahydrofuran, 1,4-dioxane and the like; aliphatic hydrocarbons such as hexane, heptane and the like; aromatic hydrocarbons such as benzene, toluene, xylene and the like; halogenated hydrocarbons such as dichloromethane, chloroform, carbon tetrachloride, trichloroethylene etc.; and the like can be mentioned. These solvents may be used in a mixture at an appropriate ratio.

The amount of compound (XII) to be used is generally about 1-10 mol, preferably about 1-2 mol, per 1 mol of compound (XI).

The reaction temperature is generally −80° C.-100° C., preferably −20° C.-50° C.

The reaction time is generally 0.5-20 hr.

(Reaction scheme 8)

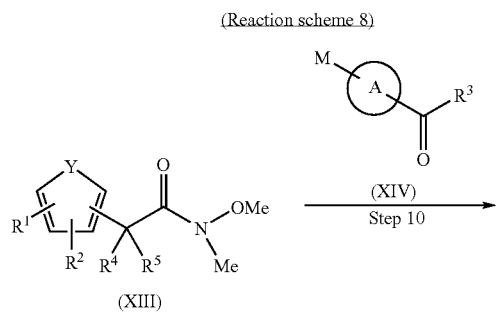

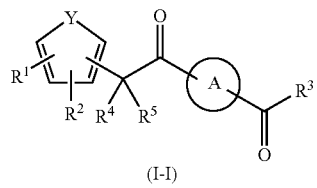

wherein M is a metal reagent (e.g., lithium, magnesium halide, zinc etc.), and other symbols are as defined above.

Step 10

Compound (I-I) can be produced by reacting compound (XIII) with compound (XIV).

This reaction is performed in a solvent inert to the reaction. Such solvent is not particularly limited as long as the reaction proceeds and, for example, ethers such as diethyl ether, tetrahydrofuran, 1,4-dioxane and the like; aliphatic hydrocarbons such as hexane, heptane and the like; aromatic hydrocarbons such as benzene, toluene, xylene and the like; and the like can be mentioned. These solvents may be used in a mixture at an appropriate ratio.

The amount of compound (XIV) to be used is generally about 1-10 mol, preferably about 1-2 mol, per 1 mol of compound (XIII).

The reaction temperature is generally −100° C.-100° C., preferably −80° C.-50° C.

The reaction time is generally 0.5-20 hr.

Now, the methods of producing the starting compounds to be used in the present invention and reactive derivatives thereof are explained in the following.

Compound (II) which is a synthetic intermediate of the object compound (I) of the present invention is a novel compound and can be produced, for example, as follows.

(Reaction scheme 9)

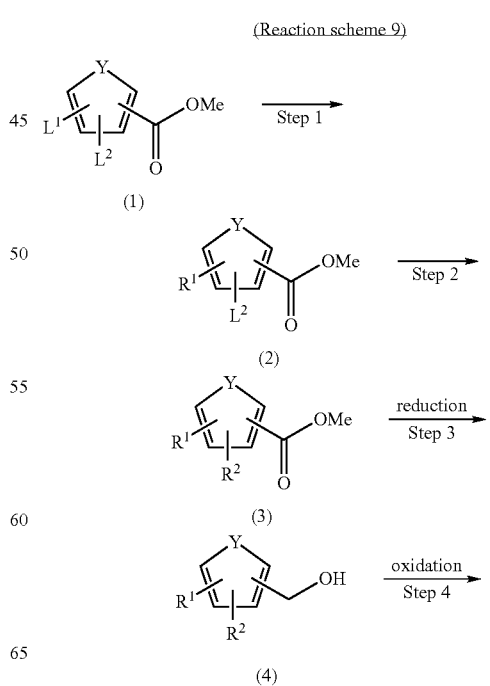

-continued

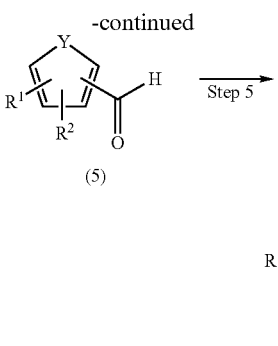

(5)

$$\text{(II)}$$

wherein L1 and L2 are leaving groups (e.g., a halogen atom (e.g., chlorine, bromine)), and other symbols are as defined above.

Step 1

Compound (2) can be produced by treating compound (1) with an organic metal reagent, reacting same with an electrophilic reagent and, where necessary, subjecting the obtained adduct to a reduction reaction to remove hydroxyl group. Compound (1) can be produced by a method known per se.

Examples of the organic metal reagent include isopropylmagnesium bromide, n-butyllithium and the like. Examples of the electrophilic reagent include aldehydes, ketones and the like. The amount of each of the organic metal reagent and the electrophilic reagent to be used is 1-10 mol, preferably 1-5 mol, per 1 mol of compound (1).

This reaction is preferably performed in a solvent inert to the reaction. Such solvent is not particularly limited as long as the reaction proceeds and, for example, ethers such as 1,4-dioxane, tetrahydrofuran, diethyl ether, tert-butyl methyl ether, diisopropyl ether, ethylene glycol dimethyl ether and the like; hydrocarbons such as n-hexane, benzene, toluene etc.; and the like can be mentioned. Two or more kinds of these solvents may be used in a mixture at an appropriate ratio.

The reaction time is generally 0.1 hr-48 hr, preferably 0.1 hr-24 hr.

The reaction temperature is generally −100° C.-100° C., preferably −80° C.-50° C.

The reduction reaction of the adduct can be performed by reaction with a reducing agent in the presence of an organic acid.

Examples of the reducing agent include sodium borohydride, triethylsilyl and the like.

Examples of the organic acid include trifluoroacetic acid and the like.

The amount of the reducing agent to be used is generally 1-50 mol, preferably 1-10 mol, per 1 mol of the adduct.

The reduction reaction of the adduct can be performed by a hydrogenation reaction. In this case, for example, a catalyst such as palladium carbon, palladium black, platinum dioxide, Raney-nickel, Raney cobalt, iron trichloride and the like can be used.

The amount of the catalyst to be used is generally about 5-1000 wt %, preferably about 10-300 wt %, relative to the adduct. The hydrogenation reaction can also be performed by using various hydrogen sources instead of gaseous hydrogen. Examples of such hydrogen source include formic acid, ammonium formate, triethylammonium formate, sodium phosphinate, hydrazine and the like.

The amount of the hydrogen source to be used is generally about 1-100 mol, preferably 1-10 mol, per 1 mol of the adduct.

The reduction reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; mineral acids such as hydrochloric acid, sulfuric acid and the like; organic acids such as formic acid, acetic acid, propionic acid, trifluoroacetic acid, methanesulfonic acid etc.; and the like can be mentioned. Two or more kinds of these solvents may be used in a mixture at an appropriate ratio.

While the reaction time varies depending on the kind and amount of the reducing agent to be used, it is generally 0.1 hr-48 hr, preferably 0.1 hr-24 hr.

The reaction temperature is generally −100° C.-150° C., preferably −80° C.-100° C.

Step 2

Compound (3) can be produced according to the production method of compound (2). In other words, it can be produced by treating compound (2) with an organic metal reagent, reacting same with an electrophilic reagent and, where necessary, subjecting the obtained adduct to a reduction reaction to remove hydroxyl group.

Compound (3) can also be produced by reacting compound (2) with a metal catalyst and, where necessary, with an organic metal reagent in the presence of a base. Examples of the organic metal reagent include boronic acid, boronic acid ester, Grignard reagent, organotin reagent, organic zinc reagent and the like. Examples of the metal catalyst include palladium catalysts (e.g., palladium acetate(II), tris(dibenzylideneacetone)dipalladium(0), bis(dibenzylideneacetone)palladium(0), tetrakis(triphenylphosphine)palladium(0), [1,1'-bis(diphenylphosphino)ferrocene]dichloropalladium dichloromethane adduct (II), bis(tris-tert-butylphosphine)palladium(0) etc.), and nickel catalysts (e.g., tetrakis(triphenylphosphine)nickel (O), dichloro[1,2-bis(diphenylphosphino)ethane]nickel (II), dichloro[1,3-bis (diphenylphosphino)propane]nickel (II), dichloro[1,4-bis (diphenylphosphino)butane]nickel (II) etc.).

This reaction may be performed in the presence of a ligand when desired. Examples of such ligand include phosphorus ligand (e.g., triphenylphosphine, 1,3-bis(diphenylphosphino) propane, 1,3-bis(diphenylphosphino)propane, 2,2'-bis (diphenylphosphino)-1,1'-binaphthyl and 4,5-bis(diphenylphosphino)-9,9-dimethylxanthene etc.).

Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate, cesium carbonate and the like; alkali metal hydrogen carbonate such as sodium hydrogen carbonate, potassium hydrogen carbonate and the like; alkali metal alkoxide having 1 to 6 carbon atoms such as sodium methoxide, sodium ethoxide, potassium tert-butoxide etc.; and the like.

The amount of the organic metal reagent to be used is generally 1-100 mol, preferably 1-10 mol, per 1 mol of compound (2).

The amount of the base to be used is generally 1-100 mol, preferably 1-10 mol, per 1 mol of compound (2).

The amount of the metal catalyst to be used is generally 0.01-1 mol, preferably 0.03-0.5 mol, per 1 mol of compound (2).

The amount of the ligand to be used is generally 0.01-2 mol, preferably 0.02-1 mol, per 1 mol of compound (2).

This reaction is preferably performed in a solvent inert to the reaction. Such solvent is not particularly limited as long as the reaction proceeds and, for example, alcohols such as methanol, ethanol, propanol, isopropanol, butanol, tert-butanol and the like; ethers such as 1,4-dioxane, tetrahydrofuran, diethyl ether, dimethoxyethane, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water; and the like can be mentioned. Two or more kinds of these solvents may be used in a mixture at an appropriate ratio.

The reaction temperature is generally $-100°$ C.-$180°$ C., preferably $-80°$ C.-$150°$ C.

The reaction time is generally 0.1 hr-48 hr, preferably 0.1 hr-24 hr.

Step 3

Compound (4) can be produced by subjecting compound (3) to a reduction reaction. The reduction reaction can be performed using a reducing agent according to a conventional method.

Examples of the reducing agent include metal hydrogen compounds such as sodium bis(2-methoxyethoxy)aluminum hydride, diisobutylaluminum hydride (DIBALH) and the like; metal hydride complex compounds such as sodium borohydride, sodium cyanoborohydride, lithium aluminum hydride, sodium aluminum hydride, calcium borohydride etc. and the like.

The amount of the reducing agent to be used is generally 1-20 mol, per 1 mol of compound (3).

This reaction is preferably performed in a solvent inert to the reaction. Such solvent is not particularly limited as long as the reaction proceeds and, for example, alcohols such as methanol, ethanol, propanol, isopropanol, butanol, isobutanol, tert-butanol and the like; halogenated hydrocarbons such as dichloromethane, chloroform, carbon tetrachloride, trichloroethylene and the like; aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, dimethoxyethane and the like, mineral acids such as hydrochloric acid, sulfuric acid and the like; organic acids such as formic acid, acetic acid, propionic acid, trifluoroacetic acid, methanesulfonic acid and the like; water; and the like can be mentioned. Two or more kinds of these solvents may be used in a mixture at an appropriate ratio.

The reaction time is 0.1 hr-48 hr, preferably 0.1 hr-24 hr.

The reaction temperature is generally $-100°$ C.-$150°$ C., preferably $-20°$ C.-$100°$ C.

Step 4

Compound (5) can be produced by subjecting compound (4) to an oxidation reaction. The oxidation reaction can be performed using an oxidant according to a conventional method.

Examples of the oxidant include activated manganese dioxide, pyridinium chlorochromate (PCC), pyridinium dichromate (PDC), Dess-Martin periodinane, dimethyl sulfoxide-acid anhydride (acetic anhydride, trifluoroacetic anhydride and the like), dimethyl sulfoxide-thionyl chloride, dimethyl sulfoxide-sulfuryl chloride, dimethyl sulfoxide-oxalyl chloride, dimethyl sulfoxide-chlorine, and dimethyl sulfoxide-dicyclohexylcarbodiimide (DCC) in the presence of acid (phosphoric acid, trifluoroacetic acid, dichloroacetic acid and the like) and the like.

The amount of the oxidant to be used is generally 1-20 mol, per 1 mol of compound (4).

This reaction is preferably performed in a solvent inert to the reaction. Such solvent is not particularly limited as long as the reaction proceeds and, for example, ethers such as diethyl ether, diisopropyl ether, diphenyl ether, tetrahydrofuran, 1,4-dioxane, 1,2-dimethoxyethane and the like; ketones such as acetone, methyl ethyl ketone and the like; halogenated hydrocarbons such as dichloromethane, chloroform, carbon tetrachloride, trichloroethylene and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; mineral acids such as hydrochloric acid, sulfuric acid and the like; organic acids such as formic acid, acetic acid, propionic acid, trifluoroacetic acid, methanesulfonic acid and the like; water; and the like can be mentioned. Two or more kinds of these solvents may be used in a mixture at an appropriate ratio.

The reaction time is 0.1 hr-48 hr, preferably 0.1 hr-24 hr.

The reaction temperature is generally $-100°$ C.-$150°$ C., preferably $-20°$ C.-$100°$ C.

Step 5

Compound (II) can be produced from compound (5) according to a method known per se. The compound can be produced by, for example, reacting compound (5) with a Grignard reagent, followed by oxidation with a Jones reagent.

This reaction is performed in a solvent inert to the reaction. Such solvent is not particularly limited as long as the reaction proceeds and, for example, ethers such as diethyl ether, tetrahydrofuran, 1,4-dioxane and the like; aliphatic hydrocarbons such as hexane, heptane and the like; aromatic hydrocarbons such as benzene, toluene, xylene and the like; and the like can be mentioned. These solvents may be used in a mixture at an appropriate ratio.

The amount of the Grignard reagent to be used is generally about 1-10 mol, preferably about 1-2 mol, per 1 mol of compound (5).

The reaction temperature is generally $-80°$ C.-$100°$ C., preferably $-20°$ C.-$50°$ C.

The reaction time is generally 0.5-20 hr.

The amount of the Jones reagent to be used is generally about 1-10 mol, preferably about 1-2 mol, per 1 mol of compound (5).

The reaction temperature is generally $-80°$ C.-$100°$ C., preferably $-20°$ C.-$50°$ C.

The reaction time is generally 0.5-20 hr.

Among compounds (II), the following compound (II-I) can be produced, for example, as follows.

(Reaction scheme 10)

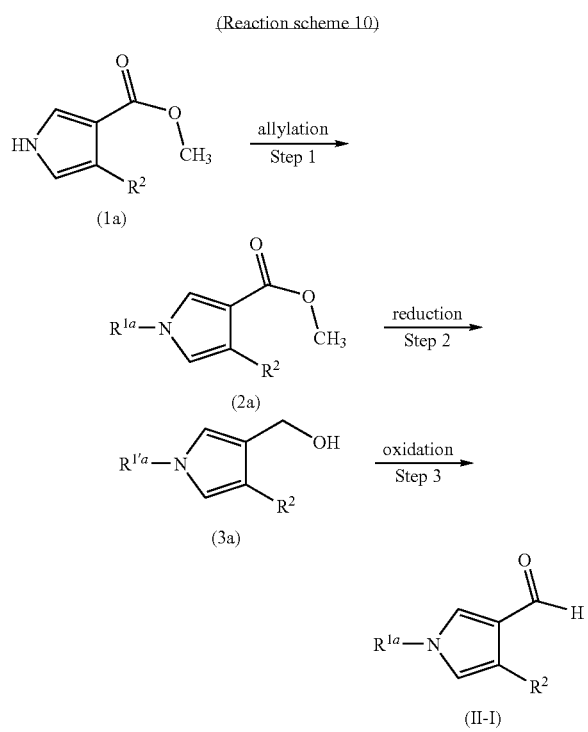

wherein $R^{1a}$ is an optionally substituted aromatic group, and other symbols are as defined above.

Here, the optionally substituted aromatic group is, for example, a group corresponding to an optionally substituted aromatic heterocyclic group from among the groups exemplified as the aforementioned optionally substituted $C_{6-14}$ aryl group and optionally substituted heterocyclic group for $R^1$.

Step 1

Compound (2a) can be produced by reacting compound (1a), an optionally substituted aromatic halogen compound corresponding to $R^{1a}$ group and a base in the presence of, where necessary, an organic metal catalyst. Compound (1a) can be produced by a method known per se, for example, according to the method described in US2007/60623, EP1803709 and the like.

As the optionally substituted aromatic halogen compound, a compound wherein an aromatic ring corresponding to the optionally substituted aromatic group for $R^{1a}$ is substituted by a halogen (e.g., iodine, fluorine) can be mentioned. The optionally substituted aromatic halogen compound can be produced by a method known per se.

The amount of the optionally substituted aromatic halogen compound to be used is generally 1-100 mol, preferably 1-10 mol, per 1 mol of compound (2a).

Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonates such as sodium carbonate, potassium carbonate, cesium carbonate and the like; alkali metal hydrogen carbonate such as sodium hydrogen carbonate, potassium hydrogen carbonate and the like; alkali metal phosphate such as potassium phosphate, sodium phosphate etc.; and the like.

The amount of the base to be used is generally 1-100 mol, preferably 1-10 mol, per 1 mol of compound (2a).

Examples of the organic metal catalyst include copper catalysts (e.g., copper(I) bromide, copper(I) iodide, copper (II) acetate, copper(I) oxide), and palladium catalysts (e.g., palladium acetate(II), tris(dibenzylideneacetone) dipalladium(0), bis(dibenzylideneacetone)palladium(0), tetrakis (triphenylphosphine)palladium(0), [1,1'-bis(diphenylphosphino)ferrocene]dichloropalladium dichloromethane adduct (II), bis(tris-tert-butylphosphine)palladium(0) etc.).

The amount of the metal catalyst to be used is generally 0.01-1 mol, preferably 0.03-0.5 mol, per 1 mol of compound (2a). This reaction may be performed in the presence of a ligand when desired. Examples of such ligand include amine ligands (e.g., trans-1,2-cyclohexanediamine), and phosphor ligands (e.g., triphenylphosphine, 1,3-bis(diphenylphosphino)propane, 1,3-bis(diphenylphosphino)propane, 2,2'-bis (diphenylphosphino)-1,1'-binaphthyl and 4,5-bis(diphenylphosphino)-9,9-dimethylxanthene etc.).

The amount of the ligand to be used is generally 0.01-2 mol, preferably 0.02-1 mol, per 1 mol of compound (2a).

This reaction is preferably performed in a solvent inert to the reaction. Such solvent is not particularly limited as long as the reaction proceeds and, for example, alcohols such as methanol, ethanol, propanol, isopropanol, butanol, tert-butanol and the like; ethers such as 1,4-dioxane, tetrahydrofuran, diethyl ether, dimethoxyethane, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide; water; and the like can be mentioned. Two or more kinds of these solvents may be used in a mixture at an appropriate ratio.

The reaction temperature is generally −100° C.-200° C., preferably −80° C.-180° C.

The reaction time is generally 0.1 hr-48 hr, preferably 0.1 hr-24 hr.

Step 2

Compound (3a) can be produced by subjecting compound (2a) to a reduction reaction. The reduction reaction can be performed in the same manner as in step 3 of reaction scheme 9.

Step 3

Compound (II-I) can be produced by subjecting compound (3a) to an oxidation reaction. The oxidation reaction can be performed in the same manner as in step 4 of reaction scheme 9.

The thus-obtained compound (I) (compound (I-A) to compound (I-I)) can be isolated and purified by known separation and purification means, for example, concentration, concentration under reduced pressure, solvent extraction, crystallization, recrystallization, phase transfer, chromatography and the like.

In addition, when compound (I) is obtained as free compounds, they can be converted to object salts by a method known per se or a method analogous thereto. When they are obtained as salts, they can be converted to free forms or other object salts by a method known per se or a method analogous thereto.

When compound (I) contains an optical isomer, a stereoisomer, a regioisomer or a rotamer, these are also encompassed in compound (I), and can be obtained as a single product according to synthesis and separation methods and the like known per se. For example, when compound (I) has an optical isomer, an optical isomer resolved from this compound is also encompassed in compound (I).

The optical isomer can be produced by a method known per se. Specifically, an optically active synthetic intermediate is used. Alternatively, the final product racemate is optically resolved by a conventional method to give an optical isomer.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, this compound and an optically active amine or an optically active alcohol are subjected to condensation reaction to give diastereomers of the amide compound or the ester compound, respectively. The separated diastereomer is converted to an optical isomer of the original compound by acid hydrolysis or base hydrolysis.

EXAMPLES

The present invention is explained in more detail in the following by referring to Examples, Experimental Examples and Formulation Examples, which are not to be construed as limitative.

$^1$H-NMR spectrum was measured using tetramethylsilane as the internal standard and Varian Gemini 200 (200 MHz), 300 (300 MHz), Bruker 300 (300 MHz) spectrometers, and all δ values are shown by ppm. Unless otherwise specified, the numerical values shown for mixed solvents are volume mixing ratios of respective solvents. Unless otherwise specified, % means weight %. In addition, unless otherwise specified, the ratio of elution solvents in silica gel chromatography means a volume mixing ratio. The room temperature (ambient temperature) in the present specification is a temperature of about 20° C. to about 30° C.

Each symbol in the Examples means the following.

DMSO: dimethyl sulfoxide, $CDCl_3$: deuterated chloroform, s: singlet, d: doublet, t: triplet, q: quartet, dd: double doublet, dt: double triplet, m: multiplet, brs: broad, J: coupling constant LC/MS analyses in Examples were performed under the following conditions.

measurement device: Waters LC/MS system

HPLC: Agilent HP1100

MS: Micromass ZMD column: CAPCELL PAK c18UG120 S-3 μm, 1.5×35 mm (manufactured by Shiseido Co., Ltd.)

solvent: SOLUTION A; 0.05% aqueous trifluoroacetic acid solution, SOLUTION B; 0.04% trifluoroacetic acid acetonitrile solution gradient cycle: 0 min. (SOLUTION A/SOLUTION B=90/10), 2.00 min. (SOLUTION A/SOLUTION B=5/95), 2.75 min. (SOLUTION A/SOLUTION B=5/95), 2.76 min. (SOLUTION A/SOLUTION B=90/10), 3.60 min. (SOLUTION A/SOLUTION B=90/10)

injection volume: 2 μL, flow rate: 0.5 mL/min, detection method: UV 220 nm,

MS conditions ionization method: ESI

Purification by preparative HLPC in Examples was performed under the following conditions.

instrument: Gilson Inc., High throughput purification system
column: YMC CombiPrep ODS-A S-5 μm, 50×20 mm, or CombiPrep Hydrosphere C18 S-5 μm, 50×20 mm solvent: SOLUTION A; 0.1% aqueous trifluoroacetic acid solution, SOLUTION B; 0.1% trifluoroacetic acid acetonitrile solution gradient cycle: 0 min. (SOLUTION A/SOLUTION B=95/5), 1.00 min. (SOLUTION A/SOLUTION B=95/5), 5.20 min. (SOLUTION A/SOLUTION B=5/95), 6.40 min. (SOLUTION A/SOLUTION B=5/95), 6.50 min. (SOLUTION A/SOLUTION B=95/5), 6.60 min. (SOLUTION A/SOLUTION B=95/5), or 0 min. (SOLUTION A/SOLUTION B=98/2), 1.00 min. (SOLUTION A/SOLUTION B=98/2), 5.00 min. (SOLUTION A/SOLUTION B=0/100), 6.40 min. (SOLUTION A/SOLUTION B=0/100), 6.50 min. (SOLUTION A/SOLUTION B=98/2), 6.60 min. (SOLUTION A/SOLUTION B=98/2)

flow rate: 20 mL/min, detection method: UV 220 nm

Example 1

3-{[4-({2-ethyl-5-[4-(trifluoromethyl)phenyl]-3-furyl}methoxy)benzoyl]amino}propanoic acid

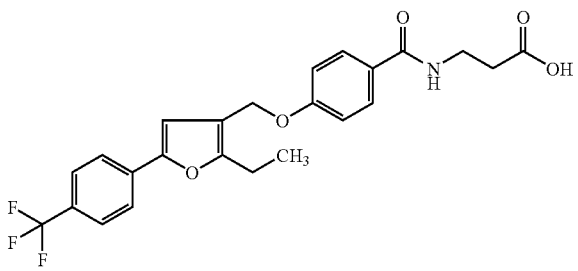

(1) methyl 2-ethyl-5-[4-(trifluoromethyl)phenyl]-3-furoate

To a solution of 2-chloro-4'-(trifluoromethyl)acetophenone (50.9 g) and methyl 3-oxopentanoate (25 g) in toluene (500 mL) was added dropwise 1,8-azabicyclo[5.4.0]-7-undecene (28.7 mL) under ice-cooling over 30 min or longer. After the completion of the dropwise addition, and the mixture was stirred under ice-cooling for 30 min, and at room temperature for 2 hr. The resulting precipitate was filtered, and washed with toluene. The obtained toluene solution was passed through silica gel, and the silica gel was washed with ethyl acetate-hexane (1:1). The collected solution was concentrated under reduced pressure to remove ethyl acetate-hexane to give a toluene solution. To this toluene solution was added 4-toluenesulfonic acid monohydrate (7.2 g), and the mixture was stirred at 100° C. for 2 hr. The reaction mixture was washed with aqueous sodium hydrogen carbonate solution, and the aqueous layer was extracted with ethyl acetate. The organic layer was collected, and dried over magnesium sulfate. The solvent was evaporated under reduced pressure. The residue was purified by silica gel chromatography (0% ethyl acetate/hexane to 10% ethyl acetate/hexane), and crystallized from ethyl acetate/hexane to give the title compound (16.3 g, 29%) as a white solid.

$^1$H NMR (300 MHz, CHLOROFORM-d) δ ppm 1.33 (t, J=7.54 Hz, 3H) 3.10 (q, J=7.54 Hz, 2H) 3.86 (s, 3H) 7.62 (d, J=8.29 Hz, 2H) 7.74 (d, J=8.10 Hz, 2H)

(2) {2-ethyl-5-[4-(trifluoromethyl)phenyl]-3-furyl}methanol

A solution of methyl 2-ethyl-5-[4-(trifluoromethyl)phenyl]-3-furoate (7.46 g) obtained by the above-mentioned reaction in tetrahydrofuran (50 mL) was added dropwise to a suspension of lithium aluminum hydride (0.95 g) in tetrahydrofuran (100 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane), and crystallized from ethyl acetate/hexane to give the title compound (6.33 g, 93%) as a white solid.

$^1$H NMR (300 MHz, CHLOROFORM-d) δ ppm 1.30 (t, J=7.54 Hz, 3H) 2.74 (q, J=7.54 Hz, 2H) 4.54 (s, 2H) 7.52-7.64 (m, 2H) 7.65-7.78 (m, 2H)

(3) 4-({2-ethyl-5-[4-(trifluoromethyl)phenyl]-3-furyl}methoxy)benzoic acid

To a solution of {2-ethyl-5-[4-(trifluoromethyl)phenyl]-3-furyl}methanol (324 mg) obtained by the above-mentioned reaction and methyl 4-hydroxybenzoate (228 mg) in tetrahydrofuran (10 mL) were added tributylphosphine (0.6 mL) and 1,1'-(azodicarbonyl)dipiperidine (606 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-({2-ethyl-5-[4-(trifluoromethyl)phenyl]-3-furyl}methoxy)benzoate as a white solid. The obtained methyl 4-({2-ethyl-5-[4-(trifluoromethyl)phenyl]-3-furyl}methoxy)benzoate was dissolved in methanol (5 mL) and tetrahydrofuran (5 mL), 2N sodium hydroxide (2.0 mL) were added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (236 mg, 86%).

$^1$H NMR (300 MHz, CHLOROFORM-d) δ ppm 1.33 (t, J=7.54 Hz, 3H) 2.79 (q, J=7.54 Hz, 2H) 4.96 (s, 2H) 6.79 (s, 1H) 7.03 (d, J=9.04 Hz, 2H) 7.61 (d, J=8.29 Hz, 2H) 7.73 (d, J=8.29 Hz, 2H) 8.08 (d, J=8.85 Hz, 2H)

(4) 3-{([4-({2-ethyl-5-[4-(trifluoromethoxy)phenyl]-3-furyl}methoxy)benzoyl]amino}propanoic acid A solution of 4-({2-ethyl-5-[4-(trifluoromethyl)phenyl]-3-furyl}methoxy)benzoic acid (117 mg) obtained by the above-mentioned reaction, ethyl β-alaninate hydrochloride (55 mg), 1-ethyl-3-(3-dimethylaminopropyl)carbodiimide hydrochloride (69 mg), hydroxybenzotriazole monohydrate (55 mg) and triethylamine (50 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N sodium hydroxide (1.0 mL), and the mixture was stirred at room temperature for 1 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (132 mg, 95%).

$^1$H NMR (300 MHz, DMSO-d$_6$) δ ppm 1.23 (t, J=7.54 Hz, 3H) 2.47-2.51 (m, 2H) 2.80 (q, J=7.54 Hz, 2H) 3.38-3.53 (m, 2H) 5.02 (s, 2H) 7.08 (d, J=9.04 Hz, 2H) 7.21 (s, 1H) 7.75 (d, J=8.48 Hz, 2H) 7.81-7.88 (m, 4H) 8.39 (brs, 1H) 12.25 (brs, 1H)

Example 2

3-{[4-({2-ethyl-5-[4-(trifluoromethyl)phenyl]-3-furyl}methoxy)benzoyl](methyl)amino}propanoic acid

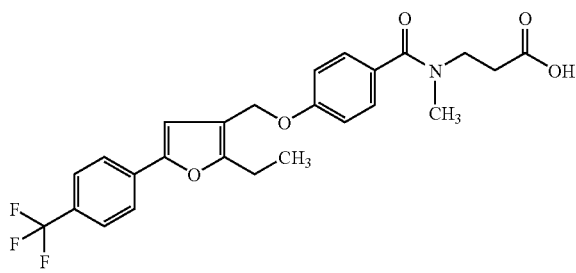

An operation similar to that in Example 1 (4) was performed using 4-({2-ethyl-5-[4-(trifluoromethyl)phenyl]-3-furyl}methoxy)benzoic acid (117 mg) as well as ethyl 3-(methylamino)propanoate (47 mg) to give the title compound (128 mg, 90%) as an oil.

$^1$H NMR (300 MHz, DMSO-$d_6$) δ ppm 1.23 (t, J=7.54 Hz, 3H) 2.54 (t, J=7.35 Hz, 2H) 2.80 (q, J=7.47 Hz, 2H) 2.93 (s, 3H) 3.33 (brs, 2H) 5.00 (s, 2H) 7.06 (d, J=8.85 Hz, 2H) 7.21 (s, 1H) 7.36 (d, J=8.67 Hz, 2H) 7.75 (d, J=8.48 Hz, 2H) 7.87 (d, J=8.10 Hz, 2H)

Example 3

3-{[4-(1-{2-ethyl-5-[4-(trifluoromethyl)phenyl]-3-furyl}ethoxy)benzoyl]amino}propanoic acid

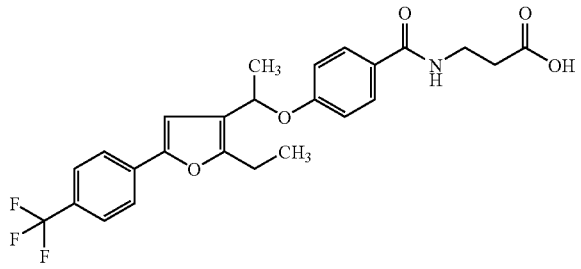

(1) 2-ethyl-5-[4-(trifluoromethyl)phenyl]-3-furaldehyde

A suspension of {2-ethyl-5-[4-(trifluoromethyl)phenyl]-3-furyl}methanol (2.7 g) and manganese dioxide (6.8 g) in diethyl ether (20 mL) and tetrahydrofuran (20 mL) was stirred overnight at 40° C. Manganese dioxide was filtered off, and the filtrate was evaporated under reduced pressure. The residue was purified by silica gel chromatography (5% ethyl acetate/hexane to 20% ethyl acetate/hexane), and crystallized from ethyl acetate/hexane to give the title compound (0.66 g, 24%) as a yellow solid.

$^1$H NMR (300 MHz, CHLOROFORM-d) δ ppm 1.42 (t, J=7.54 Hz, 3H) 3.08 (q, J=7.54 Hz, 2H) 7.04 (s, 1H) 7.66 (d, J=8.29 Hz, 2H) 7.76 (d, J=8.10 Hz, 2H) 10.00 (s, 1H)

(2) 1-{2-ethyl-5-[4-(trifluoromethyl)phenyl]-3-furyl}ethanol

To a solution of 2-ethyl-5-[4-(trifluoromethyl)phenyl]-3-furaldehyde (402 mg) obtained by the above-mentioned reaction in tetrahydrofuran (10 mL) was added dropwise 1N methyl magnesium bromide-tetrahydrofuran solution (3.0 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (5% ethyl acetate/hexane to 25% ethyl acetate/hexane) to give the title compound (350 mg, 82%) as an oil.

$^1$H NMR (300 MHz, CHLOROFORM-d) δ ppm 1.29 (t, J=7.63 Hz, 3H) 1.50 (d, J=6.59 Hz, 3H) 1.60 (brs, 1H) 2.65-2.86 (m, 2H) 4.86-4.93 (m, 1H) 6.78 (s, 1H) 7.60 (d, J=8.29 Hz, 2H) 7.71 (d, J=8.10 Hz, 2H)

(3) 4-(1-{2-ethyl-5-[4-(trifluoromethyl)phenyl]-3-furyl}ethoxy)benzoic acid

An operation similar to that in Example 1 (3) was performed using 1-{2-ethyl-5-[4-(trifluoromethyl)phenyl]-3-furyl}ethanol (341 mg) to give the title compound (289 mg, 43%) as an oil.

$^1$H NMR (300 MHz, CHLOROFORM-d) δ ppm 1.28 (t, J=7.54 Hz, 3H) 1.66 (d, J=6.40 Hz, 3H) 2.75 (qd, J=7.54, 2.26 Hz, 2H) 5.39 (q, J=6.40 Hz, 1H) 6.71 (s, 1H) 6.92 (d, J=9.04 Hz, 2H) 7.58 (d, J=8.29 Hz, 2H) 7.68 (d, J=8.29 Hz, 2H) 7.99 (d, J=8.67 Hz, 2H)

(4) 3-{[4-({2-ethyl-5-[4-(trifluoromethoxy)phenyl]-3-furyl}methoxy)benzoyl]amino}propanoic acid An operation similar to that in Example 1 (4) was performed using 4-(1-{2-ethyl-5-[4-(trifluoromethyl)phenyl]-3-furyl}ethoxy)benzoic acid (121 mg) to give the title compound (136 mg, 95%) as a white crystal.

$^1$H NMR (300 MHz, DMSO-$d_6$) δ ppm 1.20 (q, J=7.57 Hz, 3H) 1.58 (d, J=6.44 Hz, 3H) 2.39-2.48 (m, 2H) 2.79 (q, J=7.57 Hz, 2H) 3.35-3.53 (m, 2H) 5.62 (q, J=6.31 Hz, 1H) 6.99 (d, J=8.71 Hz, 2H) 7.17 (s, 1H) 7.63-7.78 (m, 4H) 7.83 (d, J=8.33 Hz, 2H) 8.33 (t, J=5.49 Hz, 1H)

Example 4

3-{[4-(1-{2-ethyl-5-[4-(trifluoromethyl)phenyl]-3-furyl}ethoxy)benzoyl](methyl)amino}propanoic acid

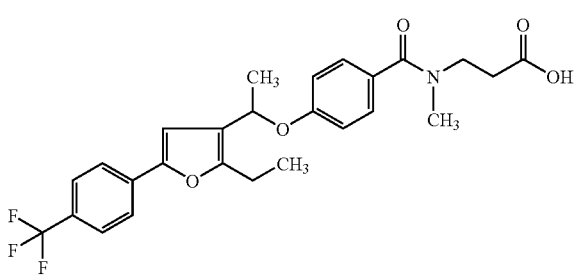

An operation similar to that in Example 1 (4) was performed using 4-(1-{2-ethyl-5-[4-(trifluoromethyl)phenyl]-3-furyl}ethoxy)benzoic acid (121 mg) as well as ethyl 3-(methylamino)propanoate (47 mg) to give the title compound (145 mg, 99%) as an oil.

$^1$H NMR (300 MHz, DMSO-$d_6$) δ ppm 1.17 (t, J=7.57 Hz, 3H) 1.58 (d, J=6.44 Hz, 3H) 2.54 (brs, 2H) 2.78 (q, J=7.57 Hz, 2H) 2.90 (s, 3H) 3.33 (brs, 2H) 5.57 (q, J=6.18 Hz, 1H) 6.97 (d, J=8.71 Hz, 2H) 7.18 (s, 1H) 7.30 (d, J=8.33 Hz, 2H) 7.73 (d, J=8.33 Hz, 2H) 7.84 (d, J=7.95 Hz, 2H)

Example 5

3-{[4-(1-{2-ethyl-5-[4-(trifluoromethyl)phenyl]-3-furyl}-3-methylbutoxy)benzoyl]amino}propanoic acid

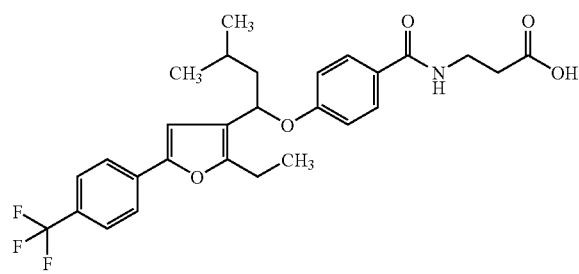

(1) 1-{2-ethyl-5-[4-(trifluoromethyl)phenyl]-3-furyl}-3-methylbutan-1-ol

An operation similar to that in Example 3 (2) was performed using 2-ethyl-5-[4-(trifluoromethyl)phenyl]-3-furaldehyde (805 mg) and 1N isobutylmagnesium bromide-tetrahydrofuran solution (6.0 mL) to give the title compound (819 mg, 83%) as an oil.

$^1$H NMR (300 MHz, CHLOROFORM-d) δ ppm 0.95 (d, J=6.40 Hz, 6H) 1.30 (t, J=7.54 Hz, 3H) 1.51-1.81 (m, 3H) 2.74 (qd, J=7.57, 1.79 Hz, 2H) 4.71-4.77 (m, 1H) 6.75 (s, 1H) 7.60 (d, J=8.85 Hz, 2H) 7.71 (d, J=8.85 Hz, 2H)

(2) 4-(1-{2-ethyl-5-[4-(trifluoromethyl)phenyl]-3-furyl}-3-methylbutoxy)benzoic acid An operation similar to that in Example 1 (3) was performed using 1-{2-ethyl-5-[4-(trifluoromethyl)phenyl]-3-furyl}-3-methylbutan-1-ol (816 mg) to give the title compound (402 mg, 50%) as a white crystal.

$^1$H NMR (300 MHz, CHLOROFORM-d) δ ppm 0.95 (d, J=6.82 Hz, 3H) 1.01 (t, J=6.82 Hz, 3H) 1.60-1.69 (m, 1H) 1.75-1.81 (m, 1H) 1.99-2.08 (m, 1H) 2.71-2.89 (m, 2H) 5.14-5.35 (m, 1H) 6.68 (s, 1H) 6.90 (d, J=9.09 Hz, 1H) 7.58 (d, J=8.33 Hz, 2H) 7.67 (d, J=8.33 Hz, 2H) 7.98 (d, J=8.71 Hz, 2H)

(3) 3-{[4-(1-{2-ethyl-5-[4-(trifluoromethyl)phenyl]-3-furyl}-3-methylbutoxy)benzoyl]amino}propanoic acid An operation similar to that in Example 1 (4) was performed using 4-(1-{2-ethyl-5-[4-(trifluoromethyl)phenyl]-3-furyl}-3-methylbutoxy)benzoic acid (179 mg) to give the title compound (205 mg, 99%) as a white crystal.

$^1$H NMR (300 MHz, DMSO-$d_6$) δ ppm 0.93 (d, J=6.06 Hz, 3H) 0.98 (d, J=6.06 Hz, 3H) 1.18 (t, J=7.57 Hz, 3H) 1.54-1.75 (m, 2H) 1.81-2.05 (m, 1H) 2.46 (t, J=7.00 Hz, 2H) 2.81 (dd, J=7.57, 2.27 Hz, 2H) 3.39 (q, J=7.19 Hz, 2H) 5.43 (t, J=6.63 Hz, 1H) 6.98 (d, J=8.71 Hz, 2H) 7.14 (s, 1H) 7.62-7.77 (m, 4H) 7.82 (d, J=8.33 Hz, 2H) 8.31 (t, J=5.30 Hz, 1H)

Example 6

3-{[4-(1-{2-ethyl-5-[4-(trifluoromethyl)phenyl]-3-furyl}-3-methylbutoxy)benzoyl](methyl)amino}propanoic acid

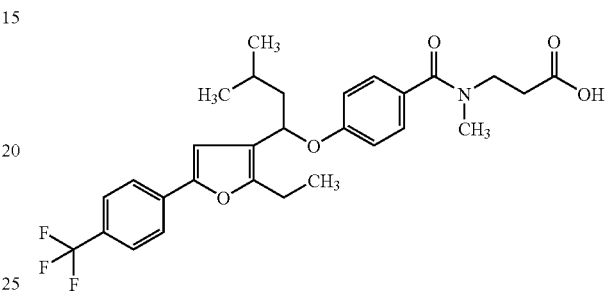

An operation similar to that in Example 1 (4) was performed using 4-(1-{2-ethyl-5-[4-(trifluoromethyl)phenyl]-3-furyl}-3-methylbutoxy)benzoic acid (179 mg) as well as ethyl 3-(methylamino)propanoate (67 mg) to give the title compound (203 mg, 99%) as an oil.

$^1$H NMR (300 MHz, DMSO-$d_6$) δ ppm 0.93 (d, J=6.25 Hz, 3H) 0.97 (d, J=6.25 Hz, 3H) 1.17 (t, J=7.57 Hz, 3H) 1.61-1.74 (m, 2H) 1.83-2.06 (m, 1H) 2.50-2.53 (m, 2H) 2.79 (q, J=7.57 Hz, 2H) 2.89 (s, 3H) 3.52 (brs, 2H) 5.36-5.40 (m, 1H) 6.96 (d, J=8.71 Hz, 2H) 7.16 (s, 1H) 7.29 (d, J=8.71 Hz, 2H) 7.72 (d, J=8.33 Hz, 2H) 7.83 (d, J=8.33 Hz, 2H)

Example 7

3-{[4-(cyclohexyl{2-ethyl-5-[4-(trifluoromethyl)phenyl]-3-furyl}methoxy)benzoyl]amino}propanoic acid

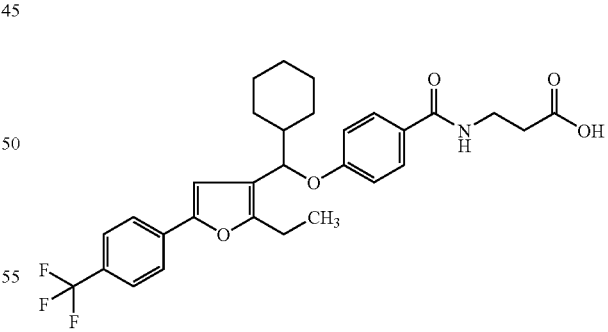

(1) cyclohexyl{2-ethyl-5-[4-(trifluoromethyl)phenyl]-3-furyl}methanol

An operation similar to that in Example 3 (2) was performed using 2-ethyl-5-[4-(trifluoromethyl)phenyl]-3-furaldehyde (1.21 g) and 1N cyclohexylmagnesium bromide-tetrahydrofuran solution (6.8 mL) to give the title compound (1.21 g, 76%) as a yellow crystal.

¹H NMR (300 MHz, CHLOROFORM-d) δ ppm 0.81-1.32 (m, 8H) 1.43-1.74 (m, 4H) 1.74-1.89 (m, 1H) 2.03-2.11 (m, 1H) 2.70 (qd, J=7.54, 3.39 Hz, 2H) 4.32 (dd, J=7.91, 2.83 Hz, 1H) 6.71 (s, 1H) 7.60 (d, J=8.29 Hz, 2H) 7.65-7.81 (d, J=8.29 Hz, 2H)

(2) 4-(cyclohexyl{2-ethyl-5-[4-(trifluoromethyl) phenyl]-3-furyl}methoxy)benzoic acid An operation similar to that in Example 1 (3) was performed using cyclohexyl{2-ethyl-5-[4-(trifluoromethyl)phenyl]-3-furyl}methanol (529 mg) to give the title compound (341 mg, 45%) as a white crystal.

¹H NMR (300 MHz, CHLOROFORM-d) δ ppm 0.97-1.30 (m, 8H) 1.54-1.92 (m, 5H) 2.06-2.12 (m, 1H) 2.74 (ddd, J=14.32, 7.44, 7.25 Hz, 2H) 4.85 (d, J=7.54 Hz, 1H) 6.62 (s, 1H) 6.88 (d, J=8.85 Hz, 2H) 7.57 (d, J=8.48 Hz, 2H) 7.69 (d, J=8.29 Hz, 2H) 7.95 (d, J=9.04 Hz, 2H)

(3) 3-{[4-(cyclohexyl{2-ethyl-5-[4-(trifluoromethyl) phenyl]-3-furyl}methoxy)benzoyl]amino}propanoic acid An operation similar to that in Example 1 (4) was performed using 4-(cyclohexyl{2-ethyl-5-[4-(trifluoromethyl) phenyl]-3-furyl}methoxy)benzoic acid (165 mg) to give the title compound (190 mg, 99%) as a white crystal.

¹H NMR (300 MHz, DMSO-d₆) δ ppm 0.93-1.34 (m, 8H) 1.51-1.91 (m, 5H) 1.99-2.09 (m, 1H) 2.45 (t, J=7.06 Hz, 2H) 2.79 (dd, J=7.35, 6.22 Hz, 2H) 3.35-3.45 (m, 2H) 5.12 (d, J=7.72 Hz, 1H) 6.94 (d, J=9.04 Hz, 2H) 7.05 (s, 1H) 7.66-7.73 (m, 4H) 7.82 (d, J=8.29 Hz, 2H) 8.29 (t, J=5.46 Hz, 1H)

Example 8

3-{[4-(cyclohexyl{2-ethyl-5-[4-(trifluoromethyl) phenyl]-3-furyl}methoxy)benzoyl](methyl) amino}propanoic acid

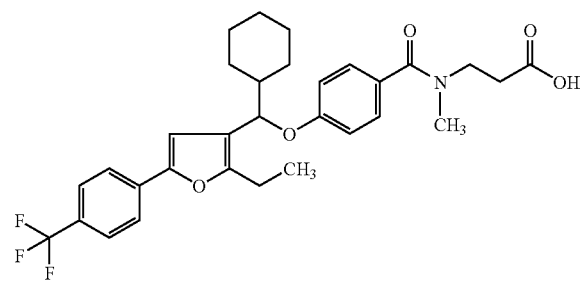

An operation similar to that in Example 1 (4) was performed using 4-(cyclohexyl{2-ethyl-5-[4-(trifluoromethyl) phenyl]-3-furyl}methoxy)benzoic acid (165 mg) as well as ethyl 3-(methylamino)propanoate (55 mg) to give the title compound (178 mg, 91%) as an amorphous compound.

¹H NMR (300 MHz, DMSO-d₆) δ ppm 0.95-1.30 (m, 8H) 1.51-1.91 (m, 5H) 1.91-2.11 (m, 1H) 2.49-2.52 (m, 2H) 2.66-2.84 (m, 2H) 2.88 (s, 3H) 3.51 (brs, 2H) 5.07 (d, J=7.72 Hz, 1H) 6.92 (d, J=8.85 Hz, 2H) 7.07 (s, 1H) 7.27 (d, J=8.67 Hz, 2H) 7.71 (d, J=8.48 Hz, 2H) 7.83 (d, J=8.29 Hz, 2H)

Example 9

3-({4-[(cyclohexyl{2-ethyl-5-[4-(trifluoromethyl) phenyl]-3-furyl}methyl)amino]benzoyl}amino)propanoic acid

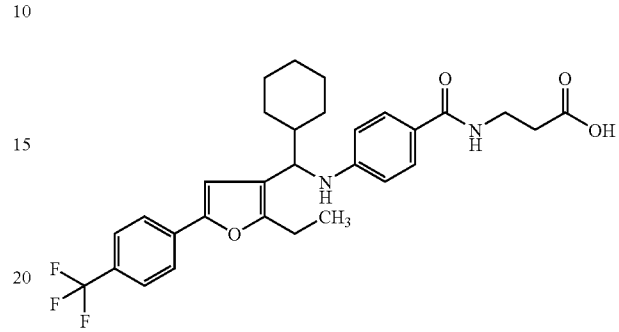

(1) 3-[chloro(cyclohexyl)methyl]-2-ethyl-5-[4-(trifluoromethyl)phenyl]furan

To a solution of cyclohexyl {2-ethyl-5-[4-(trifluoromethyl)phenyl]-3-furyl}methanol (705 mg) in toluene (10 mL) was added thionyl chloride (290 μL), and the mixture was stirred at 100° C. for 1 hr. The reaction mixture was cooled, neutralized with saturated aqueous sodium hydrogen carbonate, and poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (742 mg, 100%) as a yellow solid.

¹H NMR (300 MHz, CHLOROFORM-d) δ ppm 0.83-1.32 (m, 8H) 1.55-1.86 (m, 5H) 2.18-2.28 (m, 1H) 2.57-2.82 (m, 2H) 4.61 (d, J=8.67 Hz, 1H) 6.74 (s, 1H) 7.60 (d, J=8.29 Hz, 2H) 7.72 (d, J=8.29 Hz, 2H)

(2) 4-[(cyclohexyl{2-ethyl-5-[4-(trifluoromethyl) phenyl]-3-furyl}methyl)amino]benzoic acid A mixture of 3-[chloro(cyclohexyl)methyl]-2-ethyl-5-[4-(trifluoromethyl)phenyl]furan (742 mg) obtained by the above-mentioned reaction, methyl 4-aminobenzoate (604 mg), sodium carbonate (424 mg) and sodium iodide (2.66 g) in N,N-dimethylacetamide (10 mL) was stirred at 100° C. overnight. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (2 mL) and tetrahydrofuran (2 mL), 2N sodium hydroxide (2.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (0% ethyl acetate/hexane to 50% ethyl acetate/hexane) to give the title compound (241 mg, 25%) as an amorphous compound.

$^1$H NMR (300 MHz, CHLOROFORM-d) δ ppm 0.91-1.36 (m, 8H) 1.62-1.82 (m, 5H) 1.96-2.01 (m, 1H) 2.75 (dd, J=7.57, 5.30 Hz, 2H) 4.09-4.16 (m, 2H) 6.52 (d, J=9.09 Hz, 2H) 6.56 (s, 1H) 7.57 (d, J=8.33 Hz, 2H) 7.67 (d, J=8.33 Hz, 2H) 7.84 (d, J=9.09 Hz, 2H)

(3) 3-({4-[(cyclohexyl{2-ethyl-5-[4-(trifluoromethyl)phenyl]-3-furyl}methyl)amino]benzoyl}amino)propanoic acid An operation similar to that in Example 1 (4) was performed using 4-[(cyclohexyl{2-ethyl-5-[4-(trifluoromethyl)phenyl]-3-furyl}methyl)amino]benzoic acid (118 mg) to give the title compound (132 mg, 97%) as an amorphous compound.
$^1$H NMR (300 MHz, DMSO-d$_6$) δ ppm 0.93-1.26 (m, 8H) 1.51-1.77 (m, 5H) 2.01-2.09 (m, 1H) 2.43 (t, J=7.16 Hz, 2H) 2.79 (dd, J=7.35, 6.03 Hz, 2H) 3.36 (q, J=5.84 Hz, 2H) 4.09-4.25 (m, 1H) 6.35 (d, J=8.10 Hz, 1H) 6.56 (d, J=8.67 Hz, 2H) 6.94 (s, 1H) 7.52 (d, J=8.85 Hz, 2H) 7.71 (d, J=8.67 Hz, 2H) 7.76 (d, J=8.67 Hz, 2H) 7.99 (t, J=5.56 Hz, 1H)

Example 10

3-[{4-[(cyclohexyl{2-ethyl-5-[4-(trifluoromethyl)phenyl]-3-furyl}methyl)amino]benzoyl}(methyl)amino]propanoic acid

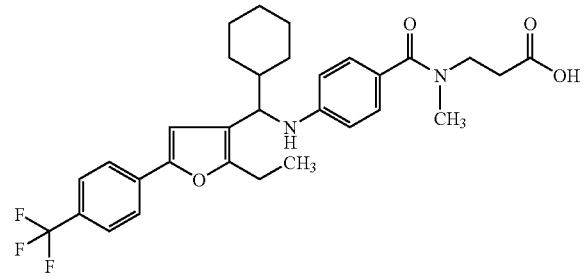

An operation similar to that in Example 1 (4) was performed using 4-[(cyclohexyl{2-ethyl-5-[4-(trifluoromethyl)phenyl]-3-furyl}methyl)amino]benzoic acid (118 mg) as well as ethyl 3-(methylamino)propanoate (39 mg) to give the title compound (104 mg, 75%) as an amorphous compound.
$^1$H NMR (300 MHz, DMSO-d$_6$) δ ppm 0.93-1.26 (m, 8H) 1.59-1.77 (m, 5H) 1.98-2.13 (m, 1H) 2.43-2.57 (m, 2H) 2.79 (dd, J=7.44, 4.62 Hz, 2H) 2.90 (s, 3H) 3.51 (t, J=7.35 Hz, 2H) 4.05-4.17 (m, 1H) 6.24 (d, J=7.91 Hz, 1H) 6.56 (d, J=8.67 Hz, 2H) 6.96 (s, 1H) 7.10 (d, J=8.67 Hz, 2H) 7.71 (d, J=8.60 Hz, 2H) 7.77 (d, J=8.60 Hz, 2H)

Example 11

3-{[4-({2-cyclohexyl-5-[4-(trifluoromethoxy)phenyl]-3-furyl}methoxy)benzoyl]amino}propanoic acid

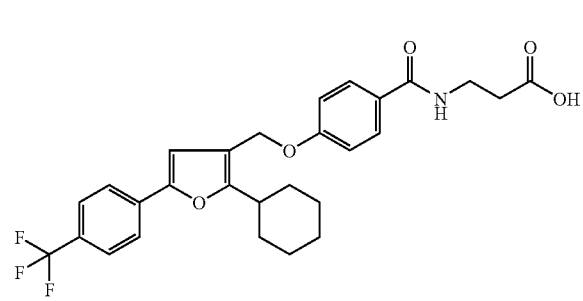

(1) ethyl 2-cyclohexyl-5-[4-(trifluoromethyl)phenyl]-3-furoate

An operation similar to that in Example 1 (1) was performed using 2-chloro-4'-(trifluoromethyl)acetophenone (13.4 g) and ethyl 3-cyclohexyl-3-oxopropanoate (9.9 g) to give the title compound (7.7 g, 40%) as a yellow crystal.
$^1$H NMR (300 MHz, CHLOROFORM-d) δ ppm 1.23-1.91 (m, 13H) 3.43-3.85 (m, 1H) 4.32 (q, J=7.19 Hz, 2H) 7.00 (s, 1H) 7.63 (d, J=8.33 Hz, 2H) 7.73 (d, J=8.33 Hz, 2H)

(2) {2-cyclohexyl-5-[4-(trifluoromethyl)phenyl]-3-furyl}methanol

An operation similar to that in Example 1 (2) was performed using ethyl 2-cyclohexyl-5-[4-(trifluoromethyl)phenyl]-3-furoate (7.3 g) to give the title compound (3.4 g, 45%) as an oil.
$^1$H NMR (300 MHz, CHLOROFORM-d) δ ppm 1.15-1.87 (m, 10H) 2.76-2.85 (m, 1H) 4.47 (d, J=4.54 Hz, 2H) 6.45 (s, 1H) 7.41-7.55 (m, 4H)

(3) 4-({2-cyclohexyl-5-[4-(trifluoromethyl)phenyl]-3-furyl}methoxy)benzoic acid

An operation similar to that in Example 1 (3) was performed using {2-cyclohexyl-5-[4-(trifluoromethyl)phenyl]-3-furyl}methanol (321 mg) to give the title compound (285 mg, 63%) as a white crystal.
$^1$H NMR (300 MHz, CHLOROFORM-d) δ ppm 1.33-1.78 (m, 8H) 1.86-1.91 (m, 2H) 2.76-2.85 (m, 1H) 4.98 (s, 2H) 6.78 (s, 1H) 7.03 (d, J=9.09 Hz, 2H) 7.61 (d, J=8.71 Hz, 2H) 7.71 (d, J=8.33 Hz, 2H) 8.05 (d, J=9.09 Hz, 2H)

(4) 3-{[4-({2-cyclohexyl-5-[4-(trifluoromethoxy)phenyl]-3-furyl}methoxy)benzoyl]amino}propanoic acid An operation similar to that in Example 1 (4) was performed using 4-({2-cyclohexyl-5-[4-(trifluoromethyl)phenyl]-3-furyl}methoxy)benzoic acid (133 mg) to give the title compound (133 mg, 98%) as a white crystal.
$^1$H NMR (300 MHz, DMSO-d$_6$) δ ppm 1.22-1.40 (m, 3H) 1.53-1.73 (m, 3H) 1.73-1.84 (m, 4H) 2.47-2.55 (m, 2H) 2.89-2.98 (m, 1H) 3.36-3.49 (m, 2H) 5.03 (s, 2H) 7.08 (d, J=8.71 Hz, 2H) 7.19 (s, 1H) 7.71-7.89 (m, 6H)

Example 12

3-{[4-({2-cyclohexyl-5-[4-(trifluoromethyl)phenyl]-3-furyl}methoxy)benzoyl](methyl)amino}propanoic acid

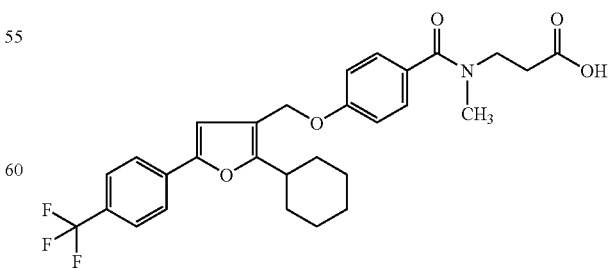

An operation similar to that in Example 1 (4) was performed using 4-({2-cyclohexyl-5-[4-(trifluoromethyl)phenyl]-3-furyl}methoxy)benzoic acid (133 mg) as well as ethyl 3-(methylamino)propanoate (47 mg) to give the title compound (151 mg, 95%) as an amorphous compound.

¹H NMR (300 MHz, DMSO-d₆) δ ppm 1.13-1.46 (m, 3H) 1.58-1.81 (m, 7H) 2.55 (t, J=7.19 Hz, 2H) 2.83-3.04 (m, 5H) 3.55 (brs, 2H) 5.01 (s, 2H) 7.06 (d, J=8.71 Hz, 2H) 7.19 (s, 1H) 7.36 (d, J=8.71 Hz, 2H) 7.75 (d, J=8.33 Hz, 2H) 7.86 (d, J=8.33 Hz, 2H)

Example 13

3-{[4-(1-{2-cyclohexyl-5-[4-(trifluoromethyl)phenyl]-3-furyl}ethoxy)benzoyl]amino}propanoic acid

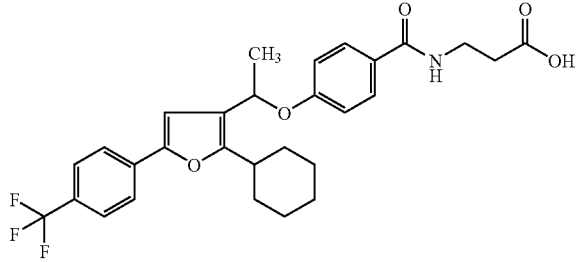

(1) 2-cyclohexyl-5-[4-(trifluoromethoxy)phenyl]-3-furaldehyde

To a solution of oxalyl chloride (0.52 mL) in tetrahydrofuran (30 mL) was added dropwise a solution of dimethyl sulfoxide (0.85 mL) in tetrahydrofuran (10 mL) at −78° C. and, after the completion of the dropwise addition, the mixture was stirred at −78° C. for 5 min. To the reaction mixture was added dropwise a solution of {2-cyclohexyl-5-[4-(trifluoromethyl)phenyl]-3-furyl}methanol (1.3 g) in tetrahydrofuran (20 mL), and the mixture was stirred at −78° C. for 15 min. Triethylamine (2.8 mL) was added dropwise, and the reaction mixture was stirred at room temperature for 15 min. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (0.42 g, 32%) as a yellow crystal.

¹H NMR (300 MHz, CHLOROFORM-d) δ ppm 1.30-1.54 (m, 3H) 1.74-2.05 (m, 7H) 3.07-3.34 (m, 1H) 7.03 (s, 1H) 7.65 (d, J=8.71 Hz, 2H) 7.75 (d, J=8.33 Hz, 2H) 10.03 (s, 1H)

(2) 1-{2-cyclohexyl-5-[4-(trifluoromethyl)phenyl]-3-furyl}ethanol

In the same manner as in Example 3 (2), the title compound (378 mg, 85%) was obtained as an oil from 2-cyclohexyl-5-[4-(trifluoromethoxy)phenyl]-3-furaldehyde (419 mg) and 1N methyl magnesium bromide-tetrahydrofuran solution (2.5 mL).

¹H NMR (300 MHz, CHLOROFORM-d) δ ppm 1.28-1.80 (m, 13H) 2.73-2.84 (m, 1H) 4.89-4.97 (m, 1H) 6.67 (s, 1H) 7.59 (d, J=8.29 Hz, 2H) 7.70 (d, J=8.29 Hz, 2H)

(3) 4-(1-{2-cyclohexyl-5-[4-(trifluoromethyl)phenyl]-3-furyl}ethoxy)benzoic acid An operation similar to that in Example 1 (3) was performed using 1-{2-cyclohexyl-5-[4-(trifluoromethyl)phenyl]-3-furyl}ethanol (372 mg) to give the title compound (291 mg, 58%) as a white crystal.

¹H NMR (300 MHz, CHLOROFORM-d) δ ppm 1.35-1.93 (m, 13H) 2.71-2.82 (m, 1H) 5.39-5.46 (m, 1H) 6.70 (s, 1H) 6.93 (d, J=8.67 Hz, 2H) 7.57 (d, J=8.48 Hz, 2H) 7.67 (d, J=8.29 Hz, 2H) 7.99 (d, J=8.85 Hz, 2H)

(4) 3-{[4-(1-{2-cyclohexyl-5-[4-(trifluoromethyl)phenyl]-3-furyl}ethoxy)benzoyl]amino}propanoic acid An operation similar to that in Example 1 (4) was performed using 4-(1-{2-cyclohexyl-5-[4-(trifluoromethyl)phenyl]-3-furyl}ethoxy)benzoic acid (138 mg) to give the title compound (137 mg, 86%) as a white crystal.

¹H NMR (300 MHz, DMSO-d₆) δ ppm 1.19-1.82 (m, 13H) 2.37-2.48 (m, 2H) 2.92-3.00 (m, 1H) 3.35-3.51 (m, 2H) 5.65 (q, J=6.18 Hz, 1H) 6.99 (d, J=9.09 Hz, 2H) 7.14 (s, 1H) 7.78-7.89 (m, 4H) 7.82 (d, J=8.33 Hz, 2H) 8.33 (t, J=5.30 Hz, 1H)

Example 14

3-{[4-(1-{2-cyclohexyl-5-[4-(trifluoromethyl)phenyl]-3-furyl}ethoxy)benzoyl](methyl)amino}propanoic acid

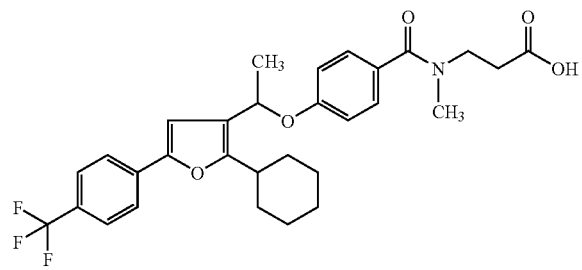

An operation similar to that in Example 1 (4) was performed using 4-(1-{2-cyclohexyl-5-[4-(trifluoromethyl)phenyl]-3-furyl}ethoxy)benzoic acid (138 mg) as well as ethyl 3-(methylamino)propanoate (47 mg) to give the title compound (138 mg, 84%) as an amorphous compound.

¹H NMR (300 MHz, DMSO-d₆) δ ppm 1.13-1.86 (m, 13H) 2.49-2.53 (m, 2H) 2.82-3.01 (m, 4H) 3.49 (brs, 2H) 5.60 (q, J=6.06 Hz, 1H) 6.97 (d, J=8.71 Hz, 2H) 7.16 (s, 1H) 7.29 (d, J=8.71 Hz, 2H) 7.73 (d, J=8.33 Hz, 2H) 7.83 (d, J=7.95 Hz, 2H)

Example 15

3-{[4-(1-{2-cyclohexyl-5-[4-(trifluoromethyl)phenyl]-3-furyl}-3-methylbutoxy)benzoyl]amino}propanoic acid

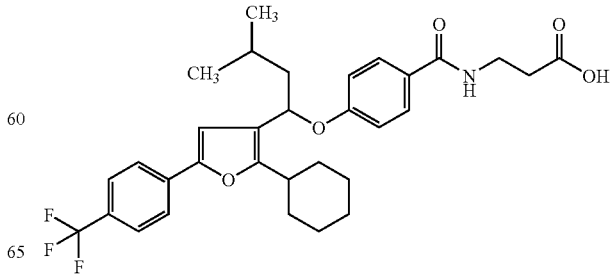

(1) 1-{2-cyclohexyl-5-[4-(trifluoromethyl)phenyl]-3-furyl}-3-methylbutan-1-ol

An operation similar to that in Example 3 (2) was performed using 2-cyclohexyl-5-[4-(trifluoromethoxy)phenyl]-3-furaldehyde (806 mg) and 1N isobutylmagnesium bromide-tetrahydrofuran solution (5.0 mL) to give the title compound (652 mg, 68%) as an oil.
$^1$H NMR (300 MHz, CHLOROFORM-d) δ ppm 0.95 (d, J=6.40 Hz, 6H) 1.19-1.97 (m, 13H) 2.71-2.81 (m, 1H) 4.77 (t, J=6.97 Hz, 1H) 6.74 (s, 1H) 7.59 (d, J=8.29 Hz, 2H) 7.70 (d, J=8.29 Hz, 2H)

(2) 4-(1-{2-cyclohexyl-5-[4-(trifluoromethyl)phenyl]-3-furyl}-3-methylbutoxy)benzoic acid An operation similar to that in Example 1 (3) was performed using 1-{2-cyclohexyl-5-[4-(trifluoromethyl)phenyl]-3-furyl}-3-methylbutan-1-ol (647 mg) to give the title compound (332 mg, 39%) as a white crystal.
$^1$H NMR (300 MHz, CHLOROFORM-d) δ ppm 0.96 (d, J=6.82 Hz, 3H) 1.00 (d, J=6.82 Hz, 3H) 1.25-2.07 (m, 13H) 2.76 (brs, 1H) 5.23-5.30 (m, 1H) 6.66 (s, 1H) 6.91 (d, J=8.71 Hz, 2H) 7.57 (d, J=8.71 Hz, 2H) 7.66 (d, J=8.33 Hz, 2H) 7.97 (d, J=9.09 Hz, 1H)

(3) 3-{[4-(1-{2-cyclohexyl-5-[4-(trifluoromethyl)phenyl]-3-furyl}-3-methylbutoxy)benzoyl]amino}propanoic acid An operation similar to that in Example 1 (4) was performed using 4-(1-{2-cyclohexyl-5-[4-(trifluoromethyl)phenyl]-3-furyl}-3-methylbutoxy)benzoic acid (150 mg) to give the title compound (171 mg, 100%) as an amorphous compound.
$^1$H NMR (300 MHz, DMSO-$d_6$) δ ppm 0.93 (d, J=6.25 Hz, 3H) 0.98 (d, J=6.25 Hz, 3H) 1.15-1.99 (m, 13H) 2.46 (t, J=7.19 Hz, 2H) 2.94-3.04 (m, 1H) 3.34-3.46 (m, 2H) 5.46 (brs, 1H) 6.98 (d, J=8.71 Hz, 2H) 7.12 (s, 1H) 7.63-7.77 (m, 4H) 7.81 (d, J=8.33 Hz, 2H) 8.32 (t, J=5.49 Hz, 1H)

Example 16

3-{[4-(1-{2-cyclohexyl-5-[4-(trifluoromethyl)phenyl]-3-furyl}-3-methylbutoxy)benzoyl](methyl)amino}propanoic acid

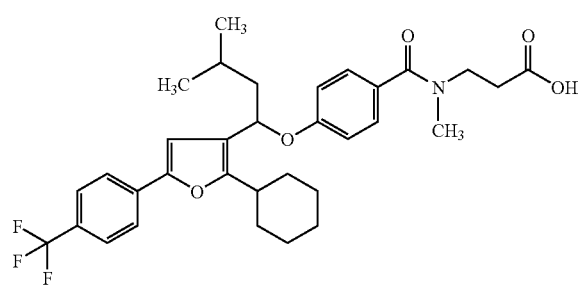

An operation similar to that in Example 1 (4) was performed using 4-(1-{2-cyclohexyl-5-[4-(trifluoromethyl)phenyl]-3-furyl}-3-methylbutoxy)benzoic acid (150 mg) as well as ethyl 3-(methylamino)propanoate (47 mg) to give the title compound (161 mg, 91%) as an amorphous compound.
$^1$H NMR (300 MHz, DMSO-$d_6$) δ ppm 0.94 (d, J=5.87 Hz, 3H) 0.97 (d, J=, 5.87 Hz, 3H) 1.15-1.99 (m, 13H) 2.50 (brs, 2H) 2.86-2.97 (m, 4H) 3.50 (brs, 2H) 5.41 (t, J=6.63 Hz, 1H) 6.97 (d, J=8.33 Hz, 2H) 7.14 (s, 1H) 7.28 (d, J=8.33 Hz, 2H) 7.72 (d, J=8.33 Hz, 2H) 7.82 (d, J=8.33 Hz, 2H)

Example 17

3-{[4-(1-{2-isopropyl-5-[4-(trifluoromethyl)phenyl]-3-furyl}-3-methylbutoxy)benzoyl]amino}propanoic acid

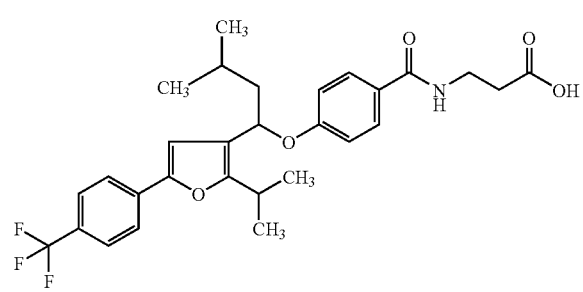

(1) methyl 2-isopropyl-5-[4-(trifluoromethyl)phenyl]-3-furoate

An operation similar to that in Example 1 (1) was performed using 2-chloro-4'-(trifluoromethyl)acetophenone (13.4 g) and methyl 4-methyl-3-oxopentanoate (7.2 g) to give the title compound (5.7 g, 36%) as an oil.
$^1$H NMR (300 MHz, CHLOROFORM-d) δ ppm 1.35 (d, J=6.97 Hz, 6H) 3.67-3.92 (m, 4H) 6.99 (s, 1H) 7.63 (d, J=8.29 Hz, 2H) 7.73 (d, J=8.10 Hz, 2H)

(2) {2-isopropyl-5-[4-(trifluoromethyl)phenyl]-3-furyl}methanol

An operation similar to that in Example 1 (2) was performed using methyl 2-isopropyl-5-[4-(trifluoromethyl)phenyl]-3-furoate (5.6 g) to give the title compound (2.9 g, 56%) as a yellow crystal.
$^1$H NMR (300 MHz, CHLOROFORM-d) δ ppm 1.34 (d, J=6.97 Hz, 6H) 3.11-3.20 (m, 1H) 4.55 (brs, 2H) 6.75 (s, 1H) 7.60 (d, J=8.29 Hz, 2H) 7.71 (d, J=8.29 Hz, 2H)

(3) 2-isopropyl-5-[4-(trifluoromethoxy)phenyl]-3-furaldehyde

To a solution of {2-isopropyl-5-[4-(trifluoromethyl)phenyl]-3-furyl}methanol (1.1 g) obtained above in methylene chloride (10 mL) was added a Dess-Martin reagent (2.0 g) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (0.99 g, 87%) as a yellow crystal.
$^1$H NMR (300 MHz, CHLOROFORM-d) δ ppm 1.45 (d, J=6.97 Hz, 6H) 3.55-3.64 (m, 1H) 7.03 (s, 1H) 7.66 (d, J=8.29 Hz, 2H) 7.76 (d, J=8.29 Hz, 2H) 10.04 (s, 1H)

(4) 1-{2-isopropyl-5-[4-(trifluoromethyl)phenyl]-3-furyl}-3-methylbutan-1-ol An operation similar to that in Example 3 (2) was performed using 2-isopropyl-5-[4-(trifluoromethoxy)phenyl]-3-furaldehyde (988 mg) and 1N isobutylmagnesium bromide-tetrahydrofuran solution (7.0 mL) to give the title compound (730 mg, 61%) as an oil.

$^1$H NMR (300 MHz, CHLOROFORM-d) δ ppm 0.95 (d, J=6.40 Hz, 6H) 1.31 (d, J=6.880 Hz, 3H) 1.35 (d, J=6.88 Hz, 3H) 1.60-1.89 (m, 2H) 3.04-3.26 (m, 1H) 4.74-4.82 (m, 1H) 6.74 (s, 1H) 7.60 (d, J=8.29 Hz, 1H) 7.71 (d, J=8.10 Hz, 2H)

(5) 4-(1-{2-isopropyl-5-[4-(trifluoromethyl)phenyl]-3-furyl}-3-methylbutoxy)benzoic acid An operation similar to that in Example 3 (2) was performed using 1-{2-isopropyl-5-[4-(trifluoromethyl)phenyl]-3-furyl}-3-methylbutan-1-ol (340 mg) to give the title compound (345 mg, 46%) as a white crystal.

$^1$H NMR (300 MHz, CHLOROFORM-d) δ ppm 0.96 (d, J=6.82 Hz, 3H) 1.01 (d, J=6.82 Hz, 3H) 1.26 (d, J=6.82 Hz, 3H) 1.35 (d, J=6.82 Hz, 3H) 1.52-1.85 (m, 2H) 1.97-2.06 (m, 1H) 3.11-3.24 (m, 1H) 5.24-5.29 (m, 1H) 6.67 (s, 1H) 6.91 (d, J=8.71 Hz, 2H) 7.57 (d, J=8.33 Hz, 2H) 7.67 (d, J=8.33 Hz, 2H) 7.97 (d, J=8.71 Hz, 2H)

(6) 3-{[4-(1-{2-isopropyl-5-[4-(trifluoromethyl)phenyl]-3-furyl}-3-methylbutoxy)benzoyl]amino}propanoic acid An operation similar to that in Example 1 (4) was performed using 4-(1-{2-isopropyl-5-[4-(trifluoromethyl)phenyl]-3-furyl}-3-methylbutoxy)benzoic acid (170 mg) to give the title compound (152 mg, 78%) as an amorphous compound.

$^1$H NMR (300 MHz, DMSO-d$_6$) δ ppm 0.93 (d, J=6.06 Hz, 3H) 0.99 (d, J=6.06 Hz, 3H) 1.19 (d, J=6.82 Hz, 3H) 1.25 (d, J=6.82 Hz, 3H) 1.64-1.73 (m, 2H) 1.91-1.99 (m, 1H) 2.35-2.48 (m, 2H) 3.35-3.43 (m, 3H) 5.45 (t, J=6.63 Hz, 1H) 6.98 (d, J=8.71 Hz, 2H) 7.12 (s, 1H) 7.71-7.74 (m, 4H) 7.82 (d, J=8.33 Hz, 2H) 8.31 (t, J=5.30 Hz, 1H)

Example 18

3-{[4-(1-{2-isopropyl-5-[4-(trifluoromethyl)phenyl]-3-furyl}-3-methylbutoxy)benzoyl](methyl)amino}propanoic acid

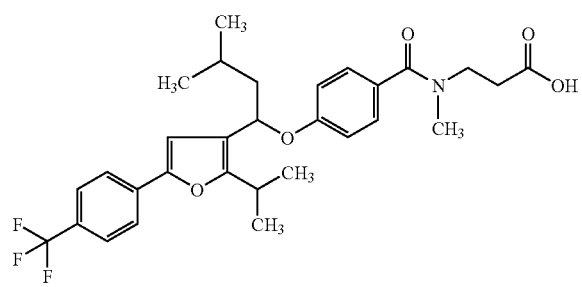

An operation similar to that in Example 1 (4) was performed using 4-(1-{2-isopropyl-5-[4-(trifluoromethyl)phenyl]-3-furyl}-3-methylbutoxy)benzoic acid (170 mg) as well as ethyl 3-(methylamino)propanoate (58 mg) to give the title compound (46 mg, 23%) as a white crystal.

$^1$H NMR (300 MHz, DMSO-d$_6$) δ ppm 0.94 (d, J=6.25 Hz, 3H) 0.95 (d, J=6.25 Hz, 3H) 1.12-1.29 (m, 6H) 1.65-1.73 (m, 2H) 1.91-2.01 (m, 1H) 2.50 (brs, 2H) 2.88 (s, 3H) 3.19-3.36 (m, 1H) 3.51 (brs, 2H) 5.40 (t, J=6.82 Hz, 1H) 6.96 (d, J=8.71 Hz, 2H) 7.14 (s, 1H) 7.28 (d, J=8.71 Hz, 2H) 7.72 (d, J=8.71 Hz, 2H) 7.83 (d, J=8.33 Hz, 2H)

Example 19

3-{[4-(cyclohexyl{2-isopropyl-5-[4-(trifluoromethyl)phenyl]-3-furyl}methoxy)benzoyl]amino}propanoic acid

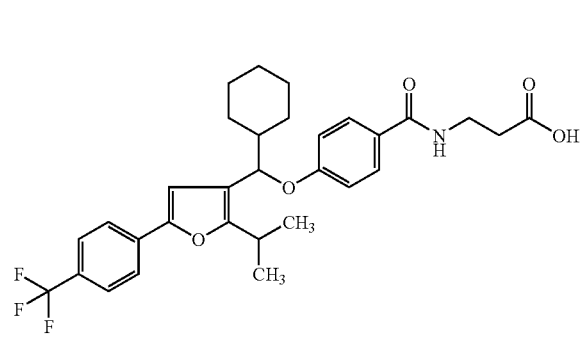

(1) cyclohexyl{2-isopropyl-5-[4-(trifluoromethyl)phenyl]-3-furyl}methanol

An operation similar to that in Example 3 (2) was performed using 2-isopropyl-5-[4-(trifluoromethoxy)phenyl]-3-furaldehyde (1.4 g) and 1N cyclohexylmagnesium bromide-tetrahydrofuran solution (7.5 mL) to give the title compound (1.6 g, 89%) as an oil.

$^1$H NMR (300 MHz, CHLOROFORM-d) δ ppm 0.83-1.41 (m, 6H) 1.49-1.72 (m, 10H) 2.07-2.18 (m, 1H) 3.04-3.14 (m, 1H) 4.34 (dd, J=8.29, 3.01 Hz, 1H) 6.70 (s, 1H) 7.58 (d, J=8.29 Hz, 2H) 7.71 (d, J=8.29 Hz, 2H)

(2) 4-(cyclohexyl{2-isopropyl-5-[4-(trifluoromethyl)phenyl]-3-furyl}methoxy)benzoic acid An operation similar to that in Example 1 (3) was performed using cyclohexyl{2-isopropyl-5-[4-(trifluoromethyl)phenyl]-3-furyl}methanol (440 mg) to give the title compound (389 mg, 67%) as an amorphous compound.

$^1$H NMR (300 MHz, CHLOROFORM-d) δ ppm 0.86-1.38 (m, 16H) 2.01-2.15 (m, 1H) 3.02-3.24 (m, 1H) 4.87 (d, J=7.72 Hz, 1H) 6.61 (s, 1H) 6.89 (d, J=8.85 Hz, 2H) 7.57 (d, J=8.29 Hz, 2H) 7.66 (d, J=8.29 Hz, 2H) 7.95 (d, J=8.85 Hz, 2H)

(3) 3-{[4-(cyclohexyl{2-isopropyl-5-[4-(trifluoromethyl)phenyl]-3-furyl}methoxy)benzoyl]amino}propanoic acid An operation similar to that in Example 1 (4) was performed using 4-(cyclohexyl{2-isopropyl-5-[4-(trifluoromethyl)phenyl]-3-furyl}methoxy)benzoic acid (195 mg) to give the title compound (158 mg, 78%) as an amorphous compound.

$^1$H NMR (300 MHz, DMSO-d$_6$) δ ppm 1.06-1.36 (m, 11H) 1.51-1.93 (m, 5H) 2.04-2.09 (m, 1H) 2.46 (t, J=7.19 Hz, 2H)

3.18-3.51 (m, 3H) 5.14 (d, J=7.95 Hz, 1H) 6.95 (d, J=8.71 Hz, 2H) 7.03 (s, 1H) 7.71-7.73 (m, 4H) 7.82 (d, J=8.33 Hz, 2H) 8.30 (t, J=5.30 Hz, 1H)

Example 20

3-{[4-(cyclohexyl{2-isopropyl-5-[4-(trifluoromethyl)phenyl]-3-furyl}methoxy)benzoyl](methyl)amino}propanoic acid

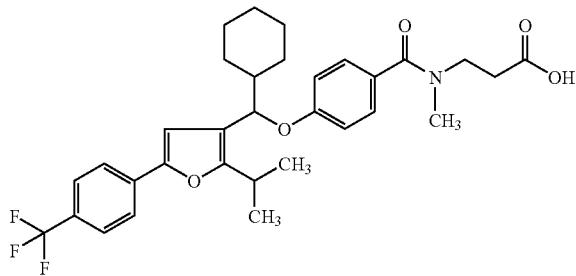

An operation similar to that in Example 1 (4) was performed using 4-(cyclohexyl{2-isopropyl-5-[4-(trifluoromethyl)phenyl]-3-furyl}methoxy)benzoic acid (195 mg) as well as ethyl 3-(methylamino)propanoate (63 mg) to give the title compound (57 mg, 25%) as an amorphous compound.

$^1$H NMR (300 MHz, DMSO-d$_6$) δ ppm 0.98-1.30 (m, 11H) 1.46-1.93 (m, 5H) 2.03-2.12 (m, 1H) 2.50 (brs, 2H) 2.87 (s, 3H) 3.15-3.36 (m, 3H) 5.08 (d, J=7.95 Hz, 1H) 6.93 (d, J=8.71 Hz, 2H) 7.06 (s, 1H) 7.26 (d, J=8.33 Hz, 2H) 7.71 (d, J=8.33 Hz, 2H) 7.82 (d, J=7.95 Hz, 2H)

Example 21

3-{[4-(3-methyl-1-{2-methyl-5-[4-(trifluoromethyl)phenyl]-3-furyl}butoxy)benzoyl]amino}propanoic acid

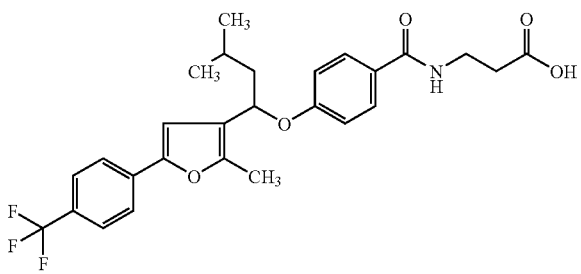

(1) methyl 2-methyl-5-[4-(trifluoromethyl)phenyl]-3-furoate

An operation similar to that in Example 1 (1) was performed using 2-chloro-4'-(trifluoromethyl)acetophenone (13.4 g) and methyl acetoacetate (5.8 g) to give the title compound (5.6 g, 39%) as a yellow crystal.

$^1$H NMR (300 MHz, CHLOROFORM-d) δ ppm 2.67 (s, 3H) 3.87 (s, 3H) 7.00 (s, 1H) 7.63 (d, J=8.33 Hz, 2H) 7.73 (d, J=7.95 Hz, 2H)

(2) {2-methyl-5-[4-(trifluoromethyl)phenyl]-3-furyl}methanol

An operation similar to that in Example 1 (2) was performed using methyl 2-methyl-5-[4-(trifluoromethyl)phenyl]-3-furoate (5.0 g) to give the title compound (4.2 g, 87%) as a yellow crystal.

$^1$H NMR (300 MHz, CHLOROFORM-d) δ ppm 2.39 (s, 3H) 4.53 (s, 2H) 6.76 (s, 1H) 7.60 (d, J=8.29 Hz, 2H) 7.71 (d, J=8.10 Hz, 2H)

(3) 2-methyl-5-[4-(trifluoromethoxy)phenyl]-3-furaldehyde

An operation similar to that in Example 17 (3) was performed using {2-methyl-5-[4-(trifluoromethyl)phenyl]-3-furyl}methanol (4.2 g) to give the title compound (2.7 g, 65%) as a yellow crystal.

$^1$H NMR (300 MHz, CHLOROFORM-d) δ ppm 2.70 (s, 3H) 7.03 (s, 1H) 7.66 (d, J=8.33 Hz, 2H) 7.76 (d, J=7.95 Hz, 2H) 9.98 (s, 1H)

(4) 1-{2-methyl-5-[4-(trifluoromethyl)phenyl]-3-furyl}-3-methylbutan-1-ol

An operation similar to that in Example 3 (2) was performed using 2-methyl-5-[4-(trifluoromethoxy)phenyl]-3-furaldehyde (1.1 g) and 1N isobutylmagnesium bromide-tetrahydrofuran solution (7.0 mL) to give the title compound (1.0 g, 73%) as a white crystal.

$^1$H NMR (300 MHz, CHLOROFORM-d) δ ppm 0.95 (d, J=6.40 Hz, 6H) 1.44-1.88 (m, 3H) 2.38 (s, 3H) 4.72 (td, 1H) 6.74 (s, 1H) 7.59 (d, J=8.29 Hz, 2H) 7.70 (d, J=8.10 Hz, 2H)

(5) 4-(1-{2-methyl-5-[4-(trifluoromethyl)phenyl]-3-furyl}-3-methylbutoxy)benzoic acid An operation similar to that in Example 1 (3) was performed using 1-{2-methyl-5-[4-(trifluoromethyl)phenyl]-3-furyl}-3-methylbutan-1-ol (250 mg) to give the title compound (203 mg, 58%) as an amorphous compound.

$^1$H NMR (300 MHz, CHLOROFORM-d) δ ppm 0.95 (d, J=6.50 Hz, 3H) 1.01 (d, J=6.50 Hz, 3H) 1.61-1.83 (m, 2H) 1.95-2.11 (m, 1H) 2.40 (s, 3H) 5.21 (dd, J=7.82, 5.93 Hz, 1H) 6.68 (s, 1H) 6.89 (d, J=8.85 Hz, 2H) 7.57 (d, J=8.67 Hz, 2H) 7.67 (d, J=8.29 Hz, 2H) 7.98 (d, J=8.85 Hz, 2H)

(6) 3-{[4-(1-{2-methyl-5-[4-(trifluoromethyl)phenyl]-3-furyl}-3-methylbutoxy)benzoyl]amino}propanoic acid An operation similar to that in Example 1 (4) was performed using 4-(1-{2-methyl-5-[4-(trifluoromethyl)phenyl]-3-furyl}-3-methylbutoxy)benzoic acid (99 mg) to give the title compound (88 mg, 76%) as a white crystal.

$^1$H NMR (300 MHz, DMSO-d$_6$) δ ppm 0.93 (d, J=6.22 Hz, 3H) 0.98 (d, J=6.22 Hz, 3H) 1.62-1.73 (m, 2H) 1.80-2.03 (m, 1H) 2.43-2.59 (m, 5H) 3.35-3.50 (m, 2H) 5.34-5.54 (m, 1H) 6.98 (d, J=8.85 Hz, 2H) 7.15 (s, 1H) 7.62-7.77 (m, 4H) 7.81 (d, J=8.10 Hz, 2H) 8.31 (t, J=5.46 Hz, 1H)

Example 22

3-{[4-(1-{2-methyl-5-[4-(trifluoromethyl)phenyl]-3-furyl}-3-methylbutoxy)benzoyl](methyl)amino}propanoic acid

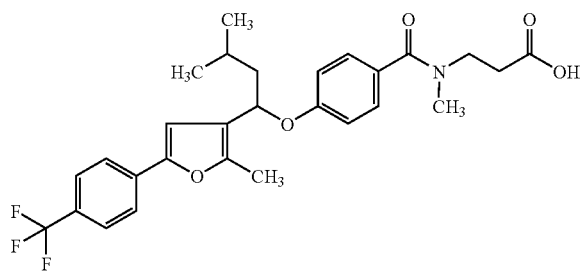

An operation similar to that in Example 1 (4) was performed using 4-(1-{2-methyl-5-[4-(trifluoromethyl)phenyl]-3-furyl}-3-methylbutoxy)benzoic acid (99 mg) as well as ethyl 3-(methylamino)propanoate (37 mg) to give the title compound (103 mg, 87%) as an amorphous compound.

$^1$H NMR (300 MHz, DMSO-$d_6$) δ ppm 0.93 (d, J=6.40 Hz, 3H) 0.97 (d, J=6.40 Hz, 3H) 1.61-1.74 (m, 2H) 1.84-2.07 (m, 1H) 2.41 (s, 3H) 2.53 (brs, 2H) 2.89 (s, 3H) 3.51 (brs, 2H) 5.36 (t, J=6.78 Hz, 1H) 6.95 (d, J=8.67 Hz, 2H) 7.16 (s, 1H) 7.28 (d, J=8.67 Hz, 2H) 7.72 (d, J=8.48 Hz, 2H) 7.82 (d, J=8.29 Hz, 2H)

Example 23

3-{[4-(cyclohexyl{2-methyl-5-[4-(trifluoromethyl)phenyl]-3-furyl}methoxy)benzoyl]amino}propanoic acid

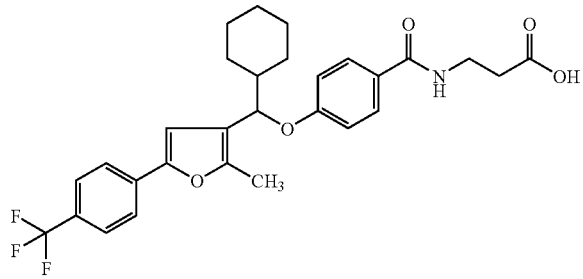

(1) cyclohexyl{2-methyl-5-[4-(trifluoromethyl)phenyl]-3-furyl}methanol

An operation similar to that in Example 3 (2) was performed using 2-methyl-5-[4-(trifluoromethoxy)phenyl]-3-furaldehyde (1.5 g) and 1N cyclohexylmagnesium bromide-tetrahydrofuran solution (10 mL) to give the title compound (1.76 g, 83%) as a white crystal.

$^1$H NMR (300 MHz, CHLOROFORM-d) δ ppm 0.82-1.40 (m, 5H) 1.42-1.90 (m, 5H) 2.03-2.10 (m, 1H) 2.35 (s, 3H) 4.32 (dd, J=7.82, 3.11 Hz, 1H) 6.71 (s, 1H) 7.59 (d, J=8.10 Hz, 2H) 7.70 (d, J=8.10 Hz, 2H)

(2) 4-(cyclohexyl{2-methyl-5-[4-(trifluoromethyl)phenyl]-3-furyl}methoxy)benzoic acid An operation similar to that in Example 1 (3) was performed using cyclohexyl{2-methyl-5-[4-(trifluoromethyl)phenyl]-3-furyl}methanol (338 mg) obtained by the above-mentioned reaction to give the title compound (261 mg, 57%) as a white crystal.

$^1$H NMR (300 MHz, CHLOROFORM-d) δ ppm 1.01-1.32 (m, 5H) 1.57-1.98 (m, 5H) 2.02-2.12 (m, 1H) 2.38 (s, 3H) 4.84 (d, J=7.16 Hz, 1H) 6.62 (s, 1H) 6.87 (d, J=8.85 Hz, 2H) 7.57 (d, J=8.48 Hz, 2H) 7.66 (d, J=8.29 Hz, 2H) 7.96 (d, J=8.85 Hz, 2H)

(3) 3-{[4-(cyclohexyl{2-methyl-5-[4-(trifluoromethyl)phenyl]-3-furyl}methoxy)benzoyl]amino}propanoic acid An operation similar to that in Example 1 (4) was performed using 4-(cyclohexyl{2-methyl-5-[4-(trifluoromethyl)phenyl]-3-furyl}methoxy)benzoic acid (128 mg) to give the title compound (125 mg, 84%) as a white crystal.

$^1$H NMR (300 MHz, DMSO-$d_6$) δ ppm 1.02-1.27 (m, 5H) 1.51-1.91 (m, 5H) 1.99-2.09 (m, 1H) 2.40 (s, 3H) 2.45 (t, J=7.25 Hz, 2H) 3.39 (d, J=5.84 Hz, 2H) 5.11 (d, J=7.54 Hz, 1H) 6.94 (d, J=8.85 Hz, 2H) 7.05 (s, 1H) 7.69-7.72 (m, 4H) 7.81 (d, J=8.29 Hz, 2H) 8.16-8.44 (m, 1H)

Example 24

3-{[4-(cyclohexyl{2-methyl-5-[4-(trifluoromethyl)phenyl]-3-furyl}methoxy)benzoyl](methyl)amino}propanoic acid

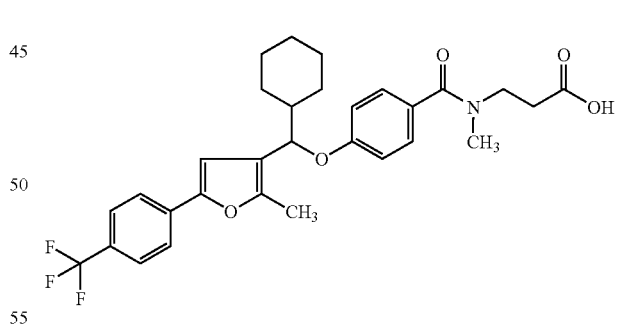

An operation similar to that in Example 1 (4) was performed using 4-(cyclohexyl{2-methyl-5-[4-(trifluoromethyl)phenyl]-3-furyl}methoxy)benzoic acid (128 mg) as well as ethyl 3-(methylamino)propanoate (45 mg) to give the title compound (134 mg, 88%) as an amorphous compound.

$^1$H NMR (300 MHz, DMSO-$d_6$) δ ppm 0.98-1.30 (m, 5H) 1.49-1.91 (m, 5H) 2.00-2.14 (m, 1H) 2.40 (s, 3H) 2.42-2.53 (m, 2H) 2.89 (s, 3H) 3.51 (brs, 2H) 5.06 (d, J=7.54 Hz, 1H) 6.92 (d, J=8.67 Hz, 2H) 7.07 (s, 1H) 7.27 (d, J=8.67 Hz, 2H) 7.71 (d, J=8.29 Hz, 2H) 7.83 (d, J=8.29 Hz, 2H)

Example 25

3-[(4-{1-[5-(4-chlorophenyl)-2-methyl-3-furyl]-3-methylbutoxy}benzoyl)amino]propanoic acid

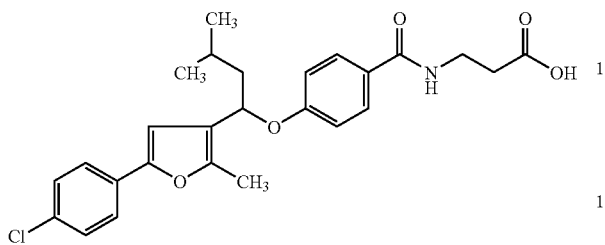

(1) ethyl 5-(4-chlorophenyl)-2-methyl-3-furoate

A mixture of 5-(4-chlorophenyl)-2-methyl-3-furancarboxylic acid (4.7 g), potassium carbonate (2.8 g) and ethyl iodide (3.7 g) in N,N-dimethylformamide (50 mL) was stirred at room temperature for 4 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (5.0 g, 95%) as a yellow crystal.

$^1$H NMR (300 MHz, CHLOROFORM-d) δ ppm 1.37 (t, J=7.16 Hz, 3H) 2.64 (s, 3H) 4.31 (q, J=7.10 Hz, 2H) 6.88 (s, 1H) 7.35 (d, J=8.85 Hz, 2H) 7.57 (d, J=8.85 Hz, 2H)

(2) [5-(4-chlorophenyl)-2-methyl-3-furyl]methanol

An operation similar to that in Example 1 (2) was performed using ethyl 5-(4-chlorophenyl)-2-methyl-3-furoate (5.0 g) to give the title compound (3.8 g, 90%) as a yellow crystal.

$^1$H NMR (300 MHz, CHLOROFORM-d) δ ppm 2.36 (s, 3H) 4.51 (s, 2H) 6.63 (s, 1H) 7.32 (d, J=8.48 Hz, 2H) 7.54 (d, J=8.67 Hz, 2H)

(3) 5-(4-chlorophenyl)-2-methyl-3-furaldehyde

An operation similar to that in Example 17 (3) was performed using [5-(4-chlorophenyl)-2-methyl-3-furyl]methanol (3.8 g) to give the title compound (3.2 g, 86%) as a yellow crystal.

$^1$H NMR (300 MHz, CHLOROFORM-d) δ ppm 2.67 (s, 3H) 6.90 (s, 1H) 7.37 (d, J=8.48 Hz, 2H) 7.59 (d, J=8.48 Hz, 2H) 9.97 (s, 1H)

(4) 1-[5-(4-chlorophenyl)-2-methyl-3-furyl]-3-methylbutan-1-ol

An operation similar to that in Example 3 (2) was performed using 5-(4-chlorophenyl)-2-methyl-3-furaldehyde (1.3 g) and 1N isobutylmagnesium bromide-tetrahydrofuran solution (10 mL) to give the title compound (1.4 g, 85%) as an oil.

$^1$H NMR (300 MHz, CHLOROFORM-d) δ ppm 0.94 (d, J=6.40 Hz, 6H) 1.26 (t, J=7.16 Hz, 1H) 1.44-1.81 (m, 3H) 2.36 (s, 3H) 4.69-4.73 (m, 1H) 6.61 (s, 1H) 7.32 (d, J=8.67 Hz, 2H) 7.54 (d, J=8.67 Hz, 2H)

(5) 4-{1-[5-(4-chlorophenyl)-2-methyl-3-furyl]-3-methylbutoxy}benzoic acid

An operation similar to that in Example 1 (3) was performed using 1-[5-(4-chlorophenyl)-2-methyl-3-furyl]-3-methylbutan-1-ol (335 mg) to give the title compound (243 mg, 50%) as an amorphous compound.

$^1$H NMR (300 MHz, CHLOROFORM-d) δ ppm 0.95 (d, J=6.63 Hz, 3H) 1.00 (d, J=6.63 Hz, 3H) 1.54-2.06 (m, 3H) 2.37 (s, 3H) 5.17-5.22 (m, 1H) 6.55 (s, 1H) 6.89 (d, J=8.71 Hz, 2H) 7.27 (d, J=8.71 Hz, 2H) 7.50 (d, J=8.33 Hz, 2H) 7.97 (d, J=9.09 Hz, 2H)

(6) 3-[(4-{1-[5-(4-chlorophenyl)-2-methyl-3-furyl]-3-methylbutoxy}benzoyl)amino]propanoic acid An operation similar to that in Example 1 (4) was performed using 4-{1-[5-(4-chlorophenyl)-2-methyl-3-furyl]-3-methylbutoxy}benzoic acid (128 mg) to give the title compound (112 mg, 79%) as a white crystal.

$^1$H NMR (300 MHz, DMSO-$d_6$) δ ppm 0.92 (d, J=5.84 Hz, 3H) 0.97 (d, J=5.84 Hz, 3H) 1.59-1.73 (m, 2H) 1.86-2.00 (m, 1H) 2.39 (s, 3H) 2.42-2.48 (m, 2H) 3.40 (d, J=5.65 Hz, 2H) 5.39 (brs, 1H) 6.91-7.02 (m, 3H) 7.42 (d, J=8.48 Hz, 2H) 7.62 (d, J=8.48 Hz, 2H) 7.73 (d, J=8.67 Hz, 2H) 8.13-8.43 (m, 1H) 12.19 (brs, 1H)

Example 26

3-[(4-{1-[5-(4-chlorophenyl)-2-methyl-3-furyl]-3-methylbutoxy}benzoyl)(methyl)amino]propanoic acid

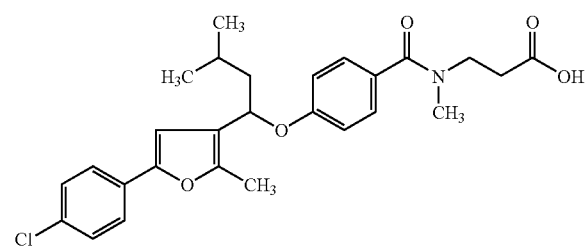

An operation similar to that in Example 1 (4) was performed using 4-{1-[5-(4-chlorophenyl)-2-methyl-3-furyl]-3-methylbutoxy}benzoic acid (128 mg) as well as ethyl 3-(methylamino)propanoate (47 mg) to give the title compound (124 mg, 86%) as an amorphous compound.

$^1$H NMR (300 MHz, DMSO-$d_6$) δ ppm 0.92 (d, J=6.22 Hz, 3H) 0.97 (d, J=6.22 Hz, 3H) 1.54-1.78 (m, 2H) 1.85-2.04 (m, 1H) 2.38 (s, 3H) 2.45-2.57 (m, 2H) 2.89 (s, 3H) 3.52 (brs, 2H) 5.29-5.42 (m, 1H) 6.93 (s, 1H) 6.97 (d, J=7.91 Hz, 2H) 7.28 (d, J=8.67 Hz, 2H) 7.42 (d, J=8.67 Hz, 2H) 7.63 (d, J=8.67 Hz, 2H)

Example 27

3-[(4-{[5-(4-chlorophenyl)-2-methyl-3-furyl](cyclohexyl)methoxy}benzoyl)amino]propanoic acid

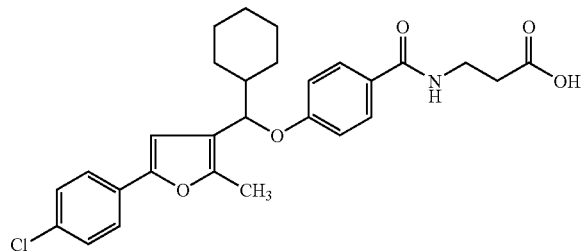

(1) [5-(4-chlorophenyl)-2-methyl-3-furyl](cyclohexyl)methanol

An operation similar to that in Example 3 (2) was performed using 5-(4-chlorophenyl)-2-methyl-3-furaldehyde (1.7 g) and 1N cyclohexylmagnesium bromide-tetrahydrofuran solution (15 mL) to give the title compound (2.0 g, 83%) as a white crystal.

$^1$H NMR (300 MHz, CHLOROFORM-d) δ ppm 0.85-1.30 (m, 5H) 1.50-1.81 (m, 5H) 2.04-2.10 (m, 1H) 2.32 (s, 3H) 4.30 (dd, J=7.82, 2.17 Hz, 1H) 6.58 (s, 1H) 7.32 (d, J=8.48 Hz, 2H) 7.54 (d, J=8.48 Hz, 2H)

(2) 4-{[5-(4-chlorophenyl)-2-methyl-3-furyl](cyclohexyl)methoxy}benzoic acid An operation similar to that in Example 1 (3) was performed using [5-(4-chlorophenyl)-2-methyl-3-furyl](cyclohexyl)methanol (366 mg) to give the title compound (257 mg, 50%) as an amorphous compound.

$^1$H NMR (300 MHz, CHLOROFORM-d) δ ppm 1.02-1.32 (m, 5H) 1.63-1.89 (m, 5H) 2.00-2.17 (m, 1H) 2.36 (s, 3H) 4.82 (d, J=7.16 Hz, 1H) 6.49 (s, 1H) 6.86 (d, J=6.97 Hz, 2H) 7.22-7.34 (m, 2H) 7.50 (d, J=6.78 Hz, 2H) 7.95 (d, J=9.04 Hz, 2H)

(3) 3-[(4-{[5-(4-chlorophenyl)-2-methyl-3-furyl](cyclohexyl)methoxy}benzoyl)amino]propanoic acid An operation similar to that in Example 1 (4) was performed using 4-{[5-(4-chlorophenyl)-2-methyl-3-furyl](cyclohexyl)methoxy}benzoic acid (120 mg) to give the title compound (131 mg, 88%) as a white crystal.

$^1$H NMR (300 MHz, DMSO-d$_6$) δ ppm 0.95-1.32 (m, 5H) 1.49-1.89 (m, 5H) 2.00-2.09 (m, 1H) 2.37 (s, 3H) 2.45 (t, J=7.25 Hz, 2H) 3.35-3.47 (m, 2H) 5.08 (d, J=7.54 Hz, 1H) 6.87 (s, 1H) 6.93 (d, J=8.85 Hz, 2H) 7.41 (d, J=8.48 Hz, 2H) 7.61 (d, J=8.48 Hz, 2H) 7.70 (d, J=8.85 Hz, 2H) 8.28 (t, J=5.46 Hz, 1H) 12.18 (brs, 1H)

Example 28

3-[(4-{[5-(4-chlorophenyl)-2-methyl-3-furyl](cyclohexyl)methoxy}benzoyl)(methyl)amino]propanoic acid

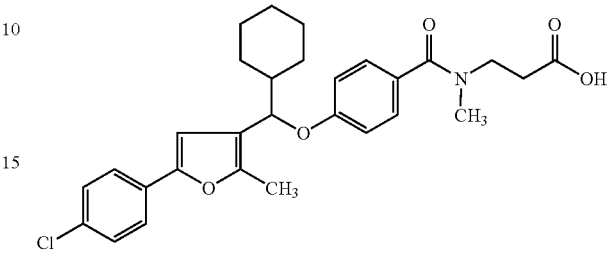

An operation similar to that in Example 1 (4) was performed using 4-{[5-(4-chlorophenyl)-2-methyl-3-furyl](cyclohexyl)methoxy}benzoic acid (120 mg) as well as ethyl 3-(methylamino)propanoate (47 mg) to give the title compound (143 mg, 93%) as an amorphous compound.

$^1$H NMR (300 MHz, DMSO-d$_6$) δ ppm 0.96-1.29 (m, 5H) 1.48-1.86 (m, 5H) 1.99-2.10 (m, 1H) 2.37 (s, 3H) 2.43-2.57 (m, 2H) 2.88 (s, 3H) 3.51 (brs, 2H) 5.02 (d, J=7.54 Hz, 1H) 6.83-6.96 (m, 3H) 7.26 (d, J=8.48 Hz, 2H) 7.41 (d, J=8.67 Hz, 2H) 7.62 (d, J=8.67 Hz, 2H)

Example 29

3-({4-[{2-ethyl-5-[4-(trifluoromethyl)phenyl]-3-furyl}(phenyl)methoxy]benzoyl}amino)propanoic acid

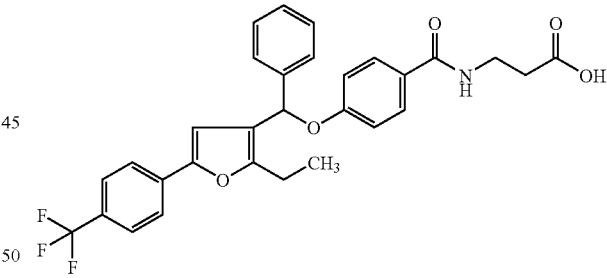

(1) {2-ethyl-5-[4-(trifluoromethyl)phenyl]-3-furyl}(phenyl)methanol

An operation similar to that in Example 3 (2) was performed using 2-ethyl-5-[4-(trifluoromethyl)phenyl]-3-furaldehyde (1.0 g) and 1N phenylmagnesium bromide-tetrahydrofuran solution (8.0 mL) to give the title compound (1.2 g, 87%) as a yellow crystal.

$^1$H NMR (300 MHz, CHLOROFORM-d) δ ppm 1.26 (t, J=7.16 Hz, 3H) 2.10 (brs, 1H) 2.77 (qd, J=7.54, 1.13 Hz, 2H) 5.83 (d, J=2.45 Hz, 1H) 6.63 (s, 1H) 7.18-7.34 (m, 2H) 7.34-7.49 (m, 3H) 7.57 (d, J=8.67 Hz, 2H) 7.67 (d, J=8.29 Hz, 2H)

(2) 4-[{2-ethyl-5-[4-(trifluoromethyl)phenyl]-3-furyl}(phenyl)methoxy]benzoic acid An operation similar to that in Example 1 (3) was performed using {2-ethyl-5-[4-(trifluoromethyl)phenyl]-3-furyl}(phenyl)methanol (346 mg) to give the title compound (239 mg, 52%) as a white crystal.

$^1$H NMR (300 MHz, CHLOROFORM-d) δ ppm 1.29 (t, J=7.57 Hz, 3H) 2.69-2.89 (m, 2H) 6.28 (s, 1H) 6.61 (s, 1H) 7.00 (d, J=8.71 Hz, 2H) 7.29-7.49 (m, 5H) 7.58 (d, J=8.33 Hz, 2H) 7.67 (d, J=8.33 Hz, 2H) 8.00 (d, J=9.09 Hz, 2H)

(3) 3-({4-[{2-ethyl-5-[4-(trifluoromethyl)phenyl]-3-furyl}(phenyl)methoxy]benzoyl}amino)propanoic acid An operation similar to that in Example 1 (4) was performed using 4-[{2-ethyl-5-[4-(trifluoromethyl)phenyl]-3-furyl}(phenyl)methoxy]benzoic acid (117 mg) to give the title compound (114 mg, 85%) as a white crystal.

$^1$H NMR (300 MHz, DMSO-$d_6$) δ ppm 1.18 (t, J=7.44 Hz, 3H) 2.37-2.55 (m, 2H) 2.81-2.92 (m, 2H) 3.35-3.47 (m, 2H) 6.63 (s, 1H) 7.09 (d, J=8.85 Hz, 2H) 7.12 (s, 1H) 7.29-7.47 (m, 3H) 7.54 (d, J=7.35 Hz, 2H) 7.63-7.79 (m, 4H) 7.83 (d, J=8.10 Hz, 2H) 8.33 (brs, 1H)

Example 30

3-[{4-[{2-ethyl-5-[4-(trifluoromethyl)phenyl]-3-furyl}(phenyl)methoxy]benzoyl}(methyl)amino]propanoic acid

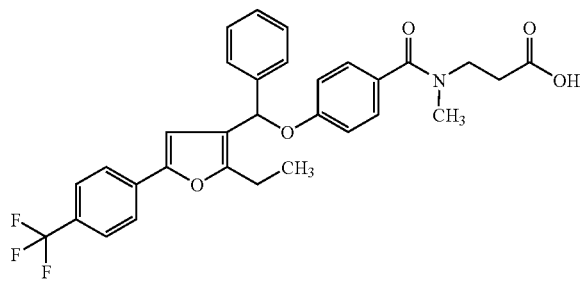

An operation similar to that in Example 1 (4) was performed using 4-[{2-ethyl-5-[4-(trifluoromethyl)phenyl]-3-furyl}(phenyl)methoxy]benzoic acid (117 mg) as well as ethyl 3-(methylamino)propanoate (39 mg) to give the title compound (117 mg, 98%) as an amorphous compound.

$^1$H NMR (300 MHz, DMSO-$d_6$) δ ppm 1.17 (t, J=7.54 Hz, 3H) 2.49-2.54 (m, 2H) 2.78-2.94 (m, 5H) 3.53 (brs, 2H) 6.58 (s, 1H) 7.06 (d, J=8.67 Hz, 2H) 7.12 (s, 1H) 7.24-7.34 (m, 2H) 7.39-7.42 (m, 3H) 7.55 (d, J=7.16 Hz, 2H) 7.71 (d, J=8.29 Hz, 2H) 7.84 (d, J=8.10 Hz, 2H)

Example 31

3-({4-[(3-methyl-1-{2-methyl-5-[4-(trifluoromethyl)phenyl]-3-furyl}butyl)amino]benzoyl}amino)propanoic acid

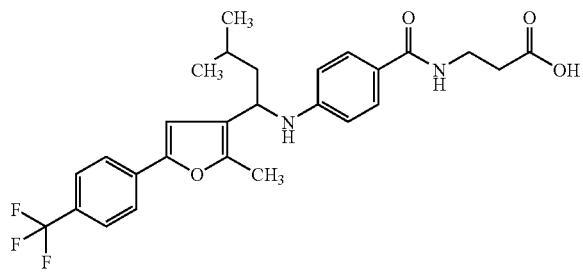

(1) 3-(1-chloro-3-methylbutyl)-2-methyl-5-[4-(trifluoromethyl)phenyl]furan

An operation similar to that in Example 9 (1) was performed using 3-methyl-1-{2-methyl-5-[4-(trifluoromethyl)phenyl]-3-furyl}butan-1-ol (781 mg) to give the title compound (827 mg, 100%) as an oil.

$^1$H NMR (300 MHz, CHLOROFORM-d) δ ppm 0.95 (d, J=6.50 Hz, 6H) 1.63-1.92 (m, 2H) 2.01-2.10 (m, 1H) 2.39 (s, 3H) 4.95 (t, J=7.63 Hz, 1H) 6.76 (s, 1H) 7.60 (d, J=8.29 Hz, 2H) 7.73 (d, J=8.10 Hz, 2H)

(2) 4-[(3-methyl-1-{2-methyl-5-[4-(trifluoromethyl)phenyl]-3-furyl}butyl)amino]benzoic acid An operation similar to that in Example 9 (2) was performed using 3-(1-chloro-3-methylbutyl)-2-methyl-5-[4-(trifluoromethyl)phenyl]furan (827 mg) to give the title compound (201 mg, 18%) as an amorphous compound.

$^1$H NMR (300 MHz, CHLOROFORM-d) δ ppm 0.94 (d, J=6.12 Hz, 3H) 1.00 (d, J=6.12 Hz, 3H) 1.58-1.84 (m, 3H) 2.42 (s, 3H) 4.41 (t, J=6.88 Hz, 1H) 6.53 (d, J=8.85 Hz, 2H) 6.62 (s, 1H) 7.58 (d, J=8.48 Hz, 2H) 7.67 (d, J=8.29 Hz, 2H) 7.87 (d, J=8.85 Hz, 2H)

(3) 3-({4-[(3-methyl-1-{2-methyl-5-[4-(trifluoromethyl)phenyl]-3-furyl}butyl)amino]benzoyl}amino)propanoic acid An operation similar to that in Example 1 (4) was performed using 4-[(3-methyl-1-{2-methyl-5-[4-(trifluoromethyl)phenyl]-3-furyl}butyl)amino]benzoic acid (129 mg) to give the title compound (126 mg, 83%) as an amorphous compound.

$^1$H NMR (300 MHz, DMSO-$d_6$) δ ppm 0.89 (d, 6.22 Hz, 3H) 0.95 (d, 6.22 Hz, 3H) 1.50-1.79 (m, 3H) 2.34-2.47 (m, 5H) 3.37 (q, J=5.84 Hz, 2H) 4.40 (d, J=7.35 Hz, 1H) 6.39 (d, J=7.54 Hz, 1H) 6.56 (d, J=8.85 Hz, 2H) 7.01 (s, 1H) 7.55 (d, J=8.67 Hz, 2H) 7.71 (d, J=8.60 Hz, 2H) 7.76 (d, J=8.60 Hz, 2H) 8.01 (t, J=5.37 Hz, 1H) 12.17 (brs, 1H)

Example 32

3-(methyl{4-[(3-methyl-1-{2-methyl-5-[4-(trifluoromethyl)phenyl]-3-furyl}butyl)amino]benzoyl}(methyl)amino)propanoic acid

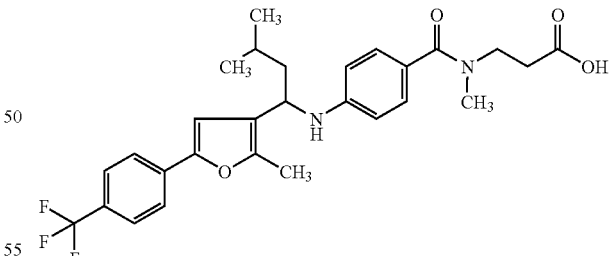

An operation similar to that in Example 1 (4) was performed using 4-[(3-methyl-1-{2-methyl-5-[4-(trifluoromethyl)phenyl]-3-furyl}butyl)amino]benzoic acid (129 mg) as well as ethyl 3-(methylamino)propanoate (37 mg) to give the title compound (128 mg, 83%) as an amorphous compound.

$^1$H NMR (300 MHz, DMSO-$d_6$) δ ppm 0.90 (d, J=6.40 Hz, 3H) 0.96 (d, J=6.40 Hz, 3H) 1.43-1.81 (m, 3H) 2.41 (s, 3H) 2.47-2.52 (m, 2H) 2.90 (s, 3H) 3.52 (t, J=7.25 Hz, 2H) 4.36 (q, J=7.35 Hz, 1H) 6.29 (d, J=7.54 Hz, 1H) 6.56 (d, J=8.48 Hz, 2H) 7.12 (d, J=8.48 Hz, 2H) 7.71 (d, J=8.48 Hz, 2H) 7.78 (d, J=8.29 Hz, 2H)

Example 33

3-({4-[(cyclohexyl{2-methyl-5-[4-(trifluoromethyl)phenyl]-3-furyl}methyl)amino]benzoyl}amino)propanoic acid

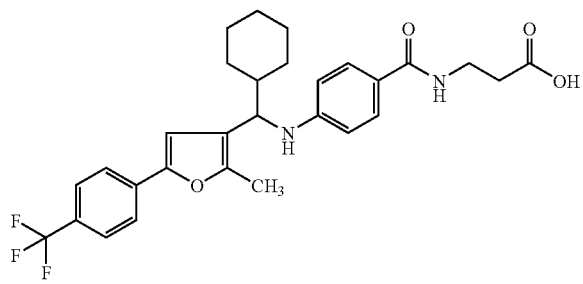

(1) 3-[chloro(cyclohexyl)methyl]-2-methyl-5-[4-(trifluoromethyl)phenyl]furan An operation similar to that in Example 9 (1) was performed using cyclohexyl{2-methyl-5-[4-(trifluoromethyl)phenyl]-3-furyl}methanol (1.3 g) to give the title compound (1.4 g, 100%) as a yellow crystal.

$^1$H NMR (300 MHz, CHLOROFORM-d) δ ppm 0.83-1.32 (m, 5H) 1.54-1.89 (m, 5H) 2.17-2.26 (m, 1H) 2.35 (s, 3H) 4.60 (d, J=8.67 Hz, 1H) 6.74 (s, 1H) 7.60 (d, J=8.29 Hz, 2H) 7.71 (d, J=8.10 Hz, 2H)

(2) 4-[(cyclohexyl{2-methyl-5-[4-(trifluoromethyl)phenyl]-3-furyl}methyl)amino]benzoic acid An operation similar to that in Example 9 (2) was performed using cyclohexyl{2-methyl-5-[4-(trifluoromethyl)phenyl]-3-furyl}methanol (1.4 g) to give the title compound (461 mg, 25%) as an amorphous compound.

$^1$H NMR (300 MHz, CHLOROFORM-d) δ ppm 0.99-1.31 (m, 5H) 1.59-1.83 (m, 5H) 1.94-2.00 (m, 1H) 2.40 (s, 3H) 4.12 (q, J=6.59 Hz, 1H) 6.50 (d, J=8.85 Hz, 2H) 6.56 (s, 1H) 7.56 (d, J=8.29 Hz, 2H) 7.66 (d, J=8.10 Hz, 2H) 7.84 (d, J=8.85 Hz, 2H)

(3) 3-({4-[(cyclohexyl{2-methyl-5-[4-(trifluoromethyl)phenyl]-3-furyl}methyl)amino]benzoyl}amino)propanoic acid An operation similar to that in Example 1 (4) was performed using 4-[(cyclohexyl{2-methyl-5-[4-s (trifluoromethyl)phenyl]-3-furyl}methyl)amino]benzoic acid (229 mg) to give the title compound (231 mg, 87%) as an amorphous compound.

$^1$H NMR (300 MHz, DMSO-d$_6$) δ ppm 0.89-1.27 (m, 5H) 1.53-1.79 (m, 5H) 1.99-2.01 (m, 1H) 2.43 (t, J=7.16 Hz, 2H) 2.40 (s, 3H) 3.37 (q, J=5.84 Hz, 2H) 4.14 (t, J=7.72 Hz, 1H) 6.36 (d, J=7.91 Hz, 1H) 6.56 (d, J=8.67 Hz, 2H) 6.95 (s, 1H) 7.53 (d, J=8.85 Hz, 2H) 7.70 (d, J=8.85 Hz, 2H) 7.75 (d, J=8.48 Hz, 2H) 7.99 (t, J=5.46 Hz, 1H) 12.15 (brs, 1H)

Example 34

3-[{4-[(cyclohexyl{2-ethyl-5-[4-(trifluoromethyl)phenyl]-3-furyl}methyl)amino]benzoyl}(methyl)amino]propanoic acid

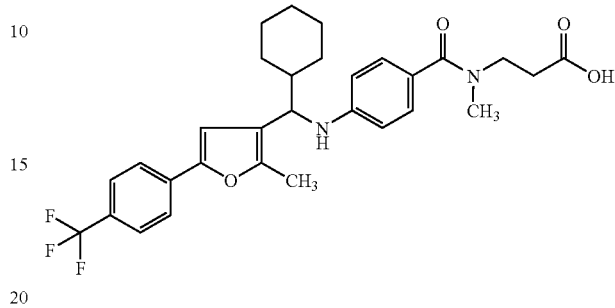

An operation similar to that in Example 1 (4) was performed using 4-[(cyclohexyl{2-methyl-5-[4-(trifluoromethyl)phenyl]-3-furyl}methyl)amino]benzoic acid (229 mg) as well as ethyl 3-(methylamino)propanoate (79 mg) to give the title compound (236 mg, 87%) as an amorphous compound.

$^1$H NMR (300 MHz, DMSO-d$_6$) δ ppm 0.90-1.31 (m, 5H) 1.52-1.76 (m, 5H) 1.96-2.10 (m, 1H) 2.40 (s, 3H) 2.48-2.52 (m, 2H) 2.90 (s, 3H) 3.52 (t, J=7.35 Hz, 2H) 4.10 (dt, J=9.04, 8.29 Hz, 1H) 6.26 (d, J=7.91 Hz, 1H) 6.56 (d, J=8.67 Hz, 2H) 6.97 (s, 1H) 7.11 (d, J=8.67 Hz, 2H) 7.71 (d, J=8.60 Hz, 2H) 7.76 (d, J=8.60 Hz, 2H)

Example 35

3-{[4-({[5-(4-chlorophenyl)-2-methyl-3-furyl](cyclohexyl)methyl}amino)benzoyl]amino}propanoic acid

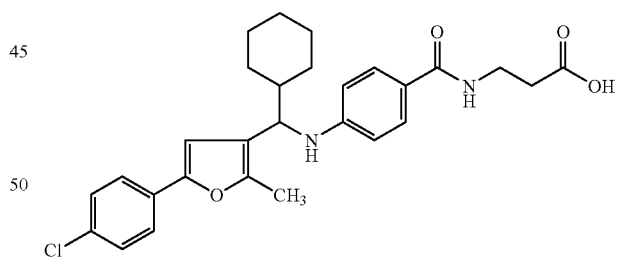

(1) 3-[chloro(cyclohexyl)methyl]-5-(4-chlorophenyl)-2-methylfuran

An operation similar to that in Example 9 (1) was performed using [5-(4-chlorophenyl)-2-methyl-3-furyl](cyclohexyl)methanol (1.2 g) to give the title compound (1.3 g, 100%) as an oil.

$^1$H NMR (300 MHz, CHLOROFORM-d) δ ppm 0.82-1.38 (m, 5H) 1.62-1.88 (m, 5H) 2.16-2.27 (m, 1H) 2.32 (s, 3H) 4.59 (d, J=8.48 Hz, 1H) 6.59 (s, 1H) 7.32 (d, J=8.85 Hz, 2H) 7.55 (d, J=8.67 Hz, 2H)

(2) 4-({[5-(4-chlorophenyl)-2-methyl-3-furyl](cyclohexyl)methyl}amino)benzoic acid An operation similar to that in Example 9 (2) was performed using 3-[chloro(cyclohexyl)methyl]-5-(4-chlorophenyl)-2-methylfuran (1.3 g) to give the title compound (0.9 g, 54%) as an amorphous compound.

$^1$H NMR (300 MHz, CHLOROFORM-d) δ ppm 0.97-1.30 (m, 5H) 1.57-1.85 (m, 5H) 1.95-2.00 (m, 1H) 2.37 (s, 3H) 4.09-4.16 (m, 1H) 6.43 (s, 1H) 6.50 (d, J=8.85 Hz, 2H) 7.14-7.37 (m, 2H) 7.50 (d, J=8.67 Hz, 2H) 7.84 (d, J=8.85 Hz, 2H)

(3) 3-{[4-({[5-(4-chlorophenyl)-2-methyl-3-furyl](cyclohexyl)methyl}amino)benzoyl]amino}propanoic acid An operation similar to that in Example 1 (4) was performed using 4-({[5-(4-chlorophenyl)-2-methyl-3-furyl](cyclohexyl)methyl}amino)benzoic acid (424 mg) to give the title compound (435 mg, 87%) as an amorphous compound.

$^1$H NMR (300 MHz, DMSO-d$_6$) δ ppm 0.90-1.24 (m, 5H) 1.52-1.77 (m, 5H) 1.99-2.06 (m, 1H) 2.36 (s, 3H) 2.43 (t, J=7.16 Hz, 2H) 3.37 (q, J=5.84 Hz, 2H) 4.09 (t, J=7.72 Hz, 1H) 6.34 (d, J=8.10 Hz, 1H) 6.55 (d, J=8.67 Hz, 2H) 6.78 (s, 1H) 7.41 (d, J=8.85 Hz, 2H) 7.52 (d, J=8.76 Hz, 2H) 7.56 (dd, J=8.76 Hz, 2H) 7.98 (t, J=5.46 Hz, 1H)

Example 36

3-{[4-({[5-(4-chlorophenyl)-2-methyl-3-furyl](cyclohexyl)methyl}amino)benzoyl](methyl)amino}propanoic acid

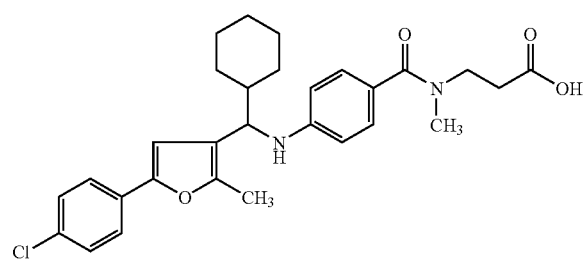

An operation similar to that in Example 1 (4) was performed using 4-({[5-(4-chlorophenyl)-2-methyl-3-furyl](cyclohexyl)methyl}amino)benzoic acid (424 mg) as well as ethyl 3-(methylamino)propanoate (157 mg) to give the title compound (461 mg, 90%) as an amorphous compound.

$^1$H NMR (300 MHz, DMSO-d$_6$) δ ppm 0.90-1.23 (m, 5H) 1.52-1.77 (m, 5H) 1.97-2.06 (m, 1H) 2.37 (s, 3H) 2.47-2.54 (m, 2H) 2.90 (s, 3H) 3.52 (t, J=7.25 Hz, 2H) 3.09-4.09 (m, 1H) 6.24 (d, J=7.91 Hz, 1H) 6.54 (d, J=8.67 Hz, 2H) 6.79 (s, 1H) 7.10 (d, J=8.48 Hz, 2H) 7.41 (d, J=8.67 Hz, 2H) 7.57 (d, J=8.67 Hz, 2H) 12.24 (brs, 1H)

Example 37

3-({4-[cyclohexyl(2-methyl-5-phenyl-3-furyl)methoxy]benzoyl}amino)propanoic acid

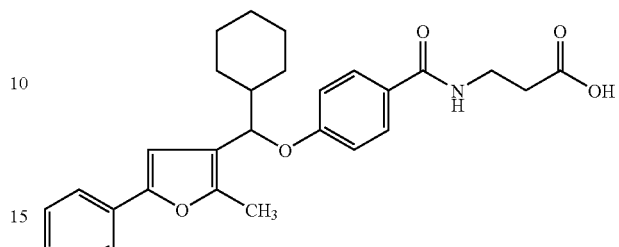

(1) ethyl 5-phenyl-2-methyl-3-furoate

An operation similar to that in Example 25 (1) was performed using 5-phenyl-2-methyl-3-furancarboxylic acid (4.0 g) to give the title compound (4.6 g, 100%) as an oil.

$^1$H NMR (300 MHz, CHLOROFORM-d) δ ppm 1.38 (t, J=7.00 Hz, 3H) 2.65 (s, 3H) 4.32 (q, J=7.07 Hz, 2H) 6.88 (s, 1H) 7.21-7.31 (m, 1H) 7.36-7.41 (m, 2H) 7.61-7.65 (m, 2H)

(2) (2-methyl-5-phenyl-3-furyl)methanol

An operation similar to that in Example 1 (2) was performed using ethyl 5-phenyl-2-methyl-3-furoate (5.0 g) to give the title compound (3.8 g, 90%) as a yellow crystal.

$^1$H NMR (300 MHz, CHLOROFORM-d) δ ppm 2.37 (s, 3H) 4.52 (s, 2H) 6.64 (s, 1H) 7.20-7.26 (m, 1H) 7.34-7.39 (m, 2H) 7.61-7.64 (m, 2H)

(3) 2-methyl-5-phenyl-3-furaldehyde

An operation similar to that in Example 17 (3) was performed using (2-methyl-5-phenyl-3-furyl)methanol (3.7 g) to give the title compound (2.6 g, 70%) as a white crystal.

$^1$H NMR (300 MHz, CHLOROFORM-d) δ ppm 2.68 (s, 3H) 6.91 (s, 1H) 7.27-7.35 (m, 1H) 7.38-7.43 (m, 2H) 7.65-7.68 (m, 2H) 9.97 (s, 1H)

(4) cyclohexyl(2-methyl-5-phenyl-3-furyl)methanol

In the same manner as in Example 3 (2), the title compound (1.4 g, 85%) was obtained as an oil from 2-methyl-5-phenyl-3-furaldehyde (2.6 g) and 1N cyclohexylmagnesium bromide-tetrahydrofuran solution (21 mL).

$^1$H NMR (300 MHz, CHLOROFORM-d) δ ppm 0.81-1.31 (m, 5H) 1.51-1.92 (m, 5H) 2.05-2.11 (m, 1H) 2.33 (s, 3H) 4.30 (dt, J=7.91, 3.01 Hz, 1H) 6.59 (s, 1H) 7.14-7.30 (m, 1H) 7.33-7.38 (m, 2H) 7.61-7.64 (m, 2H)

(5) 4-[cyclohexyl(2-methyl-5-phenyl-3-furyl)methoxy]benzoic acid

An operation similar to that in Example 1 (3) was performed using cyclohexyl(2-methyl-5-phenyl-3-furyl)methanol (406 mg) to give the title compound (273 mg, 47%) as an amorphous compound.

$^1$H NMR (300 MHz, CHLOROFORM-d) δ ppm 1.02-1.33 (m, 5H) 1.63-1.91 (m, 5H) 1.99-2.15 (m, 1H) 2.36 (s, 3H) 4.82 (d, J=7.35 Hz, 1H) 6.51 (s, 1H) 6.87 (d, J=9.04 Hz, 2H) 7.12-7.23 (m, 1H) 7.30-7.35 (m, 2H) 7.57-7.62 (m, 2H) 7.95 (d, J=8.85 Hz, 2H)

(6) 3-({4-[cyclohexyl(2-methyl-5-phenyl-3-furyl)methoxy]benzoyl}amino)propanoic acid An operation similar to that in Example 1 (4) was performed using 4-[cyclohexyl(2-methyl-5-phenyl-3-furyl)methoxy]benzoic acid (137 mg) to give the title compound (149 mg, 92%) as an amorphous compound.

$^1$H NMR (300 MHz, DMSO-$d_6$) δ ppm 0.96-1.29 (m, 5H) 1.51-1.91 (m, 5H) 2.02-2.06 (m, 1H) 2.37 (s, 3H) 2.43 (t, J=7.00 Hz, 2H) 3.39 (q, J=5.68 Hz, 2H) 5.08 (d, J=7.19 Hz, 1H) 6.80 (s, 1H) 6.93 (d, J=8.71 Hz, 2H) 7.19-7.25 (m, 1H) 7.33-7.38 (m, 2H) 7.58-7.61 (m, 2H) 7.71 (d, J=8.71 Hz, 2H) 8.30 (t, J=5.11 Hz, 1H)

Example 38

3-[{4-[(cyclohexyl{2-methyl-5-[4-(trifluoromethyl)phenyl]-3-furyl}methyl)amino]benzoyl}(methyl)amino]propanoic acid

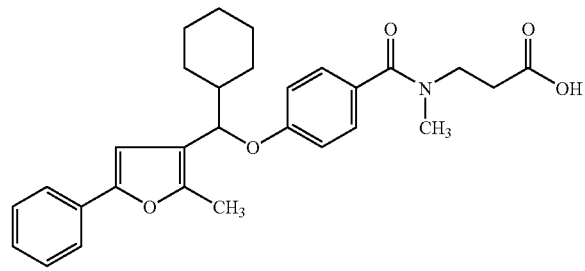

An operation similar to that in Example 1 (4) was performed using 4-[cyclohexyl(2-methyl-5-phenyl-3-furyl)methoxy]benzoic acid (137 mg) as well as ethyl 3-(methylamino)propanoate (55 mg) to give the title compound (147 mg, 88%) as an amorphous compound.

$^1$H NMR (300 MHz, DMSO-$d_6$) δ ppm 0.94-1.26 (m, 5H) 1.47-1.88 (m, 5H) 1.98-2.21 (m, 1H) 2.37 (s, 3H) 2.41-2.56 (m, 2H) 2.88 (s, 3H) 3.50 (brs, 2H) 5.02 (d, J=6.06 Hz, 1H) 6.82 (s, 1H) 6.91 (d, J=7.19 Hz, 2H) 7.16-7.44 (m, 5H) 7.61 (d, J=6.82 Hz, 2H)

Example 39

3-[(4-{[cyclohexyl(2-methyl-5-phenyl-3-furyl)methyl]amino}benzoyl)amino]propanoic acid

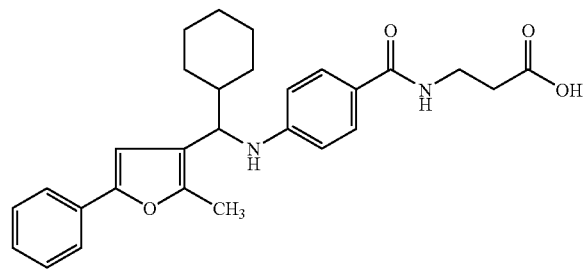

(1) 3-[chloro(cyclohexyl)methyl]-5-phenyl-2-methylfuran

An operation similar to that in Example 9 (1) was performed using cyclohexyl(2-methyl-5-phenyl-3-furyl)methanol (1.6 g) to give the title compound (1.5 g, 85%) as an oil.

$^1$H NMR (300 MHz, CHLOROFORM-d) δ ppm 0.88-1.32 (m, 5H) 1.57-1.89 (m, 5H) 2.19-2.24 (m, 1H) 2.36 (s, 3H) 4.61 (d, J=8.48 Hz, 1H) 6.60 (s, 1H) 7.07-7.38 (m, 7H) 7.63 (d, J=8.48 Hz, 2H)

(2) 4-{[cyclohexyl(2-methyl-5-phenyl-3-furyl)methyl]amino}benzoic acid

An operation similar to that in Example 9 (2) was performed using 3-[chloro(cyclohexyl)methyl]-5-phenyl-2-methylfuran (1.4 g) to give the title compound (0.6 g, 36%) as an amorphous compound.

$^1$H NMR (300 MHz, CHLOROFORM-d) δ ppm 0.96-1.28 (m, 5H) 1.53-1.85 (m, 5H) 1.92-2.01 (m, 1H) 2.38 (s, 3H) 4.12 (q, J=6.94 Hz, 1H) 6.45 (s, 1H) 6.51 (d, J=8.71 Hz, 2H) 7.16-7.21 (m, 1H) 7.30-7.35 (m, 2H) 7.57-7.59 (m, 2H) 7.84 (d, J=8.71 Hz, 2H)

(3) 3-[(4-{[cyclohexyl(2-methyl-5-phenyl-3-furyl)methyl]amino}benzoyl)amino]propanoic acid An operation similar to that in Example 1 (4) was performed using 4-{[cyclohexyl(2-methyl-5-phenyl-3-furyl)methyl]amino}benzoic acid (312 mg) to give the title compound (319 mg, 88%) as an amorphous compound.

$^1$H NMR (300 MHz, DMSO-$d_6$) δ ppm 0.93-1.33 (m, 5H) 1.54-1.76 (m, 5H) 1.98-2.06 (m, 1H) 2.36 (s, 3H) 2.39 (t, J=6.82 Hz, 2H) 3.35 (q, J=6.56 Hz, 2H) 4.10 (t, J=7.95 Hz, 1H) 6.33 (d, J=8.33 Hz, 1H) 6.55 (d, J=9.09 Hz, 2H) 6.73 (s, 1H) 7.19-7.24 (m, 1H) 7.33-7.39 (m, 2H) 7.50-7.56 (m, 4H) 8.01 (brs, 1H)

Example 40

3-[{4-[(cyclohexyl{2-ethyl-5-[4-(trifluoromethyl)phenyl]-3-furyl}methyl)amino]benzoyl}(methyl)amino]propanoic acid

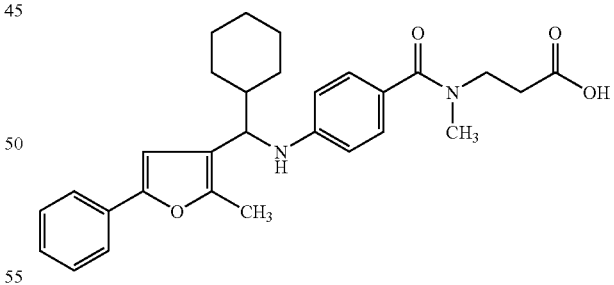

An operation similar to that in Example 1 (4) was performed using 4-{[cyclohexyl(2-methyl-5-phenyl-3-furyl)methyl]amino}benzoic acid (312 mg) as well as ethyl 3-(methylamino)propanoate (126 mg) to give the title compound (301 mg, 79%) as an amorphous compound.

$^1$H NMR (300 MHz, DMSO-$d_6$) δ ppm 0.93-1.25 (m, 5H) 1.53-1.75 (m, 5H) 2.02-2.09 (m, 1H) 2.37 (s, 3H) 2.45 (t, J=7.38 Hz, 2H) 2.89 (s, 3H) 3.50 (t, J=7.38 Hz, 2H) 4.06 (t, J=7.57 Hz, 1H) 6.23 (d, J=7.95 Hz, 1H) 6.55 (d, J=8.71 Hz, 2H) 6.74 (s, 1H) 7.10 (d, J=8.71 Hz, 2H) 7.19-7.24 (m, 1H) 7.34-7.39 (m, 2H) 7.55-7.57 (m, 2H)

Example 41

3-[(4-{cyclohexyl[5-(4-fluorophenyl)-2-methyl-3-furyl]methoxy}benzoyl)amino]propanoic acid

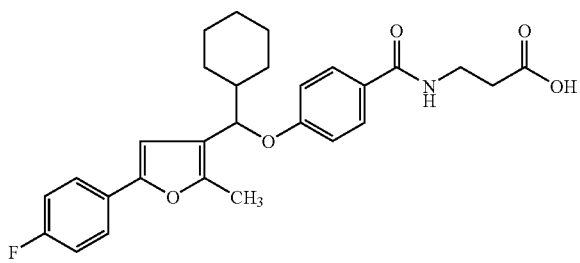

(1) methyl 5-(4-fluorophenyl)-2-methyl-3-furoate

An operation similar to that in Example 1 (1) was performed using 2-chloro-4'-fluoroacetophenone (13.4 g) and methyl acetoacetate (8.6 g) to give the title compound (7.4 g, 63%) as a yellow crystal.
$^1$H NMR (300 MHz, CHLOROFORM-d) δ ppm 2.64 (s, 3H) 3.85 (s, 3H) 6.81 (s, 1H) 7.03-7.12 (m, 2H) 7.57-7.63 (m, 2H)

(2) [5-(4-fluorophenyl)-2-methyl-3-furyl]methanol

An operation similar to that in Example 1 (2) was performed using methyl 5-(4-fluorophenyl)-2-methyl-3-furoate (7.4 g) to give the title compound (5.2 g, 80%) as a white crystal.
$^1$H NMR (300 MHz, CHLOROFORM-d) δ ppm 2.36 (s, 3H) 4.51 (d, J=4.92 Hz, 2H) 7.01-7.09 (m, 2H) 7.55-7.62 (m, 2H)

(3) 5-(4-fluorophenyl)-2-methyl-3-furaldehyde

An operation similar to that in Example 17 (3) was performed using [5-(4-fluorophenyl)-2-methyl-3-furyl]methanol (5.1 g) to give the title compound (2.1 g, 40%) as a yellow crystal.
$^1$H NMR (300 MHz, CHLOROFORM-d) δ ppm 2.67 (s, 3H) 6.84 (s, 1H) 7.06-7.14 (m, 2H) 7.60-7.66 (m, 2H) 9.96 (s, 1H)

(4) cyclohexyl[5-(4-fluorophenyl)-2-methyl-3-furyl]methanol

An operation similar to that in Example 3 (2) was performed using 5-(4-fluorophenyl)-2-methyl-3-furaldehyde (2.0 g) and 1N cyclohexylmagnesium bromide-tetrahydrofuran solution (15 mL) to give the title compound (2.4 g, 83%) as a white crystal.
$^1$H NMR (300 MHz, CHLOROFORM-d) δ ppm 0.85-1.36 (m, 5H) 1.50-1.91 (m, 5H) 2.05-2.13 (m, 1H) 2.32 (s, 3H) 4.29 (dd, J=3.41 Hz, 1H) 6.52 (s, 1H) 6.98-7.10 (m, 2H) 7.56-7.61 (m, 2H)

(5) 4-{cyclohexyl[5-(4-fluorophenyl)-2-methyl-3-furyl]methoxy}benzoic acid

An operation similar to that in Example 1 (3) was performed using cyclohexyl[5-(4-fluorophenyl)-2-methyl-3-furyl]methanol (577 mg) to give the title compound (330 mg, 40%) as an amorphous compound.
$^1$H NMR (300 MHz, CHLOROFORM-d) δ ppm 1.01-1.32 (m, 5H) 1.62-1.91 (m, 5H) 2.05-2.11 (m, 1H) 2.35 (s, 3H) 4.81 (d, J=7.16 Hz, 1H) 6.43 (s, 1H) 6.87 (d, J=9.04 Hz, 2H) 6.99-7.05 (m, 2H) 7.52-7.56 (m, 2H) 7.95 (d, J=8.85 Hz, 2H)

(6) 3-[(4-{cyclohexyl[5-(4-fluorophenyl)-2-methyl-3-furyl]methoxy}benzoyl)amino]propanoic acid An operation similar to that in Example 1 (4) was performed using 4-{cyclohexyl[5-(4-fluorophenyl)-2-methyl-3-furyl]methoxy}benzoic acid (163 mg) to give the title compound (159 mg, 83%) as an amorphous compound.
$^1$H NMR (300 MHz, DMSO-$d_6$) δ ppm 0.96-1.27 (m, 5H) 1.49-1.90 (m, 5H) 1.99-2.09 (m, 1H) 2.37 (s, 3H) 2.43 (t, J=6.97 Hz, 2H) 3.39 (q, J=5.65 Hz, 2H) 5.07 (d, J=7.54 Hz, 1H) 6.79 (s, 1H) 6.93 (d, J=8.67 Hz, 2H) 7.17-7.22 (m, 2H) 7.61-7.64 (m, 2H) 7.71 (d, J=8.67 Hz, 2H) 8.30 (brs, 1H)

Example 42

3-[(4-{cyclohexyl[5-(4-fluorophenyl)-2-methyl-3-furyl]methoxy}benzoyl)(methyl)amino]propanoic acid

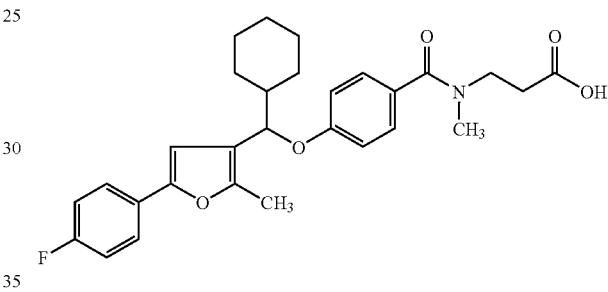

An operation similar to that in Example 1 (4) was performed using 4-{cyclohexyl[5-(4-fluorophenyl)-2-methyl-3-furyl]methoxy}benzoic acid (163 mg) as well as ethyl 3-(methylamino)propanoate (63 mg) to give the title compound (161 mg, 82%) as an amorphous compound.
$^1$H NMR (300 MHz, DMSO-$d_6$) δ ppm 0.99-1.29 (m, 5H) 1.48-1.87 (m, 5H) 1.99-2.13 (m, 1H) 2.36 (s, 3H) 2.47-2.55 (m, 2H) 2.88 (s, 3H) 3.50 (brs, 2H) 5.00 (brs, 1H) 6.80 (s, 1H) 6.86-6.94 (m, 2H) 7.17-7.28 (m, 4H) 7.60-7.67 (m, 2H)

Example 43

3-[(4-{cyclohexyl[5-(2,4-difluorophenyl)-2-methyl-3-furyl]methoxy}benzoyl)amino]propanoic acid

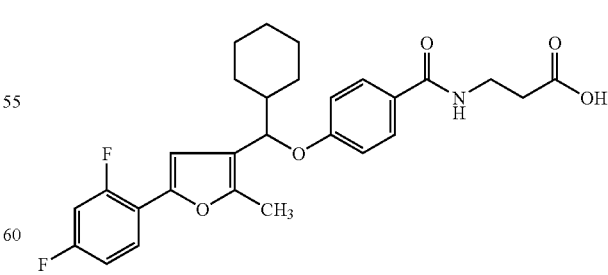

(1) methyl 5-(2,4-difluorophenyl)-2-methyl-3-furoate

An operation similar to that in Example 1 (1) was performed using 2-chloro-2',4'-difluorophenylacetophenone (19 g) and methyl acetoacetate (11 g) to give the title compound (10.3 g, 41%) as a yellow crystal.

¹H NMR (300 MHz, CHLOROFORM-d) δ ppm 2.66 (s, 3H) 3.86 (s, 3H) 6.81-7.02 (m, 3H) 7.60-7.95 (m, 1H)

(2) [5-(2,4-difluorophenyl)-2-methyl-3-furyl]methanol

An operation similar to that in Example 1 (2) was performed using methyl 5-(2,4-difluorophenyl)-2-methyl-3-furoate (10 g) to give the title compound (7.0 g, 78%) as a white crystal.

¹H NMR (300 MHz, CHLOROFORM-d) δ ppm 2.37 (s, 3H) 4.52 (d, J=5.46 Hz, 2H) 6.76 (d, J=3.77 Hz, 1H) 6.80-7.00 (m, 2H) 7.71-7.78 (m, 1H)

(3) 5-(2,4-difluorophenyl)-2-methyl-3-furaldehyde

An operation similar to that in Example 17 (3) was performed using [5-(2,4-difluorophenyl)-2-methyl-3-furyl]methanol (6.0 g) to give the title compound (2.5 g, 36%) as a yellow crystal.

¹H NMR (300 MHz, CHLOROFORM-d) δ ppm 2.68 (s, 3H) 6.81-7.00 (m, 2H) 7.04 (d, J=3.41 Hz, 1H) 7.72-7.80 (m, 1H) 9.98 (s, 1H)

(4) cyclohexyl[5-(2,4-difluorophenyl)-2-methyl-3-furyl]methanol

An operation similar to that in Example 3 (2) was performed using 5-(2,4-difluorophenyl)-2-methyl-3-furaldehyde (2.4 g) and 1N cyclohexylmagnesium bromide-tetrahydrofuran solution (16.5 mL) to give the title compound (2.6 g, 76%) as a white crystal.

¹H NMR (300 MHz, CHLOROFORM-d) δ ppm 0.86-1.31 (m, 5H) 1.48-1.82 (m, 5H) 2.05-2.12 (m, 1H) 2.33 (s, 3H) 4.30 (dd, J=7.72, 2.83 Hz, 1H) 6.71 (d, J=3.77 Hz, 1H) 6.80-6.99 (m, 2H) 7.70-7.78 (m, 1H)

(5) 4-{cyclohexyl[5-(2,4-difluorophenyl)-2-methyl-3-furyl]methoxy}benzoic acid An operation similar to that in Example 1 (3) was performed using cyclohexyl[5-(2,4-difluorophenyl)-2-methyl-3-furyl]methanol (613 mg) to give the title compound (472 mg, 55%) as an amorphous compound.

¹H NMR (300 MHz, CHLOROFORM-d) δ ppm 1.02-1.34 (m, 5H) 1.44-1.90 (m, 5H) 2.05-2.15 (m, 1H) 2.35 (s, 3H) 4.83 (d, J=7.35 Hz, 1H) 6.63 (d, J=3.77 Hz, 1H) 6.84-6.92 (m, 4H) 7.66-7.74 (m, 1H) 7.95 (d, J=6.97 Hz, 2H)

(6) 3-[(4-{cyclohexyl[5-(2,4-difluorophenyl)-2-methyl-3-furyl]methoxy}benzoyl)amino]propanoic acid An operation similar to that in Example 1 (4) was performed using 4-{cyclohexyl[5-(2,4-difluorophenyl)-2-methyl-3-furyl]methoxy}benzoic acid (235 mg) to give the title compound (272 mg, 99%) as an amorphous compound.

¹H NMR (300 MHz, DMSO-d₆) δ ppm 0.97-1.30 (m, 5H) 1.54-1.86 (m, 5H) 2.01-2.05 (m, 1H) 2.29-2.47 (m, 5H) 3.32-3.52 (m, 2H) 5.13 (d, J=7.19 Hz, 1H) 6.67 (d, J=3.79 Hz, 1H) 6.94 (d, J=8.71 Hz, 2H) 7.14 (td, J=8.52, 2.27 Hz, 1H) 7.34 (ddd, J=11.64, 9.18, 2.65 Hz, 1H) 7.60-7.80 (m, 3H) 8.32 (t, J=5.30 Hz, 1H)

Example 44

3-[(4-{cyclohexyl[5-(2,4-difluorophenyl)-2-methyl-3-furyl]methoxy}benzoyl)(methyl)amino]propanoic acid

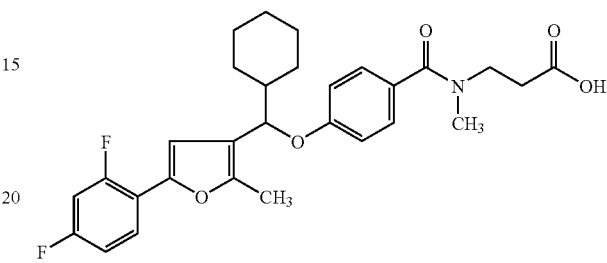

An operation similar to that in Example 1 (4) was performed using 4-{cyclohexyl[5-(2,4-difluorophenyl)-2-methyl-3-furyl]methoxy}benzoic acid (235 mg) as well as ethyl 3-(methylamino)propanoate (86 mg) to give the title compound (267 mg, 95%) as an amorphous compound.

¹H NMR (300 MHz, DMSO-d₆) δ ppm 0.97-1.29 (m, 5H) 1.51-1.92 (m, 5H) 2.01-2.05 (m, 1H) 2.38 (s, 3H) 2.45 (brs, 2H) 2.88 (s, 3H) 3.49 (brs, 2H) 5.07 (d, J=7.57 Hz, 1H) 6.68 (d, J=3.79 Hz, 1H) 6.91 (d, J=8.71 Hz, 2H) 7.14 (td, J=8.61, 2.46 Hz, 1H) 7.26 (d, J=8.33 Hz, 2H) 7.34 (ddd, J=11.74, 9.28, 2.46 Hz, 1H) 7.73 (td, J=8.80, 6.63 Hz, 1H)

Example 45

3-{[4-({cyclohexyl[5-(4-fluorophenyl)-2-methyl-3-furyl]methyl}amino)benzoyl]amino}propanoic acid

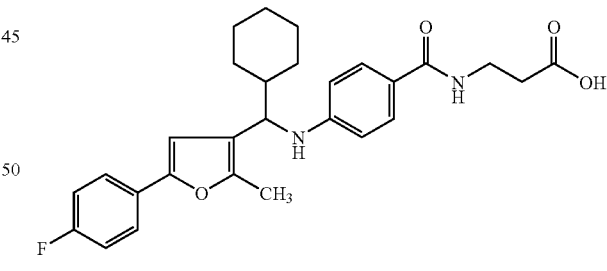

(1) 3-[chloro(cyclohexyl)methyl]-5-(4-fluorophenyl)-2-methylfuran

An operation similar to that in Example 9 (1) was performed using cyclohexyl[5-(4-fluorophenyl)-2-methyl-3-furyl]methanol (1.7 g) to give the title compound (1.5 g, 85%) as an oil.

¹H NMR (300 MHz, CHLOROFORM-d) δ ppm 0.88-1.32 (m, 5H) 1.64-1.85 (m, 5H) 2.18-2.24 (m, 1H) 2.32 (s, 3H) 4.60 (d, J=8.67 Hz, 1H) 6.55 (s, 1H) 6.95-7.11 (m, 2H) 7.56-7.62 (m, 2H)

(2) 4-({cyclohexyl[5-(4-fluorophenyl)-2-methyl-3-furyl]methyl}amino)benzoic acid An operation similar to that in Example 9 (2) was performed using 3-[chloro(cyclohexyl)methyl]-5-(4-fluorophenyl)-2-methylfuran (1.5 g) to give the title compound (0.7 g, 35%) as an amorphous compound.

$^1$H NMR (300 MHz, CHLOROFORM-d) δ ppm 1.00-1.28 (m, 5H) 1.62-1.74 (m, 5H) 1.92-1.99 (m, 1H) 2.37 (s, 3H) 4.11 (t, J=7.00 Hz, 1H) 6.37 (s, 1H) 6.50 (d, J=8.71 Hz, 2H) 6.99-7.05 (m, 2H) 7.52-7.61 (m, 2H) 7.84 (d, J=8.71 Hz, 2H)

(3) 3-{[4-({cyclohexyl[5-(4-fluorophenyl)-2-methyl-3-furyl]methyl}amino)benzoyl]amino}propanoic acid An operation similar to that in Example 1 (4) was performed using 4-({cyclohexyl[5-(4-fluorophenyl)-2-methyl-3-furyl]methyl}amino)benzoic acid (346 mg) to give the title compound (347 mg, 88%) as an amorphous compound.

$^1$H NMR (300 MHz, DMSO-$d_6$) δ ppm 0.91-1.28 (m, 5H) 1.52-1.75 (m, 5H) 1.95-2.08 (m, 1H) 2.36 (s, 3H) 2.42 (t, J=7.06 Hz, 2H) 3.24-3.52 (m, 2H) 4.09 (t, J=7.63 Hz, 1H) 6.33 (d, J=7.91 Hz, 1H) 6.55 (d, J=8.67 Hz, 2H) 6.70 (s, 1H) 7.17-7.23 (m, 2H) 7.45-7.61 (m, 4H) 8.00 (brs, 1H)

Example 46

3-{[4-({cyclohexyl[5-(4-fluorophenyl)-2-methyl-3-furyl]methyl}amino)benzoyl](methyl)amino}propanoic acid

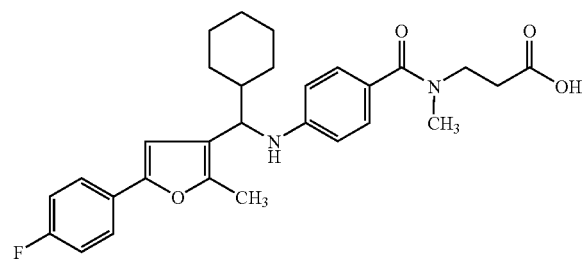

An operation similar to that in Example 1 (4) was performed using 4-({cyclohexyl[5-(4-fluorophenyl)-2-methyl-3-furyl]methyl}amino)benzoic acid (346 mg) as well as ethyl 3-(methylamino)propanoate (131 mg) to give the title compound (378 mg, 90%) as an amorphous compound.

$^1$H NMR (300 MHz, DMSO-$d_6$) δ ppm 0.91-1.26 (m, 5H) 1.55-1.76 (m, 5H) 2.01-2.05 (m, 1H) 2.36 (s, 3H) 2.41-2.47 (m, 2H) 2.89 (s, 3H) 3.50 (brs, 2H) 4.05 (brs, 1H) 6.23 (d, J=7.72 Hz, 1H) 6.54 (d, J=8.48 Hz, 2H) 6.71 (s, 1H) 7.10 (d, J=8.48 Hz, 2H) 7.17-7.22 (m, 2H) 7.57-7.61 (m, 2H)

Example 47

3-{[4-({cyclohexyl[5-(2,4-difluorophenyl)-2-methyl-3-furyl]methyl}amino)benzoyl]amino}propanoic acid

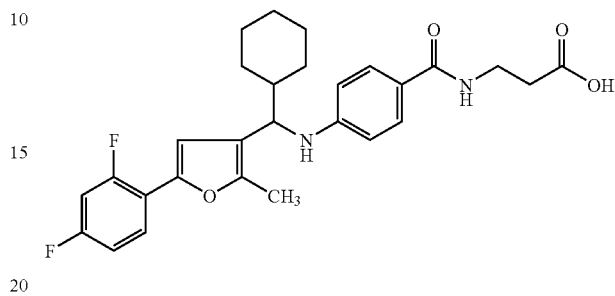

(1) 3-[chloro(cyclohexyl)methyl]-5-(2,4-difluorophenyl)-2-methylfuran

An operation similar to that in Example 9 (1) was performed using cyclohexyl[5-(2,4-difluorophenyl)-2-methyl-3-furyl]methanol (1.8 g) to give the title compound (1.6 g, 84%) as a yellow crystal.

$^1$H NMR (300 MHz, CHLOROFORM-d) δ ppm 0.84-1.37 (m, 5H) 1.63-1.91 (m, 5H) 2.21-2.25 (m, 1H) 2.43 (s, 3H) 4.61 (d, J=8.71 Hz, 1H) 6.75 (d, J=3.79 Hz, 1H) 6.80-7.00 (m, 2H) 7.66-7.83 (m, 1H)

(2) 4-({cyclohexyl[5-(2,4-difluorophenyl)-2-methyl-3-furyl]methyl}amino)benzoic acid An operation similar to that in Example 9 (2) was performed using 3-[chloro(cyclohexyl)methyl]-5-(2,4-difluorophenyl)-2-methylfuran (1.6 g) to give the title compound (1.4 g, 65%) as an amorphous compound.

$^1$H NMR (300 MHz, CHLOROFORM-d) δ ppm 0.97-1.32 (m, 5H) 1.61-1.84 (m, 5H) 1.95-2.00 (m, 1H) 2.37 (s, 3H) 4.09-4.16 (m, 1H) 6.50 (d, J=8.85 Hz, 2H) 6.57 (d, J=3.77 Hz, 1H) 6.79-6.92 (m, 2H) 7.68-7.76 (m, 1H) 7.84 (d, J=8.85 Hz, 2H).

(3) 3-{[4-({cyclohexyl[5-(2,4-difluorophenyl)-2-methyl-3-furyl]methyl}amino)benzoyl]amino}propanoic acid An operation similar to that in Example 1 (4) was performed using 4-({cyclohexyl[5-(2,4-difluorophenyl)-2-methyl-3-furyl]methyl}amino)benzoic acid (511 mg) to give the title compound (401 mg, 68%) as an amorphous compound.

$^1$H NMR (300 MHz, DMSO-$d_6$) δ ppm 0.92-1.25 (m, 5H) 1.53-1.76 (m, 5H) 2.01-2.06 (m, 1H) 2.31-2.45 (m, 5H) 3.36 (q, J=6.03 Hz, 2H) 4.13 (brs, 1H) 6.40 (d, J=8.67 Hz, 1H) 6.55 (d, J=8.85 Hz, 2H) 6.71 (d, J=3.77 Hz, 1H) 7.10-7.16 (m, 1H) 7.32-7.36 (m, 1H) 7.52 (d, J=8.48 Hz, 2H) 7.69-7.75 (m, 1H) 8.01 (brs, 1H)

Example 48

3-{[4-({cyclohexyl[5-(2,4-difluorophenyl)-2-methyl-3-furyl]methyl}amino)benzoyl](methyl)amino}propanoic acid

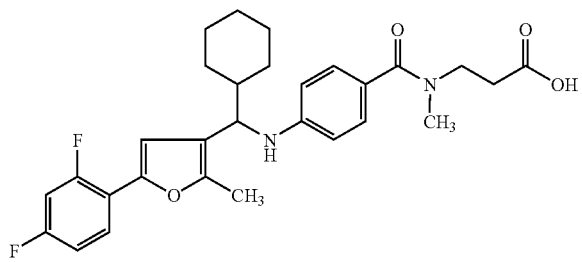

An operation similar to that in Example 1 (4) was performed using 4-({cyclohexyl[5-(2,4-difluorophenyl)-2-methyl-3-furyl]methyl}amino)benzoic acid (511 mg) as well as ethyl 3-(methylamino)propanoate (197 mg) to give the title compound (464 mg, 76%) as an amorphous compound.

$^1$H NMR (300 MHz, DMSO-d$_6$) δ ppm 0.92-1.26 (m, 5H) 1.52-1.77 (m, 5H) 2.01-2.07 (m, 1H) 2.38 (s, 3H) 2.45-2.51 (m, 2H) 2.90 (s, 3H) 3.51 (t, J=7.35 Hz, 2H) 4.09 (brs, 1H) 6.30 (d, J=8.48 Hz, 1H) 6.54 (d, J=8.67 Hz, 2H) 6.72 (d, J=3.77 Hz, 1H) 7.10 (d, J=8.48 Hz, 2H) 7.11-7.17 (m, 1H) 7.32-7.36 (m, 1H) 7.67-7.75 (m, 1H)

Example 49

3-{[4-(cyclohexyl{2-ethyl-5-[4-(trifluoromethoxy)phenyl]-3-furyl}methoxy)benzoyl]amino}propanoic acid

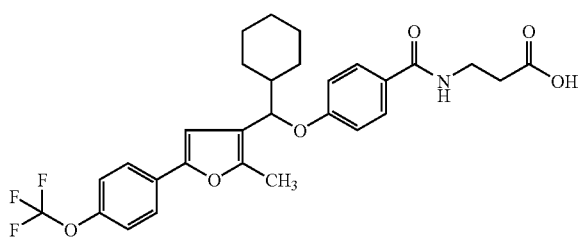

(1) methyl 5-bromo-2-methyl-3-furoate

To a solution of methyl 2-methyl-3-furoate (7.0 g) in N,N-dimethylformamide (50 mL) was added N-bromosuccinimide (10.7 g) over 45 min under ice-cooling, and the mixture was stirred under ice-cooling for 30 min and at room temperature overnight. The reaction mixture was poured into water, and the mixture was extracted with ethyl acetate. The organic layer was collected, and dried over magnesium sulfate. The solvent was evaporated under reduced pressure. The residue was purified by silica gel chromatography (0% ethyl acetate/hexane to 5% ethyl acetate/hexane) to give the title compound (7.9 g, 72%) as an oil.

$^1$H NMR (300 MHz, CHLOROFORM-d) δ ppm 2.56 (s, 3H) 3.82 (s, 2H) 6.55 (s, 1H)

(2) methyl 2-methyl-5-[4-(trifluoromethoxy)phenyl]-3-furoate

A mixture of methyl 5-bromo-2-methyl-3-furoate (2.2 g) obtained by the above-mentioned reaction, 4-(trifluoromethoxy)phenylboronic acid (2.5 g), tetrakis(triphenylphosphine)palladium(0) (0.58 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 12% ethyl acetate/hexane), and crystallized from ethyl acetate/hexane to give the title compound (2.5 g, 84%) as a white solid.

$^1$H NMR (300 MHz, CHLOROFORM-d) δ ppm 2.65 (s, 3H) 3.86 (s, 3H) 6.88 (s, 1H) 7.23 (d, J=9.09 Hz, 2H) 7.65 (d, J=9.09 Hz, 2H)

(3) {2-methyl-5-[4-(trifluoromethoxy)phenyl]-3-furyl}methanol

An operation similar to that in Example 1 (2) was performed using methyl 2-methyl-5-[4-(trifluoromethoxy)phenyl]-3-furoate (2.5 g) to give the title compound (2.3 g, 100%) as an oil.

$^1$H NMR (300 MHz, CHLOROFORM-d) δ ppm 2.37 (s, 3H) 4.52 (s, 2H) 6.64 (s, 1H) 7.20 (d, J=8.10 Hz, 2H) 7.62 (d, J=8.85 Hz, 2H)

(4) 2-methyl-5-[4-(trifluoromethoxy)phenyl]-3-furaldehyde

An operation similar to that in Example 17 (3) was performed using {2-methyl-5-[4-(trifluoromethoxy)phenyl]-3-furyl}methanol (2.3 g) to give the title compound (1.4 g, 63%) as a yellow crystal.

$^1$H NMR (300 MHz, CHLOROFORM-d) δ ppm 2.68 (s, 3H) 6.91 (s, 1H) 7.11-7.35 (m, 2H) 7.67 (d, J=8.71 Hz, 2H) 9.97 (s, 1H)

(5) cyclohexyl{2-methyl-5-[4-(trifluoromethyl)phenyl]-3-furyl}methanol

An operation similar to that in Example 3 (2) was performed using 2-methyl-5-[4-(trifluoromethoxy)phenyl]-3-furaldehyde (1.4 g) and 1N cyclohexylmagnesium bromide-tetrahydrofuran solution (8.0 mL) to give the title compound (1.0 g, 57%) as a white crystal.

$^1$H NMR (300 MHz, CHLOROFORM-d) δ ppm 1.04-1.37 (m, 5H) 1.49-1.83 (m, 5H) 2.04-2.12 (m, 1H) 2.33 (s, 3H) 4.30 (dd, J=7.95, 3.03 Hz, 1H) 6.59 (s, 1H) 7.20 (d, J=8.33 Hz, 2H) 7.62 (d, J=9.09 Hz, 2H)

(6) 4-(cyclohexyl{2-methyl-5-[4-(trifluoromethoxy)phenyl]-3-furyl}methoxy)benzoic acid An operation similar to that in Example 1 (3) was performed using cyclohexyl{2-methyl-5-[4-(trifluoromethyl)phenyl]-3-furyl}methanol (425 mg) to give the title compound (243 mg, 42%) as an amorphous compound.

$^1$H NMR (300 MHz, CHLOROFORM-d) δ ppm 1.01-1.28 (m, 5H) 1.63-1.89 (m, 5H) 2.04-2.11 (m, 1H) 2.36 (s, 3H) 4.82 (d, J=7.19 Hz, 1H) 6.50 (s, 1H) 6.86 (d, J=8.71 Hz, 2H)

6.86 (d, J=8.71 Hz, 2H) 7.17 (d, J=8.71 Hz, 2H) 7.58 (d, J=8.71 Hz, 2H) 7.95 (d, J=8.71 Hz, 2H)

(7) 3-{[4-(cyclohexyl{2-methyl-5-[4-(trifluoromethoxy)phenyl]-3-furyl}methoxy)benzoyl]amino}propanoic acid An operation similar to that in Example 1 (4) was performed using 4-(cyclohexyl{2-methyl-5-[4-(trifluoromethoxy)phenyl]-3-furyl}methoxy)benzoic acid (119 mg) to give the title compound (133 mg, 96%) as an amorphous compound.

$^1$H NMR (300 MHz, DMSO-$d_6$) δ ppm 0.98-1.31 (m, 5H) 1.52-1.92 (m, 5H) 2.02-2.17 (m, 1H) 2.38 (s, 3H) 2.47-2.54 (m, 2H) 3.33 (q, J=5.30 Hz, 2H) 5.08 (d, J=7.57 Hz, 1H) 6.89 (s, 1H) 6.92 (d, J=8.71 Hz, 2H) 7.35 (d, J=8.33 Hz, 2H) 7.66-7.72 (m, 4H) 8.57 (brs, 1H)

Example 50

3-{[4-(cyclohexyl{2-methyl-5-[4-(trifluoromethoxy)phenyl]-3-furyl}methoxy)benzoyl](methyl)amino}propanoic acid

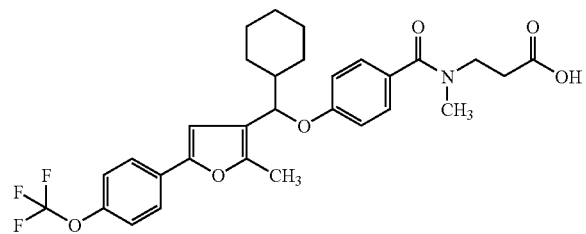

An operation similar to that in Example 1 (4) was performed using 4-(cyclohexyl{2-methyl-5-[4-(trifluoromethoxy)phenyl]-3-furyl}methoxy)benzoic acid (119 mg) as well as ethyl 3-(methylamino)propanoate (39 mg) to give the title compound (134 mg, 96%) as an amorphous compound.

$^1$H NMR (300 MHz, DMSO-$d_6$) δ ppm 0.99-1.29 (m, 5H) 1.51-1.89 (m, 5H) 2.03-2.08 (m, 1H) 2.87 (s, 3H) 3.33 (brs, 2H) 5.03 (d, J=7.57 Hz, 1H) 6.79-6.99 (m, 3H) 7.26 (d, J=8.71 Hz, 2H) 7.35 (d, J=8.33 Hz, 2H) 7.72 (d, J=8.71 Hz, 2H)

Example 51

3-[(4-{cyclohexyl[5-(2,4-dichlorophenyl)-2-methyl-3-furyl]methoxy}benzoyl)amino]propanoic acid

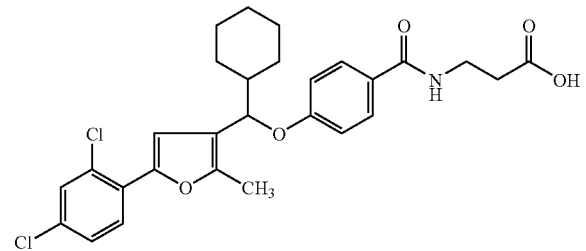

(1) methyl 5-(2,4-dichlorophenyl)-2-methyl-3-furoate

An operation similar to that in Example 49 (2) was performed using methyl 5-bromo-2-methyl-3-furoate (3.3 g) and 2,4-dichlorophenylboronic acid (3.4 g) to give the title compound (2.3 g, 54%) as a yellow crystal.

$^1$H NMR (300 MHz, CHLOROFORM-d) δ ppm 2.66 (s, 3H) 3.86 (s, 3H) 7.30 (dd, J=8.71, 2.27 Hz, 1H) 7.34 (s, 1H) 7.46 (d, J=2.27 Hz, 1H) 7.76 (d, J=8.71 Hz, 1H)

(2) [5-(2,4-dichlorophenyl)-2-methyl-3-furyl]methanol

An operation similar to that in Example 1 (2) was performed using methyl 5-(2,4-dichlorophenyl)-2-methyl-3-furoate (2.3 g) to give the title compound (2.1 g, 99%) as a yellow crystal.

$^1$H NMR (300 MHz, CHLOROFORM-d) δ ppm 2.38 (s, 3H) 4.54 (s, 2H) 7.12 (s, 1H) 7.19-7.33 (m, 1H) 7.43 (d, J=2.26 Hz, 1H) 7.77 (d, J=8.48 Hz, 1H)

(3) 5-(2,4-dichlorophenyl)-2-methyl-3-furaldehyde

An operation similar to that in Example 17 (3) was performed using [5-(2,4-difluorophenyl)-2-methyl-3-furyl]methanol (2.1 g) to give the title compound (1.3 g, 64%) as a yellow crystal.

$^1$H NMR (300 MHz, CHLOROFORM-d) δ ppm 2.68 (s, 3H) 7.15-7.35 (m, 1H) 7.38 (s, 1H) 7.48 (d, J=2.26 Hz, 1H) 7.77 (d, J=8.48 Hz, 1H) 9.99 (s, 1H)

(4) cyclohexyl[5-(2,4-dichlorophenyl)-2-methyl-3-furyl]methanol

An operation similar to that in Example 3 (2) was performed using 5-(2,4-dichlorophenyl)-2-methyl-3-furaldehyde (1.3 g) and 1N cyclohexylmagnesium bromide-tetrahydrofuran solution (7.5 mL) to give the title compound (1.3 g, 77%) as a white crystal.

$^1$H NMR (300 MHz, CHLOROFORM-d) δ ppm 0.83-1.31 (m, 5H) 1.45-1.82 (m, 5H) 1.73-1.89 (m, 1H) 2.04-2.10 (m, 1H) 2.34 (s, 3H) 4.23-4.46 (m, 1H) 7.07 (s, 1H) 7.26 (dd, J=8.52, 2.08 Hz, 1H) 7.42 (d, J=2.27 Hz, 1H) 7.77 (d, J=8.71 Hz, 1H)

(5) 4-{cyclohexyl[5-(2,4-dichlorophenyl)-2-methyl-3-furyl]methoxy}benzoic acid

In the same manner as in Example 1 (3), the title compound (338 mg, 63%) was obtained as a white crystal from cyclohexyl[5-(2,4-dichlorophenyl)-2-methyl-3-furyl]methanol (407 mg).

$^1$H NMR (300 MHz, CHLOROFORM-d) δ ppm 1.03-1.32 (m, 5H) 1.48-1.89 (m, 5H) 2.04-2.11 (m, 1H) 2.35 (s, 3H) 4.84 (d, J=7.19 Hz, 1H) 6.88 (d, J=9.09 Hz, 2H) 7.00 (s, 1H) 7.24 (dd, J=5.87, 2.46 Hz, 1H) 7.40 (d, J=2.27 Hz, 1H) 7.74 (d, J=8.71 Hz, 1H) 7.95 (d, J=9.09 Hz, 2H)

(6) 3-[(4-{cyclohexyl[5-(2,4-dichlorophenyl)-2-methyl-3-furyl]methoxy}benzoyl)amino]propanoic acid In the same manner as in Example 1 (4), the title compound (188 mg, 98%) was obtained as an amorphous compound from 4-{cyclohexyl[5-(2,4-dichlorophenyl)-2-methyl-3-furyl]methoxy}benzoic acid (165 mg).

¹H NMR (300 MHz, DMSO-d₆) δ ppm 1.02-1.29 (m, 5H) 1.54-1.86 (m, 5H) 2.00-2.05 (m, 1H) 2.38 (s, 3H) 2.44 (t, J=7.00 Hz, 2H) 3.34-3.47 (m, 2H) 5.15 (d, J=7.57 Hz, 1H) 6.95 (d, J=8.71 Hz, 2H) 7.05 (s, 1H) 7.46 (dd, J=8.71, 2.27 Hz, 1H) 7.67 (d, J=2.27 Hz, 1H) 7.70 (d, J=8.71 Hz, 2H) 7.76 (d, J=8.71 Hz, 1H) 8.30 (t, J=5.49 Hz, 1H)

Example 52

3-[(4-{cyclohexyl[5-(2,4-dichlorophenyl)-2-methyl-3-furyl]methoxy}benzoyl)(methyl)amino]propanoic acid

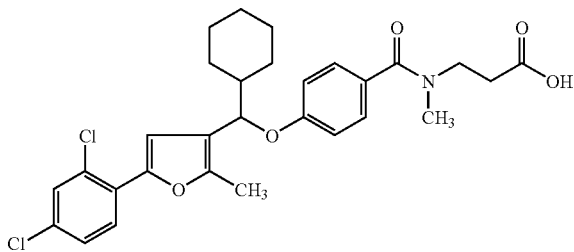

An operation similar to that in Example 1 (4) was performed using 4-{cyclohexyl[5-(2,4-dichlorophenyl)-2-methyl-3-furyl]methoxy}benzoic acid (165 mg) as well as ethyl 3-(methylamino)propanoate (56 mg) to give the title compound (192 mg, 98%) as an amorphous compound.

¹H NMR (300 MHz, DMSO-d₆) δ ppm 1.00-1.28 (m, 5H) 1.53-1.85 (m, 5H) 1.99-2.07 (m, 1H) 2.38 (s, 3H) 2.44-2.47 (m, 2H) 2.88 (s, 3H) 3.31 (brs, 2H) 5.09 (d, J=7.57 Hz, 1H) 6.92 (d, J=8.71 Hz, 2H) 7.07 (s, 1H) 7.26 (d, J=8.33 Hz, 2H) 7.47 (dd, J=8.71, 2.27 Hz, 1H) 7.67 (d, J=1.89 Hz, 1H) 7.78 (d, J=8.33 Hz, 1H)

Example 53

3-({4-[(cyclohexyl{2-methyl-5-[4-(trifluoromethoxy)phenyl]-3-furyl}methyl)amino]benzoyl}amino)propanoic acid

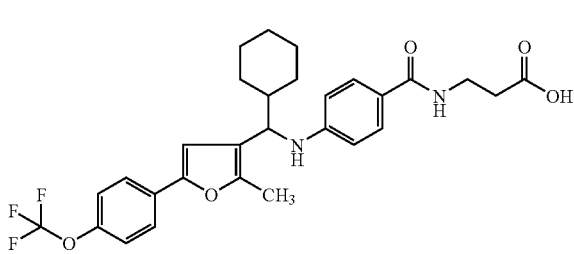

(1) 3-[chloro(cyclohexyl)methyl]-2-methyl-5-[4-(trifluoromethoxy)phenyl]furan

An operation similar to that in Example 9 (1) was performed using cyclohexyl{2-methyl-5-[4-(trifluoromethoxy)phenyl]-3-furyl}methanol (1.9 g) to give the title compound (1.9 g, 92%) as an oil.

¹H NMR (300 MHz, CHLOROFORM-d) δ ppm 0.88-1.33 (m, 5H) 1.62-1.85 (m, 5H) 2.17-2.24 (m, 1H) 2.33 (s, 3H) 4.60 (d, J=8.33 Hz, 1H) 6.62 (s, 1H) 7.05-7.36 (m, 2H) 7.63 (d, J=8.71 Hz, 2H)

(2) 4-[(cyclohexyl{2-methyl-5-[4-(trifluoromethoxy)phenyl]-3-furyl}methyl)amino]benzoic acid An operation similar to that in Example 9 (2) was performed using cyclohexyl{2-methyl-5-[4-(trifluoromethoxy)phenyl]-3-furyl}methanol (1.9 g) to give the title compound (0.73 g, 31%) as an amorphous compound.

¹H NMR (300 MHz, CHLOROFORM-d) δ ppm 0.96-1.31 (m, 5H) 1.61-1.83 (m, 5H) 1.88-2.02 (m, 1H) 2.38 (s, 3H) 4.12 (d, J=7.10 Hz, 1H) 6.44 (s, 1H) 6.50 (d, J=8.67 Hz, 2H) 7.17 (d, J=8.48 Hz, 2H) 7.58 (d, J=8.85 Hz, 2H) 7.84 (d, J=8.85 Hz, 2H)

(3) 3-({4-[(cyclohexyl{2-methyl-5-[4-(trifluoromethoxy)phenyl]-3-furyl}methyl)amino]benzoyl}amino)propanoic acid An operation similar to that in Example 1 (4) was performed using 4-[(cyclohexyl{2-methyl-5-[4-(trifluoromethoxy)phenyl]-3-furyl}methyl)amino]benzoic acid (355 mg) to give the title compound (295 mg, 97%) as an amorphous compound.

¹H NMR (300 MHz, DMSO-d₆) δ ppm 0.93-1.25 (m, 5H) 1.53-1.78 (m, 5H) 1.98-2.05 (m, 1H) 2.31-2.44 (m, 5H) 3.27-3.46 (m, 2H) 4.11 (t, J=7.95 Hz, 1H) 6.34 (d, J=7.95 Hz, 1H) 6.55 (d, J=8.71 Hz, 2H) 6.80 (s, 1H) 7.35 (d, J=7.95 Hz, 2H) 7.52 (d, J=8.71 Hz, 2H) 7.66 (d, J=9.09 Hz, 2H) 8.01 (t, J=5.11 Hz, 1H)

Example 54

3-[{4-[(cyclohexyl{2-methyl-5-[4-(trifluoromethoxy)phenyl]-3-furyl}methyl)amino]benzoyl}(methyl)amino]propanoic acid

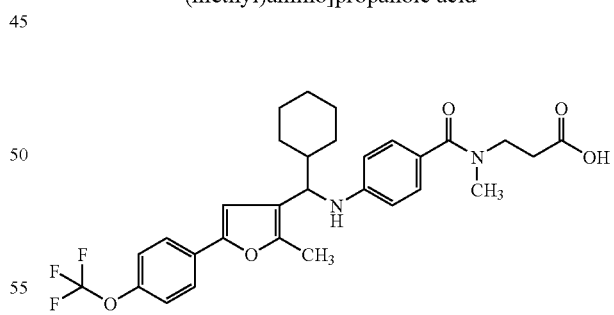

An operation similar to that in Example 1 (4) was performed using 4-[(cyclohexyl{2-methyl-5-[4-(trifluoromethoxy)phenyl]-3-furyl}methyl)amino]benzoic acid (355 mg) as well as ethyl 3-(methylamino)propanoate (118 mg) to give the title compound (401 mg, 96%) as an amorphous compound.

¹H NMR (300 MHz, DMSO-d₆) δ ppm 0.92-1.27 (m, 5H) 1.54-1.77 (m, 5H) 2.00-2.08 (m, 1H) 2.37 (s, 3H) 2.41-2.48 (m, 2H) 2.89 (s, 3H) 3.44-3.61 (m, 2H) 4.07 (s, 1H) 6.23 (s, 1H) 6.55 (d, J=8.67 Hz, 2H) 6.81 (s, 1H) 7.10 (d, J=8.67 Hz, 2H) 7.35 (d, J=8.10 Hz, 2H) 7.67 (d, J=8.85 Hz, 2H)

Example 55

3-{[4-({cyclohexyl[5-(2,4-dichlorophenyl)-2-methyl-3-furyl]methyl}amino)benzoyl]amino}propanoic acid

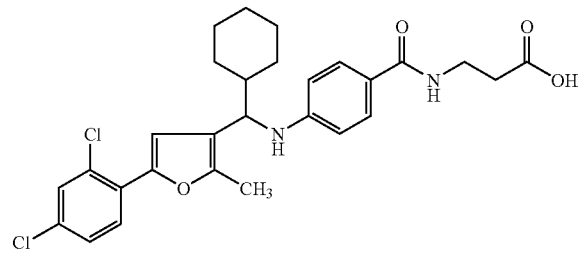

(1) 3-[chloro(cyclohexyl)methyl]-5-(2,4-dichlorophenyl)-2-methylfuran

An operation similar to that in Example 9 (1) was performed using cyclohexyl[5-(2,4-dichlorophenyl)-2-methyl-3-furyl]methanol (1.7 g) to give the title compound (1.8 g, 100%) as a yellow crystal.

$^1$H NMR (300 MHz, CHLOROFORM-d) δ ppm 0.77-1.34 (m, 5H) 1.55-1.93 (m, 5H) 2.17-2.25 (m, 1H) 2.34 (s, 3H) 4.61 (d, J=8.67 Hz, 1H) 7.09 (s, 1H) 7.26 (dd, J=8.67, 2.17 Hz, 1H) 7.43 (d, J=2.07 Hz, 1H) 7.76 (d, J=8.67 Hz, 1H)

(2) 4-({cyclohexyl[5-(2,4-dichlorophenyl)-2-methyl-3-furyl]methyl}amino)benzoic acid An operation similar to that in Example 9 (2) was performed using 3-[chloro(cyclohexyl)methyl]-5-(2,4-dichlorophenyl)-2-methylfuran (1.8 g) to give the title compound (0.99 g, 43%) as a yellow crystal.

$^1$H NMR (300 MHz, DMSO-d$_6$) δ ppm 0.83-1.33 (m, 5H) 1.51-1.78 (m, 5H) 1.99-2.07 (m, 1H) 2.40 (s, 3H) 4.16 (t, J=8.33 Hz, 1H) 6.58 (d, J=8.71 Hz, 2H) 6.68 (d, J=8.33 Hz, 1H) 7.12 (s, 1H) 7.46 (dd, J=8.71, 2.27 Hz, 1H) 7.60 (d, J=8.71 Hz, 2H) 7.66 (d, J=2.27 Hz, 1H) 7.77 (d, J=8.71 Hz, 1H) 11.93 (s, 1H)

(3) 3-{[4-({cyclohexyl[5-(2,4-dichlorophenyl)-2-methyl-3-furyl]methyl}amino)benzoyl]amino}propanoic acid An operation similar to that in Example 1 (4) was performed using 4-({cyclohexyl[5-(2,4-dichlorophenyl)-2-methyl-3-furyl]methyl}amino)benzoic acid (458 mg) to give the title compound (466 mg, 89%) as an amorphous compound.

$^1$H NMR (300 MHz, DMSO-d$_6$) δ ppm 0.91-1.27 (m, 5H) 1.52-1.77 (m, 5H) 1.99-2.06 (m, 1H) 2.32-2.45 (m, 5H) 3.32-3.40 (m, 2H) 4.03-4.25 (m, 1H) 6.40 (s, 1H) 6.56 (d, J=8.67 Hz, 2H) 7.12 (s, 1H) 7.46 (dd, J=8.67, 2.07 Hz, 1H) 7.52 (d, J=8.67 Hz, 2H) 7.66 (d, J=2.07 Hz, 1H) 7.76 (d, J=8.67 Hz, 1H) 8.00 (brs, 1H)

Example 56

3-{[4-({cyclohexyl[5-(2,4-dichlorophenyl)-2-methyl-3-furyl]methyl}amino)benzoyl](methyl)amino}propanoic acid

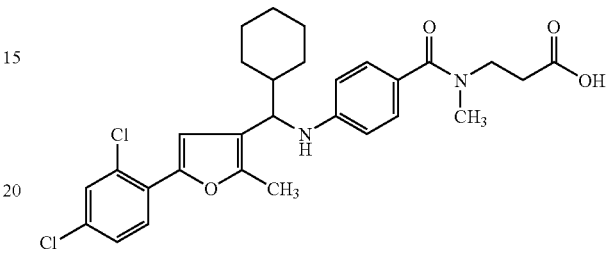

An operation similar to that in Example 1 (4) was performed using 4-({cyclohexyl[5-(2,4-dichlorophenyl)-2-methyl-3-furyl]methyl}amino)benzoic acid (458 mg) as well as ethyl 3-(methylamino)propanoate (157 mg) to give the title compound (465 mg, 85%) as an amorphous compound.

$^1$H NMR (300 MHz, DMSO-d$_6$) δ ppm 0.93-1.27 (m, 5H) 1.52-1.77 (m, 5H) 1.99-2.08 (m, 1H) 2.39 (s, 3H) 2.44 (brs, 2H) 2.89 (s, 3H) 3.54-3.56 (m, 2H) 4.06-4.15 (m, 1H) 6.31 (d, J=8.29 Hz, 1H) 6.55 (d, J=8.48 Hz, 2H) 7.08-7.13 (m, 3H) 7.46 (dd, J=8.67, 2.26 Hz, 1H) 7.66 (d, J=2.26 Hz, 1H) 7.77 (d, J=8.67 Hz, 1H)

Example 57

3-[(4-{cyclohexyl[5-(4-fluoro-2-methylphenyl)-2-methyl-3-furyl]methoxy}benzoyl)amino]propanoic acid

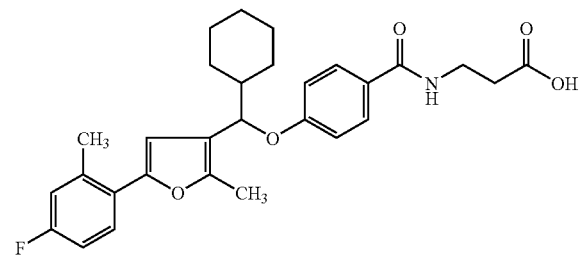

(1) methyl 5-(4-fluoro-2-methylphenyl)-2-methyl-3-furoate

An operation similar to that in Example 49 (2) was performed using methyl 5-bromo-2-methyl-3-furoate (4.4 g) and 4-fluoro-2-methylphenylboronic acid (3.7 g) to give the title compound (4.2 g, 85%) as a white crystal.

$^1$H NMR (300 MHz, CHLOROFORM-d) δ ppm 2.47 (s, 3H) 2.65 (s, 3H) 3.86 (s, 3H) 6.70 (s, 1H) 6.81-7.05 (m, 2H) 7.49-7.76 (m, 1H)

(2) [5-(4-fluoro-2-methylphenyl)-2-methyl-3-furyl]methanol

An operation similar to that in Example 1 (2) was performed using methyl 5-(4-fluoro-2-methylphenyl)-2-methyl-3-furoate (4.2 g) to give the title compound (3.5 g, 95%) as a white crystal.

$^1$H NMR (300 MHz, CHLOROFORM-d) δ ppm 1.43 (brs, 1H) 2.36 (s, 3H) 2.46 (s, 3H) 4.53 (s, 2H) 6.46 (s, 1H) 6.89-6.95 (m, 2H) 7.59-7.64 (m, 1H)

(3) 5-(4-fluoro-2-methylphenyl)-2-methyl-3-furaldehyde

An operation similar to that in Example 17 (3) was performed using [5-(4-fluoro-2-methylphenyl)-2-methyl-3-furyl]methanol (3.5 g) to give the title compound (2.6 g, 75%) as a white crystal.

$^1$H NMR (300 MHz, CHLOROFORM-d) δ ppm 2.47 (s, 3H) 2.67 (s, 3H) 6.74 (s, 1H) 6.85-7.09 (m, 2H) 7.61-7.66 (m, 1H) 9.98 (s, 1H)

(4) cyclohexyl[5-(4-fluoro-2-methylphenyl)-2-methyl-3-furyl]methanol

An operation similar to that in Example 3 (2) was performed using 5-(4-fluoro-2-methylphenyl)-2-methyl-3-furaldehyde (2.6 g) and 1N cyclohexylmagnesium bromide-tetrahydrofuran solution (18 mL) to give the title compound (2.6 g, 72%) as an oil.

$^1$H NMR (300 MHz, CHLOROFORM-d) δ ppm 0.74-1.38 (m, 5H) 1.43-1.86 (m, 5H) 2.05-2.13 (m, 1H) 2.32 (s, 3H) 2.47 (s, 3H) 4.31 (d, J=8.10 Hz, 1H) 6.41 (s, 1H) 6.78-7.05 (m, 2H) 7.60-7.65 (m, 1H)

(5) 4-{cyclohexyl[5-(4-fluoro-2-methylphenyl)-2-methyl-3-furyl]methoxy}benzoic acid An operation similar to that in Example 1 (3) was performed using cyclohexyl[5-(4-fluoro-2-methylphenyl)-2-methyl-3-furyl]methanol (604 mg) to give the title compound (144 mg, 17%) as an oil.

$^1$H NMR (300 MHz, CHLOROFORM-d) δ ppm 0.96-1.36 (m, 5H) 1.63-1.94 (m, 5H) 2.05-2.14 (m, 1H) 2.35 (s, 3H) 2.41 (s, 3H) 4.01-4.08 (m, 1H) 4.84 (d, J=7.16 Hz, 1H) 6.32 (s, 1H) 6.84-6.91 (m, 4H) 7.55-7.62 (m, 1H) 7.96 (d, J=8.85 Hz, 2H)

(6) 3-[(4-{cyclohexyl[5-(4-fluoro-2-methylphenyl)-2-methyl-3-furyl]methoxy}benzoyl)amino]propanoic acid An operation similar to that in Example 1 (4) was performed using 4-{cyclohexyl[5-(4-fluoro-2-methylphenyl)-2-methyl-3-furyl]methoxy}benzoic acid (139 mg) to give the title compound (157 mg, 96%) as an amorphous compound.

$^1$H NMR (300 MHz, DMSO-d$_6$) δ ppm 0.94-1.37 (m, 5H) 1.52-1.92 (m, 5H) 2.02-2.08 (m, 1H) 2.35 (s, 3H) 2.38 (s, 3H) 2.43 (t, J=7.19 Hz, 2H) 3.29-3.55 (m, 2H) 5.10 (d, J=7.19 Hz, 1H) 6.54 (s, 1H) 6.94 (d, J=8.71 Hz, 2H) 7.05-7.14 (m, 2H) 7.56-7.61 (m, 1H) 7.71 (d, J=8.71 Hz, 2H) 8.32 (t, J=5.30 Hz, 1H)

Example 58

3-[(4-{cyclohexyl[5-(4-fluoro-2-methylphenyl)-2-methyl-3-furyl]methoxy}benzoyl)(methyl)amino]propanoic acid

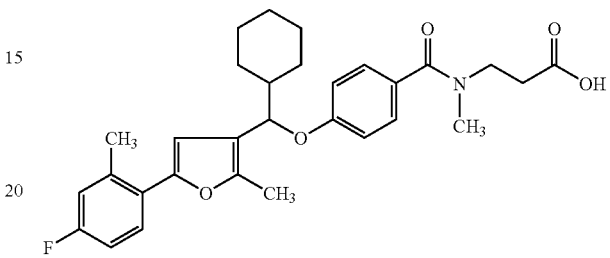

An operation similar to that in Example 1 (4) was performed using 4-{cyclohexyl[5-(4-fluoro-2-methylphenyl)-2-methyl-3-furyl]methoxy}benzoic acid (139 mg) as well as ethyl 3-(methylamino)propanoate (52 mg) to give the title compound (127 mg, 76%) as an amorphous compound.

$^1$H NMR (300 MHz, DMSO-d$_6$) δ ppm 1.01-1.28 (m, 5H) 1.53-1.88 (m, 5H) 2.02-2.09 (m, 1H) 2.35 (s, 3H) 2.38 (s, 3H) 2.41-2.49 (m, 2H) 2.88 (s, 3H) 3.34 (brs, 2H) 5.04 (d, J=7.19 Hz, 1H) 6.55 (s, 1H) 6.92 (d, J=8.33 Hz, 2H) 6.99-7.18 (m, 2H) 7.26 (d, J=8.33 Hz, 2H) 7.58-7.62 (m, 1H)

Example 59

3-{[4-({cyclohexyl[5-(4-fluoro-2-methylphenyl)-2-methyl-3-furyl]methyl}amino)benzoyl]amino}propanoic acid

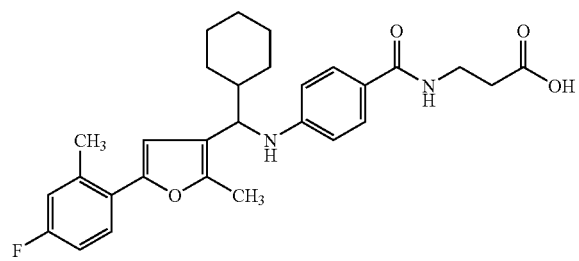

(1) 3-[chloro(cyclohexyl)methyl]-5-(4-fluoro-2-methylphenyl)-2-methylfuran

An operation similar to that in Example 9 (1) was performed using cyclohexyl[5-(4-fluoro-2-methylphenyl)-2-methyl-3-furyl]methanol (1.6 g) to give the title compound (1.7 g, 100%) as a yellow crystal.

$^1$H NMR (300 MHz, CHLOROFORM-d) δ ppm 0.88-1.31 (m, 5H) 1.62-1.91 (m, 5H) 2.17-2.28 (m, 1H) 2.32 (s, 3H) 2.36 (s, 3H) 4.62 (d, J=8.33 Hz, 1H) 6.42 (s, 1H) 6.90-6.95 (m, 2H) 7.54-7.72 (m, 1H)

(2) 4-({cyclohexyl[5-(4-fluoro-2-methylphenyl)-2-methyl-3-furyl]methyl}amino)benzoic acid An operation similar to that in Example 9 (2) was performed using 3-[chloro(cyclohexyl)methyl]-5-(4-fluoro-2-methylphenyl)-2-methylfuran (1.7 g) to give the title compound (0.96 g, 41%) as a yellow crystal.

$^1$H NMR (300 MHz, CHLOROFORM-d) δ ppm 1.01-1.31 (m, 5H) 1.50-1.84 (m, 5H) 1.93-2.01 (m, 1H) 2.37 (s, 3H) 2.41 (s, 3H) 4.12 (d, J=7.16 Hz, 1H) 6.25 (s, 1H) 6.52 (d, J=8.67 Hz, 2H) 6.87-6.92 (m, 2H) 7.57-7.62 (m, 1H) 7.85 (d, J=8.67 Hz, 2H)

(3) 3-{[4-({cyclohexyl[5-(4-fluoro-2-methylphenyl)-2-methyl-3-furyl]methyl}amino)benzoyl]amino}propanoic acid An operation similar to that in Example 1 (4) was performed using 4-({cyclohexyl[5-(4-fluoro-2-methylphenyl)-2-methyl-3-furyl]methyl}amino)benzoic acid (464 mg) to give the title compound (514 mg, 95%) as an amorphous compound.

$^1$H NMR (300 MHz, DMSO-d$_6$) δ ppm 0.91-1.27 (m, 5H) 1.54-1.77 (m, 5H) 1.99-2.08 (m, 1H) 2.36 (s, 3H) 2.39-2.43 (m, 5H) 3.25-3.48 (m, 2H) 4.01-4.26 (m, 1H) 6.34 (d, J=8.48 Hz, 1H) 6.55-6.58 (m, 3H) 7.03-7.14 (m, 2H) 7.52 (d, J=8.67, 2H) 7.56-7.61 (m, 1H) 8.02 (brs, 1H)

Example 60

3-{[4-({cyclohexyl[5-(4-fluoro-2-methylphenyl)-2-methyl-3-furyl]methyl}amino)benzoyl](methyl)amino}propanoic acid

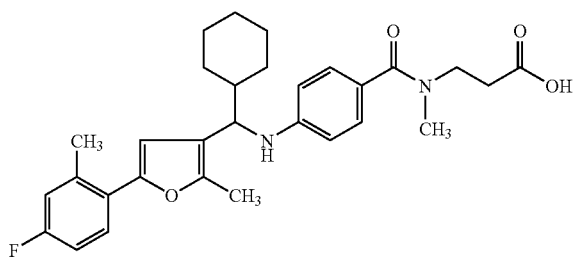

An operation similar to that in Example 1 (4) was performed using 4-({cyclohexyl[5-(4-fluoro-2-methylphenyl)-2-methyl-3-furyl]methyl}amino)benzoic acid (464 mg) as well as ethyl 3-(methylamino)propanoate (171 mg) to give the title compound (552 mg, 99%) as an amorphous compound.

$^1$H NMR (300 MHz, DMSO-d$_6$) δ ppm 0.84-1.35 (m, 5H) 1.45-1.83 (m, 5H) 2.00-2.08 (m, 1H) 2.36 (s, 3H) 2.39 (s, 3H) 2.40-2.48 (m, 2H) 2.90 (s, 3H) 3.44-3.61 (m, 2H) 4.02-4.19 (m, 1H) 6.23 (d, J=8.48 Hz, 1H) 6.45-6.70 (m, 3H) 6.90-7.21 (m, 4H) 7.57-7.62 (m, 1H)

Example 61

3-({4-[(5-tert-butyl-2-methyl-3-furyl)(cyclohexyl)methoxy]benzoyl}amino)propanoic acid

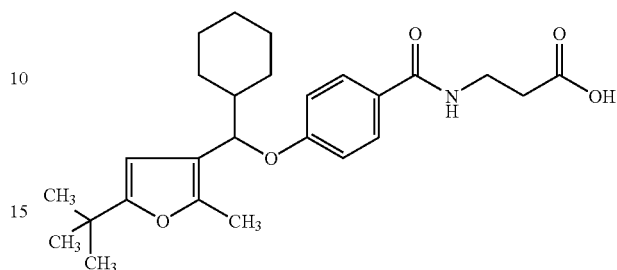

(1) ethyl 5-tert-butyl-2-methyl-3-furoate

An operation similar to that in Example 25 (1) was performed using 5-tert-butyl-2-methyl-3-furancarboxylic acid (3.6 g) to give the title compound (4.2 g, 100%) as an oil.

$^1$H NMR (300 MHz, CHLOROFORM-d) δ ppm 1.25 (s, 9H) 1.34 (t, J=7.16 Hz, 3H) 2.53 (s, 3H) 4.27 (q, J=7.16 Hz, 2H) 6.19 (s, 1H)

(2) (5-tert-butyl-2-methyl-3-furyl)methanol

An operation similar to that in Example 1 (2) was performed using ethyl 5-phenyl-2-methyl-3-furoate (4.2 g) to give the title compound (3.2 g, 95%) as an oil.

$^1$H NMR (300 MHz, CHLOROFORM-d) δ ppm 1.27 (s, 9H) 2.25 (s, 3H) 4.43 (s, 2H) 5.92 (s, 1H)

(3) 5-tert-butyl-2-methyl-3-furaldehyde

An operation similar to that in Example 17 (3) was performed using (5-tert-butyl-2-methyl-3-furyl)methanol (3.2 g) to give the title compound (2.5 g, 80%) as an oil.

$^1$H NMR (300 MHz, CHLOROFORM-d) δ ppm 1.26 (s, 9H) 2.55 (s, 3H) 6.24 (s, 1H) 9.88 (s, 1H)

(4) (5-tert-butyl-2-methyl-3-furyl)(cyclohexyl)methanol

An operation similar to that in Example 3 (2) was performed using 5-tert-butyl-2-methyl-3-furaldehyde (2.5 g) and 1N cyclohexylmagnesium bromide-tetrahydrofuran solution (23 mL) to give the title compound (2.3 g, 62%) as an oil.

$^1$H NMR (300 MHz, CHLOROFORM-d) δ ppm 0.70-1.35 (m, 14H) 1.37-1.86 (m, 5H) 2.02-2.11 (m, 1H) 2.20 (s, 3H) 4.20 (dd, J=8.10, 2.07 Hz, 1H) 5.84 (s, 1H)

(5) 4-[(5-tert-butyl-2-methyl-3-furyl)(cyclohexyl)methoxy]benzoic acid

An operation similar to that in Example 1 (3) was performed using (5-tert-butyl-2-methyl-3-furyl)(cyclohexyl)methanol (501 mg) to give the title compound (222 mg, 30%) as a white crystal.

$^1$H NMR (300 MHz, CHLOROFORM-d) δ ppm 0.95-1.30 (m, 14H) 1.46-1.84 (m, 5H) 2.01-2.09 (m, 1H) 2.23 (s, 3H) 4.72 (d, J=7.57 Hz, 1H) 5.76 (s, 1H) 6.85 (d, J=9.09 Hz, 2H) 7.94 (d, J=9.09 Hz, 2H)

(6) 3-({4-[(5-tert-butyl-2-methyl-3-furyl)(cyclohexyl)methoxy]benzoyl}amino)propanoic acid An operation similar to that in Example 1 (4) was performed using 4-[(5-tert-butyl-2-methyl-3-furyl)(cyclohexyl)methoxy]benzoic acid (111 mg) to give the title compound (131 mg, 99%) as an amorphous compound.
$^1$H NMR (300 MHz, DMSO-$d_6$) δ ppm 0.94-1.26 (m, 14H) 1.42-1.80 (m, 5H) 1.94-2.04 (m, 1H) 2.24 (s, 3H) 2.44 (t, J=7.06 Hz, 2H) 3.35-3.50 (m, 2H) 4.95 (d, J=7.54 Hz, 1H) 5.87 (s, 1H) 6.89 (d, J=8.85 Hz, 2H) 7.70 (d, J=8.85 Hz, 2H) 8.33 (s, 1H)

Example 62

3-[{4-[(5-tert-butyl-2-methyl-3-furyl)(cyclohexyl)methoxy]benzoyl}(methyl)amino]propanoic acid

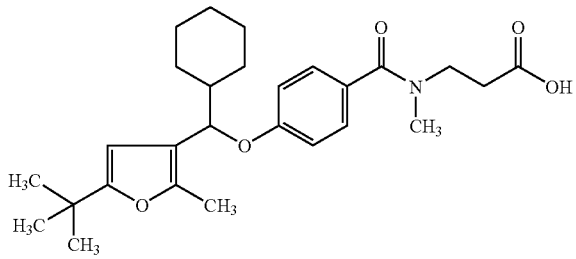

An operation similar to that in Example 1 (4) was performed using 4-[(5-tert-butyl-2-methyl-3-furyl)(cyclohexyl)methoxy]benzoic acid (111 mg) as well as ethyl 3-(methylamino)propanoate (47 mg) to give the title compound (110 mg, 81%) as an amorphous compound.
$^1$H NMR (300 MHz, DMSO-$d_6$) δ ppm 0.91-1.27 (m, 14H) 1.43-1.78 (m, 5H) 1.96-2.04 (m, 1H) 2.24 (s, 3H) 2.44 (brs, 2H) 2.89 (s, 3H) 3.50 (brs, 2H) 4.90 (d, J=7.72 Hz, 1H) 5.88 (s, 1H) 6.86 (d, J=8.67 Hz, 2H) 7.25 (d, J=8.67 Hz, 2H)

Example 63

3-[(4-{[5-(4-chloro-2-methylphenyl)-2-methyl-3-furyl](cyclohexyl)methoxy}benzoyl)amino]propanoic acid

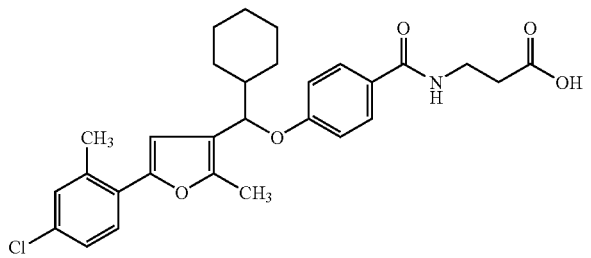

(1) ethyl 5-(4-chloro-2-methylphenyl)-2-methyl-3-furoate

An operation similar to that in Example 49 (2) was performed using methyl 5-bromo-2-methyl-3-furoate (4.4 g) and 4-chloro-2-methylphenylphenylboronic acid (4.1 g) to give the title compound (3.2 g, 60%) as a white crystal.
$^1$H NMR (300 MHz, CHLOROFORM-d) δ ppm 2.46 (s, 3H) 2.65 (s, 3H) 3.86 (s, 3H) 6.76 (s, 1H) 7.08-7.33 (m, 2H) 7.61 (d, J=8.71 Hz, 1H)

(2) [5-(4-chloro-2-methylphenyl)-2-methyl-3-furyl]methanol

An operation similar to that in Example 1 (2) was performed using ethyl 5-(4-chloro-2-methylphenyl)-2-methyl-3-furoate (3.2 g) to give the title compound (2.8 g, 100%) as a white crystal.
$^1$H NMR (300 MHz, CHLOROFORM-d) δ ppm 2.37 (s, 3H) 2.46 (s, 3H) 4.53 (brs, 2H) 6.52 (s, 1H) 7.18-7.21 (m, 2H) 7.61 (d, J=9.09 Hz, 1H)

(3) 5-(4-chloro-2-methylphenyl)-2-methyl-3-furaldehyde

An operation similar to that in Example 17 (3) was performed using [5-(4-chloro-2-methylphenyl)-2-methyl-3-furyl]methanol (2.8 g) to give the title compound (1.7 g, 60%) as a white crystal.
$^1$H NMR (300 MHz, CHLOROFORM-d) δ ppm 2.47 (s, 3H) 2.67 (s, 3H) 6.80 (s, 1H) 7.18-7.26 (m, 2H) 7.62 (d, J=8.71 Hz, 1H) 9.98 (s, 1H)

(4) [5-(4-chloro-2-methylphenyl)-2-methyl-3-furyl](cyclohexyl)methanol

An operation similar to that in Example 3 (2) was performed using 5-(4-chloro-2-methylphenyl)-2-methyl-3-furaldehyde (1.6 g) and 1N cyclohexylmagnesium bromide-tetrahydrofuran solution (10 mL) to give the title compound (1.7 g, 77%) as a white crystal.
$^1$H NMR (300 MHz, CHLOROFORM-d) δ ppm 0.76-1.38 (m, 5H) 1.45-1.90 (m, 5H) 2.05-2.11 (m, 1H) 2.33 (s, 3H) 2.46 (s, 3H) 4.32 (d, J=7.72 Hz, 1H) 6.47 (s, 1H) 7.11-7.24 (m, 2H) 7.62 (d, J=9.04 Hz, 1H)

(5) 4-{[5-(4-chloro-2-methylphenyl)-2-methyl-3-furyl](cyclohexyl)methoxy}benzoic acid An operation similar to that in Example 1 (3) was performed using [5-(4-chloro-2-methylphenyl)-2-methyl-3-furyl](cyclohexyl)methanol (478 mg) to give the title compound (326 mg, 50%) as an amorphous compound.
$^1$H NMR (300 MHz, CHLOROFORM-d) δ ppm 0.94-1.39 (m, 5H) 1.62-1.91 (m, 5H) 2.05-2.11 (m, 1H) 2.35 (s, 3H) 2.40 (s, 3H) 4.84 (d, J=7.57 Hz, 1H) 6.38 (s, 1H) 6.87 (d, J=9.09 Hz, 2H) 7.10-7.21 (m, 2H) 7.58 (d, J=9.09 Hz, 1H) 7.96 (d, J=8.71 Hz, 2H)

(6) 3-[(4-{[5-(4-chloro-2-methylphenyl)-2-methyl-3-furyl](cyclohexyl)methoxy}benzoyl)amino]propanoic acid An operation similar to that in Example 1 (4) was performed using 4-{[5-(4-chloro-2-methylphenyl)-2-methyl-3-furyl](cyclohexyl)methoxy}benzoic acid (162 mg) to give the title compound (179 mg, 95%) as an amorphous compound.
$^1$H NMR (300 MHz, DMSO-$d_6$) δ ppm 0.86-1.33 (m, 5H) 1.52-1.91 (m, 5H) 2.00-2.07 (m, 1H) 2.37 (s, 3H) 2.38 (s, 3H) 2.45-2.50 (m, 2H) 3.34-3.40 (m, 2H) 5.11 (d, J=7.35 Hz, 1H) 6.62 (s, 1H) 6.94 (d, J=8.67 Hz, 2H) 7.27 (dd, J=8.48, 2.07

Hz, 1H) 7.34 (d, J=2.07 Hz, 1H) 7.59 (d, J=8.48 Hz, 1H) 7.70 (d, J=8.67 Hz, 2H) 8.38 (brs, 1H)

Example 64

3-[(4-{[5-(4-chloro-2-methylphenyl)-2-methyl-3-furyl](cyclohexyl)methoxy}benzoyl)(methyl)amino]propanoic acid

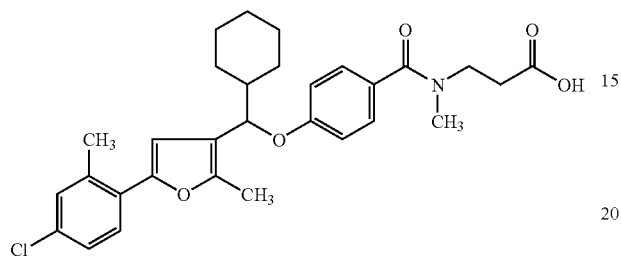

An operation similar to that in Example 1 (4) was performed using 4-{5-(4-chloro-2-methylphenyl)-2-methyl-3-furyl](cyclohexyl)methoxy}benzoic acid (162 mg) as well as ethyl 3-(methylamino)propanoate (59 mg) to give the title compound (194 mg, 99%) as an amorphous compound.

¹H NMR (300 MHz, DMSO-d₆) δ ppm 0.97-1.32 (m, 5H) 1.56-1.92 (m, 5H) 2.00-2.09 (m, 1H) 2.36 (s, 3H) 2.38 (s, 3H) 2.43-2.50 (m, 2H) 2.88 (s, 3H) 3.51 (brs, 2H) 5.06 (d, J=7.54 Hz, 1H) 6.63 (s, 1H) 6.92 (d, J=8.67 Hz, 2H) 7.22-7.29 (m, 3H) 7.34 (d, J=1.70 Hz, 1H) 7.60 (d, J=8.48 Hz, 1H)

Example 65

3-{[4-({[5-(4-chloro-2-methylphenyl)-2-methyl-3-furyl](cyclohexyl)methyl}amino)benzoyl]amino}propanoic acid

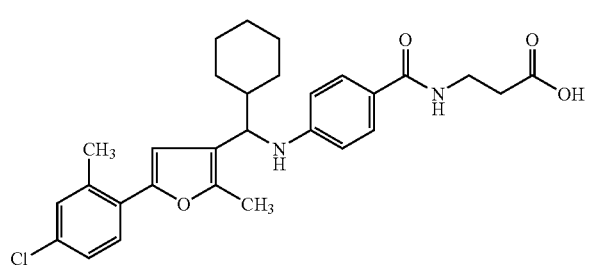

(1) 3-[chloro(cyclohexyl)methyl]-5-(4-chloro-2-methylphenyl)-2-methylfuran

An operation similar to that in Example 9 (1) was performed using [5-(4-chloro-2-methylphenyl)-2-methyl-3-furyl](cyclohexyl)methanol (1.1 g) to give the title compound (1.2 g, 100%) as an oil.

¹H NMR (300 MHz, CHLOROFORM-d) δ ppm 0.76-1.38 (m, 5H) 1.59-1.97 (m, 5H) 2.17-2.26 (m, 1H) 2.33 (s, 3H) 2.36 (s, 3H) 4.62 (d, J=8.67 Hz, 1H) 6.48 (s, 1H) 7.05-7.33 (m, 2H) 7.61 (d, J=8.67 Hz, 1H)

(2) 4-({[5-(4-chloro-2-methylphenyl)-2-methyl-3-furyl](cyclohexyl)methyl}amino)benzoic acid An operation similar to that in Example 9 (2) was performed using 3-[chloro(cyclohexyl)methyl]-5-(4-chloro-2-methylphenyl)-2-methylfuran (1.2 g) to give the title compound (0.7 g, 49%) as a yellow crystal.

¹H NMR (300 MHz, CHLOROFORM-d) δ ppm 0.97-1.34 (m, 5H) 1.63-1.85 (m, 5H) 1.89-2.03 (m, 1H) 2.37 (s, 3H) 2.40 (s, 3H) 4.02-4.25 (m, 1H) 6.31 (s, 1H) 6.51 (d, J=7.35 Hz, 2H) 7.03-7.22 (m, 2H) 7.58 (d, J=9.04 Hz, 1H) 7.85 (d, J=7.35 Hz, 2H)

(3) 3-{[4-({[5-(4-chloro-2-methylphenyl)-2-methyl-3-furyl](cyclohexyl)methyl}amino)benzoyl]amino}propanoic acid An operation similar to that in Example 1 (4) was performed using 4-({[5-(4-chloro-2-methylphenyl)-2-methyl-3-furyl](cyclohexyl)methyl}amino)benzoic acid (372 mg) to give the title compound (383 mg, 89%) as an amorphous compound.

¹H NMR (300 MHz, DMSO-d₆) δ ppm 0.80-1.32 (m, 5H) 1.54-1.78 (m, 5H) 1.98-2.08 (m, 1H) 2.36 (s, 3H) 2.39-2.44 (m, 5H) 3.22-3.47 (m, 2H) 4.14 (t, J=8.14 Hz, 1H) 6.34 (d, J=8.33 Hz, 1H) 6.57 (d, J=9.09 Hz, 2H) 6.65 (s, 1H) 7.27 (dd, J=8.33, 2.27 Hz, 1H) 7.33 (d, J=1.89 Hz, 1H) 7.52 (d, J=8.71 Hz, 2H) 7.58 (d, J=8.33 Hz, 1H) 8.01 (t, J=5.68 Hz, 1H)

Example 66

3-{[4-({[5-(4-chloro-2-methylphenyl)-2-methyl-3-furyl](cyclohexyl)methyl}amino)benzoyl](methyl)amino}propanoic acid

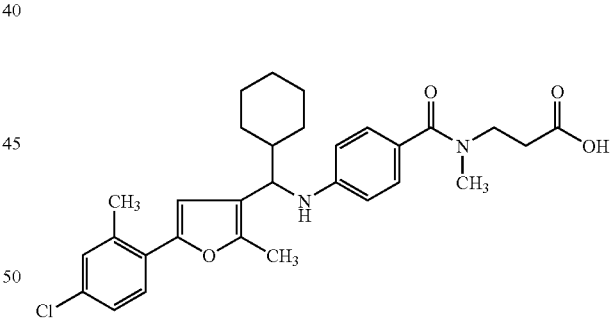

An operation similar to that in Example 1 (4) was performed using 4-({[5-(4-chloro-2-methylphenyl)-2-methyl-3-furyl](cyclohexyl)methyl}amino)benzoic acid (372 mg) as well as ethyl 3-(methylamino)propanoate (131 mg) to give the title compound (394 mg, 89%) as an amorphous compound.

¹H NMR (300 MHz, DMSO-d₆) δ ppm 0.91-1.29 (m, 5H) 1.53-1.78 (m, 5H) 1.98-2.08 (m, 1H) 2.36 (s, 3H) 2.39 (s, 3H) 2.46 (t, J=7.19 Hz, 2H) 2.90 (s, 3H) 3.51 (t, J=7.38 Hz, 2H) 4.10 (t, J=7.95 Hz, 1H) 6.23 (d, J=8.33 Hz, 1H) 6.56 (d, J=8.71 Hz, 2H) 6.66 (s, 1H) 7.10 (d, J=8.71 Hz, 2H) 7.27 (dd, J=8.33, 2.27 Hz, 1H) 7.33 (d, J=2.27 Hz, 1H) 7.59 (d, J=8.71 Hz, 1H)

Example 67

3-[(4-{[(5-tert-butyl-2-methyl-3-furyl)(cyclohexyl)methyl]amino}benzoyl)amino]propanoic acid

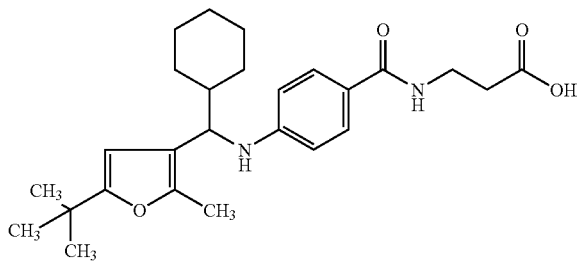

(1) 3-[chloro(cyclohexyl)methyl]-5-tert-butyl-2-methylfuran

An operation similar to that in Example 9 (1) was performed using (5-tert-butyl-2-methyl-3-furyl)(cyclohexyl)methanol (1.7 g) to give the title compound (1.8 g, 100%) as an oil.

(2) 4-({[(5-tert-butyl-2-methyl-3-furyl)(cyclohexyl)methyl]amino}benzoic acid An operation similar to that in Example 9 (2) was performed using 3-[chloro(cyclohexyl)methyl]-5-tert-butyl-2-methylfuran (1.8 g) to give the title compound (0.46 g, 17%) as an amorphous compound.
$^1$H NMR (300 MHz, CHLOROFORM-d) δ ppm 0.64-1.44 (m, 14H) 1.49-1.82 (m, 5H) 1.89-1.98 (m, 1H) 2.11 (s, 3H) 3.96-4.06 (m, 1H) 5.69 (s, 1H) 6.50 (d, J=8.71 Hz, 2H) 7.85 (d, J=9.09 Hz, 2H)

(3) 3-[(4-{[(5-tert-butyl-2-methyl-3-furyl)(cyclohexyl)methyl]amino}benzoyl)amino]propanoic acid An operation similar to that in Example 1 (4) was performed using 4-{[(5-tert-butyl-2-methyl-3-furyl)(cyclohexyl)methyl]amino}benzoic acid (222 mg) to give the title compound (31 mg, 12%) as an amorphous compound.
$^1$H NMR (300 MHz, DMSO-$d_6$) δ ppm 0.85-1.24 (m, 14H) 1.43-1.73 (m, 5H) 1.94-2.00 (m, 1H) 2.23 (s, 3H) 2.35-2.43 (m, 2H) 3.35 (brs, 2H) 3.99 (brs, 1H) 5.87 (s, 1H) 6.21-6.28 (m, 1H) 6.52 (d, J=8.48 Hz, 2H) 7.51 (d, J=8.48 Hz, 2H) 8.05 (brs, 1H)

Example 68

3-[(4-{[(5-tert-butyl-2-methyl-3-furyl)(cyclohexyl)methyl]amino}benzoyl)(methyl)amino]propanoic acid

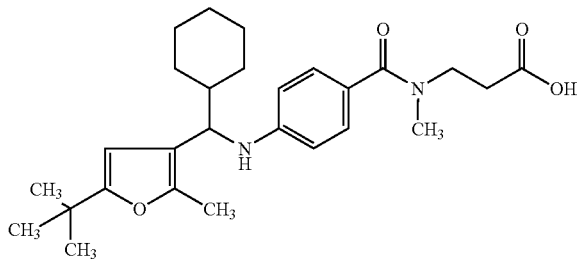

An operation similar to that in Example 1 (4) was performed using 4-{[(5-tert-butyl-2-methyl-3-furyl)(cyclohexyl)methyl]amino}benzoic acid (222 mg) as well as ethyl 3-(methylamino)propanoate (94 mg) to give the title compound (52 mg, 19%) as an amorphous compound.
$^1$H NMR (300 MHz, DMSO-$d_6$) δ ppm 0.83-1.24 (m, 14H) 1.43-1.73 (m, 5H) 1.93-2.02 (m, 1H) 2.23 (s, 3H) 2.46-2.56 (m, 2H) 2.91 (s, 3H) 3.52 (brs, 2H) 3.96 (brs, 1H) 5.88 (s, 1H) 6.14 (d, J=8.67 Hz, 1H) 6.51 (d, J=8.67 Hz, 2H) 7.10 (d, J=8.48 Hz, 2H)

Example 69

3-({[4-(cyclohexyl{2-ethyl-5-[4-(trifluoromethyl)phenyl]thiophen-3-yl}methoxy)phenyl]carbonyl}amino)propanoic acid

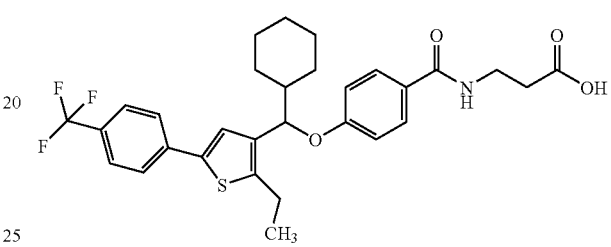

(1) 2,5-dibromothiophene-3-carboxylic acid

To a solution of 3-thiophenecarboxylic acid (25.3 g) in acetic acid (200 mL) was added dropwise bromine (21.3 mL), and the mixture was stirred at 50° C. for 1 day. The reaction mixture was concentrated under reduced pressure, and the residue was washed with diisopropyl ether to give the title compound (17.3 g, 31%) as a white solid.
$^1$H NMR (300 MHz, CDCl$_3$) δ ppm 7.40 (m, 1H)

(2) ethyl 2,5-dibromothiophene-3-carboxylate

To a solution of 2,5-dibromothiophene-3-carboxylic acid (33.5 g) synthesized above in ethanol (300 mL) was added dropwise thionyl chloride (4.23 mL), and the mixture was stirred at room temperature overnight and then stirred with heating under reflux for 3 hr. The reaction mixture was concentrated under reduced pressure, saturated aqueous sodium hydrogen carbonate solution was added to the residue, and the mixture was extracted with ethyl acetate. The extract was washed with brine, dried over magnesium sulfate, and concentrated under reduced pressure. The residue was purified by silica gel column chromatography (ethyl acetate:hexane=4:1, volume ratio) to give the title compound (33.4 g, 92%) as a white solid.
$^1$H NMR (300 MHz, CDCl$_3$) δ ppm 1.37 (t, J=7.2 Hz, 3H) 4.33 (q, J=7.2 Hz, 2H) 7.34 (m, 1H)

(3) ethyl 5-bromo-2-(1-hydroxyethyl)thiophene-3-carboxylate

Ethyl 2,5-dibromothiophene-3-carboxylate (22.3 g) synthesized above was dissolved in tetrahydrofuran (200 mL), and 1.0M isopropylmagnesium bromide-tetrahydrofuran solution (78.0 mL) was added dropwise at −45° C. After stirring under an argon atmosphere for 1 hr, acetaldehyde (19.9 mL) was added dropwise, and the mixture was stirred at −45° C. for 1 hr, and at room temperature for 2 hr. Saturated aqueous ammonium chloride solution was added to quench the reaction, and the mixture was extracted with ethyl acetate. The extract was washed with brine, dried over magnesium sulfate, and concentrated under reduced pressure. The residue was purified by silica gel column chromatography (ethyl acetate:hexane=3:17, volume ratio) to give the title compound (9.63 g, 49%) as a yellow oil.

$^1$H NMR (300 MHz, CDCl$_3$) δ 1.37 (t, J=7.2 Hz, 3H) 1.59 (d, J=6.6 Hz, 3H) 3.93 (d, J=3.9 Hz, 1H) 4.32 (d, J=7.2 Hz, 2H) 5.38-5.49 (m, 1H) 7.36 (s, 1H)

(4) ethyl 5-bromo-2-ethylthiophene-3-carboxylate

To a solution of ethyl 5-bromo-2-(1-hydroxyethyl)thiophene-3-carboxylate (11.0 g) synthesized above in trifluoroacetic acid (100 mL) was added dropwise triethylsilane (18.8 mL). After stirring at room temperature for 1 hr, the reaction mixture was concentrated under reduced pressure. The residue was purified by silica gel column chromatography (ethyl acetate:hexane=1:19, volume ratio) to give the title compound (9.67 g, 94%) as a pale-yellow oil.

$^1$H NMR (300 MHz, CDCl$_3$) δ ppm 1.30 (t, J=7.5 Hz, 3H) 1.35 (t, J=7.2 Hz, 3H) 3.16 (q, J=7.5 Hz, 2H) 4.29 (q, J=7.2 Hz, 2H) 7.33 (s, 1H)

(5) ethyl 2-ethyl-5-[4-(trifluoromethyl)phenyl]thiophene-3-carboxylate

To a mixture of ethyl 5-bromo-2-ethylthiophene-3-carboxylate (4.61 g) synthesized above, 4-(trifluoromethyl)phenylboronic acid (5.00 g), sodium carbonate (3.71 g), water (20 mL) and N,N-dimethylformamide (100 mL) was added [1,1'-bis(diphenylphosphino)ferrocene]dichloropalladium(II).dichloromethane adduct (1.43 g). The reaction mixture was deaerated, and stirred under an argon atmosphere at 80° C. for 2 hr. Saturated aqueous ammonium chloride solution was added to quench the reaction, and the mixture was extracted with ethyl acetate. The extract was washed with saturated sodium hydrogen carbonate and brine, dried over magnesium sulfate, and concentrated under reduced pressure. The residue was purified by silica gel column chromatography (ethyl acetate:hexane=1:19, volume ratio) to give the title compound (5.18 g, 90%) as a white solid.

$^1$H NMR (300 MHz, CDCl$_3$) δ ppm 1.33-1.42 (m, 6H) 3.25 (q, J=7.5 Hz, 2H) 4.34 (q, J=7.2 Hz, 2H) 7.58-7.69 (m, 5H)

(6) 2-ethyl-5-[4-(trifluoromethyl)phenyl]thiophene-3-carbaldehyde

To a solution (100 mL) of ethyl 2-ethyl-5-[4-(trifluoromethyl)phenyl]thiophene-3-carboxylate (5.18 g) synthesized above in tetrahydrofuran was added lithium aluminum hydride (721 mg) at 0° C., and the mixture was stirred for 1 hr. Water (720 μL) was added to quench the reaction, 1N aqueous sodium hydroxide solution (3.60 mL) was added, and the mixture was stirred at room temperature for 1 hr. The resulting insoluble material was filtered off, and the filtrate was concentrated under reduced pressure to give a pale-yellow oil. To a solution of the obtained oil in tetrahydrofuran (100 mL) was added activated manganese dioxide (24.6 g), and the mixture was stirred at room temperature overnight. Manganese dioxide was filtered off, and the filtrate was concentrated under reduced pressure. The residue was purified by silica gel column chromatography (ethyl acetate:hexane=1:4, volume ratio) to give the title compound (4.38 g, 98%) as a brown oil.

$^1$H NMR (300 MHz, CDCl$_3$) δ ppm 1.44 (t, J=7.5 Hz, 3H) 3.26 (q, J=7.5 Hz, 2H) 7.61-7.69 (m, 5H) 10.04 (s, 1H)

(7) cyclohexyl{2-ethyl-5-[4-(trifluoromethyl)phenyl]thiophen-3-yl}methanol

To a solution of 2-ethyl-5-[4-(trifluoromethyl)phenyl]thiophene-3-carbaldehyde (2.00 g) synthesized above in tetrahydrofuran (40 mL) was added dropwise 1.0M cyclohexylmagnesium bromide-tetrahydrofuran solution (14.1 mL) at 0° C., and the mixture was stirred for 1 hr. Saturated aqueous ammonium chloride solution was added to quench the reaction, and the mixture was extracted with ethyl acetate. The extract was washed with brine, dried over magnesium sulfate, and concentrated under reduced pressure. The residue was purified by silica gel column chromatography (hexane to ethyl acetate:hexane=1:4, volume ratio) to give the title compound (2.29 g, 88%) as a yellow oil.

$^1$H NMR (300 MHz, CDCl$_3$) δ ppm 0.82-0.97 (m, 1H) 1.00-1.36 (m, 7H) 1.38-1.48 (m, 1H) 1.59-1.74 (m, 3H) 1.74-1.86 (m, 2H) 2.08-2.19 (m, 1H) 2.72-2.95 (m, 2H) 4.44 (dd, J=8.1, 2.7 Hz, 1H) 7.29 (s, 1H) 7.58 (d, J=8.4 Hz, 2H) 7.65 (d, J=8.4 Hz, 2H)

(8) 4-(cyclohexyl{2-ethyl-5-[4-(trifluoromethyl)phenyl]thiophen-3-yl}methoxy)benzoic acid To a mixture of cyclohexyl{2-ethyl-5-[4-(trifluoromethyl)phenyl]thiophen-3-yl}methanol (648 mg) synthesized above, methyl 4-hydroxybenzoate (321 mg), 1,1'-(azodicarbonyl)dipiperidine (888 mg) and tetrahydrofuran (20 mL) was added tributylphosphine (877 μL), and the mixture was stirred at room temperature for 1 hr. The reaction mixture was concentrated under reduced pressure, the precipitate was removed by filtration, and washed with diisopropyl ether. The filtrate was concentrated under reduced pressure, and the residue was purified by silica gel column chromatography (ethyl acetate:hexane=1:9, volume ratio) to give a yellow oil. To a mixture of the obtained oil, tetrahydrofuran (10 mL) and ethanol (10 mL) was added 2N aqueous sodium hydroxide solution (5 mL), and the mixture was stirred at 50° C. for 2 hr. 1N Hydrochloric acid (10 mL) was added to the reaction mixture, the organic solvent was evaporated under reduced pressure, and the mixture was extracted with ethyl acetate. The extract was washed with brine, dried over magnesium sulfate, and concentrated under reduced pressure. The residue was purified by silica gel column chromatography (ethyl acetate:hexane=1:4, volume ratio) to give the title compound (413 mg, 85%) as a white solid.

$^1$H NMR (300 MHz, CDCl$_3$) δ ppm 0.93-1.40 (m, 8H) 1.50-1.60 (m, 1H) 1.62-1.94 (m, 4H) 2.07-2.17 (m, 1H) 2.80-3.03 (m, 3H) 4.95 (d, J=7.5 Hz, 1H) 6.85 (d, J=9.0 Hz, 2H) 7.16 (s, 1H) 7.54 (d, J=8.7 Hz, 2H) 7.59 (d, J=8.7 Hz, 2H) 7.93 (d, J=9.0 Hz, 2H)

(9) 3-({[4-(cyclohexyl{2-ethyl-5-[4-(trifluoromethyl)phenyl]thiophen-3-yl}methoxy)phenyl]carbonyl}amino)propanoic acid To a mixture of 4-(cyclohexyl{2-ethyl-5-[4-(trifluoromethyl)phenyl]thiophen-3-yl}methoxy)benzoic acid (251 mg) synthesized above, ethyl β-alaninate hydrochloride (94.8 mg), 1-hydroxybenzotriazole monohydrate (94.5 mg), triethylamine (86.0 μL) and N,N-dimethylformamide (10 mL) was added 1-ethyl-3-(3-dimethylaminopropyl)carbodiimide hydrochloride (118 mg), and the mixture was stirred at room temperature for 3 hr. Saturated aqueous ammonium chloride solution was added to quench the reaction, and the mixture was extracted with ethyl acetate. The extract was washed with brine, dried over magnesium sulfate, and concentrated under reduced pressure. The residue was purified by silica gel column chromatography (hexane to ethyl acetate:hexane=2:3, volume ratio) to give a colorless oil. To a mixture of the obtained oil, tetrahydrofuran (5 mL) and ethanol (5 mL) was added 1N aqueous sodium hydroxide solution (2 mL), and the mixture was stirred at room temperature for 1 hr. 1N Hydrochloric acid (2.5 mL) was added to the reaction mixture, the organic solvent was evaporated under reduced pressure, and the mixture was extracted with ethyl acetate. The extract was washed with water and brine, dried over magnesium sulfate and concentrated under reduced pressure to give a white solid. The solid was recrystallized from ethyl acetate-hexane to give the title compound (117 mg, 40%) as a colorless crystal.

$^1$H NMR (300 MHz, CDCl$_3$) δ ppm 0.98-1.39 (m, 8H) 1.49-1.60 (m, 1H) 1.63-1.95 (m, 4H) 2.07-2.18 (m, 1H) 2.67 (t, J=5.7 Hz, 2H) 2.78-3.02 (m, 2H) 3.62-3.72 (m, 2H) 4.92 (d, J=7.3 Hz, 1H) 6.62 (t, J=6.0 Hz, 1H) 6.83 (d, J=8.9 Hz, 2H) 7.16 (s, 1H) 7.51-7.65 (m, 6H)

Example 70

3-[{[4-(cyclohexyl{2-ethyl-5-[4-(trifluoromethyl)phenyl]thiophen-3-yl}methoxy)phenyl]carbonyl}(methyl)amino]propanoic acid

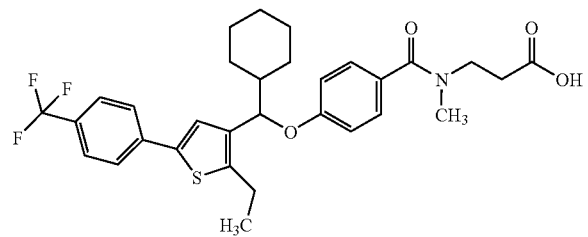

An operation similar to that in Example 69-(9) was performed using 4-(cyclohexyl{2-ethyl-5-[4-(trifluoromethyl)phenyl]thiophen-3-yl}methoxy)benzoic acid (250 mg) synthesized in Example 69 (8) and ethyl 3-(methylamino)propanoate (80.5 mg) to give the title compound (147 mg, 50%).

$^1$H NMR (300 MHz, CDCl$_3$) δ ppm 0.98-1.39 (m, 8H) 1.48-1.59 (m, 1H) 1.62-1.94 (m, 4H) 2.07-2.19 (m, 1H) 2.59-2.77 (m, 2H) 2.78-3.01 (m, 2H) 3.02 (s, 3H) 3.65-3.77 (m, 2H) 4.89 (d, J=7.5 Hz, 1H) 6.82 (d, J=8.9 Hz, 2H) 7.19 (s, 1H) 7.29 (d, J=8.5 Hz, 2H) 7.52-7.64 (m, 4H)

Example 71

3-[({4-[(cyclohexyl{2-ethyl-5-[4-(trifluoromethyl)phenyl]thiophen-3-yl}methyl)amino]phenyl}carbonyl)amino]propanoic acid

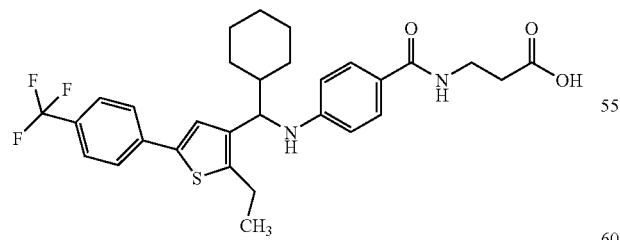

(1) 3-[chloro(cyclohexyl)methyl]-2-ethyl-5-[4-(trifluoromethyl)phenyl]thiophene

To a solution of cyclohexyl{2-ethyl-5-[4-(trifluoromethyl)phenyl]thiophen-3-yl}methanol (2.29 g) synthesized in Example 69 (7) in toluene (25 mL) was added thionyl chloride (907 μL), and the mixture was stirred at 100° C. for 1 hr. The reaction mixture was cooled to 0° C., saturated aqueous sodium hydrogen carbonate solution was added to quench the reaction, and the mixture was extracted with ethyl acetate. The extract was washed with brine, dried over magnesium sulfate, and concentrated under reduced pressure. The residue was purified by silica gel column chromatography (ethyl acetate:hexane=1:4, volume ratio) to give the title compound (2.08 g, 86%) as a pale-brown solid.

$^1$H NMR (300 MHz, CDCl$_3$) δ ppm 0.80-1.48 (m, 8H) 1.49-1.97 (m, 5H) 2.22-2.37 (m, 1H) 2.71-2.91 (m, 2H) 4.70 (d, J=9.6 Hz, 1H) 7.30 (s, 1H) 7.59 (d, J=8.6 Hz, 2H) 7.65 (d, J=8.6 Hz, 2H)

(2) 4-[(cyclohexyl{2-ethyl-5-[4-(trifluoromethyl)phenyl]thiophen-3-yl}methyl)amino]benzoic acid To a mixture of 3-[chloro(cyclohexyl)methyl]-2-ethyl-5-[4-(trifluoromethyl)phenyl]thiophene (1.00 g) synthesized above, methyl 4-aminobenzoate (780 mg), sodium iodide (1.55 g) and N,N-dimethylacetamide (10 mL) was added sodium carbonate (547 mg), and the mixture was stirred under an argon atmosphere at 100° C. overnight. Saturated aqueous ammonium chloride solution was added to quench the reaction, and the mixture was extracted with ethyl acetate. The extract was washed with brine, dried over magnesium sulfate and concentrated under reduced pressure to give a dark-brown oil. To a mixture of the obtained oil, tetrahydrofuran (10 mL) and ethanol (10 mL) was added 1N aqueous sodium hydroxide solution (10 mL), and the mixture was stirred at 60° C. for 1 hr, and stirred with heating under reflux for 30 min. 1N Hydrochloric acid (10 mL) was added to the reaction mixture, the organic solvent was evaporated under reduced pressure, and the mixture was extracted with ethyl acetate. The extract was washed with brine, dried over magnesium sulfate, and concentrated under reduced pressure. The residue was purified by silica gel column chromatography (ethyl acetate:hexane=3:7, volume ratio) to give a brown oil. The obtained oil was dissolved in ethyl acetate, washed with 1N hydrochloric acid and brine, dried over magnesium sulfate and concentrated under reduced pressure to give the title compound (369 mg, 29%) as a pale-brown solid.

$^1$H NMR (300 MHz, CDCl$_3$) δ ppm 0.94-1.32 (m, 5H) 1.38 (t, J=7.5 Hz, 3H) 1.55-1.86 (m, 5H) 1.96-2.06 (m, 1H) 2.83-3.01 (m, 2H) 4.26 (d, J=7.5 Hz, 2H) 6.49 (d, J=8.9 Hz, 2H) 7.09 (s, 1H) 7.54 (d, J=8.7 Hz, 2H) 7.59 (d, J=8.7 Hz, 2H) 7.82 (d, J=8.9 Hz, 2H)

(3) 3-[({4-[(cyclohexyl{2-ethyl-5-[4-(trifluoromethyl)phenyl]thiophen-3-yl}methyl)amino]phenyl}carbonyl)amino]propanoic acid An operation similar to that in Example 69 (9) was performed using 4-[(cyclohexyl{2-ethyl-5-[4-(trifluoromethyl)phenyl]thiophen-3-yl}methyl)amino]benzoic acid (120 mg) synthesized above to give the title compound (75.2 mg, 55%).

$^1$H NMR (300 MHz, CDCl$_3$) δ ppm 0.94-1.30 (m, 5H) 1.38 (t, J=7.6 Hz, 3H) 1.53-1.85 (m, 5H) 1.96-2.06 (m, 1H) 2.66 (t, J=5.7 Hz, 2H) 2.80-3.03 (m, 2H) 3.60-3.70 (m, 2H) 4.23 (d, J=7.2 Hz, 1H) 6.49 (d, J=8.7 Hz, 2H) 6.54 (t, J=6.4 Hz, 1H) 7.09 (s, 1H) 7.49-7.62 (m, 6H)

Example 72

3-[({4-[(cyclohexyl{2-ethyl-5-[4-(trifluoromethyl)phenyl]thiophen-3-yl}methyl)amino]phenyl}carbonyl)(methyl)amino]propanoic acid

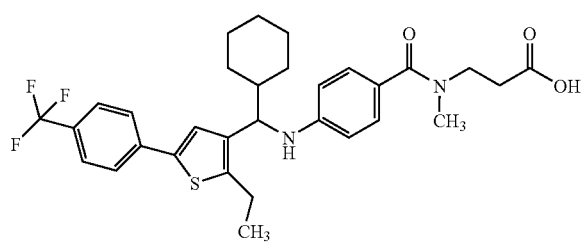

An operation similar to that in Example 69 (9) was performed using 4-[(cyclohexyl{2-ethyl-5-[4-(trifluoromethyl)phenyl]thiophen-3-yl}methyl)amino]benzoic acid (143 mg) synthesized in Example 71 (2) and ethyl 3-(methylamino)propanoate (45.9 mg) to give the title compound (77.4 mg, 46%).

$^1$H NMR (300 MHz, CDCl$_3$) δ ppm 0.93-1.31 (m, 5H) 1.37 (t, J=7.4 Hz, 3H) 1.54-1.86 (m, 5H) 1.96-2.08 (m, 1H) 2.69 (t, J=6.2 Hz, 2H) 2.80-3.03 (m, 2H) 3.06 (s, 3H) 3.71 (t, J=6.2 Hz, 2H) 4.21 (d, J=7.3 Hz, 1H) 6.48 (d, J=8.7 Hz, 2H) 7.11 (s, 1H) 7.20-7.28 (m, 2H) 7.52-7.63 (m, 4H)

Example 73

3-{[(4-{cyclohexyl[2-ethyl-5-(1-ethylpropyl)thiophen-3-yl]methoxy}phenyl)carbonyl]amino}propanoic acid

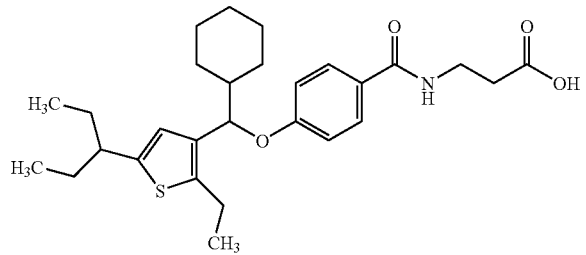

(1) ethyl 2-ethyl-5-(1-ethyl-1-hydroxypropyl)thiophene-3-carboxylate

To a solution of ethyl 5-bromo-2-ethylthiophene-3-carboxylate (3.00 g) synthesized in Example 69 (4) in tetrahydrofuran (50 mL) was added dropwise 1.0M isopropylmagnesium bromide-tetrahydrofuran solution (13.7 mL) at −45° C. After stirring under an argon atmosphere for 1 hr, 1.0M isopropylmagnesium bromide-tetrahydrofuran solution (13.7 mL) was added dropwise, and the mixture was stirred for 1 hr. 3-Heptanone (6.04 mL) was added dropwise, and the mixture was stirred at −45° C. for 1 hr, and at room temperature for 1 hr. Saturated aqueous ammonium chloride solution was added to quench the reaction, and the mixture was extracted with ethyl acetate. The extract was washed with brine, dried over magnesium sulfate, and concentrated under reduced pressure. The residue was purified by silica gel column chromatography (ethyl acetate:hexane=3:17, volume ratio) to give the title compound (3.06 g, quantitative) as a colorless oil.

$^1$H NMR (300 MHz, CDCl$_3$) δ ppm 0.87 (t, J=7.5 Hz, 6H) 1.31 (t, J=7.5 Hz, 3H) 1.36 (t, J=7.2 Hz, 3H) 1.79-1.89 (m, 4H) 3.17 (q, J=7.5 Hz, 2H) 4.29 (q, J=7.2 Hz, 2H) 7.12 (s, 1H)

(2) ethyl 2-ethyl-5-(1-ethylpropyl)thiophene-3-carboxylate

To a solution of ethyl 2-ethyl-5-(1-ethyl-1-hydroxypropyl)thiophene-3-carboxylate (3.71 g) synthesized above in trifluoroacetic acid (35 mL) was added triethylsilane (6.61 mL), and the mixture was stirred at room temperature for 2 hr and concentrated under reduced pressure. The residue was purified by silica gel column chromatography (hexane alone) to give the title compound (2.28 g, 65%) as a colorless oil.

$^1$H NMR (300 MHz, CDCl$_3$) δ ppm 0.85 (t, J=7.4 Hz, 6H) 1.30 (t, J=7.5 Hz, 3H) 1.36 (t, J=7.2 Hz, 3H) 1.44-1.76 (m, 4H) 2.49-2.60 (m, 1H) 3.16 (q, J=7.5 Hz, 2H) 4.28 (q, J=7.2 Hz, 2H) 7.04 (s, 1H)

(3) 2-ethyl-5-(1-ethylpropyl)thiophene-3-carbaldehyde

To a solution (40 mL) of ethyl 2-ethyl-5-(1-ethylpropyl)thiophene-3-carboxylate (1.98 g) synthesized above in tetrahydrofuran was added 1.5M diisobutylaluminum hydride-toluene solution (15.5 mL) at 0° C., and the mixture was stirred for 1 hr. 1N Hydrochloric acid was added to quench the reaction, and the mixture was extracted with ethyl acetate. The extract was washed with 1N hydrochloric acid and brine, dried over magnesium sulfate and concentrated under reduced pressure to give a colorless oil. To a solution of the obtained oil in tetrahydrofuran (40 mL) was added activated manganese dioxide (10.0 g), and the mixture was stirred at room temperature overnight. Manganese dioxide was filtered off, and the filtrate was concentrated under reduced pressure. The residue was purified by silica gel column chromatography (ethyl acetate:hexane=1:19, volume ratio) to give the title compound (1.40 g, 86%) as a yellow oil.

$^1$H NMR (300 MHz, CDCl$_3$) δ ppm 0.85 (t, J=7.2 Hz, 6H) 1.36 (t, J=7.5 Hz, 3H) 1.42-1.78 (m, 4H) 2.51-2.63 (m, 1H) 3.17 (q, J=7.5 Hz, 2H) 7.03 (s, 1H) 9.95 (s, 1H)

(4) cyclohexyl[2-ethyl-5-(1-ethylpropyl)thiophen-3-yl]methanol

An operation similar to that in Example 69 (7) was performed using 2-ethyl-5-(1-ethylpropyl)thiophene-3-carbaldehyde (1.63 g) synthesized above to give the title compound (1.44 g, 63%).

$^1$H NMR (300 MHz, CDCl$_3$) δ ppm 0.79-0.88 (m, 6H) 0.96-1.39 (m, 9H) 1.42-1.83 (m, 9H) 2.06-2.16 (m, 1H) 2.49-2.60 (m, 1H) 2.64-2.86 (m, 2H) 4.35 (dd, J=8.3, 3.2 Hz, 1H) 6.59 (s, 1H)

(5)-4-{cyclohexyl[2-ethyl-5-(1-ethylpropyl)thiophen-3-yl]methoxy}benzoic acid An operation similar to that in Example 69 (8) was performed using cyclohexyl[2-ethyl-5-(1-ethylpropyl)thiophen-3-yl]methanol (440 mg) synthesized above to give the title compound (458 mg, 74%).

$^1$H NMR (300 MHz, CDCl$_3$) δ ppm 0.70 (t, J=7.2 Hz, 3H) 0.77 (t, J=7.2 Hz, 3H) 0.78-0.89 (m, 1H) 0.95-1.31 (m, 8H) 1.38-1.91 (m, 9H) 2.04-2.14 (m, 1H) 2.41-2.52 (m, 1H) 2.69-2.90 (m, 2H) 4.87 (d, J=7.5 Hz, 1H) 6.47 (s, 1H) 6.81 (d, J=8.7 Hz, 2H) 7.91 (d, J=8.7 Hz, 2H)

(6) 3-{[(4-{cyclohexyl[2-ethyl-5-(1-ethylpropyl)thiophen-3-yl]methoxy}phenyl)carbonyl]amino}propanoic acid An operation similar to that in Example 69 (9) was performed using 4-{cyclohexyl[2-ethyl-5-(1-ethylpropyl)thiophen-3-yl]methoxy}benzoic acid (200 mg) synthesized above to give the title compound (124 mg, 53%).

$^1$H NMR (300 MHz, CDCl$_3$) δ ppm 0.69 (t, J=7.3 Hz, 3H) 0.75 (t, J=7.3 Hz, 3H) 0.90-1.31 (m, 8H) 1.33-1.89 (m, 9H) 2.01-2.12 (m, 1H) 2.25-2.37 (m, 2H) 2.38-2.51 (m, 1H) 2.60-2.86 (m, 2H) 3.35-3.51 (m, 2H) 4.79 (d, J=7.3 Hz, 1H) 6.47 (s, 1H) 6.71 (d, J=8.7 Hz, 2H) 6.95-7.08 (m, 1H) 7.57 (d, J=8.7 Hz, 2H)

Example 74

3-{[(4-{cyclohexyl[2-ethyl-5-(1-ethylpropyl)thiophen-3-yl]methoxy}phenyl)carbonyl](methyl)amino}propanoic acid

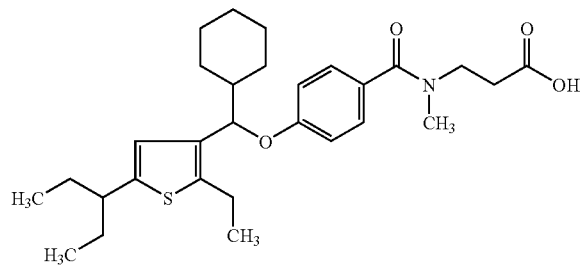

An operation similar to that in Example 69 (9) was performed using 4-{cyclohexyl[2-ethyl-5-(1-ethylpropyl)thiophen-3-yl]methoxy}benzoic acid (212 mg) synthesized in Example 73 (5) and ethyl 3-(methylamino)propanoate (80.4 mg) to give the title compound (99.2 mg, 39%).

$^1$H NMR (300 MHz, CDCl$_3$) δ ppm 0.71 (t, J=7.3 Hz, 3H) 0.77 (t, J=7.3 Hz, 3H) 0.92-1.31 (m, 8H) 1.35-1.89 (m, 9H) 2.03-2.15 (m, 1H) 2.34-2.54 (m, 3H) 2.64-2.94 (m, 5H) 3.52-3.68 (m, 2H) 4.79 (d, J=7.3 Hz, 1H) 6.49 (s, 1H) 6.74 (d, J=8.8 Hz, 2H) 7.19 (d, J=8.8 Hz, 2H)

Example 75

3-({[4-({cyclohexyl[2-ethyl-5-(1-ethylpropyl)thiophen-3-yl]methyl}amino)phenyl]carbonyl}amino)propanoic acid

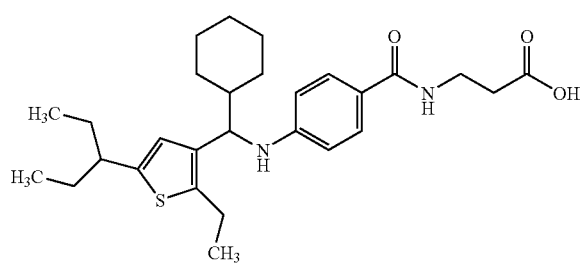

(1) 3-[chloro(cyclohexyl)methyl]-2-ethyl-5-(1-ethylpropyl)thiophene

An operation similar to that in Example 71 (1) was performed using cyclohexyl[2-ethyl-5-(1-ethylpropyl)thiophen-3-yl]methanol (1.00 g) synthesized in Example 73 (4) to give the title compound (1.05 g, 99%).

$^1$H NMR (300 MHz, CDCl$_3$) δ ppm 0.74-0.89 (m, 7H) 0.95-1.32 (m, 7H) 1.41-1.92 (m, 9H) 2.23-2.43 (m, 1H) 2.49-2.60 (m, 1H) 2.63-2.84 (m, 2H) 4.65 (d, J=9.0 Hz, 1H) 6.62 (s, 1H)

(2) 4-({cyclohexyl[2-ethyl-5-(1-ethylpropyl)thiophen-3-yl]methyl}amino)benzoic acid An operation similar to that in Example 71 (2) was performed using 3-[chloro(cyclohexyl)methyl]-2-ethyl-5-(1-ethylpropyl)thiophene (1.05 g) synthesized above to give the title compound (691 mg, 50%).

$^1$H NMR (300 MHz, CDCl$_3$) δ ppm 0.70-0.82 (m, 6H) 0.90-1.33 (m, 8H) 1.36-1.83 (m, 9H) 1.90-2.03 (m, 1H) 2.41-2.54 (m, 1H) 2.69-2.92 (m, 2H) 4.21 (d, J=7.2 Hz, 1H) 6.42 (s, 1H) 6.48 (d, J=8.7 Hz, 2H) 7.82 (d, J=8.7 Hz, 2H)

(3) 3-({[4-({cyclohexyl[2-ethyl-5-(1-ethylpropyl)thiophen-3-yl]methyl}amino)phenyl]carbonyl}amino)propanoic acid An operation similar to that in Example 69 (9) was performed using 4-({cyclohexyl[2-ethyl-5-(1-ethylpropyl)thiophen-3-yl]methyl}amino)benzoic acid (263 mg) synthesized above to give the title compound (186 mg, 60%).

$^1$H NMR (300 MHz, CDCl$_3$) δ ppm 0.67-0.83 (m, 6H) 0.90-1.31 (m, 9H) 1.35-1.82 (m, 9H) 1.90-2.03 (m, 1H) 2.40-2.52 (m, 1H) 2.61 (t, J=5.6 Hz, 2H) 2.68-2.90 (m, 2H) 3.57-3.69 (m, 2H) 4.16 (d, J=7.5 Hz, 1H) 6.42 (s, 1H) 6.46 (d, J=8.7 Hz, 2H) 6.62 (t, J=5.8 Hz, 1H) 7.51 (d, J=8.7 Hz, 2H)

Example 76

3-[{[4-({cyclohexyl[2-ethyl-5-(1-ethylpropyl)thiophen-3-yl]methyl}amino)phenyl]carbonyl}(methyl)amino]propanoic acid

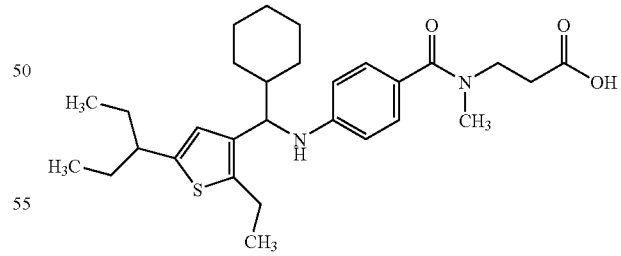

An operation similar to that in Example 69 (9) was performed using 4-({cyclohexyl[2-ethyl-5-(1-ethylpropyl)thiophen-3-yl]methyl}amino)benzoic acid (250 mg) synthesized in Example 75 (2) and ethyl 3-(methylamino)propanoate (95.1 mg) to give the title compound (186 mg, 62%).

$^1$H NMR (300 MHz, CDCl$_3$) δ ppm 0.73 (t, J=6.7 Hz, 3H) 0.78 (t, J=6.7 Hz, 3H) 0.90-1.33 (m, 9H) 1.36-1.83 (m, 9H) 1.91-2.03 (m, 1H) 2.41-2.53 (m, 1H) 2.64-2.92 (m, 4H) 3.06

(s, 3H) 3.72 (t, J=6.1 Hz, 2H) 4.16 (d, J=7.2 Hz, 1H) 6.42 (s, 1H) 6.47 (d, J=8.6 Hz, 2H) 7.23 (d, J=8.6 Hz, 2H)

Example 77

3-[({4-[cyclohexyl(5-cyclohexyl-2-ethylthiophen-3-yl)methoxy]phenyl}carbonyl)amino]propanoic acid

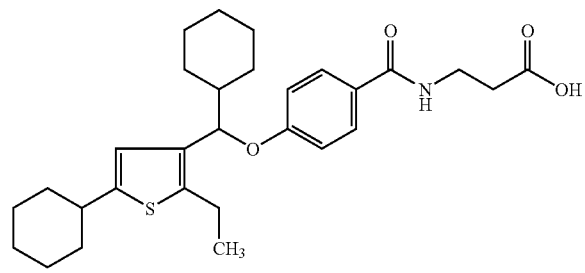

(1) (5-bromo-2-ethylthiophen-3-yl)(cyclohexyl)methanol

To a solution (40 mL) of ethyl 5-bromo-2-ethylthiophene-3-carboxylate (3.69 g) synthesized in Example 69 (4) in tetrahydrofuran was added 1.5M diisobutylaluminum hydride-toluene solution (26.4 mL) at 0° C., and the mixture was stirred for 1 hr. 1N Hydrochloric acid was added to quench the reaction, and the mixture was extracted with ethyl acetate. The extract was washed with 1N hydrochloric acid and brine, dried over magnesium sulfate and concentrated under reduced pressure to give a pale-yellow oil. To a solution of the obtained oil in tetrahydrofuran (30 mL) was added activated manganese dioxide (15.8 g), and the mixture was stirred at room temperature overnight and at 50° C. for 2 hr. Manganese dioxide was filtered off, and the filtrate was concentrated under reduced pressure to give a brown oil. To a solution of the obtained oil in tetrahydrofuran (60 mL) was added dropwise 1.0M cyclohexylmagnesium bromide-tetrahydrofuran solution (39.6 mL) at −78° C., and the mixture was stirred for 1 hr. Saturated aqueous ammonium chloride solution was added to quench the reaction, and the mixture was extracted with ethyl acetate. The extract was washed with brine, dried over magnesium sulfate, and concentrated under reduced pressure. The residue was purified by silica gel column chromatography (ethyl acetate:hexane=3:17, volume ratio) to give the title compound (2.53 g, 60%) as a yellow oil.

$^1$H NMR (300 MHz, CDCl$_3$) δ ppm 0.77-0.92 (m, 1H) 0.95-1.43 (m, 8H) 1.60-1.71 (m, 3H) 1.74-1.84 (m, 1H) 2.04-2.18 (m, 1H) 2.63-2.90 (m, 2H) 4.33-4.39 (m, 1H) 7.25 (s, 1H)

(2) methyl 4-[(5-bromo-2-ethylthiophen-3-yl) (cyclohexyl)methoxy]benzoate

To a mixture of (5-bromo-2-ethylthiophen-3-yl)(cyclohexyl)methanol (1.50 g) synthesized above, methyl 4-hydroxybenzoate (904 mg), 1,1'-(azodicarbonyl)dipiperidine (2.50 g) and tetrahydrofuran (30 mL) was added tributylphosphine (2.47 mL), and the mixture was stirred at room temperature for 3 hr. The reaction mixture was concentrated under reduced pressure, and the precipitate was removed by filtration and washed with diisopropyl ether. The filtrate was concentrated under reduced pressure, and the residue was purified by silica gel column chromatography (ethyl acetate: hexane=1:9, volume ratio) to give the title compound (1.20 g, 55%).

$^1$H NMR (300 MHz, CDCl$_3$) δ ppm 0.97-1.35 (m, 8H) 1.42-1.56 (m, 1H) 1.61-1.92 (m, 4H) 2.02-2.14 (m, 1H) 2.72-2.94 (m, 2H) 3.85 (s, 3H) 4.85 (d, J=7.5 Hz, 1H) 6.75-6.81 (m, 3H) 7.88 (d, J=8.7 Hz, 2H)

(3) methyl 4-[cyclohexyl(5-cyclohexyl-2-ethylthiophen-3-yl)methoxy]benzoate

To a solution of methyl 4-[(5-bromo-2-ethylthiophen-3-yl)(cyclohexyl)methoxy]benzoate (1.20 g) synthesized above in N-methylpyrrolidone (30 mL) were added 0.5M cyclohexylzinc bromide-tetrahydrofuran solution (8.22 mL) and bis(tri-tert-butylphosphine)palladium (70.0 mg) at 0° C., and the mixture was stirred for 1 hr under an argon atmosphere while heating to 80° C. Saturated aqueous ammonium chloride solution was added to quench the reaction, and the mixture was extracted with ethyl acetate. The extract was washed with brine, dried over magnesium sulfate, and concentrated under reduced pressure. The residue was purified by silica gel column chromatography (ethyl acetate:hexane=1:19, volume ratio) to give the title compound (0.56 g, 46%) as a colorless oil.

$^1$H NMR (300 MHz, CDCl$_3$) δ 0.93-1.41 (m, 12H) 1.44-1.52 (m, 1H) 1.62-1.88 (m, 8H) 1.90-2.00 (m, 2H) 2.02-2.13 (m, 1H) 2.56-2.68 (m, 1H) 2.69-2.94 (m, 2H) 3.84 (s, 3H) 4.85 (d, J=7.5 Hz, 1H) 6.50 (s, 1H) 6.79 (d, J=8.7 Hz, 2H) 7.86 (d, J=8.7 Hz, 2H)

(4) 4-[cyclohexyl(5-cyclohexyl-2-ethylthiophen-3-yl)methoxy]benzoic acid

To a mixture of methyl 4-[cyclohexyl(5-cyclohexyl-2-ethylthiophen-3-yl)methoxy]benzoate (560 mg) synthesized above, tetrahydrofuran (10 mL) and ethanol (10 mL) was added 1N aqueous sodium hydroxide solution (5 mL), and the mixture was stirred with heating under reflux overnight. The reaction mixture was concentrated under reduced pressure, 1N hydrochloric acid was added, and the mixture was extracted with ethyl acetate. The extract was washed with brine, dried over magnesium sulfate and concentrated under reduced pressure to give a white solid. The obtained solid was recrystallized from ethyl acetate-hexane to give the title compound (194 mg, 36%) as a colorless crystal.

$^1$H NMR (300 MHz, CDCl$_3$) δ ppm 0.93-1.42 (m, 12H) 1.43-1.88 (m, 9H) 1.90-2.01 (m, 2H) 2.03-2.15 (m, 1H) 2.55-2.69 (m, 1H) 2.70-2.97 (m, 2H) 4.87 (d, J=7.6 Hz, 1H) 6.51 (s, 1H) 6.82 (d, J=9.1 Hz, 2H) 7.92 (d, J=9.1 Hz, 2H)

(5) 3-[({4-[cyclohexyl(5-cyclohexyl-2-ethylthiophen-3-yl)methoxy]phenyl}carbonyl)amino]propanoic acid An operation similar to that in Example 69 (9) was performed using 4-[cyclohexyl(5-cyclohexyl-2-ethylthiophen-3-yl)methoxy]benzoic acid (200 mg) synthesized above to give the title compound (113 mg, 48%).

$^1$H NMR (300 MHz, CDCl$_3$) δ ppm 0.90-1.39 (t, 13H) 1.41-1.51 (m, 1H) 1.59-1.84 (m, 7H) 1.88-1.99 (m, 2H) 2.01-2.12 (m, 1H) 2.37-2.50 (m, 2H) 2.53-2.89 (m, 3H) 3.47-3.57

(m, 2H) 4.80 (d, J=7.6 Hz, 1H) 6.50 (s, 1H) 6.74 (d, J=8.7 Hz, 2H) 6.76-6.87 (m, 1H) 7.56 (d, J=8.7 Hz, 2H)

Example 78

3-[({4-[cyclohexyl(5-cyclohexyl-2-ethylthiophen-3-yl)methoxy]phenyl}carbonyl)(methyl)amino]propanoic acid

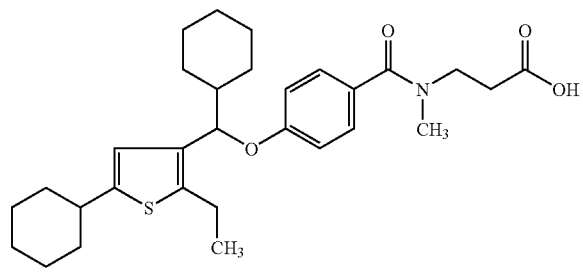

An operation similar to that in Example 69 (9) was performed using 4-[cyclohexyl(5-cyclohexyl-2-ethylthiophen-3-yl)methoxy]benzoic acid (200 mg) synthesized in Example 77 (4) and ethyl 3-(methylamino)propanoate (73.8 mg) to give the title compound (103 mg, 43%).
$^1$H NMR (300 MHz, CDCl$_3$) δ ppm 0.92-1.53 (m, 14H) 1.60-1.86 (m, 7H) 1.91-2.01 (m, 2H) 2.03-2.14 (m, 1H) 2.57-2.90 (m, 5H) 3.00 (s, 3H) 3.64-3.77 (m, 2H) 4.80 (d, J=7.6 Hz, 1H) 6.52 (s, 1H) 6.78 (d, J=8.7 Hz, 2H) 7.26 (d, J=8.7 Hz, 2H)

Example 79

3-{[(4-{[cyclohexyl(5-cyclohexyl-2-ethylthiophen-3-yl)methyl]amino}phenyl)carbonyl]amino}propanoic acid

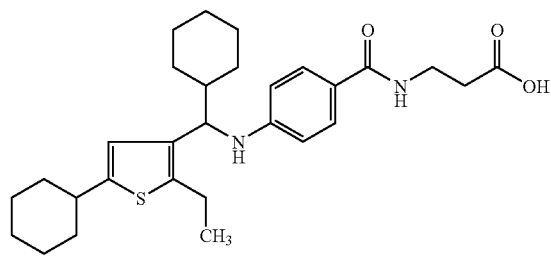

(1) cyclohexyl(5-cyclohexyl-2-ethylthiophen-3-yl)methanol

An operation similar to that in Example 77 (3) was performed using (5-bromo-2-ethylthiophen-3-yl)(cyclohexyl)methanol (1.03 g) synthesized in Example 77 (1) to give the title compound (562 mg, 54%).
$^1$H NMR (300 MHz, CDCl$_3$) δ ppm 0.74-0.91 (m, 1H) 0.95-1.48 (m, 13H) 1.54-1.84 (m, 8H) 1.98-2.16 (m, 3H) 2.63-2.85 (m, 3H) 4.35 (dd, J=8.1, 3.0 Hz, 1H) 6.63 (s, 1H)

(2) 3-[chloro(cyclohexyl)methyl]-5-cyclohexyl-2-ethylthiophene

An operation similar to that in Example 71 (1) was performed using cyclohexyl(5-cyclohexyl-2-ethylthiophen-3-yl)methanol (562 mg) synthesized above to give the title compound (596 mg, quantitative).
$^1$H NMR (300 MHz, CDCl$_3$) δ ppm 0.74-0.89 (m, 1H) 0.95-1.56 (m, 13H) 1.60-1.87 (m, 7H) 1.98-2.07 (m, 2H) 2.22-2.33 (m, 1H) 2.62-2.83 (m, 3H) 4.65 (d, J=9.3 Hz, 1H) 6.65 (s, 1H)

(3) 4-{[cyclohexyl(5-cyclohexyl-2-ethylthiophen-3-yl)methyl]amino}benzoic acid

An operation similar to that in Example 71 (2) was performed using 3-[chloro(cyclohexyl)methyl]-5-cyclohexyl-2-ethylthiophene (596 mg) synthesized above to give the title compound (584 mg, 75%).
$^1$H NMR (300 MHz, CDCl$_3$) δ ppm 0.83-1.43 (m, 12H) 1.46-1.83 (m, 9H) 1.91-2.03 (m, 3H) 2.58-2.93 (m, 3H) 4.21 (d, J=7.6 Hz, 1H) 6.45 (s, 1H) 6.48 (d, J=8.9 Hz, 2H) 7.82 (d, J=8.9 Hz, 2H)

(4) 3-{[(4-{[cyclohexyl(5-cyclohexyl-2-ethylthiophen-3-yl)methyl]amino}phenyl)carbonyl]amino}propanoic acid An operation similar to that in Example 69 (9) was performed using 4-{[cyclohexyl(5-cyclohexyl-2-ethylthiophen-3-yl)methyl]amino}benzoic acid (254 mg) synthesized above to give the title compound (89.2 mg, 30%).
$^1$H NMR (300 MHz, CDCl$_3$) δ ppm 0.86-1.42 (m, 13H) 1.45-1.83 (m, 8H) 1.90-2.02 (m, 3H) 2.57-2.90 (m, 5H) 3.58-3.68 (m, 2H) 4.16 (d, J=7.6 Hz, 1H) 6.41-6.50 (m, 3H) 6.55-6.63 (m, 1H) 7.51 (d, J=8.7 Hz, 2H)

Example 80

3-{[(4-{[cyclohexyl(5-cyclohexyl-2-ethylthiophen-3-yl)methyl]amino}phenyl)carbonyl](methyl)amino}propanoic acid

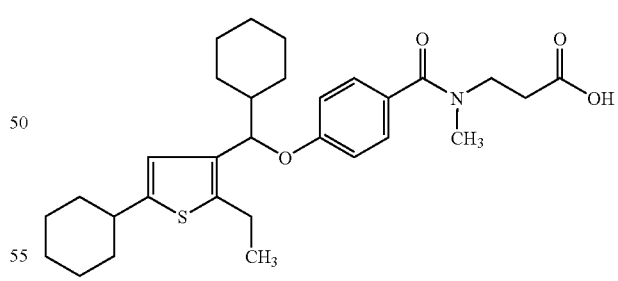

An operation similar to that in Example 69 (9) was performed using 4-{[cyclohexyl(5-cyclohexyl-2-ethylthiophen-3-yl)methyl]amino}benzoic acid (233 mg) synthesized in Example 79 (3) and ethyl 3-(methylamino)propanoate (86.0 mg) to give the title compound (208 mg, 74%).
$^1$H NMR (300 MHz, CDCl$_3$) δ ppm 0.89-1.43 (m, 13H) 1.45-1.84 (m, 8H) 1.89-2.04 (m, 3H) 2.55-2.92 (m, 5H) 3.07 (s, 3H) 3.72 (t, J=6.5 Hz, 2H) 4.15 (d, J=7.3 Hz, 1H) 6.41-6.50 (m, 3H) 7.24 (d, J=8.7 Hz, 2H)

Example 81

3-{[(4-{cyclohexyl[2-ethyl-5-(2-methylpropyl) thiophen-3-yl]methoxy}phenyl)carbonyl] amino}propanoic acid

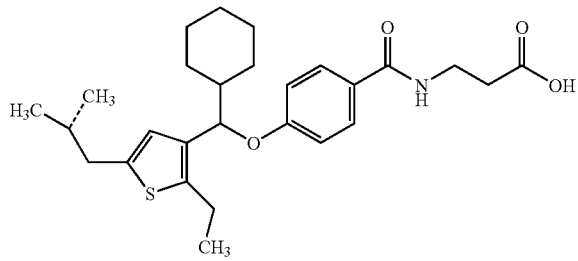

(1) ethyl 2-ethyl-5-(2-methylpropyl)thiophene-3-carboxylate

To a solution of ethyl 5-bromo-2-ethylthiophene-3-carboxylate (5.00 g) synthesized in Example 69 (4) in tetrahydrofuran (50 mL) was added dropwise 1.0M isopropylmagnesium bromide-tetrahydrofuran solution (28.5 mL) at −40° C., and the mixture was stirred for 1.5 hr under an argon atmosphere. Isobutylaldehyde (8.67 mL) was added dropwise, and the mixture was stirred at −40° C. for 1 hr and at room temperature for 1 hr. Saturated aqueous ammonium chloride solution was added to quench the reaction, and the mixture was extracted with ethyl acetate. The extract was washed with brine, dried over magnesium sulfate, and concentrated under reduced pressure. To a solution of the residue in trifluoroacetic acid (50 mL) was added triethylsilane (9.10 mL), and the mixture was stirred at room temperature for 3 hr, and concentrated under reduced pressure. The residue was purified by silica gel column chromatography (ethyl acetate: hexane=1:24, volume ratio) to give the title compound (3.67 g, 80%) as a pale-yellow oil.

$^1$H NMR (300 MHz, CDCl$_3$) δ ppm 0.94 (d, J=6.6 Hz, 6H) 1.29 (t, J=7.5 Hz, 3H) 1.35 (t, J=7.2 Hz, 3H) 1.77-1.93 (m, 1H) 2.57 (d, J=6.6 Hz, 2H) 3.15 (q, J=7.5 Hz, 2H) 4.28 (q, J=7.2 Hz, 2H) 7.02 (s, 1H)

(2) 2-ethyl-5-(2-methylpropyl)thiophene-3-carbaldehyde

An operation similar to that in Example 73 (3) was performed using ethyl 2-ethyl-5-(2-methylpropyl)thiophene-3-carboxylate (3.67 g) synthesized above to give the title compound (2.18 g, 73%).

$^1$H NMR (300 MHz, CDCl$_3$) δ ppm 0.94 (d, J=6.6 Hz, 6H) 1.36 (t, J=7.5 Hz, 3H) 1.78-1.94 (m, 1H) 2.57-2.62 (m, 1H) 3.16 (q, J=7.5 Hz, 2H) 7.01 (s, 1H) 9.95 (s, 1H)

(3) cyclohexyl[2-ethyl-5-(2-methylpropyl)thiophen-3-yl]methanol

An operation similar to that in Example 69 (7) was performed using 2-ethyl-5-(2-methylpropyl)thiophene-3-carbaldehyde (2.18 g) synthesized above to give the title compound (2.53 g, 81%).

$^1$H NMR (300 MHz, CDCl$_3$) δ ppm 0.76-1.41 (m, 16H) 1.54-1.70 (m, 3H) 1.74-1.89 (m, 2H) 2.07-2.16 (m, 1H) 2.58 (d, J=6.6 Hz, 2H) 2.65-2.83 (m, 2H) 4.35 (dd, J=8.3, 3.2 Hz, 1H) 6.59 (s, 1H)

(4) 4-{cyclohexyl[2-ethyl-5-(2-methylpropyl) thiophen-3-yl]methoxy}benzoic acid An operation similar to that in Example 69 (8) was performed using cyclohexyl[2-ethyl-5-(2-methylpropyl) thiophen-3-yl]methanol (700 mg) synthesized above to give the title compound (713 mg, 71%).

$^1$H NMR (300 MHz, CDCl$_3$) δ ppm 0.83 (d, J=6.8 Hz, 3H) 0.86 (d, J=6.8 Hz, 3H) 0.93-1.32 (m, 9H) 1.44-1.90 (m, 5H) 2.03-2.14 (m, 1H) 2.51 (d, J=7.2 Hz, 2H) 2.69-2.93 (m, 2H) 4.88 (d, J=7.6 Hz, 1H) 6.48 (s, 1H) 6.82 (d, J=8.7 Hz, 2H) 7.92 (d, J=8.7 Hz, 2H)

(5) 3-{[(4-{cyclohexyl[2-ethyl-5-(2-methylpropyl) thiophen-3-yl]methoxy}phenyl)carbonyl] amino}propanoic acid An operation similar to that in Example 69 (9) was performed using 4-{cyclohexyl[2-ethyl-5-(2-methylpropyl) thiophen-3-yl]methoxy}benzoic acid (258 mg) synthesized above to give the title compound (173 mg, 57%).

$^1$H NMR (300 MHz, CDCl$_3$) δ ppm 0.76-0.90 (m, 6H) 0.92-1.32 (m, 9H) 1.43-1.54 (m, 1H) 1.60-1.89 (m, 4H) 2.03-2.13 (m, 1H) 2.45-2.55 (m, 4H) 2.66-2.90 (m, 2H) 3.52-3.63 (m, 2H) 4.82 (d, J=7.5 Hz, 1H) 6.47 (s, 1H) 6.71-6.82 (m, 3H) 7.57 (d, J=8.9 Hz, 2H)

Example 82

3-{[(4-{cyclohexyl[2-ethyl-5-(2-methylpropyl) thiophen-3-yl]methoxy}phenyl)carbonyl](methyl) amino}propanoic acid

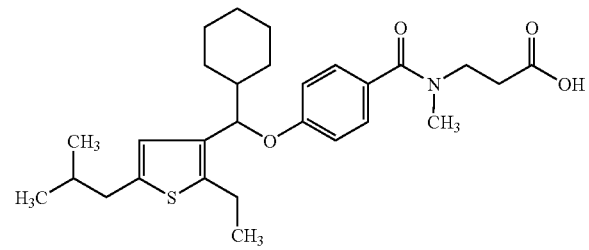

An operation similar to that in Example 69 (9) was performed using 4-{cyclohexyl[2-ethyl-5-(2-methylpropyl) thiophen-3-yl]methoxy}benzoic acid (256 mg) synthesized in Example 81 (4) and ethyl 3-(methylamino)propanoate (101 mg) to give the title compound (159 mg, 51%).

$^1$H NMR (300 MHz, CDCl$_3$) δ ppm 0.80-0.91 (m, 6H) 0.93-1.29 (m, 9H) 1.43-1.54 (m, 1H) 1.62-1.89 (m, 4H) 2.04-2.15 (m, 1H) 2.52 (d, J=7.2 Hz, 2H) 2.63-2.90 (m, 4H) 3.02 (s, 3H) 3.65-3.78 (m, 2H) 4.81 (d, J=7.5 Hz, 1H) 6.49 (s, 1H) 6.79 (d, J=8.6 Hz, 2H) 7.26 (d, J=8.6 Hz, 2H)

Example 83

3-({[4-({cyclohexyl[2-ethyl-5-(2-methylpropyl)thiophen-3-yl]methyl}amino)phenyl]carbonyl}amino)propanoic acid

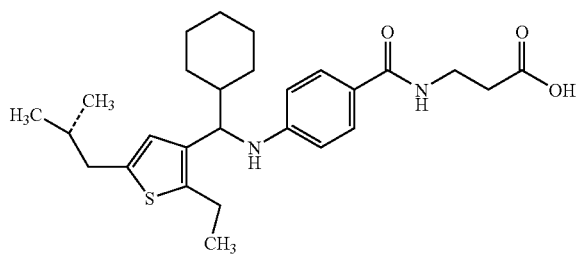

(1) 4-({cyclohexyl[2-ethyl-5-(2-methylpropyl)thiophen-3-yl]methyl}amino)benzoic acid To a solution of cyclohexyl[2-ethyl-5-(2-methylpropyl)thiophen-3-yl]methanol (1.25 g) synthesized in Example 81 (3) in toluene (25 mL) was added thionyl chloride (650.7 μL), and the mixture was stirred at 100° C. for 1 hr. The reaction mixture was cooled to 0° C., saturated aqueous sodium hydrogen carbonate solution was added to quench the reaction, and the mixture was extracted with ethyl acetate. The extract was washed with brine, dried over magnesium sulfate, and concentrated under reduced pressure. To a mixture of the residue, methyl 4-aminobenzoate (1.35 g), sodium iodide (1.34 g) and N,N-dimethylacetamide (20 mL) was added sodium carbonate (945 mg), and the mixture was stirred under an argon atmosphere at 100° C. overnight. 1N Hydrochloric acid was added to quench the reaction, and the mixture was extracted with ethyl acetate. The extract was washed with 1N hydrochloric acid and brine, dried over magnesium sulfate, and concentrated under reduced pressure. The residue was purified by silica gel column chromatography (ethyl acetate:hexane=1:9, volume ratio) to give a pale-brown oil. To a mixture of the obtained oil, tetrahydrofuran (10 mL) and ethanol (10 mL) was added 1N aqueous sodium hydroxide solution (10 mL), and the mixture was stirred with heating under reflux overnight. The reaction mixture was acidified with 1N hydrochloric acid, and extracted with ethyl acetate. The extract was washed with brine, dried over magnesium sulfate, and concentrated under reduced pressure. The residue was purified by silica gel column chromatography (ethyl acetate:hexane=1:3, volume ratio) to give a pale-brown solid. The obtained solid was recrystallized from ethyl acetate-hexane to give the title compound (528 mg, 30%) as a white solid.

$^1$H NMR (300 MHz, CDCl$_3$) δ ppm 0.83-0.90 (m, 6H) 0.91-1.33 (m, 8H) 1.47-1.84 (m, 6H) 1.92-2.03 (m, 1H), 2.52 (d, J=7.0 Hz, 2H) 2.69-2.93 (m, 2H) 4.21 (d, J=7.5 Hz, 1H) 6.41 (s, 1H) 6.48 (d, J=8.8 Hz, 2H) 7.82 (d, J=8.8 Hz, 2H)

(2) 3-({[4-({cyclohexyl[2-ethyl-5-(2-methylpropyl)thiophen-3-yl]methyl}amino)phenyl]carbonyl}amino)propanoic acid An operation similar to that in Example 69 (9) was performed using 4-({cyclohexyl[2-ethyl-5-(2-methylpropyl)thiophen-3-yl]methyl}amino)benzoic acid (250 mg) synthesized above to give the title compound (132 mg, 45%).

$^1$H NMR (300 MHz, CDCl$_3$) δ ppm 0.82-0.89 (m, 6H) 0.91-1.33 (m, 8H) 1.46-1.84 (m, 6H) 1.92-2.02 (m, 1H) 2.51 (d, J=7.0 Hz, 2H) 2.58-2.68 (m, 2H) 2.68-2.91 (m, 2H) 3.59-3.71 (m, 2H) 4.16 (d, J=7.5 Hz, 1H) 6.41 (s, 1H) 6.46 (d, J=8.7 Hz, 2H) 6.55-6.68 (m, 1H) 7.51 (d, J=8.7 Hz, 2H)

Example 84

3-[{[4-({cyclohexyl[2-ethyl-5-(2-methylpropyl)thiophen-3-yl]methyl}amino)phenyl]carbonyl}(methyl)amino]propanoic acid

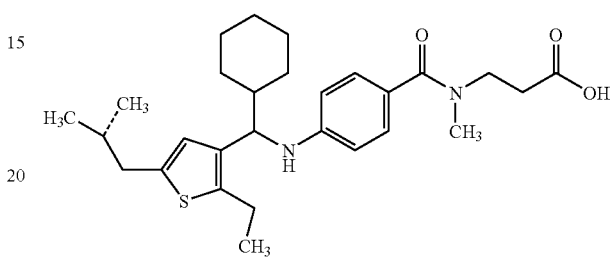

An operation similar to that in Example 69 (9) was performed using 4-({cyclohexyl[2-ethyl-5-(2-methylpropyl)thiophen-3-yl]methyl}amino)benzoic acid (250 mg) synthesized in Example 83 (1) and ethyl 3-(methylamino)propanoate (98.5 mg) to give the title compound (232 mg, 76%).

$^1$H NMR (300 MHz, CDCl$_3$) δ ppm 0.82-0.90 (m, 6H) 0.90-1.33 (m, 8H) 1.47-1.86 (m, 6H) 1.93-2.03 (m, 1H) 2.52 (d, J=7.0 Hz, 2H) 2.63-2.91 (m, 4H) 3.05 (s, 3H) 3.72 (t, J=6.5 Hz, 2H) 4.15 (d, J=7.3 Hz, 1H) 6.41 (s, 1H) 6.46 (d, J=8.6 Hz, 2H) 7.22 (d, J=8.6 Hz, 2H)

Example 85

3-{[(4-{cyclohexyl[5-(3,6-dihydro-2H-thiopyran-4-yl)-2-ethylthiophen-3-yl]methoxy}phenyl)carbonyl]amino}propanoic acid

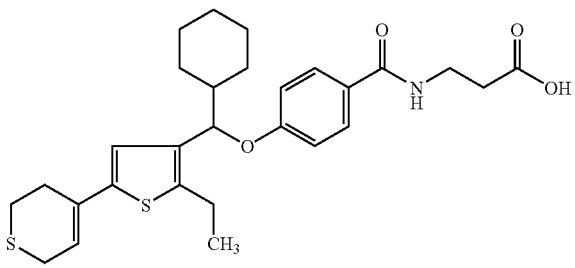

(1) ethyl 2-ethyl-5-(4-hydroxytetrahydro-2H-thiopyran-4-yl)thiophene-3-carboxylate An operation similar to that in Example 73 (1) was performed using ethyl 5-bromo-2-ethylthiophene-3-carboxylate (5.00 g) synthesized in Example 69 (4) and tetrahydro-4H-thiopyran-4-one (6.62 g) to give the title compound (4.16 g, 73%).

$^1$H NMR (300 MHz, CDCl$_3$) δ ppm 1.31 (t, J=7.5 Hz, 3H) 1.36 (t, J=7.2 Hz, 3H) 1.78 (s, 1H) 2.17-2.24 (m, 4H) 2.46-2.56 (m, 2H) 3.04-3.16 (m, 2H) 3.17 (q, J=7.5 Hz, 2H) 4.29 (q, J=7.2 Hz, 2H) 7.24 (s, 1H)

(2) 2-ethyl-5-(4-hydroxytetrahydro-2H-thiopyran-4-yl)thiophene-3-carbaldehyde An operation similar to that in Example 73 (3) was performed using ethyl 2-ethyl-5-(4-hydroxytetrahydro-2H-thiopyran-4-yl)thiophene-3-carboxylate (4.16 g) synthesized above to give the title compound (2.28 g, 64%).

$^1$H NMR (300 MHz, CDCl$_3$) δ ppm 1.38 (t, J=7.5 Hz, 3H) 1.82 (s, 1H) 2.16-2.24 (m, 4H) 2.46-2.56 (m, 2H) 3.04-3.24 (m, 4H) 7.22 (s, 1H) 9.96 (s, 1H)

(3) 4-{4-[cyclohexyl(hydroxy)methyl]-5-ethylthiophen-2-yl}tetrahydro-2H-thiopyran-4-ol An operation similar to that in Example 69 (7) was performed using 2-ethyl-5-(4-hydroxytetrahydro-2H-thiopyran-4-yl)thiophene-3-carbaldehyde (2.28 g) synthesized above to give the title compound (2.28 g, 75%).

$^1$H NMR (300 MHz, CDCl$_3$) δ ppm 0.76-0.93 (m, 1H) 0.96-1.41 (m, 8H) 1.51-1.85 (m, 6H) 2.04-2.14 (m, 1H) 2.16-2.25 (m, 4H) 2.45-2.56 (m, 2H) 2.66-2.87 (m, 2H) 3.03-3.16 (m, 2H) 4.34-4.41 (m, 1H) 6.84 (s, 1H)

(4) 4-{cyclohexyl[5-(3,6-dihydro-2H-thiopyran-4-yl)-2-ethylthiophen-3-yl]methoxy}benzoic acid An operation similar to that in Example 69 (8) was performed using 4-{4-[cyclohexyl(hydroxy)methyl]-5-ethylthiophen-2-yl}tetrahydro-2H-thiopyran-4-ol (1.01 g) synthesized above to give the title compound (706 mg, 54%).

$^1$H NMR (300 MHz, CDCl$_3$) δ ppm 0.94-1.36 (m, 8H) 1.44-1.56 (m, 1H) 1.61-1.90 (m, 4H) 2.03-2.14 (m, 1H) 2.58-2.66 (m, 2H) 2.72-2.96 (m, 4H) 3.24-3.30 (m, 2H) 4.88 (d, J=7.2 Hz, 1H) 6.16-6.22 (m, 1H) 6.74 (s, 1H) 6.82 (d, J=8.9 Hz, 2H) 7.93 (d, J=8.9 Hz, 2H)

(5) 3-{[(4-{cyclohexyl[5-(3,6-dihydro-2H-thiopyran-4-yl)-2-ethylthiophen-3-yl]methoxy}phenyl)carbonyl]amino}propanoic acid An operation similar to that in Example 69 (9) was performed using 4-{cyclohexyl[5-(3,6-dihydro-2H-thiopyran-4-yl)-2-ethylthiophen-3-yl]methoxy}benzoic acid (250 mg) synthesized above to give the title compound (88.4 mg, 32%).

$^1$H NMR (300 MHz, CDCl$_3$) δ ppm 0.93-1.31 (m, 8H) 1.44-1.54 (m, 1H) 1.61-1.89 (m, 4H) 2.03-2.16 (m, 1H) 2.56-2.93 (m, 8H) 3.23-3.29 (m, 2H) 3.61-3.71 (m, 2H) 4.84 (d, J=7.5 Hz, 1H) 6.15-6.21 (m, 1H) 6.61-6.70 (m, 1H) 6.73 (s, 1H) 6.79 (d, J=8.7 Hz, 2H) 7.60 (d, J=8.7 Hz, 2H)

Example 86

3-{[(4-{cyclohexyl[5-(3,6-dihydro-2H-thiopyran-4-yl)-2-ethylthiophen-3-yl]methoxy}phenyl)carbonyl](methyl)amino}propanoic acid

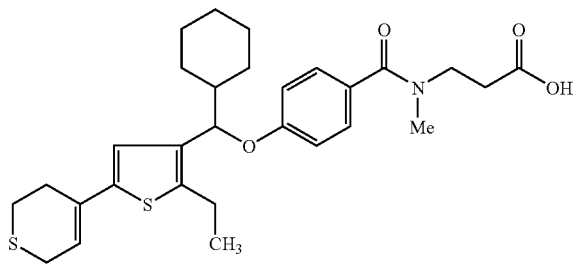

An operation similar to that in Example 69 (9) was performed using 4-{cyclohexyl[5-(3,6-dihydro-2H-thiopyran-4-yl)-2-ethylthiophen-3-yl]methoxy}benzoic acid (234 mg) synthesized in Example 85 (4) and ethyl 3-(methylamino)propanoate (79.8 mg) to give the title compound (89.2 mg, 33%).

$^1$H NMR (300 MHz, CDCl$_3$) δ ppm 0.82-1.34 (m, 8H) 1.42-1.55 (m, 1H) 1.60-1.89 (m, 4H) 2.03-2.16 (m, 1H) 2.55-2.92 (m, 8H) 3.02 (s, 3H) 3.22-3.31 (m, 2H) 3.61-3.81 (m, 2H) 4.81 (d, J=7.7 Hz, 1H) 6.19 (t, J=4.3 Hz, 1H) 6.75 (s, 1H) 6.78 (d, J=8.7 Hz, 2H) 7.23-7.32 (m, 2H)

Example 87

3-[({4-[(cyclohexyl{2-ethyl-5-[4-(trifluoromethyl)phenyl]furan-3-yl}methyl)amino]phenyl}carbonyl)(methyl)amino]propanoic acid

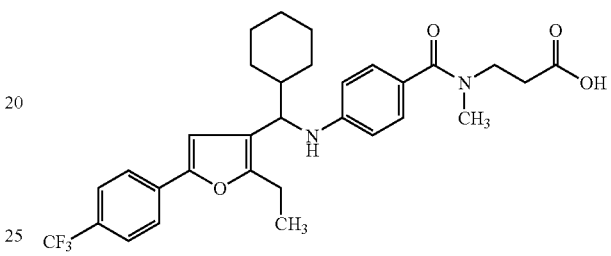

Ethyl 3-[({4-[(cyclohexyl{2-ethyl-5-[4-(trifluoromethyl)phenyl]furan-3-yl}methyl)amino]phenyl}carbonyl)(methyl)amino]propanoate (880 mg) which is a synthetic intermediate in Example 10 was dissolved in ethanol-hexane (1:1, volume ratio), and the solution was subjected to HPLC using CHIRALPAK AD (50 mmID×500 mL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 12 min were collected, and concentrated. The obtained amorphous compound (359 mg) was dissolved in ethanol (5 mL) and tetrahydrofuran (5 mL), 1N lithium hydroxide (2 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (330 mg, 97%).

$^1$H NMR (300 MHz, DMSO-d$_6$) δ ppm 0.91-1.26 (m, 8H) 1.59-1.77 (m, 5H) 1.98-2.13 (m, 1H) 2.43-2.57 (m, 2H) 2.69-2.85 (m, 2H) 2.89 (s, 3H) 3.51 (t, J=7.35 Hz, 2H) 4.05-4.17 (m, 1H) 6.24 (d, J=7.91 Hz, 1H) 6.56 (d, J=8.67 Hz, 2H) 6.96 (s, 1H) 7.10 (d, J=8.67 Hz, 2H) 7.71 (d, J=8.60 Hz, 2H) 7.77 (q, J=8.60 Hz, 3H)

Example 88

3-[({4-[(cyclohexyl{2-ethyl-5-[4-(trifluoromethyl)phenyl]furan-3-yl}methyl)amino]phenyl}carbonyl)(methyl)amino]propanoic acid

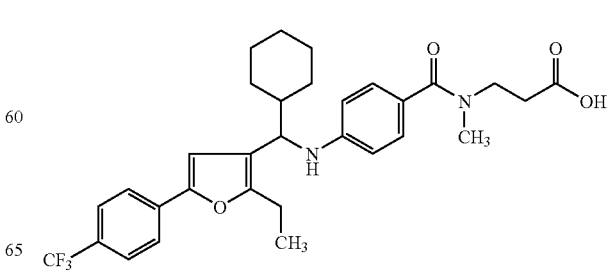

Ethyl 3-[({4-[(cyclohexyl{2-ethyl-5-[4-(trifluoromethyl)phenyl]furan-3-yl}methyl)amino]phenyl}carbonyl)(methyl)amino]propanoate (880 mg) which is a synthetic intermediate in Example 10 was dissolved in ethanol-hexane (1:1, volume ratio), and the solution was subjected to HPLC using CHIRALPAK AD (50 mmID×500 mL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 29 min were collected, and concentrated. The obtained amorphous compound (355 mg) was dissolved in ethanol (5 mL) and tetrahydrofuran (5 mL), 1N lithium hydroxide (2 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (336 mg, 99%).

$^1$H NMR (300 MHz, DMSO-$d_6$) δ ppm 0.91-1.26 (m, 8H) 1.59-1.77 (m, 5H) 1.98-2.13 (m, 1H) 2.43-2.57 (m, 2H) 2.69-2.85 (m, 2H) 2.89 (s, 3H) 3.51 (t, J=7.35 Hz, 2H) 4.05-4.17 (m, 1H) 6.24 (d, J=7.91 Hz, 1H) 6.56 (d, J=8.67 Hz, 2H) 6.96 (s, 1H) 7.10 (d, J=8.67 Hz, 2H) 7.71 (d, J=8.60 Hz, 2H) 7.77 (q, J=8.60 Hz, 3H)

Example 89

3-{[(4-{cyclohexyl[2-methyl-5-(pyridin-3-yl)furan-3-yl]methoxy}phenyl)carbonyl]amino}propanoic acid

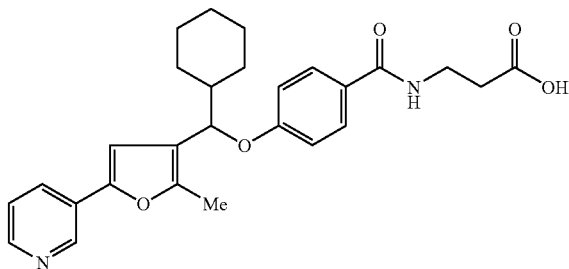

(1) 5-bromo-2-methylfuran-3-carbaldehyde

A solution of methyl 5-bromo-2-methyl-3-furancarboxylate (Example 49 (1)) (7.5 g) in tetrahydrofuran (30 mL) was added dropwise to a suspension of lithium aluminum hydride (1.9 g) in tetrahydrofuran (30 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (5% ethyl acetate/hexane to 40% ethyl acetate/hexane) to give (5-bromo-2-methylfuran-3-yl)methanol (5.7 g, 60%) as an oil. A suspension of the obtained (5-bromo-2-methylfuran-3-yl)methanol (5.5 g) and manganese dioxide (15 g) in tetrahydrofuran (100 mL) was stirred at 40° C. for 2 days. Manganese dioxide was filtered off, and the filtrate was evaporated under reduced pressure. The residue was purified by silica gel chromatography (0% ethyl acetate/hexane to 20% ethyl acetate/hexane), and crystallized from ethyl acetate/hexane to give the title compound (2.8 g, 51%) as a white solid.

$^1$H NMR (300 MHz, CHLOROFORM-d) δ ppm 2.59 (s, 3H) 6.62 (s, 1H) 9.85 (s, 1H)

(2) 2-methyl-5-(pyridin-3-yl)furan-3-carbaldehyde

A mixture of 5-bromo-2-methylfuran-3-carbaldehyde (1.9 g) obtained by the above-mentioned reaction, 3-pyridineboronic acid (1.5 g), tetrakis(triphenylphosphine)palladium(0) (0.6 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 50% ethyl acetate/hexane), and crystallized from ethyl acetate/hexane to give the title compound (1.3 g, 73%) as a white solid.

$^1$H NMR (300 MHz, CHLOROFORM-d) δ ppm 2.70 (s, 3H) 7.01 (s, 1H) 7.34 (dd, J=5.11, 7.76 Hz, 1H) 7.92 (dt, J=2.04, 8.05 Hz, 1H) 8.55 (dd, J=1.70, 4.73 Hz, 1H) 8.93 (d, J=1.89 Hz, 1H) 9.99 (s, 1H)

(3) cyclohexyl[2-methyl-5-(pyridin-3-yl)furan-3-yl]methanol

To a solution of 2-methyl-5-(pyridin-3-yl)furan-3-carbaldehyde (2.1 g) obtained by the above-mentioned reaction in tetrahydrofuran (30 mL) was added dropwise 1N cyclohexylmagnesium bromide-tetrahydrofuran solution (15 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (2.4 g, 81%) as an oil.

$^1$H NMR (300 MHz, CHLOROFORM-d) δ ppm 0.77-1.36 (m, 5H) 1.41-1.90 (m, 5H) 2.04-2.09 (m, 1H) 2.34 (s, 3H) 4.32 (dd, J=2.46, 7.76 Hz, 1H) 6.69 (s, 1H) 7.19-7.34 (m, 2H) 7.87 (dt, J=2.04, 8.05 Hz, 1H) 8.44 (dd, J=1.70, 4.73 Hz, 1H) 8.87 (d, J=1.89 Hz, 1H)

(4) 4-{cyclohexyl[2-methyl-5-(pyridin-3-yl)furan-3-yl]methoxy}benzoic acid

To a solution of cyclohexyl[2-methyl-5-(pyridin-3-yl)furan-3-yl]methanol (407 mg) obtained by the above-mentioned reaction and methyl 4-hydroxybenzoate (274 mg) in tetrahydrofuran (20 mL) were added tributylphosphine (0.7 mL) and 1,1'-(azodicarbonyl)dipiperidine (757 mg), and the mixture was stirred at room temperature overnight. The solvent was evaporated under reduced pressure, and the residue was purified by silica gel column (5% ethyl acetate/hexane to 25% ethyl acetate/hexane) to give methyl 4-{cyclohexyl[2-methyl-5-(pyridin-3-yl)furan-3-yl]methoxy}benzoate as an amorphous compound. The obtained methyl 4-{cyclohexyl[2-methyl-5-(pyridin-3-yl)furan-3-yl]methoxy}benzoate was dissolved in methanol (5 mL) and tetrahydrofuran (5 mL), 2N sodium hydroxide (2.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced-pressure, and the residue was crystallized from ethyl acetate/hexane to give the title compound (275 mg, 47%).

$^1$H NMR (300 MHz, CHLOROFORM-d) δ ppm 1.02-1.33 (m, 5H) 1.63-1.89 (m, 5H) 2.06-2.11 (m, 2H) 2.38 (s, 3H) 4.84 (d, J=6.97 Hz, 1H) 6.62 (s, 1H) 6.87 (d, J=8.85 Hz, 2H) 7.87 (t, J=1.88 Hz, 1H) 7.95 (d, J=8.85 Hz, 2H) 8.43-8.44 (m, 1H) 8.85 (s, 1H)

(5) 3-{[(4-{cyclohexyl[2-methyl-5-(pyridin-3-yl)furan-3-yl]methoxy}phenyl)carbonyl]amino}propanoic acid A solution of 4-{cyclohexyl[2-methyl-5-(pyridin-3-yl)furan-3-yl]methoxy}benzoic acid (137 mg) obtained by the above-mentioned reaction, ethyl β-alaninate hydrochloride (65 mg), 1-ethyl-3-(3-dimethylaminopropyl)carbodiimide hydrochloride (81 mg), hydroxybenzotriazole monohydrate (64 mg) and triethylamine (59 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (104 mg, 90%).

$^1$H NMR (300 MHz, DMSO-d$_6$) δ ppm 0.97-1.97 (m, 7H) 1.44-1.93 (m, 5H) 2.03-2.07 (m, 1H) 2.39 (s, 3H) 2.45 (t, J=7.16 Hz, 3H) 3.39 (d, J=5.46 Hz, 2H) 5.10 (d, J=7.54 Hz, 1H) 6.93 (d, J=8.85 Hz, 2H) 7.00 (s, 1H) 7.38 (dd, J=7.91, 4.71 Hz, 1H) 7.71 (d, J=8.85 Hz, 2H) 7.95 (dt, J=8.01, 1.74 Hz, 1H) 8.24-8.33 (m, 1H) 8.41 (dd, J=4.71, 1.51 Hz, 1H) 8.84 (d, J=2.07 Hz, 1H) 12.17 (brs, 1H)

Example 90

3-{[(4-{cyclohexyl[2-methyl-5-(pyridin-3-yl)furan-3-yl]methoxy}phenyl)carbonyl](methyl)amino}propanoic acid

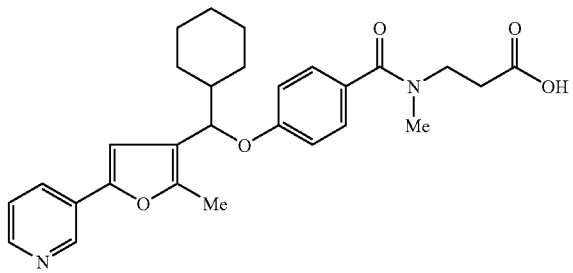

A solution of 4-{cyclohexyl[2-methyl-5-(pyridin-3-yl)furan-3-yl]methoxy}benzoic acid (137 mg), ethyl 3-(methylamino)propanoate (55 mg), 1-ethyl-3-(3-dimethylaminopropyl)carbodiimide hydrochloride (81 mg), hydroxybenzotriazole monohydrate (64 mg) and triethylamine (59 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (104 mg, 90%).

$^1$H NMR (300 MHz, DMSO-d$_6$) δ ppm 0.90-1.28 (m, 5H) 1.52-1.93 (m, 5H) 2.05 (d, J=11.68 Hz, 1H) 2.39 (s, 3H) 2.50-2.56 (m, 2H) 2.81-2.96 (m, 3H) 3.32 (s, 3H) 3.51 (brs, 2H) 5.04 (d, J=7.54 Hz, 1H) 6.91 (d, J=8.67 Hz, 2H) 7.01 (s, 1H) 7.27 (d, J=8.67 Hz, 2H) 7.38 (dd, J=8.10, 4.71 Hz, 1H) 7.96 (dt, J=7.91, 1.79 Hz, 1H) 8.42 (d, J=3.58 Hz, 1H) 8.76-8.96 (m, 1H) 12.26 (s, 1H)

Example 91

3-{[(4-{cyclohexyl[5-(4-methoxyphenyl)-2-methylfuran-3-yl]methoxy}phenyl)carbonyl]amino}propanoic acid

(1) 5-(4-methoxyphenyl)-2-methylfuran-3-carbaldehyde

A mixture of 5-bromo-2-methylfuran-3-carbaldehyde (1.9 g), 4-methoxyphenylboronic acid (1.8 g), tetrakis(triphenylphosphine)palladium(0) (0.6 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 25% ethyl acetate/hexane), and crystallized from ethyl acetate/hexane to give the title compound (1.9 g, 91%) as a white solid.

$^1$H NMR (300 MHz, CHLOROFORM-d) δ ppm 2.65 (s, 3H) 3.84 (s, 3H) 6.77 (d, J=3.77 Hz, 1H) 6.93 (d, J=8.85 Hz, 2H) 7.59 (d, J=8.85 Hz, 2H) 9.95 (s, 1H)

(2) cyclohexyl[5-(4-methoxyphenyl)-2-methylfuran-3-yl]methanol

To a solution of 5-(4-methoxyphenyl)-2-methylfuran-3-carbaldehyde (1.9 g) obtained by the above-mentioned reaction in tetrahydrofuran (30 mL) was added dropwise 1N cyclohexylmagnesium bromide-tetrahydrofuran solution (13.5 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (2.6 g, 95%) as an oil.

$^1$H NMR (300 MHz, CHLOROFORM-d) δ ppm 0.73-1.37 (m, 5H) 1.50-1.81 (m, 5H) 2.05 (d, J=4.33 Hz, 1H) 2.31 (s, 3H) 3.83 (s, 3H) 4.28 (dd, J=7.91, 2.83 Hz, 1H) 6.45 (s, 1H) 6.90 (d, J=8.85 Hz, 2H) 7.55 (d, J=9.04 Hz, 2H)

(4) 4-{cyclohexyl[5-(4-methoxyphenyl)-2-methylfuran-3-yl]methoxy}benzoic acid

To a solution of cyclohexyl[5-(4-methoxyphenyl)-2-methylfuran-3-yl]methanol (601 mg) obtained by the above-mentioned reaction and methyl 4-hydroxybenzoate (365 mg) in tetrahydrofuran (20 mL) were added tributylphosphine (1.0 mL) and 1,1'-(azodicarbonyl)dipiperidine (1.0 g), and the mixture was stirred at room temperature overnight. The solvent was evaporated under reduced pressure, and the residue was purified by silica gel column (0% ethyl acetate/hexane to 12% ethyl acetate/hexane) to give methyl 4-{cyclohexyl[5-(4-methoxyphenyl)-2-methylfuran-3-yl]methoxy}benzoate as an amorphous compound. The obtained methyl 4-{cyclohexyl[5-(4-methoxyphenyl)-2-methylfuran-3-yl]methoxy}benzoate was dissolved in methanol (5 mL) and tetrahydrofuran (5 mL), 2N sodium hydroxide (2.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (362 mg, 38%).

$^1$H NMR (300 MHz, CHLOROFORM-d) δ ppm 0.92-1.37 (m, 5H) 1.59-1.94 (m, 5H) 2.01-2.22 (m, 1H) 2.34 (s, 3H) 3.81 (s, 3H) 4.80 (d, J=7.57 Hz, 1H) 6.36 (s, 1H) 6.87 (d, J=7.57 Hz, 4H) 7.50 (d, J=9.09 Hz, 2H) 7.95 (d, J=9.09 Hz, 2H)

(5) 3-{[(4-{cyclohexyl[5-(4-methoxyphenyl)-2-methylfuran-3-yl]methoxy}phenyl)carbonyl]amino}propanoic acid A solution of 4-{cyclohexyl[5-(4-methoxyphenyl)-2-methylfuran-3-yl]methoxy}benzoic acid (181 mg) obtained by the above-mentioned reaction, ethyl β-alaninate hydrochloride (77 mg), 1-ethyl-3-(3-dimethylaminopropyl)carbodiimide hydrochloride (96 mg), hydroxybenzotriazole monohydrate (77 mg) and triethylamine (70 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (204 mg, 99%).

$^1$H NMR (300 MHz, DMSO-d$_6$) δ ppm 0.96-1.31 (m, 5H) 1.50-1.89 (m, 5H) 2.02 (brs, 1H) 2.35 (s, 3H) 2.44 (t, J=7.16 Hz, 2H) 3.24-3.49 (m, 2H) 3.75 (s, 3H) 5.05 (d, J=7.54 Hz, 1H) 6.63 (s, 1H) 6.92 (d, J=8.85 Hz, 4H) 7.52 (d, J=8.85 Hz, 2H) 7.70 (d, J=8.67 Hz, 2H) 8.30 (t, J=5.37 Hz, 1H)

Example 92

3-{[(4-{cyclohexyl[5-(4-methoxyphenyl)-2-methylfuran-3-yl]methoxy}phenyl)carbonyl](methyl)amino}propanoic acid

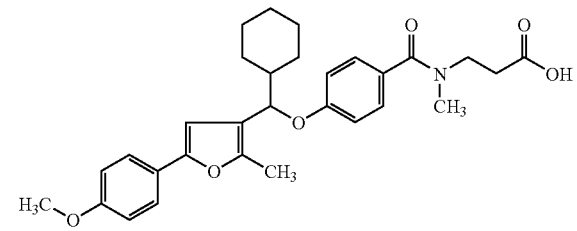

A solution of 4-{cyclohexyl[5-(4-methoxyphenyl)-2-methylfuran-3-yl]methoxy}benzoic acid (181 mg), ethyl 3-(methylamino)propanoate (66 mg), 1-ethyl-3-(3-dimethylaminopropyl)carbodiimide hydrochloride (96 mg), hydroxybenzotriazole monohydrate (77 mg) and triethylamine (70 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (211 mg, 97%).

$^1$H NMR (300 MHz, DMSO-d$_6$) δ ppm 0.97-1.17 (m, 5H) 1.52-1.87 (m, 5H) 2.03-2.07 (m, 1H) 2.35 (s, 3H) 2.44-2.57 (m, 2H) 2.88 (s, 3H) 3.75 (s, 3H) 4.99 (d, J=7.54 Hz, 1H) 6.65 (s, 1H) 6.91 (t, J=8.57 Hz, 4H) 7.26 (d, J=8.67 Hz, 2H) 7.53 (d, J=8.67 Hz, 2H)

Example 93

3-({[4-({cyclohexyl[2-methyl-5-(pyridin-3-yl)furan-3-yl]methyl}amino)phenyl]carbonyl}amino)propanoic acid

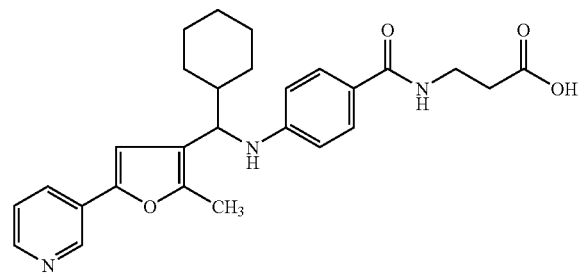

(1) 3-{4-[chloro(cyclohexyl)methyl]-5-methylfuran-2-yl}pyridine

To a solution of cyclohexyl[2-methyl-5-(pyridin-3-yl)furan-3-yl]methanol (1.6 g) in toluene (20 mL) was added thionyl chloride (1.3 mL), and the mixture was stirred at room temperature for 4 hr. The solvent was evaporated under reduced pressure to give the title compound (1.7 g, 100%) as an amorphous compound.

$^1$H NMR (300 MHz, CHLOROFORM-d) δ ppm 0.89-1.33 (m, 5H) 1.54-1.93 (m, 5H) 2.09-2.25 (m, 1H) 2.39 (s, 3H) 4.59 (d, J=8.33 Hz, 1H) 7.01 (s, 1H) 7.87 (dd, J=8.14, 5.49 Hz, 1H) 8.40-8.50 (m, 1H) 8.53 (d, J=5.68 Hz, 1H) 8.98 (d, J=1.89 Hz, 1H)

(2) 4-({cyclohexyl[2-methyl-5-(pyridin-3-yl)furan-3-yl]methyl}amino)benzoic acid A mixture of 3-{4-[chloro(cyclohexyl)methyl]-5-methylfuran-2-yl}pyridine (1.7 g) obtained by the above-mentioned reaction, methyl 4-aminobenzoate (1.8 g), sodium carbonate (1.27 g) and sodium iodide (3.6 g) in N,N-dimethylacetamide (20 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Sodium hydroxide (6 mL) was added, and the mixture was stirred at 70° C. for 3 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (25% ethyl acetate/hexane to 75% ethyl acetate/hexane) to give the title compound (1.2 g, 52%) as an amorphous compound.

$^1$H NMR (300 MHz, CHLOROFORM-d) δ ppm 1.01-1.30 (m, 5H) 1.58-1.84 (m, 5H) 1.90-2.02 (m, 1H) 2.40 (s, 3H) 4.12 (m, 1H) 6.53 (d, J=7.57 Hz, 2H) 6.55 (s, 1H) 7.85 (d, J=9.09 Hz, 2H) 8.43 (d, J=4.54 Hz, 1H) 8.84 (s, 1H)

(3) 3-({[4-({cyclohexyl[2-methyl-5-(pyridin-3-yl)furan-3-yl]methyl}amino)phenyl]carbonyl}amino)propanoic acid A solution of 4-({cyclohexyl[2-methyl-5-(pyridin-3-yl)furan-3-yl]methyl}amino)benzoic acid (586 mg) obtained by the above-mentioned reaction, ethyl β-alaninate hydrochloride (276 mg), 1-ethyl-3-(3-dimethylaminopropyl)carbodiimide hydrochloride (345 mg), hydroxybenzotriazole monohydrate (276 mg) and triethylamine (250 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (3.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (685 mg, 99%).

$^1$H NMR (300 MHz, DMSO-d$_6$) δ ppm 0.97-1.20 (m, 5H) 1.56-1.77 (m, 7H) 2.01-2.06 (m, 1H) 2.38 (s, 3H) 2.43 (t, J=7.00 Hz, 2H) 3.36 (q, J=5.68 Hz, 2H) 4.12 (t, J=7.76 Hz, 1H) 6.35 (d, J=7.95 Hz, 1H) 6.55 (d, J=9.09 Hz, 2H) 6.89 (s, 1H) 7.38 (dd, J=7.38, 4.73 Hz, 1H) 7.52 (d, J=9.09 Hz, 2H) 7.90 (dd, J=8.14, 2.08 Hz, 1H) 7.98 (t, J=5.49 Hz, 1H) 8.41 (dd, J=4.92, 1.51 Hz, 1H) 8.79 (d, J=1.51 Hz, 1H) 12.14 (brs, 1H)

Example 94

3-[{[4-({cyclohexyl[2-methyl-5-(pyridin-3-yl)furan-3-yl]methyl}amino)phenyl]carbonyl}(methyl)amino]propanoic acid

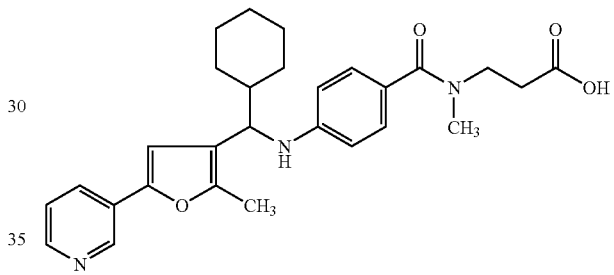

A solution of 4-({cyclohexyl[2-methyl-5-(pyridin-3-yl)furan-3-yl]methyl}amino)benzoic acid (586 mg), ethyl 3-(methylamino)propanoate (236 mg), 1-ethyl-3-(3-dimethylaminopropyl)carbodiimide hydrochloride (345 mg), hydroxybenzotriazole monohydrate (276 mg) and triethylamine (250 μl) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (3.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (544 mg, 88%).

$^1$H NMR (300 MHz, DMSO-d$_6$) δ ppm 0.90-1.27 (m, 5H) 1.56-1.76 (m, 5H) 2.02-2.06 (m, 1H) 2.39 (s, 3H) 2.42-2.59 (m, 2H) 2.89 (s, 3H) 3.51 (t, J=7.38 Hz, 2'H) 4.08 (t, J=7.38 Hz, 1H) 6.24 (d, J=7.95 Hz, 1H) 6.55 (d, J=8.33 Hz, 2H) 6.90 (s, 1H) 7.10 (d, J=8.33 Hz, 2H) 7.38 (dd, J=7.95, 4.92 Hz, 1H) 7.91 (d, J=7.95 Hz, 1H) 8.41 (d, J=3.41 Hz, 1H) 8.80 (d, J=1.89 Hz, 1H)

Example 95

3-{[(4-{cyclohexyl[2-methyl-5-(pyridin-4-yl)furan-3-yl]methoxy}phenyl)carbonyl]amino}propanoic acid

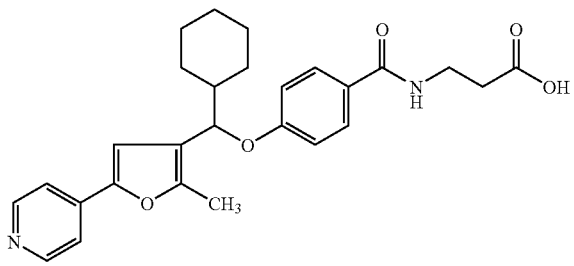

(1) 2-methyl-5-(pyridin-4-yl)furan-3-carbaldehyde

A mixture of 5-bromo-2-methylfuran-3-carbaldehyde (1.9 g) obtained by the above-mentioned reaction, 4-pyridineboronic acid (1.5 g), tetrakis(triphenylphosphine)palladium(0) (0.6 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 50% ethyl acetate/hexane), and crystallized from ethyl acetate/hexane to give the title compound (0.7 g, 38%) as a white solid.

$^1$H NMR (300 MHz, CHLOROFORM-d) δ ppm 2.71 (s, 3H) 7.15 (s, 1H) 7.51 (d, J=6.06 Hz, 2H) 8.64 (d, J=6.06 Hz, 2H) 9.99 (s, 1H)

(3) cyclohexyl[2-methyl-5-(pyridin-4-yl)furan-3-yl]methanol

To a solution of 2-methyl-5-(pyridin-4-yl)furan-3-carbaldehyde (1.3 g) obtained by the above-mentioned reaction in tetrahydrofuran (20 mL) was added dropwise 1N cyclohexylmagnesium bromide-tetrahydrofuran solution (10 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.3 g, 69%) as an oil.

$^1$H NMR (300 MHz, CHLOROFORM-d) δ ppm 0.73-1.39 (m, 5H) 1.42-1.96 (m, 5H) 2.05-2.08 (m, 1H) 2.35 (s, 3H) 4.33 (d, J=7.72 Hz, 1H) 6.83 (s, 1H) 7.45 (d, J=6.22 Hz, 2H) 8.47-8.65 (m, 2H)

(4) 4-{cyclohexyl[2-methyl-5-(pyridin-4-yl)furan-3-yl]methoxy}benzoic acid

To a solution of cyclohexyl[2-methyl-5-(pyridin-4-yl)furan-3-yl]methanol (407 mg) obtained by the above-mentioned reaction and methyl 4-hydroxybenzoate (274 mg) in tetrahydrofuran (20 mL) were added tributylphosphine (0.7 mL) and 1,1'-(azodicarbonyl)dipiperidine (757 mg), and the mixture was stirred at room temperature overnight. The solvent was evaporated under reduced pressure, and the residue was purified by silica gel column (5% ethyl acetate/hexane to 30% ethyl acetate/hexane) to give methyl 4-{cyclohexyl[2-methyl-5-(pyridin-4-yl)furan-3-yl]methoxy}benzoate as an amorphous compound. The obtained methyl 4-{cyclohexyl[2-methyl-5-(pyridin-4-yl)furan-3-yl]methoxy}benzoate was dissolved in methanol (5 mL) and tetrahydrofuran (5 mL), 2N sodium hydroxide (2.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine and dried over magnesium sulfate, and the solvent was evaporated under reduced pressure to give the title compound (261 mg, 45%).

$^1$H NMR (300 MHz, CHLOROFORM-d) δ ppm 1.02-1.32 (m, 5H) 1.52-2.16 (m, 6H) 2.41 (s, 3H) 4.85 (d, J=7.19 Hz, 1H) 6.85 (d, J=8.71 Hz, 3H) 7.52 (d, J=5.30 Hz, 2H) 7.95 (d, J=9.09 Hz, 2H) 8.55 (brs, 2H)

(5) 3-{[(4-{cyclohexyl[2-methyl-5-(pyridin-4-yl)furan-3-yl]methoxy}phenyl)carbonyl]amino}propanoic acid A solution of 4-{cyclohexyl[2-methyl-5-(pyridin-4-yl)furan-3-yl]methoxy}benzoic acid (129 mg) obtained by the above-mentioned reaction, ethyl β-alaninate hydrochloride (61 mg), 1-ethyl-3-(3-dimethylaminopropyl)carbodiimide hydrochloride (77 mg), hydroxybenzotriazole monohydrate (61 mg) and triethylamine (56 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (124 mg, 83%).

$^1$H NMR (300 MHz, DMSO-d$_6$) δ ppm 1.06-1.27 (m, 5H) 1.47-1.94 (m, 5H) 2.02-2.06 (m, 1H) 2.41 (s, 3H) 2.45 (t, J=7.25 Hz, 2H) 3.21-3.52 (m, 2H) 5.12 (d, J=7.35 Hz, 1H) 6.93 (d, J=8.85 Hz, 2H) 7.17 (s, 1H) 7.54 (dd, J=4.71, 1.51 Hz, 2H) 7.71 (d, J=8.85 Hz, 2H) 8.20-8.39 (m, 1H) 8.51 (dd, J=4.52, 1.51 Hz, 2H) 12.17 (s, 1H)

Example 96

3-{[(4-{cyclohexyl[2-methyl-5-(pyridin-4-yl)furan-3-yl]methoxy}phenyl)carbonyl](methyl)amino}propanoic acid

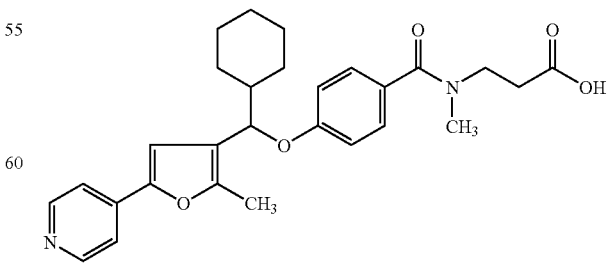

A solution of 4-{cyclohexyl[2-methyl-5-(pyridin-4-yl)furan-3-yl]methoxy}benzoic acid (137 mg), ethyl 3-(methylamino)propanoate (52 mg), 1-ethyl-3-(3-dimethylaminopropyl)carbodiimide hydrochloride (77 mg), hydroxybenzotriazole monohydrate (61 mg) and triethylamine (56 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL), 1N sodium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (130 mg, 84%).

$^1$H NMR (300 MHz, DMSO-$d_6$) δ ppm 1.01-1.27 (m, 5H) 1.49-1.87 (m, 5H) 2.03-2.06 (m, 1H) 2.41 (s, 3H) 2.47-2.57 (m, 2H) 2.88 (brs, 2H) 5.06 (d, J=7.54 Hz, 1H) 6.91 (d, J=8.67 Hz, 2H) 7.18 (s, 1H) 7.27 (d, J=8.48 Hz, 2H) 7.48-7.63 (m, 2H) 8.51 (d, J=6.03 Hz, 2H) 12.26 (brs, 1H)

Example 97

3-({[4-({cyclohexyl[2-methyl-5-(pyridin-4-yl)furan-3-yl]methyl}amino)phenyl]carbonyl}amino)propanoic acid

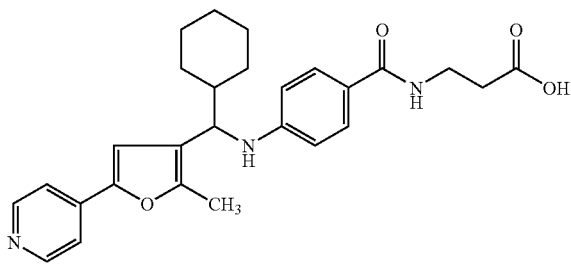

(1) 4-{4-[chloro(cyclohexyl)methyl]-5-methylfuran-2-yl}pyridine

To a solution of cyclohexyl[2-methyl-5-(pyridin-4-yl)furan-3-yl]methanol (0.9 g) in toluene (10 mL) was added thionyl chloride (0.7 mL), and the mixture was stirred at room temperature overnight. The solvent was evaporated under reduced pressure to give the title compound (0.9 g, 100%) as a yellow crystal.

$^1$H NMR (300 MHz, CHLOROFORM-d) δ ppm 0.80-1.40 (m, 5H) 1.46-1.95 (m, 5H) 2.15-2.18 (m, 1H) 2.44 (s, 3H) 4.59 (d, J=8.33 Hz, 1H) 7.29 (s, 1H) 7.91 (d, J=6.82 Hz, 2H) 8.59 (d, J=6.82 Hz, 2H)

(2) 4-({cyclohexyl[2-methyl-5-(pyridin-4-yl)furan-3-yl]methyl}amino)benzoic acid A mixture of 4-{4-[chloro(cyclohexyl)methyl]-5-methylfuran-2-yl}pyridine (0.9 g) obtained by the above-mentioned reaction, methyl 4-aminobenzoate (1.0 g), sodium carbonate (0.7 g) and sodium iodide (2.0 g) in N,N-dimethylacetamide (10 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (4 mL) was added, and the mixture was stirred at 70° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (25% ethyl acetate/hexane to 75% ethyl acetate/hexane) to give the title compound (0.7 g, 60%) as an amorphous compound.

$^1$H NMR (300 MHz, CHLOROFORM-d) δ ppm 0.89-1.37 (m, 5H) 1.68-1.87 (m, 5H) 1.96 (d, J=12.12 Hz, 1H) 2.41 (s, 3H) 4.12 (d, J=6.94 Hz, 1H) 6.49 (d, J=8.71 Hz, 2H) 6.69 (s, 1H) 7.42 (d, J=6.44 Hz, 2H) 7.85 (d, J=8.71 Hz, 2H) 8.54 (d, J=6.06 Hz, 2H)

(3) 3-({[4-({cyclohexyl[2-methyl-5-(pyridin-4-yl)furan-3-yl]methyl}amino)phenyl]carbonyl}amino)propanoic acid A solution of 4-({cyclohexyl[2-methyl-5-(pyridin-4-yl)furan-3-yl]methyl}amino)benzoic acid (390 mg) obtained by the above-mentioned reaction, ethyl β-alaninate hydrochloride (184 mg), 1-ethyl-3-(3-dimethylaminopropyl)carbodiimide hydrochloride (230 mg), hydroxybenzotriazole monohydrate (184 mg) and triethylamine (116 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (2.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (404 mg, 88%).

$^1$H NMR (300 MHz, DMSO-$d_6$) δ ppm 0.92-1.27 (m, 5H) 1.55-1.77 (m, 5H) 2.01-2.05 (m, 1H) 2.40-2.47 (m, 5H) 3.35-3.39 (m, 2H) 4.14 (t, J=7.76 Hz, 1H) 6.37 (d, J=7.95 Hz, 1H) 6.55 (d, J=8.71 Hz, 2H) 7.07 (s, 1H) 7.39-7.57 (m, 5H) 7.98 (t, J=5.49 Hz, 1H) 8.51 (d, J=6.44 Hz, 2H) 12.14 (s, 1H)

Example 98

3-[{[4-({cyclohexyl[2-methyl-5-(pyridin-4-yl)furan-3-yl]methyl}amino)phenyl]carbonyl}(methyl)amino]propanoic acid

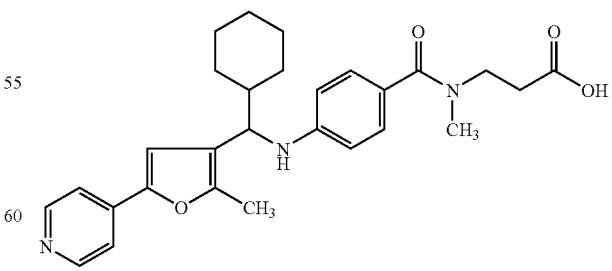

A solution of 4-({cyclohexyl[2-methyl-5-(pyridin-4-yl)furan-3-yl]methyl}amino)benzoic acid (390 mg), ethyl 3-(methylamino)propanoate (157 mg), 1-ethyl-3-(3-dimethylaminopropyl)carbodiimide hydrochloride (230 mg), hydroxybenzotriazole monohydrate (184 mg) and triethylamine (116 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (2.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (400 mg, 84%).

$^1$H NMR (300 MHz, DMSO-$d_6$) δ ppm 0.86-1.37 (m, 5H) 1.54-1.76 (m, 4H) 1.95-2.10 (m, 1H) 2.40 (s, 3H) 2.45-2.50 (m, 2H) 2.89 (s, 3H) 3.51 (t, J=7.38 Hz, 2H) 4.10 (t, J=7.76 Hz, 1H) 6.26 (d, J=7.95 Hz, 1H) 6.55 (d, J=8.71 Hz, 2H) 7.07 (s, 1H) 7.08 (d, J=4.54 Hz, 2H) 7.49 (d, J=6.06 Hz, 2H) 8.51 (d, J=6.06 Hz, 2H)

Example 99

3-[({4-[cyclobutyl(2-methyl-5-phenylfuran-3-yl)methoxy]phenyl}carbonyl)amino]propanoic acid

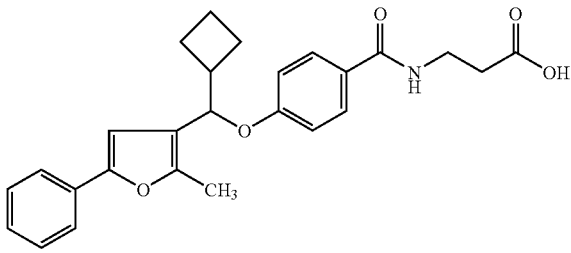

(1) ethyl 2-methyl-5-phenyl-3-furancarboxylate

A suspension of 2-methyl-5-phenyl-3-furancarboxylic acid (5.0 g), ethyl iodide (4.7 g) and potassium carbonate (3.5 g) in N,N-dimethylformamide (50 mL) was stirred at room temperature for 4 hr. The reaction mixture was poured into water, and the mixture was extracted with ethyl acetate. The organic layer was washed with 1N hydrochloric acid, and dried over magnesium sulfate. The solvent was evaporated under reduced pressure to give the title compound (5.7 g, 100%) as an oil.

$^1$H NMR (300 MHz, CHLOROFORM-d) δ ppm 1.38 (t, J=7.11 Hz, 3H) 2.65 (s, 3H) 4.32 (q, J=7.11 Hz, 2H) 6.89 (s, 1H) 7.24-7.30 (m, 1H) 7.39 (t, J=7.25 Hz, 2H) 7.64 (d, J=7.54 Hz, 2H)

(2) (2-methyl-5-phenylfuran-3-yl)methanol

A solution of ethyl 2-methyl-5-phenyl-3-furancarboxylate (5.7 g) in tetrahydrofuran (30 mL) was added dropwise to a suspension of lithium aluminum hydride (1.0 g) in tetrahydrofuran (30 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (4.7 g, 100%) as an oil.

$^1$H NMR (300 MHz, CHLOROFORM-d) δ ppm 1.40 (brs, 1H) 2.37 (s, 3H) 4.51 (s, 2H) 6.63 (s, 1H) 7.14-7.29 (m, 1H) 7.36 (t, J=7.57 Hz, 2H) 7.62 (d, J=7.19 Hz, 2H)

(3) 2-methyl-5-phenylfuran-3-carbaldehyde

To a solution of (2-methyl-5-phenylfuran-3-yl)methanol (4.7 g) obtained by the above-mentioned reaction in methylene chloride (30 mL) was added a Dess-Martin reagent (12.7 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (3.6 g, 78%) as a yellow crystal.

$^1$H NMR (300 MHz, CHLOROFORM-d) δ ppm 2.67 (s, 3H) 6.91 (s, 1H) 7.21-7.35 (m, 1H) 7.40 (t, J=7.57 Hz, 2H) 7.66 (d, J=7.57 Hz, 2H) 9.97 (s, 1H)

(3) cyclobutyl (2-methyl-5-phenylfuran-3-yl)methanol

To a solution of 2-methyl-5-phenylfuran-3-carbaldehyde (1.3 g) obtained by the above-mentioned reaction in tetrahydrofuran (30 mL) was added dropwise 0.9N cyclobutylmagnesium bromide-diethyl ether solution (11.7 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (1.6 g, 93%) as an oil.

$^1$H NMR (300 MHz, CHLOROFORM-d) δ ppm 1.61-1.77 (m, 2H) 1.82-2.08 (m, 3H) 2.14-2.20 (m, 1H) 2.38 (s, 3H) 2.54-2.82 (m, 1H) 4.54 (dd, J=8.33, 1.89 Hz, 1H) 6.56 (s, 1H) 7.22 (d, J=7.57 Hz, 1H) 7.35 (t, J=7.57 Hz, 2H) 7.61 (d, J=7.19 Hz, 2H)

(4) 4-[cyclobutyl(2-methyl-5-phenylfuran-3-yl)methoxy]benzoic acid

To a solution of cyclobutyl(2-methyl-5-phenylfuran-3-yl)methanol (364 mg) obtained by the above-mentioned reaction and methyl 4-hydroxybenzoate (274 mg) in tetrahydrofuran (20 mL) were added tributylphosphine (0.7 mL) and 1,1'-(azodicarbonyl)dipiperidine (757 mg), and the mixture was stirred at room temperature overnight. The solvent was evaporated under reduced pressure, and the residue was purified by silica gel column (0% ethyl acetate/hexane to 12% ethyl acetate/hexane) to give methyl 4-[cyclobutyl(2-methyl-5-phenylfuran-3-yl)methoxy]benzoate as an oil. The obtained methyl 4-[cyclobutyl(2-methyl-5-phenylfuran-3-yl)methoxy]benzoate was dissolved in methanol (5 mL) and tetrahydrofuran (5 mL). 2N Lithium hydroxide (1.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (276 mg, 47%) as an amorphous compound.

$^1$H NMR (300 MHz, CHLOROFORM-d) δ ppm 1.70-2.25 (m, 4H) 2.39 (s, 3H) 2.73-2.97 (m, 1H) 5.02 (d, J=7.95 Hz, 1H) 6.50 (s, 1H) 6.90 (d, J=8.71 Hz, 2H) 7.20 (d, J=7.57 Hz, 1H) 7.32 (t, J=7.57 Hz, 2H) 7.57 (d, J=7.19 Hz, 2H) 7.96 (d, J=8.71 Hz, 2H)

(5) 3-[({4-[cyclobutyl(2-methyl-5-phenylfuran-3-yl)methoxy]phenyl}carbonyl)amino]propanoic acid A solution of 4-[cyclobutyl(2-methyl-5-phenylfuran-3-yl)methoxy]benzoic acid (127 mg) obtained by the above-mentioned reaction, ethyl β-alaninate hydrochloride (65 mg), 1-ethyl-3-(3-dimethylaminopropyl)carbodiimide hydrochloride (81 mg), hydroxybenzotriazole monohydrate (64 mg) and triethylamine (59 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (126 mg, 83%).

$^1$H NMR (300 MHz, DMSO-d$_6$) δ ppm 1.75-2.21 (m, 6H) 2.41 (s, 3H) 2.45 (t, J=7.19 Hz, 2H) 2.77-2.91 (m, 1H) 3.34-3.48 (m, 2H) 5.32 (d, J=8.33 Hz, 1H) 6.81 (s, 1H) 6.95 (d, J=8.71 Hz, 2H) 7.23 (d, J=7.57 Hz, 1H) 7.35 (t, J=7.57 Hz, 2H) 7.58 (d, J=7.19 Hz, 2H) 7.71 (d, J=8.71 Hz, 2H) 8.29 (t, J=5.30 Hz, 1H)

Example 100

3-[({4-[cyclobutyl(2-methyl-5-phenylfuran-3-yl)methoxy]phenyl}carbonyl)(methyl)amino]propanoic acid

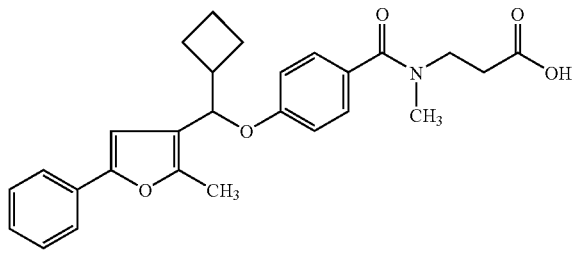

A solution of 4-[cyclobutyl(2-methyl-5-phenylfuran-3-yl)methoxy]benzoic acid (127 mg), ethyl 3-(methylamino)propanoate (55 mg), 1-ethyl-3-(3-dimethylaminopropyl)carbodiimide hydrochloride (81 mg), hydroxybenzotriazole monohydrate (64 mg) and triethylamine (59 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (2.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (115 mg, 73%).

$^1$H NMR (300 MHz, DMSO-d$_6$) δ ppm 1.76-2.22 (m, 6H) 2.40 (s, 3H) 2.46-2.50 (m, 2H) 2.72-2.97 (m, 4H) 3.51 (brs, 2H) 5.26 (d, J=8.33 Hz, 1H) 6.83 (s, 1H) 6.93 (d, J=8.71 Hz, 2H) 7.20-7.28 (m, 3H) 7.36 (t, J=7.57 Hz, 2H) 7.59 (d, J=7.57 Hz, 2H)

Example 101

3-{[(4-{[cyclobutyl(2-methyl-5-phenylfuran-3-yl)methyl]amino}phenyl)carbonyl]amino}propanoic acid

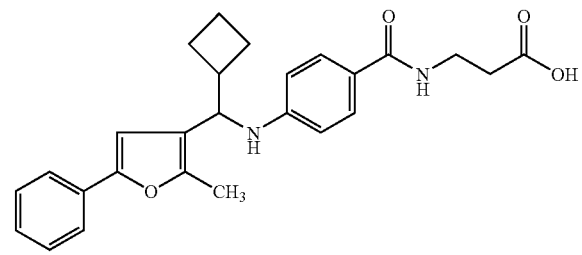

(1) 3-[chloro(cyclobutyl)methyl]-2-methyl-5-phenylfuran

To a solution of cyclobutyl(2-methyl-5-phenylfuran-3-yl)methanol (1.3 g) in toluene (10 mL) was added thionyl chloride (1.2 mL), and the mixture was stirred at room temperature overnight. The solvent was evaporated under reduced pressure to give the title compound (1.4 g, 100%) as an oil.

(2) 4-{[cyclobutyl(2-methyl-5-phenylfuran-3-yl)methyl]amino}benzoic acid

A mixture of 3-[chloro(cyclobutyl)methyl]-2-methyl-5-phenylfuran (1.4 g) obtained by the above-mentioned reaction, methyl 4-aminobenzoate (1.7 g), sodium carbonate (1.2 g) and sodium iodide (3.3 g) in N,N-dimethylacetamide (10 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (6 mL) was added, and the mixture was stirred at 70° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.4 g, 18%) as an amorphous compound.

¹H NMR (300 MHz, CHLOROFORM-d) δ ppm 1.80-1.97 (m, 5H) 2.06-2.25 (m, 1H) 2.42 (s, 3H) 2.60-2.69 (m, 1H) 4.23 (d, J=9.09 Hz, 1H) 6.45 (s, 1H) 6.52 (d, J=9.09 Hz, 2H) 7.20 (d, J=7.19 Hz, 1H) 7.32 (t, J=7.57 Hz, 2H) 7.57 (d, J=7.19 Hz, 2H) 7.84 (d, J=8.71 Hz, 2H)

(3) 3-{[(4-{[cyclobutyl(2-methyl-5-phenylfuran-3-yl)methyl]amino}phenyl)carbonyl]amino}propanoic acid A solution of 4-{[cyclobutyl(2-methyl-5-phenylfuran-3-yl)methyl]amino}benzoic acid (181 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (190 mg, 88%).

¹H NMR (300 MHz, DMSO-d₆) δ ppm 1.67-1.91 (m, 5H) 2.07-2.13 (m, 1H) 2.40-2.44 (m, 5H) 2.61-2.69 (m, 1H) 3.25-3.47 (m, 2H) 4.28 (d, J=7.95 Hz, 1H) 6.26 (d, J=7.57 Hz, 1H) 6.55 (d, J=9.09 Hz, 2H) 6.72 (s, 1H) 7.22 (d, J=7.19 Hz, 1H) 7.35 (t, J=7.57 Hz, 2H) 7.53 (dd, J=7.95, 3.79 Hz, 4H) 7.99 (t, J=5.49 Hz, 1H)

Example 102

3-{[(4-{[cyclobutyl(2-methyl-5-phenylfuran-3-yl)methyl]amino}phenyl)carbonyl](methyl)amino}propanoic acid

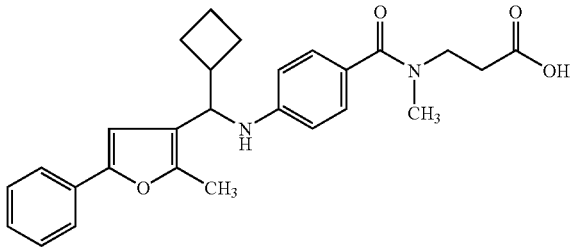

A solution of 4-{[cyclobutyl(2-methyl-5-phenylfuran-3-yl)methyl]amino}benzoic acid (181 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (206 mg, 92%).

¹H NMR (300 MHz, DMSO-d₆) δ ppm 1.71-1.87 (m, 5H) 2.08-2.15 (m, 5H) 2.41 (s, 3H) 2.46-2.50 (m, 2H) 2.60-2.73 (m, 1H) 2.89 (s, 3H) 3.51 (t, J=7.38 Hz, 2H) 4.23 (d, J=7.57 Hz, 1H) 6.15 (d, J=7.57 Hz, 1H) 6.54 (d, J=8.33 Hz, 2H) 6.73 (s, 1H) 7.11 (d, J=8.71 Hz, 2H) 7.22 (d, J=7.19 Hz, 1H) 7.36 (t, J=7.76 Hz, 2H) 7.55 (d, J=7.19 Hz, 2H)

Example 103

3-[({4-[(2-methyl-5-phenylfuran-3-yl)(tetrahydro-2H-pyran-4-yl)methoxy]phenyl}carbonyl)amino]propanoic acid

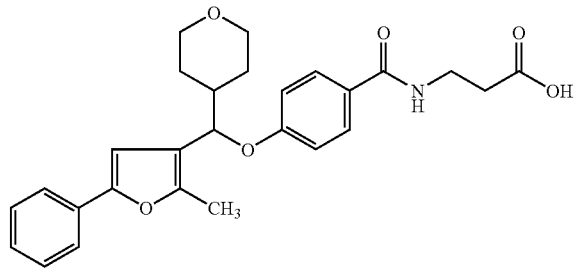

(1) (2-methyl-5-phenylfuran-3-yl)(tetrahydro-2H-pyran-4-yl)methanol

To a solution of 2-methyl-5-phenylfuran-3-carbaldehyde (1.9 g) in tetrahydrofuran (30 mL) was added dropwise bromo(tetrahydro-2H-pyran-4-yl)magnesium-diethyl ether solution (30 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel column (10% ethyl acetate/hexane to 40% ethyl acetate/hexane) to give the title compound (2.3 g, 86%) as an oil.

¹H NMR (300 MHz, CHLOROFORM-d) δ ppm 1.12-1.54 (m, 4H) 1.72 (brs, 1H) 1.80-2.04 (m, 2H) 2.34 (s, 3H) 3.23-3.49 (m, 2H) 3.85-3.98 (m, 1H) 4.02-4.08 (m, 1H) 4.31 (d, J=8.33 Hz, 1H) 6.59 (s, 1H) 7.13-7.30 (m, 1H) 7.36 (t, J=7.57 Hz, 2H) 7.62 (d, J=7.19 Hz, 2H)

(2) 4-[(2-methyl-5-phenylfuran-3-yl)(tetrahydro-2H-pyran-4-yl)methoxy]benzoic acid To a solution of (2-methyl-5-phenylfuran-3-yl)(tetrahydro-2H-pyran-4-yl)methanol (545 mg) obtained by the above-mentioned reaction and methyl 4-hydroxybenzoate (365 mg) in tetrahydrofuran (20 mL) were added tributylphosphine (1.0 mL) and 1,1'-(azodicarbonyl)dipiperidine (1.0 g), and the mixture was stirred at room temperature overnight. The solvent was evaporated under reduced pressure, and the residue was purified by silica gel column (0% ethyl acetate/hexane to 30% ethyl acetate/hexane) to give methyl 4-[(2-methyl-5-phenylfuran-3-yl)(tetrahydro-2H-pyran-4-yl)methoxy]benzoate as an oil. The obtained methyl 4-[(2-methyl-5-phenylfuran-3-yl)(tetrahydro-2H-pyran-4-yl)methoxy]benzoate was dissolved in methanol (4 mL) and tetrahydrofuran (4 mL). 2N Lithium hydroxide (2.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (361 mg, 47%) as an amorphous compound.

$^1$H NMR (300 MHz, CHLOROFORM-d) δ ppm 1.40-1.59 (m, 3H) 1.87-2.24 (m, 2H) 2.38 (s, 3'H) 3.34-3.47 (m, 2H) 3.96-4.09 (m, 2H) 4.83 (d, J=7.54 Hz, 1H) 6.51 (s, 1H) 6.87 (d, J=8.85 Hz, 2H) 7.22 (d, J=7.16 Hz, 1H) 7.33 (t, J=7.54 Hz, 2H) 7.57 (d, J=7.35 Hz, 2H) 7.96 (d, J=8.85 Hz, 2H)

(3) 3-[({4-[(2-methyl-5-phenylfuran-3-yl)(tetrahydro-2H-pyran-4-yl)methoxy]phenyl}carbonyl)amino]propanoic acid A solution of 4-[(2-methyl-5-phenylfuran-3-yl)(tetrahydro-2H-pyran-4-yl)methoxy]benzoic acid (177 mg) obtained by the above-mentioned reaction, ethyl β-alaninate hydrochloride (77 mg), 1-ethyl-3-(3-dimethylaminopropyl)carbodiimide hydrochloride (96 mg), hydroxybenzotriazole monohydrate (77 mg) and triethylamine (70 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (189 mg, 90%).

$^1$H NMR (300 MHz, DMSO-d$_6$) δ ppm 1.30-1.49 (m, 3H) 1.89-1.94 (m, 1H) 2.04-2.13 (m, 1H) 2.39 (s, 3H) 2.44 (t, J=7.06 Hz, 2H) 3.23-3.48 (m, 3H) 3.83-3.94 (m, 2H) 5.14 (d, J=7.91 Hz, 1H) 6.83 (s, 1H) 6.95 (d, J=8.85 Hz, 2H) 7.24 (d, J=7.35 Hz, 1H) 7.36 (t, J=7.63 Hz, 2H) 7.59 (d, J=7.35 Hz, 2H) 7.71 (d, J=8.85 Hz, 2H) 8.30 (s, 1H)

Example 104

3-{[(4-{[(2-methyl-5-phenylfuran-3-yl)(tetrahydro-2H-pyran-4-yl)methyl]amino}phenyl)carbonyl]amino}propanoic acid

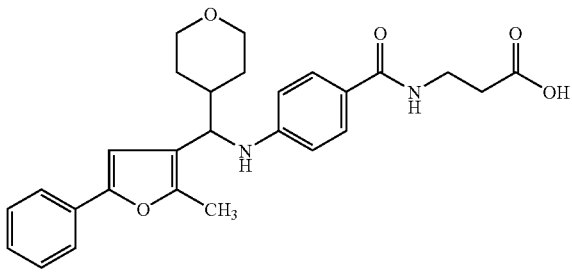

(1) 4-[chloro(2-methyl-5-phenylfuran-3-yl)methyl]tetrahydro-2H-pyran

To a solution of (2-methyl-5-phenylfuran-3-yl)(tetrahydro-2H-pyran-4-yl)methanol (1.8 g) in toluene (20 mL) was added thionyl chloride (1.4 mL), and the mixture was stirred at room temperature overnight. The solvent was evaporated under reduced pressure to give the title compound (1.9 g, 100%) as an oil.

$^1$H NMR (300 MHz, CHLOROFORM-d) δ ppm 1.14-1.54 (m, 3H) 1.97-2.25 (m, 2H) 2.35 (m, 3H) 3.17-3.50 (m, 2H) 3.84-4.17 (m, 2H) 4.57 (d, J=9.09 Hz, 1H) 6.61 (s, 1H) 7.09-7.30 (m, 1H) 7.36 (t, J=7.57 Hz, 2H) 7.62 (d, J=7.19 Hz, 2H)

(2) 4-{[(2-methyl-5-phenylfuran-3-yl)(tetrahydro-2H-pyran-4-yl)methyl]amino}benzoic acid A mixture of 4-[chloro(2-methyl-5-phenylfuran-3-yl)methyl]tetrahydro-2H-pyran (1.9 g) obtained by the above-mentioned reaction, methyl 4-aminobenzoate (2.0 g), sodium carbonate (1.4 g) and sodium iodide (3.9 g) in N,N-dimethylacetamide (20 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (6 mL), 2 N lithium hydroxide (6 mL) was added, and the mixture was stirred at 70° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (1.5 g, 65%).

$^1$H NMR (300 MHz, DMSO-d$_6$) δ ppm 1.22-1.44 (m, 3H) 1.84-1.92 (m, 2H) 2.39 (s, 3H) 3.25 (q, J=13.38 Hz, 2H) 3.81-3.93 (m, 2H) 34.18 (brs, 1H) 6.60 (d, J=8.85 Hz, 2H) 6.63-6.71 (m, 1H) 6.75 (s, 1H) 7.23 (d, J=7.35 Hz, 1H) 7.37 (t, J=7.63 Hz, 2H) 7.58 (dd, J=15.07, 8.10 Hz, 4H)

(3) 3-{[(4-{[(2-methyl-5-phenylfuran-3-yl)(tetrahydro-2H-pyran-4-yl)methyl]amino}phenyl)carbonyl]amino}propanoic acid A solution of 4-{[(2-methyl-5-phenylfuran-3-yl)(tetrahydro-2H-pyran-4-yl)methyl]amino}benzoic acid (744 mg) obtained by the above-mentioned reaction, ethyl β-alaninate hydrochloride (353 mg), 1-ethyl-3-(3-dimethylaminopropyl)carbodiimide hydrochloride (441 mg), hydroxybenzotriazole monohydrate (352 mg) and triethylamine (321 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (5 mL), tetrahydrofuran (3 mL) and 1N lithium hydroxide (5.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (694 mg, 80%).

$^1$H NMR (300 MHz, DMSO-d$_6$) δ ppm 1.13-1.50 (m, 6H) 1.83-1.94 (m, 2H) 2.38 (s, 3H) 2.42 (t, J=7.19 Hz, 2H) 3.34 (dd, J=12.12, 4.92 Hz, 4H) 3.87 (ddd, J=14.20, 10.98, 10.79 Hz, 2H) 4.16 (t, J=8.14 Hz, 1H) 6.37 (d, J=8.33 Hz, 1H) 6.57 (d, J=9.09 Hz, 2H) 6.75 (s, 1H) 7.23 (d, J=7.19 Hz, 1H) 7.36 (t, J=7.76 Hz, 2H) 7.54 (dd, J=7.76, 5.87 Hz, 4H) 7.99 (t, J=5.49 Hz, 1H) 12.18 (brs, 1H)

Example 105

3-{methyl[(4-{[(2-methyl-5-phenylfuran-3-yl)(tetrahydro-2H-pyran-4-yl)methyl]amino}phenyl)carbonyl]amino}propanoic acid

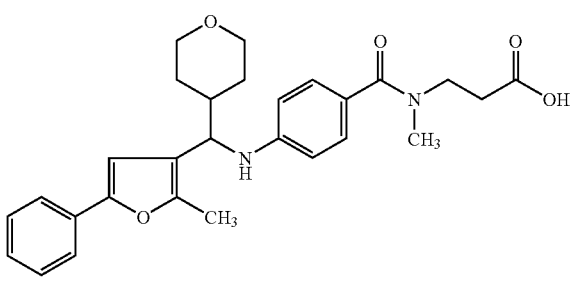

A solution of 4-{[(2-methyl-5-phenylfuran-3-yl)(tetrahydro-2H-pyran-4-yl)methyl]amino}benzoic acid (744 mg), ethyl 3-(methylamino)propanoate (302 mg), 1-ethyl-3-(3-dimethylaminopropyl)carbodiimide hydrochloride (441 mg), hydroxybenzotriazole monohydrate (352 mg) and triethylamine (321 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure.

To the residue were added ethanol (5 mL), tetrahydrofuran (5 mL) and 1N lithium hydroxide (3.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (725 mg, 75%).

$^1$H NMR (300 MHz, DMSO-$d_6$) δ ppm 1.16-1.47 (m, 3H) 1.83-1.94 (m, 2H) 2.38 (s, 3H) 2.43-2.55 (m, 2H) 2.90 (s, 3H) 3.14-3.42 (m, 2H) 3.51 (t, J=7.19 Hz, 2H) 3.85 (dd, J=13.82, 10.79 Hz, 2H) 4.12 (t, J=7.95 Hz, 1H) 6.28 (d, J=7.95 Hz, 1H) 6.57 (d, J=8.71 Hz, 2H) 6.76 (s, 1H) 7.11 (d, J=8.71 Hz, 2H) 7.23 (d, J=7.57 Hz, 1H) 7.36 (t, J=7.76 Hz, 2H) 7.56 (d, J=7.19 Hz, 2H)

Example 106

3-({[4-(cyclohexyl{2-(methoxymethyl)-5-[4-(trifluoromethyl)phenyl]furan-3-yl}methoxy)phenyl]carbonyl}amino)propanoic acid

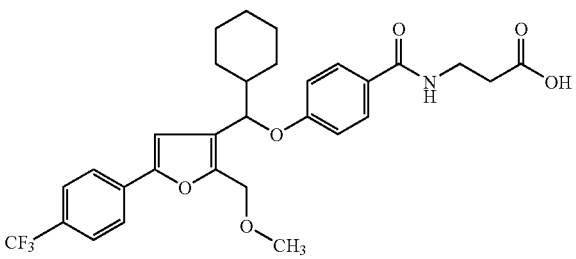

(1) methyl 5-bromo-2-(bromomethyl)furan-3-carboxylate

To a solution of methyl 2-methyl-3-furancarboxylate (14.0 g) in N,N-dimethylformamide (100 mL) was added N-bromosuccinimide (39.2 g) at 0° C. over 45 min or longer. The mixture was stirred at 0° C. for 30 min, and at 40° C. overnight. The reaction mixture was poured into water, and the mixture was extracted with diethyl ether. The organic layer was washed with water, and dried over magnesium sulfate. The solvent was evaporated under reduced pressure, and the residue was purified by silica gel chromatography (0% ethyl acetate/hexane to 10% ethyl acetate/hexane) to give the title compound (11.4 g, 38%) as an oil.

$^1$H NMR (300 MHz, CHLOROFORM-d) δ ppm 3.87 (s, 3H) 4.76 (s, 2H) 6.63 (s, 1H)

(2) methyl 5-bromo-2-(methoxymethyl)furan-3-carboxylate

To a solution of methyl 5-bromo-2-(bromomethyl)furan-3-carboxylate (3.0 g) in methanol (30 mL) was added sodium methoxide (0.8 g) at 0° C., and the mixture was stirred at room temperature overnight. The reaction mixture was poured into water, and the mixture was acidified with 1N hydrochloric acid and extracted with ethyl acetate. The organic layer was washed with water, and dried over magnesium sulfate. The solvent was evaporated under reduced pressure, and the residue was purified by silica gel chromatography (0% ethyl acetate/hexane to 20% ethyl acetate/hexane) to give the title compound (1.9 g, 77%) as an oil.

$^1$H NMR (300 MHz, CHLOROFORM-d) δ ppm 3.41 (s, 3H) 3.85 (s, 3H) 4.70 (s, 2H) 6.63 (s, 1H)

(3) methyl 2-(methoxymethyl)-5-[4-(trifluoromethyl)phenyl]furan-3-carboxylate A mixture of methyl 5-bromo-2-(methoxymethyl)furan-3-carboxylate (1.9 g) obtained by the above-mentioned reaction, 4-(trifluoromethyl)phenylboronic acid (1.7 g), tetrakis(triphenylphosphine)palladium(0) (0.4 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 25% ethyl acetate/hexane) to give the title compound (1.9 g, 81%) as an oil.

$^1$H NMR (300 MHz, CHLOROFORM-d) δ ppm 3.46 (s, 3H) 3.89 (s, 3H) 4.82 (s, 2H) 7.06 (s, 1H) 7.66 (d, J=8.10 Hz, 2H) 7.80 (d, J=8.48 Hz, 2H)

(4) 2-(methoxymethyl)-5-[4-(trifluoromethyl)phenyl]furan-3-yl}methanol

A solution of methyl 2-(methoxymethyl)-5-[4-(trifluoromethyl)phenyl]furan-3-carboxylate (4.2 g) obtained by the above-mentioned reaction in tetrahydrofuran (30 mL) was added dropwise to a suspension of lithium aluminum hydride (0.5 g) in tetrahydrofuran (30 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (3.8 g, 100%) as an oil.

$^1$H NMR (300 MHz, CHLOROFORM-d) δ ppm 2.01 (t, J=5.84 Hz, 1H) 3.43 (s, 3H) 4.53 (s, 2H) 4.62 (d, J=5.65 Hz, 2H) 6.79 (s, 1H) 7.62 (d, J=8.29 Hz, 2H) 7.75 (d, J=8.29 Hz, 2H)

(5) 2-(methoxymethyl)-5-[4-(trifluoromethyl)phenyl]furan-3-carbaldehyde

To a solution of 2-(methoxymethyl)-5-[4-(trifluoromethyl)phenyl]furan-3-yl}methanol (3.8 g) obtained by the above-mentioned reaction in methylene chloride (30 mL) was added a Dess-Martin reagent (8.6 g) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (3.2 g, 84%) as a yellow crystal.

$^1$H NMR (300 MHz, CHLOROFORM-d) δ ppm 3.50 (s, 3H) 4.78 (s, 2H) 7.10 (s, 1H) 7.67 (d, J=7.95 Hz, 2H) 7.80 (d, J=8.33 Hz, 2H) 10.12 (s, 1H)

(6) cyclohexyl{2-(methoxymethyl)-5-[4-(trifluoromethyl)phenyl]furan-3-yl}methanol To a solution of 2-(methoxymethyl)-5-[4-(trifluoromethyl)phenyl]furan-3-carbaldehyde (3.1 g) obtained by the above-mentioned reaction in tetrahydrofuran (30 mL) was added dropwise 1N cyclohexylmagnesium bromide-tetrahydrofuran solution (16.5 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (2.9 g, 72%) as an oil.

$^1$H NMR (300 MHz, CHLOROFORM-d) δ ppm 0.85-1.38 (m, 5H) 1.48-1.95 (m, 5H) 2.01-2.04 (m, 1H) 2.08 (d, J=3.79 Hz, 1H) 3.42 (s, 3H) 4.43 (dd, J=7.19, 3.79 Hz, 1H) 4.49 (s, 2H) 6.74 (s, 1H) 7.62 (d, J=8.71 Hz, 2H) 7.76 (d, J=8.71 Hz, 2H)

(7) 4-(cyclohexyl{2-(methoxymethyl)-5-[4-(trifluoromethyl)phenyl]furan-3-yl}methoxy)benzoic acid To a solution of cyclohexyl{2-(methoxymethyl)-5-[4-(trifluoromethyl)phenyl]furan-3-yl}methanol (553 mg) obtained by the above-mentioned reaction and methyl 4-hydroxybenzoate (274 mg) in tetrahydrofuran (20 mL) were added tributylphosphine (0.7 mL) and 1,1'-(azodicarbonyl)dipiperidine (757 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-(cyclohexyl{2-(methoxymethyl)-5-[4-(trifluoromethyl)phenyl]furan-3-yl}methoxy)benzoate as an amorphous compound. The obtained methyl 4-(cyclohexyl{2-(methoxymethyl)-5-[4-(trifluoromethyl)phenyl]furan-3-yl}methoxy)benzoate was dissolved in methanol (2 mL) and tetrahydrofuran (2 mL). 2N Lithium hydroxide (1.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (195 mg, 27%) as an amorphous compound.

$^1$H NMR (300 MHz, CHLOROFORM-d) δ ppm 0.96-1.40 (m, 5H) 1.57-1.98 (m, 5H) 2.09 (d, J=14.01 Hz, 1H) 3.42 (s, 3H) 4.37-4.61 (m, 2H) 4.44 (d, J=12.87 Hz, 1H) 4.58 (d, J=12.87 Hz, 1H) 5.01 (d, J=7.19 Hz, 1H) 6.69 (s, 1H) 6.96 (d, J=9.09 Hz, 2H) 7.59 (d, J=8.33 Hz, 2H) 7.71 (d, J=8.33 Hz, 2H) 7.95 (d, J=8.71 Hz, 2H)

(8) 3-({[4-(cyclohexyl{2-(methoxymethyl)-5-[4-(trifluoromethyl)phenyl]furan-3-yl}methoxy)phenyl]carbonyl}amino)propanoic acid A solution of 4-(cyclohexyl{2-(methoxymethyl)-5-[4-(trifluoromethyl)phenyl]furan-3-yl}methoxy)benzoic acid (98 mg) obtained by the above-mentioned reaction, ethyl β-alaninate hydrochloride (37 mg), 1-ethyl-3-(3-dimethylaminopropyl)carbodiimide hydrochloride (46 mg), hydroxybenzotriazole monohydrate (37 mg) and triethylamine (33 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (96 mg, 86%).

$^1$H NMR (300 MHz, DMSO-d$_6$) δ ppm 0.91-1.37 (m, 5H) 1.44-1.94 (m, 5H) 2.02-2.06 (m, 1H) 2.41 (t, J=7.00 Hz, 2H) 3.38 (q, J=7.00 Hz, 2H) 4.41-4.66 (m, 2H) 5.21 (d, J=7.57 Hz, 1H) 6.99 (d, J=8.71 Hz, 2H) 7.15 (s, 1H) 7.70 (d, J=9.09 Hz, 2H) 7.74 (d, J=8.71 Hz, 2H) 7.87 (d, J=8.33 Hz, 2H) 8.35 (brs, 1H)

Example 107

3-[{[4-(cyclohexyl{2-(methoxymethyl)-5-[4-(trifluoromethyl)phenyl]furan-3-yl}methoxy)phenyl]carbonyl}(methyl)amino]propanoic acid

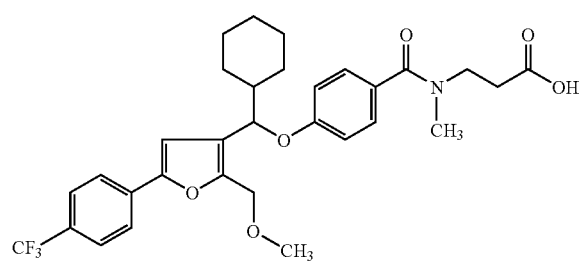

A solution of 4-(cyclohexyl{2-(methoxymethyl)-5-[4-(trifluoromethyl)phenyl]furan-3-yl}methoxy)benzoic acid (98 mg), ethyl 3-(methylamino)propanoate (31 mg), 1-ethyl-3-(3-dimethylaminopropyl)carbodiimide hydrochloride (46 mg), hydroxybenzotriazole monohydrate (37 mg) and triethylamine (33 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (93 mg, 81%).

$^1$H NMR (300 MHz, DMSO-$d_6$) δ ppm 0.98-1.31 (m, 5H) 1.47-1.89 (m, 5H) 2.03-2.05 (m, 1H) 2.41-2.55 (m, 2H) 2.88 (s, 3H) 3.29 (brs, 2H) 4.53 (q, J=12.62 Hz, 2H) 5.16 (d, J=7.19 Hz, 1H) 6.98 (d, J=7.95 Hz, 2H) 7.17 (s, 1H) 7.26 (d, J=7.57 Hz, 2H) 7.75 (d, J=7.57 Hz, 2H) 7.88 (d, J=7.57 Hz, 2H)

Example 108

3-({[4-(cyclohexyl{2-(ethoxymethyl)-5-[4-(trifluoromethyl)phenyl]furan-3-yl}methoxy)phenyl]carbonyl}amino)propanoic acid

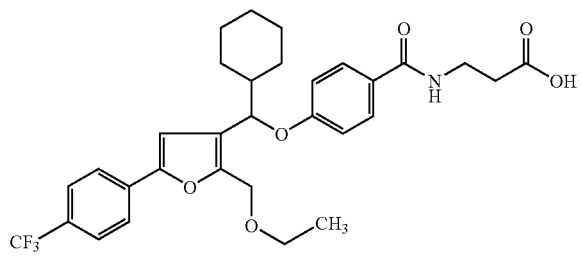

(1) methyl 5-bromo-2-(ethoxymethyl)furan-3-carboxylate

To a solution of methyl 5-bromo-2-(bromomethyl)furan-3-carboxylate (4.5 g) in ethanol (50 mL) was added 20% sodium ethoxide-ethanol solution (7.8 g) at 0° C., and the mixture was stirred at 0° C. for 2 hr and at room temperature overnight. The reaction was poured into water, and the mixture was acidified with 1N hydrochloric acid and extracted with ethyl acetate. The organic layer was washed with water, and dried over magnesium sulfate. The solvent was evaporated under reduced pressure, and the residue was purified by silica gel chromatography (0% ethyl acetate/hexane to 15% ethyl acetate/hexane) to give the title compound (2.8 g, 67%) as an oil.

$^1$H NMR (300 MHz, CHLOROFORM-d) δ ppm 1.23 (t, J=7.00 Hz, 3H) 1.35 (t, J=7.00 Hz, 3H) 3.58 (q, J=6.82 Hz, 2H) 4.30 (q, J=7.19 Hz, 2H) 4.74 (s, 2H) 6.63 (s, 1H)

(2) methyl 2-(ethoxymethyl)-5-[4-(trifluoromethyl)phenyl]furan-3-carboxylate

A mixture of methyl 5-bromo-2-(ethoxymethyl)furan-3-carboxylate (2.7 g) obtained by the above-mentioned reaction, 4-(trifluoromethyl)phenylboronic acid (2.3 g), tetrakis(triphenylphosphine)palladium(0) (0.6 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane) to give the title compound (2.8 g, 81%) as an oil.

$^1$H NMR (300 MHz, CHLOROFORM-d) δ ppm 1.26 (t, J=7.00 Hz, 3H) 1.39 (t, J=7.19 Hz, 3H) 3.64 (q, J=7.19 Hz, 2H) 4.35 (q, J=7.19 Hz, 2H) 4.86 (s, 2H) 7.06 (s, 1H) 7.59-7.70 (m, 2H) 7.80 (d, J=8.33 Hz, 2H)

(3) 2-(ethoxymethyl)-5-[4-(trifluoromethyl)phenyl]furan-3-yl}methanol

A solution of methyl 2-(ethoxymethyl)-5-[4-(trifluoromethyl)phenyl]furan-3-carboxylate (2.7 g) obtained by the above-mentioned reaction in tetrahydrofuran (30 mL) was added dropwise to a suspension of lithium aluminum hydride (0.3 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (2.4 g, 100%) as an oil.

$^1$H NMR (300 MHz, CHLOROFORM-d) δ ppm 1.26 (t, J=6.82 Hz, 3H) 2.09 (t, J=5.87 Hz, 1H) 3.61 (q, J=6.82 Hz, 2H) 4.58 (s, 2H) 4.61 (d, J=5.68 Hz, 2H) 6.78 (s, 1H) 7.62 (d, J=8.33 Hz, 2H) 7.74 (d, J=8.33 Hz, 2H)

(4) 2-(ethoxymethyl)-5-[4-(trifluoromethyl)phenyl]furan-3-carbaldehyde

To a solution of 2-(ethoxymethyl)-5-[4-(trifluoromethyl)phenyl]furan-3-yl}methanol (2.4 g) obtained by the above-mentioned reaction in methylene chloride (25 mL) was added a Dess-Martin reagent (5.0 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane), and crystallized from ethyl acetate/hexane to give the title compound (3.2 g, 84%) as a white crystal.

$^1$H NMR (300 MHz, CHLOROFORM-d) δ ppm 1.28 (t, J=7.00 Hz, 3H) 3.67 (q, J=6.82 Hz, 2H) 4.83 (s, 2H) 7.10 (s, 1H) 7.67 (d, J=8.33 Hz, 2H) 7.80 (d, J=8.33 Hz, 2H) 10.14 (s, 1H)

(5) cyclohexyl{2-(methoxymethyl)-5-[4-(trifluoromethyl)phenyl]furan-3-yl}methanol To a solution of 2-(ethoxymethyl)-5-[4-(trifluoromethyl)phenyl]furan-3-carbaldehyde (2.1 g) obtained by the above-mentioned reaction in tetrahydrofuran (30 mL) was added dropwise 1N cyclohexylmagnesium bromide-tetrahydrofuran solution (10.5 mL) at 0° C. and, after the completion of the dropwise addition, and the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (2.2 g, 84%) as an oil.

$^1$H NMR (300 MHz, CHLOROFORM-d) δ ppm 0.94-1.32 (m, 8H) 1.49-1.94 (m, 5H) 1.99-2.06 (m, 1H) 2.20 (d, J=3.79 Hz, 1H) 3.60 (q, J=6.82 Hz, 2H) 4.44 (dd, J=7.38, 3.60 Hz, 1H) 4.54 (s, 2H) 6.73 (s, 1H) 7.61 (d, J=8.33 Hz, 2H) 7.75 (d, J=8.33 Hz, 2H)

(6) 4-(cyclohexyl{2-(ethoxymethyl)-5-[4-(trifluoromethyl)phenyl]furan-3-yl}methoxy)benzoic acid To a solution of cyclohexyl{2-(methoxymethyl)-5-[4-(trifluoromethyl)phenyl]furan-3-yl}methanol (574 mg) obtained by the above-mentioned reaction and methyl 4-hydroxybenzoate (274 mg) in tetrahydrofuran (20 mL) were added tributylphosphine (0.7 mL) and 1,1'-(azodicarbonyl)dipiperidine (757 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-(cyclohexyl{2-(ethoxymethyl)-5-[4-(trifluoromethyl)phenyl]furan-3-yl}methoxy)benzoate as an amorphous compound. The obtained methyl 4-(cyclohexyl{2-(ethoxymethyl)-5-[4-(trifluoromethyl)phenyl]furan-3-yl}methoxy)benzoate was dissolved in methanol (2 mL) and tetrahydrofuran (2 mL). 2N Lithium hydroxide (1.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (289 mg, 38%) as an amorphous compound.

$^1$H NMR (300 MHz, CHLOROFORM-d) δ ppm 1.02-1.32 (m, 8H) 1.38-1.95 (m, 5H) 2.04-2.11 (m, 1H) 3.59 (q, J=7.19 Hz, 2H) 4.50 (d, J=12.49 Hz, 1H) 4.62 (d, J=12.49 Hz, 1H) 5.03 (d, J=7.19 Hz, 1H) 6.69 (s, 1H) 6.98 (d, J=8.71 Hz, 2H) 7.58 (d, J=8.33 Hz, 2H) 7.71 (d, J=8.33 Hz, 2H) 7.94 (d, J=8.71 Hz, 2H)

(7) 3-({[4-(cyclohexyl{2-(ethoxymethyl)-5-[4-(trifluoromethyl)phenyl]furan-3-yl}methoxy)phenyl]carbonyl}amino)propanoic acid A solution of 4-(cyclohexyl{2-(ethoxymethyl)-5-[4-(trifluoromethyl)phenyl]furan-3-yl}methoxy)benzoic acid (141 mg) obtained by the above-mentioned reaction, ethyl β-alaninate hydrochloride (52 mg), 1-ethyl-3-(3-dimethylaminopropyl)carbodiimide hydrochloride (65 mg), hydroxybenzotriazole monohydrate (52 mg) and triethylamine (47 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (141 mg, 88%).

$^1$H NMR (300 MHz, DMSO-d$_6$) δ ppm 0.99-1.29 (m, 8H) 1.45-1.95 (m, 5H) 2.02-2.05 (m, 1H) 2.40 (t, J=7.19 Hz, 2H) 3.30-3.44 (m, 2H) 3.53 (q, J=7.19 Hz, 2H) 4.52 (d, J=12.87 Hz, 1H) 4.62 (d, J=12.87 Hz, 1H) 5.21 (d, J=7.19 Hz, 1H) 7.00 (d, J=8.71 Hz, 2H) 7.14 (s, 1H) 7.69 (d, J=8.71 Hz, 2H) 7.74 (d, J=8.33 Hz, 2H) 7.87 (d, J=7.95 Hz, 2H) 8.36 (br. s., 1H)

Example 109

3-[{[4-(cyclohexyl{2-(ethoxymethyl)-5-[4-(trifluoromethyl)phenyl]furan-3-yl}methoxy)phenyl]carbonyl}(methyl)amino]propanoic acid

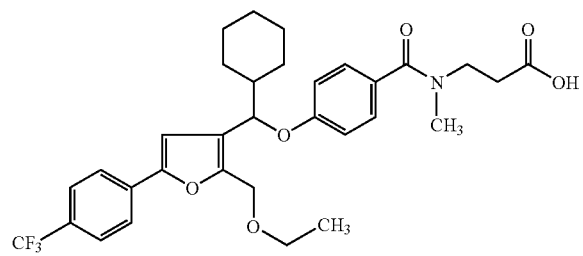

A solution of 4-(cyclohexyl{2-(ethoxymethyl)-5-[4-(trifluoromethyl)phenyl]furan-3-yl}methoxy)benzoic acid (141 mg), ethyl 3-(methylamino)propanoate (45 mg), 1-ethyl-3-(3-dimethylaminopropyl)carbodiimide hydrochloride (65 mg), hydroxybenzotriazole monohydrate (52 mg) and triethylamine (47 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (93 mg, 81%).

$^1$H NMR (300 MHz, DMSO-d$_6$) δ ppm 1.01-1.25 (m, 8H) 1.42-1.95 (m, 5H) 2.02-2.06 (m, 1H) 2.40-2.48 (m, 2H) 2.87 (s, 3H) 3.51 (q, J=6.94 Hz, 2H) 4.52 (d, J=12.87 Hz, 1H) 4.61 (d, J=12.87 Hz, 1H) 5.16 (d, J=7.57 Hz, 1H) 6.98 (d, J=8.71 Hz, 2H) 7.16 (s, 1H) 7.24 (d, J=8.71 Hz, 2H) 7.74 (d, J=8.71 Hz, 2H) 7.88 (d, J=8.33 Hz, 2H)

Example 110

3-[({4-[cyclohexyl(2,5-dimethylfuran-3-yl)methoxy]phenyl}carbonyl)amino]propanoic acid

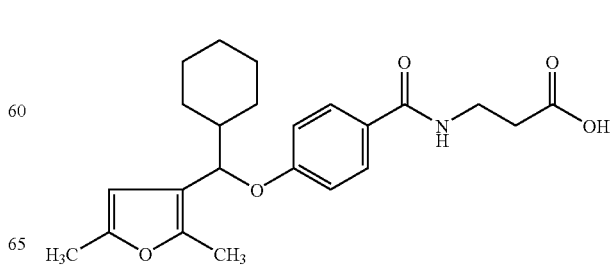

(1) (2,5-dimethylfuran-3-yl)methanol

A solution of 2,5-dimethylfuran-3-carbonyl chloride (5.0 g) in tetrahydrofuran (20 mL) was added dropwise to a suspension of sodium borohydride (3.4 g) in tetrahydrofuran (50 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (3.8 g, 100%) as an oil.

$^1$H NMR (300 MHz, CHLOROFORM-d) δ ppm 2.24 (s, 6H) 4.41 (d, J=5.68 Hz, 2H) 5.94 (s, 1H)

(2) 2,5-dimethylfuran-3-carbaldehyde

To a solution of (2,5-dimethylfuran-3-yl)methanol (3.8 g) obtained by the above-mentioned reaction in methylene chloride (30 mL) was added a Dess-Martin reagent (15.3 g) at 0° C., and the mixture was stirred at 0° C. for 3 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (2.1 g, 56%) as an oil.

$^1$H NMR (300 MHz, CHLOROFORM-d) δ ppm 2.27 (s, 3H) 2.54 (s, 3H) 6.25 (s, 1H) 9.87 (s, 1H)

(3) cyclohexyl(2,5-dimethylfuran-3-yl)methanol

To a solution of 2,5-dimethylfuran-3-carbaldehyde (1.3 g) obtained by the above-mentioned reaction in tetrahydrofuran (30 mL) was added dropwise 1N cyclohexylmagnesium bromide-diethyl ether solution (25.5 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (3.1 g, 89%) as an oil.

$^1$H NMR (300 MHz, CHLOROFORM-d) δ ppm 0.72-1.37 (m, 5H) 1.39-1.95 (m, 5H) 1.99-2.11 (m, 1H) 2.19 (s, 3H) 2.26 (s, 3H) 4.20 (dd, J=7.95, 2.65 Hz, 1H) 5.88 (s, 1H)

(4) 4-[cyclohexyl(2,5-dimethylfuran-3-yl)methoxy]benzoic acid

To a solution of cyclohexyl(2,5-dimethylfuran-3-yl)methanol (521 mg) obtained by the above-mentioned reaction and methyl 4-hydroxybenzoate (456 mg) in tetrahydrofuran (20 mL) were added tributylphosphine (1.2 mL) and 1,1'-(azodicarbonyl)dipiperidine (1.2 g), and the mixture was stirred at room temperature overnight. The solvent was evaporated under reduced pressure, and the residue was purified by silica gel column (0% ethyl acetate/hexane to 12% ethyl acetate/hexane) to give methyl 4-[cyclohexyl(2,5-dimethylfuran-3-yl)methoxy]benzoate as an oil. The obtained methyl 4-[cyclohexyl(2,5-dimethylfuran-3-yl)methoxy]benzoate was dissolved in methanol (5 mL) and tetrahydrofuran (5 mL). 2N Lithium hydroxide (1.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel column (0% ethyl acetate/hexane to 30% ethyl acetate/hexane) to give the title compound (501 mg, 61%) as a white crystal.

$^1$H NMR (300 MHz, CHLOROFORM-d) δ ppm 0.88-1.38 (m, 5H) 1.40-1.92 (m, 5H) 2.02-2.07 (m, 1H) 2.17 (s, 3H) 2.23 (s, 3H) 4.73 (d, J=7.19 Hz, 1H) 5.80 (s, 1H) 6.83 (d, J=8.71 Hz, 2H) 7.95 (d, J=8.71 Hz, 2H)

(5) 3-[({4-[cyclohexyl(2,5-dimethylfuran-3-yl)methoxy]phenyl}carbonyl)amino]propanoic acid A solution of 4-[cyclohexyl(2,5-dimethylfuran-3-yl)methoxy]benzoic acid (246 mg) obtained by the above-mentioned reaction, ethyl β-alaninate hydrochloride (138 mg), 1-ethyl-3-(3-dimethylaminopropyl)carbodiimide hydrochloride (173 mg), hydroxybenzotriazole monohydrate (138 mg) and triethylamine (125 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (188 mg, 63%).

$^1$H NMR (300 MHz, DMSO-$d_6$) δ ppm 0.83-1.29 (m, 5H) 1.40-1.83 (m, 5H) 1.99 (d, J=12.87 Hz, 1H) 2.12 (s, 3H) 2.22 (s, 4H) 2.44 (t, J=7.19 Hz, 2H) 3.32-3.50 (m, 2H) 4.96 (d, J=7.57 Hz, 1H) 5.88 (s, 1H) 6.86 (d, J=8.71 Hz, 2H) 7.69 (d, J=8.71 Hz, 2H) 8.21-8.42 (m, 1H)

Example 111

3-[({4-[cyclohexyl(2,5-dimethylfuran-3-yl)methoxy]phenyl}carbonyl)(methyl)amino]propanoic acid

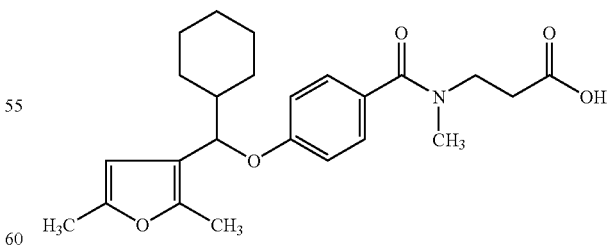

A solution of 4-[cyclohexyl(2,5-dimethylfuran-3-yl)methoxy]benzoic acid (246 mg) obtained by the above-mentioned reaction, ethyl 3-(methylamino)propanoate (118 mg), 1-ethyl-3-(3-dimethylaminopropyl)carbodiimide hydrochloride (173 mg), hydroxybenzotriazole monohydrate (138 mg) and triethylamine (125 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (102 mg, 33%).

$^1$H NMR (300 MHz, DMSO-$d_6$) δ ppm 0.89-1.29 (m, 5H) 1.41-1.83 (m, 5H) 1.98-1.02 (m, 1H) 2.13 (s, 3H) 2.22 (s, 3H) 2.42-2.52 (m, 2H) 2.89 (s, 3H) 3.51 (brs, 2H) 4.90 (d, J=7.57 Hz, 1H) 5.90 (s, 1H) 6.84 (d, J=8.71 Hz, 2H) 7.24 (d, J=8.71 Hz, 2H)

Example 112

3-{[(4-{cyclohexyl[2-methyl-5-(pyridin-2-yl)furan-3-yl]methoxy}phenyl)carbonyl]amino}propanoic acid

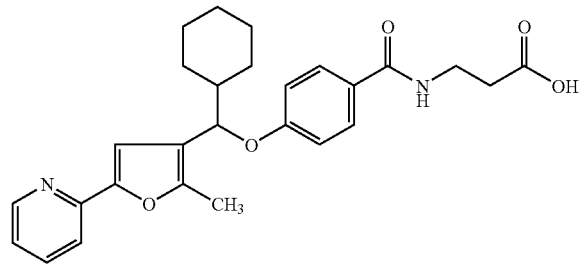

(1) 2-methyl-5-(pyridin-2-yl)furan-3-carbaldehyde

A mixture of 5-bromo-2-methylfuran-3-carbaldehyde (4.9 g), bis(pinacolato)diboron (7.3 g), 1,1'-bis(diphenylphosphino)ferrocene-palladium(II)dichloride dichloromethane complex (1.1 g), potassium acetate (7.7 g) and dimethyl sulfoxide (50 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. A mixture of the residue, 2-bromopyridine (4.9 g), tetrakis(triphenylphosphine)palladium(0) (1.5 g), 2N aqueous sodium carbonate solution (31 mL) and 1,2-dimethoxyethane (60 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 35% ethyl acetate/hexane), and crystallized from ethyl acetate/hexane to give the title compound (0.8 g, 17%) as a yellow solid.

$^1$H NMR (300 MHz, CHLOROFORM-d) δ ppm 2.72 (s, 3H) 7.22 (d, J=6.06 Hz, 1H) 7.24-7.33 (m, 1H) 7.59-7.70 (m, 1H) 7.73 (dd, J=7.57, 1.89 Hz, 1H) 8.63 (d, J=4.92 Hz, 1H) 10.00 (s, 1H)

(2) cyclohexyl[2-methyl-5-(pyridin-2-yl)furan-3-yl]methanol

To a solution of 2-methyl-5-(pyridin-2-yl)furan-3-carbaldehyde (0.8 g) obtained by the above-mentioned reaction in tetrahydrofuran (20 mL) was added dropwise 1N cyclohexylmagnesium bromide-tetrahydrofuran solution (7 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (5% ethyl acetate/hexane to 40% ethyl acetate/hexane) to give the title compound (1.0 g, 83%) as an oil.

$^1$H NMR (300 MHz, CHLOROFORM-d) δ ppm 0.80-1.37 (m, 5H) 1.60-1.89 (m, 5H) 2.04-2.09 (m, 1H) 2.37 (s, 3H) 4.32 (dd, J=7.95, 3.41 Hz, 1H) 6.98 (s, 1H) 7.11 (ddd, J=7.00, 5.11, 1.51 Hz, 1H) 7.56-7.77 (m, 2H) 8.57 (d, J=4.16 Hz, 1H)

(4) 4-{cyclohexyl[2-methyl-5-(pyridin-2-yl)furan-3-yl]methoxy}benzoic acid

To a solution of cyclohexyl[2-methyl-5-(pyridin-2-yl)furan-3-yl]methanol (271 mg) obtained by the above-mentioned reaction and methyl 4-hydroxybenzoate (183 mg) in tetrahydrofuran (20 mL) were added tributylphosphine (0.5 mL) and 1,1'-(azodicarbonyl)dipiperidine (505 mg), and the mixture was stirred at room temperature overnight. The solvent was evaporated under reduced pressure, and the residue was purified by silica gel column (0% ethyl acetate/hexane to 20% ethyl acetate/hexane) to give methyl 4-{cyclohexyl[2-methyl-5-(pyridin-2-yl)furan-3-yl]methoxy}benzoate as an amorphous compound. The obtained methyl 4-{cyclohexyl[2-methyl-5-(pyridin-2-yl)furan-3-yl]methoxy}benzoate was dissolved in methanol (3 mL) and tetrahydrofuran (3 mL). 2N Lithium hydroxide (1.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (174 mg, 46%).

$^1$H NMR (300 MHz, CHLOROFORM-d) δ ppm 1.00-1.30 (m, 5H) 1.66-1.91 (m, 5H) 2.05-2.11 (m, 1H) 2.39 (s, 3H) 4.86 (d, J=7.19 Hz, 1H) 6.87 (d, J=9.09 Hz, 2H) 6.94 (s, 1H) 7.11 (d, J=6.06 Hz, 1H) 7.50-7.76 (m, 2H) 7.94 (d, J=9.09 Hz, 2H) 8.57 (d, J=4.92 Hz, 1H)

(5) 3-{[(4-{cyclohexyl[2-methyl-5-(pyridin-2-yl)furan-3-yl]methoxy}phenyl)carbonyl]amino}propanoic acid A solution of 4-{cyclohexyl[2-methyl-5-(pyridin-2-yl)furan-3-yl]methoxy}benzoic acid (86 mg) obtained by the above-mentioned reaction, ethyl β-alaninate hydrochloride (40 mg), 1-ethyl-3-(3-dimethylaminopropyl)carbodiimide hydrochloride (50 mg), hydroxybenzotriazole monohydrate (40 mg) and triethylamine (36 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10% mL) was added. The mixture was neutralized with 1N hydrochloric acid under ice-cooling, and stirred for 1 hr. The resulting precipitate was collected by filtration and dried to give the title compound (85 mg, 84%).

$^1$H NMR (300 MHz, DMSO-$d_6$) δ ppm 0.97-1.28 (m, 5H) 1.48-1.92 (m, 5H) 2.01-2.07 (m, 1H) 2.40 (s, 3H) 2.45 (t, J=7.35 Hz, 2H) 3.39 (q, J=5.84 Hz, 2H) 5.14 (d, J=7.35 Hz, 1H) 6.88-7.03 (m, 3H) 7.22 (dd, J=6.97, 5.27 Hz, 1H) 7.59 (d, J=8.10 Hz, 2H) 7.70 (d, J=8.85 Hz, 2H) 7.78 (t, J=7.72 Hz, 1H) 8.28 (t, J=5.37 Hz, 1H) 8.50 (d, J=4.71 Hz, 1H) 12.17 (s, 1H)

Example 113

3-{[(4-{cyclohexyl[2-methyl-5-(pyridin-2-yl)furan-3-yl]methoxy}phenyl)carbonyl](methyl)amino}propanoic acid

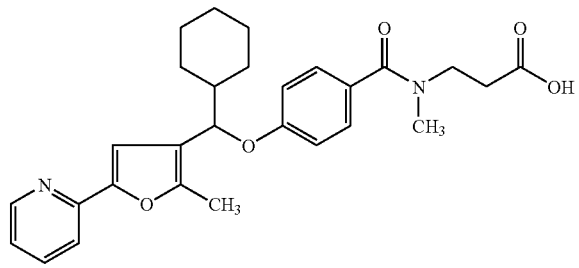

A solution of 4-{cyclohexyl[2-methyl-5-(pyridin-2-yl)furan-3-yl]methoxy}benzoic acid (86 mg), ethyl 3-(methylamino)propanoate (34 mg), 1-ethyl-3-(3-dimethylaminopropyl)carbodiimide hydrochloride (50 mg), hydroxybenzotriazole monohydrate (40 mg) and triethylamine (36 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (85 mg, 81%).

$^1$H NMR (300 MHz, DMSO-$d_6$) δ ppm 0.89-1.31 (m, 5H) 1.54-1.87 (m, 5H) 2.02-2.06 (m, 1H) 2.39 (s, 3H) 2.47-2.52 (m, 2H) 2.88 (s, 3H) 3.53 (d, J=7.16 Hz, 2H) 5.08 (d, J=7.35 Hz, 1H) 6.94 (d, J=5.46 Hz, 2H) 6.95 (s, 1H) 7.20-7.28 (m, 3H) 7.61 (d, J=7.91 Hz, 1H) 7.79 (t, J=1.13 Hz, 1H) 8.50 (d, J=4.33 Hz, 1H) 12.27 (brs, 1H)

Example 114

3-({[4-({cyclohexyl[2-methyl-5-(pyridin-2-yl)furan-3-yl]methyl}amino)phenyl]carbonyl}amino)propanoic acid

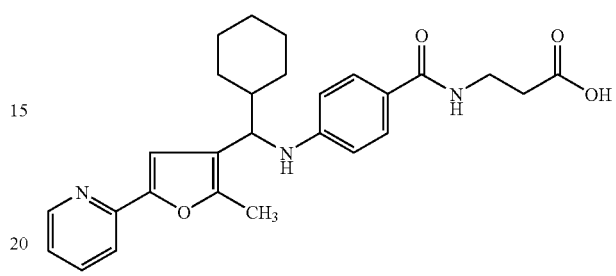

(1) 2-{4-[chloro(cyclohexyl)methyl]-5-methylfuran-2-yl}pyridine hydrochloride

To a solution of cyclohexyl[2-methyl-5-(pyridin-2-yl)furan-3-yl]methanol (0.7 g) in toluene (20 mL) was added thionyl chloride (1.3 mL), and the mixture was stirred at room temperature for 2 hr. The solvent was evaporated under reduced pressure to give the title compound (0.8 g, 100%) as a yellow crystal.

$^1$H NMR (300 MHz, CHLOROFORM-d) δ ppm 0.82-1.40 (m, 5H) 1.38-2.04 (m, 5H) 2.22 (d, J=10.22 Hz, 1H) 2.46 (s, 3H) 4.58 (d, J=8.71 Hz, 1H) 7.54 (t, J=6.63 Hz, 1H) 8.00 (d, J=7.95 Hz, 1H) 8.23 (t, J=7.95 Hz, 1H) 8.34 (s, 1H) 8.69 (d, J=6.44 Hz, 1H)

(2) 4-({cyclohexyl[2-methyl-5-(pyridin-2-yl)furan-3-yl]methyl}amino)benzoic acid A mixture of 2-{4-[chloro(cyclohexyl)methyl]-5-methylfuran-2-yl}pyridine hydrochloride (0.8 g) obtained by the above-mentioned reaction, methyl 4-aminobenzoate (0.8 g), sodium carbonate (0.6 g) and sodium iodide (1.6 g) in N,N-dimethylacetamide (20 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (4 mL) and tetrahydrofuran (4 mL). 2N Lithium hydroxide (3 mL) was added, and the mixture was stirred at 70° C. for 3 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (25% ethyl acetate/hexane to 75% ethyl acetate/hexane) to give the title compound (0.5 g, 53%) as a white crystal.

$^1$H NMR (300 MHz, DMSO-$d_6$) δ ppm 0.93-1.20 (m, 5H) 1.53-1.78 (m, 5H) 2.04 (d, J=11.30 Hz, 1H) 2.40 (s, 3H) 4.16 (s, 1H) 6.58 (d, J=8.85 Hz, 2H) 6.61-6.75 (m, 1H) 6.98 (s, 1H) 7.20 (ddd, J=7.49, 4.85, 1.04 Hz, 1H) 7.50-7.67 (m, 4H) 7.77 (dd, J=7.72, 1.88 Hz, 1H) 8.49 (ddd, J=4.90, 1.70, 0.94 Hz, 1H)

(3) 3-({[4-({cyclohexyl[2-methyl-5-(pyridin-2-yl)furan-3-yl]methyl}amino)phenyl]carbonyl}amino)propanoic acid A solution of 4-({cyclohexyl[2-methyl-5-(pyridin-2-yl)furan-3-yl]methyl}amino)benzoic acid (254 mg) obtained by the above-mentioned reaction, ethyl β-alaninate hydrochloride (120 mg), 1-ethyl-3-(3-dimethylaminopropyl)carbodiimide hydrochloride (150 mg), hydroxybenzotriazole monohydrate (119 mg) and triethylamine (109 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.3 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (275 mg, 92%).

$^1$H NMR (300 MHz, DMSO-$d_6$) δ ppm 0.94-1.25 (m, 5H) 1.54-1.77 (m, 5H) 2.02-2.05 (m, 1H) 2.34-2.46 (m, 5H) 3.36 (q, J=5.84 Hz, 2H) 4.06-4.24 (m, 1H) 6.38 (d, J=8.48 Hz, 1H) 6.56 (d, J=8.67 Hz, 2H) 6.97 (s, 1H) 7.20 (dd, J=6.97, 5.27 Hz, 1H) 7.52 (d, J=8.38 Hz, 2H) 7.54 (d, J=10.64 Hz, 1H) 7.78 (td, J=7.77, 1.79 Hz, 1H) 7.92-8.07 (m, 2H) 8.49 (d, J=3.96 Hz, 1H) 12.15 (brs, 1H)

Example 115

3-[{[4-({cyclohexyl[2-methyl-5-(pyridin-2-yl)furan-3-yl]methyl}amino)phenyl]carbonyl}(methyl)amino]propanoic acid

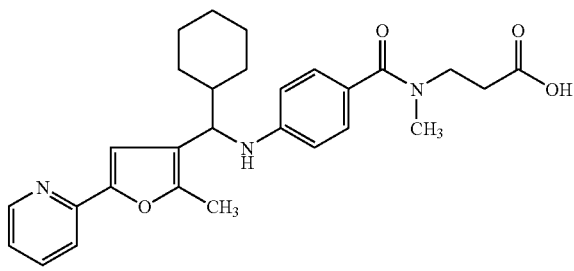

A solution of 4-({cyclohexyl[2-methyl-5-(pyridin-2-yl)furan-3-yl]methyl}amino)benzoic acid (254 mg), ethyl 3-(methylamino)propanoate (102 mg), 1-ethyl-3-(3-dimethylaminopropyl)carbodiimide hydrochloride (150 mg), hydroxybenzotriazole monohydrate (119 mg) and triethylamine (109 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.3 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (269 mg, 87%).

$^1$H NMR (300 MHz, DMSO-$d_6$) δ ppm 0.90-1.26 (m, 5H) 1.59-1.78 (m, 5H) 2.02-2.07 (m, 1H) 2.40 (s, 3H) 2.47-2.51 (m, 2H) 2.90 (s, 3H) 3.52 (t, J=7.35 Hz, 2H) 4.11 (t, J=8.19 Hz, 1H) 6.29 (d, J=8.29 Hz, 1H) 6.56 (d, J=8.67 Hz, 2H) 6.99 (s, 1H) 7.10 (d, J=8.48 Hz, 2H) 7.21 (d, J=7.35 Hz, 1H) 7.56 (d, J=8.10 Hz, 1H) 7.78 (td, J=7.72, 1.70 Hz, 1H) 8.49 (d, J=4.90 Hz, 1H)

Example 116

3-({[4-(cyclohexyl{3-methyl-5-[4-(trifluoromethyl)phenyl]furan-2-yl}methoxy)phenyl]carbonyl}amino)propanoic acid

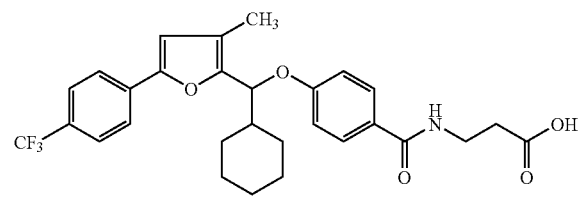

(1) methyl 5-bromo-3-methylfuran-2-carboxylate

To a solution of methyl 3-methylfuran-2-carboxylate (5.6 g) in chloroform (40 mL) was added dropwise bromine (2.3 mL) at 0° C. and, after the completion of the dropwise addition, the mixture was stirred at 0° C. for 30 min, at room temperature for 1 hr, and at 50° C. overnight. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 10% ethyl acetate/hexane), and crystallized from ethyl acetate/hexane to give the title compound (5.3 g, 60%) as a white solid.

$^1$H NMR (300 MHz, CHLOROFORM-d) δ ppm 2.34 (s, 3H) 3.89 (s, 3H) 6.31 (s, 1H)

(2) methyl 3-methyl-5-[4-(trifluoromethyl)phenyl]furan-2-carboxylate

A mixture of methyl 5-bromo-3-methylfuran-2-carboxylate (5.2 g) obtained by the above-mentioned reaction, 4-(trifluoromethyl)phenylboronic acid (5.0 g), tetrakis(triphenylphosphine)palladium(0) (1.4 g), 2N aqueous sodium carbonate solution (26 mL) and 1,2-dimethoxyethane (50 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (3.9 g, 57%) as a white solid.

¹H NMR (300 MHz, CHLOROFORM-d) δ ppm 2.41 (s, 3H) 3.93 (s, 3H) 6.72 (s, 1H) 7.66 (d, J=8.33 Hz, 2H) 7.85 (d, J=8.33 Hz, 2H)

(3) {3-methyl-5-[4-(trifluoromethyl)phenyl]furan-2-yl}methanol

A solution of methyl 3-methyl-5-[4-(trifluoromethyl)phenyl]furan-2-carboxylate (3.8 g) in tetrahydrofuran (30 mL) was added dropwise to a suspension of lithium aluminum hydride (0.5 g) in tetrahydrofuran (30 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (3.4 g, 97%) as a white solid.
¹H NMR (300 MHz, CHLOROFORM-d) δ ppm 1.70 (t, J=5.93 Hz, 1H) 2.11 (s, 3H) 4.66 (d, J=5.84 Hz, 2H) 6.61 (s, 1H) 7.61 (m, J=8.29 Hz, 2H) 7.73 (m, J=8.10 Hz, 2H)

(4) 3-methyl-5-[4-(trifluoromethyl)phenyl]furan-2-carbaldehyde

To a solution of {3-methyl-5-[4-(trifluoromethyl)phenyl]furan-2-yl}methanol (3.3 g) obtained by the above-mentioned reaction in methylene chloride (30 mL) was added a Dess-Martin reagent (8.3 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (2.1 g, 56%) as an oil.
¹H NMR (300 MHz, CHLOROFORM-d) δ ppm 2.45 (s, 3H) 6.80 (s, 1H) 7.45-7.65 (m, 1H) 7.69 (d, J=8.29 Hz, 2H) 7.89 (d, J=8.29 Hz, 2H) 9.83 (s, 1H)

(5) cyclohexyl{3-methyl-5-[4-(trifluoromethyl)phenyl]furan-2-yl}methanol

To a solution of 3-methyl-5-[4-(trifluoromethyl)phenyl]furan-2-carbaldehyde in tetrahydrofuran (20 mL) obtained by the above-mentioned reaction was added 1N cyclohexylmagnesium bromide-tetrahydrofuran solution (7.5 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (0.9 g, 54%) as an oil.
¹H NMR (300 MHz, CHLOROFORM-d) δ ppm 0.78-1.48 (m, 5H) 1.61-1.97 (m, 5H) 2.09-2.23 (m, 1H) 3.61 (brs, 1H) 4.42 (dd, J=8.33, 5.30 Hz, 1H) 6.58 (s, 1H) 7.60 (d, J=8.33 Hz, 2H) 7.71 (d, J=7.95 Hz, 2H)

(6) 4-(cyclohexyl{3-methyl-5-[4-(trifluoromethyl)phenyl]furan-2-yl}methoxy)benzoic acid To a solution of cyclohexyl{3-methyl-5-[4-(trifluoromethyl)phenyl]furan-2-yl}methanol (271 mg) obtained by the above-mentioned reaction and methyl 4-hydroxybenzoate (146 mg) in tetrahydrofuran (20 mL) were added tributylphosphine (0.4 mL) and 1,1'-(azodicarbonyl)dipiperidine (404 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-(cyclohexyl{3-methyl-5-[4-(trifluoromethyl)phenyl]furan-2-yl}methoxy)benzoate as an oil. The obtained methyl 4-(cyclohexyl{3-methyl-5-[4-(trifluoromethyl)phenyl]furan-2-yl}methoxy)benzoate was dissolved in methanol (2 mL) and tetrahydrofuran (2 mL). 2N Lithium hydroxide (1.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (138 mg, 39%).
¹H NMR (300 MHz, CHLOROFORM-d) δ ppm 1.45-1.71 (m, 10H) 2.16 (d, J=3.01 Hz, 1H) 4.96 (d, J=7.72 Hz, 1H) 6.53 (s, 1H) 6.91 (d, J=8.85 Hz, 2H) 7.60 (d, J=8.29 Hz, 2H) 7.70 (d, J=8.29 Hz, 2H) 7.95 (d, J=9.04 Hz, 2H)

(7) 3-({[4-(cyclohexyl{3-methyl-5-[4-(trifluoromethyl)phenyl]furan-2-yl}methoxy)phenyl]carbonyl}amino)propanoic acid A solution of 4-(cyclohexyl{3-methyl-5-[4-(trifluoromethyl)phenyl]furan-2-yl}methoxy)benzoic acid (69 mg) obtained by the above-mentioned reaction, ethyl β-alaninate hydrochloride (28 mg), 1-ethyl-3-(3-dimethylaminopropyl)carbodiimide hydrochloride (35 mg), hydroxybenzotriazole monohydrate (28 mg) and triethylamine (25 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.3 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (80 mg, 100%).
¹H NMR (300 MHz, DMSO-d₆) δ ppm 0.93-1.34 (m, 6H) 1.40-1.77 (m, 4H) 2.07-2.12 (m, 4H) 2.43 (t, J=7.00 Hz, 2H) 3.24-3.49 (m, 2H) 5.25 (d, J=7.95 Hz, 1H) 6.95 (s, 1H) 6.98 (d, J=8.71 Hz, 2H) 7.70-7.76 (m, 4H) 7.81 (d, J=8.33 Hz, 2H) 8.25-8.44 (m, 1H)

Example 117

3-[{[4-(cyclohexyl{3-methyl-5-[4-(trifluoromethyl)phenyl]furan-2-yl}methoxy)phenyl]carbonyl}(methyl)amino]propanoic acid

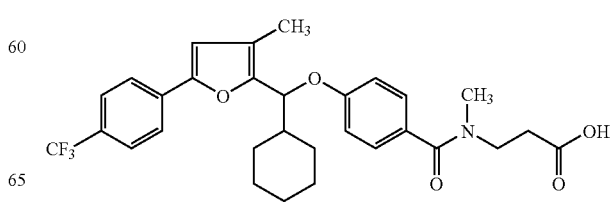

A solution of 4-(cyclohexyl{3-methyl-5-[4-(trifluoromethyl)phenyl]furan-2-yl}methoxy)benzoic acid (69 mg), ethyl 3-(methylamino)propanoate (24 mg), 1-ethyl-3-(3-dimethylaminopropyl)carbodiimide hydrochloride (35 mg), hydroxybenzotriazole monohydrate (28 mg) and triethylamine (25 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.3 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (45 mg, 55%).

$^1$H NMR (300 MHz, DMSO-$d_6$) δ ppm 0.98-1.47 (m, 6H) 1.55-1.79 (m, 4H) 2.05-2.15 (m, 6H) 2.88 (s, 3H) 3.43-3.70 (m, 2H) 5.20 (brs, 1H) 6.79 (s, 1H) 6.91-7.03 (m, 2H) 7.15-7.29 (m, 2H) 7.69-7.97 (m, 4H)

Example 118

3-[({4-[(cyclohexyl{2-(ethoxymethyl)-5-[4-(trifluoromethyl)phenyl]furan-3-yl}methyl)amino]phenyl}carbonyl)amino]propanoic acid

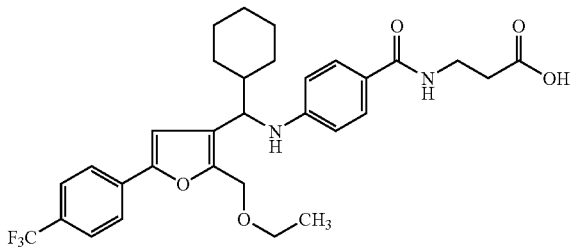

(1) 3-[chloro(cyclohexyl)methyl]-2-(ethoxymethyl)-5-[4-(trifluoromethyl)phenyl]furan To a solution of cyclohexyl{2-(ethoxymethyl)-5-[4-(trifluoromethyl)phenyl]furan-3-yl}methanol (1.8 g) in tetrahydrofuran (30 mL) were added oxalyl chloride (0.6 mL) and triethylamine (1.0 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.9 g, 100%).

(2) 4-[(cyclohexyl{2-(ethoxymethyl)-5-[4-(trifluoromethyl)phenyl]furan-3-yl}methyl)amino]benzoic acid A mixture of 3-[chloro(cyclohexyl)methyl]-2-(ethoxymethyl)-5-[4-(trifluoromethyl)phenyl]furan (1.9 g) obtained by the above-mentioned reaction, methyl 4-aminobenzoate (1.4 g), sodium carbonate (0.5 g) and sodium iodide (2.8 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (4 mL) and tetrahydrofuran (4 mL). 2N Lithium hydroxide (2 mL) was added, and the mixture was stirred at 80° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (5% ethyl acetate/hexane to 40% ethyl acetate/hexane) to give the title compound (0.2 g, 9%) as an amorphous compound.

$^1$H NMR (300 MHz, CHLOROFORM-d) δ ppm 0.99-1.29 (m, 8H) 1.56-1.87 (m, 5H) 1.90-2.02 (m, 1H) 3.59 (q, J=6.94 Hz, 2H) 4.31 (d, J=6.82 Hz, 1H) 4.43-4.67 (m, 2H) 6.59 (d, J=8.71 Hz, 2H) 6.63 (s, 1H) 7.59 (d, J=8.33 Hz, 2H) 7.71 (d, J=8.33 Hz, 2H) 7.84 (d, J=8.71 Hz, 2H)

(3) 3-[({4-[(cyclohexyl{2-(ethoxymethyl)-5-[4-(trifluoromethyl)phenyl]furan-3-yl}methyl)amino]phenyl}carbonyl)amino]propanoic acid A solution of 4-[(cyclohexyl{2-(ethoxymethyl)-5-[4-(trifluoromethyl)phenyl]furan-3-yl}methyl)amino]benzoic acid (100 mg) obtained by the above-mentioned reaction, ethyl β-alaninate hydrochloride (37 mg), 1-ethyl-3-(3-dimethylaminopropyl)carbodiimide hydrochloride (46 mg), hydroxybenzotriazole monohydrate (37 mg) and triethylamine (33 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (98 mg, 87%).

$^1$H NMR (300 MHz, DMSO-$d_6$) δ ppm 0.91-1.23 (m, 8H) 1.47-1.83 (m, 5H) 2.01-2.05 (m, 1H) 2.42 (t, J=7.19 Hz, 2H) 3.21-3.43 (m, 2H) 3.55 (q, J=6.82 Hz, 2H) 4.25 (t, J=7.95 Hz, 1H) 4.45-4.69 (m, 2H) 6.37 (d, J=8.33 Hz, 1H) 6.62 (d, J=8.71 Hz, 2H) 7.03 (s, 1H) 7.51 (d, J=8.71 Hz, 2H) 7.74 (d, J=8.71 Hz, 2H) 7.81 (d, J=8.33 Hz, 2H) 8.01 (t, J=5.49 Hz, 1H)

Example 119

3-[({4-[(cyclohexyl{2-(ethoxymethyl)-5-[4-(trifluoromethyl)phenyl]furan-3-yl}methyl)amino]phenyl}carbonyl)(methyl)amino]propanoic acid

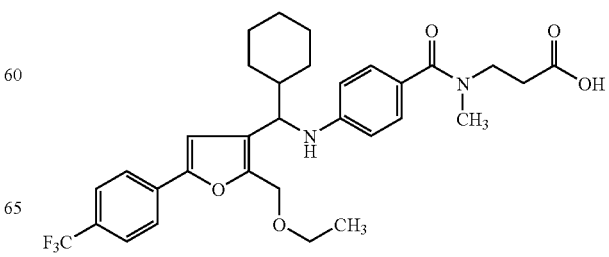

A solution of 4-[(cyclohexyl{2-(ethoxymethyl)-5-[4-(trifluoromethyl)phenyl]furan-3-yl}methyl)amino]benzoic acid (100 mg), ethyl β-alaninate hydrochloride (37 mg), ethyl 3-(methylamino)propanoate (31 mg), 1-ethyl-3-(3-dimethylaminopropyl)carbodiimide hydrochloride (46 mg), hydroxybenzotriazole monohydrate (37 mg) and triethylamine (33 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (81 mg, 69%).

$^1$H NMR (300 MHz, DMSO-d$_6$) δ ppm 0.95-1.23 (m, B H) 1.55-1.77 (m, 5H) 1.96-2.10 (m, 1H) 2.41-2.49 (m, 2H) 2.89 (s, 3H) 3.42-3.63 (m, 4H) 4.21 (t, J=7.76 Hz, 1H) 4.42-4.70 (m, 2H) 6.27 (d, J=7.95 Hz, 1H) 6.62 (d, J=8.71 Hz, 2H) 7.04 (s, 1H) 7.08 (d, J=8.33 Hz, 2H) 7.74 (d, J=8.71 Hz, 2H) 7.82 (d, J=8.71 Hz, 2H)

Example 120

3-[({4-[(cyclohexyl{3-methyl-5-[4-(trifluoromethyl)phenyl]furan-2-yl}methyl)amino]phenyl}carbonyl)amino]propanoic acid

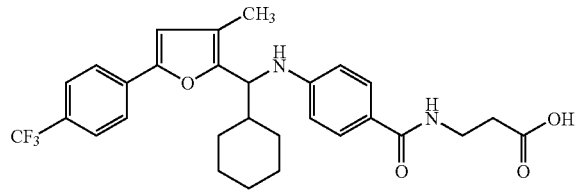

(1) 2-[chloro(cyclohexyl)methyl]-3-methyl-5-[4-(trifluoromethyl)phenyl]furan

To a solution of cyclohexyl{3-methyl-5-[4-(trifluoromethyl)phenyl]furan-2-yl}methanol (0.7 g) in dichloromethane (5 mL) were added oxalyl chloride (0.3 mL) and triethylamine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.8 g, 100%).

(2) 4-[(cyclohexyl{3-methyl-5-[4-(trifluoromethyl)phenyl]furan-2-yl}methyl)amino]benzoic acid A mixture of 2-[chloro(cyclohexyl)methyl]-3-methyl-5-[4-(trifluoromethyl)phenyl]furan (0.8 g) obtained by the above-mentioned reaction, methyl 4-aminobenzoate (0.7 g), sodium carbonate (0.5 g) and sodium iodide (1.3 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (3 mL) and tetrahydrofuran (5 mL). 2N Lithium hydroxide (1 mL) was added, and the mixture was stirred at 80° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.2 g, 15%) as an amorphous compound.

$^1$H NMR (300 MHz, CHLOROFORM-d) δ ppm 0.96-1.31 (m, 5H) 1.49-1.91 (m, 5H) 1.97-2.16 (m, 4H) 4.31-4.37 (m, 1H) 6.54 (s, 1H) 6.57 (d, J=8.71 Hz, 2H) 7.59 (d, J=8.33 Hz, 2H) 7.66 (d, J=8.71 Hz, 2H) 7.86 (d, J=8.71 Hz, 2H)

(3) 3-[({4-[(cyclohexyl{3-methyl-5-[4-(trifluoromethyl)phenyl]furan-2-yl}methyl)amino]phenyl}carbonyl)amino]propanoic acid A solution of 4-[(cyclohexyl{3-methyl-5-[4-(trifluoromethyl)phenyl]furan-2-yl}methyl)amino]benzoic acid (92 mg) obtained by the above-mentioned reaction, ethyl β-alaninate hydrochloride (37 mg), 1-ethyl-3-(3-dimethylaminopropyl)carbodiimide hydrochloride (46 mg), hydroxybenzotriazole monohydrate (37 mg) and triethylamine (33 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (74 mg, 70%).

$^1$H NMR (300 MHz, DMSO-d$_6$) δ ppm 0.89-1.33 (m, 5H) 1.38-1.89 (m, 5H) 2.02-2.06 (m, 4H) 2.41 (t, J=7.19 Hz, 2H) 3.22-3.46 (m, 2H) 4.34 (t, J=8.33 Hz, 1H) 6.53 (d, J=8.33 Hz, 1H) 6.60 (d, J=8.71 Hz, 2H) 6.90 (s, 1H) 7.53 (d, J=9.09 Hz, 2H) 7.74 (d, J=8.71 Hz, 2H) 7.80 (d, J=8.71 Hz, 2H) 8.03 (t, J=5.68 Hz, 1H)

Example 121

3-[({4-[(cyclohexyl{3-methyl-5-[4-(trifluoromethyl)phenyl]furan-2-yl}methyl)amino]phenyl}carbonyl)(methyl)amino]propanoic acid

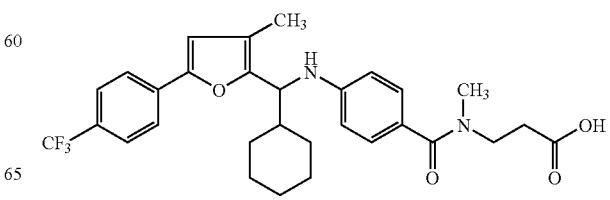

A solution of 4-[(cyclohexyl{3-methyl-5-[4-(trifluoromethyl)phenyl]furan-2-yl}methyl)amino]benzoic acid (92 mg), ethyl β-alaninate hydrochloride (37 mg), ethyl 3-(methylamino)propanoate (31 mg), 1-ethyl-3-(3-dimethylaminopropyl)carbodiimide hydrochloride (46 mg), hydroxybenzotriazole monohydrate (37 mg) and triethylamine (33 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (81 mg, 69%).

$^1$H NMR (300 MHz, DMSO-$d_6$) δ ppm 0.86-1.32 (m, 5H) 1.38-1.89 (m, 5H) 2.04-2.07 (m, 4H) 2.47-2.51 (m, 2H) 2.89 (s, 3H) 3.51 (t, J=7.19 Hz, 2H) 4.30 (t, J=7.95 Hz, 1H) 6.43 (d, J=7.95 Hz, 1H) 6.60 (d, J=8.71 Hz, 2H) 6.91 (s, 1H) 7.11 (d, J=8.71 Hz, 2H) 7.74 (d, J=8.33 Hz, 2H) 7.81 (d, J=7.95 Hz, 2H)

Example 122

3-[({4-[(cyclohexyl{2-ethyl-5-[4-(trifluoromethyl)phenyl]furan-3-yl}methyl)amino]phenyl}carbonyl)amino]-2-hydroxypropanoic acid

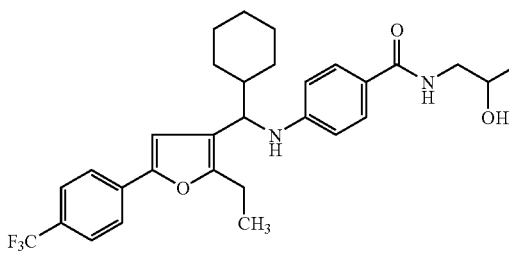

(1) methyl 3-amino-2-hydroxypropanoate hydrochloride

To a solution of 3-amino-2-hydroxypropanoic acid (0.7 g) in methanol (15 mL) was added thionyl chloride (2.5 mL) at 0° C., and the mixture was stirred at 0° C. for 2 hr and then at room temperature overnight. The solvent was evaporated under reduced pressure to give the title compound (1.6 g, 100%) as an oil.

$^1$H NMR (300 MHz, DMSO-$d_6$) δ ppm 2.91 (ddd, J=13.44, 8.14, 5.68 Hz, 1H) 3.05-3.14 (ddd, J=12.87, 6.06, 3.79 Hz, 1H) 3.68 (s, 3H) 4.38 (dd, J=8.71, 3.79 Hz, 1H) 8.12 (brs, 2H)

(2) 3-[({4-[(cyclohexyl{2-ethyl-5-[4-(trifluoromethyl)phenyl]furan-3-yl}methyl)amino]phenyl}carbonyl)amino]-2-hydroxypropanoic acid A solution of methyl 3-amino-2-hydroxypropanoate hydrochloride (75 mg) obtained above, 4-[(cyclohexyl{2-ethyl-5-[4-(trifluoromethyl)phenyl]furan-3-yl}methyl)amino]benzoic acid (189 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.7 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (190 mg, 86%).

$^1$H NMR (300 MHz, DMSO-$d_6$) δ ppm 0.94-1.24 (m, 8H) 1.54-1.78 (m, 5H) 2.03-2.06 (m, 1H) 2.72-2.88 (m, 2H) 3.40-3.56 (m, 1H) 4.01-4.17 (m, 2H) 6.37 (d, J=7.91 Hz, 1H) 6.57 (d, J=8.67 Hz, 2H) 6.95 (s, 1H) 7.54 (d, J=8.67 Hz, 2H) 7.71 (d, J=8.67 Hz, 2H) 7.76 (d, J=8.48 Hz, 2H) 7.98 (brs, 1H)

Example 123

3-{[(4-{[cyclohexyl(5-phenyl-2-methylfuran-3-yl)methyl]amino}phenyl)carbonyl]amino}-2-hydroxypropanoic acid

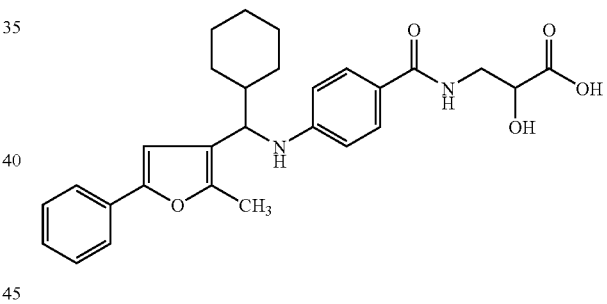

A solution of 4-{[cyclohexyl(5-phenyl-2-methylfuran-3-yl)methyl]amino}benzoic acid (156 mg), methyl 3-amino-2-hydroxypropanoate hydrochloride (75 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (168 mg, 88%).

$^1$H NMR (300 MHz, DMSO-$d_6$) δ ppm 0.92-1.26 (m, 5H) 1.53-1.77 (m, 5H) 2.01-2.05 (m, 1H) 2.37 (s, 3H) 3.31-3.35

(m, 2H) 3.41-3.50 (m, 1H) 4.06 (dd, J=6.88, 4.99 Hz, 2H) 6.35 (d, J=8.10 Hz, 1H) 6.56 (d, J=8.85 Hz, 2H) 6.73 (s, 1H) 7.21 (t, J=7.35 Hz, 1H) 7.36 (t, J=7.72 Hz, 2H) 7.47-7.64 (m, 4H) 7.96 (s, 1H)

Example 124

3-{[(4-{[3-methyl-1-(2-methyl-5-phenylfuran-3-yl)butyl]amino}phenyl)carbonyl]amino}propanoic acid

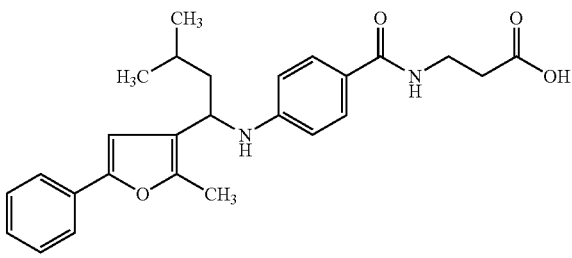

(1) 3-methyl-1-(2-methyl-5-phenylfuran-3-yl)butan-1-ol

To a solution of 2-methyl-5-phenylfuran-5-carbaldehyde (1.3 g) in tetrahydrofuran (30 mL) was added dropwise 1N cyclobutylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 20% ethyl acetate/hexane) to give the title compound (1.5 g, 87%) as a yellow crystal.

$^1$H NMR (300 MHz, CHLOROFORM-d) δ ppm 0.94 (d, J=6.44 Hz, 6H) 1.48-1.87 (m, 3H) 2.37 (s, 3H) 4.71 (td, J=6.91, 2.46 Hz, 1H) 6.62 (s, 1H) 7.20-7.26 (m, 1H) 7.35 (t, J=7.57 Hz, 2H) 7.62 (d, J=7.19 Hz, 2H)

(2) 3-(1-chloro-3-methylbutyl)-2-methyl-5-phenylfuran

To a solution of 3-methyl-1-(2-methyl-5-phenylfuran-3-yl)butan-1-ol (1.5 g) in toluene (20 mL) was added thionyl chloride (0.9 mL), and the mixture was stirred at room temperature overnight. The solvent was evaporated under reduced pressure to give the title compound (1.6 g, 100%) as an oil.

$^1$H NMR (300 MHz, CHLOROFORM-d) δ ppm 0.94 (dd, J=6.59, 3.39 Hz, 6H) 1.66-1.80 (m, 1H) 1.82-1.91 (m, 1H) 1.95-2.15 (m, 1H) 2.37 (s, 3H) 4.96 (t, J=7.63 Hz, 1H) 6.64 (s, 1H) 7.19-7.27 (m, 1H) 7.36 (t, J=7.54 Hz, 2H) 7.62 (d, J=7.35 Hz, 2H)

(3) 4-{[3-methyl-1-(2-methyl-5-phenylfuran-3-yl)butyl]amino}benzoic acid

A mixture of 3-(1-chloro-3-methylbutyl)-2-methyl-5-phenylfuran (1.6 g) obtained by the above-mentioned reaction, methyl 4-aminobenzoate (1.8 g), sodium carbonate (1.3 g) and sodium iodide (3.6 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (6 mL) and tetrahydrofuran (6 mL). 2N Lithium hydroxide (6 mL) was added, and the mixture was stirred at 70° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.1 g, 51%) as an amorphous compound.

$^1$H NMR (300 MHz, CHLOROFORM-d) δ ppm 0.96 (dd, J=18.55, 6.06 Hz, 6H) 1.53-1.87 (m, 3H) 2.40 (s, 3H) 4.40 (t, J=7.00 Hz, 1H) 6.50 (s, 1H) 6.53 (d, J=8.71 Hz, 2H) 7.17-7.21 (m, 1H) 7.33 (t, J=7.76 Hz, 2H) 7.58 (d, J=7.19 Hz, 2H) 7.87 (d, J=8.71 Hz, 2H)

(4) 3-{[(4-{[3-methyl-1-(2-methyl-5-phenylfuran-3-yl)butyl]amino}phenyl)carbonyl]amino}propanoic acid A solution of 4-{[3-methyl-1-(2-methyl-5-phenylfuran-3-yl)butyl]amino}benzoic acid (182 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (178 mg, 82%).

$^1$H NMR (300 MHz, DMSO-$d_6$) δ ppm 0.92 (dd, J=18.65, 6.22 Hz, 6H) 1.45-1.85 (m, 3H) 2.38-2.44 (m, 5H) 3.21-3.48 (m, 2H) 4.37 (q, J=7.16 Hz, 1H) 6.36 (d, J=7.54 Hz, 1H) 6.56 (d, J=8.85 Hz, 2H) 6.77 (s, 1H) 7.19-7.24 (m, 1H) 7.36 (t, J=7.72 Hz, 2H) 7.55 (dd, J=7.91, 6.03 Hz, 4H) 8.02 (s, 1H)

Example 125

3-{methyl[(4-{[3-methyl-1-(2-methyl-5-phenylfuran-3-yl)butyl]amino}phenyl)carbonyl]amino}propanoic acid

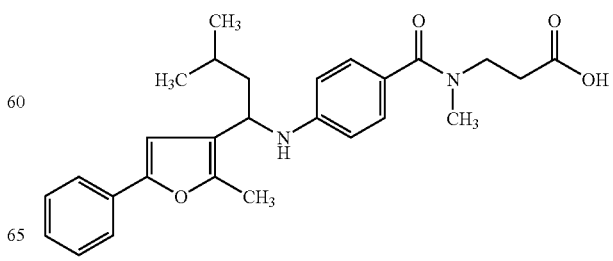

A solution of 4-{[3-methyl-1-(2-methyl-5-phenylfuran-3-yl)butyl]amino}benzoic acid (182 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure to give ethyl 3-{methyl[(4-{[3-methyl-1-(2-methyl-5-phenylfuran-3-yl)butyl]amino}phenyl)carbonyl]amino}propanoate. Ethyl 3-{methyl[(4-{[3-methyl-1-(2-methyl-5-phenylfuran-3-yl)butyl]amino}phenyl)carbonyl]amino}propanoate was dissolved in ethanol (2 mL) and tetrahydrofuran (2 mL) and 1N lithium hydroxide (1.0 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (186 mg, 83%).

$^1$H NMR (300 MHz, DMSO-$d_6$) δ ppm 0.92 (dd, J=18.08, 6.22 Hz, 6H) 1.50-1.76 (m, 3H) 2.38 (s, 3H) 2.46-2.51 (m, 2H) 2.90 (s, 3H) 3.47-3.58 (m, 2H) 4.30-4.37 (m, 1H) 6.25 (d, J=7.54 Hz, 1H) 6.55 (d, J=8.67 Hz, 2H) 6.79 (s, 1H) 7.12 (d, J=8.67 Hz, 2H) 7.22 (t, J=7.35 Hz, 1H) 7.36 (t, J=7.54 Hz, 2H) 7.57 (d, J=7.16 Hz, 2H)

Example 126

3-{[(4-{[cyclopentyl(2-methyl-5-phenylfuran-3-yl)methyl]amino}phenyl)carbonyl]amino}propanoic acid

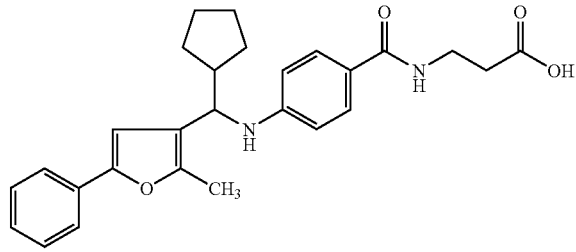

(1) cyclopentyl(2-methyl-5-phenylfuran-3-yl)methanol

To a solution of 2-methyl-5-phenylfuran-3-carbaldehyde (1.3 g) in tetrahydrofuran (30 mL) was added dropwise 1N cyclopentylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 20% ethyl acetate/hexane) to give the title compound (0.9 g, 50%) as a white crystal.

$^1$H NMR (300 MHz, CHLOROFORM-d) δ ppm 1.06-1.16 (m, 1H) 1.40-1.78 (m, 6H) 1.90-1.99 (m, 1H) 2.19-2.32 (m, 1H) 2.36 (s, 3H) 4.35 (dd, J=8.90, 2.08 Hz, 1H) 6.63 (s, 1H) 7.19-7.24 (m, 1H) 7.35 (t, J=7.76 Hz, 2H) 7.62 (d, J=7.19 Hz, 2H)

(2) 3-[chloro(cyclopentyl)methyl]-2-methyl-5-phenylfuran

To a solution of cyclopentyl(2-methyl-5-phenylfuran-3-yl)methanol (0.9 g) in toluene (20 mL) was added thionyl chloride (0.5 mL), and the mixture was stirred at room temperature overnight. The solvent was evaporated under reduced pressure to give the title compound (1.0 g, 100%) as an oil.

$^1$H NMR (300 MHz, CHLOROFORM-d) δ ppm 1.09-1.17 (m, 1H) 1.46-1.80 (m, 6H) 2.01-2.10 (m, 1H) 2.31-2.39 (m, 4H) 4.67 (d, J=9.61 Hz, 1H) 6.65 (s, 1H) 7.10-7.30 (m, 1H) 7.36 (t, J=7.54 Hz, 2H) 7.62 (dd, J=8.38, 1.22 Hz, 2H)

(3) 4-{[cyclopentyl(2-methyl-5-phenylfuran-3-yl)methyl]amino}benzoic acid

A mixture of 3-[chloro(cyclopentyl)methyl]-2-methyl-5-phenylfuran (1.0 g) obtained by the above-mentioned reaction, methyl 4-aminobenzoate (1.1 g), sodium carbonate (0.7 g) and sodium iodide (2.1 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (4 mL) was added, and the mixture was stirred at 70° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.7 g, 50%) as an amorphous compound.

$^1$H NMR (300 MHz, CHLOROFORM-d) δ ppm 1.20-1.32 (m, 1H) 1.33-1.76 (m, 6H) 1.81-2.00 (m, 1H) 2.16-2.32 (m, 1H) 2.41 (s, 3H) 4.11 (dd, J=7.91, 4.90 Hz, 1H) 6.48 (s, 1H) 6.50 (d, J=2.45 Hz, 2H) 7.19 (dt, J=7.39, 1.58 Hz, 1H) 7.28-7.41 (m, 2H) 7.57 (d, J=7.35 Hz, 2H) 7.84 (d, J=8.85 Hz, 2H)

(4) 3-{[(4-{[cyclopentyl(2-methyl-5-phenylfuran-3-yl)methyl]amino}phenyl)carbonyl]amino}propanoic acid A solution of 4-{[cyclopentyl(2-methyl-5-phenylfuran-3-yl)methyl]amino}benzoic acid (150 mg) obtained by the above-mentioned reaction, ethyl β-alaninate hydrochloride (74 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (160 mg, 90%).

¹H NMR (300 MHz, DMSO-d₆) δ ppm 1.12-1.23 (m, 1H) 1.33-1.68 (m, 6H) 1.86-1.98 (m, 1H) 2.15-2.31 (m, 4H) 2.39 (s, 3H) 3.17-3.48 (m, 2H) 4.11 (brs, 1H) 6.37 (brs, 1H) 6.54 (d, J=7.57 Hz, 2H) 6.76 (s, 1H) 7.16-7.23 (m, 1H) 7.27-7.42 (m, 2H) 7.43-7.67 (m, 4H) 8.02 (brs, 1H)

Example 127

3-{[(4-{[cyclopentyl(2-methyl-5-phenylfuran-3-yl)methyl]amino}phenyl)carbonyl](methyl)amino}propanoic acid

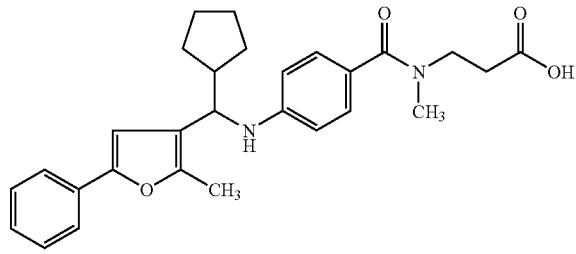

A solution of 4-{[cyclopentyl(2-methyl-5-phenylfuran-3-yl)methyl]amino}benzoic acid (150 mg), ethyl 3-(methylamino)propanoate (63 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (186 mg, 83%).

¹H NMR (300 MHz, DMSO-d₆) δ ppm 1.14-1.27 (m, 1H) 1.29-1.74 (m, 6H) 1.87-1.96 (m, 1H) 2.16-2.29 (m, 1H) 2.39 (s, 3H) 2.46-2.49 (m, 2H) 2.89 (s, 3H) 3.51 (t, J=7.38 Hz, 2H) 4.07 (t, J=8.52 Hz, 1H) 6.28 (d, J=7.95 Hz, 1H) 6.54 (d, J=8.71 Hz, 2H) 6.77 (s, 1H) 7.10 (d, J=8.33 Hz, 2H) 7.22 (d, J=7.19 Hz, 1H) 7.36 (t, J=7.57 Hz, 2H) 7.55 (d, J=7.19 Hz, 2H)

Example 128

3-{[(4-{[1-(2-methyl-5-phenylfuran-3-yl)pentyl]amino}phenyl)carbonyl]amino}propanoic acid

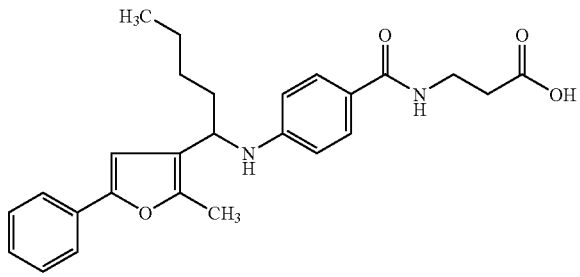

(1) 1-(2-methyl-5-phenylfuran-3-yl)pentan-1-ol

To a solution of 2-methyl-5-phenylfuran-3-carbaldehyde (1.3 g) in tetrahydrofuran (30 mL) was added dropwise 1N butylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 20% ethyl acetate/hexane) to give the title compound (1.6 g, 93%) as an oil.

¹H NMR (300 MHz, CHLOROFORM-d) δ ppm 0.90 (t, J=7.06 Hz, 3H) 1.21-1.41 (m, 4H) 1.66-1.71 (m, 1H) 1.82-1.88 (m, 1H) 2.35 (s, 3H) 4.61 (t, J=6.12 Hz, 1H) 6.62 (s, 1H) 7.14-7.27 (m, 1H) 7.35 (t, J=7.63 Hz, 2H) 7.62 (dd, J=8.48, 1.32 Hz, 2H)

(2) 3-(1-chloropentyl)-2-methyl-5-phenylfuran

To a solution of 1-(2-methyl-5-phenylfuran-3-yl)pentan-1-ol (1.6 g) in toluene (20 mL) was added thionyl chloride (1.0 mL), and the mixture was stirred at room temperature overnight. The solvent was evaporated under reduced pressure to give the title compound (1.7 g, 100%) as an oil.

¹H NMR (300 MHz, CHLOROFORM-d) δ ppm 0.91 (d, J=13.94 Hz, 3H) 1.22-1.52 (m, 4H) 1.89-2.21 (m, 2H) 2.36 (s, 3H) 4.86 (t, J=7.35 Hz, 1H) 6.64 (s, 1H) 7.09-7.30 (m, 1H) 7.36 (t, J=7.63 Hz, 2H) 7.62 (d, J=7.16 Hz, 2H)

(3) 4-{[1-(2-methyl-5-phenylfuran-3-yl)pentyl]amino}benzoic acid

A mixture of 3-(1-chloropentyl)-2-methyl-5-phenylfuran (1.7 g) obtained by the above-mentioned reaction, methyl 4-aminobenzoate (2.0 g), sodium carbonate (1.4 g) and sodium iodide (3.9 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (10 mL). 2N Lithium hydroxide (10 mL) was added, and the mixture was stirred at 70° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.6 g, 67%) as an amorphous compound.

¹H NMR (300 MHz, CHLOROFORM-d) δ ppm 0.90 (t, J=13.63 Hz, 3H) 1.21-1.48 (m, 4H) 1.67-1.79 (m, 1H) 1.82-1.98 (m, 1H) 2.38% (s, 3H) 4.30 (dd, J=7.95, 6.06 Hz, 1H) 6.50 (s, 1H) 6.53 (d, J=8.71 Hz, 2H) 7.17-7.22 (m, 1H) 7.33 (t, J=7.76 Hz, 2H) 7.59 (d, J=7.19 Hz, 2H) 7.87 (d, J=8.71 Hz, 2H)

(4) 3-{[(4-{[1-(2-methyl-5-phenylfuran-3-yl)pentyl]amino}phenyl)carbonyl]amino}propanoic acid A solution of 4-{[1-(2-methyl-5-phenylfuran-3-yl)amino}benzoic acid (182 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (206 mg, 95%).

$^1$H NMR (300 MHz, DMSO-$d_6$) δ ppm 0.87 (t, J=13.75 Hz, 3H) 1.13-1.44 (m, 4H) 1.60-1.71 (m, 1H) 1.78-1.86 (m, 1H) 2.37 (s, 3H) 2.43 (t, J=7.06 Hz, 2H) 3.25-3.45 (m, 2H) 4.23-4.41 (m, 1H) 6.37 (d, J=7.54 Hz, 1H) 6.55 (d, J=8.85 Hz, 2H) 6.77 (s, 1H) 7.19-7.24 (m, 2H) 7.36 (t, J=7.72 Hz, 2H) 7.52-7.57 (m, 4H) 8.00 (s, 2H) 12.18 (brs, 1H)

Example 129

3-{methyl[(4-{[1-(2-methyl-5-phenylfuran-3-yl)pentyl]amino}phenyl)carbonyl]amino}propanoic acid

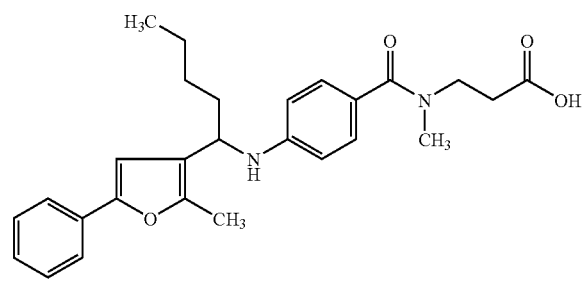

A solution of 4-{[1-(2-methyl-5-phenylfuran-3-yl)pentyl]amino}benzoic acid (182 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (211 mg, 94%).

$^1$H NMR (300 MHz, DMSO-$d_6$) δ ppm 0.87 (t, J=6.97 Hz, 3H) 1.19-1.46 (m, 4H) 2.27-2.42 (m, 5H) 2.47-2.51 (m, 2H) 2.90 (s, 3H) 3.49-3.53 (m, 2H) 4.18-4.35 (m, 1H) 6.26-6.28 (m, 1H) 6.54 (d, J=8.67 Hz, 2H) 6.79 (s, 1H) 7.12 (d, J=8.48 Hz, 2H) 7.19-7.24 (m, 1H) 7.36 (t, J=7.72 Hz, 2H) 7.57 (d, J=7.35 Hz, 2H)

Example 130

3-{[(4-{[3,3-dimethyl-1-(2-methyl-5-phenylfuran-3-yl)butyl]amino}phenyl)carbonyl]amino}propanoic acid

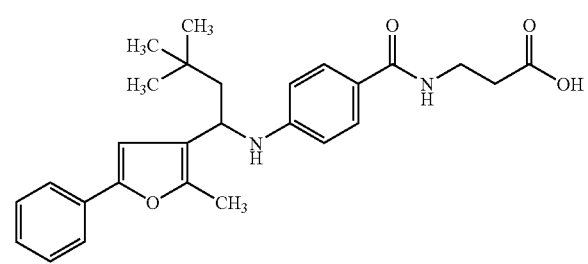

(1) 3,3-dimethyl-1-(2-methyl-5-phenylfuran-3-yl)butan-1-ol

To a solution of 2-methyl-5-phenylfuran-3-carbaldehyde (1.1 g) in tetrahydrofuran (20 mL) was added dropwise 1N chloro(2,2-dimethylpropyl)magnesium-tetrahydrofuran solution (9 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 15% ethyl acetate/hexane) to give the title compound (1.1 g, 70%) as an oil.

$^1$H NMR (300 MHz, CHLOROFORM-d) δ ppm 0.97 (s, 9H) 1.46 (d, J=3.03 Hz, 1H) 1.58-1.69 (m, 1H) 1.74-1.91 (m, 1H) 2.36 (s, 3H) 4.78 (ddd, J=7.48, 5.02, 3.03 Hz, 1H) 6.63 (s, 1H) 7.19-7.24 (m, 1H) 7.35 (t, J=7.57 Hz, 2H) 7.62 (d, J=7.19 Hz, 2H)

(2) 3-(1-chloro-3,3-dimethylbutyl)-2-methyl-5-phenylfuran

To a solution of 3,3-dimethyl-1-(2-methyl-5-phenylfuran-3-yl)butan-1-ol (1.1 g) in toluene (15 mL) was added thionyl chloride (0.6 mL), and the mixture was stirred at room temperature overnight. The solvent was evaporated under reduced pressure to give the title compound (1.1 g, 100%) as an oil.

(3) 4-{[3,3-dimethyl-1-(2-methyl-5-phenylfuran-3-yl)butyl]amino}benzoic acid A mixture of 3-(1-chloro-3,3-dimethylbutyl)-2-methyl-5-phenylfuran (1.1 g) obtained by the above-mentioned reaction, methyl 4-aminobenzoate (1.2 g), sodium carbonate (0.9 g) and sodium iodide (2.4 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (6 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.2 g, 20%) as an amorphous compound.

$^1$H NMR (300 MHz, CHLOROFORM-d) δ ppm 0.98 (s, 9H) 1.76 (dd, J=10.98, 6.06 Hz, 2H) 2.40 (s, 3H) 4.44 (t, J=6.06 Hz, 1H) 6.50-6.53 (m, 3H) 7.17-7.22 (m, 1H) 7.33 (t, J=7.57 Hz, 2H) 7.58 (d, J=7.19 Hz, 2H) 7.86 (d, J=8.71 Hz, 2H)

(4) 3-{[(4-{[3,3-dimethyl-1-(2-methyl-5-phenylfuran-3-yl)butyl]amino}phenyl)carbonyl]amino}propanoic acid A solution of 4-{[3,3-dimethyl-1-(2-methyl-5-phenylfuran-3-yl)butyl]amino}benzoic acid (113 mg) obtained by the above-mentioned reaction, ethyl β-alaninate hydrochloride (55 mg), 1-ethyl-3-(3-dimethylaminopropyl)carbodiimide hydrochloride (69 mg), hydroxybenzotriazole monohydrate (55 mg) and triethylamine (51 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (104 mg, 77%).

$^1$H NMR (300 MHz, DMSO-d$_6$) δ ppm 0.94 (s, 9H) 1.60 (dd, J=14.03, 5.18 Hz, 1H) 1.86 (d, J=6.97 Hz, 1H) 2.38 (s, 3H) 2.43 (t, J=7.25 Hz, 2H) 3.37 (d, J=5.84 Hz, 2H) 4.36-4.43 (m, 1H) 6.29 (d, J=8.10 Hz, 1H) 6.55 (d, J=8.85 Hz, 2H) 6.79 (s, 1H) 7.19-7.24 (m, 1H) 7.36 (t, J=7.63 Hz, 2H) 7.53-7.57 (m, 4H) 7.93-8.06 (m, 1H) 12.16 (brs, 1H)

Example 131

3-{[(4-{[3,3-dimethyl-1-(2-methyl-5-phenylfuran-3-yl)butyl]amino}phenyl)carbonyl](methyl)amino}propanoic acid

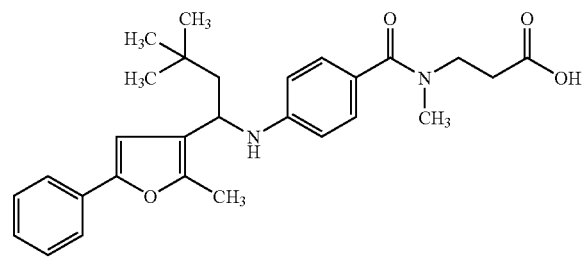

A solution of 4-{[(3,3-dimethyl-1-(2-methyl-5-phenylfuran-3-yl)butyl]amino}benzoic acid (113 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (107 mg, 77%).

$^1$H NMR (300 MHz, DMSO-d$_6$) δ ppm 0.94 (s, 9H) 1.59 (dd, J=14.03, 4.99 Hz, 1H) 1.86 (dd, J=14.03, 7.44 Hz, 1H) 2.38 (s, 3H) 2.47-2.51 (m, 2H) 2.90 (s, 3H) 3.52 (t, J=7.25 Hz, 2H) 4.28-4.44 (m, 1H) 6.11-6.28 (m, 1H) 6.55 (m, J=8.48 Hz, 2H) 6.81 (s, 1H) 7.13 (d, J=8.48 Hz, 2H) 7.17-7.28 (m, 1H) 7.36 (t, J=7.63 Hz, 2H) 7.50-7.63 (m, 2H)

Example 132

3-({[4-({cyclohexyl[5-(6-methoxypyridin-3-yl)-2-methylfuran-3-yl]methyl}amino)phenyl]carbonyl}amino)propanoic acid

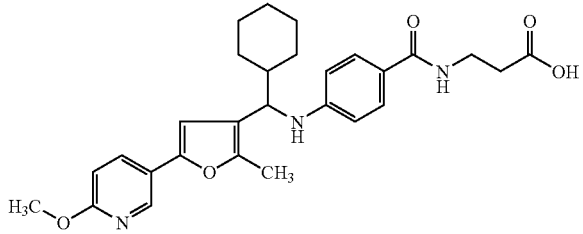

(1) methyl 5-(6-fluoropyridin-3-yl)-2-methylfuran-3-carboxylate

A mixture of methyl 5-bromo-2-methyl-3-furancarboxylate (2.6 g), 2-fluoropyridine-5-boronic acid (2.1 g), tetrakis(triphenylphosphine)palladium(0) (0.7 g), 2N aqueous sodium carbonate solution (15 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (2.5 g, 87%) as a white solid.

$^1$H NMR (300 MHz, CHLOROFORM-d) δ ppm 2.66 (s, 3H) 3.86 (s, 3H) 6.92 (s, 1H) 6.97 (dd, J=8.57, 2.35 Hz, 1H) 8.00 (ddd, J=8.52, 7.49, 2.64 Hz, 1H) 8.50 (d, J=2.45 Hz, 1H)

(2) [5-(6-fluoropyridin-3-yl)-2-methylfuran-3-yl]methanol

A solution of methyl 5-(6-fluoropyridin-3-yl)-2-methylfuran-3-carboxylate (2.4 g) obtained by the above-mentioned reaction in tetrahydrofuran (20 mL) was added dropwise to a suspension of lithium aluminum hydride (0.4 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (2.0 g, 100%) as a white solid.

$^1$H NMR (300 MHz, CHLOROFORM-d) δ ppm 1.45 (t, J=5.49 Hz, 1H) 2.37 (s, 3H) 4.53 (d, J=5.30 Hz, 2H) 6.67 (s, 1H) 6.94 (dd, J=7.95, 3.03 Hz, 1H) 7.98 (td, J=8.05, 2.46 Hz, 1H) 8.47 (d, J=2.27 Hz, 1H)

(3) 5-(6-fluoropyridin-3-yl)-2-methylfuran-3-carbaldehyde

To a solution of [5-(6-fluoropyridin-3-yl)-2-methylfuran-3-yl]methanol (2.0 g) obtained by the above-mentioned reaction in methylene chloride (15 mL) was added a Dess-Martin reagent (5.1 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 35% ethyl acetate/hexane) to give the title compound (1.6 g, 77%) as a white crystal.

$^1$H NMR (300 MHz, CHLOROFORM-d) δ ppm 2.69 (s, 3H) 6.96 (s, 1H) 6.99 (dd, J=8.48, 3.01 Hz, 1H) 8.02 (ddd, J=8.57, 7.54, 2.54 Hz, 1H) 8.53 (d, J=2.45 Hz, 1H) 9.98 (s, 1H)

(4) cyclohexyl[5-(6-fluoropyridin-3-yl)-2-methylfuran-3-yl]methanol

To a solution of 5-(6-fluoropyridin-3-yl)-2-methylfuran-3-carbaldehyde (1.5 g) obtained by the above-mentioned reaction in tetrahydrofuran (20 mL) was added dropwise 1N cyclohexylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (2.0 g, 94%) as an oil.

$^1$H NMR (300 MHz, CHLOROFORM-d) δ ppm 0.76-1.39 (m, 5H) 1.43-1.96 (m, 5H) 2.05-2.10 (m, 1H) 2.33 (s, 3H) 4.31 (dd, J=7.82, 2.92 Hz, 1H) 6.62 (s, 1H) 6.93 (dd, J=8.57, 2.92 Hz, 1H) 7.98 (td, J=8.10, 2.45 Hz, 1H) 8.47 (d, J=2.45 Hz, 1H)

(5) 5-{4-[chloro(cyclohexyl)methyl]-5-methylfuran-2-yl}-2-fluoropyridine

To a solution of cyclohexyl[5-(6-fluoropyridin-3-yl)-2-methylfuran-3-yl]methanol (2.0 g) obtained by the above-mentioned reaction in toluene (20 mL) was added thionyl chloride (1.0 mL), and the mixture was stirred at room temperature for 4 hr. The solvent was evaporated under reduced pressure to give the title compound (2.2 g, 100%) as an amorphous compound.

$^1$H NMR (300 MHz, CHLOROFORM-d) δ ppm 0.73-1.43 (m, 5H) 1.62-1.97 (m, 5H) 2.21 (d, J=12.49 Hz, 2H) 2.34 (s, 3H) 4.59 (d, J=8.33 Hz, 1H) 6.65 (s, 1H) 6.94 (dd, J=8.33, 2.65 Hz, 1H) 7.97 (dd, J=8.14, 2.08 Hz, 1H) 8.48 (d, J=2.27 Hz, 1H)

(6) 4-({cyclohexyl[5-(6-methoxypyridin-3-yl)-2-methylfuran-3-yl]methyl}amino)benzoic acid A mixture of 5-{4-[chloro(cyclohexyl)methyl]-5-methylfuran-2-yl}-2-fluoropyridine (2.2 g) obtained by the above-mentioned reaction, methyl 4-aminobenzoate (2.1 g), sodium carbonate (1.5 g) and sodium iodide (4.2 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (10 mL). 2N Sodium hydroxide (7 mL) was added, and the mixture was stirred at 70° C. overnight. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 30% ethyl acetate/hexane) to give the title compound (2.0 g, 68%) as an amorphous compound.

$^1$H NMR (300 MHz, CHLOROFORM-d) δ ppm 1.00-1.39 (m, 5H) 1.56-1.85 (m, 5H) 1.95-1.99 (m, 1H) 2.37 (s, 3H) 3.94 (s, 3H) 4.12 (d, J=7.19 Hz, 2H) 6.35 (s, 1H) 6.51 (d, J=9.09 Hz, 2H) 6.71 (d, J=8.71 Hz, 1H) 7.75 (dd, J=8.52, 2.46 Hz, 1H) 7.85 (d, J=8.71 Hz, 2H) 8.39 (d, J=1.89 Hz, 1H)

(7) 3-({[4-({cyclohexyl[5-(6-methoxypyridin-3-yl)-2-methylfuran-3-yl]methyl}amino)phenyl]carbonyl}amino)propanoic acid A solution of 4-({cyclohexyl[5-(6-methoxypyridin-3-yl)-2-methylfuran-3-yl]methyl}amino)benzoic acid (168 mg) obtained by the above-mentioned reaction, ethyl β-alaninate hydrochloride (74 mg), 1-ethyl-3-(3-dimethylaminopropyl) carbodiimide hydrochloride (92 mg), hydroxybenzotriazole monohydrate (74 mg) and triethylamine (67 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.7 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (145 mg, 74%).

$^1$H NMR (300 MHz, DMSO-d$_6$) δ ppm 0.92-1.25 (m, 5H) 1.52-1.56 (m, 5H) 2.01-2.06 (m, 1H) 2.36 (s, 3H) 2.40 (t, J=7.00 Hz, 2H) 3.35 (q, J=6.06 Hz, 3H) 3.85 (s, 3H) 4.09 (t, J=7.76 Hz, 1H) 6.33 (d, J=7.95 Hz, 1H) 6.54 (m, J=8.71 Hz, 2H) 6.67 (s, 1H) 6.83 (d, J=8.71 Hz, 1H) 7.52 (d, J=8.71 Hz, 2H) 7.86 (dd, J=8.71, 2.65 Hz, 1H) 7.97-8.09 (m, 1H) 8.37 (d, J=2.65 Hz, 1H)

Example 133

3-[{[4-({cyclohexyl[5-(6-methoxypyridin-3-yl)-2-methylfuran-3-yl]methyl}amino)phenyl]carbonyl}(methyl)amino]propanoic acid

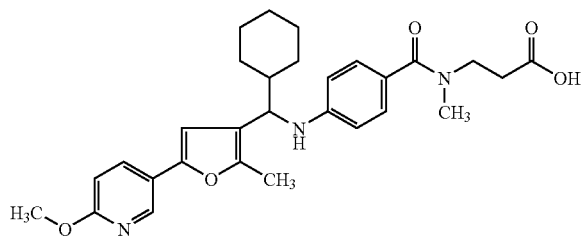

A solution of 4-({cyclohexyl[5-(6-methoxypyridin-3-yl)-2-methylfuran-3-yl]methyl}amino)benzoic acid (168 mg), ethyl 3-(methylamino)propanoate (63 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure to give ethyl 3-[{[4-({cyclohexyl[5-(6-methoxypyridin-3-yl)-2-methylfuran-3-yl]methyl}amino)phenyl]carbonyl}(methyl)amino]propanoate. The obtained ethyl 3-[{[4-({cyclohexyl[5-(6-methoxypyridin-3-yl)-2-methylfuran-3-yl]methyl}amino)phenyl]carbonyl}(methyl)amino]propanoate was dissolved in ethanol (2 mL) and tetrahydrofuran (2 mL). 1N Lithium hydroxide (0.6 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (118 mg, 60%).

$^1$H NMR (300 MHz, DMSO-$d_6$) δ ppm 0.90-1.24 (m, 5H) 1.54-1.75 (m, 5H) 2.02-2.05 (m, 1H) 2.36 (s, 3H) 2.41-2.48 (m, 2H) 2.90 (s, 3H) 3.51 (t, J=7.38 Hz, 2H) 3.85 (s, 3H) 4.05 (t, J=7.95 Hz, 1H) 6.23 (d, J=7.95 Hz, 1H) 6.54 (d, J=8.71 Hz, 2H) 6.69 (s, 1H) 6.83 (d, J=8.71 Hz, 1H) 7.10 (d, J=8.71 Hz, 2H) 7.87 (dd, J=8.71, 2.65 Hz, 1H) 8.38 (d, J=1.89 Hz, 1H)

Example 134

3-{[(4-{[1,4-dioxaspiro[4.5]dec-8-yl(2-methyl-5-phenylfuran-3-yl)methyl]amino}phenyl)carbonyl]amino}propanoic acid

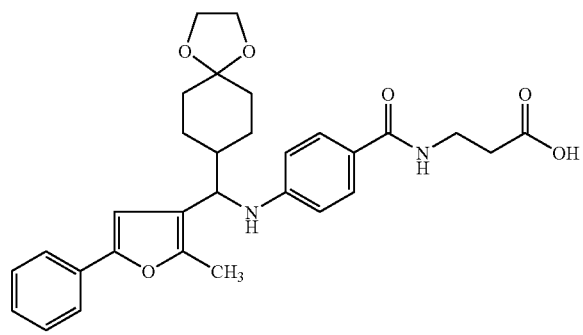

(1) 1,4-dioxaspiro[4.5]dec-8-yl(2-methyl-5-phenylfuran-3-yl)methanol

To a solution of 2-methyl-5-phenylfuran-3-carbaldehyde (2.4 g) in tetrahydrofuran (30 mL) was added dropwise 0.4N bromo(1,4-dioxaspiro[4.5]dec-8-yl)magnesium-tetrahydrofuran solution (33.5 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 30% ethyl acetate/hexane) to give the title compound (3.9 g, 91%) as a yellow crystal.

$^1$H NMR (300 MHz, CHLOROFORM-d) δ ppm 1.10-1.76 (m, 7H) 1.83 (m, 1H) 2.14 (dd, J=9.47, 2.65 Hz, 1H) 2.32 (s, 3H) 3.94 (d, J=1.89 Hz, 4H) 4.34 (dd, J=8.14, 2.84 Hz, 1H) 6.60 (s, 1H) 7.19-7.24 (m, 1H) 7.35 (t, J=7.76 Hz, 2H) 7.62 (d, J=7.19 Hz, 2H)

(2) 8-[chloro(2-methyl-5-phenylfuran-3-yl)methyl]-1,4-dioxaspiro[4.5]decane

To a solution of 1,4-dioxaspiro[4.5]dec-8-yl(2-methyl-5-phenylfuran-3-yl)methanol (0.7 g) in toluene (20 mL) were added thionyl chloride (0.2 mL) and pyridine (0.2 mL), and the mixture was stirred at 0° C. for 2 hr. The reaction mixture was poured into water, and the mixture was extracted with ethyl acetate. The organic layer was washed with saturated brine, and dried over magnesium sulfate. The solvent was evaporated under reduced pressure to give the title compound (0.7 g, 100%) as an oil.

$^1$H NMR (300 MHz, CHLOROFORM-d) δ ppm 1.15-1.75 (m, 7H) 1.77-1.98 (m, 1H) 2.19-2.34 (m, 1H) 2.32 (s, 3H) 3.87-4.01 (m, 2H) 4.63 (d, J=9.09 Hz, 1H) 6.62 (s, 1H) 7.10-7.25 (m, 1H) 7.36 (t, J=7.57 Hz, 2H) 7.63 (d, J=7.19 Hz, 2H)

(3) 3-{[(4-{[1,4-dioxaspiro[4.5]dec-8-yl(2-methyl-5-phenylfuran-3-yl)methyl]amino}phenyl)carbonyl]amino}propanoic acid A mixture of 8-[chloro(2-methyl-5-phenylfuran-3-yl)methyl]-1,4-dioxaspiro[4.5]decane (694 mg) obtained by the above-mentioned reaction, ethyl 3-{[(4-aminophenyl)carbonyl]amino}propanoate (567 mg), sodium carbonate (254 mg) and sodium iodide (360 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (40% ethyl acetate/hexane to 70% ethyl acetate/hexane) to give ethyl 3-{[(4-{[1,4-dioxaspiro[4.5]dec-8-yl(2-methyl-5-phenylfuran-3-yl)methyl]amino}phenyl)carbonyl]amino}propanoate. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (95 mg, 20%).

$^1$H NMR (300 MHz, DMSO-$d_6$) δ ppm 1.18-1.74 (m, 8H) 1.95-2.03 (m, 1H) 2.37-2.42 (m, 4H) 3.29-3.38 (m, 2H) 3.78-3.84 (m, 4H) 4.17 (t, J=7.91 Hz, 1H) 6.37 (d, J=8.29 Hz, 1H) 6.56 (d, J=8.48 Hz, 2H) 6.74 (s, 1H) 7.14-7.26 (m, 1H) 7.33-7.38 (m, 2H) 7.46-7.63 (m, 4H)

Example 135

3-{[(4-{[1,4-dioxaspiro[4.5]dec-8-yl(2-methyl-5-phenylfuran-3-yl)methyl]amino}phenyl)carbonyl](methyl)amino}propanoic acid

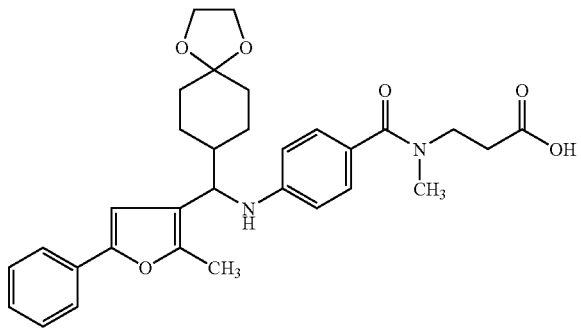

A mixture of 8-[chloro(2-methyl-5-phenylfuran-3-yl)methyl]-1,4-dioxaspiro[4.5]decane (694 mg) obtained by the above-mentioned reaction, ethyl 3-{[(4-aminophenyl)carbonyl](methyl)amino}propanoate (601 mg), sodium carbonate (254 mg) and sodium iodide (360 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (40% ethyl acetate/hexane to 70% ethyl acetate/hexane) to give ethyl 3-{[(4-{[1,4-dioxaspiro[4.5]dec-8-yl(2-methyl-5-phenylfuran-3-yl)methyl]amino}phenyl)carbonyl]amino}propanoate. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (84 mg, 23%).

$^1$H NMR (300 MHz, DMSO-$d_6$) δ ppm 1.15-1.75 (m, 8H) 1.99-2.03 (m, 1H) 2.37 (s, 3H) 2.43 (t, J=7.44 Hz, 2H) 2.89 (s, 3H) 3.47-3.52 (m, 2H) 3.82 (s, 4H) 4.13 (t, J=7.25 Hz, 1H) 6.27 (d, J=8.29 Hz, 1H) 6.56 (d, J=8.29 Hz, 2H) 6.76 (s, 1H) 7.10 (d, J=8.29 Hz, 2H) 7.20-7.24 (m, 1H) 7.36 (t, J=7.63 Hz, 2H) 7.56 (d, J=7.54 Hz, 2H)

Example 136

3-{[(4-{[(2-methyl-5-phenylfuran-3-yl)(4-oxocyclohexyl)methyl]amino}phenyl)carbonyl]amino}propanoic acid

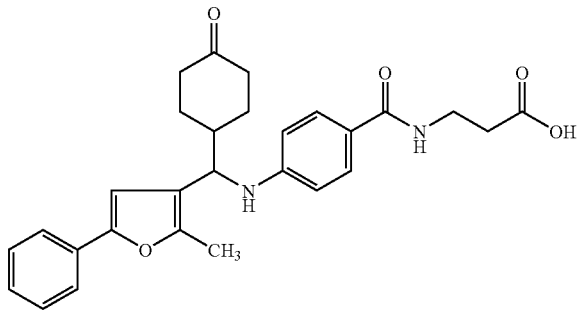

(1) ethyl 3-{[(4-{[(2-methyl-5-phenylfuran-3-yl)(4-oxocyclohexyl)methyl]amino}phenyl)carbonyl]amino}propanoate A mixture of ethyl 3-{[(4-{[1,4-dioxaspiro[4.5]dec-8-yl(2-methyl-5-phenylfuran-3-yl)methyl]amino}phenyl)carbonyl]amino}propanoate (234 mg) obtained by the above-mentioned reaction, 1N hydrochloric acid (5 mL) and tetrahydrofuran (10 mL) was stirred overnight at room temperature. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (50% ethyl acetate/hexane to 70% ethyl acetate/hexane) to give the title compound (121 mg, 80%) as an amorphous compound.

(2) 3-{[(4-{[(2-methyl-5-phenylfuran-3-yl)(4-oxocyclohexyl)methyl]amino}phenyl)carbonyl]amino}propanoic acid To ethyl 3-{[(4-{[(2-methyl-5-phenylfuran-3-yl)(4-oxocyclohexyl)methyl]amino}phenyl)carbonyl]amino}propanoate (151 mg) obtained by the above-mentioned reaction were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (103 mg, 73%).

$^1$H NMR (300 MHz, CHLOROFORM-d) δ ppm 1.47-1.71 (m, 2H) 2.01-2.17 (m, 5H) 2.30-2.44 (m, 5H) 2.63-2.68 (m, 2H) 3.62-3.69 (m, 2H) 4.19-4.24 (m, 1H) 6.47 (s, 1H) 6.54 (d, J=8.33 Hz, 2H) 7.21-7.36 (m, 5H) 7.57 (d, J=7.19 Hz, 2H)

Example 137

3-{methyl[(4-{[(2-methyl-5-phenylfuran-3-yl)(4-oxocyclohexyl)methyl]amino}phenyl)carbonyl]amino}propanoic acid

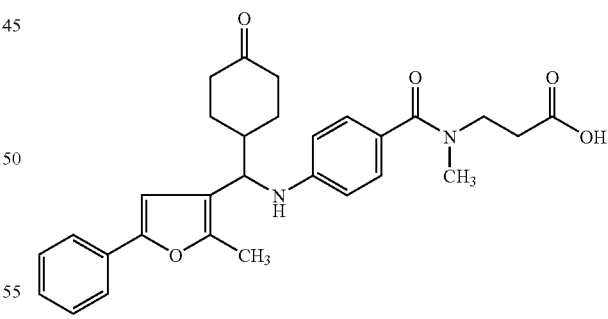

(1) ethyl 3-{methyl[(4-{[(2-methyl-5-phenylfuran-3-yl)(4-oxocyclohexyl)methyl]amino}phenyl)carbonyl]amino}propanoate A mixture of ethyl 3-{[(4-{[1,4-dioxaspiro[4.5]dec-8-yl(2-methyl-5-phenylfuran-3-yl)methyl]amino}phenyl)carbonyl](methyl)amino}propanoate (280 mg) obtained by the above-mentioned reaction, 1N hydrochloric acid (5 mL) and tetrahydrofuran (10 mL) was stirred overnight at room temperature. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (50% ethyl acetate/hexane to 70% ethyl acetate/hexane) to give the title compound (204 mg, 79%) as an amorphous compound.

(2) 3-{methyl[(4-{[(2-methyl-5-phenylfuran-3-yl)(4-oxocyclohexyl)methyl]amino}phenyl)carbonyl]amino}propanoic acid To ethyl 3-{methyl[(4-{[(2-methyl-5-phenylfuran-3-yl)(4-oxocyclohexyl)methyl]amino}phenyl)carbonyl]amino}propanoate (155 mg) obtained by the above-mentioned reaction were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (88 mg, 60%).
$^1$H NMR (300 MHz, DMSO-d$_6$) δ ppm 1.42-1.61 (m, 2H) 1.82-1.92 (m, 1H) 2.11-2.42 (m, 9H) 2.46-2.50 (m, 2H) 2.90 (s, 3H) 3.51 (t, J=7.35 Hz, 2H) 4.24-4.30 (m, 1H) 6.37 (d, J=8.10 Hz, 1H) 6.59 (d, J=8.67 Hz, 2H) 6.80 (s, 1H) 7.12 (d, J=8.48 Hz, 2H) 77.20-7.25 (m, 1H) 7.37 (t, J=7.72 Hz, 2H) 7.56 (d, J=7.35 Hz, 2H)

Example 138

3-{[(4-{[(4-hydroxycyclohexyl)(2-methyl-5-phenyl-furan-3-yl)methyl]amino}phenyl)carbonyl]amino}propanoic acid

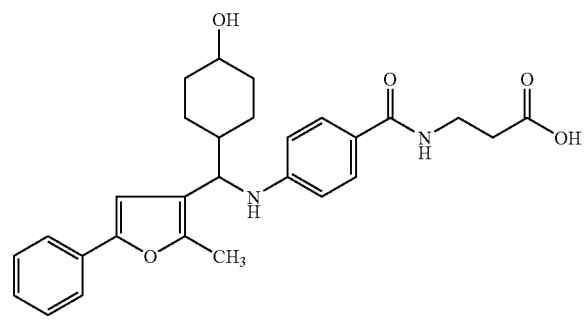

(1) ethyl 3-{[(4-{[(4-hydroxycyclohexyl)(2-methyl-5-phenylfuran-3-yl)methyl]amino}phenyl)carbonyl]amino}propanoate To a solution of ethyl 3-{[(4-{[(2-methyl-5-phenylfuran-3-yl)(4-oxocyclohexyl)methyl]amino}phenyl)carbonyl]amino}propanoate (302 mg) obtained by the above-mentioned reaction in tetrahydrofuran (5 mL) and methanol (5 mL) was added sodium borohydride (23 mg), and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (50% ethyl acetate/hexane to 100% ethyl acetate/hexane) to give the title compound (258 mg, 85%) as an amorphous compound.

(2) 3-{[(4-{[(4-hydroxycyclohexyl)(2-methyl-5-phenylfuran-3-yl)methyl]amino}phenyl)carbonyl]amino}propanoic acid To ethyl 3-{[(4-{[(4-hydroxycyclohexyl)(2-methyl-5-phenylfuran-3-yl)methyl]amino}phenyl)carbonyl]amino}propanoate (252 mg) obtained by the above-mentioned reaction were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (238 mg, 100%).
$^1$H NMR (300 MHz, DMSO-d$_6$) δ ppm 0.91-1.26 (m, 4H) 1.45-1.69 (m, 2H) 1.73-1.92 (m, 2H) 1.94-2.11 (m, 1H) 2.36 (s, 3H) 2.41 (t, J=7.38 Hz, 2H) 3.20-3.46 (m, 2H) 4.08 (t, J=7.95 Hz, 1H) 4.48 (brs, 1H) 6.35 (d, J=7.95 Hz, 1H) 6.54 (d, J=8.71 Hz, 2H) 6.72 (s, 1H) 7.15-7.27 (m, 1H) 7.36 (t, J=7.57 Hz, 2H) 7.45-7.61 (m, 4H) 8.01 (t, J=5.68 Hz, 1H)

Example 139

3-{[(4-{[(4-hydroxycyclohexyl)(2-methyl-5-phenyl-furan-3-yl)methyl]amino}phenyl)carbonyl](methyl)amino}propanoic acid

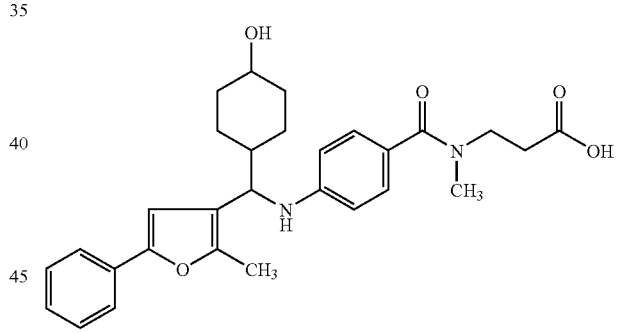

(1) ethyl 3-{[(4-{[(4-hydroxycyclohexyl)(2-methyl-5-phenylfuran-3-yl)methyl]amino}phenyl)carbonyl](methyl)amino}propanoate To a solution of ethyl 3-{methyl[(4-{[(2-methyl-5-phenyl-furan-3-yl)(4-oxocyclohexyl)methyl]amino}phenyl)carbonyl]amino}propanoate (258 mg) obtained by the above-mentioned reaction in tetrahydrofuran (5 mL) and methanol (5 mL) was added sodium borohydride (23 mg), and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (50% ethyl acetate/hexane to 100% ethyl acetate/hexane) to give the title compound (156 mg, 60%) as an amorphous compound.

(2) 3-{[(4-{[(4-hydroxycyclohexyl)(2-methyl-5-phenylfuran-3-yl)methyl]amino}phenyl)carbonyl](methyl)amino}propanoic acid To ethyl 3-{[(4-{[(4-hydroxycyclohexyl)(2-methyl-5-phenylfuran-3-yl)methyl]amino}phenyl)carbonyl](methyl)amino}propanoate (252 mg) obtained by the above-mentioned reaction were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (238 mg, 100%).
$^1$H NMR (300 MHz, DMSO-$d_6$) δ ppm 0.97-1.20 (m, 4H) 1.52-1.63 (m, 2H) 1.76-1.90 (m, 2H) 1.98-2.06 (m, 1H) 2.36 (s, 3H) 2.40-2.48 (m, 2H) 2.89 (s, 3H) 3.50 (t, J=7.38 Hz, 2H) 3.96-4.19 (m, 1H) 4.48 (brs, 1H) 6.25 (d, J=7.95 Hz, 1H) 6.53 (d, J=8.71 Hz, 2H) 6.74 (s, 1H) 7.10 (d, J=8.33 Hz, 2H) 7.21 (t, J=7.19 Hz, 1H) 7.36 (t, J=7.57 Hz, 2H) 7.56 (d, J=7.19 Hz, 2H)

Example 140

3-[({4-[(cyclohexyl{2-ethyl-5-[4-(trifluoromethyl)phenyl]furan-3-yl}methyl)amino]phenyl}carbonyl)(methyl)amino]-2-hydroxypropanoic acid

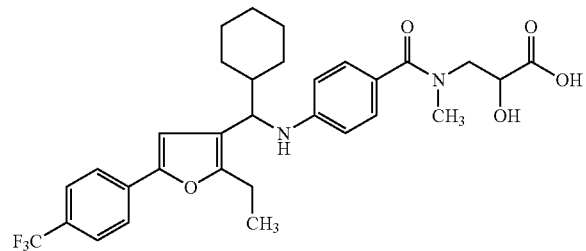

(1) methyl 2-hydroxy-3-{[(2-nitrophenyl)sulfonyl]amino}propanoate

To a solution of methyl 3-amino-2-hydroxypropanoate hydrochloride (0.8 g) in N,N-dimethylformamide (10 mL) were added triethylamine (1.1 mL) and 2-nitrobenzenesulfonyl chloride (1.1 g) at 0° C., and the mixture was stirred at 0° C. for 2 hr and then at room temperature overnight. The reaction mixture was poured into water, and the mixture was extracted with ethyl acetate. The organic layer was washed with saturated brine, and dried over magnesium sulfate. The solvent was evaporated under reduced pressure to give the title compound (1.1 g, 89%) as an oil.
$^1$H NMR (300 MHz, CHLOROFORM-d) δ ppm 2.96-3.19 (m, 1H) 3.47 (d, J=4.14 Hz, 2H) 3.82 (s, 3H) 4.30 (t, J=4.62 Hz, 1H) 5.80 (brs, 1H) 7.68-7.81 (m, 2H) 7.83-7.95 (m, 1H) 8.08-8.19 (m, 2H)

(2) methyl 2-hydroxy-3-{methyl[(2-nitrophenyl)sulfonyl]amino}propanoate

A mixture of methyl 2-hydroxy-3-{[(2-nitrophenyl)sulfonyl]amino}propanoate (1.1 g), cesium carbonate (1.4 g), methyl iodide (0.3 mL) and N,N-dimethylformamide (10 mL) was stirred overnight at room temperature. The reaction mixture was poured into water, and the mixture was extracted with ethyl acetate. The organic layer was washed with saturated brine, and dried over magnesium sulfate. The solvent was evaporated under reduced pressure to give the title compound (1.1 g, 100%) as an oil.
$^1$H NMR (300 MHz, CHLOROFORM-d) δ ppm 3.03 (s, 3H) 3.51-3.73 (m, 2H) 3.84 (s, 3H) 4.43 (td, J=6.15, 3.98 Hz, 1H) 7.59-7.78 (m, 3H) 7.99-8.08 (m, 1H)

(3) methyl 3-[(tert-butoxycarbonyl)(methyl)amino]-2-hydroxypropanoate

To a solution of methyl 2-hydroxy-3-{methyl[(2-nitrophenyl)sulfonyl]amino}propanoate (1.1 g) in N,N-dimethylformamide (10 mL) were added thioglycolic acid (1.0 g) and lithium hydroxide monohydrate (0.9 g), and the mixture was stirred at room temperature overnight. To the reaction mixture was added di-tert-butyl dicarbonate (1.5 g), and the mixture was stirred at room temperature overnight. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 40% ethyl acetate/hexane) to give the title compound (0.2 g, 20%) as an oil.
$^1$H NMR (300 MHz, CHLOROFORM-d) δ ppm 1.46 (s, 9H) 2.94 (s, 3H) 3.29-3.69 (m, 2H) 3.79 (s, 3H) 4.38 (d, J=3.79 Hz, 1H)

(4) methyl 2-hydroxy-3-(methylamino)propanoate hydrochloride

A mixture of methyl 3-[(tert-butoxycarbonyl)(methyl)amino]-2-hydroxypropanoate (0.2 g) and 4N hydrochloric acid-ethyl acetate (5 mL) was stirred at room temperature for 1 hr. The solvent was evaporated under reduced pressure, to give the title compound (0.1 g, 100%) as a yellow crystal.
$^1$H NMR (300 MHz, DMSO-$d_6$) δ ppm 2.57 (s, 3H) 3.03-3.11 (m, 1H) 3.21-3.26 (m, 1H) 3.70 (s, 3H) 4.42-4.44 (m, 1H)

(5) 3-[({4-[(cyclohexyl{2-ethyl-5-[4-(trifluoromethyl)phenyl]furan-3-yl}methyl)amino]phenyl}carbonyl)(methyl)amino]-2-hydroxypropanoic acid A solution of 4-[(cyclohexyl{2-ethyl-5-[4-(trifluoromethyl)phenyl]furan-3-yl}methyl)amino]benzoic acid (141 mg), methyl 2-hydroxy-3-(methylamino)propanoate hydrochloride (61 mg), 1-ethyl-3-(3-dimethylaminopropyl)carbodiimide hydrochloride (69 mg), hydroxybenzotriazole monohydrate (55 mg) and triethylamine (50 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (107 mg, 64%).
$^1$H NMR (300 MHz, DMSO-$d_6$) δ ppm 0.93-1.27 (m, 8H) 1.53-1.76 (m, 5H) 1.21 (t, J=7.44 Hz, 12H) 1.36 (s, 9H) 1.63 (d, J=3.58 Hz, 12H) 2.03-2.08 (m, 1H) 2.68-2.88 (m, 2H) 2.93 (s, 3H) 3.03-3.37 (m, 2H) 3.62 (brs, 1H) 3.97 (brs, 1H) 4.07-4.13 (m, 1H) 6.20 (d, J=7.91 Hz, 1H) 6.54 (d, J=8.67 Hz, 2H) 6.96 (s, 1H) 7.13 (d, J=8.48 Hz, 2H) 7.65-7.74 (m, 2H) 7.74-7.84 (m, 2H)

Example 141

3-{[(4-{[cyclohexyl(2-methyl-5-phenylfuran-3-yl)methyl]amino}phenyl)carbonyl](methyl)amino}-2-hydroxypropanoic acid

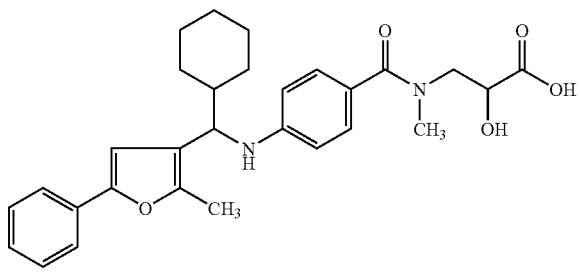

A solution of 4-{[cyclohexyl(2-methyl-5-phenylfuran-3-yl)methyl]amino}benzoic acid (117 mg), methyl 2-hydroxy-3-(methylamino)propanoate hydrochloride (61 mg), 1-ethyl-3-(3-dimethylaminopropyl)carbodiimide hydrochloride (69 mg), hydroxybenzotriazole monohydrate (55 mg) and triethylamine (50 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (98 mg, 69%).

$^1$H NMR (300 MHz, DMSO-d$_6$) δ ppm 0.94-1.19 (m, 5H) 1.50-1.81 (m, 5H) 2.04 (d, J=12.81 Hz, 1H) 2.37 (s, 3H) 2.95 (s, 3H) 3.33 (brs, 1H) 3.36-3.51 (m, 1H) 3.65 (d, J=11.87 Hz, 1H) 4.06 (t, J=7.82 Hz, 1H) 4.11-4.23 (m, 1H) 6.22 (d, J=7.72 Hz, 1H) 6.54 (d, J=8.67 Hz, 2H) 6.74 (s, 1H) 7.13 (d, J=8.29 Hz, 2H) 7.17-7.28 (m, 1H) 7.36 (t, J=7.72 Hz, 2H) 7.49-7.61 (m, 2H)

Example 142

3-({[4-({cyclohexyl[5-(6-fluoropyridin-3-yl)-2-methylfuran-3-yl]methyl}amino)phenyl]carbonyl}amino)propanoic acid

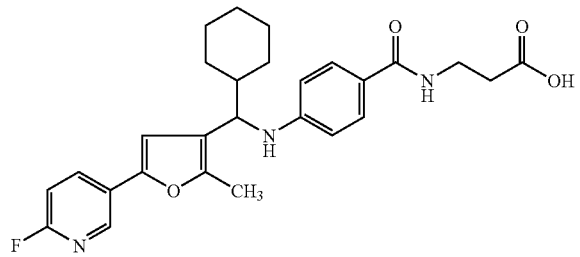

Example 142 (continued)

3-({[4-({cyclohexyl[5-(6-fluoropyridin-3-yl)-2-methylfuran-3-yl]methyl}amino)phenyl]carbonyl}amino)propanoic acid A mixture of 5-{4-[chloro(cyclohexyl)methyl]-5-methylfuran-2-yl}-2-fluoropyridine (0.8 g), ethyl 3-{[(4-aminophenyl)carbonyl]amino}propanoate (0.7 g), sodium carbonate (0.3 g) and sodium iodide (0.5 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane). To the residue were added ethanol (3 mL), tetrahydrofuran (3 mL) and 1N lithium hydroxide (3.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (753 mg, 62%).

$^1$H NMR (300 MHz, DMSO-d$_6$) δ ppm 0.83-1.22 (m, 5H) 1.49-1.81 (m, 5H) 2.03 (d, J=13.38 Hz, 1H) 2.31-2.44 (m, 5H) 3.18-3.48 (m, 2H) 4.11 (t, J=7.63 Hz, 1H) 6.36 (d, J=7.72 Hz, 1H) 6.54 (d, J=8.85 Hz, 2H) 6.86 (s, 1H) 7.19 (dd, J=8.67, 2.64 Hz, 1H) 7.51 (d, J=8.48 Hz, 1H) 8.04 (brs, 1H) 8.12 (td, J=8.19, 2.45 Hz, 1H) 8.43 (d, J=2.07 Hz, 1H)

Example 143

3-[{[4-({cyclohexyl[5-(6-fluoropyridin-3-yl)-2-methylfuran-3-yl]methyl}amino)phenyl]carbonyl}(methyl)amino]propanoic acid

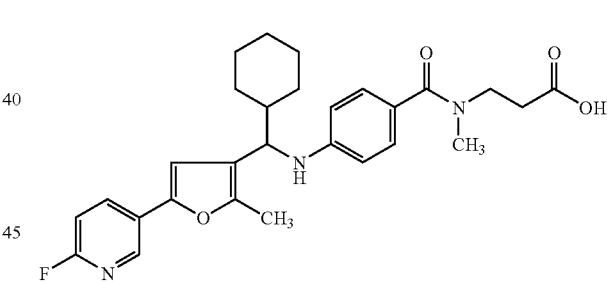

A mixture of 5-{4-[chloro(cyclohexyl)methyl]-5-methylfuran-2-yl}-2-fluoropyridine (0.77 g), ethyl 3-{[(4-aminophenyl)carbonyl](methyl)amino}propanoate (0.75 g), sodium carbonate (0.3 g) and sodium iodide (0.5 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane). To the residue were added ethanol (3 mL), tetrahydrofuran (3 mL) and 1N lithium hydroxide (2.7 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (667 mg, 54%).

¹H NMR (300 MHz, DMSO-d₆) δ ppm 0.90-1.30 (m, 5H) 1.46-1.81 (m, 5H) 2.04 (d, J=15.07 Hz, 1H) 2.28-2.46 (m, 5H) 2.89 (s, 3H) 3.43-3.58 (m, 2H) 4.07 (t, J=6.69 Hz, 1H) 6.25 (d, J=7.91 Hz, 1H) 6.54 (d, J=8.48 Hz, 2H) 6.87 (s, 1H) 7.09 (d, J=8.29 Hz, 2H) 7.19 (d, J=10.36 Hz, 1H) 8.03-8.23 (m, 1H) 8.44 (s, 1H)

Example 144

3-({[4-({cyclohexyl[5-(5-fluoropyridin-2-yl)-2-methylfuran-3-yl]methyl}amino)phenyl]carbonyl}amino)propanoic acid

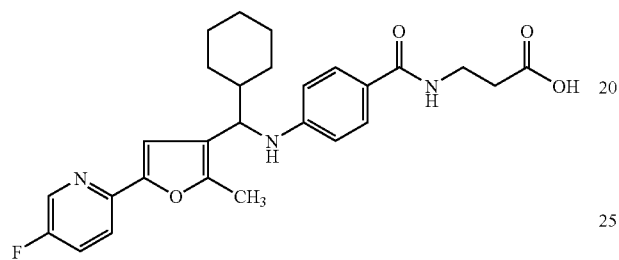

(1) cyclohexyl[5-(5-fluoropyridin-2-yl)-2-methylfuran-3-carbaldehyde

A mixture of 5-bromo-2-methylfuran-3-carbaldehyde (1.9 g), bis(pinacolato)diboron (3.1 g), 1,1'-bis(diphenylphosphino)ferrocene-palladium(II)dichloride dichloromethane complex (0.2 g), potassium acetate (2.9 g) and dimethyl sulfoxide (50 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. A mixture of the residue, 2-bromo-5-fluoropyridine (2.6 g), tetrakis(triphenylphosphine)palladium(0) (0.6 g), 2N aqueous sodium carbonate solution (12 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane), and crystallized from ethyl acetate/hexane to give the title compound (0.3 g, 14%) as a yellow solid.

¹H NMR (300 MHz, CHLOROFORM-d) δ ppm 2.71 (s, 3H) 7.21 (s, 1H) 7.46 (td, J=8.38, 2.83 Hz, 1H) 7.67 (dd, J=8.95, 4.05 Hz, 1H) 8.49 (d, J=2.83 Hz, 1H) 9.99 (s, 1H)

(2) cyclohexyl[5-(5-fluoropyridin-2-yl)-2-methylfuran-3-yl]methanol

To a solution of cyclohexyl[5-(5-fluoropyridin-2-yl)-2-methylfuran-3-carbaldehyde (0.5 g) obtained by the above-mentioned reaction in tetrahydrofuran (20 mL) was added dropwise 1N cyclohexylmagnesium bromide-tetrahydrofuran solution (4 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (0.7 g, 97%) as an oil.

¹H NMR (300 MHz, CHLOROFORM-d) δ ppm 0.86-1.34 (m, 5H) 1.51-1.81 (m, 5H) 1.99-2.14 (m, 1H) 2.36 (s, 3H) 4.32 (dd, J=7.91, 3.20 Hz, 1H) 6.91 (s, 1H) 7.41 (td, J=8.48, 2.83 Hz, 1H) 7.62 (dd, J=8.76, 4.43 Hz, 1H) 8.43 (d, J=2.83 Hz, 1H)

(3) 2-{4-[chloro(cyclohexyl)methyl]-5-methylfuran-2-yl}-5-fluoropyridine

To a solution of cyclohexyl[5-(5-fluoropyridin-2-yl)-2-methylfuran-3-yl]methanol (0.7 g) in toluene (10 mL) was added thionyl chloride (0.3 mL), and the mixture was stirred at room temperature for 2 hr. The solvent was evaporated under reduced pressure to give the title compound (0.7 g, 100%) as a yellow crystal.

¹H NMR (300 MHz, CHLOROFORM-d) δ ppm 0.88-1.30 (m, 5H) 1.67-1.91 (m, 5H) 2.21 (d, J=12.87 Hz, 1H) 2.37 (s, 3H) 4.59 (d, J=8.71 Hz, 1H) 7.08-7.20 (m, 1H) 7.51 (td, J=8.33, 3.03 Hz, 1H) 7.69 (dd, J=8.90, 4.35 Hz, 1H) 8.46 (d, J=2.65 Hz, 1H)

(4) 3-({[4-({cyclohexyl[5-(5-fluoropyridin-2-yl)-2-methylfuran-3-yl]methyl}amino)phenyl]carbonyl}amino)propanoic acid A mixture of 2-{4-[chloro(cyclohexyl)methyl]-5-methylfuran-2-yl}-5-fluoropyridine (0.4 g), ethyl 3-{[(4-aminophenyl)carbonyl]amino}propanoate (0.3 g), sodium carbonate (0.2 g) and sodium iodide (0.2 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane). To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (285 mg, 52%).

¹H NMR (300 MHz, DMSO-d₆) δ ppm 0.89-1.28 (m, 5H) 1.48-1.81 (m, 5H) 2.01-2.07 (m, 1H) 2.33-2.46 (m, 5H) 3.19-3.46 (m, 2H) 4.14 (t, J=8.19 Hz, 1H) 6.37 (d, J=8.67 Hz, 1H) 6.56 (d, J=8.67 Hz, 2H) 6.93 (s, 1H) 7.51 (d, J=8.85 Hz, 2H) 7.57-7.67 (m, 1H) 7.67-7.81 (m, 1H) 8.02 (s, 1H) 8.49 (d, J=2.83 Hz, 1H)

Example 145

3-[{[4-({cyclohexyl[5-(5-fluoropyridin-2-yl)-2-methylfuran-3-yl]methyl}amino)phenyl]carbonyl}(methyl)amino]propanoic acid

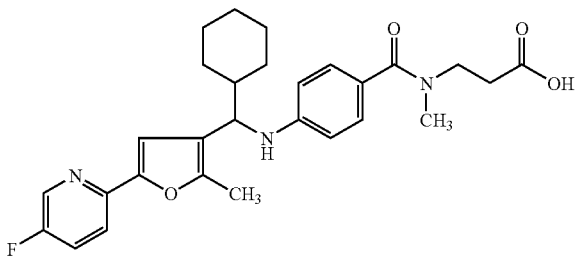

A mixture of 5-{4-[chloro(cyclohexyl)methyl]-5-methylfuran-2-yl}-2-fluoropyridine (0.37 g), ethyl 3-{[(4-aminophenyl)carbonyl](methyl)amino}propanoate (0.35 g), sodium carbonate (0.2 g) and sodium iodide (0.2 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane). To the residue were added ethanol (2 mL), tetrahydrofuran (2 mL) and 1N lithium hydroxide (1.1 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (245 mg, 42%).

$^1$H NMR (300 MHz, DMSO-$d_6$) δ ppm 0.89-1.29 (m, 5H) 1.48-1.83 (m, 5H) 2.04 (d, J=11.87 Hz, 1H) 2.39 (s, 3H) 2.42-2.48 (m, 2H) 2.89 (s, 3H) 3.50 (t, J=7.35 Hz, 2H) 4.11 (t, J=8.01 Hz, 1H) 6.28 (d, J=8.67 Hz, 1H) 6.55 (m, J=8.67 Hz, 2H) 6.94 (s, 1H) 7.10 (d, J=8.48 Hz, 2H) 7.57-7.67 (m, 1H) 7.67-7.80 (m, 1H) 8.50 (d, J=3.01 Hz, 1H)

Example 146

3-({[4-({cyclohexyl[2-(methoxymethyl)-5-(6-methoxypyridin-3-yl)furan-3-yl]methyl}amino)phenyl]carbonyl}amino)propanoic acid

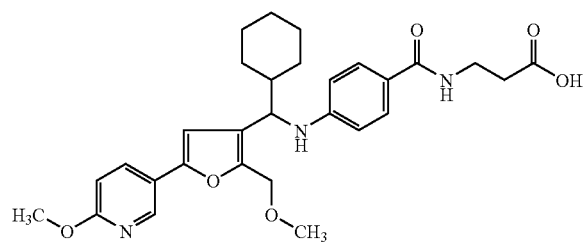

(1) methyl 2-(methoxymethyl)-5-(6-methoxypyridin-3-yl)furan-3-carboxylate

A mixture of methyl 5-bromo-2-(methoxymethyl)furan-3-carboxylate (3.0 g), 2-methoxy-5-pyridineboronic acid (2.1 g), tetrakis(triphenylphosphine)palladium(0) (0.7 g), 2N aqueous sodium carbonate solution (14 mL) and 1,2-dimethoxyethane (30 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 25% ethyl acetate/hexane), and crystallized from ethyl acetate/hexane to give the title compound (2.8 g, 84%) as a white crystal.

$^1$H NMR (300 MHz, CHLOROFORM-d) δ ppm 3.45 (s, 3H) 3.88 (s, 3H) 3.97 (s, 3H) 4.79 (s, 2H) 6.78 (d, J=8.10 Hz, 1H) 6.85 (s, 1H) 7.86 (dd, J=8.67, 2.45 Hz, 1H) 8.50 (d, J=1.88 Hz, 1H)

(2) [2-(methoxymethyl)-5-(6-methoxypyridin-3-yl)furan-3-yl]methanol

A solution of methyl 2-(methoxymethyl)-5-(6-methoxypyridin-3-yl)furan-3-carboxylate (2.8 g) obtained by the above-mentioned reaction in tetrahydrofuran (20 mL) was added dropwise to a suspension of lithium aluminum hydride (0.4 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (2.5 g, 100%) as a white crystal.

$^1$H NMR (300 MHz, CHLOROFORM-d) δ ppm 1.89 (t, J=5.87 Hz, 1H) 3.42 (s, 3H) 3.96 (s, 3H) 4.51 (s, 2H) 4.61 (d, J=6.06 Hz, 2H) 6.59 (s, 1H) 6.77 (d, J=8.71 Hz, 1H) 7.84 (dd, J=8.52, 2.46 Hz, 1H) 8.47 (d, J=2.65 Hz, 1H)

(3) 2-(methoxymethyl)-5-(6-methoxypyridin-3-yl)furan-3-carbaldehyde

To a solution of [2-(methoxymethyl)-5-(6-methoxypyridin-3-yl)furan-3-yl]methanol (2.5 g) obtained by the above-mentioned reaction in methylene chloride (30 mL) was added a Dess-Martin reagent (5.1 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 40% ethyl acetate/hexane) to give the title compound (2.0 g, 81%) as a white crystal.

$^1$H NMR (300 MHz, CHLOROFORM-d) δ ppm 3.48 (s, 3H) 3.98 (s, 3H) 4.76 (s, 2H) 6.80 (dd, J=8.67, 0.75 Hz, 1H) 6.86-6.95 (m, 1H) 7.85 (dd, J=8.76, 2.54 Hz, 1H) 8.51 (d, J=1.88 Hz, 1H) 10.10 (s, 1H)

(4) cyclohexyl[2-(methoxymethyl)-5-(6-methoxypyridin-3-yl)furan-3-yl]methanol To a solution of 2-(methoxymethyl)-5-(6-methoxypyridin-3-yl)furan-3-carbaldehyde (2.0 g) obtained by the above-mentioned reaction in tetrahydrofuran (30 mL) was added dropwise 1N cyclohexylmagnesium bromide-tetrahydrofuran solution (12 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (2.1 g, 72%) as an oil.

$^1$H NMR (300 MHz, CHLOROFORM-d) δ ppm 0.91-1.31 (m, 5H) 1.47-1.87 (m, 5H) 1.98-2.15 (m, 2H) 3.41 (s, 3H) 3.96 (s, 3H) 4.41 (dd, J=7.38, 3.60 Hz, 1H) 4.47 (s, 2H) 6.53 (s, 1H) 6.76 (d, J=7.95 Hz, 1H) 7.84 (dd, J=8.71, 2.65 Hz, 1H) 8.47 (d, J=1.89 Hz, 1H)

(5) 5-{4-[chloro(cyclohexyl)methyl]-5-(methoxymethyl)furan-2-yl}-2-methoxypyridine To a solution of cyclohexyl[2-(methoxymethyl)-5-(6-methoxypyridin-3-yl)furan-3-yl]methanol (0.8 g) in toluene (10 mL) were added thionyl chloride (0.2 mL) and pyridine (0.3 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.8 g, 100%) as an oil.

(6) 3-({[4-({cyclohexyl[2-(methoxymethyl)-5-(6-methoxypyridin-3-yl)furan-3-yl]methyl}amino)phenyl]carbonyl}amino)propanoic acid A mixture of 5-{4-[chloro(cyclohexyl)methyl]-5-(methoxymethyl)furan-2-yl}-2-methoxypyridine (0.4 g), ethyl 3-{[(4-aminophenyl)carbonyl]amino}propanoate (0.3 g), sodium carbonate (0.2 g) and sodium iodide (0.2 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 70% ethyl acetate/hexane). To the residue were added ethanol (2 mL), tetrahydrofuran (2 mL) and 1N lithium hydroxide (0.45 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (104 mg, 16%).

$^1$H NMR (300 MHz, DMSO-d$_6$) δ ppm 0.84-1.27 (m, 5H) 1.43-1.83 (m, 5H) 1.95-2.09 (m, 1H) 2.43 (t, J=7.00 Hz, 2H) 3.34-3.48 (m, 5H) 3.86 (s, 3H) 4.21 (t, J=8.14 Hz, 1H) 4.38-4.67 (m, 2H) 6.36 (d, J=8.33 Hz, 1H) 6.59-6.65 (m, 2H) 6.77 (s, 1H) 6.86 (d, J=8.33 Hz, 1H) 7.51 (d, J=8.71 Hz, 2H) 7.91 (dd, J=8.71, 2.27 Hz, 1H) 8.00 (t, J=5.49 Hz, 1H) 8.42 (d, J=2.27 Hz, 1H) 12.18 (brs, 1H)

Example 147

3-[{[4-({cyclohexyl[2-(methoxymethyl)-5-(6-methoxypyridin-3-yl)furan-3-yl]methyl}amino)phenyl]carbonyl}(methyl)amino]propanoic acid

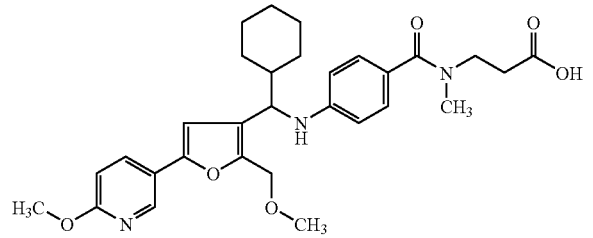

A mixture of 5-{4-[chloro(cyclohexyl)methyl]-5-(methoxymethyl)furan-2-yl}-2-methoxypyridine (0.4 g), ethyl 3-{[(4-aminophenyl)carbonyl](methyl)amino}propanoate (0.4 g), sodium carbonate (0.2 g) and sodium iodide (0.2 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 70% ethyl acetate/hexane). To the residue were added ethanol (2 mL), tetrahydrofuran (2 mL) and 1N lithium hydroxide (0.45 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (91 mg, 14%).

$^1$H NMR (300 MHz, DMSO-d$_6$) δ ppm 0.83-1.32 (m, 5H) 1.60-1.80 (m, 5H) 2.04 (d, J=11.74 Hz, 1H) 2.47-2.51 (m, 2H) 2.89 (s, 3H) 3.23-3.38 (m, 5H) 3.51 (t, J=7.19 Hz, 2H) 3.87 (s, 3H) 4.18 (t, J=7.95 Hz, 1H) 4.50 (q, J=12.62 Hz, 2H) 6.25 (d, J=7.95 Hz, 1H) 6.51-6.65 (m, 2H) 6.79 (s, 1H) 6.86 (d, J=8.33 Hz, 1H) 7.09 (d, J=8.33 Hz, 2H) 7.92 (dd, J=8.71, 2.65 Hz, 1H) 8.43 (d, J=2.27 Hz, 1H) 12.26 (brs, 1H)

Example 148

3-({[4-({1-[5-(6-methoxypyridin-3-yl)-2-methylfuran-3-yl]-3-methylbutyl}amino)phenyl]carbonyl}amino)propanoic acid

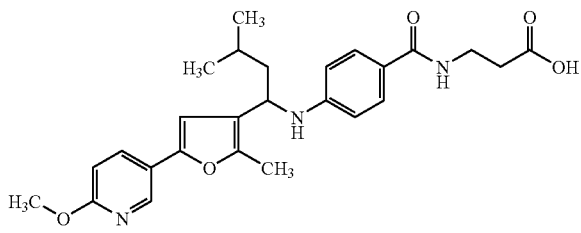

(1) methyl 5-(6-methoxypyridin-3-yl)-2-methylfuran-3-carboxylate

A mixture of methyl 5-bromo-2-methyl-3-furancarboxylate (2.2 g), 2-methoxy-5-pyridineboronic acid (1.8 g), tetrakis(triphenylphosphine)palladium(0) (0.6 g), 2N aqueous sodium carbonate solution (12 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (2.0 g, 81%) as a white solid.

$^1$H NMR (300 MHz, CHLOROFORM-d) δ ppm 2.65 (s, 3H) 3.85 (s, 3H) 3.97 (s, 3H) 6.76-6.79 (m, 2H) 7.80 (dd, J=8.67, 2.64 Hz, 1H) 8.45 (d, J=1.88 Hz, 1H)

(2) [5-(6-methoxypyridin-3-yl)-2-methylfuran-3-yl]methanol

A solution of methyl 5-(6-methoxypyridin-3-yl)-2-methylfuran-3-carboxylate (2.0 g) obtained by the above-mentioned reaction in tetrahydrofuran (20 mL) was added dropwise to a suspension of lithium aluminum hydride (0.3 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane), and crystallized from ethyl acetate/hexane to give the title compound (1.7 g, 100%) as a white solid.

$^1$H NMR (300 MHz, CHLOROFORM-d) δ ppm 1.40 (s, 1H) 2.36 (s, 3H) 3.96 (s, 3H) 4.51 (d, J=5.68 Hz, 2H) 6.55 (s, 1H) 6.75 (d, J=8.71 Hz, 1H) 7.79 (dd, J=8.52, 2.46 Hz, 1H) 8.43 (d, J=2.65 Hz, 1H)

(3) 5-(6-methoxypyridin-3-yl)-2-methylfuran-3-carbaldehyde

To a solution of [5-(6-methoxypyridin-3-yl)-2-methylfuran-3-yl]methanol (1.8 g) obtained by the above-mentioned reaction in methylene chloride (20 mL) was added a Dess-Martin reagent (4.0 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (10% ethyl acetate/hexane to 40% ethyl acetate/hexane), and crystallized from ethyl acetate/hexane to give the title compound (1.5 g, 88%) as a white solid.

$^1$H NMR (300 MHz, CHLOROFORM-d) δ ppm 2.67 (s, 3H) 3.97 (s, 3H) 6.79 (d, J=8.71 Hz, 1H) 6.82 (s, 1H) 7.81 (dd, J=8.52, 2.46 Hz, 1H) 8.48 (d, J=1.89 Hz, 1H) 9.96 (s, 1H)

(4) 1-[5-(6-methoxypyridin-3-yl)-2-methylfuran-3-yl]-3-methylbutan-1-ol

To a solution of 5-(6-methoxypyridin-3-yl)-2-methylfuran-3-carbaldehyde (1.5 g) obtained by the above-mentioned reaction in tetrahydrofuran (20 mL) was added dropwise 1N isobutylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (5% ethyl acetate/hexane to 65% ethyl acetate/hexane) to give the title compound (1.7 g, 90%) as an oil.

$^1$H NMR (300 MHz, CHLOROFORM-d) δ ppm 0.95 (d, J=6.44 Hz, 6H) 1.60-1.69 (m, 1H) 1.69-1.89 (m, 2H) 2.36 (s, 3H) 3.96 (s, 3H) 4.71 (td, J=7.00, 3.41 Hz, 1H) 6.52 (s, 1H) 6.74 (d, J=8.71 Hz, 1H) 7.79 (dd, J=8.71, 2.27 Hz, 1H) 8.43 (d, J=2.27 Hz, 1H)

(5) 5-[4-(1-chloro-3-methylbutyl)-5-methylfuran-2-yl]-2-methoxypyridine

To a solution of 1-[5-(6-methoxypyridin-3-yl)-2-methylfuran-3-yl]-3-methylbutan-1-ol (0.7 g) obtained by the above-mentioned reaction in toluene (20 mL) were added thionyl chloride (0.3 mL) and pyridine (0.3 mL) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure to give the title compound (0.8 g, 100%) as an amorphous compound.

$^1$H NMR (300 MHz, CHLOROFORM-d) δ ppm 0.94 (dd, J=6.44, 3.41 Hz, 6H) 1.72 (dq, J=13.30, 6.67 Hz, 2H) 1.95-2.17 (m, 1H) 2.04 (t, J=6.82 Hz, 4H) 2.37 (s, 3H) 3.98 (s, 3H) 4.95 (t, J=7.57 Hz, 1H) 6.55 (s, 1H) 6.77 (d, J=8.71 Hz, 1H) 7.81 (dd, J=8.71, 2.65 Hz, 1H) 8.44 (d, J=1.89 Hz, 1H)

(6) 3-({[4-({1-[5-(6-methoxypyridin-3-yl)-2-methylfuran-3-yl]-3-methylbutyl}amino)phenyl]carbonyl}amino)propanoic acid A mixture of 5-[4-(1-chloro-3-methylbutyl)-5-methylfuran-2-yl]-2-methoxypyridine (382 mg) obtained by the above-mentioned reaction, ethyl 3-{[(4-aminophenyl)carbonyl]amino}propanoate (378 mg), sodium carbonate (170 mg) and sodium iodide (240 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 65% ethyl acetate/hexane) to give ethyl 3-({[4-({1-[5-(6-methoxypyridin-3-yl)-2-methylfuran-3-yl]-3-methylbutyl}amino)phenyl]carbonyl}amino)propanoate. The obtained ethyl 3-({[4-({1-[5-(6-methoxypyridin-3-yl)-2-methylfuran-3-yl]-3-methylbutyl}amino)phenyl]carbonyl}amino)propanoate was dissolved in ethanol (2 mL) and tetrahydrofuran (2 mL) and 1N lithium hydroxide (0.9 mL) was added, and the mixture was stirred at room temperature for 1 hr. The solvent was evaporated under reduced pressure, water (10 mL) was added, and the mixture was neutralized with 1N hydrochloric acid under ice-cooling, and stirred for 1 hr. The resulting precipitate was collected by filtration and dried to give the title compound (191 mg, 32%).

$^1$H NMR (300 MHz, DMSO-d$_6$) δ ppm 0.92 (dd, J=18.17, 6.06 Hz, 6H) 1.46-1.80 (m, 3H) 2.33-2.46 (m, 5H) 3.29-3.48 (m, 2H) 3.85 (s, 3H) 4.36 (q, J=7.45 Hz, 1H) 6.36 (d, J=7.57 Hz, 1H) 6.55 (d, J=8.71 Hz, 2H) 6.73 (s, 1H) 6.83 (d, J=8.71 Hz, 1H) 7.54 (d, J=8.33 Hz, 2H) 7.87 (dd, J=8.71, 2.27 Hz, 1H) 7.97-8.12 (m, 1H) 8.38 (d, J=2.27 Hz, 1H)

Example 149

3-[{[4-({1-[5-(6-methoxypyridin-3-yl)-2-methylfuran-3-yl]-3-methylbutyl}amino)phenyl]carbonyl}(methyl)amino]propanoic acid

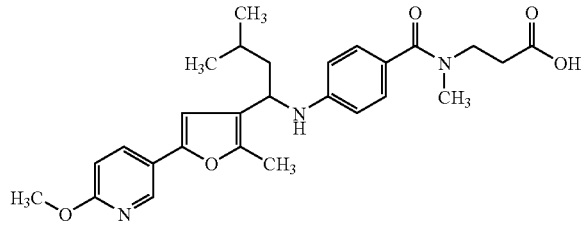

A mixture of 5-[4-(1-chloro-3-methylbutyl)-5-methylfuran-2-yl]-2-methoxypyridine (382 mg), ethyl 3-{[(4-aminophenyl)carbonyl](methyl)amino}propanoate (400 mg), sodium carbonate (170 mg) and sodium iodide (240 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 65% ethyl acetate/hexane) to give ethyl 3-[{[4-({1-[5-(6-methoxypyridin-3-yl)-2-methylfuran-3-yl]-3-methylbutyl}amino)phenyl]carbonyl}(methyl) amino]propanoate. The obtained ethyl 3-[{[4-({1-[5-(6-methoxypyridin-3-yl)-2-methylfuran-3-yl]-3-methylbutyl}amino)phenyl]carbonyl}(methyl)amino] propanoate was dissolved in ethanol (2 mL) and tetrahydrofuran (2 mL) and 1N lithium hydroxide (0.7 mL) were added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (153 mg, 25%).

$^1$H NMR (300 MHz, DMSO-$d_6$) δ ppm 0.92 (dd, J=17.61, 6.25 Hz, 6H) 1.49-1.75 (m, 3H) 2.47-2.51 (m, 2H) 2.38 (s, 3H) 2.90 (s, 3H) 3.52 (t, J=7.57 Hz, 2H) 3.85 (s, 3H) 4.32 (d, J=7.57 Hz, 1H) 6.26 (d, J=7.19 Hz, 1H) 6.54 (d, J=8.71 Hz, 2H) 6.74 (s, 1H) 6.83 (d, J=8.71 Hz, 1H) 7.12 (d, J=8.71 Hz, 2H) 7.88 (dd, J=8.71, 2.27 Hz, 1H) 8.39 (d, J=2.27 Hz, 1H)

Example 150

3-({[4-({1-[5-(4-methoxyphenyl)-2-methylfuran-3-yl]-3-methylbutyl}amino)phenyl]carbonyl}amino) propanoic acid

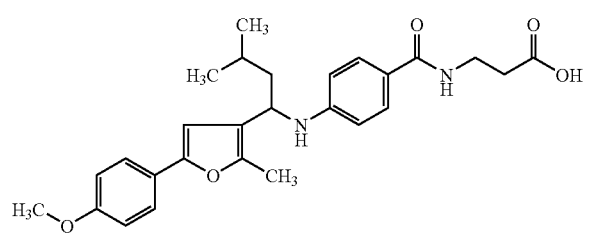

(1) methyl 5-(4-methoxyphenyl)-2-methylfuran-3-carboxylate

A mixture of methyl 5-bromo-2-methyl-3-furancarboxylate (2.6 g), 4-methoxy-phenylboronic acid (2.3 g), tetrakis(triphenylphosphine)palladium(0) (0.7 g), 2N aqueous sodium carbonate solution (15 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 15% ethyl acetate/hexane), and crystallized from ethyl acetate/hexane to give the title compound (2.6 g, 88%) as a white solid.

$^1$H NMR (300 MHz, CHLOROFORM-d) δ ppm 2.63 (s, 3H) 3.85 (s, 3H) 3.84 (s, 3H) 6.73 (s, 1H) 6.92 (d, J=8.71 Hz, 2H) 7.56 (d, J=8.71 Hz, 2H)

(2) [5-(4-methoxyphenyl)-2-methylfuran-3-yl]methanol

A solution of methyl 5-(4-methoxyphenyl)-2-methylfuran-3-carboxylate (2.3 g) obtained by the above-mentioned reaction in tetrahydrofuran (20 mL) was added dropwise to a suspension of lithium aluminum hydride (0.4 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (2.3 g, 100%) as a white solid.

$^1$H NMR (300 MHz, CHLOROFORM-d) δ ppm 1.36 (t, J=5.49 Hz, 1H) 2.35 (s, 3H) 3.83 (s, 3H) 4.50 (d, J=5.30 Hz, 2H) 6.50 (s, 1H) 6.90 (d, J=8.71 Hz, 8H) 7.55 (d, J=8.71 Hz, 8H)

(3) 5-(4-methoxyphenyl)-2-methylfuran-3-carbaldehyde

To a solution of [5-(4-methoxyphenyl)-2-methylfuran-3-yl]methanol (2.3 g) obtained by the above-mentioned reaction in methylene chloride (20 mL) was added a Dess-Martin reagent (5.3 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 30% ethyl acetate/hexane), and crystallized from ethyl acetate/hexane to give the title compound (1.5 g, 67%) as a white solid.

$^1$H NMR (300 MHz, CHLOROFORM-d) δ ppm 2.66 (s, 3H) 3.84 (s, 3H) 6.76 (s, 1H) 6.93 (d, J=8.71 Hz, 2H) 7.59 (d, J=8.71 Hz, 2H) 9.96 (s, 1H)

(4) 1-[5-(4-methoxyphenyl)-2-methylfuran-3-yl]-3-methylbutan-1-ol

To a solution of 5-(4-methoxyphenyl)-2-methylfuran-3-carbaldehyde (1.5 g) obtained by the above-mentioned reaction in tetrahydrofuran (20 mL) was added dropwise 1N isobutylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.5 g, 79%) as an oil.

$^1$H NMR (300 MHz, CHLOROFORM-d) δ ppm 0.94 (d, J=6.44 Hz, 6H) 1.48-1.81 (m, 3H) 2.35 (s, 3H) 3.83 (s, 3H) 4.70 (t, J=6.82 Hz, 1H) 6.48 (s, 1H) 6.90 (d, J=9.09 Hz, 2H) 7.55 (d, J=9.09 Hz, 2H)

(5) 3-(1-chloro-3-methylbutyl)-5-(4-methoxyphenyl)-2-methylfuran

To a solution of 1-[5-(4-methoxyphenyl)-2-methylfuran-3-yl]-3-methylbutan-1-ol (0.7 g) obtained by the above-mentioned reaction in toluene (20 mL) were added thionyl chloride (0.3 mL) and pyridine (0.3 mL) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure to give the title compound (0.7 g, 100%) as an amorphous compound.

$^1$H NMR (300 MHz, CHLOROFORM-d) δ ppm 0.93 (dd, J=6.63, 3.98 Hz, 6H) 1.69-1.91 (m, 2H) 1.99-2.08 (m, 1H) 2.36 (s, 3H) 3.83 (s, 3H) 6.50 (s, 1H) 6.90 (d, J=9.09 Hz, 2H) 7.55 (d, J=9.09 Hz, 2H)

(6) 3-({[4-({1-[5-(4-methoxyphenyl)-2-methylfuran-3-yl]-3-methylbutyl}amino)phenyl]carbonyl}amino)propanoic acid A mixture of 5-[4-(1-chloro-3-methylbutyl)-5-methylfuran-2-yl]-2-methoxypyridine (381 mg) obtained by the above-mentioned reaction, ethyl 3-{[(4-aminophenyl)carbonyl]amino}propanoate (378 mg), sodium carbonate (170 mg) and sodium iodide (240 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 65% ethyl acetate/hexane). To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (195 mg, 32%).

$^1$H NMR (300 MHz, DMSO-d$_6$) δ ppm 0.92 (dd, J=18.55, 6.06 Hz, 6H) 1.58 (qd, J=12.43, 6.63 Hz, 2H) 1.71 (dd, J=12.12, 6.82 Hz, 1H) 2.36 (s, 3H) 2.42 (t, J=7.19 Hz, 2H) 3.31-3.47 (m, 2H) 3.75 (s, 3H) 4.35 (q, J=7.19 Hz, 1H) 6.34 (d, J=7.57 Hz, 1H) 6.55 (d, J=8.71 Hz, 2H) 6.60 (s, 1H) 6.93 (d, J=8.71 Hz, 2H) 7.49 (d, J=8.71 Hz, 2H) 7.54 (d, J=8.71 Hz, 2H) 8.02 (t, J=5.30 Hz, 1H)

Example 151

3-[{[4-({1-[5-(4-methoxyphenyl)-2-methylfuran-3-yl]-3-methylbutyl}amino)phenyl]carbonyl}(methyl)amino]propanoic acid

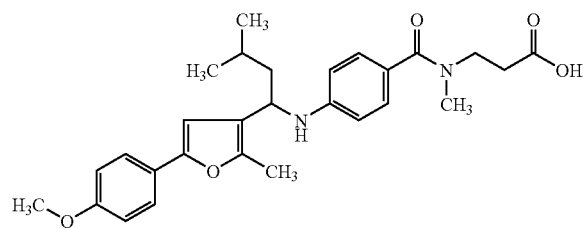

A mixture of 5-[4-(1-chloro-3-methylbutyl)-5-methylfuran-2-yl]-2-methoxypyridine (382 mg), ethyl 3-{[(4-aminophenyl)carbonyl](methyl)amino}propanoate (400 mg), sodium carbonate (170 mg) and sodium iodide (240 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 65% ethyl acetate/hexane) to give ethyl 3-[{[4-({1-[5-(4-methoxyphenyl)-2-methylfuran-3-yl]-3-methylbutyl}amino)phenyl]carbonyl}(methyl)amino]propanoate. Ethyl 3-[{[4-({1-[5-(4-methoxyphenyl)-2-methylfuran-3-yl]-3-methylbutyl}amino)phenyl]carbonyl}(methyl)amino]propanoate was dissolved in ethanol (2 mL) and tetrahydrofuran (2 mL) and 1N lithium hydroxide (1.0 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (210 mg, 34%).

$^1$H NMR (300 MHz, DMSO-d$_6$) δ ppm 0.92 (dd, J=17.98, 6.25 Hz, 6H) 1.56-1.82 (m, 3H) 2.36 (s, 3H) 2.46-2.51 (m, 2H) 2.90 (s, 3H) 3.52 (t, J=7.38 Hz, 2H) 3.76 (s, 3H) 4.31 (d, J=7.57 Hz, 1H) 6.24 (d, J=7.57 Hz, 1H) 6.54 (d, J=8.71 Hz, 2H) 6.62 (s, 1H) 6.93 (d, J=8.71 Hz, 2H) 7.12 (d, J=8.71 Hz, 2H) 7.50 (d, J=8.71 Hz, 2H) 12.31 (brs, 1H)

Example 152

3-({[4-({1-[2-(methoxymethyl)-5-phenylfuran-3-yl]-3-methylbutyl}amino)phenyl]carbonyl}amino)propanoic acid

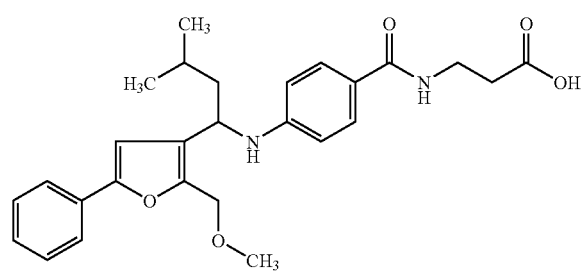

(1) methyl 2-(methoxymethyl)-5-phenylfuran-3-carboxylate

A mixture of methyl 5-bromo-2-(methoxymethyl)-3-furancarboxylate (3.7 g), phenylboronic acid (2.2 g), tetrakis(triphenylphosphine)palladium(0) (0.9 g), 2N aqueous sodium carbonate solution (18 mL) and 1,2-dimethoxyethane (30 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 15% ethyl acetate/hexane) to give the title compound (3.2 g, 87%) as an oil.

$^1$H NMR (300 MHz, CHLOROFORM-d) δ ppm 3.45 (s, 3H) 3.88 (s, 3H) 4.80 (s, 2H) 6.94 (s, 1H) 7.27-7.36 (m, 1H) 7.36-7.46 (m, 2H) 7.69 (d, J=7.19 Hz, 2H)

(2) [2-(methoxymethyl)-5-phenylfuran-3-yl]methanol

A solution of methyl 2-(methoxymethyl)-5-phenylfuran-3-carboxylate (3.2 g) obtained by the above-mentioned reaction in tetrahydrofuran (20 mL) was added dropwise to a suspension of lithium aluminum hydride (0.5 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure to give the title compound (2.8 g, 100%) as a white solid.

$^1$H NMR (300 MHz, CHLOROFORM-d) δ ppm 1.92 (t, J=5.87 Hz, 1H) 3.42 (s, 3H) 4.52 (s, 2H) 4.61 (d, J=5.68 Hz, 2H) 6.68 (s, 1H) 7.24-7.29 (m, 1H) 7.38 (t, J=7.38 Hz, 2H) 7.66 (d, J=7.19 Hz, 2H)

(3) 2-(methoxymethyl)-5-phenylfuran-3-carbaldehyde

To a solution of [2-(methoxymethyl)-5-phenylfuran-3-yl] methanol (2.8 g) obtained by the above-mentioned reaction in methylene chloride (30 mL) was added a Dess-Martin reagent (6.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 30% ethyl acetate/hexane) to give the title compound (2.4 g, 85%) as an oil.

$^1$H NMR (300 MHz, CHLOROFORM-d) δ ppm 3.48 (s, 3H) 4.77 (s, 2H) 6.98 (s, 1H) 7.31-7.36 (m, 1H) 7.42 (t, J=7.57 Hz, 2H) 7.70 (d, J=7.57 Hz, 2H) 10.11 (s, 1H)

(4) 1-[2-(methoxymethyl)-5-phenylfuran-3-yl]-3-methylbutan-1-ol

To a solution of 2-(methoxymethyl)-5-phenylfuran-3-carbaldehyde (2.4 g) obtained by the above-mentioned reaction in tetrahydrofuran (30 mL) was added dropwise 1N isobutylmagnesium bromide-tetrahydrofuran solution (15 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.8 g, 61%) as an oil.

$^1$H NMR (300 MHz, CHLOROFORM-d) δ ppm 0.89-1.02 (m, 6H) 1.47-1.64 (m, 1H) 1.65-1.87 (m, 2H) 2.07 (d, J=3.58 Hz, 1H) 3.42 (s, 3H) 4.52 (s, 2H) 4.72-4.89 (m, 1H) 6.65 (s, 1H) 7.23-7.29 (m, 1H) 7.31-7.43 (m, 2H) 7.61-7.71 (m, 2H)

(5) 3-(1-chloro-3-methylbutyl)-2-(methoxymethyl)-5-phenylfuran

To a solution of 1-[2-(methoxymethyl)-5-phenylfuran-3-yl]-3-methylbutan-1-ol (0.8 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure to give the title compound (0.9 g, 100%) as an oil.

$^1$H NMR (300 MHz, CHLOROFORM-d) δ ppm 0.95 (d, J=6.44 Hz, 6H) 1.74-1.96 (m, 2H) 1.98-2.15 (m, 1H) 3.40 (s, 3H) 4.42-4.59 (m, 2H) 5.06 (t, J=7.95 Hz, 1H) 6.72 (s, 1H) 7.21-7.31 (m, 1H) 7.38 (t, J=7.38 Hz, 2H) 7.67 (d, J=6.82 Hz, 2H)

(6) 3-({[4-({1-[2-(methoxymethyl)-5-phenylfuran-3-yl]-3-methylbutyl}amino)phenyl]carbonyl}amino) propanoic acid A mixture of 3-(1-chloro-3-methylbutyl)-2-(methoxymethyl)-5-phenylfuran (439 mg) obtained by the above-mentioned reaction, ethyl 3-{[(4-aminophenyl)carbonyl]amino}propanoate (425 mg), sodium carbonate (191 mg) and sodium iodide (270 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 40% ethyl acetate/hexane). To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (63 mg, 9%).

$^1$H NMR (300 MHz, DMSO-d$_6$) δ ppm 0.92 (dd, J=17.42, 6.44 Hz, 6H) 1.49-1.82 (m, 3H) 2.43 (t, J=7.19 Hz, 2H) 3.23-3.46 (m, 2H) 3.32 (s, 3H) 4.38-4.63 (m, 3H) 6.39 (d, J=7.9.5 Hz, 1H) 6.59 (d, J=8.71 Hz, 2H) 6.86 (s, 1H) 7.28 (d, J=7.57 Hz, 2H) 7.25-7.30 (m, 1H) 7.40 (t, J=7.57 Hz, 2H) 7.53 (d, J=8.71 Hz, 2H) 7.61 (d, J=7.57 Hz, 2H) 8.02 (t, J=5.49 Hz, 1H)

Example 153

3-[{[4-({1-[2-(methoxymethyl)-5-phenylfuran-3-yl]-3-methylbutyl}amino)phenyl]carbonyl}(methyl) amino]propanoic acid

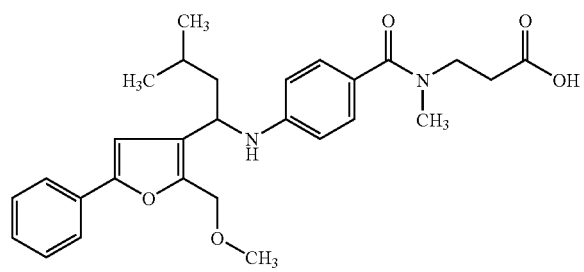

A mixture of 3-(1-chloro-3-methylbutyl)-2-(methoxymethyl)-5-phenylfuran (439 mg), ethyl 3-{[(4-aminophenyl)carbonyl](methyl)amino}propanoate (451 mg), sodium carbonate (191 mg) and sodium iodide (270 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 60% ethyl acetate/hexane). To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (63 mg, 9%).

$^1$H NMR (300 MHz, DMSO-$d_6$) δ ppm 0.92 (dd, J=16.85, 6.25 Hz, 6H) 1.50-1.81 (m, 3H) 2.44-2.51 (m, 2H) 2.90 (s, 3H) 3.20-3.41 (m, 2H) 3.51 (brs, 1H) 4.42-4.52 (m, 3H) 6.29 (d, J=7.19 Hz, 1H) 6.59 (d, J=7.95 Hz, 2H) 6.88 (s, 1H) 7.11 (d, J=7.95 Hz, 2H) 7.29-7.30 (m, 4H) 7.40 (t, J=7.57 Hz, 2H) 7.62 (d, J=7.19 Hz, 2H) 12.31 (brs, 1H)

Example 154

3-({[4-({1-[5-(4-fluoro-2-methylphenyl)-2-methylfuran-3-yl]-3-methylbutyl}amino)phenyl]carbonyl}amino)propanoic acid

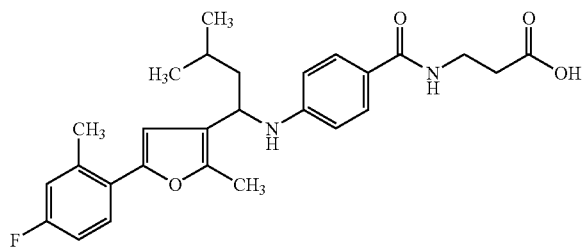

(1) methyl 5-(4-fluoro-2-methylphenyl)-2-methylfuran-3-carboxylate

A mixture of methyl 5-bromo-2-methyl-3-furancarboxylate (2.2 g), 4-fluoro-2-methylphenylboronic acid (1.9 g), tetrakis(triphenylphosphine)palladium(0) (0.6 g), 2N aqueous sodium carbonate solution (12 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (2.3 g, 91%) as a white solid.

$^1$H NMR (300 MHz, CHLOROFORM-d) δ ppm 2.47 (s, 3H) 2.64 (s, 3H) 3.86 (s, 3H) 6.70 (s, 1H) 6.88-7.01 (m, 2H) 7.62 (dd, J=9.47, 6.06 Hz, 1H)

(2) [5-(4-fluoro-2-methylphenyl)-2-methylfuran-3-yl]methanol

A solution of methyl 5-(4-fluoro-2-methylphenyl)-2-methylfuran-3-carboxylate (2.2 g) obtained by the above-mentioned reaction in tetrahydrofuran (20 mL) was added dropwise to a suspension of lithium aluminum hydride (0.3 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (2.0 g, 100%) as a white solid.

$^1$H NMR (300 MHz, CHLOROFORM-d) δ ppm 1.41 (t, J=5.43 Hz, 1H) 2.36 (s, 3H) 2.47 (s, 3H) 4.54 (d, J=5.68 Hz, 2H) 6.46 (s, 1H) 6.84-7.02 (m, 2H) 7.59-7.64 (m, 1H)

(3) 5-(4-fluoro-2-methylphenyl)-2-methylfuran-3-carbaldehyde

To a solution of [5-(4-fluoro-2-methylphenyl)-2-methylfuran-3-yl]methanol (2.0 g) obtained by the above-mentioned reaction in methylene chloride (20 mL) was added a Dess-Martin reagent (4.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 30% ethyl acetate/hexane), and crystallized from ethyl acetate/hexane to give the title compound (1.7 g, 88%) as a white solid.

$^1$H NMR (300 MHz, CHLOROFORM-d) δ ppm 2.47 (s, 3H) 2.67 (s, 3H) 6.74 (s, 1H) 6.88-7.04 (m, 2H) 7.57-7.71 (m, 1H) 9.98 (s, 1H)

(4) 1-[5-(4-fluoro-2-methylphenyl)-2-methylfuran-3-yl]-3-methylbutan-1-ol

To a solution of 5-(4-fluoro-2-methylphenyl)-2-methylfuran-3-carbaldehyde (1.7 g) obtained by the above-mentioned reaction in tetrahydrofuran (30 mL) was added dropwise 1N isobutylmagnesium bromide-tetrahydrofuran solution (9 mL) at 0° C. and, after the completion of the dropwise addition, the mixture was stirred at 0° C. for 1 hr. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 25% ethyl acetate/hexane) to give the title compound (1.9 g, 86%) as an oil.

$^1$H NMR (300 MHz, CHLOROFORM-d) δ ppm 0.95 (d, J=6.44 Hz, 6H) 1.45-1.86 (m, 3H) 2.36 (s, 3H) 2.47 (s, 3H) 4.73 (td, J=7.00, 3.41 Hz, 1H) 6.43 (s, 1H) 6.85-7.00 (m, 2H) 7.62 (dd, J=9.28, 5.87 Hz, 1H)

(5) 3-(1-chloro-3-methylbutyl)-5-(4-fluoro-2-methylphenyl)-2-methylfuran

To a solution of 1-[5-(4-fluoro-2-methylphenyl)-2-methylfuran-3-yl]-3-methylbutan-1-ol (0.8 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure to give the title compound (0.9 g, 100%) as an amorphous compound.

$^1$H NMR (300 MHz, CHLOROFORM-d) δ ppm 0.95 (dd, J=6.50, 2.35 Hz, 6H) 1.73-1.94 (m, 2H) 2.01-2.10 (m, 1H) 2.36 (s, 3H) 2.47 (s, 3H) 4.96 (t, J=8.10 Hz, 1H) 6.45 (s, 1H) 6.94 (d, J=8.67 Hz, 2H) 7.61 (dd, J=9.23, 5.84 Hz, 1H)

(6) 3-({[4-({1-[5-(4-fluoro-2-methylphenyl)-2-methylfuran-3-yl]-3-methylbutyl}amino)phenyl]carbonyl}amino)propanoic acid A mixture of 3-(1-chloro-3-methylbutyl)-5-(4-fluoro-2-methylphenyl)-2-methylfuran (442 mg) obtained by the above-mentioned reaction, ethyl 3-{[(4-aminophenyl)carbonyl]amino}propanoate (425 mg), sodium carbonate (191 mg) and sodium iodide (270 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 50% ethyl acetate/hexane). To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (181 mg, 26%).

$^1$H NMR (300 MHz, DMSO-d$_6$) δ ppm 0.92 (dd, J=18.17, 4.54 Hz, 6H) 1.48-1.82 (m, 3H) 2.38 (s, 3H) 2.39 (s, 3H) 2.44-2.51 (m, 2H) 3.35 (brs, 2H) 4.41 (brs, 1H) 6.36 (d, J=7.19 Hz, 1H) 6.57 (d, J=8.33 Hz, 3H) 6.91-7.26 (m, 2H) 7.49-7.68 (m, 3H) 8.04 (brs, 1H) 12.17 (s, 1H)

Example 155

3-[{[4-({1-[5-(4-fluoro-2-methylphenyl)-2-methylfuran-3-yl]-3-methylbutyl}amino)phenyl]carbonyl}(methyl)amino]propanoic acid

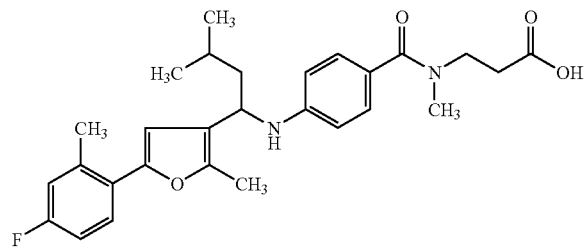

A mixture of 3-(1-chloro-3-methylbutyl)-5-(4-fluoro-2-methylphenyl)-2-methylfuran (442 mg), ethyl 3-{[(4-aminophenyl)carbonyl](methyl)amino}propanoate (451 mg), sodium carbonate (191 mg) and sodium iodide (270 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 50% ethyl acetate/hexane). To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (188 mg, 26%).

$^1$H NMR (300 MHz, DMSO-d$_6$) δ ppm 0.92 (dd, J=17.61, 6.25 Hz, 6H) 1.45-1.79 (m, 3H) 2.37 (s, 3H) 2.39 (s, 3H) 2.44-2.51 (m, 2H) 2.90 (s, 3H) 3.52 (t, J=7.38 Hz, 2H) 4.37 (d, J=7.57 Hz, 1H) 6.25 (d, J=8.33 Hz, 1H) 6.56 (d, J=8.33 Hz, 2H) 6.60 (s, 1H) 6.99-7.19 (m, 4H) 7.59 (dd, J=8.71, 6.06 Hz, 1H)

Example 156

3-({[4-({1-[5-(4-fluoro-2-methylphenyl)-2-(methoxymethyl)furan-3-yl]-3-methylbutyl}amino)phenyl]carbonyl}amino)propanoic acid

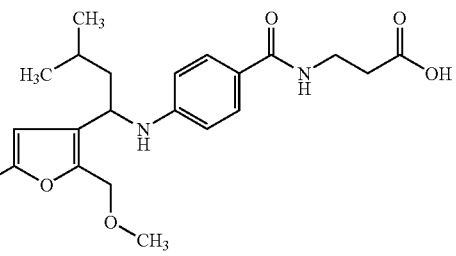

(1) methyl 5-(4-fluoro-2-methylphenyl)-2-(methoxymethyl)furan-3-carboxylate

A mixture of methyl 5-bromo-2-(methoxymethyl)-3-furancarboxylate (2.5 g), 4-fluoro-2-methylphenylboronic acid (1.9 g), tetrakis(triphenylphosphine)palladium(0) (0.6 g), 2N aqueous sodium carbonate solution (12 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane) to give the title compound (2.6 g, 92%) as an oil.

$^1$H NMR (300 MHz, CHLOROFORM-d) δ ppm 2.48 (s, 3H) 3.45 (s, 3H) 3.88 (s, 3H) 4.80 (s, 2H) 6.77 (s, 1H) 6.90-7.04 (m, 2H) 7.60-7.74 (m, 1H)

(2) [5-(4-fluoro-2-methylphenyl)-2-(methoxymethyl)furan-3-yl]methanol

A solution of methyl 5-(4-fluoro-2-methylphenyl)-2-(methoxymethyl)furan-3-carboxylate (2.5 g) obtained by the above-mentioned reaction in tetrahydrofuran (20 mL) was added dropwise to a suspension of lithium aluminum hydride (0.3 g) in tetrahydrofuran (20 mL) at 0° C. and, after the completion of the dropwise addition, the mixture was stirred for 30 min at 0° C. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (2.3 g, 100%) as an oil.

¹H NMR (300 MHz, CHLOROFORM-d) δ ppm 1.95 (t, J=5.87 Hz, 1H) 2.47 (s, 3H) 3.42 (s, 3H) 4.52 (s, 2H) 4.62 (d, J=6.06 Hz, 2H) 6.50 (s, 1H) 6.91-6.97 (m, 2H) 7.61-7.65 (m, 1H)

(3) 5-(4-fluoro-2-methylphenyl)-2-(methoxymethyl)furan-3-carbaldehyde

To a solution of [5-(4-fluoro-2-methylphenyl)-2-(methoxymethyl)furan-3-yl]methanol (2.3 g) obtained by the above-mentioned reaction in methylene chloride (20 mL) was added Dess-Martin reagent (4.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 30% ethyl acetate/hexane) to give the title compound (1.8 g, 80%) as an oil.
¹H NMR (300 MHz, CHLOROFORM-d) δ ppm 2.48 (s, 3H) 3.48 (s, 3H) 4.76 (s, 2H) 6.82 (s, 1H) 6.87-7.16 (m, 2H) 7.54-7.79 (m, 1H) 10.12 (s, 1H)

(4) 1-[5-(4-fluoro-2-methylphenyl)-2-(methoxymethyl)furan-3-yl]-3-methylbutan-1-ol To a solution of 5-(4-fluoro-2-methylphenyl)-2-(methoxymethyl)furan-3-carbaldehyde (1.7 g) obtained by the above-mentioned reaction in tetrahydrofuran (30 mL) was added dropwise 1N isobutylmagnesium bromide-tetrahydrofuran solution (8.4 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 25% ethyl acetate/hexane) to give the title compound (1.6 g, 74%) as an oil.
¹H NMR (300 MHz, CHLOROFORM-d) δ ppm 0.97 (d, J=6.44 Hz, 6H) 1.53-1.59 (m, 1H) 1.69-1.92 (m, 8H) 2.07 (d, J=3.79 Hz, 1H) 2.47 (s, 3H) 3.41 (s, 3H) 4.51 (s, 2H) 4.80-4.85 (m, 1H) 6.47 (s, 1H) 6.80-7.00 (m, 2H) 7.63 (dd, J=9.09, 6.06 Hz, 1H)

(5) 3-(1-chloro-3-methylbutyl)-5-(4-fluoro-2-methylphenyl)-2-(methoxymethyl)furan To a solution of 1-[5-(4-fluoro-2-methylphenyl)-2-(methoxymethyl)furan-3-yl]-3-methylbutan-1-ol (0.9 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure to give the title compound (1.0 g, 100%) as an oil.
¹H NMR (300 MHz, CHLOROFORM-d) δ ppm 0.95 (d, J=6.59 Hz, 6H) 1.67-1.94 (m, 2H) 2.02-2.09 (m, 1H) 2.48 (s, 13H) 3.40 (s, 3H) 4.40-4.60 (m, 2H) 5.08 (dd, J=8.38, 6.69 Hz, 1H) 6.53 (s, 1H) 6.86-7.02 (m, 2H) 7.56-7.69 (m, 1H)

(6) 3-({[4-({1-[5-(4-fluoro-2-methylphenyl)-2-(methoxymethyl)furan-3-yl]-3-methylbutyl}amino)phenyl]carbonyl}amino)propanoic acid A mixture of 3-(1-chloro-3-methylbutyl)-5-(4-fluoro-2-methylphenyl)-2-(methoxymethyl)furan (487 mg) obtained by the above-mentioned reaction, ethyl 3-{[(4-aminophenyl)carbonyl]amino}propanoate (425 mg), sodium carbonate (191 mg) and sodium iodide (270 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 50% ethyl acetate/hexane). To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (30 mg, 4%).
¹H NMR (300 MHz, DMSO-d₆) δ ppm 0.92 (dd, J=17.42, 6.44 Hz, 6H) 1.49-1.81 (m, 3H) 2.41 (s, 3H) 2.45 (t, J=7.95 Hz, 2H) 3.30-3.40 (m, 5H) 4.46-4.57 (m, 3H) 6.39 (d, J=8.33 Hz, 1H) 6.60 (d, J=8.71 Hz, 2H) 6.69 (s, 1H) 7.13 (ddd, J=13.44, 10.79, 2.65 Hz, 2H) 7.54 (d, J=8.71 Hz, 2H) 7.60 (dd, J=8.71, 6.06 Hz, 1H) 8.02 (brs, 1H) 12.16 (brs, 1H)

Example 157

3-[{[4-({1-[5-(4-fluoro-2-methylphenyl)-2-(methoxymethyl)furan-3-yl]-3-methylbutyl}amino)phenyl]carbonyl}(methyl)amino]propanoic acid

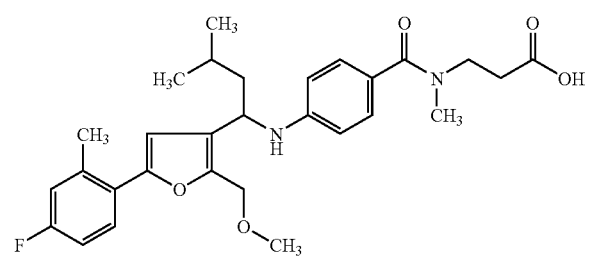

A mixture of 3-(1-chloro-3-methylbutyl)-5-(4-fluoro-2-methylphenyl)-2-(methoxymethyl)furan (487 mg), ethyl 3-{[(4-aminophenyl)carbonyl](methyl)amino}propanoate (451 mg), sodium carbonate (191 mg) and sodium iodide (270 mg) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 60% ethyl acetate/hexane). To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (45 mg, 6%).

$^1$H NMR (300 MHz, DMSO-$d_6$) δ ppm 0.92 (dd, J=16.28, 6.44 Hz, 6H) 1.46-1.80 (m, 1H) 2.41 (s, 3H) 2.45-2.51 (m, 2H) 2.90 (s, 3H) 3.29 (s, 2H) 3.52 (t, J=7.38 Hz, 2H) 4.45-4.52 (m, 3H) 6.28 (d, J=8.33 Hz, 1H) 6.60 (d, J=8.71 Hz, 2H) 6.70 (s, 1H) 7.01-7.21 (m, 4H) 7.61 (dd, J=8.71, 6.06 Hz, 1H) 12.25 (s, 1H)

Example 158

3-{[(4-{[1-(2-ethyl-5-phenylfuran-3-yl)-3-methylbutyl]amino}phenyl)carbonyl]amino}propanoic acid

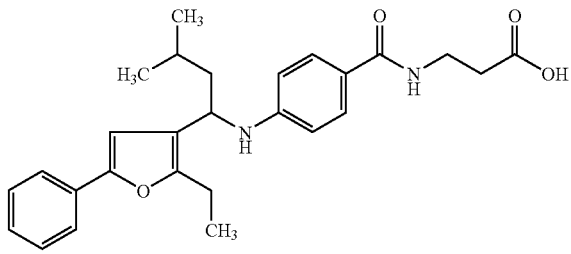

(1) methyl 2-ethyl-5-phenylfuran-3-carboxylate

To a solution of phenacyl bromide (10 g) and methyl 3-oxopentanoate (6.5 g) in toluene (100 mL) was added dropwise 1,8-azabicyclo[5.4.0]-7-undecene (7.5 mL) over 30 min or more under ice-cooling. After the completion of the dropwise addition, the mixture was stirred for 30 min under ice-cooling and then at room temperature for 2 hr. The resulting precipitate was filtered, and washed with toluene. The obtained toluene solution was passed through silica gel, and the silica gel was washed with ethyl acetate-hexane (1:1). The collected solutions were concentrated under reduced pressure to remove ethyl acetate-hexane to give a toluene solution. To this toluene solution was added 4-toluenesulfonic acid monohydrate (1.9 g), and the mixture was stirred at 100° C. for 2 hr. The reaction mixture was washed with aqueous sodium hydrogen carbonate solution, and the aqueous layer was extracted with ethyl acetate. The organic layers were collected, and dried over magnesium sulfate. The solvent was evaporated under reduced pressure. The residue was purified by silica gel chromatography (0% ethyl acetate/hexane to 5% ethyl acetate/hexane) to give the title compound (6.7 g, 58%) as an oil.

$^1$H NMR (300 MHz, CHLOROFORM-d) δ ppm 1.32 (t, J=7.54 Hz, 3H) 3.08 (q, J=7.66 Hz, 2H) 3.85 (s, 3H) 6.88 (s, 1H) 7.20-7.30 (m, 1H) 7.34-7.45 (m, 2H) 7.59-7.69 (m, 2H)

(2) (2-ethyl-5-phenylfuran-3-yl)methanol

A solution of methyl 2-ethyl-5-phenylfuran-3-carboxylate (6.7 g) obtained by the above-mentioned reaction in tetrahydrofuran (30 mL) was added dropwise to a suspension of lithium aluminum hydride (1.1 g) in tetrahydrofuran (30 mL) at 0° C. and, after the completion of the dropwise addition, the mixture was stirred for 30 min at 0° C. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (5.9 g, 100%) as an oil.

$^1$H NMR (300 MHz, CHLOROFORM-d) δ ppm 1.29 (t, J=7.54 Hz, 3H) 1.37 (t, J=5.56 Hz, 1H) 2.73 (q, J=7.54 Hz, 2H) 4.52 (d, J=5.46 Hz, 2H) 6.64 (s, 1H) 7.15-7.25 (m, 1H) 7.30-7.43 (m, 2H) 7.55-7.68 (m, 2H)

(3) 2-ethyl-5-phenylfuran-3-carbaldehyde

To a solution of (2-ethyl-5-phenylfuran-3-yl)methanol (5.9 g) obtained by the above-mentioned reaction in methylene chloride (30 mL) was added Dess-Martin reagent (14.8 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 25% ethyl acetate/hexane) to give the title compound (4.8 g, 83%) as an oil.

$^1$H NMR (300 MHz, CHLOROFORM-d) δ ppm 1.41 (t, J=7.57 Hz, 3H) 3.05 (q, J=7.57 Hz, 2H) 6.91 (s, 1H) 7.27-7.35 (m, 1H) 7.41 (t, J=7.38 Hz, 2H) 7.67 (d, J=6.82 Hz, 2H) 9.99 (s, 8H)

(4) 1-(2-ethyl-5-phenylfuran-3-yl)-3-methylbutan-1-ol

To a solution of 2-ethyl-5-phenylfuran-3-carbaldehyde (1.4 g) obtained by the above-mentioned reaction in tetrahydrofuran (20 mL) was added dropwise 1N isobutylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (1.5 g, 80%) as an oil.

$^1$H NMR (300 MHz, CHLOROFORM-d) δ ppm 0.94 (d, J=6.44 Hz, 6H) 1.29 (t, J=7.38 Hz, 3H) 1.49-1.82 (m, 3H) 2.68-2.76 (m, 2H) 4.73 (td, J=7.00, 3.03 Hz, 1H) 6.62 (s, 1H) 7.22 (t, J=7.38 Hz, 1H) 7.36 (t, J=7.57 Hz, 2H) 7.63 (d, J=7.19 Hz, 2H)

(5) 3-(1-chloro-3-methylbutyl)-2-ethyl-5-phenylfuran

To a solution of 1-(2-ethyl-5-phenylfuran-3-yl)-3-methylbutan-1-ol (1.4 g) obtained by the above-mentioned reaction in toluene (20 mL) were added thionyl chloride (0.5 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.5 g, 100%) as an oil.

$^1$H NMR (300 MHz, CHLOROFORM-d) δ ppm 0.94 (dd, J=6.63, 3.22 Hz, 6H) 1.30 (t, J=7.57 Hz, 3H) 1.69-1.92 (m, 2H) 1.96-2.12 (m, 1H) 2.63-2.83 (m, 2H) 4.98 (t, J=7.76 Hz, 1H) 6.64 (s, 1H) 7.19 (t, J=6.82 Hz, 1H) 7.36 (t, J=7.57 Hz, 2H) 7.63 (d, J=7.19 Hz, 2H)

(6) 4-{[1-(2-ethyl-5-phenylfuran-3-yl)-3-methylbutyl]amino}benzoic acid

A mixture of 3-(1-chloro-3-methylbutyl)-2-ethyl-5-phenylfuran (1.5 g) obtained by the above-mentioned reaction, methyl 4-aminobenzoate (1.7 g), sodium carbonate (1.2 g) and sodium iodide (3.3 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (10 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 40% ethyl acetate/hexane) to give the title compound (1.3 g, 63%) as an amorphous compound.

$^1$H NMR (300 MHz, CHLOROFORM-d) δ ppm 0.96 (dd, J=17.98, 6.25 Hz, 6H) 1.30 (t, J=7.57 Hz, 3H) 1.53-1.86 (m, 3H) 2.75 (qd, J=7.57, 2.65 Hz, 2H) 4.42 (t, J=7.00 Hz, 1H) 6.50 (s, 1H) 6.54 (d, J=8.71 Hz, 2H) 7.18-7.23 (m, 1H) 7.34 (t, J=7.57 Hz, 2H) 7.59 (d, J=7.19 Hz, 2H) 7.87 (d, J=8.71 Hz, 2H).

(7) 3-{[(4-{[1-(2-ethyl-5-phenylfuran-3-yl)-3-methylbutyl]amino}phenyl)carbonyl]amino}propanoic acid A solution of 4-{[1-(2-ethyl-5-phenylfuran-3-yl)-3-methylbutyl]amino}benzoic acid (189 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (185 mg, 83%).

$^1$H NMR (300 MHz, DMSO-d$_6$) δ ppm 0.92 (dd, J=17.80, 6.06 Hz, 6H) 1.21 (t, J=7.38 Hz, 3H) 1.46-1.80 (m, 3H) 2.42 (t, J=7.00 Hz, 2H) 2.66-2.89 (m, 2H) 3.22-3.50 (m, 2H) 4.38 (q, J=7.19 Hz, 1H) 6.36 (d, J=7.95 Hz, 1H) 6.56 (d, J=8.71 Hz, 2H) 6.77 (s, 1H) 7.14-7.28 (m, 1H) 7.37 (t, J=7.76 Hz, 2H) 7.52-7.58 (m, 4H) 8.03 (t, J=5.30 Hz, 1H)

Example 159

3-{[(4-{[1-(2-ethyl-5-phenylfuran-3-yl)-3-methylbutyl]amino}phenyl)carbonyl](methyl)amino}propanoic acid

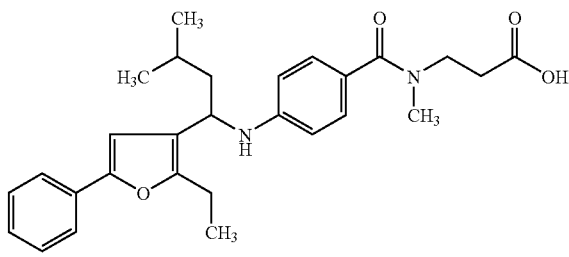

A solution of 4-{[1-(2-ethyl-5-phenylfuran-3-yl)-3-methylbutyl]amino}benzoic acid (189 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide 110 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (163 mg, 84%).

$^1$H NMR (300 MHz, DMSO-d$_6$) δ ppm 0.92 (dd, J=17.23, 6.25 Hz, 6H) 1.20 (t, J=7.57 Hz, 3H) 1.50-1.76 (m, 3H) 2.45-2.53 (m, 2H) 2.66-2.84 (m, 2H) 2.89 (s, 3H) 3.51 (t, J=7.38 Hz, 2H) 4.35 (d, J=7.57 Hz, 1H) 6.25 (d, J=7.57 Hz, 1H) 6.56 (d, J=8.71 Hz, 2H) 6.79 (s, 1H) 7.11 (d, J=8.71 Hz, 2H) 7.20-7.25 (m, 1H) 7.37 (t, J=7.76 Hz, 2H) 7.58 (d, J=7.19 Hz, 2H)

Example 160

3-{[(4-{[cyclopentyl(2-ethyl-5-phenylfuran-3-yl)methyl]amino}phenyl)carbonyl]amino}propanoic acid

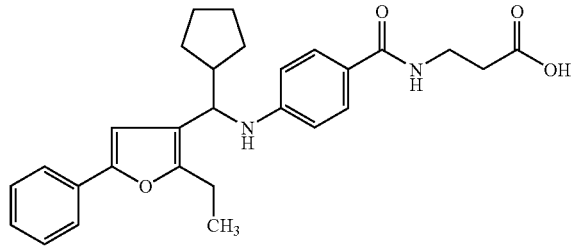

(1) cyclopentyl(2-ethyl-5-phenylfuran-3-yl)methanol

To a solution of 2-ethyl-5-phenylfuran-3-carbaldehyde (1.4 g) obtained by the above-mentioned reaction in tetrahydrofuran (20 mL) was added dropwise 1N cyclopentylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (1.0 g, 51%) as a yellow crystal.

$^1$H NMR (300 MHz, CHLOROFORM-d) δ ppm 1.03-1.16 (m, 1H) 1.27 (t, J=7.07 Hz, 3H) 1.45-1.78 (m, 6H) 1.93-1.97 (m, 1H) 2.19-2.32 (m, 1H) 2.72 (qd, J=7.51, 2.46 Hz, 2H) 4.35 (dd, J=9.09, 3.03 Hz, 1H) 6.63 (s, 1H) 7.22 (t, J=7.38 Hz, 1H) 7.36 (t, J=7.57 Hz, 2H) 7.63 (d, J=7.19 Hz, 2H)

(2) 3-[chloro(cyclopentyl)methyl]-2-ethyl-5-phenylfuran

To a solution of cyclopentyl(2-ethyl-5-phenylfuran-3-yl)methanol (1.0 g) obtained by the above-mentioned reaction in toluene (20 mL) were added thionyl chloride (0.3 mL) and pyridine (0.3 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.0 g, 100%) as an oil.

¹H NMR (300 MHz, CHLOROFORM-d) δ ppm 1.06-1.19 (m, 1H) 1.29 (t, J=7.57 Hz, 3H) 1.45-1.76 (m, 6H) 2.02-2.10 (m, 1H) 2.42-2.62 (m, 1H) 2.71 (qd, J=7.57, 2.27 Hz, 2H) 4.68 (d, J=9.47 Hz, 1H) 6.65 (s, 1H) 7.09-7.25 (m, 1H) 7.36 (t, J=7.76 Hz, 2H) 7.63 (d, J=7.19 Hz, 2H)

(3) 4-{[2-cyclopentyl-1-(2-ethyl-5-phenylfuran-3-yl)ethyl]amino}benzoic acid

A mixture of 3-[chloro(cyclopentyl)methyl]-2-ethyl-5-phenylfuran (1.0 g) obtained by the above-mentioned reaction, methyl 4-aminobenzoate (1.1 g), sodium carbonate (0.7 g) and sodium iodide (2.1 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (6 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 40% ethyl acetate/hexane) to give the title compound (0.8 g, 67%) as an amorphous compound.

¹H NMR (300 MHz, CHLOROFORM-d) δ ppm 1.24-1.34 (m, 4H) 1.51-1.71 (m, 6H) 1.81-1.97 (m, 1H) 2.19-2.28 (m, 1H) 2.64-2.91 (m, 2H) 4.12 (d, J=7.19 Hz, 1H) 6.48 (s, 1H) 6.52 (d, J=8.71 Hz, 2H) 7.16-7.21 (m, 1H) 7.32 (t, J=7.57 Hz, 2H) 7.58 (d, J=7.19 Hz, 2H) 7.83 (d, J=8.71 Hz, 2H)

(4) 3-{[(4-{[cyclopentyl(2-ethyl-5-phenylfuran-3-yl)methyl]amino}phenyl)carbonyl]amino}propanoic acid A solution of 4-{[2-cyclopentyl-1-(2-ethyl-5-phenylfuran-3-yl)ethyl]amino}benzoic acid (195 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (203 mg, 90%).

¹H NMR (300 MHz, DMSO-d₆) δ ppm 1.16-1.25 (m, 4H) 1.32-1.66 (m, 6H) 1.87-1.95 (m, 1H) 2.20-2.27 (m, 1H) 2.40 (t, J=7.19 Hz, 2H) 2.68-2.88 (m, 2H) 3.22-3.47 (m, 2H) 4.11 (t, J=8.52 Hz, 1H) 6.38 (d, J=7.95 Hz, 1H) 6.54 (d, J=9.09 Hz, 2H) 6.75 (s, 1H) 7.19-7.24 (m, 1H) 7.36 (t, J=7.57 Hz, 2H) 7.50-7.55 (m, 4H) 8.03 (t, J=5.30 Hz, 1H)

Example 161

3-{[(4-{[cyclopentyl(2-ethyl-5-phenylfuran-3-yl)methyl]amino}phenyl)carbonyl](methyl)amino}propanoic acid

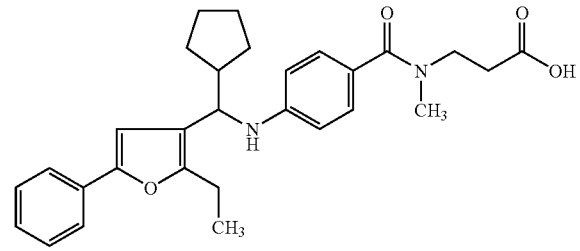

A solution of 4-{[2-cyclopentyl-1-(2-ethyl-5-phenylfuran-3-yl)ethyl]amino}benzoic acid (195 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (199 mg, 86%).

¹H NMR (300 MHz, DMSO-d₆) δ ppm 1.18-1.23 (m, 4H) 1.36-1.74 (m, 6H) 1.87-2.01 (m, 1H) 2.15-2.33 (m, 1H) 2.45-2.54 (m, 2H) 2.70-2.84 (m, 2H) 2.89 (s, 3H) 3.50 (t, J=7.00 Hz, 2H) 4.08 (t, J=8.71 Hz, 1H) 6.28 (d, J=8.33 Hz, 1H) 6.54 (d, J=8.71 Hz, 2H) 6.77 (s, 1H) 7.10 (d, J=8.71 Hz, 2H) 7.15-7.28 (m, 1H) 7.37 (t, J=7.57 Hz, 2H) 7.56 (d, J=7.95 Hz, 2H)

Example 162

3-{[(3-methoxy-4-{[3-methyl-1-(2-methyl-5-phenylfuran-3-yl)butyl]amino}phenyl)carbonyl]amino}propanoic acid

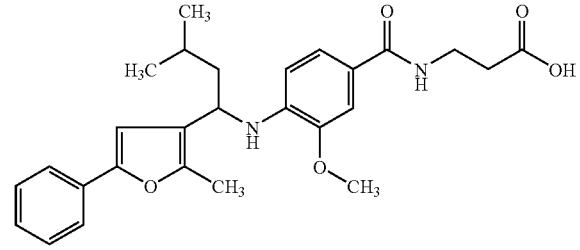

(1) 3-methoxy-4-{[3-methyl-1-(2-methyl-5-phenylfuran-3-yl)butyl]amino}benzoic acid A mixture of 3-(1-chloro-3-methylbutyl)-2-methyl-5-phenylfuran (1.3 g), methyl 4-amino-3-methoxybenzoate (1.1 g), sodium carbonate (1.1 g) and sodium iodide (3.0 g) in N,N- dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (6 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.0 g, 50%) as an amorphous compound.

$^1$H NMR (300 MHz, CHLOROFORM-d) δ ppm 0.85-1.07 (m, 6H) 1.57-1.90 (m, 3H) 2.40 (s, 3H) 3.91 (s, 3H) 4.39 (t, J=7.00 Hz, 1H) 6.48 (d, J=8.71 Hz, 1H) 6.51 (s, 1H) 7.17-7.22 (m, 1H) 7.33 (t, J=7.57 Hz, 2H) 7.41 (d, J=1.89 Hz, 1H) 7.59 (d, J=7.19 Hz, 2H) 7.63 (dd, J=8.33, 1.89 Hz, 1H)

(2) 3-{[(3-methoxy-4-{[3-methyl-1-(2-methyl-5-phenylfuran-3-yl)butyl]amino}phenyl)carbonyl]amino}propanoic acid A solution of 3-methoxy-4-{[3-methyl-1-(2-methyl-5-phenylfuran-3-yl)butyl]amino}benzoic acid (197 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (205 mg, 88%).

$^1$H NMR (300 MHz, DMSO-d$_6$) δ ppm 0.92 (dd, J=19.50, 6.25 Hz, 6H) 1.53-1.67 (m, 2H) 1.77-1.88 (m, 1H) 2.32-2.47 (m, 5H) 3.37-3.41 (m, 2H) 3.84 (s, 3H) 4.43 (q, J=7.57 Hz, 1H) 5.22 (d, J=7.95 Hz, 1H) 6.51 (d, J=8.33 Hz, 1H) 6.87 (s, 1H) 7.16-7.43 (m, 5H) 7.56 (d, J=7.19 Hz, 2H) 8.15 (s, 1H)

Example 163

3-{[(3-methoxy-4-{[3-methyl-1-(2-methyl-5-phenylfuran-3-yl)butyl]amino}phenyl)carbonyl](methyl)amino}propanoic acid

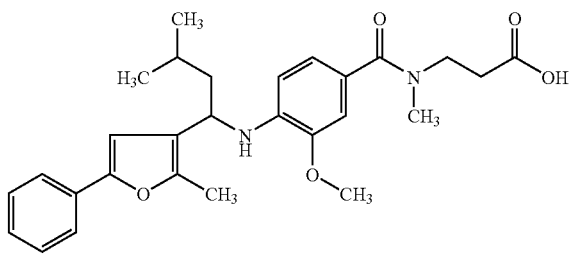

A solution of 3-methoxy-4-{[3-methyl-1-(2-methyl-5-phenylfuran-3-yl)butyl]amino}benzoic acid (197 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (168 mg, 95%).

$^1$H NMR (300 MHz, DMSO-d$_6$) δ ppm 0.92 (dd, J=19.12, 6.25 Hz, 6H) 1.43-1.68 (m, 2H) 1.76-1.84 (m, 1H) 2.39 (s, 3H) 2.50-2.55 (m, 2H) 2.92 (s, 3H) 3.53 (t, J=7.19 Hz, 2H) 3.81 (s, 3H) 4.39 (d, J=7.57 Hz, 1H) 5.11 (d, J=7.95 Hz, 1H) 6.49 (d, J=8.71 Hz, 1H) 6.77-6.87 (m, 2H) 6.89 (s, 1H) 7.23 (d, J=7.19 Hz, 1H) 7.36 (t, J=7.76 Hz, 2H) 7.57 (d, J=7.19 Hz, 2H)

Example 164

3-{[(3-fluoro-4-{[3-methyl-1-(2-methyl-5-phenylfuran-3-yl)butyl]amino}phenyl)carbonyl]amino}propanoic acid

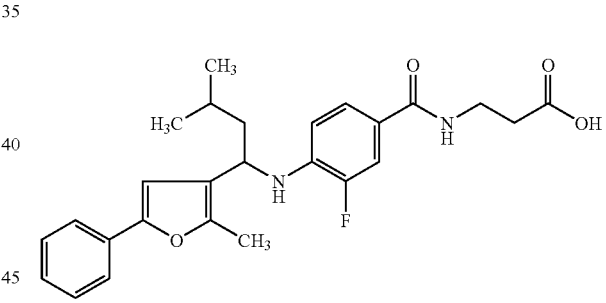

(1) 3-fluoro-4-{[3-methyl-1-(2-methyl-5-phenylfuran-3-yl)butyl]amino}benzoic acid A mixture of 3-(1-chloro-3-methylbutyl)-2-methyl-5-phenylfuran (1.3 g), methyl 4-amino-3-fluorobenzoate (1.7 g), sodium carbonate (1.1 g) and sodium iodide (3.0 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (6 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.7 g, 40%) as an amorphous compound.

¹H NMR (300 MHz, CHLOROFORM-d) δ ppm 0.97 (dd, J=17.80, 6.44 Hz, 6H) 1.55-1.88 (m, 3H) 2.41 (s, 3H) 4.41 (t, J=6.82 Hz, 1H) 4.58 (brs, 1H) 6.50 (s, 1H) 6.57 (t, J=8.33 Hz, 1H) 7.12-7.24 (m, 1H) 7.33 (t, J=7.76 Hz, 2H) 7.52-7.77 (m, 3H)

(2) 3-{[(3-fluoro-4-{[3-methyl-1-(2-methyl-5-phenylfuran-3-yl)butyl]amino}phenyl)carbonyl]amino}propanoic acid A solution of 3-fluoro-4-{[3-methyl-1-(2-methyl-5-phenylfuran-3-yl)butyl]amino}benzoic acid (191 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (225 mg, 99%).

¹H NMR (300 MHz, DMSO-d₆) δ ppm 0.92 (dd, J=16.66, 6.06 Hz, 6H) 1.50-1.70 (m, 2H) 1.70-1.98 (m, 1H) 2.32-2.47 (m, 5H) 3.34-3.40 (m, 2H) 4.47 (t, J=7.57 Hz, 1H) 6.02 (dd, J=8.14, 2.08 Hz, 1H) 6.69 (t, J=8.90 Hz, 1H) 6.86 (s, 1H) 7.15-7.28 (m, 1H) 7.36 (t, J=7.76 Hz, 2H) 7.42-7.51 (m, 2H) 7.54 (d, J=7.19 Hz, 2H) 8.19 (t, J=5.30 Hz, 1H)

Example 165

3-{[(3-fluoro-4-{[3-methyl-1-(2-methyl-5-phenylfuran-3-yl)butyl]amino}phenyl)carbonyl](methyl)amino}propanoic acid

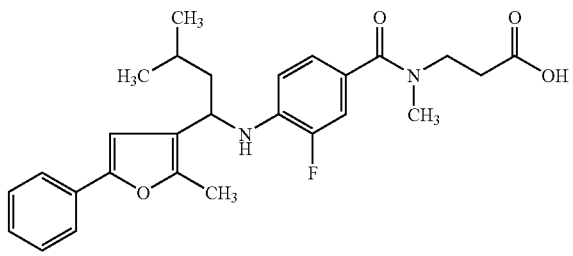

A solution of 3-fluoro-4-{[3-methyl-1-(2-methyl-5-phenylfuran-3-yl)butyl]amino}benzoic acid (191 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (173 mg, 82%).

¹H NMR (300 MHz, DMSO-d₆) δ ppm 0.92 (dd, J=15.90, 6.06 Hz, 6H) 1.45-1.72 (m, 2H) 1.84-1.88 (m, 1H) 2.31-2.40 (m, 4H) 2.90 (s, 3H) 3.52 (t, J=7.00 Hz, 2H) 4.44 (t, J=7.57 Hz, 1H) 5.89 (d, J=6.44 Hz, 1H) 6.67 (t, J=8.52 Hz, 1H) 6.87 (s, 1H) 6.94-7.13 (m, 2H) 7.23 (d, J=7.57 Hz, 1H) 7.19 (s, 1H) 7.37 (t, J=7.76 Hz, 2H) 7.55 (d, J=7.57 Hz, 2H)

Example 166

3-[{[4-({cyclohexyl[5-(6-methoxypyridin-3-yl)-2-methylfuran-3-yl]methyl}amino)phenyl]carbonyl}(methyl)amino]propanoic acid

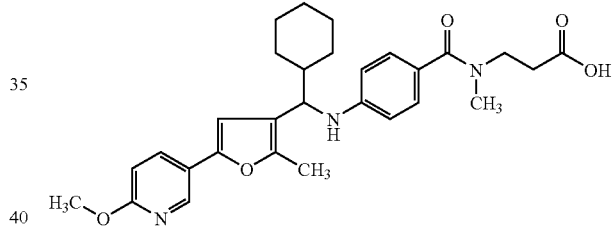

Ethyl 3-[{[4-({cyclohexyl[5-(6-methoxypyridin-3-yl)-2-methylfuran-3-yl]methyl}amino)phenyl]carbonyl}(methyl)amino]propanoate (1388 mg) which is a synthetic intermediate in Example 13.3 was dissolved in ethanol-hexane (6:4, volume ratio), and the solution was subjected to HPLC using CHIRALPAK AD (50 mmID×500 mL, manufactured by DAICEL CHEMICAL INDUSTRIES, LTD.) and eluted with ethanol-hexane (6:4, volume ratio) as mobile phase at 30° C., a flow rate 60 mL/min. The fractions showing a peak with retention time 20 min were collected, and concentrated. The obtained amorphous compound (682 mg) was dissolved in ethanol (3 mL) and tetrahydrofuran (3 mL), 1N lithium hydroxide (2.5 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (614 mg, 96%).

¹H NMR (300 MHz, DMSO-d₆) δ ppm 0.89-1.28 (m, 5H) 1.47-1.85 (m, 5H) 2.02-2.08 (m, 1H) 2.36 (s, 3H) 2.42-2.49 (m, 3H) 2.90 (s, 3H) 3.51 (t, J=7.19 Hz, 2H) 3.85 (s, 3H) 4.05 (t, J=7.76 Hz, 1H) 6.25 (d, J=7.95 Hz, 1H) 6.54 (m, J=8.71 Hz, 2H) 6.69 (s, 1H) 6.83 (d, J=8.71 Hz, 1H) 7.10 (m, J=8.33 Hz, 2H) 7.87 (dd, J=8.71, 2.65 Hz, 1H) 8.38 (d, J=2.27 Hz, 1H)

Example 167

3-[{[4-({cyclohexyl[5-(6-methoxypyridin-3-yl)-2-methylfuran-3-yl]methyl}amino)phenyl]carbonyl}(methyl)amino]propanoic acid

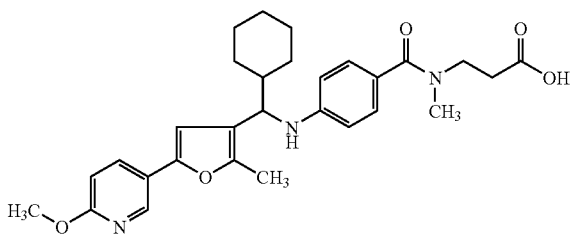

Ethyl 3-[{[4-({cyclohexyl[5-(6-methoxypyridin-3-yl)-2-methylfuran-3-yl]methyl}amino)phenyl]carbonyl}(methyl)amino]propanoate (1388 mg) which is a synthetic intermediate in Example 133 was dissolved in ethanol-hexane (6:4, volume ratio), and the solution was subjected to HPLC using CHIRALPAK AD (50 mmID×500 mL, manufactured by DAICEL CHEMICAL INDUSTRIES, LTD.) and eluted with ethanol-hexane (6:4, volume ratio) as mobile phase at 30° C., a flow rate 60 mL/min. The fractions showing a peak with retention time 29 min were collected, and concentrated. The obtained amorphous compound (681 mg) was dissolved in ethanol (3 mL) and tetrahydrofuran (3 mL), 1N lithium hydroxide (2.5 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (601 mg, 94%).

$^1$H NMR (300 MHz, DMSO-$d_6$) δ ppm 0.89-1.28 (m, 5H) 1.47-1.85 (m, 5H) 2.02-2.08 (m, 1H) 2.36 (s, 3H) 2.42-2.49 (m, 3H) 2.90 (s, 3H) 3.51 (t, J=7.19 Hz, 2H) 3.85 (s, 3H) 4.05 (t, J=7.76 Hz, 1H) 6.25 (d, J=7.95 Hz, 1H) 6.54 (m, J=8.71 Hz, 2H) 6.69 (s, 1H) 6.83 (d, J=8.71 Hz, 1H) 7.10 (m, J=8.33 Hz, 2H) 7.87 (dd, J=8.71, 2.65 Hz, 1H) 8.38 (d, J=2.27 Hz, 1H)

Example 168

3-{methyl[(4-{[3-methyl-1-(2-methyl-5-phenylfuran-3-yl)butyl]amino}phenyl)carbonyl]amino}propanoic acid

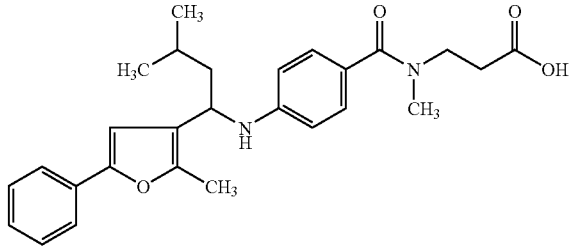

Ethyl 3-{methyl[(4-{[3-methyl-1-(2-methyl-5-phenylfuran-3-yl)butyl]amino}phenyl)carbonyl]amino}propanoate (2.54 g) which is a synthetic intermediate in Example 125 was dissolved in ethanol-hexane (1:1, volume ratio), and the solution was subjected to HPLC using CHIRALPAK AD (50 mmID×500 mL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 12 min was collected, and concentrated. The obtained amorphous compound (1.24 g) was dissolved in ethanol (5 mL) and tetrahydrofuran (5 mL), 1N lithium hydroxide (5.5 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (1.1 g, 97%).

$^1$H NMR (300 MHz, DMSO-$d_6$) δ ppm 0.92 (dd, J=18.18, 6.31 Hz, 6H) 1.42-1.83 (m, 3H) 2.38 (s, 3H) 2.46-2.51 (m, 2H) 2.90 (s, 3H) 3.43-3.59 (m, 2H) 4.23-4.44 (m, 1H) 6.27 (d, J=7.35 Hz, 1H) 6.55 (d, J=8.67 Hz, 2H) 6.79 (s, 1H) 7.12 (d, J=8.48 Hz, 2H) 7.22 (t, J=7.35 Hz, 1H) 7.36 (t, J=7.63 Hz, 2H) 7.57 (d, J=7.16 Hz, 2H)

Example 169

3-{methyl[(4-{[3-methyl-1-(2-methyl-5-phenylfuran-3-yl)butyl]amino}phenyl)carbonyl]amino}propanoic acid

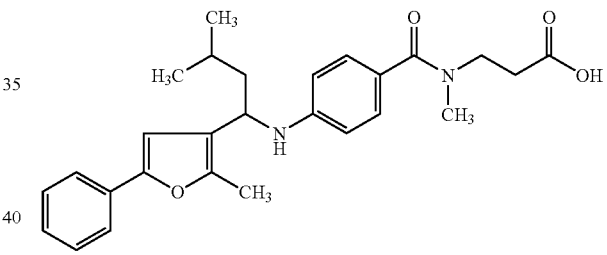

Ethyl 3-{methyl[(4-{[3-methyl-1-(2-methyl-5-phenylfuran-3-yl)butyl]amino}phenyl)carbonyl]amino}propanoate (2.54 g) which is a synthetic intermediate in Example 125 was dissolved in ethanol-hexane (1:1, volume ratio), and the solution was subjected to HPLC using CHIRALPAK AD (50 mmID×500 mL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 20 min was collected, and concentrated. The obtained amorphous compound (1.24 g) was dissolved in ethanol (5 mL) and tetrahydrofuran (5 mL), 1N lithium hydroxide (5.5 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (1.1 g, 97%).

$^1$H NMR (300 MHz, DMSO-$d_6$) δ ppm 0.92 (dd, J=18.18, 6.31 Hz, 6H) 1.42-1.83 (m, 3H) 2.38 (s, 3H) 2.46-2.51 (m, 2H) 2.90 (s, 3H) 3.43-3.59 (m, 2H) 4.23-4.44 (m, 1H) 6.27 (d, J=7.35 Hz, 1H) 6.55 (d, J=8.67 Hz, 2H) 6.79 (s, 1H) 7.12 (d, J=8.48 Hz, 2H) 7.22 (t, J=7.35 Hz, 1H) 7.36 (t, J=7.63 Hz, 2H) 7.57 (d, J=7.16 Hz, 2H)

Example 170

3-{[(4-{[1-(2-cyclopropyl-5-phenylfuran-3-yl)-3-methylbutyl]amino}phenyl)carbonyl]amino}propanoic acid

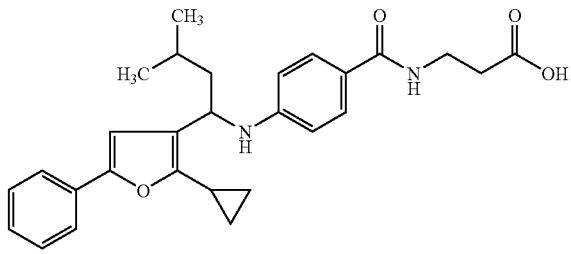

(1) methyl 2-cyclopropyl-5-phenylfuran-3-carboxylate

To a solution of phenacyl bromide (10 g) and methyl 3-cyclopropyl-3-oxopentanoate (6.5 g) in toluene (100 mL) was added dropwise 1,8-azabicyclo[5.4.0]-7-undecene (7.5 mL) over 30 min or more under ice-cooling. After the completion of the dropwise addition, the mixture was stirred for 30 min under ice-cooling, and then at room temperature for 2 hr. The resulting precipitate was filtered, and washed with toluene. The obtained toluene solution was passed through silica gel, and the silica gel was washed with ethyl acetate-hexane (1:1). The collected solutions were concentrated under reduced pressure to remove ethyl acetate-hexane to give a toluene solution. To this toluene solution was added 4-toluenesulfonic acid monohydrate (1.9 g), and the mixture was stirred at 100° C. for 2 hr. The reaction mixture was washed with aqueous sodium hydrogen carbonate solution, and the aqueous layer was extracted with ethyl acetate. The organic layers were collected, and dried over magnesium sulfate. The solvent was evaporated under reduced pressure. The residue was purified by silica gel chromatography (0% ethyl acetate/hexane to 5% ethyl acetate/hexane) to give the title compound (7.1 g, 59%) as a white solid.
$^1$H NMR (300 MHz, CHLOROFORM-d) δ ppm 1.03-1.22 (m, 4H) 2.73-2.93 (m, 1H) 3.87 (s, 3H) 6.86 (s, 1H) 7.23-7.27 (m, 1H) 7.36 (t, J=7.57 Hz, 2H) 7.55 (d, J=7.19 Hz, 2H)

(2) (2-cyclopropyl-5-phenylfuran-3-yl)methanol

A solution of methyl 2-cyclopropyl-5-phenylfuran-3-carboxylate (7.0 g) obtained by the above-mentioned reaction in tetrahydrofuran (50 mL) was added dropwise to a suspension of lithium aluminum hydride (1.1 g) in tetrahydrofuran (30 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 40% ethyl acetate/hexane) to give the title compound (5.8 g, 94%) as a white crystal.
$^1$H NMR (300 MHz, CHLOROFORM-d) δ ppm 0.86-1.11 (m, 4H) 1.41 (t, J=5.65 Hz, 5H) 1.98 (tt, J=8.24, 5.32 Hz, 1H) 4.61 (d, J=5.46 Hz, 2H) 6.63 (s, 1H) 7.11-7.25 (m, 1H) 7.30-7.42 (m, 2H) 7.47-7.65 (m, 2H)

(3) 2-cyclopropyl-5-phenylfuran-3-carbaldehyde

To a solution of (2-cyclopropyl-5-phenylfuran-3-yl)methanol (5.8 g) obtained by the above-mentioned reaction in methylene chloride (30 mL) was added Dess-Martin reagent (13.7 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (4.8 g, 83%) as a yellow crystal.
$^1$H NMR (300 MHz, CHLOROFORM-d) δ ppm 1.13-1.33 (m, 4H) 2.42-2.59 (m, 1H) 6.90 (s, 1H) 7.27-7.33 (m, 1H) 7.34-7.43 (m, 2H) 7.52-7.62 (m, 2H) 10.07 (s, 1H)

(4) 1-(2-cyclopropyl-5-phenylfuran-3-yl)-3-methylbutan-1-ol

To a solution of 2-cyclopropyl-5-phenylfuran-3-carbaldehyde (1.5 g) obtained by the above-mentioned reaction in tetrahydrofuran (20 mL) was added dropwise 1N isobutylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (1.8 g, 94%) as an oil.
$^1$H NMR (300 MHz, CHLOROFORM-d) δ ppm 0.89-1.11 (m, 10H) 1.52-1.85 (m, 4H) 1.97 (tt, J=8.10, 5.46 Hz, 1H) 4.88 (td, J=7.02, 3.30 Hz, 1H) 6.62 (s, 1H) 7.15-7.24 (m, 1H) 7.29-7.39 (m, 2H) 7.51-7.60 (m, 2H)

(5) 3-(1-chloro-3-methylbutyl)-2-cyclopropyl-5-phenylfuran

To a solution of 1-(2-cyclopropyl-5-phenylfuran-3-yl)-3-methylbutan-1-ol (1.1 g) obtained by the above-mentioned reaction in toluene (20 mL) were added thionyl chloride (0.6 mL) and pyridine (0.6 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.8 g, 100%) as an oil.

(6) 4-{[1-(2-cyclopropyl-5-phenylfuran-3-yl)-3-methylbutyl]amino}benzoic acid

A mixture of 3-(1-chloro-3-methylbutyl)-2-cyclopropyl-5-phenylfuran (1.8 g) obtained by the above-mentioned reaction, methyl 4-aminobenzoate (2.0 g), sodium carbonate (1.4 g) and sodium iodide (3.9 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (6 mL) and tetrahydrofuran (6 mL), 2N lithium hydroxide (6.5 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 40% ethyl acetate/hexane) to give the title compound (0.5 g, 21%) as an amorphous compound.

$^1$H NMR (300 MHz, CHLOROFORM-d) δ ppm 0.81-1.11 (m, 10H) 1.55-1.88 (m, 3H) 1.98 (ddd, J=13.44, 7.76, 5.68 Hz, 1H) 4.56 (t, J=7.00 Hz, 1H) 6.50 (s, 1H) 6.60 (d, J=9.09 Hz, 2H) 7.15-7.20 (m, 1H) 7.31 (t, J=7.57 Hz, 2H) 7.52 (d, J=7.19 Hz, 2H) 7.88 (d, J=8.71 Hz, 2H)

(7) 3-{[(4-{[1-(2-cyclopropyl-5-phenylfuran-3-yl)-3-methylbutyl]amino}phenyl)carbonyl]amino}propanoic acid A solution of 4-{[1-(2-cyclopropyl-5-phenylfuran-3-yl)-3-methylbutyl]amino}benzoic acid (264 mg) obtained by the above-mentioned reaction, ethyl β-alaninate hydrochloride (126 mg), 1-ethyl-3-(3-dimethylaminopropyl)carbodiimide hydrochloride (157 mg), hydroxybenzotriazole monohydrate (126 mg) and triethylamine (114 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (195 mg, 61%).

$^1$H NMR (300 MHz, DMSO-d$_6$) δ ppm 0.75-1.06 (m, 10H) 1.56-1.79 (m, 3H) 2.12-2.32 (m, 1H) 2.42 (t, J=7.19 Hz, 2H) 3.34 (d, J=6.44 Hz, 2H) 4.50 (brs, 1H) 6.39 (d, J=7.57 Hz, 1H) 6.61 (d, J=9.09 Hz, 2H) 6.75 (s, 1H) 7.17-7.22 (m, 1H) 7.32-7.37 (m, 2H) 7.50-7.56 (m, 4H) 8.15 (brs, 1H)

Example 171

3-{[(4-{[1-(2-cyclopropyl-5-phenylfuran-3-yl)-3-methylbutyl]amino}phenyl)carbonyl](methyl)amino}propanoic acid

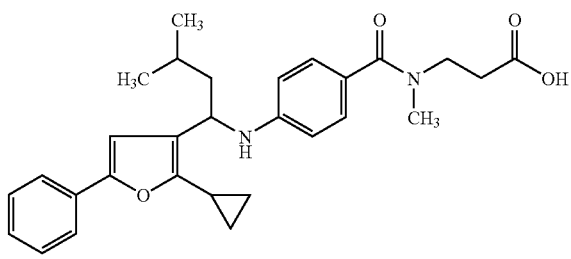

A solution of 4-{[1-(2-cyclopropyl-5-phenylfuran-3-yl)-3-methylbutyl]amino}benzoic acid (264 mg), ethyl 3-(methylamino)propanoate (108 mg), 1-ethyl-3-(3-dimethylaminopropyl)carbodiimide hydrochloride (157 mg), hydroxybenzotriazole monohydrate (126 mg) and triethylamine (114 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (153 mg, 48%).

$^1$H NMR (300 MHz, DMSO-d$_6$) δ ppm 0.77-1.07 (m, 10H) 1.55-1.79 (m, 3H) 2.12-2.31 (m, 1H) 2.37-2.48 (m, 2H) 2.90 (s, 3H) 3.51 (t, J=7.38 Hz, 2H) 4.47 (q, J=6.94 Hz, 1H) 6.28 (d, J=7.57 Hz, 1H) 6.61 (d, J=8.71 Hz, 2H) 6.78 (s, 1H) 7.13 (d, J=8.71 Hz, 2H) 7.16-7.25 (m, 1H) 7.28-7.42 (m, 2H) 7.52 (d, J=7.19 Hz, 2H)

Example 172

3-{[(2-methoxy-4-{[3-methyl-1-(2-methyl-5-phenylfuran-3-yl)butyl]amino}phenyl)carbonyl]amino}propanoic acid

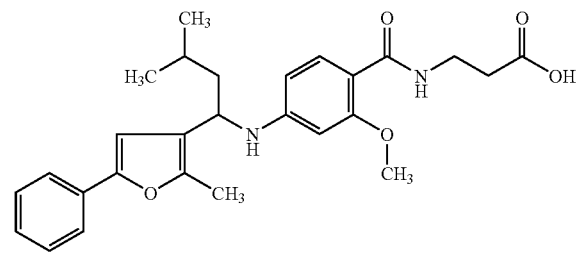

(1) 2-methoxy-4-{[3-methyl-1-(2-methyl-5-phenylfuran-3-yl)butyl]amino}benzoic acid A mixture of 3-(1-chloro-3-methylbutyl)-2-methyl-5-phenylfuran (1.3 g), methyl 4-amino-2-methoxybenzoate (1.1 g), sodium carbonate (1.1 g) and sodium iodide (3.0 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (5 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane) to give the title compound (0.9 g, 46%) as an amorphous compound.

$^1$H NMR (300 MHz, CHLOROFORM-d) δ ppm 0.98 (dd, J=18.55, 6.44 Hz, 6H) 1.60-1.87 (m, 3H) 2.41 (s, 3H) 3.95 (s, 3H) 4.29-4.49 (m, 2H) 6.08 (d, J=2.27 Hz, 1H) 6.28 (dd, J=8.71, 1.89 Hz, 1H) 6.50 (s, 1H) 7.19-7.32 (m, 1H) 7.35 (t, J=7.57 Hz, 2H) 7.59 (d, J=7.19 Hz, 1H) 7.92 (d, J=8.71 Hz, 1H) 10.36 (brs, 1H)

(2) 3-{[(2-methoxy-4-{[3-methyl-1-(2-methyl-5-phenylfuran-3-yl)butyl]amino}phenyl)carbonyl]amino}propanoic acid A solution of 2-methoxy-4-{[3-methyl-1-(2-methyl-5-phenylfuran-3-yl)butyl]amino}benzoic acid (197 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (107 mg, 47%).

$^1$H NMR (300 MHz, DMSO-d$_6$) δ ppm 0.92 (dd, J=19.31, 6.06 Hz, 6H) 1.42-1.65 (m, 2H) 1.42-1.65 (m, 2H) 1.65-1.83 (m, 1H) 2.31-2.45 (m, 5H) 3.40 (q, J=6.44 Hz, 2H) 3.80 (s, 3H) 4.39 (q, J=6.94 Hz, 1H) 6.09-6.29 (m, 2H) 6.49 (d, J=7.57 Hz, 1H) 6.78 (s, 1H) 7.12-7.28 (m, 1H) 7.37 (t, J=7.76 Hz, 2H) 7.57 (d, J=7.19 Hz, 2H) 7.62 (d, J=8.33 Hz, 2H) 8.13 (t, J=5.30 Hz, 1H)

Example 173

3-{[(2-methoxy-4-{[3-methyl-1-(2-methyl-5-phenyl-furan-3-yl)butyl]amino}phenyl)carbonyl](methyl)amino}propanoic acid

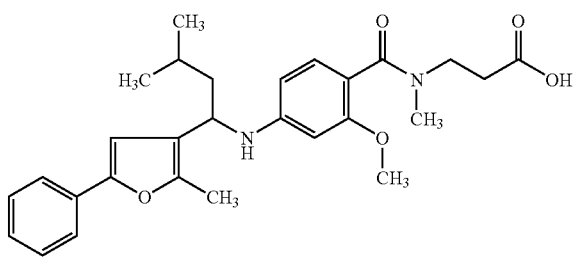

A solution of 2-methoxy-4-{[3-methyl-1-(2-methyl-5-phenylfuran-3-yl)butyl]amino}benzoic acid (197 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (103 mg, 44%).

$^1$H NMR (300 MHz, DMSO-d$_6$) δ ppm 0.92 (dd, J=18.93, 6.06 Hz, 6H) 1.41-1.67 (m, 3H) 2.24-2.46 (m, 5H) 2.63-2.78 (m, 3H) 3.52 (brs, 2H) 3.67 (s, 3H) 4.33 (d, J=7.57 Hz, 1H) 6.14-6.34 (m, 3H) 6.69-6.84 (m, 2H) 7.12-7.28 (m, 1H) 7.37 (t, J=7.57 Hz, 2H) 7.57 (d, J=7.57 Hz, 2H)

Example 174

3-({[4-({1-[5-(4-fluoro-2-methoxyphenyl)-2-methyl-furan-3-yl]-3-methylbutyl}amino)phenyl]carbonyl}amino)propanoic acid

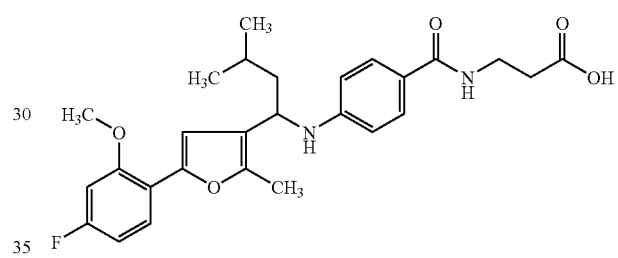

(1) methyl 5-(4-fluoro-2-methoxyphenyl)-2-methyl-furan-3-carboxylate

A mixture of methyl 5-bromo-2-methyl-3-furancarboxylate (2.2 g), 4-fluoro-2-methoxyphenylboronic acid (2.0 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (1.3 g, 51%) as a white solid.

$^1$H NMR (300 MHz, CHLOROFORM-d) δ ppm 2.64 (s, 3H) 3.85 (s, 3H) 3.94 (s, 3H) 6.64-6.81 (m, 2H) 7.06 (s, 1H) 7.75 (dd, J=8.52, 6.63 Hz, 1H)

(2) [5-(4-fluoro-2-methoxyphenyl)-2-methylfuran-3-yl]methanol

A solution of methyl 5-(4-fluoro-2-methoxyphenyl)-2-methylfuran-3-carboxylate (1.3 g) obtained by the above-mentioned reaction in tetrahydrofuran (20 mL) was added dropwise to a suspension of lithium aluminum hydride (0.2 g) in tetrahydrofuran (20 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (1.2 g, 100%) as a white solid.

$^1$H NMR (300 MHz, CHLOROFORM-d) δ ppm 2.36 (s, 3H) 3.92 (s, 3H) 4.52 (d, J=5.68 Hz, 2H) 6.63-6.77 (m, 2H) 6.85 (s, 1H) 7.73 (d, J=7.19 Hz, 1H)

(3) 5-(4-fluoro-2-methoxyphenyl)-2-methylfuran-3-carbaldehyde

To a solution of [5-(4-fluoro-2-methoxyphenyl)-2-methylfuran-3-yl]methanol (1.2 g) obtained by the above-mentioned reaction in methylene chloride (15 mL) was added Dess-Martin reagent (2.5 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (0.7 g, 61%) as a white crystal.

$^1$H NMR (300 MHz, CHLOROFORM-d) δ ppm 2.66 (s, 3H) 3.94 (s, 3H) 6.61-6.82 (m, 2H) 7.12 (s, 1H) 7.51-7.99 (m, 1H) 9.97 (s, 1H)

(4) 1-[5-(4-fluoro-2-methoxyphenyl)-2-methylfuran-3-yl]-3-methylbutan-1-ol

To a solution of 5-(4-fluoro-2-methoxyphenyl)-2-methylfuran-3-carbaldehyde (0.7 g) obtained by the above-mentioned reaction in tetrahydrofuran (20 mL) was added dropwise 1N isobutylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) the title compound (0.7 g, 85%) as an oil.

$^1$H NMR (300 MHz, CHLOROFORM-d) δ ppm 0.95 (d, J=6.44 Hz, 6H) 1.46-1.83 (m, 3H) 2.35 (s, 3H) 3.93 (s, 3H) 4.72 (td, J=7.00, 2.65 Hz, 1H) 6.59-6.76 (m, 2H) 6.82 (s, 1H) 7.75 (dd, J=8.33, 6.82 Hz, 1H)

(5) 3-(1-chloro-3-methylbutyl)-5-(4-fluoro-2-methoxyphenyl)-2-methylfuran

To a solution of 1-[5-(4-fluoro-2-methoxyphenyl)-2-methylfuran-3-yl]-3-methylbutan-1-ol (0.7 g) obtained by the above-mentioned reaction in toluene (20 mL) were added thionyl chloride (0.2 mL) and pyridine (0.2 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.8 g, 100%) as a white crystal.

$^1$H NMR (300 MHz, CHLOROFORM-d) δ ppm 0.94 (dd, J=6.44, 3.03 Hz, 6H) 1.66-1.95 (m, 2H) 1.98-2.18 (m, 1H) 2.36 (s, 3H) 3.94 (s, 3H) 4.96 (t, J=7.95 Hz, 1H) 6.62-6.75 (m, 2H) 6.83 (s, 1H) 7.74 (dd, J=8.52, 6.63 Hz, 1H)

(6) 4-({1-[5-(4-fluoro-2-methoxyphenyl)-2-methylfuran-3-yl]-3-methylbutyl}amino)benzoic acid A mixture of 3-(1-chloro-3-methylbutyl)-5-(4-fluoro-2-methoxyphenyl)-2-methylfuran (0.8 g) obtained by the above-mentioned reaction, methyl 4-aminobenzoate (0.8 g), sodium carbonate (0.5 g) and sodium iodide (1.5 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (4 mL) and tetrahydrofuran (6 mL), 2N lithium hydroxide (3 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (15% ethyl acetate/hexane to 50% ethyl acetate/hexane) to give the title compound (0.7 g, 64%) as an amorphous compound.

$^1$H NMR (300 MHz, CHLOROFORM-d) δ ppm 0.97 (dd, J=19.31, 6.06 Hz, 6H) 1.51-1.84 (m, 3H) 2.38 (s, 3H) 3.91 (s, 3H) 4.40 (t, J=7.00 Hz, 1H) 6.54 (d, J=8.71 Hz, 2H) 6.59-6.77 (m, 3H) 7.74 (dd, J=8.71, 6.82 Hz, 1H) 7.87 (d, J=8.71 Hz, 2H)

(7) 3-({[4-({1-[5-(4-fluoro-2-methoxyphenyl)-2-methylfuran-3-yl]-3-methylbutyl}amino)phenyl]carbonyl}amino)propanoic acid A solution of 4-({1-[5-(4-fluoro-2-methoxyphenyl)-2-methylfuran-3-yl]-3-methylbutyl}amino)benzoic acid (206 mg) obtained by the above-mentioned reaction, ethyl β-alaninate hydrochloride (74 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (220 mg, 91%).

$^1$H NMR (300 MHz, DMSO-$d_6$) δ ppm 0.92 (dd, J=18.55, 6.44 Hz, 6H) 1.45-1.78 (m, 3H) 2.37 (s, 3H) 2.42 (t, J=7.19 Hz, 2H) 3.30-3.45 (m, 2H) 3.89 (s, 3H) 4.36 (q, J=7.57 Hz, 1H) 6.41 (d, J=7.95 Hz, 1H) 6.54 (d, J=8.71 Hz, 2H) 6.76 (s, 1H) 6.81 (td, J=8.42, 2.46 Hz, 1H) 6.99 (dd, J=11.36, 2.27 Hz, 1H) 7.53 (d, J=8.71 Hz, 2H) 7.63 (dd, J=8.71, 6.82 Hz, 1H) 8.02 (t, J=5.49 Hz, 1H)

Example 175

3-[{[4-({1-[5-(4-fluoro-2-methoxyphenyl)-2-methyl-furan-3-yl]-3-methylbutyl}amino)phenyl]carbonyl}(methyl)amino]propanoic acid

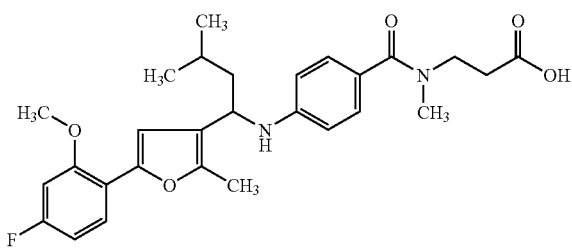

A solution of 4-({1-[5-(4-fluoro-2-methoxyphenyl)-2-methylfuran-3-yl]-3-methylbutyl}amino)benzoic acid (206 mg), ethyl 3-(methylamino)propanoate (63 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (217 mg, 87%).

$^1$H NMR (300 MHz, DMSO-d$_6$) δ ppm 0.91 (dd, J=17.98, 6.25 Hz, 6H) 1.45-1.78 (m, 3H) 2.37 (s, 3H) 2.41-2.48 (m, 2H) 2.89 (s, 3H) 3.51 (t, J=7.38 Hz, 2H) 3.89 (s, 3H) 4.32 (q, J=7.19 Hz, 1H) 6.30 (d, J=7.57 Hz, 1H) 6.54 (d, J=8.71 Hz, 2H) 6.71-6.86 (m, 2H) 6.99 (dd, J=11.36, 2.65 Hz, 1H) 7.11 (d, J=8.71 Hz, 2H) 7.63 (dd, J=8.71, 7.19 Hz, 1H)

Example 176

3-({[4-({1-[5-(2-methoxyphenyl)-2-methylfuran-3-yl]-3-methylbutyl}amino)phenyl]carbonyl}amino)propanoic acid

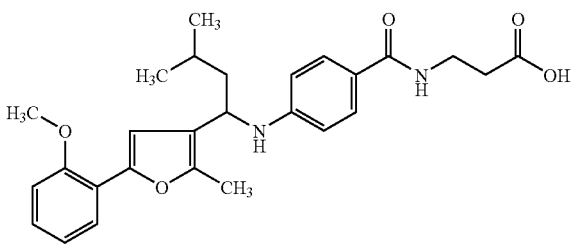

(1) methyl 5-(2-methoxyphenyl)-2-methylfuran-3-carboxylate

A mixture of methyl 5-bromo-2-methyl-3-furancarboxylate (2.2 g), 2-methoxyphenylboronic acid (1.8 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (2.3 g, 92%) as a white solid.

$^1$H NMR (300 MHz, CHLOROFORM-d) δ ppm 2.65 (s, 3H) 3.86 (s, 3H) 3.96 (s, 3H) 6.95-7.04 (m, 2H) 7.14 (s, 1H) 7.23-7.28 (m, 1H) 7.81 (dd, J=7.76, 1.70 Hz, 1H)

(2) [5-(2-methoxyphenyl)-2-methylfuran-3-yl]methanol

A solution of methyl 5-(2-methoxyphenyl)-2-methylfuran-3-carboxylate (2.2 g) obtained by the above-mentioned reaction in tetrahydrofuran (20 mL) was added dropwise to a suspension of lithium aluminum hydride (0.3 g) in tetrahydrofuran (20 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (2.0 g, 100%) as a white solid.

$^1$H NMR (300 MHz, CHLOROFORM-d) δ ppm 1.35 (t, J=5.49 Hz, 1H) 2.37 (s, 3H) 3.94 (s, 3H) 4.53 (d, J=5.68 Hz, 2H) 6.90-7.05 (m, 3H) 7.16-7.25 (m, 1H) 7.81 (dd, J=7.76, 1.70 Hz, 1H)

(3) 5-(2-methoxyphenyl)-2-methylfuran-3-carbaldehyde

To a solution of [5-(2-methoxyphenyl)-2-methylfuran-3-yl]methanol (2.0 g) obtained by the above-mentioned reaction in methylene chloride (15 mL) was added Dess-Martin reagent (4.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (1.1 g, 59%) as a white crystal.

$^1$H NMR (300 MHz, CHLOROFORM-d) δ ppm 2.67 (s, 3H) 3.95 (s, 3H) 6.91-7.08 (m, 2H) 7.20 (s, 1H) 7.27-7.30 (m, 1H) 7.82 (dd, J=7.76, 1.70 Hz, 1H) 9.98 (s, 8H)

(4) 1-[5-(2-methoxyphenyl)-2-methylfuran-3-yl]-3-methylbutan-1-ol

To a solution of 5-(2-methoxyphenyl)-2-methylfuran-3-carbaldehyde (1.1 g) obtained by the above-mentioned reaction in tetrahydrofuran (20 mL) was added dropwise 1N isobutylmagnesium bromide-tetrahydrofuran solution (7.5 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.2 g, 88%) as an oil.

$^1$H NMR (300 MHz, CHLOROFORM-d) δ ppm 0.95 (d, J=6.44 Hz, 6H) 1.51-1.84 (m, 3H) 2.37 (s, 3H) 3.94 (s, 3H) 4.72 (td, J=7.00, 3.03 Hz, 1H) 6.90 (s, 1H) 6.92-7.06 (m, 2H) 7.21 (td, J=7.76, 1.51 Hz, 1H) 7.81 (dd, J=7.76, 1.70 Hz, 1H)

(5) 3-(1-chloro-3-methylbutyl)-5-(2-methoxyphenyl)-2-methylfuran

To a solution of 1-[5-(2-methoxyphenyl)-2-methylfuran-3-yl]-3-methylbutan-1-ol (1.2 g) obtained by the above-mentioned reaction in toluene (20 mL) were added thionyl chloride (0.5 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.3 g, 100%) as an oil.

$^1$H NMR (300 MHz, CHLOROFORM-d) δ ppm 0.94 (dd, J=6.59, 2.64 Hz, 6H) 1.65-1.93 (m, 2H) 1.97-2.17 (m, 1H) 2.37 (s, 3H) 3.95 (s, 3H) 4.99 (t, J=7.35 Hz, 1H) 6.84-7.07 (m, 4H) 7.80 (dd, J=7.72, 1.70 Hz, 1H)

(6) 4-({1-[5-(2-methoxyphenyl)-2-methylfuran-3-yl]-3-methylbutyl}amino)benzoic acid A mixture of 3-(1-chloro-3-methylbutyl)-5-(2-methoxyphenyl)-2-methylfuran (1.3 g) obtained by the above-mentioned reaction, methyl 4-aminobenzoate (1.3 g), sodium carbonate (0.9 g) and sodium iodide (2.6 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (4 mL) and tetrahydrofuran (6 mL), 2N lithium hydroxide (4.5 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (25% ethyl acetate/hexane to 50% ethyl acetate/hexane) to give the title compound (0.9 g, 55%) as an amorphous compound.

$^1$H NMR (300 MHz, CHLOROFORM-d) δ ppm 0.85-1.11 (m, 6H) 1.52-1.85 (m, 3H) 2.39 (s, 3H) 3.93 (s, 3H) 4.42 (t, J=7.19 Hz, 1H) 6.54 (d, J=8.71 Hz, 2H) 6.79 (s, 1H) 6.92 (d, J=8.33 Hz, 1H) 6.98 (t, J=7.57 Hz, 1H) 7.12-7.23 (m, 1H) 7.80 (dd, J=7.76, 1.70 Hz, 1H) 7.87 (d, J=8.71 Hz, 2H)

(7) 3-({[4-({1-[5-(2-methoxyphenyl)-2-methylfuran-3-yl]-3-methylbutyl}amino)phenyl]carbonyl}amino)propanoic acid A solution of 4-({1-[5-(2-methoxyphenyl)-2-methylfuran-3-yl]-3-methylbutyl}amino)benzoic acid (197 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (205 mg, 88%).

$^1$H NMR (300 MHz, DMSO-d$_6$) δ ppm 0.92 (dd, J=18.74, 6.25 Hz, 6H) 1.46-1.79 (m, 3H) 2.38 (s, 3H) 2.43 (t, J=7.19 Hz, 2H) 3.31-3.46 (m, 2H) 3.87 (s, 3H) 4.37 (q, J=7.45 Hz, 1H) 6.41 (d, J=7.95 Hz, 1H) 6.55 (d, J=8.71 Hz, 2H) 6.82 (s, 1H) 6.97 (t, J=7.38 Hz, 1H) 7.06 (d, J=7.57 Hz, 1H) 7.12-7.25 (m, 1H) 7.54 (d, J=8.71 Hz, 2H) 7.63 (dd, J=7.57, 1.51 Hz, 1H) 7.99 (t, J=5.30 Hz, 1H)

Example 177

3-[{[4-({1-[5-(2-methoxyphenyl)-2-methylfuran-3-yl]-3-methylbutyl}amino)phenyl]carbonyl}(methyl)amino]propanoic acid

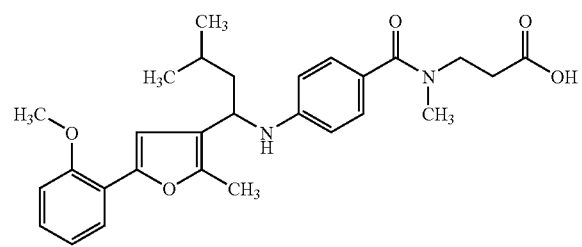

A solution of 4-({1-[5-(2-methoxyphenyl)-2-methylfuran-3-yl]-3-methylbutyl}amino)benzoic acid (197 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (212 mg, 89%).

$^1$H NMR (300 MHz, DMSO-d$_6$) δ ppm 0.92 (dd, J=18.17, 6.06 Hz, 6H) 1.45-1.79 (m, 3H) 2.38 (s, 3H) 2.42-2.49 (m, 2H) 2.90 (s, 3H) 3.52 (t, J=7.38 Hz, 2H) 3.88 (s, 3H) 4.33 (q, J=7.57 Hz, 1H) 6.30 (d, J=7.57 Hz, 1H) 6.54 (d, J=8.71 Hz, 2H) 6.83 (s, 1H) 6.97 (t, J=7.57 Hz, 1H) 7.02-7.09 (m, 1H) 7.12 (m, J=8.71 Hz, 2H) 7.16-7.29 (m, 1H) 7.64 (dd, J=7.76, 1.70 Hz, 1H)

Example 178

3-({[4-({1-[5-(3-methoxyphenyl)-2-methylfuran-3-yl]-3-methylbutyl}amino)phenyl]carbonyl}amino)propanoic acid

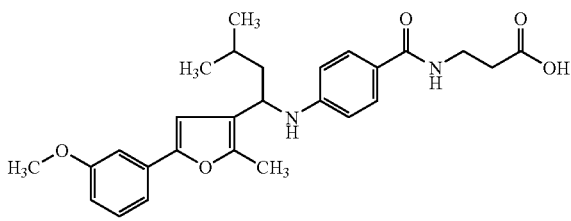

(1) methyl 5-(3-methoxyphenyl)-2-methylfuran-3-carboxylate

A mixture of methyl 5-bromo-2-methyl-3-furancarboxylate (2.2 g), 3-methoxyphenylboronic acid (1.8 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (2.3 g, 92%) as a white solid.
$^1$H NMR (300 MHz, CHLOROFORM-d) δ ppm 2.65 (s, 3H) 3.86 (s, 6H) 6.83 (dd, J=7.95, 1.51 Hz, 1H) 6.88 (s, 1H) 7.16-7.32 (m, 3H)

(2) [5-(3-methoxyphenyl)-2-methylfuran-3-yl]methanol

A solution of methyl 5-(3-methoxyphenyl)-2-methylfuran-3-carboxylate (2.2 g) obtained by the above-mentioned reaction in tetrahydrofuran (20 mL) was added dropwise to a suspension of lithium aluminum hydride (0.3 g) in tetrahydrofuran (20 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (2.0 g, 100%) as a white solid.
$^1$H NMR (300 MHz, CHLOROFORM-d) δ ppm 1.40 (t, J=5.49 Hz, 1H) 2.37 (s, 3H) 3.85 (s, 3H) 4.51 (d, J=4.92 Hz, 2H) 6.64 (s, 1H) 6.79 (dd, J=7.95, 1.51 Hz, 1H) 7.10-7.36 (m, 3H)

(3) 5-(3-methoxyphenyl)-2-methylfuran-3-carbaldehyde

To a solution of [5-(3-methoxyphenyl)-2-methylfuran-3-yl]methanol (2.0 g) obtained by the above-mentioned reaction in methylene chloride (15 mL) was added Dess-Martin reagent (4.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (1.5 g, 79%) as a white crystal.
$^1$H NMR (300 MHz, CHLOROFORM-d) δ ppm 2.68 (s, 3H) 3.86 (s, 3H) 6.86 (d, J=7.95 Hz, 1H) 6.91 (s, 1H) 7.13-7.18 (m, 1H) 7.21-7.39 (m, 2H) 9.97 (s, 1H)

(4) 1-[5-(3-methoxyphenyl)-2-methylfuran-3-yl]-3-methylbutan-1-ol

To a solution of 5-(3-methoxyphenyl)-2-methylfuran-3-carbaldehyde (1.1 g) obtained by the above-mentioned reaction in tetrahydrofuran (20 mL) was added dropwise 1N isobutylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.8 g, 93%) as an oil.
$^1$H NMR (300 MHz, CHLOROFORM-d) δ ppm 0.94 (d, J=6.44 Hz, 6H) 1.49-1.82 (m, 3H) 2.37 (s, 3H) 3.85 (s, 3H) 4.71 (td, J=7.00, 3.41 Hz, 1H) 6.62 (s, 1H) 6.73-6.78 (m, 1H) 7.12-7.18 (m, 1H) 7.21-7.25 (m, 2H)

(5) 3-(1-chloro-3-methylbutyl)-5-(3-methoxyphenyl)-2-methylfuran

To a solution of 1-[5-(3-methoxyphenyl)-2-methylfuran-3-yl]-3-methylbutan-1-ol (1.2 g) obtained by the above-mentioned reaction in toluene (20 mL) were added thionyl chloride (0.7 mL) and pyridine (0.8 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.9 g, 100%) as an oil.
$^1$H NMR (300 MHz, CHLOROFORM-d) δ ppm 0.94 (dd, J=6.50, 3.49 Hz, 6H) 1.64-1.94 (m, 2H) 1.96-2.13 (m, 1H) 2.37 (s, 3H) 3.85 (s, 3H) 4.95 (t, J=7.63 Hz, 1H) 6.64 (s, 1H) 6.79 (ddd, J=7.82, 2.54, 1.32 Hz, 1H) 7.05-7.22 (m, 3H)

(6) 4-({1-[5-(3-methoxyphenyl)-2-methylfuran-3-yl]-3-methylbutyl}amino)benzoic acid A mixture of 3-(1-chloro-3-methylbutyl)-5-(3-methoxyphenyl)-2-methylfuran (1.9 g) obtained by the above-mentioned reaction, methyl 4-aminobenzoate (1.4 g), sodium carbonate (1.4 g) and sodium iodide (2.6 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (4 mL) and tetrahydrofuran (6 mL), 2N lithium hydroxide (6.5 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane) to give the title compound (1.4 g, 56%) as an amorphous compound.

$^1$H NMR (300 MHz, CHLOROFORM-d) δ ppm 0.96 (dd, J=18.36, 6.25 Hz, 6H) 1.52-1.84 (m, 3H) 2.40 (s, 3H) 3.83 (s, 3H) 4.39 (t, J=7.00 Hz, 1H) 6.50 (s, 1H) 6.53 (d, J=9.09 Hz, 2H) 6.76 (dd, J=7.95, 1.51 Hz, 1H) 7.13 (d, J=2.27 Hz, 1H) 7.15-7.25 (m, 2H) 7.87 (d, J=8.71 Hz, 2H)

(7) 3-({[4-({1-[5-(3-methoxyphenyl)-2-methylfuran-3-yl]-3-methylbutyl}amino)phenyl]carbonyl}amino)propanoic acid A solution of 4-({1-[5-(3-methoxyphenyl)-2-methylfuran-3-yl]-3-methylbutyl}amino)benzoic acid (197 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (207 mg, 88%).

$^1$H NMR (300 MHz, DMSO-d$_6$) δ ppm 0.92 (dd, J=18.55, 6.06 Hz, 6H) 1.45-1.87 (m, 3H) 2.38 (s, 3H) 2.43 (t, J=7.19 Hz, 2H) 3.32-3.43 (m, 2H) 3.77 (s, 3H) 4.36 (q, J=7.32 Hz, 1H) 6.34 (d, J=7.95 Hz, 1H) 6.55 (d, J=8.71 Hz, 2H) 6.73-6.79 (m, 2H) 7.08 (d, J=2.27 Hz, 1H) 7.14 (d, J=7.95 Hz, 1H) 7.27 (t, J=7.95 Hz, 1H) 7.54 (d, J=8.71 Hz, 2H) 7.99 (t, J=5.49 Hz, 1H) 12.15 (brs, 1H)

Example 179

3-[{[4-({1-[5-(3-methoxyphenyl)-2-methylfuran-3-yl]-3-methylbutyl}amino)phenyl]carbonyl}(methyl)amino]propanoic acid

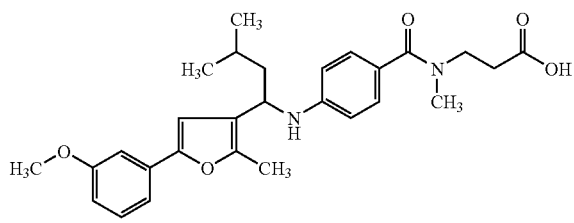

A solution of 4-({1-[5-(3-methoxyphenyl)-2-methylfuran-3-yl]-3-methylbutyl}amino)benzoic acid (197 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure to give ethyl 3-[{[4-({1-[5-(3-methoxyphenyl)-2-methylfuran-3-yl]-3-methylbutyl}amino)phenyl]carbonyl}(methyl)amino]propanoate. The obtained ethyl 3-[{[4-({1-[5-(3-methoxyphenyl)-2-methylfuran-3-yl]-3-methylbutyl}amino)phenyl]carbonyl}(methyl)amino]propanoate was dissolved in ethanol (2 mL) and tetrahydrofuran (2 mL), 1N lithium hydroxide (1.0 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (216 mg, 91%).

$^1$H NMR (300 MHz, DMSO-d$_6$) δ ppm 0.92 (dd, J=17.98, 6.25 Hz, 6H) 1.46-1.79 (m, 3H) 2.38 (s, 3H) 2.41-2.48 (m, 2H) 2.90 (s, 3H) 3.52 (t, J=7.38 Hz, 2H) 3.78 (s, 3H) 4.33 (q, J=7.07 Hz, 1H) 6.24 (d, J=7.57 Hz, 1H) 6.55 (d, J=8.71 Hz, 2H) 6.73-6.85 (m, 2H) 7.01-7.19 (m, 4H) 7.27 (t, J=7.95 Hz, 1H) 12.26 (brs, 1H)

Example 180

3-({[4-({1-[5-(4-methoxy-2-methylphenyl)-2-methylfuran-3-yl]-3-methylbutyl}amino)phenyl]carbonyl}amino)propanoic acid

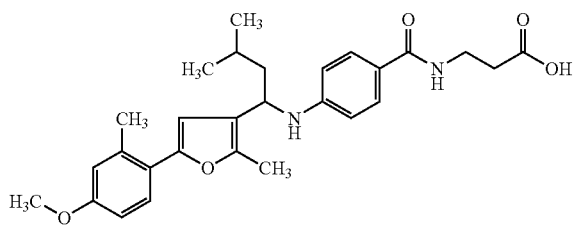

(1) 5-(4-methoxy-2-methylphenyl)-2-methylfuran-3-carbaldehyde

A mixture of 5-bromo-2-methylfuran-3-carbaldehyde (1.5 g), 4-methoxy-2-methylphenylboronic acid (1.7 g), tetrakis(triphenylphosphine)palladium(0) (0.5 g), 2N aqueous sodium carbonate solution (10 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (1.7 g, 94%) as a pale-yellow solid.

¹H NMR (300 MHz, CHLOROFORM-d) δ ppm 2.46 (s, 3H) 2.66 (s, 3H) 3.83 (s, 3H) 6.67 (s, 1H) 6.75-6.87 (m, 2H) 7.60 (dd, J=7.63, 1.41 Hz, 1H) 9.97 (s, 1H)

(2) 1-[5-(4-methoxy-2-methylphenyl)-2-methylfuran-3-yl]-3-methylbutan-1-ol

To a solution of 5-(4-methoxy-2-methylphenyl)-2-methylfuran-3-carbaldehyde (1.7 g) obtained by the above-mentioned reaction in tetrahydrofuran (20 mL) was added dropwise 1N isobutylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.6 g, 76%) as an oil.
¹H NMR (300 MHz, CHLOROFORM-d) δ ppm 0.95 (d, J=6.59 Hz, 6H) 1.50-1.83 (m, 3H) 2.35 (s, 3H) 2.46 (s, 3H) 3.82 (s, 3H) 4.72 (td, J=7.02, 2.17 Hz, 1H) 6.37 (s, 1H) 6.72-6.83 (m, 2H) 7.53-7.63 (m, 1H)

(5) 3-(1-chloro-3-methylbutyl)-5-(4-methoxy-2-methylphenyl)-2-methylfuran

To a solution of 1-[5-(4-methoxy-2-methylphenyl)-2-methylfuran-3-yl]-3-methylbutan-1-ol (1.7 g) obtained by the above-mentioned reaction in toluene (20 mL) were added thionyl chloride (0.6 mL) and pyridine (0.7 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.7 g, 100%) as an oil.
¹H NMR (300 MHz, CHLOROFORM-d) δ ppm 0.94 (dd, J=6.59, 2.45 Hz, 6H) 1.68-1.89 (m, 2H) 2.01-2.08 (m, 1H) 2.36 (s, 3H) 3.82 (s, 3H) 4.98 (t, J=7.63 Hz, 1H) 6.38 (s, 1H) 6.73-6.84 (m, 2H) 7.51-7.61 (m, 1H)

(6) 4-({1-[5-(4-methoxy-2-methylphenyl)-2-methylfuran-3-yl]-3-methylbutyl}amino)benzoic acid A mixture of 3-(1-chloro-3-methylbutyl)-5-(4-methoxy-2-methylphenyl)-2-methylfuran (1.7 g) obtained by the above-mentioned reaction, methyl 4-aminobenzoate (1.7 g), sodium carbonate (1.2 g) and sodium iodide (3.3 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (5.5 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (15% ethyl acetate/hexane to 50% ethyl acetate/hexane) to give the title compound (1.0 g, 46%) as an amorphous compound.
¹H NMR (300 MHz, CHLOROFORM-d) δ ppm 0.97 (dd, J=19.31, 6.06 Hz, 6H) 1.54-1.85 (m, 3H) 2.38 (s, 3H) 2.41 (s, 3H) 3.80 (s, 3H) 4.41 (t, J=7.00 Hz, 1H) 6.25 (s, 1H) 6.54 (d, J=9.09 Hz, 2H) 6.68-6.81 (m, 2H) 7.55 (d, J=8.71 Hz, 1H) 7.88 (d, J=8.71 Hz, 2H)

(7) 3-({[4-({1-[5-(4-methoxy-2-methylphenyl)-2-methylfuran-3-yl]-3-methylbutyl}amino)phenyl]carbonyl}amino)propanoic acid A solution of 4-({1-[5-(4-methoxy-2-methylphenyl)-2-methylfuran-3-yl]-3-methylbutyl}amino)benzoic acid (204 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (2327 mg, 97%).
¹H NMR (300 MHz, DMSO-d₆) δ ppm 0.92 (dd, J=17.80, 4.92 Hz, 6H) 1.46-1.79 (m, 3H) 2.36 (s, 6H) 2.39-2.46 (m, 2H) 3.33-3.49 (m, 2H) 3.75 (s, 3H) 4.39 (brs, 1H) 6.32 (brs, 1H) 6.47 (s, 1H) 6.57 (d, J=7.95 Hz, 2H) 6.69-6.93 (m, 2H) 7.37-7.61 (m, 3H) 7.85-8.12 (m, 1H) 12.14 (brs, 1H)

Example 181

3-[{[4-({1-[5-(4-methoxy-2-methylphenyl)-2-methylfuran-3-yl]-3-methylbutyl}amino)phenyl]carbonyl}(methyl)amino]propanoic acid

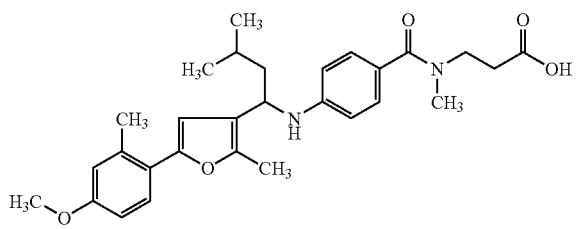

A solution of 4-({1-[5-(4-methoxy-2-methylphenyl)-2-methylfuran-3-yl]-3-methylbutyl}amino)benzoic acid (253 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (183 mg, 74%).

$^1$H NMR (300 MHz, DMSO-$d_6$) δ ppm 0.92 (dd, J=17.61, 6.25 Hz, 6H) 1.46-1.79 (m, 3H) 2.36 (s, 6H) 2.44-2.55 (m, 2H) 2.91 (s, 3H) 3.53 (t, J=7.19 Hz, 2H) 3.75 (s, 3H) 4.35 (q, J=7.70 Hz, 1H) 6.23 (d, J=7.95 Hz, 1H) 6.47 (s, 1H) 6.56 (d, J=8.71 Hz, 2H) 6.72-6.84 (m, 2H) 7.12 (d, J=8.71 Hz, 2H) 7.48 (d, J=8.33 Hz, 1H) 12.25 (brs, 1H)

Example 182

3-[{[4-({1-[2-ethyl-5-(4-methoxyphenyl)furan-3-yl]-3-methylbutyl}amino)phenyl]carbonyl}amino]propanoic acid

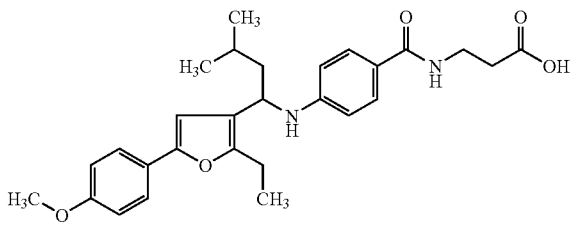

(1) methyl 2-ethyl-5-(4-methoxyphenyl)furan-3-carboxylate

To a solution of 2-bromo-4'-methoxyacetophenone (13.7 g) and methyl 3-oxopentanoate (7.8 g) in toluene (100 mL) was added dropwise 1,8-azabicyclo[5.4.0]-7-undecene (9.1 mL) over 30 min or more under ice-cooling. After the completion of the dropwise addition, the mixture was stirred for 30 min under ice-cooling, and then at room temperature for 2 hr. The resulting precipitate was filtered, and washed with toluene. The obtained toluene solution was passed through silica gel, and the silica gel was washed with ethyl acetate-hexane (1:1). The collected solutions were concentrated under reduced pressure to remove ethyl acetate-hexane to give a toluene solution. To this toluene solution was added 4-toluenesulfonic acid monohydrate (2.3 g), and the mixture was stirred at 100° C. for 2 hr. The reaction mixture was washed with aqueous sodium hydrogen carbonate solution, and the aqueous layer was extracted with ethyl acetate. The organic layers were collected, and dried over magnesium sulfate. The solvent was evaporated under reduced pressure. The residue was purified by silica gel chromatography (0% ethyl acetate/hexane to 5% ethyl acetate/hexane) to give the title compound (9.2 g, 59%) as an oil.

$^1$H NMR (300 MHz, CHLOROFORM-d) δ ppm 1.31 (t, J=7.57 Hz, 3H) 3.06 (q, J=7.57 Hz, 2H) 3.82 (s, 3H) 3.85 (s, 3H) 6.73 (s, 1H) 6.92 (d, J=8.71 Hz, 2H) 7.57 (d, J=8.71 Hz, 2H)

(2) [2-ethyl-5-(4-methoxyphenyl)furan-3-yl]methanol

A solution of methyl 2-ethyl-5-(4-methoxyphenyl)furan-3-carboxylate (9.1 g) obtained by the above-mentioned reaction in tetrahydrofuran (30 mL) was added dropwise to a suspension of lithium aluminum hydride (1.3 g) in tetrahydrofuran (30 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (8.1 g, 100%) as an oil.

$^1$H NMR (300 MHz, CHLOROFORM-d) δ ppm 1.28 (t, J=7.54 Hz, 3H) 2.71 (q, J=7.60 Hz, 2H) 3.83 (s, 3H) 4.50 (d, J=3.96 Hz, 2H) 6.50 (s, 1H) 6.90 (d, J=8.85 Hz, 2H) 7.56 (d, J=8.85 Hz, 2H)

(3) 2-ethyl-5-(4-methoxyphenyl)furan-3-carbaldehyde

To a solution of [2-ethyl-5-(4-methoxyphenyl)furan-3-yl]methanol (8.1 g) obtained by the above-mentioned reaction in methylene chloride (30 mL) was added Dess-Martin reagent (17.8 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (5.3 g, 65%) as an oil.

$^1$H NMR (300 MHz, CHLOROFORM-d) δ ppm 1.39 (t, J=7.54 Hz, 3H) 3.03 (q, J=7.54 Hz, 2H) 3.84 (s, 3H) 6.77 (s, 1H) 6.94 (d, J=9.04 Hz, 2H) 7.59 (d, J=8.85 Hz, 2H) 9.97 (s, 1H)

(4) 1-[(2-ethyl-5-(4-methoxyphenyl)furan-3-yl)]-3-methylbutan-1-ol

To a solution of 2-ethyl-5-(4-methoxyphenyl)furan-3-carbaldehyde (1.6 g) obtained by the above-mentioned reaction in tetrahydrofuran (20 mL) was added dropwise 1N isobutylmagnesium bromide-tetrahydrofuran solution (10.5 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 25% ethyl acetate/hexane) to give the title compound (1.8 g, 87%) as an oil.

$^1$H NMR (300 MHz, CHLOROFORM-d) δ ppm 0.94 (d, J=6.22 Hz, 6H) 1.28 (t, J=7.54 Hz, 3H) 1.48-1.82 (m, 3H) 2.71 (qd, J=7.54, 2.07. Hz, 2H) 3.83 (s, 3H) 4.61-4.77 (m, 1H) 6.48 (s, 1H) 6.90 (d, J=8.85 Hz, 2H) 7.56 (d, J=8.85 Hz, 2H)

(5) 3-(1-chloro-3-methylbutyl)-2-ethyl-5-(4-methoxyphenyl)furan

To a solution of 1-[(2-ethyl-5-(4-methoxyphenyl)furan-3-yl)]-3-methylbutan-1-ol (1.7 g) obtained by the above-mentioned reaction in toluene (20 mL) were added thionyl chloride (0.7 mL) and pyridine (0.7 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.8 g, 100%) as an oil.

$^1$H NMR (300 MHz, CHLOROFORM-d) δ ppm 0.93 (dd, J=6.59, 3.58 Hz, 6H) 1.29 (t, J=7.54 Hz, 3H) 1.63-1.80 (m, 2H) 1.95-2.12 (m, 1H) 2.71 (qd, J=7.57, 1.60 Hz, 2H) 3.83 (s, 3H) 4.98 (t, J=7.63 Hz, 1H) 6.50 (s, 1H) 6.90 (d, J=8.85 Hz, 2H) 7.56 (d, J=8.85 Hz, 2H)

(6) 4-({1-[2-ethyl-5-(4-methoxyphenyl)furan]-3-methylbutyl}amino)benzoic acid

A mixture of 3-(1-chloro-3-methylbutyl)-2-ethyl-5-(4-methoxyphenyl)furan (1.8 g) obtained by the above-mentioned reaction, methyl 4-aminobenzoate (1.4 g), sodium carbonate (1.0 g) and sodium iodide (2.7 g) in N,N-dimethylacetamide (10 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (6 mL) was added, and the mixture was stirred at 70° C. for 5 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (15% ethyl acetate/hexane to 50% ethyl acetate/hexane) to give the title compound (1.3 g, 53%) as an amorphous compound.

$^1$H NMR (300 MHz, CHLOROFORM-d) δ ppm 0.96 (dd, J=17.98, 6.25 Hz, 6H) 1.29 (t, J=7.95 Hz, 3H) 1.53-1.86 (m, 3H) 2.64-2.83 (m, 2H) 3.81 (s, 3H) 4.41 (t, J=7.00 Hz, 1H) 6.36 (s, 1H) 6.54 (d, J=8.71 Hz, 2H) 6.77-6.94 (m, 2H) 7.42-7.60 (m, 2H) 7.87 (d, J=8.71 Hz, 2H)

(7) 3-[{[4-({1-[2-ethyl-5-(4-methoxyphenyl)furan-3-yl]-3-methylbutyl}amino)phenyl]carbonyl}amino]propanoic acid A solution of 4-({1-[2-ethyl-5-(4-methoxyphenyl)furan]-3-methylbutyl}amino)benzoic acid (204 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (209 mg, 88%).

$^1$H NMR (300 MHz, DMSO-d$_6$) δ ppm 0.92 (dd, J=17.80, 6.06 Hz, 6% H) 1.20 (t, J=7.38 Hz, 3H) 1.46-1.78 (m, 3H) 2.41 (t, J=7.19 Hz, 2H) 2.66-2.83 (m, 2H) 3.29-3.44 (m, 2H) 3.76 (s, 3H) 4.36 (d, J=7.57 Hz, 1H) 6.32 (d, J=7.95 Hz, 1H) 6.55 (d, J=8.71 Hz, 2H) 6.59 (s, 1H) 6.94 (d, J=8.71 Hz, 2H) 7.39-7.59 (m, 4H) 7.92-8.09 (m, 1H)

Example 183

3-[{[4-({1-[2-ethyl-5-(4-methoxyphenyl)furan-3-yl]-3-methylbutyl}amino)phenyl]carbonyl}(methyl)amino]propanoic acid

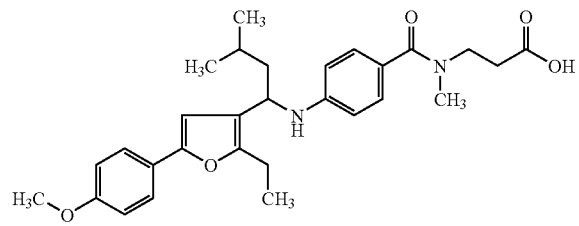

A solution of 4-({1-[2-ethyl-5-(4-methoxyphenyl)furan]-3-methylbutyl}amino)benzoic acid (204 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (174 mg, 71%).

$^1$H NMR (300 MHz, DMSO-d$_6$) δ ppm 0.92 (dd, J=17.04, 6.06 Hz, 6H) 1.20 (d, J=7.57 Hz, 3H) 1.42-1.65 (m, 3H) 2.37-2.47 (m, 2H) 2.75 (d, J=6.44 Hz, 2H) 2.89 (s, 3H) 3.51 (t, J=7.00 Hz, 2H) 3.76 (s, 3H) 4.33 (q, J=7.57 Hz, 1H) 6.21 (d, J=7.57 Hz, 1H) 6.55 (d, J=8.71 Hz, 2H) 6.61 (s, 1H) 6.94 (d, J=8.71 Hz, 2H) 7.11 (d, J=8.71 Hz, 2H) 7.50 (d, J=8.71 Hz, 2H)

Example 184

3-{[(3-methyl-4-{[3-methyl-1-(2-methyl-5-phenylfuran-3-yl)butyl]amino}phenyl)carbonyl]amino}propanoic acid

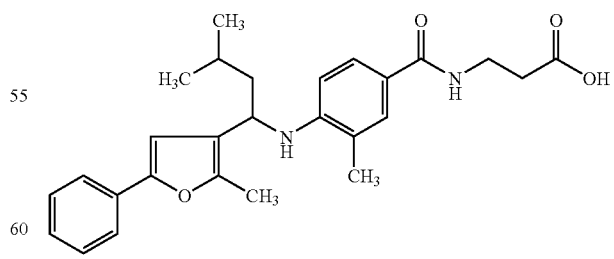

(1) 3-methyl-4-{[3-methyl-1-(2-methyl-5-phenylfuran-3-yl)butyl]amino}benzoic acid A mixture of 3-(1-chloro-3-methylbutyl)-2-methyl-5-phenylfuran (1.1 g), methyl 4-amino-3-methylbenzoate (1.0 g), sodium carbonate (0.6 g) and sodium iodide (2.4 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.5 g, 31%) as an amorphous compound.

$^1$H NMR (300 MHz, CHLOROFORM-d) δ ppm 0.84-1.12 (m, 6H) 1.54-1.87 (m, 3H) 2.17 (s, 3H) 2.40 (s, 3H) 4.45 (t, J=7.00 Hz, 1H) 6.49 (s, 1H) 6.52 (d, J=8.71 Hz, 1H) 7.14-7.24 (m, 1H) 7.33 (t, J=7.57 Hz, 2H) 7.59 (d, J=7.19 Hz, 2H) 7.77 (s, 1H) 7.82 (dd, J=8.71, 1.89 Hz, 1H)

(2) 3-{[(3-methyl-4-{[3-methyl-1-(2-methyl-5-phenylfuran-3-yl)butyl]amino}phenyl)carbonyl]amino}propanoic acid A solution of 3-methyl-4-{[3-methyl-1-(2-methyl-5-phenylfuran-3-yl)butyl]amino}benzoic acid (226 mg) obtained by the above-mentioned reaction, ethyl β-alaninate hydrochloride (111 mg), 1-ethyl-3-(3-dimethylaminopropyl)carbodiimide hydrochloride (138 mg), hydroxybenzotriazole monohydrate (110 mg) and triethylamine (100 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (256 mg, 95%).

$^1$H NMR (300 MHz, DMSO-d$_6$) δ ppm 0.79-1.06 (m, 6H) 1.50-1.70 (m, 2H) 1.74-1.97 (m, 1H) 2.17 (s, 3H) 2.32-2.46 (m, 5H) 3.28-3.44 (m, 2H) 4.44 (q, J=7.19 Hz, 1H) 5.16 (d, J=7.95 Hz, 1H) 6.48 (d, J=9.09 Hz, 1H) 6.87 (s, 1H) 7.10-7.28 (m, 1H) 7.36 (t, J=7.76 Hz, 2H) 7.41-7.50 (m, 2H) 7.54 (d, J=7.57 Hz, 2H) 8.03 (t, J=5.30 Hz, 1H)

Example 185

3-{methyl[(3-methyl-4-{[3-methyl-1-(2-methyl-5-phenylfuran-3-yl)butyl]amino}phenyl)carbonyl]amino}propanoic acid

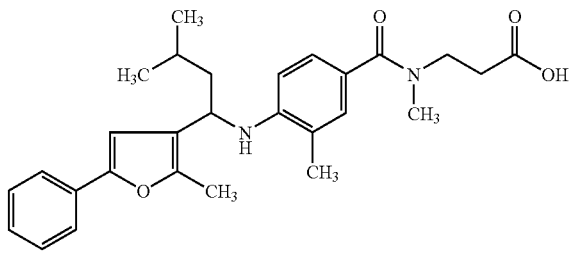

A solution of 2-methyl-4-{[3-methyl-1-(2-methyl-5-phenylfuran-3-yl)butyl]amino}benzoic acid (228 mg), ethyl 3-(methylamino)propanoate (94 mg), 1-ethyl-3-(3-dimethylaminopropyl)carbodiimide hydrochloride (138 mg), hydroxybenzotriazole monohydrate (110 mg) and triethylamine (100 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (271 mg, 97%).

$^1$H NMR (300 MHz, DMSO-d$_6$) δ ppm 0.81-1.03 (m, 6H) 1.51-1.72 (m, 2H) 1.75-1.97 (m, 1H) 2.16 (s, 3H) 2.39 (s, 3H) 2.46-2.51 (m, 2H) 2.89 (s, 3H) 3.52 (t, J=7.38 Hz, 2H) 4.33-4.49 (m, 1H) 5.05 (d, J=8.33 Hz, 1H) 6.46 (d, J=9.09 Hz, 1H) 6.88 (s, 1H) 6.97-7.08 (m, 2H) 7.14-7.26 (m, 1H) 7.36 (t, J=7.76 Hz, 2H) 7.55 (d, J=7.19 Hz, 2H)

Example 186

3-{[(2-methyl-4-{[3-methyl-1-(2-methyl-5-phenylfuran-3-yl)butyl]amino}phenyl)carbonyl]amino}propanoic acid

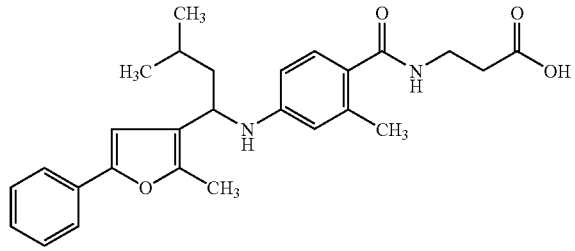

(1) 2-methyl-4-{[3-methyl-1-(2-methyl-5-phenylfuran-3-yl)butyl]amino}benzoic acid A mixture of 3-(1-chloro-3-methylbutyl)-2-methyl-5-phenylfuran (1.1 g), methyl 4-amino-2-methylbenzoate (1.1 g), sodium carbonate (0.6 g) and sodium iodide (2.4 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 70° C. for 6 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.5 g, 33%) as an oil.

$^1$H NMR (300 MHz, CHLOROFORM-d) δ ppm 0.96 (dd, J=18.27, 6.22 Hz, 6H) 1.46-1.79 (m, 3H) 2.40 (s, 3H) 2.54 (s, 3H) 4.39 (t, J=6.88 Hz, 1H) 6.31-6.42 (m, 2H) 6.50 (s, 1H) 7.13-7.24 (m, 1H) 7.33 (t, J=7.54 Hz, 2H) 7.59 (dd, J=8.38, 1.22 Hz, 2H) 7.89 (d, J=8.48 Hz, 1H)

(2) 3-{[(2-methyl-4-{[3-methyl-1-(2-methyl-5-phenylfuran-3-yl)butyl]amino}phenyl)carbonyl]amino}propanoic acid A solution of 2-methyl-4-{[3-methyl-1-(2-methyl-5-phenylfuran-3-yl)butyl]amino}benzoic acid (245 mg) obtained by the above-mentioned reaction, ethyl β-alaninate hydrochloride (120 mg), 1-ethyl-3-(3-dimethylaminopropyl)carbodiimide hydrochloride (150 mg), hydroxybenzotriazole monohydrate (119 mg) and triethylamine (109 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (234 mg, 90%).

$^1$H NMR (300 MHz, DMSO-d$_6$) δ ppm 0.92 (dd, J=18.17, 6.06 Hz, 6H) 1.45-1.78 (m, 3H) 2.23 (s, 3H) 2.33-2.46 (m, 5H) 3.24-3.46 (m, 2H) 4.24-4.42 (m, 1H) 6.06 (d, J=7.95 Hz, 1H) 6.29-6.44 (m, 2H) 6.77 (s, 1H) 7.08 (d, J=8.33 Hz, 1H) 7.13-7.25 (m, 1H) 7.36 (t, J=7.57 Hz, 2H) 7.55 (d, J=7.19 Hz, 2H) 7.80 (t, J=5.30 Hz, 1H) 12.15 (brs, 1H)

Example 187

3-{methyl[(2-methyl-4-{[3-methyl-1-(2-methyl-5-phenylfuran-3-yl)butyl]amino}phenyl)carbonyl]amino}propanoic acid

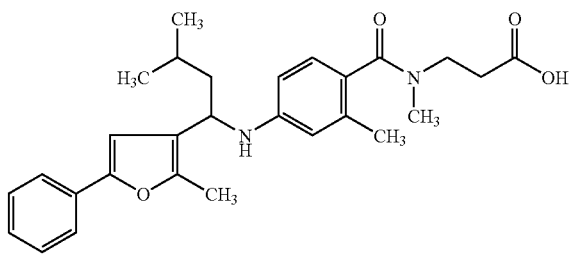

A solution of 2-methyl-4-{[3-methyl-1-(2-methyl-5-phenylfuran-3-yl)butyl]amino}benzoic acid (245 mg), ethyl 3-(methylamino)propanoate (102 mg), 1-ethyl-3-(3-dimethylaminopropyl)carbodiimide hydrochloride (150 mg), hydroxybenzotriazole monohydrate (119 mg) and triethylamine (109 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (251 mg, 94%).

$^1$H NMR (300 MHz, DMSO-d$_6$) δ ppm 0.92 (dd, J=17.61, 6.25 Hz, 6H) 1.45-1.77 (m, 3H) 2.04 (s, 3H) 2.29-2.46 (m, 5H) 3.37 (brs, 5H) 4.21-4.37 (m, 1H) 5.95 (d, J=7.19 Hz, 1H) 6.30-6.44 (m, 2H) 6.72-6.84 (m, 2H) 7.14-7.26 (m, 1H) 7.36 (t, J=7.76 Hz, 2H) 7.56 (d, J=7.19 Hz, 2H) 12.24 (brs, 1H)

Example 188

3-[{[4-({1-[5-(4-methoxyphenyl)-2-methylfuran-3-yl]-3-methylbutyl}amino)phenyl]carbonyl}(methyl)amino]propanoic acid

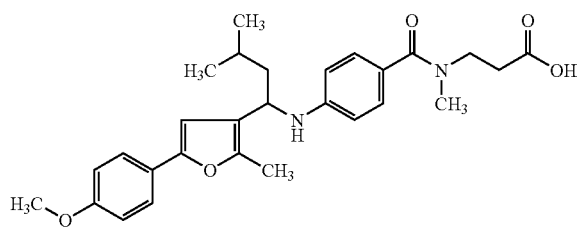

Ethyl 3-[{[4-({1-[5-(4-methoxyphenyl)-2-methylfuran-3-yl]-3-methylbutyl}amino)phenyl]carbonyl}(methyl)amino]propanoate (660 mg) which is a synthetic intermediate in Example 151 was dissolved in ethanol-hexane (1:1, volume ratio), and the solution was subjected to HPLC using CHIRALPAK AD (50 mmID×500 mL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 13.5 min were collected, and concentrated. The obtained amorphous compound (319 mg) was dissolved in ethanol (5 mL) and tetrahydrofuran (5 mL), 1N lithium hydroxide (1.3 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (288 mg, 95%).

$^1$H NMR (300 MHz, DMSO-d$_6$) δ ppm 0.92 (dd, J=17.98, 6.25 Hz, 6H) 1.43-1.81 (m, 3H) 2.36 (s, 3H) 2.46-2.51 (m, 2H) 2.90 (s, 3H) 3.52 (t, J=7.00 Hz, 2H) 3.76 (s, 3H) 4.31 (q, J=6.94 Hz, 1H) 6.23 (d, J=7.19 Hz, 1H) 6.55 (d, J=8.33 Hz, 2H) 6.61 (s, 1H) 6.93 (d, J=8.71 Hz, 2H) 7.12 (d, J=8.33 Hz, 2H) 7.49 (d, J=8.33 Hz, 2H) 12.23 (brs, 1H)

Example 189

3-[{[4-({1-[5-(4-methoxyphenyl)-2-methylfuran-3-yl]-3-methylbutyl}amino)phenyl]carbonyl}(methyl)amino]propanoic acid

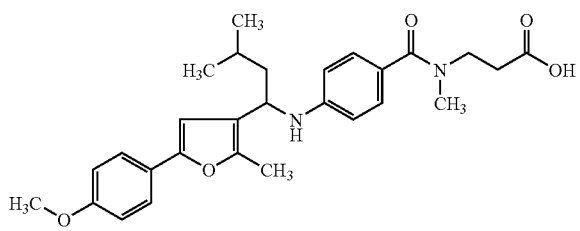

Ethyl 3-[{[4-({1-[5-(4-methoxyphenyl)-2-methylfuran-3-yl]-3-methylbutyl}amino)phenyl]carbonyl}(methyl)amino]propanoate (660 mg) which is a synthetic intermediate in Example 151 was dissolved in ethanol-hexane (1:1, volume ratio), and the solution was subjected to HPLC using CHIRALPAK AD (50 mmID×500 mL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 21.4 min were collected, and concentrated. The obtained amorphous compound (319 mg) was dissolved in ethanol (5 mL) and tetrahydrofuran (5 mL), 1N lithium hydroxide (1.3 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (284 mg, 94%).

$^1$H NMR (300 MHz, DMSO-$d_6$) δ ppm 0.92 (dd, J=17.98, 6.25 Hz, 6H) 1.43-1.81 (m, 3H) 2.36 (s, 3H) 2.46-2.51 (m, 2H) 2.90 (s, 3H) 3.52 (t, J=7.00 Hz, 2H) 3.76 (s, 3H) 4.31 (q, J=6.94 Hz, 1H) 6.23 (d, J=7.19 Hz, 1H) 6.55 (d, J=8.33 Hz, 2H) 6.61 (s, 1H) 6.93 (d, J=8.71 Hz, 2H) 7.12 (d, J=8.33 Hz, 2H) 7.49 (d, J=8.33 Hz, 2H) 12.23 (brs, 1H)

Example 190

3-[{[4-({1-[5-(3-methoxyphenyl)-2-methylfuran-3-yl]-3-methylbutyl}amino)phenyl]carbonyl}(methyl)amino]propanoic acid

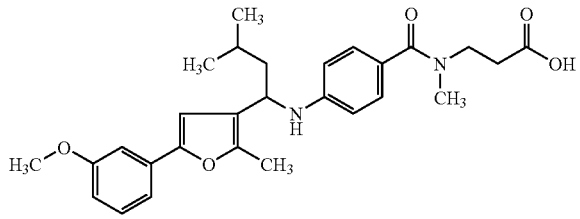

Ethyl 3-[{[4-({1-[5-(3-methoxyphenyl)-2-methylfuran-3-yl]-3-methylbutyl}amino)phenyl]carbonyl}(methyl)amino]propanoate (1200 mg) which is a synthetic intermediate in Example 151 was dissolved in ethanol-hexane (6:4, volume ratio), and the solution was subjected to HPLC using CHIRALPAK AD (50 mmID×500 mL, manufactured by DAICEL CHEMICAL INDUSTRIES, LTD.) and eluted with ethanol-hexane (6:4, volume ratio) as mobile phase at 30° C., a flow rate 60 mL/min. The fractions showing a peak with retention time 11.1 min were collected, and concentrated. The obtained amorphous compound (598 mg) was dissolved in ethanol (5 mL) and tetrahydrofuran (5 mL), lithium hydroxide (2.5 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (518 mg, 92%).

$^1$H NMR (300 MHz, DMSO-$d_6$) δ ppm 0.92 (dd, J=17.98, 6.25 Hz, 6H) 1.46-1.79 (m, 3H) 2.38 (s, 3H) 2.41-2.48 (m, 2H) 2.90 (s, 3H) 3.52 (t, J=7.38 Hz, 2H) 3.78 (s, 3H) 4.33 (q, J=6.82 Hz, 1H) 6.24 (d, J=7.57 Hz, 1H) 6.55 (d, J=8.71 Hz, 2H) 6.73-6.85 (m, 2H) 7.03-7.19 (m, 3H) 7.27 (t, J=7.95 Hz, 1H) 12.27 (brs, 1H)

Example 191

3-[{[4-({1-[5-(3-methoxyphenyl)-2-methylfuran-3-yl]-3-methylbutyl}amino)phenyl]carbonyl}(methyl)amino]propanoic acid

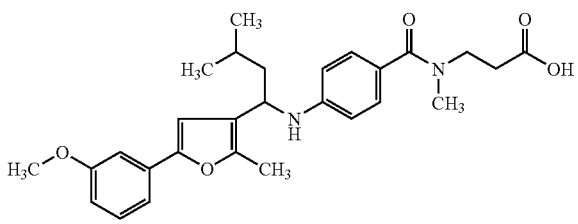

Ethyl 3-[{[4-({1-[5-(3-methoxyphenyl)-2-methylfuran-3-yl]-3-methylbutyl}amino)phenyl]carbonyl}(methyl)amino]propanoate (1200 mg) which is a synthetic intermediate in Example 151 was dissolved in ethanol-hexane (6:4, volume ratio), and the solution was subjected to HPLC using CHIRALPAK AD (50 mmID×500 mL, manufactured by DAICEL CHEMICAL INDUSTRIES, LTD.) and eluted with ethanol-hexane (6:4, volume ratio) as mobile phase at 30° C., a flow rate 60 mL/min. The fractions showing a peak with retention time 14.6 min were collected, and concentrated. The obtained amorphous compound (598 mg) was dissolved in ethanol (5 mL) and tetrahydrofuran (5 mL), 1N lithium hydroxide (2.5 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (508 mg, 90%).

$^1$H NMR (300 MHz, DMSO-$d_6$) δ ppm 0.92 (dd, J=17.98, 6.25 Hz, 6H) 1.46-1.79 (m, 3H) 2.38 (s, 3H) 2.41-2.48 (m, 2H) 2.90 (s, 3H) 3.52 (t, J=7.38 Hz, 2H) 3.78 (s, 3H) 4.33 (q, J=6.82 Hz, 1H) 6.24 (d, J=7.57 Hz, 1H) 6.55 (d, J=8.71 Hz, 2H) 6.73-6.85 (m, 2H) 7.03-7.19 (m, 3H) 7.27 (t, J=7.95 Hz, 1H) 12.27 (brs, 1H)

Example 192

3-({[4-({1-[5-(3-fluorophenyl)-2-methylfuran-3-yl]-3-methylbutyl}amino)phenyl]carbonyl}amino)propanoic acid

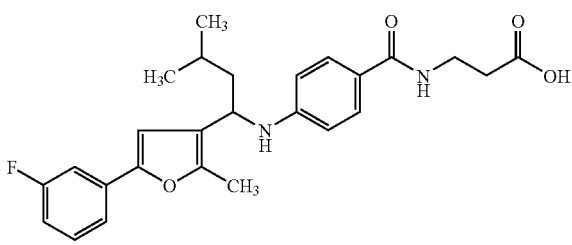

(1) methyl 5-(3-fluorophenyl)-2-methylfuran-3-carboxylate

A mixture of methyl 5-bromo-2-methyl-3-furancarboxylate (2.2 g), 3-fluorophenylboronic acid (1.7 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 15% ethyl acetate/hexane), and crystallized from ethyl acetate/hexane to give the title compound (2.1 g, 92%) as a white solid.

$^1$H NMR (300 MHz, CHLOROFORM-d) δ ppm 2.65 (s, 3H) 3.86 (s, 3H) 6.90 (s, 1H) 6.96 (dd, J=16.66, 2.65 Hz, 1H) 7.28-7.37 (m, 2H) 7.37-7.44 (m, 1H)

(2) [5-(3-fluorophenyl)-2-methylfuran-3-yl]methanol

A solution of methyl 5-(3-fluorophenyl)-2-methylfuran-3-carboxylate (2.1 g) obtained by the above-mentioned reaction in tetrahydrofuran (20 mL) was added dropwise to a suspension of lithium aluminum hydride (0.4 g) in tetrahydrofuran (20 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (1.9 g, 100%) as a white solid.

$^1$H NMR (300 MHz, CHLOROFORM-d) δ ppm 1.43 (brs, 1H) 2.37 (s, 3H) 4.52 (s, 2H) 6.66 (s, 1H) 6.91 (ddd, J=10.31, 9.00, 1.22 Hz, 1H) 7.27-7.44 (m, 3H)

(3) 5-(3-fluorophenyl)-2-methylfuran-3-carbaldehyde

To a solution of [5-(3-fluorophenyl)-2-methylfuran-3-yl]methanol (1.9 g) obtained by the above-mentioned reaction in acetonitrile (30 mL) was added Dess-Martin reagent (4.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (1.4 g, 77%) as a white crystal.

$^1$H NMR (300 MHz, CHLOROFORM-d) δ ppm 2.68 (s, 3H) 6.94 (s, 1H) 6.95-7.08 (m, 1H) 7.29-7.47 (m, 3H) 9.97 (s, 1H)

(4) 1-[5-(3-fluorophenyl)-2-methylfuran-3-yl]-3-methylbutan-1-ol

To a solution of 5-(3-fluorophenyl)-2-methylfuran-3-carbaldehyde (1.4 g) obtained by the above-mentioned reaction in tetrahydrofuran (20 mL) was added dropwise 1N isobutylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.5 g, 83%) as an oil.

$^1$H NMR (300 MHz, CHLOROFORM-d) δ ppm 0.95 (d, J=6.40 Hz, 6H) 1.49-1.82 (m, 3H) 2.36 (s, 3H) 4.71 (t, J=6.97 Hz, 1H) 6.64 (s, 1H) 6.91 (ddd, J=16.62, 2.50, 1.04 Hz, 1H) 7.31 (dt, J=10.03, 2.14 Hz, 2H) 7.35-7.44 (m, 1H)

(5) 3-(1-chloro-3-methylbutyl)-5-(3-fluorophenyl)-2-methylfuran

To a solution of 1-[5-(3-fluorophenyl)-2-methylfuran-3-yl]-3-methylbutan-1-ol (1.5 g) obtained by the above-mentioned reaction in toluene (20 mL) were added thionyl chloride (0.6 mL) and pyridine (0.7 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.6 g, 100%) as an oil.

$^1$H NMR (300 MHz, CHLOROFORM-d) δ ppm 0.94 (dd, J=6.50, 3.30 Hz, 6H) 1.64-1.94 (m, 2H) 1.97-2.11 (m, 1H) 2.37 (s, 3H) 4.94 (t, J=7.63 Hz, 1H) 6.66 (s, 1H) 6.82-7.01 (m, 1H) 7.27-7.45 (m, 3H)

(6) 4-({1-[5-(3-fluorophenyl)-2-methylfuran-3-yl]-3-methylbutyl}amino)benzoic acid A mixture of 3-(1-chloro-3-methylbutyl)-5-(3-fluorophenyl)-2-methylfuran (1.6 g) obtained by the above-mentioned reaction, methyl 4-aminobenzoate (1.3 g), sodium carbonate (0.9 g) and sodium iodide (3.4 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (6 mL) and tetrahydrofuran (6 mL), 2N lithium hydroxide (6 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.4 g, 65%) as an amorphous compound.

$^1$H NMR (300 MHz, CHLOROFORM-d) δ ppm 0.97 (dd, J=17.61, 6.25 Hz, 6H) 1.52-1.83 (m, 3H) 2.40 (s, 3H) 4.40 (t, J=7.00 Hz, 1H) 6.45-6.58 (m, 3H) 6.87-6.98 (m, 1H) 7.27-7.40 (m, 3H) 7.87 (d, J=9.09 Hz, 2H)

(7) 3-({[4-({1-[5-(3-fluorophenyl)-2-methylfuran-3-yl]-3-methylbutyl}amino)phenyl]carbonyl}amino)propanoic acid A solution of 4-({1-[5-(3-fluorophenyl)-2-methylfuran-3-yl]-3-methylbutyl}amino)benzoic acid (191 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (205 mg, 91%).

$^1$H NMR (300 MHz, DMSO-d$_6$) δ ppm 0.92 (dd, J=18.36, 6.25 Hz, 6H) 1.40-1.88 (m, 3H) 2.38 (s, 3H) 2.43 (t, J=7.19 Hz, 2H) 3.32-3.46 (m, 2H) 4.37 (q, J=7.19 Hz, 1H) 6.35 (d, J=7.57 Hz, 1H) 6.55 (d, J=8.71 Hz, 2H) 6.89 (s, 1H) 7.04 (m, 1H) 7.28-7.46 (m, 3H) 7.54 (d, J=8.71 Hz, 2H) 8.00 (t, J=5.49 Hz, 1H) 12.19 (brs, 1H)

Example 193

3-[{[4-({1-[5-(3-fluorophenyl)-2-methylfuran-3-yl]-3-methylbutyl}amino)phenyl]carbonyl}(methyl)amino]propanoic acid

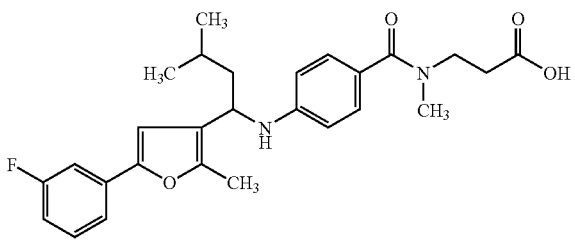

A solution of 4-({1-[5-(3-fluorophenyl)-2-methylfuran-3-yl]-3-methylbutyl}amino)benzoic acid (191 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (203 mg, 87%).

$^1$H NMR (300 MHz, DMSO-d$_6$) δ ppm 0.92 (dd, J=17.80, 6.44 Hz, 6H) 1.46-1.79 (m, 3H) 2.39 (s, 3H) 2.47-2.51 (m, 2H) 2.90 (s, 3H) 3.52 (t, J=7.38 Hz, 2H) 4.33 (q, J=7.32 Hz, 1H) 6.25 (d, J=7.57 Hz, 1H) 6.55 (d, J=8.33 Hz, 2H) 6.90 (s, 1H) 6.95-7.08 (m, 1H) 7.12 (d, J=8.71 Hz, 2H) 7.28-7.48 (m, 3H) 12.24 (brs, 1H)

Example 194

3-({[4-({1-[5-(3-chlorophenyl)-2-methylfuran-3-yl]-3-methylbutyl}amino)phenyl]carbonyl}amino)propanoic acid

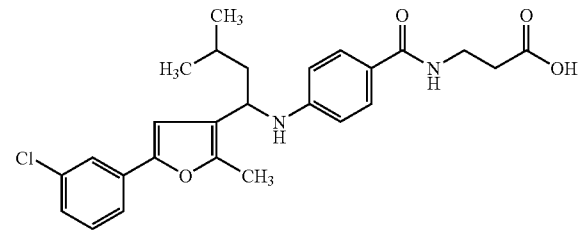

(1) methyl 5-(3-chlorophenyl)-2-methylfuran-3-carboxylate

A mixture of methyl 5-bromo-2-methyl-3-furancarboxylate (2.2 g), 3-chlorophenylboronic acid (1.9 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 15% ethyl acetate/hexane), and crystallized from ethyl acetate/hexane to give the title compound (2.3 g, 92%) as a white solid.

$^1$H NMR (300 MHz, CHLOROFORM-d) δ ppm 2.65 (s, 3H) 3.86 (s, 3H) 6.91 (s, 1H) 7.16-7.25 (m, 1H) 7.31 (t, J=7.95 Hz, 1H) 7.50 (d, J=7.57 Hz, 1H) 7.63 (s, 1H)

(2) [5-(3-chlorophenyl)-2-methylfuran-3-yl]methanol

A solution of methyl 5-(3-chlorophenyl)-2-methylfuran-3-carboxylate (2.3 g) obtained by the above-mentioned reaction in tetrahydrofuran (20 mL) was added dropwise to a suspension of lithium aluminum hydride (0.4 g) in tetrahydrofuran (20 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (2.1 g, 100%) as an oil.

$^1$H NMR (300 MHz, CHLOROFORM-d) δ ppm 1.37 (brs, 1H) 2.37 (s, 3H) 4.51 (s, 2H) 6.66 (s, 1H) 7.10-7.24 (m, 1H) 7.27-7.33 (m, 1H) 7.48 (dt, J=7.82, 1.27 Hz, 1H) 7.61 (t, J=1.79 Hz, 1H)

(3) 5-(3-chlorophenyl)-2-methylfuran-3-carbaldehyde

To a solution of [5-(3-chlorophenyl)-2-methylfuran-3-yl] methanol (2.1 g) obtained by the above-mentioned reaction in acetonitrile (30 mL) was added Dess-Martin reagent (4.7 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (1.8 g, 88%) as a white crystal.

$^1$H NMR (300 MHz, CHLOROFORM-d) δ ppm 2.68 (s, 3H) 6.94 (s, 1H) 7.27-7.39 (m, 2H) 7.52 (dt, J=7.54, 1.41 Hz, 1H) 7.65 (t, J=1.70 Hz, 1H) 9.97 (s, 1H)

(4) 1-[5-(3-chlorophenyl)-2-methylfuran-3-yl]-3-methylbutan-1-ol

To a solution of 5-(3-chlorophenyl)-2-methylfuran-3-carbaldehyde (1.4 g) obtained by the above-mentioned reaction in tetrahydrofuran (20 mL) was added dropwise 1N isobutylmagnesium bromide-tetrahydrofuran solution (12 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.9 g, 85%) as an oil.

$^1$H NMR (300 MHz, CHLOROFORM-d) δ ppm 0.95 (d, J=6.40 Hz, 6H) 1.48-1.82 (m, 3H) 2.36 (s, 3H) 4.71 (t, J=6.97 Hz, 1H) 6.65 (s, 1H) 7.19 (dd, J=1.79, 1.04 Hz, 1H) 7.27-7.32 (m, 1H) 7.44-7.52 (m, 1H) 7.61 (t, J=1.79 Hz, 1H)

(5) 3-(1-chloro-3-methylbutyl)-5-(3-fluorophenyl)-2-methylfuran

To a solution of 1-[5-(3-chlorophenyl)-2-methylfuran-3-yl]-3-methylbutan-1-ol (1.9 g) obtained by the above-mentioned reaction in toluene (20 mL) were added thionyl chloride (0.7 mL) and pyridine (0.8 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (2.0 g, 100%) as an oil.

$^1$H NMR (300 MHz, CHLOROFORM-d) δ ppm 0.94 (dd, J=6.50, 3.49 Hz, 6H) 1.63-1.92 (m, 2H) 1.97-2.12 (m, 1H) 2.37 (s, 3H) 4.94 (t, J=7.72 Hz, 1H) 6.67 (s, 1H) 7.10-7.25 (m, 2H) 7.49 (dt, J=7.72, 1.32 Hz, 1H) 7.61 (t, J=1.79 Hz, 1H)

(6) 4-({1-[5-(3-chlorophenyl)-2-methylfuran-3-yl]-3-methylbutyl}amino)benzoic acid A mixture of 3-(1-chloro-3-methylbutyl)-5-(3-chlorophenyl)-2-methylfuran (2.0 g) obtained by the above-mentioned reaction, methyl 4-aminobenzoate (1.5 g), sodium carbonate (1.1 g) and sodium iodide (4.0 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (7 mL) and tetrahydrofuran (7 mL), 2N lithium hydroxide (7 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.5 g, 54%) as an amorphous compound.

$^1$H NMR (300 MHz, CHLOROFORM-d) δ ppm 0.97 (dd, J=17.42, 6.44 Hz, 6H) 1.50-1.83 (m, 3H) 2.40 (s, 3H) 4.39 (t, J=7.00 Hz, 1H) 6.43-6.65 (m, 3H) 7.12-7.21 (m, 1H) 7.21-7.28 (m, 1H) 7.45 (d, J=7.95 Hz, 1H) 7.57 (t, J=1.89 Hz, 1H) 7.87 (d, J=9.09 Hz, 2H)

(7) 3-({[4-({1-[5-(3-chlorophenyl)-2-methylfuran-3-yl]-3-methylbutyl}amino)phenyl]carbonyl}amino) propanoic acid A solution of 4-({1-[5-(3-chlorophenyl)-2-methylfuran-3-yl]-3-methylbutyl}amino)benzoic acid (199 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (217 mg, 93%).

$^1$H NMR (300 MHz, DMSO-$d_6$) δ ppm 0.92 (dd, J=18.17, 6.44 Hz, 6H) 1.48-1.80 (m, 3H) 2.38 (s, 3H) 2.44 (t, J=7.00 Hz, 2H) 3.33-3.46 (m, 2H) 4.21-4.47 (m, 1H) 6.34 (d, J=7.57 Hz, 1H) 6.55 (d, J=8.71 Hz, 2H) 6.92 (s, 1H) 7.17-7.32 (m, 1H) 7.39 (t, J=7.95 Hz, 1H) 7.46-7.66 (m, 4H) 7.99 (t, J=5.49 Hz, 1H) 12.14 (s, 1H)

Example 195

3-[{[4-({1-[5-(3-chlorophenyl)-2-methylfuran-3-yl]-3-methylbutyl}amino)phenyl]carbonyl}(methyl)amino]propanoic acid

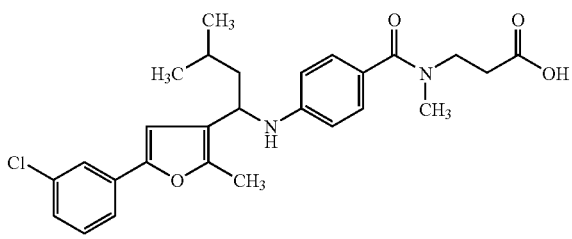

A solution of 4-({1-[5-(3-chlorophenyl)-2-methylfuran-3-yl]-3-methylbutyl}amino)benzoic acid (199 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (216 mg, 89%).

$^1$H NMR (300 MHz, DMSO-$d_6$) δ ppm 0.92 (dd, J=17.80, 6.44 Hz, 6H) 1.46-1.79 (m, 3H) 2.39 (s, 3H) 2.45-2.56 (m, 2H) 2.90 (s, 3H) 3.52 (t, J=7.38 Hz, 2H) 4.33 (q, J=7.19 Hz, 1H) 6.24 (d, J=7.57 Hz, 1H) 6.55 (d, J=8.71 Hz, 2H) 6.94 (s, 1H) 7.12 (d, J=8.33 Hz, 2H) 7.21-7.32 (m, 1H) 7.39 (t, J=7.95 Hz, 1H) 7.53 (d, J=7.95 Hz, 1H) 7.60 (s, 1H) 12.23 (s, 1H)

Example 196

3-({[4-({1-[5-(2-fluoro-5-methoxyphenyl)-2-methylfuran-3-yl]-3-methylbutyl}amino)phenyl]carbonyl}amino)propanoic acid

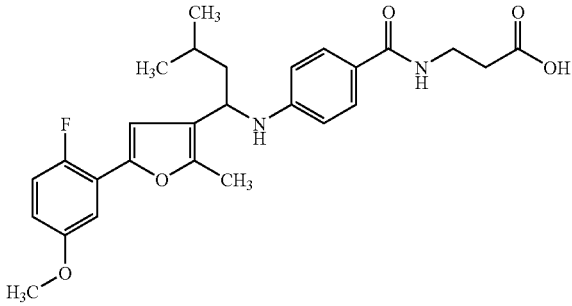

(1) 5-(2-fluoro-5-methoxyphenyl)-2-methylfuran-3-carbaldehyde

A mixture of 5-bromo-2-methylfuran-3-carbaldehyde (1.3 g), 2-fluoro-5-methoxyphenylboronic acid (1.4 g), tetrakis(triphenylphosphine)palladium(0) (0.4 g), 2N aqueous sodium carbonate solution (9 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane), and crystallized from ethyl acetate/hexane to give the title compound (1.5 g, 93%) as a white crystal.

$^1$H NMR (300 MHz, CHLOROFORM-d) δ ppm 2.69 (s, 3H) 3.85 (s, 3H) 6.69-6.85 (m, 1H) 6.95-7.17 (m, 2H) 7.22-7.33 (m, 1H) 9.98 (s, 1H)

(2) 1-[5-(2-fluoro-5-methoxyphenyl)-2-methylfuran-3-yl]-3-methylbutan-1-ol

To a solution of 5-(2-fluoro-5-methoxyphenyl)-2-methylfuran-3-carbaldehyde (1.5 g) obtained by the above-mentioned reaction in tetrahydrofuran (20 mL) was added dropwise 1N isobutylmagnesium bromide-tetrahydrofuran solution (9 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.7 g, 90%) as an oil.

$^1$H NMR (300 MHz, CHLOROFORM-d) δ ppm 0.95 (d, J=6.40 Hz, 6H) 1.50-1.83 (m, 3H) 2.38 (s, 3H) 3.83 (s, 3H) 4.72 (td, J=6.97, 3.20 Hz, 1H) 6.71 (dt, J=8.76, 3.53 Hz, 1H) 6.81 (d, J=3.77 Hz, 1H) 7.01 (dd, J=10.64, 8.95 Hz, 1H) 7.25-7.28 (m, 1H)

(3) 3-(1-chloro-3-methylbutyl)-5-(2-fluoro-5-methoxyphenyl)-2-methylfuran

To a solution of 1-[5-(2-fluoro-5-methoxyphenyl)-2-methylfuran-3-yl]-3-methylbutan-1-ol (1.7 g) obtained by the above-mentioned reaction in toluene (20 mL) were added thionyl chloride (0.6 mL) and pyridine (0.7 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.8 g, 100%) as an oil.

$^1$H NMR (300 MHz, CHLOROFORM-d) δ ppm 0.94 (dd, J=6.40, 3.20 Hz, 6H) 1.66-1.80 (m, 2H) 1.96-2.16 (m, 1H) 2.39 (s, 3H) 3.83 (s, 3H) 4.96 (t, J=7.63 Hz, 1H) 6.72 (dt, J=8.90, 3.56 Hz, 1H) 6.83 (d, J=3.58 Hz, 1H) 7.01 (dd, J=10.55, 9.04 Hz, 1H) 7.21-7.36 (m, 1H)

(4) 4-({1-[5-(2-fluoro-5-methoxyphenyl)-2-methylfuran-3-yl]-3-methylbutyl}amino)benzoic acid A mixture of 3-(1-chloro-3-methylbutyl)-5-(2-fluoro-5-methoxyphenyl)-2-methylfuran (1.8 g) obtained by the above-mentioned reaction, methyl 4-aminobenzoate (1.3 g), sodium carbonate (0.9 g) and sodium iodide (1.7 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (6 mL) and tetrahydrofuran (6 mL), 2N lithium hydroxide (6 mL) was added, and the mixture was stirred at 70° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.3 g, 55%) as an amorphous compound.

$^1$H NMR (300 MHz, CHLOROFORM-d) δ ppm 0.97 (dd, J=18.08, 6.22 Hz, 6H) 1.51-1.84 (m, 3H) 2.41 (s, 3H) 3.82 (s, 3H) 4.41 (t, J=6.97 Hz, 1H) 6.53 (d, J=8.85 Hz, 2H) 6.63-6.76 (m, 2H) 6.98 (dd, J=10.74, 9.04 Hz, 1H) 7.19-7.28 (m, 1H) 7.87 (d, J=8.85 Hz, 2H)

(5) 3-({[4-({1-[5-(2-fluoro-5-methoxyphenyl)-2-methylfuran-3-yl]-3-methylbutyl}amino)phenyl]carbonyl}amino)propanoic acid A solution of 4-({1-[5-(2-fluoro-5-methoxyphenyl)-2-methylfuran-3-yl]-3-methylbutyl}amino)benzoic acid (205 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (200 mg, 83%).

$^1$H NMR (300 MHz, DMSO-d$_6$) δ ppm 0.92 (dd, J=17.90, 6.22 Hz, 6H) 1.42-1.87 (m, 3H) 2.40-2.45 (m, 5H) 3.36 (q, J=5.65 Hz, 2H) 3.76 (s, 3H) 4.41 (d, J=7.91 Hz, 1H) 6.41 (d, J=8.29 Hz, 1H) 6.55 (d, J=8.85 Hz, 2H) 6.73-6.89 (m, 2H) 7.06-7.14 (m, 2H) 7.54 (d, J=8.85 Hz, 2H) 7.91-8.08 (m, 1H) 12.23 (brs, 1H)

Example 197

3-[{[4-({1-[5-(2-fluoro-5-methoxyphenyl)-2-methylfuran-3-yl]-3-methylbutyl}amino)phenyl]carbonyl}(methyl)amino]propanoic acid

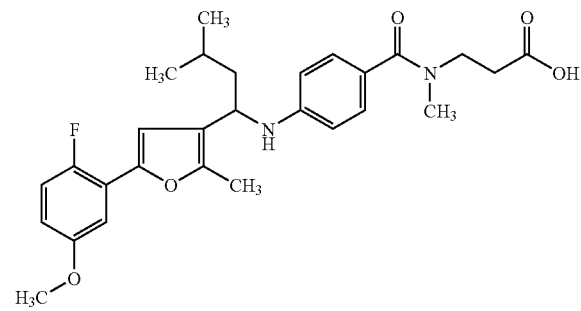

A solution of 4-({1-[5-(2-fluoro-5-methoxyphenyl)-2-methylfuran-3-yl]-3-methylbutyl}amino)benzoic acid (205 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (209 mg, 84%).

$^1$H NMR (300 MHz, DMSO-d$_6$) δ ppm 0.92 (dd, J=17.33, 6.22 Hz, 6H) 1.45-1.78 (m, 3H) 2.41 (s, 3H) 2.44-2.49 (m, 2H) 2.90 (s, 3H) 3.52 (t, J=7.35 Hz, 2H) 3.76 (s, 3H) 4.37 (q, J=7.47 Hz, 1H) 6.32 (d, J=8.10 Hz, 1H) 6.55 (d, J=8.67 Hz, 2H) 6.73-6.90 (m, 2H) 7.06-7.16 (m, 3H) 7.18 (d, J=2.07 Hz, 1H) 12.31 (brs, 1H)

Example 198

3-({[4-({1-[5-(2-fluoro-3-methoxyphenyl)-2-methylfuran-3-yl]-3-methylbutyl}amino)phenyl]carbonyl}amino)propanoic acid

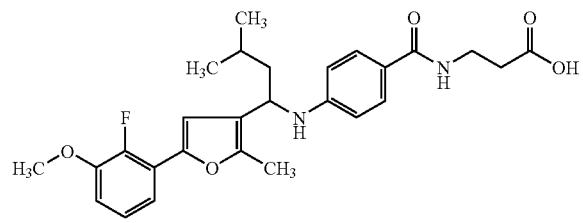

(1) 5-(2-fluoro-3-methoxyphenyl)-2-methylfuran-3-carbaldehyde

A mixture of 5-bromo-2-methylfuran-3-carbaldehyde (1.3 g), 2-fluoro-3-methoxyphenylboronic acid (1.4 g), tetrakis(triphenylphosphine)palladium(0) (0.4 g), 2N aqueous sodium carbonate solution (9 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane), and crystallized from ethyl acetate/hexane to give the title compound (1.5 g, 93%) as a yellow crystal.

$^1$H NMR (300 MHz, CHLOROFORM-d) δ ppm 2.68 (s, 3H) 3.92 (s, 3H) 6.92 (td, J=8.10, 1.51 Hz, 1H) 7.05-7.18 (m, 2H) 7.36 (ddd, J=7.96, 6.36, 1.51 Hz, 1H) 9.99 (s, 1H)

(2) 1-[5-(2-fluoro-3-methoxyphenyl)-2-methylfuran-3-yl]-3-methylbutan-1-ol

To a solution of 5-(2-fluoro-3-methoxyphenyl)-2-methylfuran-3-carbaldehyde (1.5 g) obtained by the above-mentioned reaction in tetrahydrofuran (20 mL) was added dropwise 1N isobutylmagnesium bromide-tetrahydrofuran solution (9 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.5 g, 78%) as an oil.

$^1$H NMR (300 MHz, CHLOROFORM-d) δ ppm 0.95 (d, J=6.40 Hz, 6H) 1.51-1.83 (m, 3H) 2.37 (s, 3H) 3.91 (s, 3H) 4.72 (td, J=6.92, 3.30 Hz, 1H) 6.78-6.90 (m, 2H) 7.07 (td, J=8.10, 1.51 Hz, 1H) 7.35 (ddd, J=7.96, 6.45, 1.60 Hz, 1H)

(3) 3-(1-chloro-3-methylbutyl)-5-(2-fluoro-3-methoxyphenyl)-2-methylfuran

To a solution of 1-[5-(2-fluoro-3-methoxyphenyl)-2-methylfuran-3-yl]-3-methylbutan-1-ol (1.5 g) obtained by the above-mentioned reaction in toluene (20 mL) were added thionyl chloride (0.5 mL) and pyridine (0.6 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.6 g, 100%) as an oil.

$^1$H NMR (300 MHz, CHLOROFORM-d) δ ppm 0.94 (dd, J=6.63, 2.84 Hz, 6H) 1.65-1.81 (m, 2H) 1.99-2.14 (m, 1H) 2.38 (s, 3H) 3.91 (s, 3H) 4.96 (t, J=7.76 Hz, 1H) 6.79-6.93 (m, 2H) 7.07 (td, J=7.95, 1.51 Hz, 1H) 7.35 (ddd, J=8.14, 6.44, 1.70 Hz, 1H)

(4) 4-({1-[5-(2-fluoro-3-methoxyphenyl)-2-methylfuran-3-yl]-3-methylbutyl}amino)benzoic acid A mixture of 3-(1-chloro-3-methylbutyl)-5-(2-fluoro-3-methoxyphenyl)-2-methylfuran (1.6 g) obtained by the above-mentioned reaction, methyl 4-aminobenzoate (1.1 g), sodium carbonate (0.8 g) and sodium iodide (1.5 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (5 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.2 g, 57%) as a white crystal.

$^1$H NMR (300 MHz, CHLOROFORM-d) δ ppm 0.96 (dd, J=18.27, 6.22 Hz, 6H) 1.47-1.67 (m, 3H) 2.40 (s, 3H) 3.89 (s, 3H) 4.42 (t, J=6.97, 1H) 6.54 (d, J=8.85 Hz, 2H) 6.71 (d, J=3.58 Hz, 1H) 6.82 (td, J=8.05, 1.60 Hz, 1H) 7.06 (td, J=8.10, 1.32 Hz, 1H) 7.33 (ddd, J=8.01, 6.50, 1.51 Hz, 1H) 7.86 (d, J=8.85 Hz, 2H)

(5) 3-({[4-({1-[5-(2-fluoro-3-methoxyphenyl)-2-methylfuran-3-yl]-3-methylbutyl}amino)phenyl]carbonyl}amino)propanoic acid A solution of 4-({1-[5-(2-fluoro-3-methoxyphenyl)-2-methylfuran-3-yl]-3-methylbutyl}amino)benzoic acid (205 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (207 mg, 86%).

$^1$H NMR (300 MHz, DMSO-d$_6$) δ ppm 0.92 (dd, J=17.80, 6.31 Hz, 6H) 1.46-1.79 (m, 3H) 2.34-2.47 (m, 5H) 3.35 (q, J=6.97 Hz, 2H) 3.84 (s, 3H) 4.41 (q, J=7.54 Hz, 1H) 6.43 (d, J=8.29 Hz, 1H) 6.55 (d, J=8.85 Hz, 2H) 6.77 (d, J=3.77 Hz, 1H) 7.06 (dd, J=8.10, 1.70 Hz, 1H) 7.14 (t, J=8.19 Hz, 1H) 7.21 (dd, J=6.41, 1.70 Hz, 1H) 7.54 (d, J=8.67 Hz, 2H) 8.01 (t, J=5.46 Hz, 1H) 12.20 (brs, 1H)

Example 199

3-[{[4-({1-[5-(2-fluoro-3-methoxyphenyl)-2-methylfuran-3-yl]-3-methylbutyl}amino)phenyl]carbonyl}(methyl)amino]propanoic acid

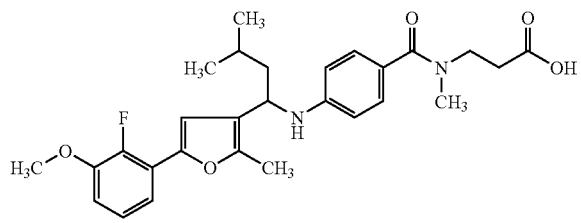

A solution of 4-({1-[5-(2-fluoro-3-methoxyphenyl)-2-methylfuran-3-yl]-3-methylbutyl}amino)benzoic acid (205 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (206 mg, 83%).

$^1$H NMR (300 MHz, DMSO-d$_6$) δ ppm 0.92 (dd, J=17.33, 6.40 Hz, 6H) 1.45-1.78 (m, 3H) 2.40 (s, 3H) 2.48-2.52 (m, 2H) 2.90 (s, 3H) 3.52 (t, J=7.35 Hz, 2H) 3.84 (s, 3H) 4.37 (q, J=7.41 Hz, 1H) 6.33 (d, J=7.91 Hz, 1H) 6.55 (d, J=8.67 Hz, 2H) 6.78 (d, J=3.58 Hz, 1H) 7.02-7.26 (m, 5H) 12.24 (brs, 1H)

Example 200

3-({[4-({1-[5-(6-chloropyridin-3-yl)-2-methylfuran-3-yl]-3-methylbutyl}amino)phenyl]carbonyl}amino)propanoic acid

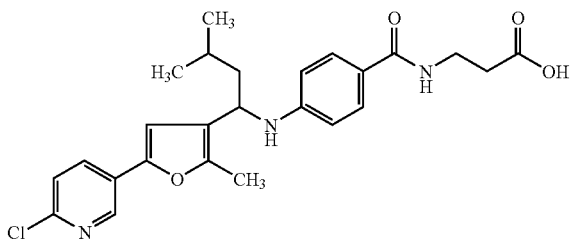

(1) 5-(6-chloropyridin-3-yl)-2-methylfuran-3-carbaldehyde

A mixture of 5-bromo-2-methylfuran-3-carbaldehyde (1.3 g), 2-chloropyridine-5-boronic acid (1.3 g), tetrakis(triphenylphosphine)palladium(0) (0.4 g), 2N aqueous sodium carbonate solution (9 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane), and crystallized from ethyl acetate/hexane to give the title compound (1.1 g, 68%) as a yellow solid.
$^1$H NMR (300 MHz, CHLOROFORM-d) δ ppm 2.70 (s, 3H) 7.01 (s, 1H) 7.37 (d, J=8.33 Hz, 1H) 7.88 (dd, J=8.33, 2.65 Hz, 1H) 8.69 (d, J=2.27 Hz, 1H) 9.98 (s, 1H)

(2) 1-[5-(6-chloropyridin-3-yl)-2-methylfuran-3-yl]-3-methylbutan-1-ol

To a solution of 5-(6-chloropyridin-3-yl)-2-methylfuran-3-carbaldehyde (1.0 g) obtained by the above-mentioned reaction in tetrahydrofuran (20 mL) was added dropwise 1N isobutylmagnesium bromide-tetrahydrofuran solution (7 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.0 g, 79%) as a yellow crystal.
$^1$H NMR (300 MHz, CHLOROFORM-d) δ ppm 0.95 (d, J=6.40 Hz, 6H) 1.45-1.60 (m, 1H) 1.60-1.90 (m, 2H) 2.37 (s, 3H) 4.72 (ddd, J=10.31, 3.72, 3.48 Hz, 1H) 6.71 (s, 1H) 7.31 (d, J=8.29 Hz, 1H) 7.83 (dd, J=8.38, 2.54 Hz, 1H) 8.63 (d, J=1.88 Hz, 1H)

(3) 2-chloro-5-[4-(1-chloro-3-methylbutyl)-5-methylfuran-2-yl]pyridine

To a solution of 1-[5-(6-chloropyridin-3-yl)-2-methylfuran-3-yl]-3-methylbutan-1-ol (1.0 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.1 g, 100%) as a yellow crystal.
$^1$H NMR (300 MHz, CHLOROFORM-d) δ ppm 0.95 (dd, J=6.44, 3.41 Hz, 6H) 1.79-1.91 (m, 2H) 2.00-2.19 (m, 1H) 2.38 (s, 3H) 4.84-5.08 (m, 1H) 6.73 (s, 1H) 7.32 (d, J=8.33 Hz, 1H) 7.84 (dd, J=8.33, 2.27 Hz, 1H) 8.64 (d, J=2.65 Hz, 1H)

(4) 4-({1-[5-(6-chloropyridin-3-yl)-2-methylfuran-3-yl]-3-methylbutyl}amino)benzoic acid A mixture of 2-chloro-5-[4-(1-chloro-3-methylbutyl)-5-methylfuran-2-yl]pyridine (1.1 g) obtained by the above-mentioned reaction, methyl 4-aminobenzoate (0.9 g), sodium carbonate (0.6 g) and sodium iodide (1.1 g) in N,N-dimethylacetamide (20 mL) was stirred overnight at 80° C. The reaction mixture was, poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.9 g, 62%) as an amorphous compound.
$^1$H NMR (300 MHz, CHLOROFORM-d) δ ppm 0.97 (dd, J=16.20, 6.22 Hz, 6H) 1.51-1.83 (m, 3H) 2.42 (s, 3H) 4.40 (t, J=6.97 Hz, 1H) 6.52 (d, J=8.85 Hz, 2H) 6.59 (s, 1H) 7.28 (d, J=8.48 Hz, 1H) 7.80 (dd, J=8.38, 2.54 Hz, 1H) 7.87 (d, J=8.85 Hz, 2H) 8.60 (d, J=1.88 Hz, 1H)

(5) 3-({[4-({1-[5-(6-chloropyridin-3-yl)-2-methylfuran-3-yl]-3-methylbutyl}amino)phenyl]carbonyl}amino)propanoic acid A solution of 4-({1-[5-(6-chloropyridin-3-yl)-2-methylfuran-3-yl]-3-methylbutyl}amino)benzoic acid (199 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (212 mg, 90%).

¹H NMR (300 MHz, DMSO-d₆) δ ppm 0.92 (dd, J=17.99, 6.31 Hz, 6H) 1.47-1.80 (m, 3H) 2.35-2.47 (m, 5H) 3.34-3.47 (m, 2H) 4.38 (q, J=7.22 Hz, 1H) 6.39 (d, J=7.54 Hz, 1H) 6.55 (d, J=8.85 Hz, 2H) 7.00 (s, 1H) 7.50 (d, J=9.04 Hz, 1H) 7.54 (d, J=8.85 Hz, 2H) 7.92-8.10 (m, 2H) 8.62 (d, J=2.07 Hz, 1H) 12.19 (brs, 1H)

Example 201

3-[{[4-({1-[5-(6-chloropyridin-3-yl)-2-methylfuran-3-yl]-3-methylbutyl}amino)phenyl]carbonyl}(methyl)amino]propanoic acid

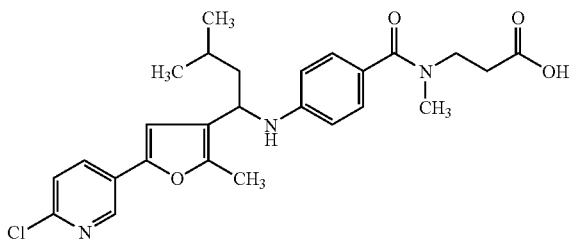

A solution of 4-({1-[5-(6-chloropyridin-3-yl)-2-methylfuran-3-yl]-3-methylbutyl}amino)benzoic acid (199 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (220 mg, 91%).

¹H NMR (300 MHz, DMSO-d₆) δ ppm 0.92 (dd, J=17.43, 6.31 Hz, 6H) 1.47-1.80 (m, 3H) 2.40 (s, 3H) 2.44-2.49 (m, 2H) 2.90 (s, 3H) 3.52 (t, J=7.25 Hz, 2H) 4.34 (q, J=7.22 Hz, 1H) 6.28 (d, J=7.35 Hz, 1H) 6.55 (d, J=8.67 Hz, 2H) 7.01 (s, 1H) 7.12 (d, J=8.67 Hz, 2H) 7.50 (d, J=8.48 Hz, 1H) 8.00 (dd, J=8.38, 2.54 Hz, 1H) 8.63 (d, J=1.88 Hz, 1H) 12.27 (brs, 1H)

Example 202

3-({[4-({cyclohexyl[5-(3,5-dimethylisoxazol-4-yl)-2-methylfuran-3-yl]methyl}amino)phenyl]carbonyl}amino)propanoic acid

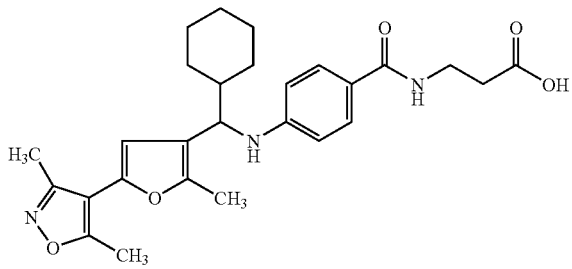

(1) 5-(3,5-dimethylisoxazol-4-yl)-2-methylfuran-3-carbaldehyde

A mixture of 5-bromo-2-methylfuran-3-carbaldehyde (1.9 g), 3,5-dimethylisoxazole-4-boronic acid (1.7 g), tetrakis(triphenylphosphine)palladium(0) (0.6 g), 2N aqueous sodium carbonate solution (9 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane), and crystallized from ethyl acetate/hexane to give the title compound (1.4 g, 69%) as a yellow crystal.

¹H NMR (300 MHz, CHLOROFORM-d) δ ppm 2.40 (s, 3H) 2.58 (s, 3H) 2.66 (s, 3H) 6.63 (s, 1H) 9.97 (s, 1H)

(2) cyclohexyl[5-(3,5-dimethylisoxazol-4-yl)-2-methylfuran-3-yl]methanol

To a solution of 5-(3,5-dimethylisoxazol-4-yl)-2-methylfuran-3-carbaldehyde (0.7 g) obtained by the above-mentioned reaction in tetrahydrofuran (20 mL) was added dropwise 1N cyclohexylmagnesium bromide-tetrahydrofuran solution (5.1 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (0.9 g, 89%) as a white crystal.

¹H NMR (300 MHz, CHLOROFORM-d) δ ppm 0.81-1.35 (m, 5H) 1.48-1.83 (m, 5H) 1.97-2.16 (m, 1H) 2.30 (s, 3H) 2.39 (s, 3H) 2.56 (s, 3H) 4.31 (dd, J=7.91, 3.01 Hz, 1H) 6.28 (s, 1H)

(3) 4-{4-[chloro(cyclohexyl)methyl]-5-methylfuran-2-yl}-3,5-dimethylisoxazole

To a solution of cyclohexyl[5-(3,5-dimethylisoxazol-4-yl)-2-methylfuran-3-yl]methanol (0.9 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.9 g, 100%) as an oil.

¹H NMR (300 MHz, CHLOROFORM-d) δ ppm 0.69-1.44 (m, 5H) 1.59-1.93 (m, 5H) 2.18 (br. s., 1H) 2.30 (s, 3H) 2.40 (s, 3H) 2.56 (s, 3H) 4.60 (d, J=8.67 Hz, 1H) 6.29 (s, 1H)

(4) 4-({cyclohexyl[5-(3,5-dimethylisoxazol-4-yl)-2-methylfuran-3-yl]methyl}amino)benzoic acid A mixture of 4-{4-[chloro(cyclohexyl)methyl]-5-methylfuran-2-yl}-3,5-dimethylisoxazole (0.9 g) obtained by the above-mentioned reaction, methyl 4-aminobenzoate (0.7 g), sodium carbonate (0.5 g) and sodium iodide (0.9 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (3 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 55% ethyl acetate/hexane) to give the title compound (0.9 g, 73%) as an amorphous compound.

$^1$H NMR (300 MHz, CHLOROFORM-d) δ ppm 0.93-1.38 (m, 5H) 1.43-1.88 (m, 5H) 1.90-2.02 (m, 1H) 2.35 (s, 3H) 2.36 (s, 3H) 2.53 (s, 3H) 4.09-4.12 (m, 1H) 6.11 (s, 1H) 6.50 (d, J=8.85 Hz, 2H) 7.85 (d, J=8.85 Hz, 2H)

(5) 3-({[4-({1-[5-(3,5-dimethylisoxazol-4-yl)-2-methylfuran-3-yl]-3-methylbutyl}amino)phenyl]carbonyl}amino)propanoic acid A solution of 4-({cyclohexyl[5-(3,5-dimethylisoxazol-4-yl)-2-methylfuran-3-yl]methyl}amino)benzoic acid (204 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (221 mg, 92%).

$^1$H NMR (300 MHz, DMSO-d$_6$) δ ppm 0.78-1.33 (m, 5H) 1.54-1.83 (m, 5H) 2.02 (d, J=12.06 Hz, 1H) 2.29 (s, 3H) 2.34 (s, 3H) 2.43 (t, J=7.16 Hz, 2H) 2.50 (s, 3H) 3.37 (q, J=5.84 Hz, 2H) 4.13 (t, J=8.29 Hz, 1H) 6.31 (d, J=8.48 Hz, 1H) 6.47 (s, 1H) 6.56 (d, J=8.85 Hz, 2H) 7.53 (d, J=8.67 Hz, 2H) 8.00 (d, J=8.29 Hz, 1H) 12.19 (brs, 1H)

Example 203

3-({[4-({cyclohexyl[5-(3,5-dimethylisoxazol-4-yl)-2-methylfuran-3-yl]methyl}amino)phenyl]carbonyl}(methyl)amino)propanoic acid

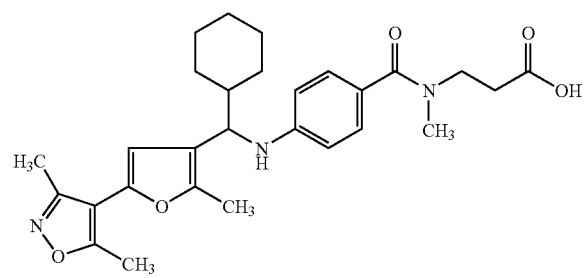

A solution of 4-({cyclohexyl[5-(3,5-dimethylisoxazol-4-yl)-2-methylfuran-3-yl]methyl}amino)benzoic acid (204 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (221 mg, 90%).

$^1$H NMR (300 MHz, DMSO-d$_6$) δ ppm 0.93-1.25 (m, 5H) 1.46-1.79 (m, 5H) 2.00 (d, J=2.64 Hz, 1H) 2.29 (s, 3H) 2.34 (s, 3H) 2.47-2.51 (m, 2H) 2.90 (s, 3H) 3.52 (t, J=7.44 Hz, 2H) 4.09 (t, J=8.10 Hz, 1H) 6.20 (d, J=8.48 Hz, 1H) 6.48 (s, 1H) 6.55 (d, J=8.85 Hz, 2H) 7.10 (d, J=8.67 Hz, 2H) 12.30 (brs, 1H)

Example 204

3-({[4-({1-[5-(3,5-dimethylisoxazol-4-yl)-2-methylfuran-3-yl]-3-methylbutyl}amino)phenyl]carbonyl}amino)propanoic acid

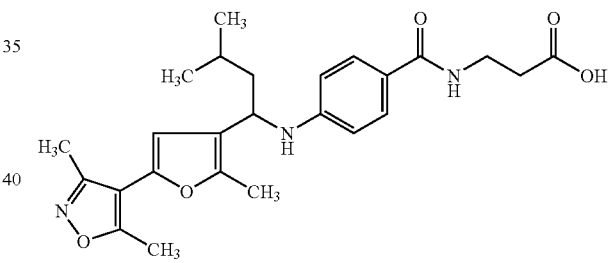

(1) 1-[5-(3,5-dimethylisoxazol-4-yl)-2-methylfuran-3-yl]-3-methylbutan-1-ol

To a solution of 5-(3,5-dimethylisoxazol-4-yl)-2-methylfuran-3-carbaldehyde (0.7 g) obtained by the above-mentioned reaction in tetrahydrofuran (20 mL) was added dropwise 1N isobutylmagnesium bromide-tetrahydrofuran solution (5.1 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (0.8 g, 89%) as an oil.

$^1$H NMR (300 MHz, CHLOROFORM-d) δ ppm 0.95 (d, J=6.40 Hz, 6H) 1.43-1.59 (m, 1H) 1.59-1.86 (m, 2H) 2.34 (s, 3H) 2.39 (s, 3H) 2.56 (s, 3H) 4.73 (dt, J=6.45, 3.84 Hz, 1H) 6.30 (s, 1H)

(2) 4-[4-(1-chloro-3-methylbutyl)-5-methylfuran-2-yl]-3,5-dimethylisoxazole

To a solution of 1-[5-(3,5-dimethylisoxazol-4-yl)-2-methylfuran-3-yl]-3-methylbutan-1-ol (0.9 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.9 g, 100%) as an oil.

$^1$H NMR (300 MHz, CHLOROFORM-d) δ ppm 0.95 (dd, J=6.50, 2.17 Hz, 6H) 1.66-1.89 (m, 2H) 1.97-2.14 (m, 1H) 2.35 (s, 3H) 2.40 (s, 3H) 2.56 (s, 3H) 4.95 (dd, J=8.19, 6.88 Hz, 1H) 6.32 (s, 1H)

(3) 4-({1-[5-(3,5-dimethylisoxazol-4-yl)-2-methylfuran-3-yl]-3-methylbutyl}amino)benzoic acid A mixture of 4-[4-(1-chloro-3-methylbutyl)-5-methylfuran-2-yl]-3,5-dimethylisoxazole (0.9 g) obtained by the above-mentioned reaction, methyl 4-aminobenzoate (0.7 g), sodium carbonate (0.5 g) and sodium iodide (0.9 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (3 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 55% ethyl acetate/hexane) to give the title compound (0.6 g, 51%) as an amorphous compound.

$^1$H NMR (300 MHz, CHLOROFORM-d) δ ppm 0.97 (dd, J=16.86, 6.31 Hz, 6H) 1.53-1.84 (m, 3H) 2.36 (s, 3H) 2.38 (s, 3H) 2.53 (s, 3H) 4.40 (t, J=7.06 Hz, 1H) 6.17 (s, 1H) 6.53 (d, J=8.85 Hz, 2H) 7.88 (d, J=8.85 Hz, 2H)

(4) 3-({[4-({1-[5-(3,5-dimethylisoxazol-4-yl)-2-methylfuran-3-yl]-3-methylbutyl}amino)phenyl]carbonyl}amino)propanoic acid A solution of 4-({1-[5-(3,5-dimethylisoxazol-4-yl)-2-methylfuran-3-yl]-3-methylbutyl}amino)benzoic acid (191 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (203 mg, 89%).

$^1$H NMR (300 MHz, DMSO-d$_6$) δ ppm 0.92 (dd, J=17.98, 6.25 Hz, 6H) 1.46-1.79 (m, 3H) 2.29 (s, 3H) 2.36 (s, 3H) 2.44 (t, J=7.19 Hz, 2H) 3.32-3.53 (m, 2H) 4.39 (q, J=7.70 Hz, 1H) 6.32 (d, J=8.33 Hz, 1H) 6.50 (s, 1H) 6.56 (d, J=9.09 Hz, 2H) 7.55 (d, J=8.71 Hz, 2H) 8.02 (t, J=5.49 Hz, 1H) 12.16 (brs, 1H)

Example 205

3-[{[4-({1-[5-(3,5-dimethylisoxazol-4-yl)-2-methylfuran-3-yl]-3-methylbutyl}amino)phenyl]carbonyl}(methyl)amino]propanoic acid

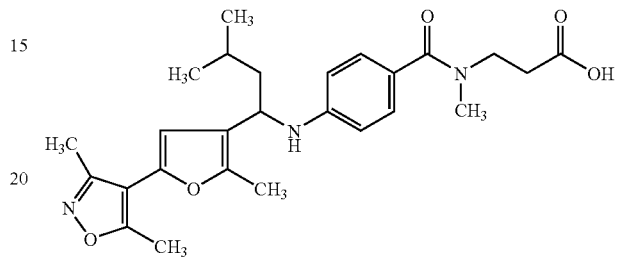

A solution of 4-({1-[5-(3,5-dimethylisoxazol-4-yl)-2-methylfuran-3-yl]-3-methylbutyl}amino)benzoic acid (191 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (191 mg, 89%).

$^1$H NMR (300 MHz, DMSO-d$_6$) δ ppm 0.92 (dd, J=17.04, 6.06 Hz, 6H) 1.45-1.78 (m, 3H) 2.30 (s, 3H) 2.36 (s, 3H) 2.47-2.51 (m, 2H) 2.91 (s, 3H) 3.52 (t, J=7.38 Hz, 2H) 4.36 (q, J=7.57 Hz, 1H) 6.22 (d, J=8.33 Hz, 1H) 6.50 (s, 1H) 6.56 (d, J=8.71 Hz, 2H) 7.12 (d, J=8.33 Hz, 2H) 12.27 (brs, 1H)

Example 206

3-({[4-({cyclohexyl[2-methyl-5-(1-methyl-1H-pyrazol-4-yl)furan-3-yl]methyl}amino)phenyl]carbonyl}amino)propanoic acid

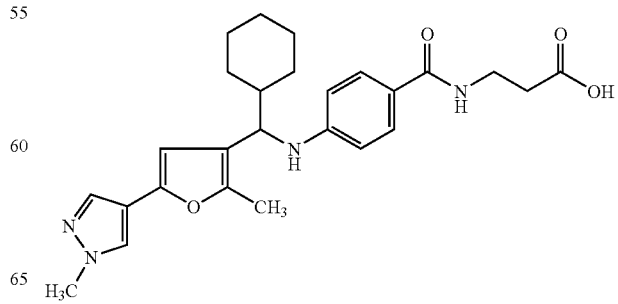

(1) 5-(1-methyl-1H-pyrazol-4-yl)-2-methylfuran-3-carbaldehyde

A mixture of 5-bromo-2-methylfuran-3-carbaldehyde (1.9 g), 1-methyl-4-(4,4,5,5-tetramethyl-1,3,2-dioxaboran-2-yl)-1H-pyrazole (2.5 g), tetrakis(triphenylphosphine)palladium (0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 55% ethyl acetate/hexane), and crystallized from ethyl acetate/hexane to give the title compound (1.5 g, 81%) as a yellow crystal.

$^1$H NMR (300 MHz, CHLOROFORM-d) δ ppm 2.62 (s, 3H) 3.94 (s, 3H) 6.57 (s, 1H) 7.59 (s, 1H) 7.69 (s, 1H) 9.93 (s, 1H)

(2) cyclohexyl[2-methyl-5-(1-methyl-1H-pyrazol-4-yl)furan-3-yl]methanol

To a solution of 5-(1-methyl-1H-pyrazol-4-yl)-2-methylfuran-3-carbaldehyde (0.8 g) obtained by the above-mentioned reaction in tetrahydrofuran (20 mL) was added dropwise 1N cyclohexylmagnesium bromide-tetrahydrofuran solution (5.1 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.0 g, 90%) as an oil.

$^1$H NMR (300 MHz, CHLOROFORM-d) δ ppm 0.72-1.40 (m, 5H) 1.44-1.88 (m, 5H) 1.99-2.14 (m, 1H) 2.27 (s, 3H) 3.91 (s, 3H) 4.26 (dd, J=7.91, 2.07 Hz, 1H) 6.25 (s, 1H) 7.53 (s, 1H) 7.65 (s, 1H)

(3) 4-{4-[chloro(cyclohexyl)methyl]-5-methylfuran-2-yl}-1-methyl-1H-pyrazole To a solution of cyclohexyl[2-methyl-5-(1-methyl-1H-pyrazol-4-yl)furan-3-yl]methanol (1.0 g) obtained by the above-mentioned reaction in toluene (20 mL) were added thionyl chloride (0.4 mL) and pyridine (0.4 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.1 g, 100%) as an oil.

$^1$H NMR (300 MHz, CHLOROFORM-d) δ ppm 0.75-1.38 (m, 5H) 1.60-1.88 (m, 5H) 2.17-2.22 (m, 1H) 2.36 (s, 3H) 3.91 (s, 3H) 4.58 (d, J=8.67 Hz, 1H) 6.28 (s, 1H) 7.54 (s, 1H) 7.66 (s, 1H)

(4) 4-({cyclohexyl[2-methyl-5-(1-methyl-1H-pyrazol-4-yl)furan-3-yl]methyl}amino)benzoic acid A mixture of 4-{4-[chloro(cyclohexyl)methyl]-5-methylfuran-2-yl}-1-methyl-1H-pyrazole (1.1 g) obtained by the above-mentioned reaction, methyl 4-aminobenzoate (0.8 g), sodium carbonate (0.6 g) and sodium iodide (1.1 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 70% ethyl acetate/hexane) to give the title compound (0.9 g, 66%) as an amorphous compound.

$^1$H NMR (300 MHz, CHLOROFORM-d) δ ppm 0.89-1.33 (m, 5H) 1.40-1.86 (m, 5H) 1.94-1.98 (m, 1H) 2.32 (s, 3H) 3.89 (s, 3H) 4.01-4.19 (m, 2H) 6.10 (s, 1H) 6.50 (d, J=9.09 Hz, 2H) 7.50 (s, 1H) 7.61 (s, 1H) 7.83 (d, J=8.71 Hz, 2H)

(5) 3-({[4-({cyclohexyl[2-methyl-5-(1-methyl-1H-pyrazol-4-yl)furan-3-yl]methyl}amino)phenyl]carbonyl}amino)propanoic acid A solution of 4-({cyclohexyl[2-methyl-5-(1-methyl-1H-pyrazol-4-yl)furan-3-yl]methyl}amino)benzoic acid (198 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (200 mg, 86%).

$^1$H NMR (300 MHz, DMSO-d$_6$) δ ppm 0.79-1.30 (m, 5H) 1.45-1.88 (m, 5H) 2.02 (d, J=10.98 Hz, 1H) 2.30 (s, 3H) 2.43 (t, J=7.19 Hz, 2H) 3.36 (q, J=6.06 Hz, 2H) 3.81 (s, 3H) 4.05 (t, J=7.95 Hz, 1H) 6.26 (s, 1H) 6.31 (d, J=7.95 Hz, 1H) 6.53 (d, J=8.71 Hz, 2H) 7.51 (d, J=8.71 Hz, 2H) 7.57 (s, 1H) 7.87 (s, 1H) 7.98 (t, J=5.49 Hz, 1H) 12.17 (brs, 1H)

Example 207

3-({[4-({cyclohexyl[2-methyl-5-(1-methyl-1H-pyrazol-4-yl)furan-3-yl]methyl}amino)phenyl]carbonyl}(methyl)amino)propanoic acid

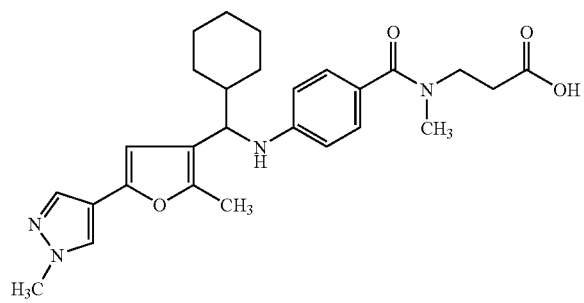

A solution of 4-({cyclohexyl[2-methyl-5-(1-methyl-1H-pyrazol-4-yl)furan-3-yl]methyl}amino)benzoic acid (198 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (160 mg, 67%).

$^1$H NMR (300 MHz, DMSO-$d_6$) δ ppm 0.71-1.32 (m, 5H) 1.47-1.80 (m, 5H) 2.02 (d, J=11.74 Hz, 1H) 2.30 (s, 3H) 2.46-2.51 (m, 2H) 2.90 (s, 3H) 3.52 (t, J=7.38 Hz, 2H) 3.81 (s, 3H) 4.01 (t, J=7.76 Hz, 1H) 6.21 (d, J=7.95 Hz, 1H) 6.27 (s, 1H) 6.52 (d, J=8.71 Hz, 2H) 7.09 (d, J=8.71 Hz, 2H) 7.58 (s, 1H) 7.88 (s, 1H) 12.27 (brs, 1H)

Example 208

3-({[4-({1-[5-(1-methyl-1H-pyrazol-4-yl)-2-methylfuran-3-yl]-3-methylbutyl}amino)phenyl]carbonyl}amino)propanoic acid

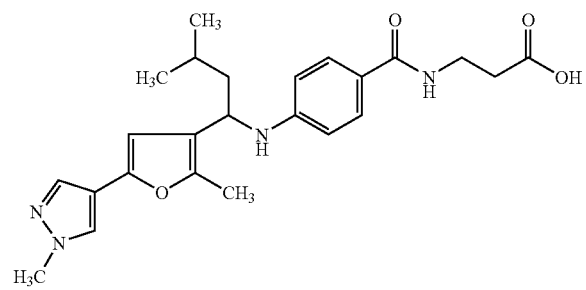

(1) 3-methyl-1-[2-methyl-5-(1-methyl-1H-pyrazol-4-yl)furan-3-yl]butan-1-ol

To a solution of 5-(1-methyl-1H-pyrazol-4-yl)-2-methylfuran-3-carbaldehyde (0.8 g) obtained by the above-mentioned reaction in tetrahydrofuran (20 mL) was added dropwise 1N isobutylmagnesium bromide-tetrahydrofuran solution (6 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.0 g, 96%) as an oil.

$^1$H NMR (300 MHz, CHLOROFORM-d) δ ppm 0.93 (d, J=5.65 Hz, 6H) 1.46-1.80 (m, 3H) 2.31 (s, 3H) 3.91 (s, 3H) 4.68 (td, J=6.97, 3.20 Hz, 1H) 6.28 (s, 1H) 7.53 (s, 1H) 7.65 (s, 1H)

(2) 4-[4-(1-chloro-3-methylbutyl)-5-methylfuran-2-yl]-1-methyl-1H-pyrazole

To a solution of 3-methyl-1-[2-methyl-5-(1-methyl-1H-pyrazol-4-yl)furan-3-yl]butan-1-ol (0.9 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.0 g, 100%) as an oil.

$^1$H NMR (300 MHz, CHLOROFORM-d) δ ppm 0.93 (dd, J=6.63, 4.35 Hz, 6H) 1.68-1.93 (m, 2H) 1.93-2.14 (m, 1H) 2.32 (s, 3H) 3.93 (s, 3H) 4.94 (t, J=7.57 Hz, 1H) 6.31 (s, 1H) 7.55 (s, 1H) 7.67 (s, 1H)

(3) 4-({1-[5-(1-methyl-1H-pyrazol-4-yl)-2-methylfuran-3-yl]-3-methylbutyl}amino)benzoic acid A mixture of 4-[4-(1-chloro-3-methylbutyl)-5-methylfuran-2-yl]-1-methyl-1H-pyrazole (1.0 g), methyl 4-aminobenzoate (0.9 g), sodium carbonate (0.6 g) and sodium iodide (1.1 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 55% ethyl acetate/hexane) to give the title compound (0.5 g, 39%) as an amorphous compound.

$^1$H NMR (300 MHz, CHLOROFORM-d) δ ppm 0.96 (dd, J=17.52, 6.22 Hz, 6H) 1.46-1.77 (m, 3H) 2.35 (s, 3H) 3.90 (s, 3H) 4.37 (t, J=6.97 Hz, 1H) 6.16 (s, 1H) 6.52 (d, J=8.85 Hz, 2H) 7.51 (s, 1H) 7.62 (s, 1H) 7.86 (d, J=8.85 Hz, 2H)

(4) 3-({[4-({1-[5-(1-methyl-1H-pyrazol-4-yl)-2-methylfuran-3-yl]-3-methylbutyl}amino)phenyl]carbonyl}amino)propanoic acid A solution of 4-({1-[5-(3,5-dimethylisoxazol-4-yl)-2-methylfuran-3-yl]-3-methylbutyl}amino)benzoic acid (184 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (200 mg, 92%).

¹H NMR (300 MHz, DMSO-d₆) δ ppm 0.91 (dd, J=17.98, 6.25 Hz, 6H) 1.43-1.76 (m, 3H) 2.32 (s, 3H) 2.44 (t, J=7.19 Hz, 2H) 3.33-3.46 (m, 2H) 3.81 (s, 3H) 4.32 (q, J=7.19 Hz, 1H) 6.30 (s, 1H) 6.33 (d, J=7.95 Hz, 1H) 6.53 (d, J=8.71 Hz, 2H) 7.53 (d, J=8.71 Hz, 2H) 7.58 (s, 1H) 7.88 (s, 1H) 7.99 (t, J=5.49 Hz, 1H) 12.15 (s, 1H)

Example 209

3-({[4-({3-methyl-1-[2-methyl-5-(1-methyl-1H-pyrazol-4-yl)furan-3-yl]butyl}amino)phenyl]carbonyl}(methyl)amino)propanoic acid

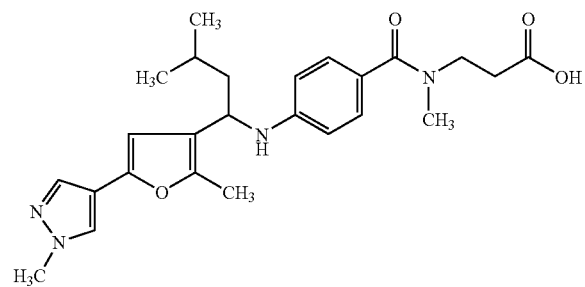

A solution of 4-({1-[5-(1-methyl-1H-pyrazol-4-yl)-2-methylfuran-3-yl]-3-methylbutyl}amino)benzoic acid (184 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (204 mg, 90%).

¹H NMR (300 MHz, DMSO-d₆) δ ppm 0.91 (dd, J=17.42, 6.06 Hz, 6H) 1.42-1.75 (m, 3H) 2.32 (s, 3H) 2.50 (t, J=1.89 Hz, 2H) 2.90 (s, 3H) 3.32 (s, 3H) 3.52 (t, J=7.38 Hz, 2H) 3.81 (s, 3H) 4.29 (q, J=7.45 Hz, 1H) 6.23 (d, J=7.57 Hz, 1H) 6.32 (s, 1H) 6.53 (d, J=8.71 Hz, 2H) 7.11 (d, J=8.71 Hz, 2H) 7.59 (s, 1H) 7.89 (s, 1H) 12.25 (s, 1H)

Example 210

3-({[4-({cyclohexyl[5-(5-methoxypyridin-3-yl)-2-methyl-furan-3-yl]methyl}amino)phenyl]carbonyl}amino)propanoic acid

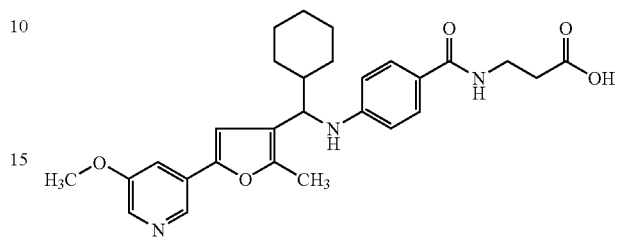

(1) 5-(5-methoxypyridin-3-yl)-2-methylfuran-3-carbaldehyde

A mixture of 5-bromo-2-methylfuran-3-carbaldehyde (1.9 g), pinacol 5-methoxy-3-pyridineborate (2.8 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (5% ethyl acetate/hexane to 50% ethyl acetate/hexane), and crystallized from ethyl acetate/hexane to give the title compound (2.0 g, 90%) as a yellow crystal.

¹H NMR (300 MHz, CHLOROFORM-d) δ ppm 2.70 (s, 3H) 3.92 (s, 3H) 7.01 (s, 1H) 7.41 (dd, J=2.73, 1.79 Hz, 1H) 8.25 (d, J=2.83 Hz, 1H) 8.54 (d, J=1.70 Hz, 1H) 9.98 (s, 1H)

(2) cyclohexyl[5-(5-methoxypyridin-3-yl)-2-methyl-furan-3-yl]methanol

To a solution of 5-(5-methoxypyridin-3-yl)-2-methylfuran-3-carbaldehyde (1.0 g) obtained by the above-mentioned reaction in tetrahydrofuran (20 mL) was added dropwise 1N cyclohexylmagnesium bromide-tetrahydrofuran solution (6.8 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 30% ethyl acetate/hexane) to give the title compound (1.2 g, 90%) as an oil.

¹H NMR (300 MHz, CHLOROFORM-d) δ ppm 0.73-1.41 (m, 5H) 1.45-1.88 (m, 5H) 2.05-2.09 (m, 1H) 2.34 (s, 3H) 3.90 (s, 3H) 4.32 (dd, J=7.82, 2.92 Hz, 1H) 6.69 (s, 1H) 7.38 (dd, J=2.73, 1.79 Hz, 1H) 8.16 (d, J=2.83 Hz, 1H) 8.49 (d, J=1.88 Hz, 1H)

(3) 3-{4-[chloro(cyclohexyl)methyl]-5-methylfuran-2-yl}-5-methoxypyridine

To a solution of cyclohexyl[5-(5-methoxypyridin-3-yl)-2-methylfuran-3-yl]methanol (1.2 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.3 g, 100%) as an oil.

$^1$H NMR (300 MHz, CHLOROFORM-d) δ ppm 0.74-1.44 (m, 5H) 1.43-1.98 (m, 5H) 2.21 (d, J=14.13 Hz, 1H) 2.35 (s, 3H) 3.90 (s, 3H) 4.60 (d, J=8.48 Hz, 1H) 6.71 (s, 1H) 7.39 (dd, J=2.73, 1.79 Hz, 1H) 8.18 (d, J=2.64 Hz, 1H) 8.50 (d, J=1.51 Hz, 1H)

(4) 4-({cyclohexyl[5-(5-methoxypyridin-3-yl)-2-methylfuran-3-yl]methyl}amino)benzoic acid A mixture of 3-{4-[chloro(cyclohexyl)methyl]-5-methyl-furan-2-yl}-5-methoxypyridine (1.3 g) obtained by the above-mentioned reaction, methyl 4-aminobenzoate (0.9 g), sodium carbonate (0.6 g) and sodium iodide (1.2 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (4 mL) and tetrahydrofuran (4 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 60% ethyl acetate/hexane) to give the title compound (0.9 g, 55%) as an amorphous compound.

$^1$H NMR (300 MHz, CHLOROFORM-d) δ ppm 1.01-1.12 (m, 5H) 1.53-1.77 (m, 5H) 1.97 (dd, J=13.09, 1.04 Hz, 1H) 2.40 (s, 3H) 3.88 (s, 3H) 4.11 (d, J=6.59 Hz, 1H) 6.51 (d, J=9.04 Hz, 2H) 6.55 (s, 1H) 7.35 (dd, J=2.73, 1.79 Hz, 1H) 7.85 (d, J=8.85 Hz, 2H) 8.14 (d, J=2.83 Hz, 1H) 8.45 (d, J=1.70 Hz, 1H)

(5) 3-({[4-({1-[5-(5-methoxypyridin-3-yl)-2-methyl-furan-3-yl]-3-methylbutyl}amino)phenyl]carbonyl}amino)propanoic acid A solution of 4-({cyclohexyl[5-(5-methoxypyridin-3-yl)-2-methylfuran-3-yl]methyl}amino)benzoic acid (210 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (219 mg, 89%).

$^1$H NMR (300 MHz, DMSO-$d_6$) δ ppm 0.81-1.34 (m, 5H) 1.47-1.68 (m, 5H) 2.03 (d, J=11.87 Hz, 1H) 2.39 (s, 3H) 2.43 (t, J=7.16 Hz, 2H) 3.35-3.47 (m, 2H) 3.86 (s, 3H) 4.11 (t, J=7.44 Hz, 1H) 6.35 (d, J=7.54 Hz, 1H) 6.55 (d, J=8.67 Hz, 2H) 6.93 (s, 1H) 7.45 (dd, J=2.64, 1.88 Hz, 1H) 7.52 (d, J=8.85 Hz, 2H) 7.98 (t, J=5.37 Hz, 1H) 8.13 (d, J=2.83 Hz, 1H) 8.40 (d, J=1.70 Hz, 1H) 12.14 (brs, 1H)

Example 211

3-({[4-({cyclohexyl[5-(5-methoxypyridin-3-yl)-2-methylfuran-3-yl]methyl}amino)phenyl]carbonyl}(methyl)amino)propanoic acid

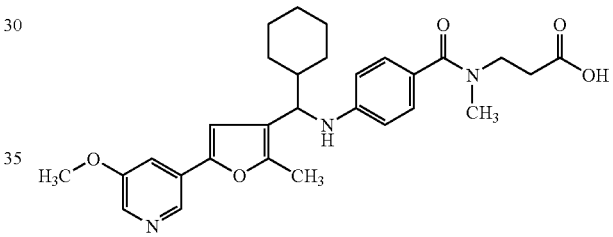

A solution of 4-({cyclohexyl[5-(5-methoxypyridin-3-yl)-2-methylfuran-3-yl]methyl}amino)benzoic acid (210 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (226 mg, 90%).

$^1$H NMR (300 MHz, DMSO-$d_6$) δ ppm 0.89-1.27 (m, 5H) 1.47-1.75 (m, 5H) 2.03 (d, J=11.87 Hz, 1H) 2.39 (s, 3H) 2.43 (t, J=7.16 Hz, 2H) 3.35-3.47 (m, 2H) 3.86 (s, 3H) 4.11 (t, J=7.44 Hz, 1H) 6.35 (d, J=7.54 Hz, 1H) 6.55 (d, J=8.67 Hz, 2H) 6.93 (s, 1H) 7.45 (dd, J=2.64, 1.88 Hz; 1H) 7.52 (d, J=8.85 Hz, 2H) 7.98 (t, J=5.37 Hz, 1H) 8.13 (d, J=2.83 Hz, 1H) 8.40 (d, J=1.70 Hz, 1H) 12.14 (brs, 1H)

Example 212

3-({[4-({1-[5-(5-methoxypyridin-3-yl)-2-methylfuran-3-yl]-3-methylbutyl}amino)phenyl]carbonyl}amino)propanoic acid

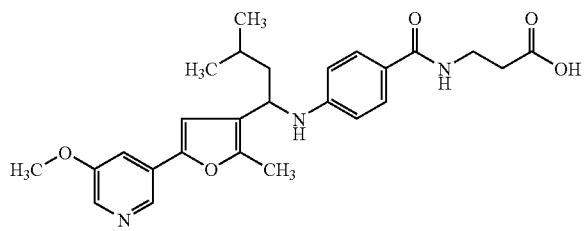

(1) 1-[5-(5-methoxypyridin-3-yl)-2-methylfuran-3-yl]-3-methylbutan-1-ol

To a solution of 5-(5-methoxypyridin-3-yl)-2-methylfuran-3-carbaldehyde (1.0 g) obtained by the above-mentioned reaction in tetrahydrofuran (20 mL) was added dropwise 1N isobutylmagnesium bromide-tetrahydrofuran solution (6.8 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.1 g, 90%) as a white crystal.

$^1$H NMR (300 MHz, CHLOROFORM-d) δ ppm 0.95 (d, J=6.40 Hz, 6H) 1.49-1.83 (m, 3H) 3.90 (s, 3H) 4.72 (td, J=7.02, 3.30 Hz, 1H) 6.72 (s, 1H) 7.38 (dd, J=2.83, 1.70 Hz, 1H) 8.16 (d, J=2.83 Hz, 1H) 8.49 (d, J=1.88 Hz, 1H)

(2) 3-[4-(1-chloro-3-methylbutyl)-5-methylfuran-2-yl]-5-methoxypyridine

To a solution of 1-[5-(5-methoxypyridin-3-yl)-2-methylfuran-3-yl]-3-methylbutan-1-ol (1.1 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.2 g, 100%) as an oil.

$^1$H NMR (300 MHz, CHLOROFORM-d) δ ppm 0.95 (dd, J=6.59, 3.20 Hz, 6H) 1.66-1.94 (m, 2H) 1.96-2.16 (m, 1H) 2.39 (s, 3H) 3.91 (s, 3H) 4.93 (d, J=7.91 Hz, 1H) 6.74 (s, 1H) 7.39 (dd, J=2.73, 1.79 Hz, 1H) 8.18 (d, J=2.64 Hz, 1H) 8.50 (d, J=1.51 Hz, 1H)

(3) 4-({1-[5-(5-methoxypyridin-3-yl)-2-methylfuran-3-yl]-3-methylbutyl}amino)benzoic acid A mixture of 3-[4-(1-chloro-3-methylbutyl)-5-methylfuran-2-yl]-5-methoxypyridine (1.2 g) obtained by the above-mentioned reaction, methyl 4-aminobenzoate (0.9 g), sodium carbonate (0.6 g) and sodium iodide (1.2 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, the title compound (0.4 g, 22%) as a yellow crystal.

$^1$H NMR (300 MHz, DMSO-d$_6$) δ ppm 0.93 (dd, J=17.80, 6.31 Hz, 6H) 1.50-1.86 (m, 3H) 2.42 (s, 3H) 3.84-3.96 (m, 2H) 4.30-4.49 (m, 1H) 6.58 (d, J=8.85 Hz, 2H) 7.08 (s, 1H) 7.62 (d, J=8.85 Hz, 2H) 8.23 (brs, 1H) 8.49 (s, 1H)

(4) 3-({[4-({1-[5-(5-methoxypyridin-3-yl)-2-methylfuran-3-yl]-3-methylbutyl}amino)phenyl]carbonyl}amino)propanoic acid A solution of 4-({1-[5-(5-methoxypyridin-3-yl)-2-methylfuran-3-yl]-3-methylbutyl}amino)benzoic acid (178 mg) obtained by the above-mentioned reaction, ethyl β-alaninate hydrochloride (83 mg), 1-ethyl-3-(3-dimethylaminopropyl)carbodiimide hydrochloride (104 mg), hydroxybenzotriazole monohydrate (83 mg) and triethylamine (75 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL), 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (116 mg, 56%).

$^1$H NMR (300 MHz, DMSO-d$_6$) δ 0.93 (dd, J=18.17, 6.44 Hz, 6H) 1.48-1.80 (m, 3H) 2.40 (s, 3H) 2.41-2.47 (m, 2H) 3.25-3.49 (m, 2H) 3.86 (s, 3H) 4.38 (q, J=7.19 Hz, 1H) 6.37 (d, J=7.57 Hz, 1H) 6.55 (d, J=9.09 Hz, 2H) 6.99 (s, 1H) 7.46 (d, J=1.89 Hz, 1H) 7.54 (d, J=8.71 Hz, 2H) 8.00 (t, J=5.30 Hz, 1H) 8.13 (d, J=2.65 Hz, 1H) 8.41 (d, J=1.51 Hz, 1H) 12.14 (d, J=1.51 Hz, 1H)

Example 213

3-({[4-({3-methyl-1-[2-methyl-5-(5-methoxypyridin-3-yl)furan-3-yl]butyl}amino)phenyl]carbonyl}(methyl)amino)propanoic acid

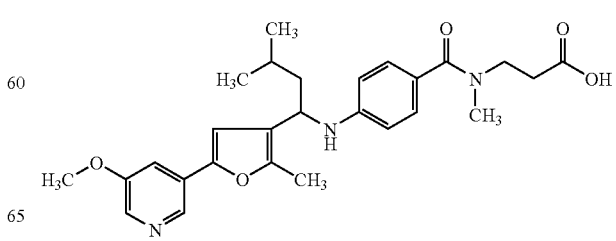

A solution of 4-({1-[5-(5-methoxypyridin-3-yl)-2-methylfuran-3-yl]-3-methylbutyl}amino)benzoic acid (178 mg), ethyl 3-(methylamino)propanoate (71 mg), 1-ethyl-3-(3-dimethylaminopropyl)carbodiimide hydrochloride (104 mg), hydroxybenzotriazole monohydrate (83 mg) and triethylamine (75 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL), 1N lithium hydroxide (0.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (119 mg, 56%).

$^1$H NMR (300 MHz, DMSO-$d_6$) δ ppm 0.93 (dd, J=17.80, 6.06 Hz, 6H) 1.48-1.81 (m, 3H) 2.40 (s, 3H) 2.44-2.58 (m, 2H) 2.90 (s, 3H) 3.52 (t, J=7.19 Hz, 2H) 3.86 (s, 3H) 4.34 (q, J=6.56 Hz, 1H) 6.27 (d, J=7.19 Hz, 1H) 6.55 (d, J=8.71 Hz, 2H) 7.00 (s, 1H) 7.12 (d, J=8.33 Hz, 2H) 7.47 (d, J=2.65 Hz, 1H) 8.13 (d, J=2.65 Hz, 1H) 8.41 (d, J=1.51 Hz, 1H) 12.24 (brs, 1H)

Example 214

3-({[4-({1-[5-(2-chloropyridin-4-yl)-2-methylfuran-3-yl]-3-methylbutyl}amino)phenyl]carbonyl}amino)propanoic acid

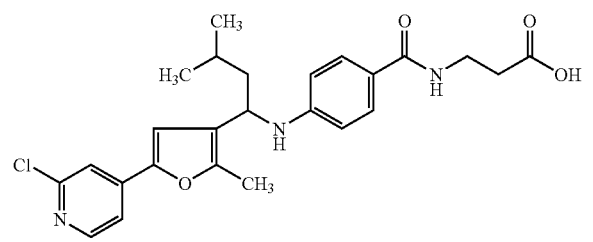

(1) 5-(2-chloropyridin-4-yl)-2-methylfuran-3-carbaldehyde

A mixture of 5-bromo-2-methylfuran-3-carbaldehyde (1.9 g), 2-chloropyridine-4-boronic acid (1.9 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (5% ethyl acetate/hexane to 50% ethyl acetate/hexane), and crystallized from ethyl acetate/hexane to give the title compound (1.2 g, 55%) as a yellow solid.

$^1$H NMR (300 MHz, CHLOROFORM-d) δ ppm 2.71 (s, 3H) 7.18 (s, 1H) 7.42 (dd, J=5.27, 1.51 Hz, 1H) 7.56 (d, J=0.75 Hz, 1H) 8.40 (d, J=5.27 Hz, 1H) 9.99 (s, 1H)

(2) 1-[5-(2-chloropyridin-4-yl)-2-methylfuran-3-yl]-3-methylbutan-1-ol

To a solution of 5-(2-chloropyridin-4-yl)-2-methylfuran-3-carbaldehyde (1.2 g) obtained by the above-mentioned reaction in tetrahydrofuran (20 mL) was added dropwise 1N isobutylmagnesium bromide-tetrahydrofuran solution (8.3 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (5% ethyl acetate/hexane to 35% ethyl acetate/hexane) to give the title compound (0.9 g, 55%) as a yellow crystal.

$^1$H NMR (300 MHz, CHLOROFORM-d) δ ppm 0.95 (d, J=6.44 Hz, 6H) 1.48-1.79 (m, 4H) 2.39 (s, 3H) 4.73 (ddd, J=10.22, 3.79, 3.41 Hz, 1H) 6.89 (s, 1H) 7.36 (dd, J=5.30, 1.51 Hz, 1H) 7.50 (s, 1H) 8.32 (d, J=5.30 Hz, 1H)

(3) 2-chloro-4-[4-(1-chloro-3-methylbutyl)-5-methylfuran-2-yl]pyridine

To a solution of 1-[5-(2-chloropyridin-4-yl)-2-methylfuran-3-yl]-3-methylbutan-1-ol (0.8 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.9 g, 100%) as an oil.

$^1$H NMR (300 MHz, CHLOROFORM-d) δ ppm 0.95 (dd, J=6.50, 2.92 Hz, 6H) 1.78-1.93 (m, 2H) 1.94-2.14 (m, 1H) 2.40 (s, 3H) 4.92 (dd, J=8.10, 7.16 Hz, 1H) 6.91 (s, 1H) 7.37 (dd, J=5.27, 1.51 Hz, 1H) 7.51 (d, J=0.94 Hz, 1H) 8.33 (d, J=5.27 Hz, 1H)

(4) 4-({1-[5-(2-chloropyridin-4-yl)-2-methylfuran-3-yl]-3-methylbutyl}amino)benzoic acid A mixture of 2-chloro-4-[4-(1-chloro-3-methylbutyl)-5-methylfuran-2-yl]pyridine (0.9 g) obtained by the above-mentioned reaction, methyl 4-aminobenzoate (0.7 g), sodium carbonate (0.5 g) and sodium iodide (0.9 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (3 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (15% ethyl acetate/hexane to 50% ethyl acetate/hexane) to give the title compound (0.5 g, 42%) as an amorphous compound.

$^1$H NMR (300 MHz, CHLOROFORM-d) δ ppm 0.98 (dd, J=16.11, 6.31 Hz, 6H) 1.49-1.71 (m, 2H) 2.43 (s, 3H) 4.41 (t, J=6.97 Hz, 1H) 6.51 (d, J=8.85 Hz, 2H) 6.76 (s, 1H) 7.32 (dd, J=5.37, 1.41 Hz, 1H) 7.46 (d, J=0.94 Hz, 1H) 7.87 (d, J=8.85 Hz, 2H) 8.30 (d, J=5.27 Hz, 1H)

(5) 3-({[4-({1-[5-(2-chloropyridin-4-yl)-2-methylfuran-3-yl]-3-methylbutyl}amino)phenyl]carbonyl}amino)propanoic acid A solution of 4-({1-[5-(2-chloropyridin-4-yl)-2-methylfuran-3-yl]-3-methylbutyl}amino)benzoic acid (239 mg) obtained by the above-mentioned reaction, ethyl β-alaninate hydrochloride (111 mg), 1-ethyl-3-(3-dimethylaminopropyl)carbodiimide hydrochloride (138 mg), hydroxybenzotriazole monohydrate (110 mg) and triethylamine (100 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (250 mg, 90%).

$^1$H NMR (300 MHz, DMSO-$d_6$) δ ppm 0.92 (dd, J=17.80, 6.31 Hz, 6H) 1.47-1.81 (m, 3H) 2.31-2.48 (m, 5H) 3.34-3.44 (m, 2H) 4.40 (q, J=7.22 Hz, 1H) 6.40 (d, J=7.54 Hz, 1H) 6.55 (d, J=8.85 Hz, 2H) 7.27 (s, 1H) 7.46-7.58 (m, 3H) 7.60 (d, J=0.94 Hz, 1H) 8.01 (t, J=5.56 Hz, 1H) 8.34 (d, J=5.27 Hz, 1H) 12.16 (brs, 1H)

Example 215

3-[{[4-({1-[5-(2-chloropyridin-4-yl)-2-methylfuran-3-yl]-3-methylbutyl}amino)phenyl]carbonyl}(methyl)amino]propanoic acid

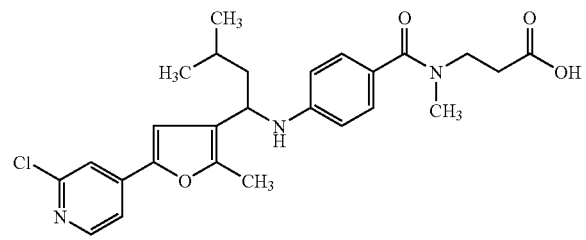

A solution of 4-({1-[5-(2-chloropyridin-4-yl)-2-methylfuran-3-yl]-3-methylbutyl}amino)benzoic acid (239 mg), ethyl 3-(methylamino)propanoate (94 mg), 1-ethyl-3-(3-dimethylaminopropyl)carbodiimide hydrochloride (138 mg), hydroxybenzotriazole monohydrate (110 mg) and triethylamine (100 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.2 and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (279 mg, 96%).

$^1$H NMR (300 MHz, DMSO-$d_6$) δ ppm 0.92 (dd, J=17.33, 6.40 Hz, 6H) 1.39-1.66 (m, 3H) 2.42 (s, 3H) 2.44-2.50 (m, 2H) 2.90 (s, 3H) 3.52 (t, J=7.35 Hz, 2H) 4.25-4.44 (m, 1H) 6.29 (d, J=7.35 Hz, 1H) 6.55 (d, J=8.67 Hz, 2H) 7.12 (d, J=8.67 Hz, 2H) 7.28 (s, 1H) 7.53 (dd, J=5.27, 1.51 Hz, 1H) 7.61 (d, J=0.94 Hz, 1H) 8.33 (d, J=5.46 Hz, 1H) 12.25 (brs, 1H)

Example 216

3-({[4-({1-[5-(5-chloropyridin-3-yl)-2-methylfuran-3-yl]-3-methylbutyl}amino)phenyl]carbonyl}amino)propanoic acid

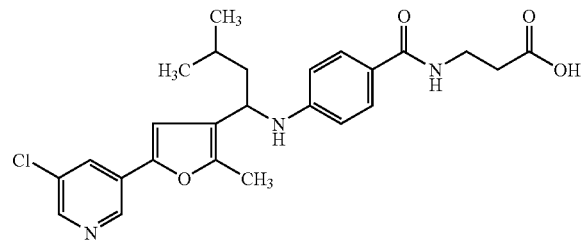

(1) 5-(5-chloropyridin-3-yl)-2-methylfuran-3-carbaldehyde

A mixture of 5-bromo-2-methylfuran-3-carbaldehyde (1.9 g), 5-chloropyridine-3-boronic acid (1.9 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane), and crystallized from ethyl acetate/hexane to give the title compound (1.1 g, 49%) as a yellow solid.

$^1$H NMR (300 MHz, CHLOROFORM-d) δ ppm 2.70 (s, 3H) 7.06 (s, 1H) 7.92 (t, J=2.08 Hz, 1H) 8.49 (d, J=2.27 Hz, 1H) 8.79 (d, J=1.89 Hz, 1H) 9.98 (s, 1H)

(2) 1-[5-(5-chloropyridin-3-yl)-2-methylfuran-3-yl]-3-methylbutan-1-ol

To a solution of 5-(5-chloropyridin-3-yl)-2-methylfuran-3-carbaldehyde (1.1 g) obtained by the above-mentioned reaction in tetrahydrofuran (20 mL) was added dropwise 1N isobutylmagnesium bromide-tetrahydrofuran solution (7.4 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.1 g, 82%) as a white crystal.

$^1$H NMR (300 MHz, CHLOROFORM-d) δ ppm 0.95 (d, J=6.59 Hz, 6H) 1.49-1.82 (m, 3H) 2.38 (s, 3H) 4.72 (td, J=6.97, 3.39 Hz, 1H) 6.76 (s, 1H) 7.87 (t, J=2.17 Hz, 1H) 8.40 (d, J=2.26 Hz, 1H) 8.73 (d, J=1.88 Hz, 1H)

(3) 3-chloro-5-[4-(1-chloro-3-methylbutyl)-5-methylfuran-2-yl]pyridine

To a solution of 1-[5-(5-chloropyridin-3-yl)-2-methylfuran-3-yl]-3-methylbutan-1-ol (1.1 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.2 g, 100%) as a white crystal.

$^1$H NMR (300 MHz, CHLOROFORM-d) δ ppm 0.95 (dd, J=6.59, 3.20 Hz, 6H) 1.64-1.94 (m, 2H) 1.94-2.18 (m, 1H) 2.39 (s, 3H) 4.92 (d, J=8.10 Hz, 1H) 6.78 (s, 1H) 7.88 (t, J=2.17 Hz, 1H) 8.42 (d, J=2.26 Hz, 1H) 8.74 (d, J=1.88 Hz, 1H)

(4) 4-({1-[5-(5-chloropyridin-3-yl)-2-methylfuran-3-yl]-3-methylbutyl}amino)benzoic acid A mixture of 3-chloro-5-[4-(1-chloro-3-methylbutyl)-5-methylfuran-2-yl]pyridine (1.2 g) obtained by the above-mentioned reaction, methyl 4-aminobenzoate (0.9 g), sodium carbonate (0.6 g) and sodium iodide (1.2 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.8 g, 51%) as an amorphous compound.

$^1$H NMR (300 MHz, CHLOROFORM-d) δ ppm 0.98 (dd, J=16.47, 6.25 Hz, 6H) 1.51-1.83 (m, 3H) 2.43 (s, 3H) 4.41 (t, J=7.00 Hz, 1H) 6.52 (d, J=9.09 Hz, 2H) 6.64 (s, 1H) 7.84 (t, J=2.08 Hz, 1H) 7.87 (d, J=8.71 Hz, 2H) 8.38 (d, J=2.27 Hz, 1H) 8.70 (d, J=1.89 Hz, 1H)

(5) 3-({[4-({1-[5-(5-chloropyridin-3-yl)-2-methylfuran-3-yl]-3-methylbutyl}amino)phenyl]carbonyl}amino)propanoic acid A solution of 4-({1-[5-(5-chloropyridin-3-yl)-2-methylfuran-3-yl]-3-methylbutyl}amino)benzoic acid (199 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (215 mg, 92%).

$^1$H NMR (300 MHz, DMSO-d$_6$) δ ppm 0.92 (dd, J=17.80, 6.06 Hz, 6H) 1.48-1.81 (m, 3H) 2.33-2.47 (m, 5H) 3.37 (d, J=5.68 Hz, 2H) 4.38 (q, J=7.19 Hz, 1H) 6.39 (d, J=7.57 Hz, 1H) 6.55 (d, J=8.71 Hz, 2H) 7.09 (s, 1H) 7.54 (d, J=8.71 Hz, 2H) 8.01 (t, J=5.49 Hz, 1H) 8.05 (t, J=2.08 Hz, 1H) 8.45 (d, J=2.27 Hz, 1H) 8.76 (d, J=1.89 Hz, 1H) 12.17 (brs, 1H)

Example 217

3-[{[4-({1-[5-(5-chloropyridin-3-yl)-2-methylfuran-3-yl]-3-methylbutyl}amino)phenyl]carbonyl}(methyl)amino]propanoic acid

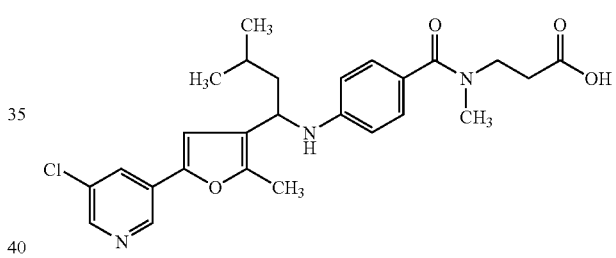

A solution of 4-({1-[5-(5-chloropyridin-3-yl)-2-methylfuran-3-yl]-3-methylbutyl}amino)benzoic acid (199 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (225 mg, 93%).

$^1$H NMR (300 MHz, DMSO-d$_6$) δ ppm 0.92 (dd, J=17.42, 6.44 Hz, 6H) 1.47-1.80 (m, 3H) 2.41 (s, 3H) 2.47-2.50 (m, 2H) 2.90 (s, 3H) 3.52 (t, J=7.38 Hz, 2H) 4.35 (q, J=7.19 Hz, 1H) 6.28 (d, J=7.19 Hz, 1H) 6.55 (d, J=8.71 Hz, 2H) 7.01-

7.23 (m, 3H) 8.06 (t, J=2.08 Hz, 1H) 8.45 (d, J=2.65 Hz, 1H) 8.76 (d, J=1.89 Hz, 1H) 12.23 (brs, 1H)

Example 218

3-({[4-({cyclohexyl[2-methyl-5-(1,3,5-trimethyl-1H-pyrazol-4-yl)furan-3-yl]methyl}amino)phenyl]carbonyl}amino)propanoic acid

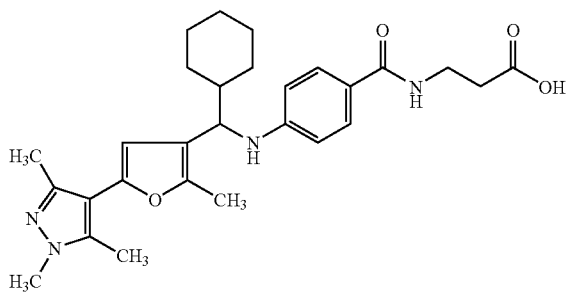

(1) 5-(1,3,5-trimethyl-1H-pyrazol-4-yl)-2-methylfuran-3-carbaldehyde

A mixture of 5-bromo-2-methylfuran-3-carbaldehyde (1.3 g), pinacol 1,3,5-trimethyl-1H-pyrazole-4-borate (2.0 g), tetrakis(triphenylphosphine)palladium(0) (0.4 g), 2N aqueous sodium carbonate solution (9 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 60% ethyl acetate/hexane), and crystallized from ethyl acetate/hexane to give the title compound (1.0 g, 66%) as a white crystal.

$^1$H NMR (300 MHz, CHLOROFORM-d) δ ppm 2.34 (s, 3H) 2.38 (s, 3H) 2.63 (s, 3H) 3.76 (s, 3H) 6.47 (s, 1H) 9.96 (s, 1H)

(2) cyclohexyl[2-methyl-5-(1,3,5-trimethyl-1H-pyrazol-4-yl)furan-3-yl]methanol To a solution of 5-(1,3,5-trimethyl-1H-pyrazol-4-yl)-2-methylfuran-3-carbaldehyde (1.0 g) obtained by the above-mentioned reaction in tetrahydrofuran (20 mL) was added dropwise 1N cyclohexylmagnesium bromide-tetrahydrofuran solution (6.9 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 60% ethyl acetate/hexane) to give the title compound (1.2 g, 89%) as an oil.

$^1$H NMR (300 MHz, CHLOROFORM-d) δ ppm 1.00-1.31 (m, 5H) 1.40-1.73 (m, 5H) 2.09 (dd, J=12.87, 1.89 Hz, 1H) 2.29 (s, 3H) 2.33 (s, 3H) 2.38 (s, 3H) 3.74 (s, 3H) 4.29 (dd, J=7.95, 3.03 Hz, 1H) 6.14 (s, 1H)

(3) 4-{4-[chloro(cyclohexyl)methyl]-5-methylfuran-2-yl}-1,3,5-trimethyl-1H-pyrazole To a solution of cyclohexyl[2-methyl-5-(1,3,5-trimethyl-1H-pyrazol-4-yl)furan-3-yl]methanol (1.2 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.3 g, 100%) as an oil.

$^1$H NMR (300 MHz, CHLOROFORM-d) δ ppm 0.73-1.38 (m, 5H) 1.57-1.86 (m, 5H) 2.21 (d, J=12.62 Hz, 1H) 2.29 (s, 3H) 2.34 (s, 3H) 2.36 (s, 3H) 2.38 (s, 3H) 3.75 (s, 3H) 4.62 (d, J=8.67 Hz, 1H) 6.15 (s, 1H)

(4) 4-({cyclohexyl[2-methyl-5-(1,3,5-trimethyl-1H-pyrazol-4-yl)furan-3-yl]methyl}amino)benzoic acid A mixture of 4-{4-[chloro(cyclohexyl)methyl]-5-methylfuran-2-yl}-1,3,5-trimethyl-1H-pyrazole (1.3 g) obtained by the above-mentioned reaction, methyl 4-aminobenzoate (0.9 g), sodium carbonate (0.6 g) and sodium iodide (1.2 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 100% ethyl acetate/hexane) to give the title compound (1.0 g, 60%) as a yellow crystal.

$^1$H NMR (300 MHz, CHLOROFORM-d) δ ppm 0.97-1.38 (m, 5H) 1.52-1.85 (m, 5H) 1.97 (d, J=11.49 Hz, 1H) 2.30 (s, 3H) 2.33 (s, 3H) 2.35 (s, 3H) 3.72 (s, 3H) 4.12 (q, J=7.16 Hz, 1H) 5.98 (s, 1H) 6.52 (d, J=8.85 Hz, 2H) 7.84 (d, J=8.85 Hz, 2H)

(5) 3-({[4-({1-[5-(1,3,5-trimethyl-1H-pyrazol-4-yl)-2-methylfuran-3-yl]-3-methylbutyl}amino)phenyl]carbonyl}amino)propanoic acid A solution of 4-({cyclohexyl[2-methyl-5-(1,3,5-trimethyl-1H-pyrazol-4-yl)methylfuran-3-yl]methyl}amino)benzoic acid (211 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (215 mg, 88%).

¹H NMR (300 MHz, DMSO-d₆) δ ppm 0.92-1.10 (m, 5H) 1.48-1.79 (m, 5H) 2.02 (d, J=12.81 Hz, 1H) 2.16 (s, 3H) 2.30 (s, 6H) 2.44 (t, J=7.06 Hz, 2H) 3.33-3.45 (m, 2H) 3.64 (s, 3H) 4.09 (t, J=8.19 Hz, 1H) 6.18 (s, 1H) 6.29 (d, J=8.48 Hz, 1H) 6.56 (d, J=8.85 Hz, 2H) 7.52 (d, J=8.67 Hz, 2H) 7.99 (t, J=5.46 Hz, 1H) 12.14 (s, 1H)

Example 219

3-({[4-({cyclohexyl[5-(1,3,5-trimethyl-1H-pyrazol-4-yl)-2-methylfuran-3-yl]methyl}amino)phenyl]carbonyl}(methyl)amino)propanoic acid

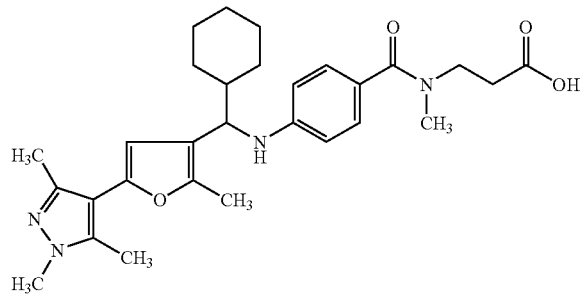

A solution of 4-({cyclohexyl[2-methyl-5-(1,3,5-trimethyl-1H-pyrazol-4-yl)furan-3-yl]methyl}amino)benzoic acid (211 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (214 mg, 85%).

¹H NMR (300 MHz, DMSO-d₆) δ ppm 0.87-1.19 (m, 5H) 1.49-1.81 (m, 5H) 1.92-2.07 (m, 1H) 2.16 (s, 3H) 2.31 (s, 6H) 2.43-2.50 (m, 2H) 2.91 (s, 3H) 3.52 (t, J=7.35 Hz, 2H) 3.64 (s, 3H) 4.06 (t, J=8.19 Hz, 1H) 6.19 (d, J=8.10 Hz, 1H) 6.19 (s, 1H) 6.55 (d, J=8.67 Hz, 2H) 7.10 (d, J=8.67 Hz, 2H) 12.25 (brs, 1H)

Example 220

3-({[4-({cyclohexyl[5-(5-methoxypyridin-2-yl)-2-methylfuran-3-yl]methyl}amino)phenyl]carbonyl}amino)propanoic acid

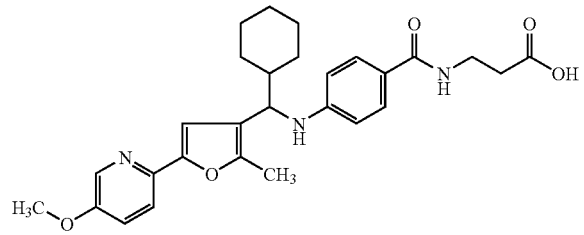

(1) [5-(5-methoxypyridin-2-yl)-2-methylfuran-3-yl]methanol

A mixture of tert-butyl({5-[(5,5-dimethyl-1,3,2-dioxaborinan-2-yl)methyl]-2-methylfuran-3-yl}methoxy)dimethylsilane (1.9 g), 2-bromo-5-methoxypyridine (2.0 g), tetrakis(triphenylphosphine)palladium(0) (0.4 g), 2N aqueous sodium carbonate solution (7 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was dissolved in tetrahydrofuran (20 mL), 1N tetrabutylammonium fluoride in tetrahydrofuran (10 mL) was added, and the mixture was stirred at room temperature for 2 hr. The reaction mixture was poured into water, and the mixture was extracted with ethyl acetate. The organic layer was washed with saturated brine, and dried over magnesium sulfate. The solvent was evaporated under reduced pressure, purified by silica gel chromatography (10% ethyl acetate/hexane to 100% ethyl acetate/hexane), and crystallized from ethyl acetate/hexane to give the title compound (1.0 g, 65%) as a white crystal.

¹H NMR (300 MHz, CHLOROFORM-d) δ ppm 1.43 (t, J=5.56 Hz, 1H) 2.39 (s, 3H) 3.88 (s, 3H) 4.52 (d, J=5.46 Hz, 2H) 6.85 (s, 1H) 7.21 (dd, J=8.76, 2.92 Hz, 1H) 7.56 (d, J=8.29 Hz, 1H) 8.29 (d, J=2.45 Hz, 1H)

(2) 5-(5-methoxypyridin-2-yl)-2-methylfuran-3-carbaldehyde

To a solution of [5-(5-methoxypyridin-2-yl)-2-methylfuran-3-yl]methanol (1.0 g) obtained by the above-mentioned reaction in acetonitrile (20 mL) was added Dess-Martin reagent (2.9 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (10% ethyl acetate/hexane to 50% ethyl acetate/hexane) to give the title compound (0.7 g, 83%) as a white crystal.

¹H NMR (300 MHz, CHLOROFORM-d) δ ppm 2.69 (s, 3H) 3.90 (s, 3H) 7.11 (s, 1H) 7.23 (d, J=2.65 Hz, 1H) 7.60 (d, J=8.71 Hz, 1H) 8.33 (d, J=2.65 Hz, 1H) 9.98 (s, 1H)

(3) cyclohexyl[5-(5-methoxypyridin-2-yl)-2-methylfuran-3-yl]methanol

To a solution of 5-(5-methoxypyridin-2-yl)-2-methylfuran-3-carbaldehyde (0.7 g) obtained by the above-mentioned reaction in tetrahydrofuran (20 mL) was added dropwise 1N cyclohexylmagnesium bromide-tetrahydrofuran solution (4.5 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.9 g, 90%) as a white crystal.

¹H NMR (300 MHz, CHLOROFORM-d) δ ppm 0.73-1.40 (m, 5H) 1.42-1.76 (m, 5H) 2.04-2.10 (m, 1H) 2.35 (s, 3H) 3.88 (s, 3H) 4.30 (dd, J=7.57, 3.41 Hz, 1H) 6.82 (s, 1H) 7.21 (dd, J=8.71, 3.03 Hz, 1H) 7.56 (d, J=8.71 Hz, 1H) 8.28 (d, J=2.65 Hz, 1H)

(4) 2-{4-[chloro(cyclohexyl)methyl]-5-methylfuran-2-yl}-5-methoxypyridine

To a solution of cyclohexyl[2-methyl-5-(5-methoxypyridin-2-yl)furan-3-yl]methanol (0.9 g) obtained by the above-mentioned reaction in toluene (20 mL) were added thionyl chloride (0.3 mL) and pyridine (0.3 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.9 g, 100%) as an oil.

¹H NMR (300 MHz, CHLOROFORM-d) δ ppm 0.83-1.31 (m, 5H) 1.45-1.96 (m, 5H) 2.22 (d, J=12.62 Hz, 1H) 2.35 (s, 3H) 3.88 (s, 3H) 4.60 (d, J=8.67 Hz, 1H) 6.87 (s, 1H) 7.06-7.35 (m, 1H) 7.57 (d, J=9.23 Hz, 1H) 8.29 (d, J=2.26 Hz, 1H)

(5) 4-({cyclohexyl[5-(5-methoxypyridin-2-yl)-2-methylfuran-3-yl]methyl}amino)benzoic acid A mixture of 2-{4-[chloro(cyclohexyl)methyl]-5-methylfuran-2-yl}-5-methoxypyridine (0.9 g) obtained by the above-mentioned reaction, methyl 4-aminobenzoate (0.6 g), sodium carbonate (0.5 g) and sodium iodide (0.8 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (3 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.7 g, 55%) as a white crystal.

¹H NMR (300 MHz, CHLOROFORM-d) δ ppm 1.00-1.33 (m, 5H) 1.46-1.84 (m, 5H) 1.98 (d, J=12.06 Hz, 1H) 2.39 (s, 3H) 3.86 (s, 3H) 4.12 (q, J=7.16 Hz, 1H) 6.44-6.56 (m, 2H) 6.72 (s, 1H) 7.19 (dd, J=8.76, 2.92 Hz, 1H) 7.54 (d, J=8.85 Hz, 1H) 7.73-7.89 (m, 2H) 8.25 (d, J=2.45 Hz, 1H)

(6) 3-({[4-({1-[5-(5-methoxypyridin-2-yl)-2-methylfuran-3-yl]-3-methylbutyl}amino)phenyl]carbonyl}amino)propanoic acid A solution of 4-({cyclohexyl[5-(5-methoxypyridin-2-yl)-2-methylfuran-3-yl]methyl}amino)benzoic acid (168 mg) obtained by the above-mentioned reaction, ethyl β-alaninate hydrochloride (74 mg), 1-ethyl-3-(3-dimethylaminopropyl) carbodiimide hydrochloride (92 mg), hydroxybenzotriazole monohydrate (74 mg) and triethylamine (67 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (171 mg, 87%).

¹H NMR (300 MHz, DMSO-d₆) δ ppm 0.92-1.25 (m, 5H) 1.45-1.85 (m, 5H) 1.94-2.12 (m, 1H) 2.37 (s, 3H) 2.43 (t, J=7.16 Hz, 2H) 3.30-3.47 (m, 2H) 3.82 (s, 3H) 4.12 (t, J=8.01 Hz, 1H) 6.36 (d, J=8.48 Hz, 1H) 6.56 (d, J=8.85 Hz, 2H) 6.80 (s, 1H) 7.27-7.45 (m, 1H) 7.52 (d, J=8.48 Hz, 3H) 7.98 (t, J=5.56 Hz, 1H) 8.21 (d, J=2.45 Hz, 1H) 12.13 (brs, 1H)

Example 221

3-({[4-({cyclohexyl[5-(5-methoxypyridin-2-yl)-2-methylfuran-3-yl]methyl}amino)phenyl]carbonyl}(methyl)amino)propanoic acid

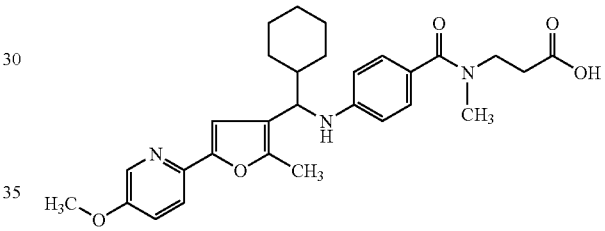

A solution of 4-({cyclohexyl[5-(5-methoxypyridin-2-yl)-2-methylfuran-3-yl]methyl}amino)benzoic acid (168 mg), ethyl 3-(methylamino)propanoate (63 mg), 1-ethyl-3-(3-dimethylaminopropyl)carbodiimide hydrochloride (92 mg), hydroxybenzotriazole monohydrate (74 mg) and triethylamine (67 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (161 mg, 80%).

¹H NMR (300 MHz, DMSO-d₆) δ ppm 0.92-1.25 (m, 5H) 1.48-1.80 (m, 5H) 2.04 (d, J=10.74 Hz, 1H) 2.37 (s, 3H) 2.41-2.49 (m, 2H) 2.90 (s, 3H) 3.52 (t, J=7.35 Hz, 2H) 3.82 (s, 3H) 3.97-4.19 (m, 2H) 6.26 (d, J=8.48 Hz, 1H) 6.55 (d, J=8.67 Hz, 2H) 6.81 (s, 1H) 7.10 (d, J=8.67 Hz, 2H) 7.39 (dd, J=8.76, 2.92 Hz, 1H) 7.47-7.60 (m, 1H) 8.21 (d, J=2.45 Hz, 1H) 12.25 (brs, 1H)

Example 222

3-({[4-({cyclohexyl[2-methyl-5-(5-methylpyridin-3-yl)furan-3-yl]methyl}amino)phenyl]carbonyl}amino)propanoic acid

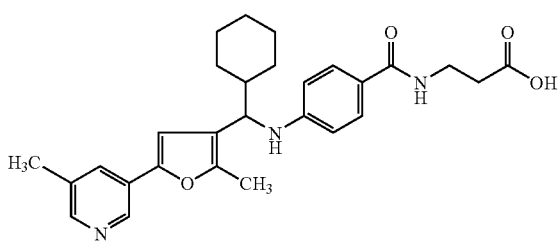

(1) 5-(5-methylpyridin-3-yl)-2-methylfuran-3-carbaldehyde

A mixture of 5-bromo-2-methylfuran-3-carbaldehyde (1.9 g), 5-methyl-3-pyridineboronic acid (1.6 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 50% ethyl acetate/hexane), and crystallized from ethyl acetate/hexane to give the title compound (1.6 g, 81%) as a white crystal.

$^1$H NMR (300 MHz, CHLOROFORM-d) δ ppm 2.39 (s, 3H) 2.69 (s, 3H) 6.99 (s, 1H) 7.73 (s, 1H) 8.38 (d, J=1.51 Hz, 1H) 8.73 (d, J=1.89 Hz, 1H) 9.98 (s, 1H)

(2) cyclohexyl[2-methyl-5-(5-methylpyridin-3-yl)furan-3-yl]methanol

To a solution of 5-(5-methylpyridin-3-yl)-2-methylfuran-3-carbaldehyde (1.6 g) obtained by the above-mentioned reaction in tetrahydrofuran (20 mL) was added dropwise 1N cyclohexylmagnesium bromide-tetrahydrofuran solution (12 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (2.0 g, 89%) as a white crystal.

$^1$H NMR (300 MHz, CHLOROFORM-d) δ ppm 0.71-1.39 (m, 5H) 1.43-1.90 (m, 5H) 1.97-2.15 (m, 1H) 2.34 (s, 3H) 2.35 (s, 3H) 4.31 (d, J=7.91 Hz, 1H) 6.67 (s, 1H) 7.70 (d, J=0.75 Hz, 1H) 8.28 (d, J=1.51 Hz, 1H) 8.68 (d, J=1.88 Hz, 1H)

(3) 3-{4-[chloro(cyclohexyl)methyl]-5-methylfuran-2-yl}-5-methylpyridine

To a solution of cyclohexyl[2-methyl-5-(2-methylpyridin-3-yl)furan-3-yl]methanol (2.0 g) obtained by the above-mentioned reaction in toluene (20 mL) were added thionyl chloride (0.8 mL) and pyridine (0.8 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (2.1 g, 100%) as an oil.

$^1$H NMR (300 MHz, CHLOROFORM-d) δ ppm 0.84-1.33 (m, 5H) 1.60-1.98 (m, 5H) 2.13-2.28 (m, 1H) 2.28-2.41 (m, 6H) 4.60 (d, J=8.71 Hz, 1H) 6.63-6.76 (m, 1H) 7.72 (s, 1H) 8.30 (s, 1H) 8.69 (s, 1H)

(4) 4-({cyclohexyl[2-methyl-5-(5-methylpyridin-3-yl)furan-3-yl]methyl}amino)benzoic acid A mixture of 3-{4-[chloro(cyclohexyl)methyl]-5-methylfuran-2-yl}-5-methylpyridine (2.1 g) obtained by the above-mentioned reaction, methyl 4-aminobenzoate (1.6 g), sodium carbonate (1.1 g) and sodium iodide (2.1 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (7 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.5 g, 19%) as a white crystal.

$^1$H NMR (300 MHz, CHLOROFORM-d) δ ppm 0.88-1.10 (m, 5H) 1.61-1.88 (m, 5H) 1.90-2.03 (m, 1H) 2.33 (s, 3H) 2.39 (s, 3H) 4.11 (d, J=6.59 Hz, 1H) 6.50 (d, J=8.85 Hz, 2H) 6.53 (s, 1H) 7.67 (s, 1H) 7.85 (d, J=8.85 Hz, 2H) 8.27 (d, J=1.51 Hz, 1H) 8.65 (d, J=1.88 Hz, 1H)

(5) 3-({[4-({1-[5-(5-methylpyridin-3-yl)-2-methylfuran-3-yl]-3-methylbutyl}amino)phenyl]carbonyl}amino)propanoic acid A solution of 4-({cyclohexyl[2-methyl-5-(5-methylpyridin-3-yl)furan-3-yl]methyl}amino)benzoic acid (162 mg) obtained by the above-mentioned reaction, ethyl β-alaninate hydrochloride (74 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (153 mg, 81%).

$^1$H NMR (300 MHz, DMSO-$d_6$) δ ppm 0.94-1.25 (m, 5H) 1.49-1.82 (m, 5H) 2.02-2.05 (m, 1H) 2.30 (s, 3H) 2.38 (s, 3H) 2.43 (t, J=7.06 Hz, 2H) 3.23-3.47 (m, 2H) 4.12 (t, J=7.82 Hz, 1H) 6.35 (d, J=8.10 Hz, 1H) 6.55 (d, J=8.48 Hz, 2H) 6.86 (s, 1H) 7.52 (d, J=8.67 Hz, 2H) 7.74 (s, 1H) 7.98 (s, 1H) 8.25 (d, J=0.94 Hz, 1H) 8.59 (d, J=1.51 Hz, 1H) 12.14 (brs, 1H)

Example 223

3-({[4-({cyclohexyl[5-(5-methoxypyridin-3-yl)-2-methylfuran-3-yl]methyl}amino)phenyl]carbonyl}(methyl)amino)propanoic acid

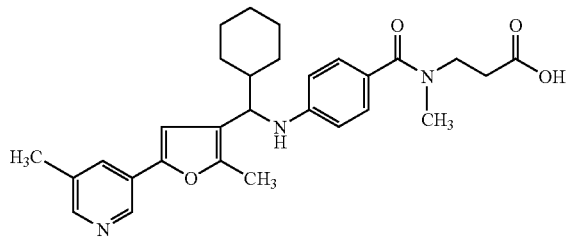

A solution of 4-({cyclohexyl[2-methyl-5-(5-methylpyridin-3-yl)furan-3-yl]methyl}amino)benzoic acid (162 mg), ethyl 3-(methylamino)propanoate (63 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (161 mg, 82%).

$^1$H NMR (300 MHz, DMSO-$d_6$) δ ppm 0.85-1.31 (m, 5H) 1.48-1.90 (m, 5H) 1.95-2.13 (m, 1H) 2.30 (s, 3H) 2.38 (s, 3H) 2.47-2.50 (m, 2H) 2.90 (s, 3H) 3.52 (t, J=7.06 Hz, 2H) 4.08 (t, J=7.06 Hz, 1H) 6.24 (d, J=7.54 Hz, 1H) 6.55 (d, J=8.48 Hz, 2H) 6.87 (s, 1H) 7.10 (d, J=8.48 Hz, 2H) 7.75 (s, 1H) 8.25 (s, 1H) 8.60 (s, 1H) 12.25 (brs, 1H)

Example 224

3-({[4-({cyclohexyl[2-methyl-5-(5-{trifluoromethyl}pyridin-2-yl)furan-3-yl]methyl}amino)phenyl]carbonyl}amino)propanoic acid

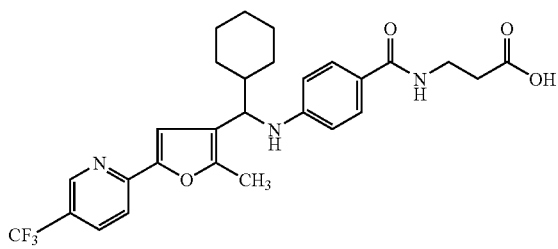

(1) [2-methyl-5-(5-{trifluoromethyl}pyridin-2-yl)furan-3-yl]methanol

A mixture of tert-butyl({5-[(5,5-dimethyl-1,3,2-dioxaborinan-2-yl)methyl]-2-methylfuran-3-yl}methoxy)dimethylsilane (2.4 g), 2-chloro-5-trifluoromethylpyridine (1.8 g), tetrakis(triphenylphosphine)palladium(0) (0.4 g), 2N aqueous sodium carbonate solution (7 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was dissolved in tetrahydrofuran (20 mL), 1N tetrabutylammonium fluoride in tetrahydrofuran (10 mL) was added, and the mixture was stirred at room temperature for 2 hr. The reaction mixture was poured into water, and the mixture was extracted with ethyl acetate. The organic layer was washed with saturated brine, and dried over magnesium sulfate. The solvent was evaporated under reduced pressure, purified by silica gel chromatography (10% ethyl acetate/hexane to 100% ethyl acetate/hexane), and crystallized from ethyl acetate/hexane to give the title compound (1.1 g, 62%) as a yellow crystal.

$^1$H NMR (300 MHz, CHLOROFORM-d) δ ppm 1.53 (t, J=5.56 Hz, 1H) 2.43 (s, 3H) 4.55 (d, J=5.46 Hz, 2H) 7.16 (s, 1H) 7.70 (d, J=8.29 Hz, 1H) 7.90 (dd, J=8.29, 1.70 Hz, 1H) 8.80 (d, J=0.94 Hz, 1H)

(2) 2-methyl-5-[5-(trifluoromethyl)pyridin-2-yl]furan-3-carbaldehyde

To a solution of [5-(5-{trifluoromethyl}pyridin-2-yl)-2-methylfuran-3-yl]methanol (1.1 g) obtained by the above-mentioned reaction in acetonitrile (20 mL) was added Dess-Martin reagent (2.7 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (10% ethyl acetate/hexane to 50% ethyl acetate/hexane) to give the title compound (1.0 g, 94%) as a white crystal.

$^1$H NMR (300 MHz, CHLOROFORM-d) δ ppm 2.74 (s, 3H) 7.43 (s, 1H) 7.77 (d, J=8.33 Hz, 1H) 7.97 (dd, J=8.14, 2.08 Hz, 1H) 8.87 (d, J=1.51 Hz, 1H) 10.01 (s, 1H)

(3) cyclohexyl{2-methyl-5-[5-(trifluoromethyl)pyridin-2-yl]furan-3-yl}methanol

To a solution of 2-methyl-5-[5-(trifluoromethyl)pyridin-2-yl]furan-3-carbaldehyde (1.0 g) obtained by the above-mentioned reaction in tetrahydrofuran (20 mL) was added dropwise 1N cyclohexylmagnesium bromide-tetrahydrofuran solution (6 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 35% ethyl acetate/hexane) to give the title compound (1.3 g, 95%) as a yellow crystal.

$^1$H NMR (300 MHz, CHLOROFORM-d) δ ppm 1.04-1.36 (m, 5H) 1.50-1.83 (m, 5H) 2.06 (d, J=14.32 Hz, 1H) 2.39 (s, 3H) 4.34 (dd, J=7.72, 3.20 Hz, 1H) 7.13 (s, 1H) 7.70 (d, J=8.29 Hz, 1H) 7.89 (dd, J=8.38, 1.79 Hz, 1H) 8.80 (d, J=2.26 Hz, 1H)

(4) 2-{4-[chloro(cyclohexyl)methyl]-5-methylfuran-2-yl}-5-(trifluoromethyl)pyridine To a solution of cyclohexyl{2-methyl-5-[5-(trifluoromethyl)pyridin-2-yl]furan-3-yl}methanol (1.3 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.4 g, 100%) as an oil.

$^1$H NMR (300 MHz, CHLOROFORM-d) δ ppm 0.84-1.36 (m, 5H) 1.59-1.95 (m, 5H) 2.21 (d, J=12.87 Hz, 1H) 2.36 (s, 2H) 4.61 (d, J=8.33 Hz, 1H) 7.16 (s, 1H) 7.71 (d, J=8.71 Hz, 1H) 7.91 (dd, J=8.33, 1.89 Hz, 1H) 8.81 (s, 1H)

(5) 4-({cyclohexyl[2-methyl-5-(5-{trifluoromethyl}pyridin-2-yl)furan-3-yl]methyl}amino)benzoic acid A mixture of 2-{4-[chloro(cyclohexyl)methyl]-5-methylfuran-2-yl}-5-(trifluoromethyl)pyridine (1.4 g) obtained by the above-mentioned reaction, methyl 4-aminobenzoate (0.9 g), sodium carbonate (0.6 g) and sodium iodide (1.1 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.2 g, 68%) as an amorphous compound.

$^1$H NMR (300 MHz, CHLOROFORM-d) δ ppm 0.88-1.20 (m, 5H) 1.62-1.83 (m, 5H) 1.98 (d, J=12.43 Hz, 1H) 2.44 (s, 3H) 4.12-4.21 (m, 1H) 6.49 (d, J=8.85 Hz, 2H) 7.02 (s, 1H) 7.68 (d, J=8.48 Hz, 1H) 7.76-7.94 (m, 3H) 8.76 (d, J=0.94 Hz, 1H)

(6) 3-({[4-({cyclohexyl[2-methyl-5-(5-{trifluoromethyl}pyridin-2-yl)furan-3-yl]methyl}amino)phenyl]carbonyl}amino)propanoic acid A solution of 4-({cyclohexyl[2-methyl-5-(5-{trifluoromethyl}pyridin-2-yl)furan-3-yl]methyl}amino)benzoic acid (229 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (242 mg, 91%).

$^1$H NMR (300 MHz, DMSO-d$_6$) δ ppm 0.93-1.26 (m, 5H) 1.46-1.79 (m, 5H) 2.03 (d, J=9.61 Hz, 1H) 2.32-2.47 (m, 5H) 3.34 (q, J=6.97 Hz, 2H) 4.19 (t, J=8.10 Hz, 1H) 6.40 (d, J=8.29 Hz, 1H) 6.57 (d, J=8.85 Hz, 2H) 7.19 (s, 1H) 7.52 (d, J=8.48 Hz, 2H) 7.74 (d, J=8.48 Hz, 1H) 7.90-8.08 (m, 1H) 8.16 (dd, J=8.48, 2.45 Hz, 1H) 8.85 (d, J=0.94 Hz, 1H) 12.10 (s, 1H)

Example 225

3-[({4-[(cyclohexyl{2-methyl-5-[5-(trifluoromethyl)pyridin-2-yl]furan-3-yl}methyl)amino]phenyl}carbonyl)(methyl)amino]propanoic acid

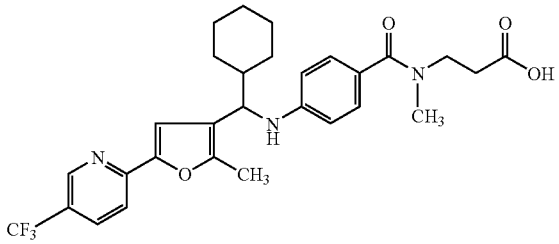

A solution of 4-({cyclohexyl[2-methyl-5-(5-{trifluoromethyl}pyridin-2-yl)furan-3-yl]methyl}amino)benzoic acid (229 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (161 mg, 80%).

$^1$H NMR (300 MHz, DMSO-d$_6$) δ ppm 0.93-1.26 (m, 5H) 1.50-1.78 (m, 5H) 1.97-2.13 (m, 1H) 2.43 (s, 3H) 2.45-2.50 (m, 2H) 2.89 (s, 3H) 3.50 (t, J=7.19 Hz, 2H) 4.15 (t, J=7.95 Hz, 1H) 6.29 (d, J=8.33 Hz, 1H) 6.56 (d, J=8.33 Hz, 2H) 7.10 (d, J=8.33 Hz, 2H) 7.20 (s, 1H) 7.74 (d, J=8.33 Hz, 1H) 8.16 (d, J=8.33 Hz, 1H) 8.85 (s, 1H) 12.36 (brs, 1H)

Example 226

3-[({4-[(cyclohexyl{2-methyl-5-[4-(methylsulfonyl)phenyl]furan-3-yl}methyl)amino]phenyl}carbonyl)amino]propanoic acid

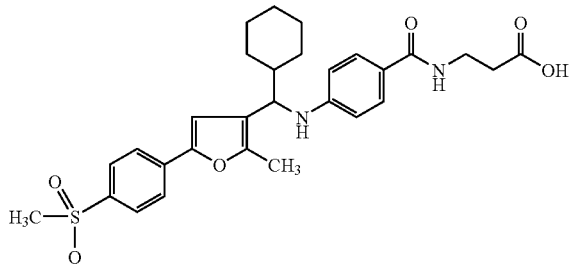

(1) 2-methyl-5-[4-(methylsulfonyl)phenyl]furan-3-carbaldehyde

A mixture of 5-bromo-2-methylfuran-3-carbaldehyde (1.5 g), 4-(methanesulfonyl)phenylboronic acid (2.0 g), tetrakis(triphenylphosphine)palladium(0) (0.5 g), 2N aqueous sodium carbonate solution (10 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 100% ethyl acetate/hexane), and crystallized from ethyl acetate/hexane to give the title compound (1.3 g, 64%) as a yellow crystal.

$^1$H NMR (300 MHz, CHLOROFORM-d) δ ppm 2.71 (s, 3H) 3.08 (s, 3H) 7.11 (s, 1H) 7.83 (d, J=8.85 Hz, 2H) 7.98 (d, J=8.85 Hz, 2H) 9.99 (s, 1H)

(2) cyclohexyl{2-methyl-5-[4-(methylsulfonyl)phenyl]furan-3-yl}methanol

To a solution of 2-methyl-5-[4-(methylsulfonyl)phenyl]furan-3-carbaldehyde (1.3 g) obtained by the above-mentioned reaction in tetrahydrofuran (20 mL) was added dropwise 1N cyclohexylmagnesium bromide-tetrahydrofuran solution (7.5 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (1.6 g, 91%) as a yellow crystal.

$^1$H NMR (300 MHz, DMSO-$d_6$) δ ppm 0.74-1.33 (m, 5H) 1.38-1.66 (m, 5H) 1.90-2.06 (m, 1H) 2.32 (s, 3H) 3.22 (s, 3H) 4.18 (dd, J=7.19, 4.16 Hz, 1H) 4.92 (d, J=4.16 Hz, 1H) 7.07 (s, 1H) 7.79-7.96 (m, 4H)

(3) 3-[chloro(cyclohexyl)methyl]-2-methyl-5-[4-(methylsulfonyl)phenyl]furan

To a solution of cyclohexyl{2-methyl-5-[4-(methylsulfonyl)phenyl]furan-3-yl}methanol (1.6 g) obtained by the above-mentioned reaction in toluene (20 mL) were added thionyl chloride (0.5 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.7 g, 100%) as an amorphous compound.

$^1$H NMR (300 MHz, CHLOROFORM-d) δ ppm 0.89-1.17 (m, 5H) 1.59-1.93 (m, 5H) 2.18 (d, J=2.83 Hz, 1H) 2.36 (d, J=1.51 Hz, 3H) 3.07 (s, 3H) 4.60 (d, J=8.48 Hz, 1H) 6.82 (s, 1H) 7.71-7.85 (m, 2H) 7.86-7.99 (m, 2H)

(4) 4-[(cyclohexyl{2-methyl-5-[4-(methylsulfonyl)phenyl]furan-3-yl}methyl)amino]benzoic acid A mixture of 3-[chloro(cyclohexyl)methyl]-2-methyl-5-[4-(methylsulfonyl)phenyl]furan (1.7 g) obtained by the above-mentioned reaction, methyl 4-aminobenzoate (1.0 g), sodium carbonate (0.7 g) and sodium iodide (1.4 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (4.5 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.9 g, 90%) as an amorphous compound.

$^1$H NMR (300 MHz, CHLOROFORM-d) δ ppm 0.89-1.43 (m, 5H) 1.63-1.88 (m, 5H) 1.97 (d, J=12.62 Hz, 1H) 2.41 (s, 3H) 3.04 (s, 3H) 6.50 (d, J=8.85 Hz, 2H) 6.64 (s, 1H) 7.72 (d, J=8.85 Hz, 2H) 7.81-7.91 (m, 4H)

(5) 3-[({4-[(cyclohexyl{2-methyl-5-[4-(methylsulfonyl)phenyl]furan-3-yl}methyl)amino]phenyl}carbonyl)amino]propanoic acid A solution of 4-[(cyclohexyl{2-methyl-5-[4-(methylsulfonyl)phenyl]furan-3-yl}methyl)amino]benzoic acid (234 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (219 mg, 82%).

$^1$H NMR (300 MHz, DMSO-$d_6$) δ ppm 0.81-1.32 (m, 5H) 1.50-1.80 (m, 5H) 2.03 (d, J=10.60 Hz, 1H) 2.40 (s, 3H) 2.41 (d, J=14.01 Hz, 2H) 3.19 (s, 3H) 3.26-3.44 (m, 2H) 4.14 (t, J=7.57 Hz, 1H) 6.35 (d, J=7.95 Hz, 1H) 6.56 (d, J=8.71 Hz, 2H) 7.00 (s, 1H) 7.52 (d, J=8.71 Hz, 2H) 7.71-7.82 (m, 2H) 7.83-7.94 (m, 2H) 8.00 (t, J=5.49 Hz, 1H) 12.20 (brs, 1H)

Example 227

3-[({4-[(cyclohexyl{2-methyl-5-[4-(methylsulfonyl)phenyl]furan-3-yl}methyl)amino]phenyl}carbonyl)(methyl)amino]propanoic acid

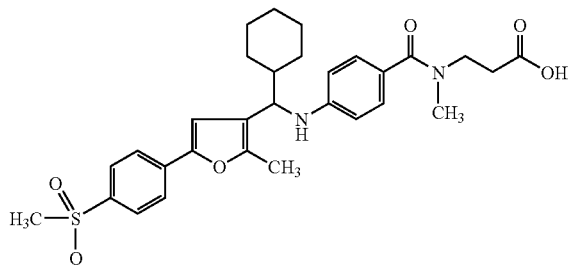

A solution of 4-[(cyclohexyl{2-methyl-5-[4-(methylsulfonyl)phenyl]furan-3-yl}methyl)amino]benzoic acid (234 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (222 mg, 80%).

$^1$H NMR (300 MHz, DMSO-$d_6$) δ ppm 0.82-1.32 (m, 5H) 1.47-1.80 (m, 5H) 2.03 (d, J=12.12 Hz, 1H) 2.40 (s, 3H) 2.42-2.49 (m, 2H) 2.89 (s, 3H) 3.20 (s, 3H) 3.50 (t, J=7.38 Hz, 2H) 4.10 (t, J=7.57 Hz, 1H) 6.25 (d, J=7.95 Hz, 1H) 6.56 (d, J=8.71 Hz, 2H) 7.02 (s, 1H) 7.10 (d, J=8.33 Hz, 2H) 7.71-7.84 (m, 2H) 7.84-7.99 (m, 2H)

Example 228

3-({[4-({cyclohexyl[2-methyl-5-(6-methylpyridin-3-yl)furan-3-yl]methyl}amino)phenyl]carbonyl}amino)propanoic acid

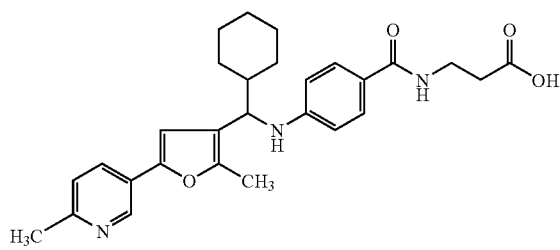

(1) 5-(6-methylpyridin-3-yl)-2-methylfuran-3-carbaldehyde

A mixture of 5-bromo-2-methylfuran-3-carbaldehyde (1.5 g), 2-methyl-5-(4,4,5,5-tetramethyl-1,3,2-dioxaborolan-2-yl)pyridine (2.1 g), tetrakis(triphenylphosphine)palladium (0) (0.5 g), 2N aqueous sodium carbonate solution (10 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (10% ethyl acetate/hexane to 50% ethyl acetate/hexane), and crystallized from ethyl acetate/hexane to give the title compound (1.3 g, 82%) as a yellow crystal.

$^1$H NMR (300 MHz, CHLOROFORM-d) δ ppm 2.59 (s, 3H) 2.69 (s, 3H) 6.95 (s, 1H) 7.19 (d, J=8.33 Hz, 1H) 7.81 (dd, J=7.95, 2.27 Hz, 1H) 8.80 (d, J=2.27 Hz, 1H) 9.97 (s, 1H)

(2) cyclohexyl[2-methyl-5-(6-methylpyridin-3-yl)furan-3-yl]methanol

To a solution of 5-(6-methylpyridin-3-yl)-2-methylfuran-3-carbaldehyde (1.3 g) obtained by the above-mentioned reaction in tetrahydrofuran (20 mL) was added dropwise 1N cyclohexylmagnesium bromide-tetrahydrofuran solution (10 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (5% ethyl acetate/hexane to 50% ethyl acetate/hexane) to give the title compound (1.7 g, 93%) as an amorphous compound.

$^1$H NMR (300 MHz, CHLOROFORM-d) δ ppm 1.00-1.31 (m, 5H) 1.44-1.95 (m, 5H) 2.00-2.16 (m, 1H) 2.33 (s, 3H) 2.55 (s, 3H) 4.30 (d, J=6.44 Hz, 1H) 6.61 (s, 1H) 7.13 (d, J=8.33 Hz, 1H) 7.77 (dd, J=7.95, 2.27 Hz, 1H) 8.74 (d, J=1.89 Hz, 1H)

(3) 3-{4-[chloro(cyclohexyl)methyl]-5-methylfuran-2-yl}-6-methylpyridine

To a solution of cyclohexyl[2-methyl-5-(6-methylpyridin-3-yl)furan-3-yl]methanol (1.7 g) obtained by the above-mentioned reaction in toluene (20 mL) were added thionyl chloride (0.7 mL) and pyridine (0.7 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.8 g, 100%) as an oil.

$^1$H NMR (300 MHz, CHLOROFORM-d) δ ppm 1.01-1.34 (m, 5H) 1.60-1.90 (m, 5H) 2.21 (d, J=12.87 Hz, 1H) 2.34 (s, 3H) 2.57 (s, 3H) 4.60 (d, J=8.71 Hz, 1H) 6.54-6.69 (m, 2H) 7.79 (dd, J=8.33, 2.27 Hz, 1H) 8.76 (d, J=1.51 Hz, 1H)

(4) 4-({cyclohexyl[2-methyl-5-(6-methylpyridin-3-yl)furan-3-yl]methyl}amino)benzoic acid A mixture of 3-{4-[chloro(cyclohexyl)methyl]-5-methylfuran-2-yl}-6-methylpyridine (1.8 g) obtained by the above-mentioned reaction, methyl 4-aminobenzoate (1.4 g), sodium carbonate (1.0 g) and sodium iodide (1.8 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (6 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 70% ethyl acetate/hexane) to give the title compound (0.6 g, 24%) as an amorphous compound.

$^1$H NMR (300 MHz, CHLOROFORM-d) δ ppm 1.00-1.32 (m, 5H) 1.53-1.85 (m, 5H) 1.97 (d, J=12.87 Hz, 1H) 2.39 (s, 3H) 2.54 (s, 3H) 4.11 (d, J=6.44 Hz, 1H) 6.48 (s, 1H) 6.51 (d, J=9.09 Hz, 2H) 7.11 (d, J=8.33 Hz, 1H) 7.74 (dd, J=7.95, 2.27 Hz, 1H) 7.85 (d, J=9.09 Hz, 2H) 8.72 (d, J=1.89 Hz, 1H)

(5) 3-({[4-({1-[5-(6-methylpyridin-3-yl)-2-methylfuran-3-yl]-3-methylbutyl}amino)phenyl]carbonyl}amino)propanoic acid A solution of 4-({cyclohexyl[2-methyl-5-(6-methylpyridin-3-yl)furan-3-yl]methyl}amino)benzoic acid (162 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (158 mg, 83%).

$^1$H NMR (300 MHz, DMSO-d$_6$) δ ppm 0.75-1.33 (m, 5H) 1.56-1.75 (m, 5H) 2.03 (d, J=11.74 Hz, 1H) 2.37 (s, 3H) 2.39-2.47 (m, 5H) 3.31-3.47 (m, 2H) 4.11 (t, J=7.76 Hz, 1H) 6.33 (d, J=7.95 Hz, 1H) 6.55 (d, J=9.09 Hz, 2H) 6.80 (s, 1H) 7.24 (d, J=7.95 Hz, 1H) 7.52 (d, J=8.71 Hz, 2H) 7.80 (dd, J=7.95, 2.27 Hz, 1H) 7.98 (t, J=5.49 Hz, 1H) 8.65 (d, J=2.27 Hz, 1H) 12.16 (brs, 1H)

Example 229

3-({[4-({cyclohexyl[5-(6-methoxypyridin-3-yl)-2-methylfuran-3-yl]methyl}amino)phenyl]carbonyl}(methyl)amino)propanoic acid

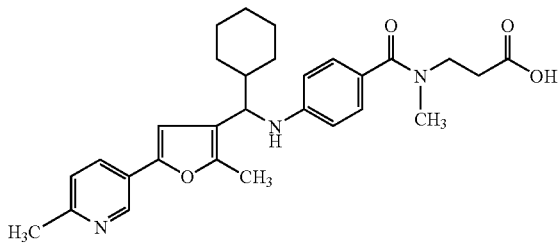

A solution of 4-({cyclohexyl[2-methyl-5-(6-methylpyridin-3-yl)furan-3-yl]methyl}amino)benzoic acid (162 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.8 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (163 mg, 83%).

$^1$H NMR (300 MHz, DMSO-d$_6$) δ ppm 0.94-1.27 (m, 5H) 1.48-1.81 (m, 5H) 2.03 (d, J=10.22 Hz, 1H) 2.37 (s, 3H) 2.41-2.47 (m, 5H) 2.90 (s, 3H) 3.51 (t, J=7.38 Hz, 2H) 4.07 (t, J=7.76 Hz, 1H) 6.23 (d, J=7.95 Hz, 1H) 6.55 (d, J=8.71 Hz, 2H) 6.81 (s, 1H) 7.10 (d, J=8.33 Hz, 2H) 7.24 (d, J=8.33 Hz, 1H) 7.81 (dd, J=7.95, 2.27 Hz, 1H) 8.66 (d, J=1.89 Hz, 1H) 12.30 (brs, 1H)

Example 230

3-[({4-[(cyclohexyl{2-[(methylsulfanyl)methyl]-5-phenylfuran-3-yl}methyl)amino]phenyl}carbonyl)amino]propanoic acid

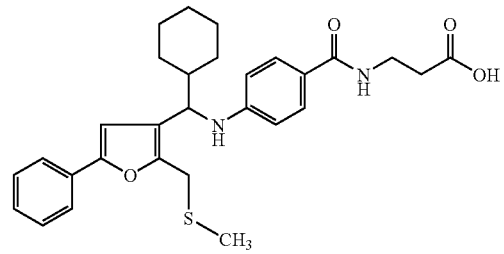

(1) methyl 5-bromo-2-[(methylsulfanyl)methyl]furan-3-carboxylate

To a solution of methyl 5-bromo-2-(bromomethyl)furan-3-carboxylate (8.9 g) in tetrahydrofuran (50 mL) was added sodium methanethiolate (2.5 g) at 0° C., and the mixture was stirred overnight at room temperature. The reaction mixture was poured into water, and the mixture was extracted with ethyl acetate. The organic layer was washed with water, and dried over magnesium sulfate. The solvent was evaporated under reduced pressure, and the residue was purified by silica gel chromatography (0% ethyl acetate/hexane to 10% ethyl acetate/hexane) to give the title compound (6.7 g, 84%) as an oil.

$^1$H NMR (300 MHz, CHLOROFORM-d) δ ppm 2.14 (s, 3H) 3.83 (s, 3H) 4.01 (s, 2H) 6.59 (s, 1H)

(2) methyl 2-[(methylsulfanyl)methyl]-5-phenylfuran-3-carboxylate

A mixture of methyl 5-bromo-2-[(methylsulfanyl)methyl]furan-3-carboxylate (6.6 g) obtained by the above-mentioned reaction, phenylboronic acid (3.7 g), tetrakis(triphenylphosphine)palladium(0) (1.5 g), 2N aqueous sodium carbonate solution (30 mL) and 1,2-dimethoxyethane (50 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane) to give the title compound (6.1 g, 81%) as an oil.

$^1$H NMR (300 MHz, CHLOROFORM-d) δ ppm 2.19 (s, 3H) 3.87 (s, 3H) 4.11 (s, 2H) 6.91 (s, 1H) 7.20-7.34 (m, 1H) 7.40 (t, J=7.57 Hz, 2H) 7.66 (d, J=7.19 Hz, 2H)

(3) {2-[(methylsulfanyl)methyl]-5-phenylfuran-3-yl}methanol

A solution of methyl 2-[(methylsulfanyl)methyl]-5-phenylfuran-3-carboxylate (6.0 g) obtained by the above-mentioned reaction in tetrahydrofuran (50 mL) was added dropwise to a suspension of lithium aluminum hydride (0.9 g) in tetrahydrofuran (50 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (5.4 g, 100%) as an oil.

$^1$H NMR (300 MHz, CHLOROFORM-d) δ ppm 2.15 (s, 3H) 3.81 (s, 2H) 4.57 (s, 2H) 6.67 (s, 1H) 7.23-7.28 (m, 1H) 7.37 (t, J=7.38 Hz, 2H) 7.64 (d, J=7.19 Hz, 2H)

(4) 2-[(methylsulfanyl)methyl]-5-phenylfuran-3-carbaldehyde

To a solution of {2-[(methylsulfanyl)methyl]-5-phenylfuran-3-yl}methanol (5.4 g) obtained by the above-mentioned reaction in acetonitrile (50 mL) was added Dess-Martin reagent (14.6 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 20% ethyl acetate/hexane) to give the title compound (3.3 g, 62%) as a yellow crystal.

$^1$H NMR (300 MHz, CHLOROFORM-d) δ ppm 2.20 (s, 3H) 4.04 (s, 2H) 6.95 (s, 1H) 7.29-7.37 (m, 1H) 7.37-7.49 (m, 2H) 7.57-7.73 (m, 2H) 10.01 (s, 1H)

(5) cyclohexyl{2-[(methylsulfanyl)methyl]-5-phenylfuran-3-yl}methanol

To a solution of 2-[(methylsulfanyl)methyl]-5-phenylfuran-3-carbaldehyde (3.3 g) obtained by the above-mentioned reaction in tetrahydrofuran (50 mL) was added dropwise 1N cyclohexylmagnesium bromide-tetrahydrofuran solution (21 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (3.2 g, 73%) as an oil.

$^1$H NMR (300 MHz, CHLOROFORM-d) δ ppm 0.82-1.36 (m, 5H) 1.59-1.85 (m, 5H) 1.88 (d, J=3.20 Hz, 1H) 2.05-2.12 (m, 1H) 2.19 (s, 3H) 3.79 (s, 3H) 4.36 (dd, J=7.82, 2.92 Hz, 1H) 6.61 (s, 1H) 7.18-7.30 (m, 1H) 7.31-7.44 (m, 2H) 7.64 (dd, J=8.48, 1.32 Hz, 2H)

(6) 3-[chloro(cyclohexyl)methyl]-2-[(methylsulfanyl)methyl]-5-phenylfuran

To a solution of cyclohexyl{2-[(methylsulfanyl)methyl]-5-phenylfuran-3-yl}methanol (3.2 g) obtained by the above-mentioned reaction in toluene (20 mL) were added thionyl chloride (1.1 mL) and pyridine (1.2 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (3.4 g, 100%) as an oil.

$^1$H NMR (300 MHz, CHLOROFORM-d) δ ppm 0.80-1.42 (m, 5H) 1.58-1.98 (m, 5H) 2.18 (s, 3H) 2.27 (d, J=1.32 Hz, 1H) 3.75 (s, 2H) 4.65 (d, J=8.67 Hz, 1H) 6.66 (s, 1H) 7.22-7.30 (m, 1H) 7.30-7.42° (m, 2H) 7.65 (dd, J=8.38, 1.22 Hz, 2H)

(7) 4-[(cyclohexyl{2-[(methylsulfanyl)methyl]-5-phenylfuran-3-yl}methyl)amino]benzoic acid A mixture of 3-[chloro(cyclohexyl)methyl]-2-[(methylsulfanyl)methyl]-5-phenylfuran (3.4 g) obtained by the above-mentioned reaction, methyl 4-aminobenzoate (2.3 g), sodium carbonate (1.6 g) and sodium iodide (3.0 g) in N,N-dimethylacetamide (30 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (10 mL) and tetrahydrofuran (10 mL), 2N lithium hydroxide (10 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (2.1 g, 49%) as an amorphous compound.

$^1$H NMR (300 MHz, CHLOROFORM-d) δ ppm 1.01-1.35 (m, 5H) 1.53-1.86 (m, 5H) 1.97 (d, J=10.98 Hz, 1H) 2.19 (s, 3H) 3.79 (s, 2H) 4.25 (d, J=6.44 Hz, 1H) 6.50 (s, 1H) 6.60 (d, J=8.71 Hz, 2H) 7.15-7.26 (m, 1H) 7.34 (t, J=7.57 Hz, 2H) 7.60 (d, J=7.19 Hz, 2H) 7.85 (d, J=8.71 Hz, 2H)

(8) ethyl 3-[({4-[(cyclohexyl{2-[(methylsulfanyl)methyl]-5-phenylfuran-3-yl}methyl)amino]phenyl}carbonyl)amino]propanoate A solution of 4-[(cyclohexyl{2-[(methylsulfanyl)methyl]-5-phenylfuran-3-yl}methyl)amino]benzoic acid (653 mg) obtained by the above-mentioned reaction, ethyl β-alaninate hydrochloride (276 mg), 1-ethyl-3-(3-dimethylaminopropyl)carbodiimide hydrochloride (345 mg), hydroxybenzotriazole monohydrate (276 mg) and triethylamine (209 μL) in N,N- dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the residue was purified by silica gel chromatography (5% ethyl acetate/hexane to 50% ethyl acetate/hexane) to give the title compound (663 mg, 83%) as an amorphous compound.

$^1$H NMR (300 MHz, CHLOROFORM-d) δ ppm 1.15-1.34 (m, 8H) 1.61-1.85 (m, 5H) 1.97 (d, J=8.71 Hz, 1H) 2.19 (s, 3H) 2.59 (t, J=5.87 Hz, 2H) 3.66 (q, J=6.06 Hz, 2H) 3.79 (s, 2H) 4.03-4.25 (m, 3H) 4.31 (d, J=6.82 Hz, 1H) 6.50 (s, 1H) 6.59 (d, J=8.71 Hz, 2H) 7.13-7.25 (m, 1H) 7.34 (t, J=7.57 Hz, 2H) 7.54-7.60 (m, 4H)

(9) 3-[({4-[(cyclohexyl{2-[(methylsulfanyl)methyl]-5-phenylfuran-3-yl}methyl)amino]phenyl}carbonyl)amino]propanoic acid Ethyl 3-[({4-[(cyclohexyl{2-[(methylsulfanyl)methyl]-5-phenylfuran-3-yl}methyl)amino]phenyl}carbonyl)amino]propanoate (114 mg) obtained by the above-mentioned reaction was dissolved in ethanol (2 mL) and tetrahydrofuran (2 mL), 1N lithium hydroxide (0.6 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (119 mg, 87%).

$^1$H NMR (300 MHz, DMSO-$d_6$) δ ppm 0.75-1.32 (m, 5H) 1.45-1.84 (m, 5H) 2.02 (d, J=12.12 Hz, 1H) 2.17 (s, 3H) 2.40 (t, J=7.00 Hz, 2H) 3.27-3.45 (m, 2H) 3.80-4.03 (m, 2H) 4.22 (t, J=7.95 Hz, 1H) 6.32 (d, J=7.95 Hz, 1H) 6.63 (d, J=8.71 Hz, 2H) 6.80 (s, 1H) 7.25 (t, J=7.38 Hz, 1H) 7.39 (t, J=7.57 Hz, 2H) 7.51 (d, J=8.71 Hz, 2H) 7.57 (d, J=7.19 Hz, 2H) 8.03 (t, J=5.49 Hz, 1H)

Example 231

3-[({4-[(cyclohexyl{2-[(methylsulfanyl)methyl]-5-phenylfuran-3-yl}methyl)amino]phenyl}carbonyl)(methyl)amino]propanoic acid

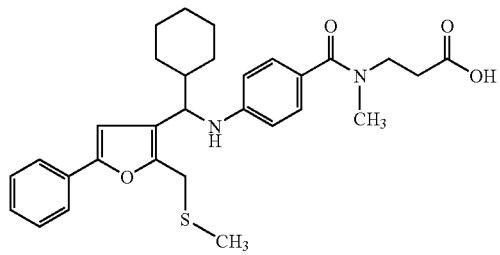

(1) ethyl 3-[({4-[(cyclohexyl{2-[(methylsulfanyl)methyl]-5-phenylfuran-3-yl}methyl)amino]phenyl}carbonyl)(methyl)amino]propanoate A solution of 4-({cyclohexyl[2-methyl-5-(5-methylpyridin-3-yl)furan-3-yl]methyl}amino)benzoic acid (653 mg) obtained by the above-mentioned reaction, ethyl 3-(methylamino)propanoate (236 mg), 1-ethyl-3-(3-dimethylaminopropyl)carbodiimide hydrochloride (345 mg), hydroxybenzotriazole monohydrate (276 mg) and triethylamine (209 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the residue was purified by silica gel chromatography (5% ethyl acetate/hexane to 50% ethyl acetate/hexane) to give the title compound (694 mg, 84%) as an amorphous compound.

$^1$H NMR (300 MHz, CHLOROFORM-d) δ ppm 0.92-1.12 (m, 8H) 1.64-1.77 (m, 5H) 1.97 (d, J=10.93 Hz, 1H) 2.18 (s, 3H) 2.62 (t, J=7.06 Hz, 2H) 3.02 (s, 3H) 3.73 (dt, J=9.94, 6.99 Hz, 2H) 3.79 (s, 2H) 4.08-4.18 (m, 3H) 6.51 (s, 1H) 6.57 (d, J=8.67 Hz, 2H) 7.16-7.29 (m, 3H) 7.35 (t, J=7.54 Hz, 2H) 7.50-7.67 (m, 2H)

(2) 3-[({4-[(cyclohexyl{2-[(methylsulfanyl)methyl]-5-phenylfuran-3-yl}methyl)amino]phenyl}carbonyl)(methyl)amino]propanoic acid Ethyl 3-[({4-[(cyclohexyl{2-[(methylsulfanyl)methyl]-5-phenylfuran-3-yl}methyl)amino]phenyl}carbonyl)(methyl)amino]propanoate (148 mg) obtained by the above-mentioned reaction was dissolved in ethanol (2 mL) and tetrahydrofuran (2 mL), 1N lithium hydroxide (0.6 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (116 mg, 82%).

$^1$H NMR (300 MHz, DMSO-$d_6$) δ ppm 0.94-1.27 (m, 5H) 1.46-1.83 (m, 5H) 2.03 (d, J=13.25 Hz, 1H) 2.15 (s, 3H) 2.46-2.51 (m, 2H) 2.89 (s, 3H) 3.51 (t, J=7.19 Hz, 2H) 3.80-4.02 (m, 2H) 4.19 (t, J=7.95 Hz, 1H) 6.22 (d, J=8.33 Hz, 1H) 6.62 (d, J=8.71 Hz, 2H) 6.82 (s, 1H) 7.09 (d, J=8.71 Hz, 2H) 7.18-7.29 (m, 1H) 7.39 (t, J=7.76 Hz, 2H) 7.58 (d, J=7.19 Hz, 2H)

Example 232

3-[({4-[(cyclohexyl{2-[(methylsulfonyl)methyl]-5-phenylfuran-3-yl}methyl)amino]phenyl}carbonyl)amino]propanoic acid

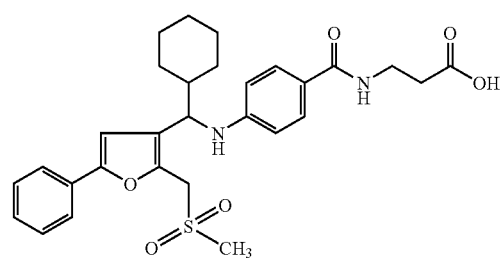

(1) ethyl 3-[({4-[(cyclohexyl{2-[(methylsulfonyl)methyl]-5-phenylfuran-3-yl}methyl)amino]phenyl}carbonyl)amino]propanoate Ethyl 3-[({4-[(cyclohexyl{2-[(methylsulfanyl)methyl]-5-phenylfuran-3-yl}methyl)amino]phenyl}carbonyl)amino]

propanoate (267 mg) was dissolved in methanol (9 mL) and water (1 mL), OXONE (0.6 g) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 75% ethyl acetate/hexane) to give the title compound (229 mg, 81%) as an amorphous compound.

$^1$H NMR (300 MHz, CHLOROFORM-d) δ ppm 1.04-1.35 (m, 8H) 1.76-1.98 (m, 6H) 2.59 (t, J=5.87 Hz, 2H) 2.93 (s, 3H) 3.67 (q, J=6.06 Hz, 2H) 4.15 (q, J=7.19 Hz, 2H) 4.33 (t, J=6.63 Hz, 1H) 4.39 (d, J=4.92 Hz, 1H) 4.55 (d, J=7.19 Hz, 1H) 6.52-6.66 (m, 4H) 7.26-7.32 (m, 1H) 7.38 (t, J=7.38 Hz, 2H) 7.56-7.62 (m, 4H)

(2) 3-[({4-[(cyclohexyl{2-[(methylsulfonyl)methyl]-5-phenylfuran-3-yl}methyl)amino]phenyl}carbonyl)amino]propanoic acid 4-({Cyclohexyl[2-methyl-5-(5-methylpyridin-3-yl)furan-3-yl]methyl}amino)benzoic acid (148 mg) obtained by the above-mentioned reaction was dissolved in ethanol (2 mL) and tetrahydrofuran (2 mL), 1N lithium hydroxide (0.8 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (178 mg, 83%).

$^1$H NMR (300 MHz, DMSO-$d_6$) δ ppm 0.93-1.23 (m, 5H) 1.51-1.82 (m, 5H) 2.00 (d, J=8.71 Hz, 1H) 2.43 (t, J=7.00 Hz, 2H) 3.10 (s, 3H) 3.36 (q, J=5.68 Hz, 2H) 4.35 (t, J=7.76 Hz, 1H) 4.70-4.94 (m, 2H) 6.32 (d, J=8.33 Hz, 1H) 6.68 (d, J=8.71 Hz, 2H) 6.91 (s, 1H) 7.27-7.32 (m, 1H) 7.42 (t, J=7.57 Hz, 2H) 7.52 (d, J=8.71 Hz, 2H) 7.61 (d, J=7.19 Hz, 2H) 8.00 (t, J=5.49 Hz, 1H) 12.16 (brs, 1H)

Example 233

3-[({4-[(cyclohexyl{2-[(methylsulfonyl)methyl]-5-phenylfuran-3-yl}methyl)amino]phenyl}carbonyl)(methyl)amino]propanoic acid

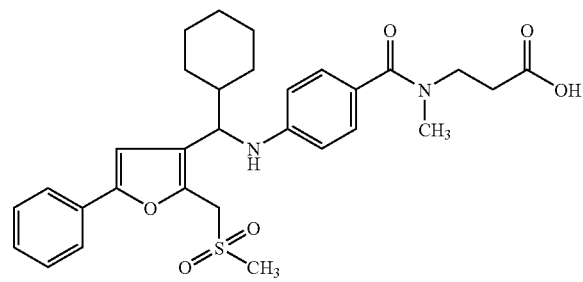

(1) ethyl 3-[({4-[(cyclohexyl{2-[(methylsulfonyl)methyl]-5-phenylfuran-3-yl}methyl)amino]phenyl}carbonyl)(methyl)amino]propanoate Ethyl 3-[({4-[(cyclohexyl{2-[(methylsulfanyl)methyl]-5-phenylfuran-3-yl}methyl)amino]phenyl}carbonyl)(methyl)amino]propanoate (274 mg) obtained by the above-mentioned reaction was dissolved in methanol (9 mL) and water (1 mL), OXONE (0.6 g) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 75% ethyl acetate/hexane) to give the title compound (241 mg, 83%) as an amorphous compound.

$^1$H NMR (300 MHz, CHLOROFORM-d) δ ppm 1.04-1.35 (m, 8H) 1.61-1.71 (m, 6H) 2.62 (t, J=6.82 Hz, 2H) 2.92 (s, 3H) 3.03 (s, 3H) 3.62-3.81 (m, 2H) 4.12 (q, J=6.94 Hz, 2H) 4.30 (d, J=6.44 Hz, 1H) 4.33-4.51 (m, 3H) 6.52-6.65 (m, 3H) 7.20-7.33 (m, 3H) 7.38 (t, J=7.38 Hz, 2H) 7.61 (d, J=6.82 Hz, 2H)

(2) 3-[({4-[(cyclohexyl{2-[(methylsulfonyl)methyl]-5-phenylfuran-3-yl}methyl)amino]phenyl}carbonyl)(methyl)amino]propanoic acid Ethyl 3-[({4-[(cyclohexyl{2-[(methylsulfonyl)methyl]-5-phenylfuran-3-yl}methyl)amino]phenyl}carbonyl)(methyl)amino]propanoate (232 mg) obtained by the above-mentioned reaction was dissolved in ethanol (2 mL) and tetrahydrofuran (2 mL), 1N lithium hydroxide (0.8 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (204 mg, 92%).

$^1$H NMR (300 MHz, DMSO-$d_6$) δ ppm 0.96-1.29 (m, 5H) 1.48-1.80 (m, 5H) 2.01 (d, J=12.87 Hz, 1H) 2.47-2.51 (m, 2H) 2.90 (s, 3H) 3.09 (s, 3H) 3.52 (t, J=7.38 Hz, 2H) 4.31 (t, J=8.14 Hz, 1H) 4.69-4.95 (m, 2H) 6.23 (d, J=8.33 Hz, 1H) 6.66 (d, J=8.71 Hz, 2H) 6.93 (s, 1H) 7.09 (d, J=8.33 Hz, 2H) 7.27-7.32 (m, 1H) 7.42 (t, J=7.57 Hz, 2H) 7.62 (d, J=7.57 Hz, 2H) 12.26 (brs, 1H)

Example 234

3-[({4-[(cyclohexyl{2-[(methylsulfinyl)methyl]-5-phenylfuran-3-yl}methyl)amino]phenyl}carbonyl)amino]propanoic acid

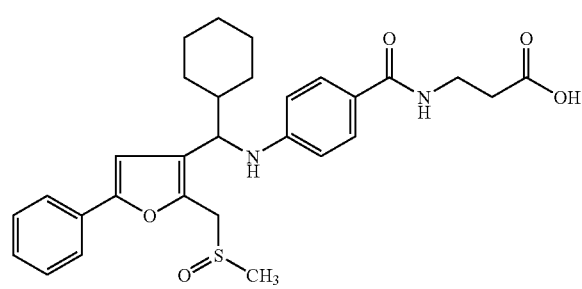

(1) ethyl 3-[({4-[(cyclohexyl{2-[(methylsulfinyl)methyl]-5-phenylfuran-3-yl}methyl)amino]phenyl}carbonyl)amino]propanoate Ethyl 3-[({4-[(cyclohexyl{2-[(methylsulfanyl)methyl]-5-phenylfuran-3-yl}methyl)amino]phenyl}carbonyl)amino]

propanoate (267 mg) was dissolved in methanol (9 mL) and water (1 mL), OXONE (277 mg) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (40% ethyl acetate/hexane to 100% ethyl acetate/hexane) to give the title compound (196 mg, 79%) as an amorphous compound.

$^1$H NMR (300 MHz, CHLOROFORM-d) δ ppm 1.02-1.34 (m, 8H) 1.61-1.99 (m, 6H) 2.50-2.66 (m, 5H) 3.67 (q, J=6.06 Hz, 2H) 3.95-4.26 (m, 4H) 4.31 (t, J=5.68 Hz, 1H) 4.89 (t, J=7.57 Hz, 1H) 6.60 (dd, J=11.55, 2.84 Hz, 4H) 7.20-7.32 (m, 1H) 7.38 (t, J=7.76 Hz, 2H) 7.56-7.61 (m, 4H)

(2) 3-[({4-[(cyclohexyl{2-[(methylsulfinyl)methyl]-5-phenylfuran-3-yl}methyl)amino]phenyl}carbonyl)amino]propanoic acid Ethyl 3-[({4-[(cyclohexyl{2-[(methylsulfinyl)methyl]-5-phenylfuran-3-yl}methyl)amino]phenyl}carbonyl)amino]propanoate (193 mg) obtained by the above-mentioned reaction was dissolved in ethanol (2 mL) and tetrahydrofuran (2 mL), 1N lithium hydroxide (0.7 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (169 mg, 92%).

$^1$H NMR (300 MHz, DMSO-$d_6$) δ ppm 0.88-1.09 (m, 5H) 1.48-1.78 (m, 5H) 2.02 (d, J=14.77 Hz, 1H) 2.43 (t, J=6.82 Hz, 2H) 2.67 (s, 3H) 3.33-3.44 (m, 2H) 4.16-4.48 (m, 3H) 6.21-6.42 (m, 1H) 6.66 (d, J=8.33 Hz, 2H) 6.88 (d, J=3.03 Hz, 1H) 7.25-7.30 (m, 1H) 7.40 (t, J=7.57 Hz, 2H) 7.50-7.53 (m, 2H) 7.59 (d, J=7.95 Hz, 2H) 7.99 (brs, 1H) 12.08 (brs, 1H)

Example 235

3-[({4-[(cyclohexyl{2-[(methylsulfinyl)methyl]-5-phenylfuran-3-yl}methyl)amino]phenyl}carbonyl)(methyl)amino]propanoic acid

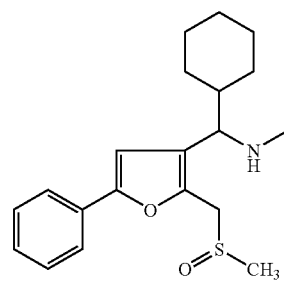

(1) ethyl 3-[({4-[(cyclohexyl{2-[(methylsulfinyl)methyl]-5-phenylfuran-3-yl}methyl)amino]phenyl}carbonyl)(methyl)amino]propanoate Ethyl 3-[({4-[(cyclohexyl{2-[(methylsulfanyl)methyl]-5-phenylfuran-3-yl}methyl)amino]phenyl}carbonyl)(methyl)amino]propanoate (274 mg) obtained by the above-mentioned reaction was dissolved in methanol (9 mL) and water (1 mL), OXONE (277 mg) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (40% ethyl acetate/hexane to 100% ethyl acetate/hexane) to give the title compound (175 mg, 69%) as an amorphous compound.

$^1$H NMR (300 MHz, CHLOROFORM-d) δ ppm 1.04-1.33 (m, 8H) 1.63-1.96 (m, 6H) 2.51-2.68 (m, 5H) 3.04 (s, 3H) 3.73 (q, J=7.07 Hz, 2H) 4.07-4.19 (m, 5H) 4.69 (brs, 1H) 6.55-6.59 (m, 3H) 7.17-7.32 (m, 3H) 7.38 (t, J=7.57 Hz, 2H) 7.60 (d, J=7.19 Hz, 2H)

(2) 3-[({4-[(cyclohexyl{2-[(methylsulfinyl)methyl]-5-phenylfuran-3-yl}methyl)amino]phenyl}carbonyl)(methyl)amino]propanoic acid Ethyl 3-[({4-[(cyclohexyl{2-[(methylsulfinyl)methyl]-5-phenylfuran-3-yl}methyl)amino]phenyl}carbonyl)(methyl)amino]propanoate (169 mg) obtained by the above-mentioned reaction was dissolved in ethanol (2 mL) and tetrahydrofuran (2 mL), 1N lithium hydroxide (0.6 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (154 mg, 96%).

$^1$H NMR (300 MHz, DMSO-$d_6$) δ ppm 0.96-1.29 (m, 5H) 1.47-1.80 (m, 5H) 2.03 (d, J=14.77 Hz, 1H) 2.38-2.50 (m, 2H) 2.67 (d, J=2.65 Hz, 3H) 2.90 (s, 3H) 3.52 (t, J=7.19 Hz, 2H) 4.22-4.41 (m, 3H) 6.24 (dd, J=11.36, 8.33 Hz, 1H) 6.65 (d, J=7.95 Hz, 2H) 6.90 (d, J=2.27 Hz, 1H) 7.09 (dd, J=8.33, 2.65 Hz, 2H) 7.25-7.30 (m, 1H) 7.41 (t, J=7.76 Hz, 2H) 7.60 (d, J=7.19 Hz, 2H) 12.25 (brs, 1H)

Example 236

3-({[4-({cyclohexyl[5-(6-methoxypyridin-2-yl)-2-methylfuran-3-yl]methyl}amino)phenyl]carbonyl}amino)propanoic acid

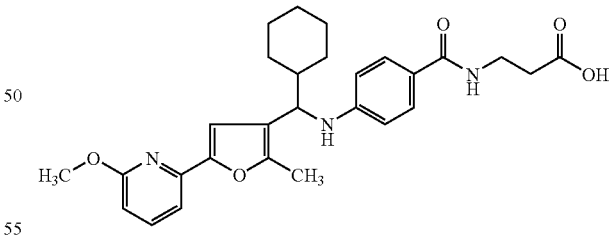

(1) [5-(6-methoxypyridin-2-yl)-2-methylfuran-3-yl]methanol

A mixture of tert-butyl({5-[(5,5-dimethyl-1,3,2-dioxaborinan-2-yl)methyl]-2-methylfuran-3-yl}methoxy)dimethylsilane (2.4 g), 2-bromo-6-methoxypyridine (1.9 g), tetrakis(triphenylphosphine)palladium(0) (0.4 g), 2N aqueous sodium carbonate solution (7 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was dissolved in tetrahydrofuran (20 mL), 1N tetrabutylammonium fluoride in tetrahydrofuran (10 mL) was added, and the mixture was stirred at room temperature for 2 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 100% ethyl acetate/hexane) to give the title compound (1.5 g, 95%) as an oil.
$^1$H NMR (300 MHz, CHLOROFORM-d) δ ppm 1.38 (t, J=5.68 Hz, 1H) 2.38 (s, 3H) 3.97 (s, 3H) 4.53 (d, J=5.68 Hz, 2H) 6.58 (d, J=7.57 Hz, 1H) 7.02 (s, 1H) 7.21 (d, J=7.95 Hz, 1H) 7.55 (d, J=8.33 Hz, 1H)

(2) 5-(6-methoxypyridin-2-yl)-2-methylfuran-3-carbaldehyde

To a solution of [5-(6-methoxypyridin-2-yl)-2-methylfuran-3-yl]methanol (1.4 g) obtained by the above-mentioned reaction in acetonitrile (20 mL) was added Dess-Martin reagent (4.2 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (10% ethyl acetate/hexane to 30% ethyl acetate/hexane) to give the title compound (1.1 g, 79%) as a white crystal.
$^1$H NMR (300 MHz, CHLOROFORM-d) δ ppm 2.69 (s, 3H) 3.98 (s, 3H) 6.66 (d, J=8.33 Hz, 1H) 7.21-7.32 (m, 1H) 7.59 (d, J=8.33 Hz, 1H) 7.63 (s, 1H) 9.99 (s, 1H)

(3) cyclohexyl[5-(6-methoxypyridin-2-yl)-2-methylfuran-3-yl]methanol

To a solution of 5-(6-methoxypyridin-2-yl)-2-methylfuran-3-carbaldehyde (1.0 g) obtained by the above-mentioned reaction in tetrahydrofuran (20 mL) was added dropwise 1N cyclohexylmagnesium bromide-tetrahydrofuran solution (6 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 35% ethyl acetate/hexane) to give the title compound (1.4 g, 92%) as an oil.
$^1$H NMR (300 MHz, CHLOROFORM-d) δ ppm 0.76-1.45 (m, 5H) 1.44-1.98 (m, 5H) 2.09 (d, J=12.49 Hz, 1H) 2.34 (s, 3H) 3.98 (s, 3H) 4.31 (dd, J=8.14, 3.22 Hz, 1H) 6.57 (d, J=7.57 Hz, 1H) 6.98 (s, 1H) 7.21 (d, J=6.82 Hz, 1H) 7.55 (d, J=8.33 Hz, 1H)

(4) 2-{4-[chloro(cyclohexyl)methyl]-5-methylfuran-2-yl}-6-methoxypyridine

To a solution of cyclohexyl[5-(6-methoxypyridin-2-yl)-2-methylfuran-3-yl]methanol (1.4 g) obtained by the above-mentioned reaction in toluene (20 mL) were added thionyl chloride (0.5 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.4 g, 100%) as an oil.
$^1$H NMR (300 MHz, CHLOROFORM-d) δ ppm 0.74-1.44 (m, 5H) 1.59-1.98 (m, 5H) 2.23 (d, J=12.87 Hz, 1H) 2.35 (s, 3H) 3.99 (s, 3H) 4.60 (d, J=8.71 Hz, 1H) 6.59 (d, J=7.57 Hz, 1H) 6.99 (s, 1H) 7.10-7.35 (m, 1H) 7.55 (d, J=7.95 Hz, 1H)

(5) 4-({cyclohexyl[5-(6-methoxypyridin-2-yl)-2-methylfuran-3-yl]methyl}amino)benzoic acid A mixture of 2-{4-[chloro(cyclohexyl)methyl]-5-methylfuran-2-yl}-6-methoxypyridine (1.4 g) obtained by the above-mentioned reaction, methyl 4-aminobenzoate (1.0 g), sodium carbonate (0.7 g) and sodium iodide (1.4 g) in N,N-dimethylacetamide (20 mL) was stirred overnight at 80° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (5 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.5 g, 79%) as an amorphous compound.
$^1$H NMR (300 MHz, CHLOROFORM-d) δ ppm 0.90-1.40 (m, 5H) 1.66-1.89 (m, 5H) 1.99 (d, J=14.13 Hz, 1H) 2.39 (s, 3H) 3.96 (s, 3H) 4.12 (d, J=6.97 Hz, 1H) 6.51 (d, J=8.85 Hz, 2H) 6.55 (d, J=7.72 Hz, 1H) 6.84 (s, 1H) 7.19 (d, J=6.97 Hz, 1H) 7.54 (dd, J=8.29, 7.54 Hz, 1H) 7.84 (d, J=8.85 Hz, 2H)

(6) 3-({[4-({cyclohexyl[5-(6-methoxypyridin-2-yl)-2-methylfuran-3-yl]methyl}amino)phenyl]carbonyl}amino)propanoic acid A solution of 4-({cyclohexyl[5-(6-methoxypyridin-2-yl)-2-methylfuran-3-yl]methyl}amino)benzoic acid (210 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (218 mg, 89%).
$^1$H NMR (300 MHz, DMSO-$d_6$) δ ppm 0.85-1.33 (m, 5H) 1.47-1.80 (m, 5H) 2.04 (d, J=12.12 Hz, 1H) 2.31-2.46 (m, 5H) 3.31-3.43 (m, 2H) 3.87 (s, 3H) 4.13 (t, J=7.95 Hz, 1H) 6.41 (d, J=8.33 Hz, 1H) 6.55 (m, J=8.71 Hz, 2H) 6.63 (d, J=7.95 Hz, 1H) 6.92 (s, 1H) 7.16 (d, J=7.19 Hz, 1H) 7.52 (d, J=8.71 Hz, 2H) 7.67 (d, J=7.95 Hz, 1H) 7.98 (t, J=5.49 Hz, 1H) 12.17 (brs, 1H)

Example 237

3-[{[4-({cyclohexyl[5-(6-methoxypyridin-2-yl)-2-methylfuran-3-yl]methyl}amino)phenyl]carbonyl}(methyl)amino]propanoic acid

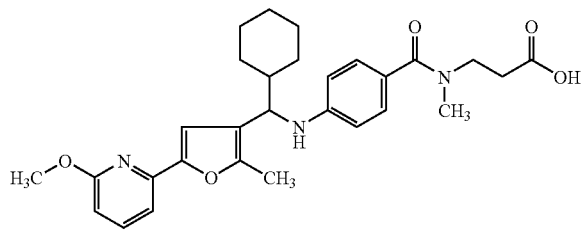

A solution of 4-({cyclohexyl[5-(6-methoxypyridin-2-yl)-2-methylfuran-3-yl]methyl}amino)benzoic acid (210 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (216 mg, 85%).

$^1$H NMR (300 MHz, DMSO-$d_6$) δ ppm 0.93-1.25 (m, 5H) 1.50-1.79 (m, 5H) 2.05 (d, J=12.49 Hz, 1H) 2.40 (s, 3H) 2.43-2.51 (m, 2H) 2.90 (s, 3H) 3.51 (t, J=7.38 Hz, 2H) 3.88 (s, 3H) 4.09 (t, J=7.95 Hz, 1H) 6.31 (d, J=8.33 Hz, 1H) 6.54 (d, J=8.71 Hz, 2H) 6.63 (d, J=7.95 Hz, 1H) 6.94 (s, 1H) 7.10 (d, J=8.71 Hz, 2H) 7.16 (d, J=7.19 Hz, 1H) 7.67 (d, J=8.33 Hz, 1H)

Example 238

3-({[4-({[5-(3-carbamoylphenyl)-2-methylfuran-3-yl](cyclohexyl)methyl}amino)phenyl]carbonyl}amino)propanoic acid

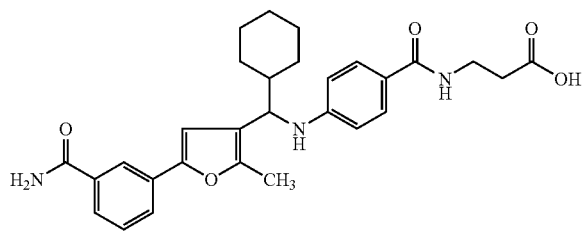

(1) methyl 3-(4-formyl-5-methylfuran-2-yl)benzoate

A mixture of 5-bromo-2-methylfuran-3-carbaldehyde (1.9 g), 3-methoxycarbonylphenylboronic acid (2.2 g), tetrakis(triphenylphosphine)palladium(0) (0.6 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 25% ethyl acetate/hexane), and crystallized from ethyl acetate/hexane to give the title compound (2.1 g, 87%) as a yellow crystal.

$^1$H NMR (300 MHz, CHLOROFORM-d) δ ppm 2.69 (s, 3H) 3.96 (s, 3H) 7.00 (s, 1H) 7.49 (t, J=7.82 Hz, 1H) 7.83 (dt, J=7.82, 1.55 Hz, 1H) 7.97 (dt, J=7.91, 1.41 Hz, 1H) 8.33 (t, J=1.60 Hz, 1H) 9.98 (s, 1H)

(2) methyl 3-{4-[cyclohexyl(hydroxy)methyl]-5-methylfuran-2-yl}benzoate

To a solution of methyl 3-(4-formyl-5-methylfuran-2-yl)benzoate (2.1 g) obtained by the above-mentioned reaction in tetrahydrofuran (20 mL) was added dropwise 1N cyclohexylmagnesium bromide-tetrahydrofuran solution (12.9 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure to give the title compound (2.5 g, 100%) as an oil.

$^1$H NMR (300 MHz, CHLOROFORM-d) δ ppm 0.82-1.42 (m, 5H) 1.61-1.79 (m, 5H) 2.07 (d, J=19.21 Hz, 1H) 2.34 (s, 3H) 3.94 (s, 3H) 4.31 (dd, J=7.91, 3.20 Hz, 1H) 6.68 (s, 1H) 7.43 (t, J=7.82 Hz, 1H) 7.80 (dt, J=7.86, 1.44 Hz, 1H) 7.88 (dd, J=7.82, 1.41 Hz, 1H) 8.28 (t, J=1.51 Hz, 1H)

(3) 3-{4-[cyclohexyl(hydroxy)methyl]-5-methylfuran-2-yl}benzoic acid

Methyl 3-{4-[cyclohexyl(hydroxy)methyl]-5-methylfuran-2-yl}benzoate (2.5 g) obtained by the above-mentioned reaction was dissolved in methanol (4 mL) and tetrahydrofuran (4 mL), 2N lithium hydroxide (4 mL) was added, and the mixture was stirred at room temperature for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.3 g, 56%) as an amorphous compound.

$^1$H NMR (300 MHz, CHLOROFORM-d) δ ppm 0.75-1.39 (m, 5H) 1.45-1.91 (m, 5H) 2.12 (d, J=8.29 Hz, 1H) 2.35 (s, 3H) 4.33 (d, J=7.72 Hz, 1H) 6.71 (s, 1H) 7.47 (t, J=7.82 Hz, 1H) 7.85 (dt, J=8.01, 1.37 Hz, 1H) 7.95 (dt, J=7.82, 1.27 Hz, 1H) 8.35 (t, J=1.60 Hz, 1H)

(4) 3-{4-[cyclohexyl(hydroxy)methyl]-5-methylfuran-2-yl}benzamide

A solution of 3-{4-[cyclohexyl(hydroxy)methyl]-5-methylfuran-2-yl}benzoic acid (1.3 g) obtained by the above-mentioned reaction, 1-ethyl-3-(3-dimethylaminopropyl)carbodiimide hydrochloride (1.2 g), hydroxybenzotriazole ammonium salt (0.9 g) in N,N-dimethylformamide (20 mL)

was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. The residue was crystallized from ethyl acetate/hexane to give the title compound (1.2 g, 96%) as a white crystal.

$^1$H NMR (300 MHz, DMSO-d$_6$) δ ppm 0.72-1.30 (m, 5H) 1.38-1.83 (m, 5H) 1.98 (d, J=13.63 Hz, 1H) 2.30 (s, 3H) 4.17 (dd, J=7.19, 4.16 Hz, 1H) 4.86 (d, J=4.16 Hz, 1H) 6.86 (s, 1H) 7.45 (t, J=7.76 Hz, 1H) 7.40 (brs, 1H) 7.73 (t, J=8.52 Hz, 2H) 8.05 (brs, 1H) 8.13 (s, 1H)

(5) 3-{4-[chloro(cyclohexyl)methyl]-5-methylfuran-2-yl}benzamide

To a solution of 3-{4-[cyclohexyl(hydroxy)methyl]-5-methylfuran-2-yl}benzamide (1.2 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.3 g, 100%) as a yellow crystal.

$^1$H NMR (300 MHz, CHLOROFORM-d) δ ppm 0.83-1.40 (m, 5H) 1.60-1.95 (m, 5H) 2.17-2.27 (m, 1H) 2.34 (s, 3H) 4.61 (d, J=8.48 Hz, 1H) 5.58 (brs, 1H) 6.12 (brs, 1H) 6.72 (s, 1H) 7.45 (t, J=7.91 Hz, 1H) 7.65 (ddd, J=7.91, 1.51, 1.32 Hz, 1H) 7.78 (dt, J=7.72, 1.41 Hz, 1H) 8.0.8 (t, J=1.60 Hz, 1H)

(6) 3-({[4-({[5-(3-carbamoylphenyl)-2-methylfuran-3-yl](cyclohexyl)methyl}amino)phenyl]carbonyl}amino)propanoic acid A mixture of 3-{4-[cyclohexyl(hydroxy)methyl]-5-methylfuran-2-yl}benzamide (0.6 g) obtained by the above-mentioned reaction, ethyl 3-{[(4-aminophenyl)carbonyl]amino}propanoate (0.7 g), sodium carbonate (0.3 g) and sodium iodide (0.6 g) in N,N-dimethylacetamide (20 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (50% ethyl acetate/hexane to 100% ethyl acetate/hexane). To the residue were added ethanol (3 mL), tetrahydrofuran (3 mL) and 1N lithium hydroxide (2.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (570 mg, 61%).

$^1$H NMR (300 MHz, DMSO-d$_6$) δ ppm 0.84-1.11 (m, 5H) 1.49-1.82 (m, 5H) 2.04 (d, J=11.11 Hz, 1H) 2.39 (s, 3H) 2.43 (t, J=7.25 Hz, 2H) 3.27-3.52 (m, 2H) 4.12 (t, J=7.72 Hz, 1H) 6.35 (d, J=8.10 Hz, 1H) 6.56 (d, J=8.85 Hz, 2H) 6.82 (s, 1H) 7.39 (brs, 1H) 7.44 (t, J=7.82 Hz, 1H) 7.52 (d, J=8.67 Hz, 2H) 7.69 (t, J=7.63 Hz, 2H) 7.98 (d, J=5.37 Hz, 1H) 8.05 (d, J=1.51 Hz, 2H) 12.08 (brs, 1H)

Example 239

3-[{[4-({[5-(3-carbamoylphenyl)-2-methylfuran-3-yl](cyclohexyl)methyl}amino)phenyl]carbonyl}(methyl)amino]propanoic acid

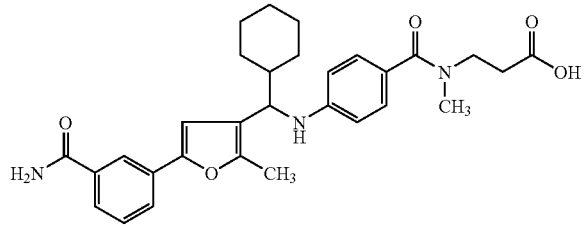

A mixture of 3-{4-[cyclohexyl(hydroxy)methyl]-5-methylfuran-2-yl}benzamide (0.6 g), ethyl 3-{[(4-aminophenyl)carbonyl](methyl)amino}propanoate (0.7 g), sodium carbonate (0.3 g) and sodium iodide (0.6 g) in N,N-dimethylacetamide (20 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (50% ethyl acetate/hexane to 100% ethyl acetate/hexane). To the residue were added ethanol (3 mL), tetrahydrofuran (3 mL) and 1N lithium hydroxide (2.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (527 mg, 54%).

$^1$H NMR (300 MHz, DMSO-d$_6$) δ ppm 0.94-1.26 (m, 5H) 1.50-1.82 (m, 5H) 2.04 (d, J=9.61 Hz, 1H) 2.39 (s, 3H) 2.42-2.50 (m, 2H) 3.32 (s, 3H) 3.52 (t, J=7.44 Hz, 2H) 4.08 (t, J=7.54 Hz, 1H) 6.25 (d, J=7.72 Hz, 1H) 6.56 (d, J=8.67 Hz, 2H) 6.83 (s, 1H) 7.10 (d, J=8.67 Hz, 2H) 7.39 (brs, 1H) 7.44 (t, J=7.72 Hz, 1H) 7.68 (dd, J=3.48, 1.60 Hz, 2H) 8.06 (d, J=1.51 Hz, 2H) 12.20 (s, 1H)

Example 240

3-({[4-({cyclohexyl[5-(6-methoxypyridazin-3-yl)-2-methylfuran-3-yl]methyl}amino)phenyl]carbonyl}amino)propanoic acid

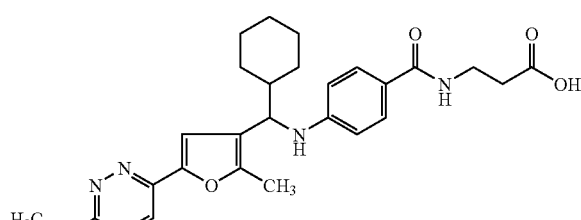

(1) [5-(6-methoxypyridazin-3-yl)-2-methylfuran-3-yl]methanol

A mixture of tert-butyl({5-[(5,5-dimethyl-1,3,2-dioxaborinan-2-yl)methyl]-2-methylfuran-3-yl}methoxy)dimethylsilane (2.4 g), 3-chloro-6-methoxypyridazine (1.5 g), tetrakis(triphenylphosphine)palladium(0) (0.4 g), 2N aqueous sodium carbonate solution (7 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was dissolved in tetrahydrofuran (20 mL), 1N tetrabutylammonium fluoride in tetrahydrofuran (10 mL) was added, and the mixture was stirred at room temperature for 2 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (40% ethyl acetate/hexane to 100% ethyl acetate/hexane) to give the title compound (1.3 g, 86%) as a white crystal.

$^1$H NMR (300 MHz, CHLOROFORM-d) δ ppm 1.46 (t, J=5.68 Hz, 1H) 2.40 (s, 3H) 4.15 (s, 3H) 4.55 (d, J=5.68 Hz, 2H) 6.98 (d, J=9.47 Hz, 1H) 7.12 (s, 1H) 7.71 (d, J=9.09 Hz, 1H)

(2) 5-(6-methoxypyridazin-2-yl)-2-methylfuran-3-carbaldehyde

To a solution of [5-(6-methoxypyridazin-3-yl)-2-methylfuran-3-yl]methanol (1.3 g) obtained by the above-mentioned reaction in acetonitrile (30 mL) was added Dess-Martin reagent (3.8 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (10% ethyl acetate/hexane to 50% ethyl acetate/hexane) to give the title compound (0.8 g, 62%) as a white crystal.

$^1$H NMR (300 MHz, CHLOROFORM-d) δ ppm 2.71 (s, 3H) 4.18 (s, 3H) 7.03 (d, J=9.09 Hz, 1H) 7.36 (s, 1H) 7.73 (d, J=9.09 Hz, 1H) 10.01 (s, 1H)

(3) cyclohexyl[5-(6-methoxypyridazin-2-yl)-2-methylfuran-3-yl]methanol

To a solution of 5-(6-methoxypyridazin-2-yl)-2-methylfuran-3-carbaldehyde (0.8 g) obtained by the above-mentioned reaction in tetrahydrofuran (20 mL) was added dropwise 1N cyclohexylmagnesium bromide-tetrahydrofuran solution (6 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.1 g, 96%) as an oil.

$^1$H NMR (300 MHz; CHLOROFORM-d) δ ppm 0.76-1.41 (m, 5H) 1.50-1.73 (m, 5H) 2.04-2.19 (m, 1H) 2.36 (s, 3H) 4.15 (s, 3H) 4.33 (dd, J=7.95, 3.41 Hz, 1H) 6.97 (d, J=9.09 Hz, 1H) 7.08 (s, 1H) 7.70 (d, J=9.09 Hz, 1H)

(4) 2-{4-[chloro(cyclohexyl)methyl]-5-methylfuran-2-yl}-6-methoxypyridazine

To a solution of cyclohexyl[5-(6-methoxypyridazin-2-yl)-2-methylfuran-3-yl]methanol (1.1 g) obtained by the above-mentioned reaction in toluene (20 mL) were added thionyl chloride (0.4 mL) and pyridine (0.4 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.1 g, 100%) as an oil.

$^1$H NMR (300 MHz, CHLOROFORM-d) δ ppm 0.74-1.49 (m, 5H) 1.57-1.97 (m, 5H) 2.22 (d, J=12.87 Hz, 1H) 2.36 (s, 3H) 4.15 (s, 3H) 4.61 (d, J=8.33 Hz, 1H) 6.98 (d, J=9.47 Hz, 1H) 7.12 (s, 1H) 7.70 (d, J=9.09 Hz, 1H)

(5) 3-({[4-({cyclohexyl[5-(6-methoxypyridazin-3-yl)-2-methylfuran-3-yl]methyl}amino)phenyl]carbonyl}amino)propanoic acid A mixture of 2-{4-[chloro(cyclohexyl)methyl]-5-methylfuran-2-yl}-6-methoxypyridazine (160 mg) obtained by the above-mentioned reaction, ethyl 3-{[(4-aminophenyl)carbonyl]amino}propanoate (236 mg), sodium carbonate (106 mg) and sodium iodide (300 mg) in N,N-dimethylacetamide (5 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 70% ethyl acetate/hexane). To the residue were added ethanol (2 mL), tetrahydrofuran (2 mL) and 1N lithium hydroxide (0.7 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (55 mg, 23%).

$^1$H NMR (300 MHz, DMSO-d$_6$) δ ppm 0.84-1.11 (m, 5H) 1.50-1.81 (m, 5H) 2.05 (d, J=9.84 Hz, 1H) 2.34-2.46 (m, 5H) 3.33-3.47 (m, 2H) 4.02 (s, 3H) 4.16 (t, J=7.95 Hz, 1H) 6.40 (d, J=8.33 Hz, 1H) 6.56 (d, J=8.71 Hz, 2H) 7.04 (s, 1H) 7.21 (d, J=9.09 Hz, 1H) 7.52 (d, J=8.71 Hz, 2H) 7.80 (d, J=9.47 Hz, 1H) 7.98 (t, J=5.49 Hz, 1H) 12.04 (s, 1H)

Example 241

3-[{[4-({cyclohexyl[5-(6-methoxypyridazin-3-yl)-2-methylfuran-3-yl]methyl}amino)phenyl]carbonyl}(methyl)amino]propanoic acid

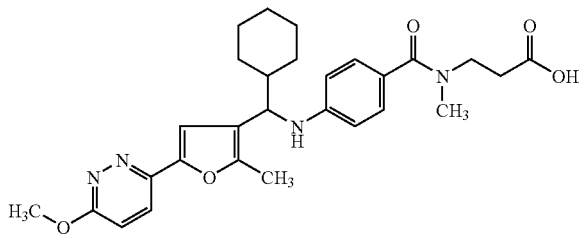

A mixture of 2-{4-[chloro(cyclohexyl)methyl]-5-methylfuran-2-yl}-6-methoxypyridazine (160 mg), ethyl 3-{[(4-aminophenyl)carbonyl](methyl)amino}propanoate (250 mg), sodium carbonate (106 mg) and sodium iodide (300 mg) in N,N-dimethylacetamide (5 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 70% ethyl acetate/hexane). To the residue were added ethanol (2 mL), tetrahydrofuran (2 mL) and 1N lithium hydroxide (0.7 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (87 mg, 38%).

$^1$H NMR (300 MHz, DMSO-d$_6$) δ ppm 0.94-1.28 (m, 5H) 1.53-1.78 (m, 5H) 2.04 (d, J=14.39 Hz, 1H) 2.41 (s, 3H) 2.47-2.51 (m, 2H) 2.90 (s, 3H) 3.52 (t, J=7.38 Hz, 2H) 4.02 (s, 3H) 4.12 (t, J=8.33 Hz, 1H) 6.30 (d, J=8.33 Hz, 1H) 6.56 (d, J=8.71 Hz, 2H) 7.05 (s, 1H) 7.10 (d, J=8.71 Hz, 2H) 7.21 (d, J=9.47 Hz, 1H) 7.80 (d, J=9.09 Hz, 1H) 12.22 (s, 1H)

Example 242

3-({[4-({cyclohexyl[2-methyl-5-(6-methylpyridazin-3-yl)furan-3-yl]methyl}amino)phenyl]carbonyl}amino)propanoic acid

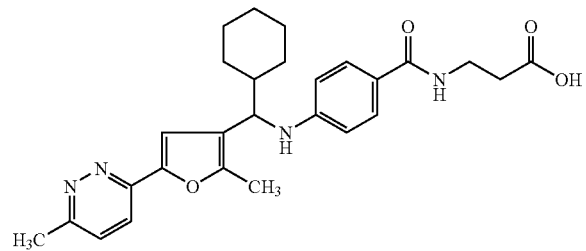

(1) [2-methyl-5-(6-methylpyridazin-3-yl)furan-3-yl]methanol

A mixture of tert-butyl({5-[(5,5-dimethyl-1,3,2-dioxaborinan-2-yl)methyl]-2-methylfuran-3-yl}methoxy)dimethylsilane (2.4 g), 3-chloro-6-methylpyridazine (1.5 g), tetrakis(triphenylphosphine)palladium(0) (0.4 g), 2N aqueous sodium carbonate solution (7 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was dissolved in tetrahydrofuran (20 mL), 1N tetrabutylammonium fluoride in tetrahydrofuran (10 mL) was added, and the mixture was stirred at room temperature for 2 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (50% ethyl acetate/hexane to 100% ethyl acetate/hexane) to give the title compound (0.44 g, 31%) as a yellow crystal.

$^1$H NMR (300 MHz, CHLOROFORM-d) δ ppm 1.80 (t, J=5.49 Hz, 1H) 2.41 (s, 3H) 2.71 (s, 3H) 4.56 (d, J=5.30 Hz, 2H) 7.27-7.39 (m, 2H) 7.67 (d, J=8.71 Hz, 1H) 8.69 (d, J=8.71 Hz, 1H)

(2) 2-methyl-5-(6-methylpyridazin-2-yl)furan-3-carbaldehyde

To a solution of [2-methyl-5-(6-methylpyridazin-3-yl)furan-3-yl]methanol (0.4 g) obtained by the above-mentioned reaction in acetonitrile (20 mL) was added Dess-Martin reagent (1.4 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (10% ethyl acetate/hexane to 50% ethyl acetate/hexane) to give the title compound (0.3 g, 62%) as a yellow crystal.

$^1$H NMR (300 MHz, CHLOROFORM-d) δ ppm 2.73 (s, 3H) 2.75 (s, 3H) 7.37 (d, J=8.67 Hz, 1H) 7.50 (s, 1H) 7.70 (d, J=8.67 Hz, 1H) 10.01 (s, 1H)

(3) cyclohexyl[2-methyl-5-(6-methylpyridazin-2-yl)furan-3-yl]methanol

To a solution of 2-methyl-5-(6-methylpyridazin-2-yl)furan-3-carbaldehyde (0.3 g) obtained by the above-mentioned reaction in tetrahydrofuran (10 mL) was added dropwise 1N cyclohexylmagnesium bromide-tetrahydrofuran solution (2 mL) at 0° C. and, after the completion of the dropwise addition, the mixture was stirred at 0° C. for 1 hr. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (30% ethyl acetate/hexane to 100% ethyl acetate/hexane) to give the title compound (0.2 g, 57%) as an oil.

$^1$H NMR (300 MHz, CHLOROFORM-d) δ ppm 0.82-1.39 (m, 5H) 1.59-1.85 (m, 5H) 1.99-2.14 (m, 1H) 2.38 (s, 3H) 2.71 (s, 3H) 4.34 (dd, J=7.76, 3.60 Hz, 1H) 7.21 (s, 1H) 7.30 (d, J=8.71 Hz, 1H) 7.66 (d, J=8.71 Hz, 1H)

(4) 3-{4-[chloro(cyclohexyl)methyl]-5-methylfuran-2-yl}-6-methylpyridazine

To a solution of cyclohexyl[2-methyl-5-(6-methylpyridazin-3-yl)furan-3-yl]methanol (0.2 g) obtained by the above-mentioned reaction in toluene (20 mL) were added thionyl chloride (0.1 mL) and pyridine (0.1 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (0.2 g, 100%) as an oil.

$^1$H NMR (300 MHz, CHLOROFORM-d) δ ppm 0.81-1.43 (m, 5H) 1.60-1.94 (m, 5H) 2.22 (d, J=13.25 Hz, 1H) 2.36 (s, 3H) 2.72 (s, 3H) 4.61 (d, J=8.33 Hz, 1H) 7.08-7.24 (m, 1H) 7.30 (d, J=8.71 Hz, 1H) 7.66 (d, J=9.09 Hz, 1H)

(5) 3-({[4-({cyclohexyl[2-methyl-5-(6-methylpyridazin-3-yl)furan-3-yl]methyl}amino)phenyl]carbonyl}amino)propanoic acid A mixture of 3-{4-[chloro(cyclohexyl)methyl]-5-methylfuran-2-yl}-6-methylpyridazine (107 mg) obtained by the above-mentioned reaction, ethyl 3-{[(4-aminophenyl)carbonyl]amino}propanoate (165 mg), sodium carbonate (74 mg) and sodium iodide (210 mg) in N,N-dimethylacetamide (5 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (30% ethyl acetate/hexane to 100% ethyl acetate/hexane). To the residue were added ethanol (2 mL), tetrahydrofuran (2 mL) and 1N lithium hydroxide (0.3 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (36 mg, 22%).

$^1$H NMR (300 MHz, DMSO-d$_6$) δ ppm 0.90-1.23 (m, 5H) 1.50-1.82 (m, 5H) 2.05 (d, J=11.87 Hz, 1H) 2.41-2.45 (m, 5H) 2.59 (s, 3H) 3.36 (q, J=6.03 Hz, 2H) 4.18 (t, J=8.38 Hz, 1H) 6.41 (d, J=9.80 Hz, 1H) 6.57 (d, J=8.85 Hz, 2H) 7.16 (s, 1H) 7.51-7.57 (m, 3H) 7.74 (d, J=8.85 Hz, 1H) 7.99 (t, J=5.37 Hz, 1H)

Example 243

3-[{[4-({cyclohexyl[2-methyl-5-(6-methylpyridazin-3-yl)furan-3-yl]methyl}amino)phenyl]carbonyl}(methyl)amino]propanoic acid

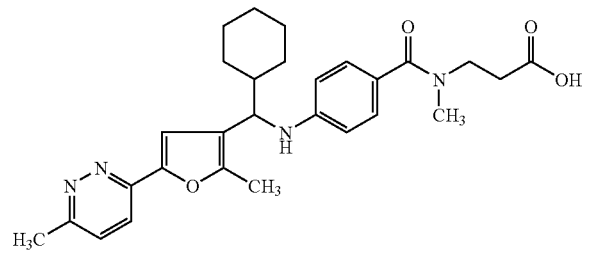

A mixture of 3-{4-[chloro(cyclohexyl)methyl]-5-methylfuran-2-yl}-6-methylpyridazine (107 mg), ethyl 3-{[(4-aminophenyl)carbonyl](methyl)amino}propanoate (175 mg), sodium carbonate (74 mg) and sodium iodide (210 mg) in N,N-dimethylacetamide (5 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (30% ethyl acetate/hexane to 100% ethyl acetate/hexane). To the residue were added ethanol (2 mL), tetrahydrofuran (2 mL) and 1N lithium hydroxide (0.3 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (56 mg, 33%).

$^1$H NMR (300 MHz, DMSO-d$_6$) δ ppm 0.94-1.27 (m, 5H) 1.48-1.80 (m, 5H) 1.97-2.13 (m, 1H) 2.42 (s, 3H) 2.47-2.51 (m, 2H) 2.60 (s, 3H) 2.90 (s, 3H) 3.52 (t, J=7.44 Hz, 2H) 4.14 (t, J=7.82 Hz, 1H) 6.30 (d, J=0.94 Hz, 1H) 6.57 (d, J=8.67 Hz, 2H) 7.10 (d, J=8.67 Hz, 2H) 7.17 (s, 1H) 7.55 (d, J=8.85 Hz, 1H) 7.75 (d, J=8.85 Hz, 1H)

Example 244

3-[({4-[(cyclohexyl{5-[6-(2-methoxyethoxy)pyridin-3-yl]-2-methylfuran-3-yl}methyl)amino]phenyl}carbonyl)amino]propanoic acid

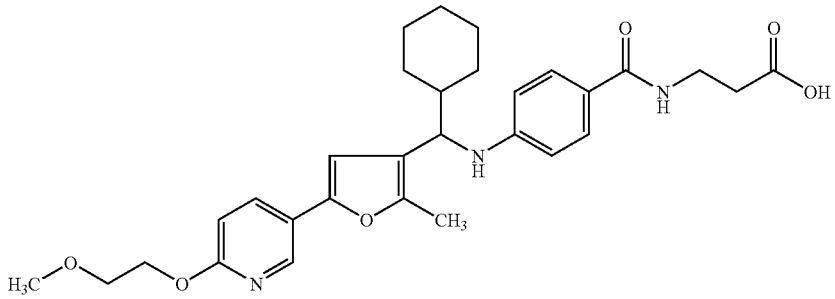

(1) 4-[(cyclohexyl{5-[6-(2-methoxyethoxy)pyridin-3-yl]-2-methylfuran-3-yl}methyl)amino]benzoic acid Methyl 4-({cyclohexyl[5-(6-fluoropyridin-3-yl)-2-methylfuran-3-yl]methyl}amino)benzoate (1.9 g) was dissolved in 2-methoxyethanol (5 mL) and tetrahydrofuran (5 mL), 2N lithium hydroxide (5 mL) was added, and the mixture was stirred overnight at 80° C. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (20% ethyl acetate/hexane to 40% ethyl acetate/hexane) to give the title compound (0.9 g, 42%) as an amorphous compound.

$^1$H NMR (300 MHz, CHLOROFORM-d) δ ppm 0.93-1.36 (m, 5H) 1.56-1.85 (m, 5H) 1.96 (d, J=10.98 Hz, 1H) 2.37 (s, 3H) 3.44 (s, 3H) 3.73-3.76 (m, 2H) 4.09-4.12 (m, 1H) 4.46-4.49 (m, 2H) 6.34 (s, 1H) 6.51 (d, J=9.09 Hz, 2H) 6.78 (d, J=8.71 Hz, 1H) 7.75 (dd, J=8.71, 2.65 Hz, 1H) 7.84 (d, J=8.71 Hz, 2H) 8.36 (d, J=1.89 Hz, 1H)

(2) 3-[({4-[(cyclohexyl{5-[6-(2-methoxyethoxy)pyridin-3-yl]-2-methylfuran-3-yl}methyl)amino]phenyl}carbonyl)amino]propanoic acid A solution of 4-[(cyclohexyl{5-[6-(2-methoxyethoxy)pyridin-3-yl]-2-methylfuran-3-yl}methyl)amino]benzoic acid (232 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (235 mg, 88%).

$^1$H NMR (300 MHz, DMSO-d$_6$) δ ppm 0.89-1.29 (m, 5H) 1.47-1.82 (m, 5H) 2.04 (d, J=13.75 Hz, 1H) 2.36 (s, 3H) 2.39-2.47 (m, 2H) 3.33-3.43 (m, 2H) 3.57-3.74 (m, 2H) 4.09 (t, J=7.72 Hz, 1H) 4.28-4.43 (m, 2H) 6.33 (d, J=7.91 Hz, 1H) 6.54 (d, J=8.67 Hz, 2H) 6.67 (s, 1H) 6.83 (d, J=8.85 Hz, 1H) 7.52 (d, J=8.67 Hz, 2H) 7.86 (dd, J=8.67, 2.45 Hz, 1H) 7.98 (t, J=5.56 Hz, 1H) 8.35 (d, J=2.45 Hz, 1H) 12.14 (brs, 1H)

Example 245

3-[({4-[(cyclohexyl{5-[6-(2-methoxyethoxy)pyridin-3-yl]-2-methylfuran-3-yl}methyl)amino]phenyl}carbonyl)(methyl)amino]propanoic acid

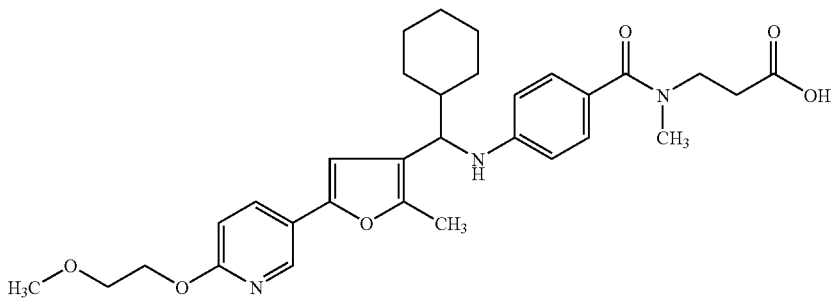

A solution of 4-[(cyclohexyl{5-[6-(2-methoxyethoxy)pyridin-3-yl]-2-methylfuran-3-yl}methyl)amino]benzoic acid (232 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (233 mg, 85%).

$^1$H NMR (300 MHz, DMSO-d$_6$) δ ppm 0.81-1.19 (m, 5H) 1.48-1.83 (m, 5H) 1.94-2.16 (m, 1H) 2.36 (s, 3H) 2.45-2.51 (m, 2H) 2.90 (s, 3H) 3.29 (s, 3H) 3.45-3.60 (m, 2H) 3.60-3.78 (m, 2H) 3.91-4.16 (m, 1H) 4.37 (d, J=3.77 Hz, 2H) 6.24 (d, J=6.40 Hz, 1H) 6.54 (d, J=8.29 Hz, 2H) 6.69 (s, 1H) 6.83 (d, J=8.67 Hz, 1H) 7.10 (d, J=8.10 Hz, 2H) 7.87 (d, J=8.85 Hz, 1H) 8.36 (brs, 1H)

Example 246

3-[({4-[(cyclohexyl{5-[6-(3-hydroxy-3-methylbutoxy)pyridin-3-yl]-2-methylfuran-3-yl}methyl)amino]phenyl}carbonyl)amino]propanoic acid

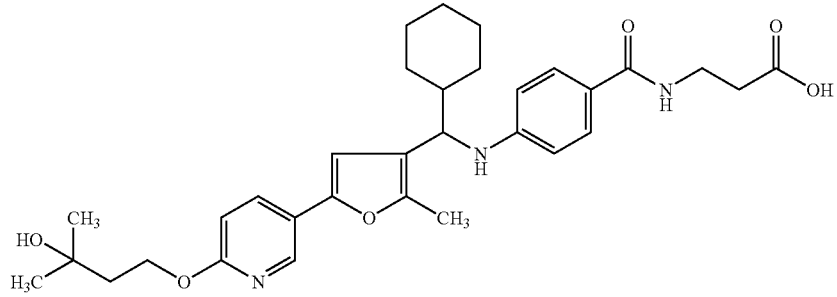

(1) 4-[(cyclohexyl{5-[6-(3-hydroxy-3-methylbutoxy)pyridin-3-yl]-2-methylfuran-3-yl}methyl)amino]benzoic acid Methyl 4-({cyclohexyl[5-(6-fluoropyridin-3-yl)-2-methylfuran-3-yl]methyl}amino)benzoate (1.7 g) and 3-methyl-1,3-butanediol (2.1 g) were dissolved in tetrahydrofuran (10 mL), 2N lithium hydroxide (4 mL) was added, and the mixture was stirred at 80° C. for 10 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (0.3 g, 16%) as an amorphous compound.

$^1$H NMR (300 MHz, CHLOROFORM-d) δ ppm 0.99-1.33 (m, 11H) 1.53-1.84 (m, 5H) 1.96-2.00 (m, 3H) 2.37 (s, 3H) 3.90 (d, J=5.68 Hz, 1H) 4.11 (d, J=7.19 Hz, 1H) 4.51 (t, J=6.44 Hz, 2H) 6.35 (s, 1H) 6.51 (d, J=8.71 Hz, 2H) 6.70 (d, J=8.71 Hz, 1H) 7.75 (dd, J=8.71, 2.65 Hz, 1H) 7.84 (d, J=9.09 Hz, 2H) 8.38 (d, J=1.89 Hz, 1H)

(2) 3-[({4-[(cyclohexyl{5-[6-(3-hydroxy-3-methylbutoxy)pyridin-3-yl]-2-methylfuran-3-yl}methyl)amino]phenyl}carbonyl)amino]propanoic acid A solution of 4-[(cyclohexyl{5-[6-(3-hydroxy-3-methylbutoxy)pyridin-3-yl]-2-methylfuran-3-yl}methyl)amino]benzoic acid (148 mg) obtained by the above-mentioned reaction, ethyl β-alaninate hydrochloride (55 mg), 1-ethyl-3-(3-dimethylaminopropyl)carbodiimide hydrochloride (69 mg), hydroxybenzotriazole monohydrate (55 mg) and triethylamine (50 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (137 mg, 81%).

$^1$H NMR (300 MHz, DMSO-d$_6$) δ ppm 0.87-1.09 (m, 5H) 1.09-1.31 (m, 6H) 1.49-1.77 (m, 5H) 1.82 (t, J=7.38 Hz, 2H) 2.03 (d, J=10.98 Hz, 1H) 2.36 (s, 3H) 2.43 (t, J=7.00 Hz, 2H) 3.33-3.45 (m, 2H) 4.09 (t, J=7.76 Hz, 1H) 4.32-4.37 (m, 3H) 6.32 (d, J=7.95 Hz, 1H) 6.54 (d, J=8.71 Hz, 2H) 6.66 (s, 1H) 6.78 (d, J=8.71 Hz, 1H) 7.52 (d, J=8.71 Hz, 2H) 7.84 (dd, J=8.71, 2.65 Hz, 1H) 7.97 (t, J=5.30 Hz, 1H) 8.35 (d, J=2.65 Hz, 1H) 12.14 (brs, 1H)

Example 247

3-[({4-[(cyclohexyl{5-[6-(3-hydroxy-3-methylbutoxy)pyridin-3-yl]-2-methylfuran-3-yl}methyl)amino]phenyl}carbonyl)(methyl)amino]propanoic acid

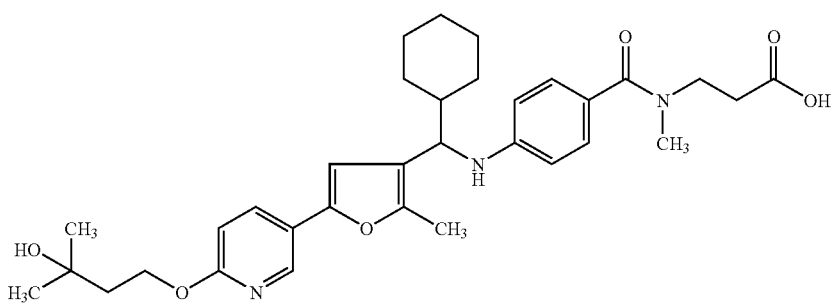

A solution of 4-[(cyclohexyl{5-[6-(3-hydroxy-3-methylbutoxy)pyridin-3-yl]-2-methylfuran-3-yl}methyl)amino]benzoic acid (148 mg), ethyl 3-(methylamino)propanoate (47 mg), 1-ethyl-3-(3-dimethylaminopropyl)carbodiimide hydrochloride (69 mg), hydroxybenzotriazole monohydrate (55 mg) and triethylamine (50 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (137 mg, 79%).

$^1$H NMR (300 MHz, DMSO-$d_6$) δ ppm 0.89-1.29 (m, 11H) 1.56-1.86 (m, 7H) 2.03 (d, J=11.74 Hz, 1H) 2.36 (s, 3H) 2.47-2.51 (m, 2H) 2.89 (s, 3H) 3.52 (t, J=7.38 Hz, 2H) 4.05 (t, J=7.57 Hz, 1H) 4.30-4.39 (m, 3H) 6.22 (d, J=7.95 Hz, 1H) 6.54 (d, J=8.33 Hz, 2H) 6.67 (s, 1H) 6.78 (d, J=8.71 Hz, 1H) 7.10 (d, J=7.95 Hz, 2H) 7.84 (dd, J=8.71, 2.27 Hz, 1H) 8.36 (d, J=2.65 Hz, 1H) 12.13 (brs, 1H)

Example 248

3-{[(4-{[cyclohexyl(2-methyl-5-{6-[3-(2-oxopyrrolidin-1-yl)propoxy]pyridin-3-yl}furan-3-yl)methyl]amino}phenyl)carbonyl]amino}propanoic acid 4.01-4.19 (m, 1H) 6.44-6.55 (m, 3H) 6.90 (dd, J=8.48, 2.64 Hz, 1H) 7.79-7.88 (m, 2H) 7.94 (ddd, J=8.52, 7.58, 2.54 Hz, 1H) 8.43 (d, J=2.45 Hz, 1H)

(2) 4-{[cyclohexyl(2-methyl-5-{6-[3-(2-oxopyrrolidin-1-yl)propoxy]pyridin-3-yl}furan-3-yl)methyl]amino}benzoic acid 1-(3-Hydroxypropyl)-2-pyrrolidine (0.4 g) was dissolved in dimethyl sulfoxide (10 mL), sodium hydride (0.1 g) was added at 0° C., and the mixture was stirred at 0° C. for 30 min. To the reaction mixture was added a solution of 4-({cyclohexyl[5-(6-fluoropyridin-3-yl)-2-methylfuran-3-yl]methyl}amino)benzoic acid (0.6 g) in dimethyl sulfoxide (20 mL), and the mixture was stirred at 0° C. for 30 min, and then at room temperature for 3 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (0.6 g, 73%) as a white crystal.

$^1$H NMR (300 MHz, DMSO-$d_6$) δ ppm 0.89-1.28 (m, 5H) 1.49-1.80 (m, 5H) 1.80-1.97 (m, 4H) 1.97-2.07 (m, 1H) 2.12-2.24 (m, 2H) 2.36 (s, 3H) 3.22-3.43 (m, 6H) 4.10 (t, J=7.95 Hz, 1H) 4.22 (t, J=6.44 Hz, 2H) 6.51-6.65 (m, 3H) 6.67 (s, 1H) 6.81 (d, J=8.33 Hz, 1H) 7.59 (d, J=8.71 Hz, 2H) 7.86 (dd, J=8.71, 2.27 Hz, 1H) 8.36 (d, J=2.27 Hz, 1H) 11.91 (brs, 1H)

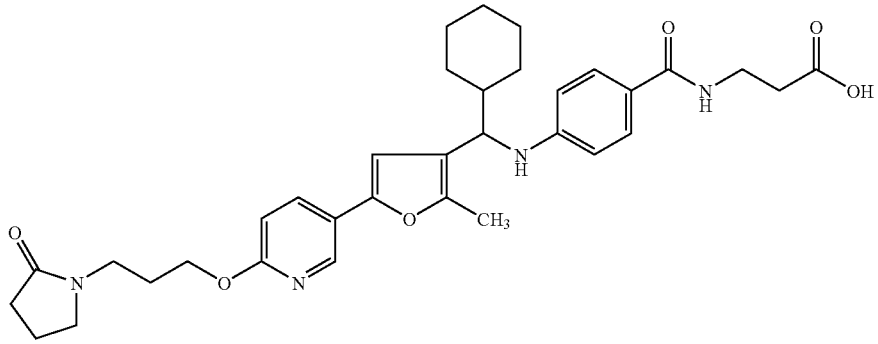

(1) 4-({cyclohexyl[5-(6-fluoropyridin-3-yl)-2-methylfuran-3-yl]methyl}amino)benzoic acid Methyl 4-({cyclohexyl[5-(6-fluoropyridin-3-yl)-2-methylfuran-3-yl]methyl}amino)benzoate (1.7 g) was dissolved in tetrahydrofuran (10 mL), 2N lithium hydroxide (4 mL) was added, and the mixture was stirred overnight at 80° C. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.2 g, 74%) as an amorphous compound.

$^1$H NMR (300 MHz, CHLOROFORM-d) δ ppm 0.97-1.30 (m, 5H) 1.47-1.83 (m, 5H) 1.93-2.00 (m, 1H) 2.39 (s, 3H)

(3) 3-{[(4-{[cyclohexyl(2-methyl-5-{6-[3-(2-oxopyrrolidin-1-yl)propoxy]pyridin-3-yl}furan-3-yl)methyl]amino}phenyl)carbonyl]amino}propanoic acid A solution of 4-{[cyclohexyl(2-methyl-5-{6-[3-(2-oxopyrrolidin-1-yl)propoxy]pyridin-3-yl}furan-3-yl)methyl]amino}benzoic acid (159 mg) obtained by the above-mentioned reaction, ethyl β-alaninate hydrochloride (55 mg), 1-ethyl-3-(3-dimethylaminopropyl)carbodiimide hydrochloride (69 mg), hydroxybenzotriazole monohydrate (55 mg) and triethylamine (50 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (150 mg, 84%).

$^1$H NMR (300 MHz, DMSO-$d_6$) δ ppm 0.92-1.30 (m, 5H) 1.47-1.80 (m, 5H) 1.81-1.97 (m, 4H) 2.02 (d, J=13.63 Hz, 1H) 2.13-2.24 (m, 2H) 2.36 (s, 3H) 2.43 (t, J=7.19 Hz, 2H) 3.28-3.43 (m, 4H) 4.09 (t, J=7.76 Hz, 1H) 4.22 (t, J=6.44 Hz, 2H) 6.32 (d, J=7.95 Hz, 1H) 6.54 (d, J=9.09 Hz, 2H) 6.67 (s, 1H) 6.81 (d, J=8.71 Hz, 1H) 7.52 (d, J=8.71 Hz, 2H) 7.85 (dd, J=8.71, 2.65 Hz, 1H) 7.97 (t, J=5.30 Hz, 1H) 8.35 (d, J=2.27 Hz, 1H) 12.12 (brs, 1H)

Example 249

3-{[(4-{[cyclohexyl(2-methyl-5-{6-[3-(2-oxopyrrolidin-1-yl)propoxy]pyridin-3-yl}furan-3-yl)methyl]amino}phenyl)carbonyl](methyl)amino}propanoic acid

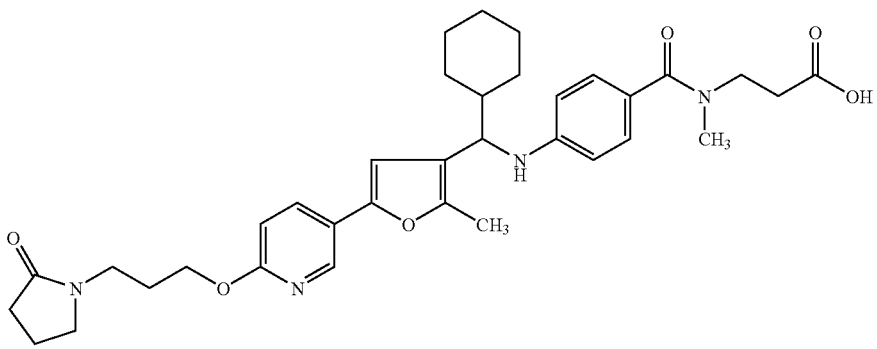

A solution of 4-{[cyclohexyl(2-methyl-5-{6-[3-(2-oxopyrrolidin-1-yl)propoxy]pyridin-3-yl}furan-3-yl)methyl]amino}benzoic acid (159 mg), ethyl 3-(methylamino)propanoate (47 mg), 1-ethyl-3-(3-dimethylaminopropyl)carbodiimide hydrochloride (69 mg), hydroxybenzotriazole monohydrate (55 mg) and triethylamine (50 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (135 mg, 73%).

$^1$H NMR (300 MHz, DMSO-$d_6$) δ ppm 0.90-1.29 (m, 5H) 1.47-1.81 (m, 5H) 1.81-1.98 (m, 4H) 1.98-2.12 (m, 1H) 2.12-2.23 (m, 2H) 2.36 (s, 3H) 2.46-2.51 (m, 2H) 2.90 (s, 3H) 3.28-3.37 (m, 4H) 3.51 (t, J=7.19 Hz, 2H) 4.05 (t, J=7.38 Hz, 1H) 4.22 (t, J=6.44 Hz, 2H) 6.22 (d, J=7.57 Hz, 1H) 6.54 (d, J=8.71 Hz, 2H) 6.68 (s, 1H) 6.81 (d, J=9.09 Hz, 1H) 7.10 (d, J=8.33 Hz, 2H) 7.86 (dd, J=8.71, 2.65 Hz, 1H) 8.36 (d, J=1.89 Hz, 1H) 12.22 (brs, 1H)

Example 250

3-[({4-[(cyclohexyl{2-[(methylsulfonyl)methyl]-5-[4-(trifluoromethyl)phenyl]furan-3-yl}methyl)amino]phenyl}carbonyl)amino]propanoic acid

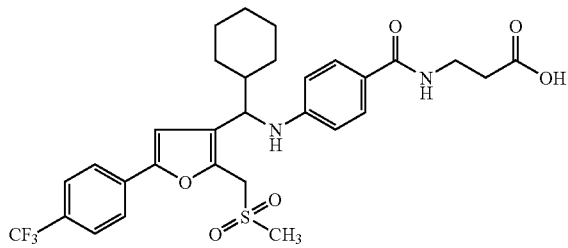

(1) methyl 2-[(methylsulfanyl)methyl]-5-[4-(trifluoromethyl)phenyl]furan-3-carboxylate A mixture of methyl 5-bromo-2-[(methylsulfanyl)methyl]furan-3-carboxylate (5.3 g), 4-(trifluoromethyl)phenylboronic acid (4.6 g), tetrakis(triphenylphosphine)palladium(0) (1.2 g), 2N aqueous sodium carbonate solution (24 mL) and 1,2-dimethoxyethane (50 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane) to give the title compound (5.0 g, 75%) as an oil.
$^1$H NMR (300 MHz, CHLOROFORM-d) δ ppm 2.19 (s, 3H) 3.88 (s, 3H) 4.11 (s, 2H) 7.03 (s, 1H) 7.59-7.69 (m, 2H) 7.70-7.85 (m, 2H)

(2) {2-[(methylsulfanyl)methyl]-5-[4-(trifluoromethyl)phenyl]furan-3-yl}methanol A solution of methyl 2-[(methylsulfanyl)methyl]-5-[4-(trifluoromethyl)phenyl]furan-3-carboxylate (5.0 g) obtained by the above-mentioned reaction in tetrahydrofuran (20 mL) was added dropwise to a suspension of lithium aluminum hydride (0.6 g) in tetrahydrofuran (50 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The residue was purified by silica gel chromatography (0% ethyl acetate/hexane to 30% ethyl acetate/hexane) to give the title compound (4.5 g, 100%) as an oil.
$^1$H NMR (300 MHz, CHLOROFORM-d) δ ppm 1.76 (t, J=5.75 Hz, 1H) 2.16 (s, 3H) 3.82 (s, 2H) 4.59 (d, J=5.84 Hz, 2H) 6.79 (s, 1H) 7.53-7.67 (m, 2H) 7.67-7.81 (m, 2H)

(3) 2-[(methylsulfanyl)methyl]-5-[4-(trifluoromethyl)phenyl]furan-3-carbaldehyde To a solution of {2-[(methylsulfanyl)methyl]-5-[4-(trifluoromethyl)phenyl]furan-3-yl}methanol (4.5 g) obtained by the above-mentioned reaction in acetonitrile (50 mL) was added Dess-Martin reagent (9.5 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 25% ethyl acetate/hexane) to give the title compound (3.6 g, 80%) as a yellow crystal.
$^1$H NMR (300 MHz, CHLOROFORM-d) δ ppm 2.20 (s, 3H) 4.05 (s, 2H) 7.07 (s, 1H) 7.59-7.72 (m, 2H) 7.72-7.85 (m, 2H) 10.03 (s, 1H)

(4) cyclohexyl{2-[(methylsulfanyl)methyl]-5-[4-(trifluoromethyl)phenyl]furan-3-yl}methanol To a solution of 2-[(methylsulfanyl)methyl]-5-[4-(trifluoromethyl)phenyl]furan-3-carbaldehyde (3.6 g) obtained by the above-mentioned reaction in tetrahydrofuran (50 mL) was added dropwise 1N cyclohexylmagnesium bromide-tetrahydrofuran solution (15 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 25% ethyl acetate/hexane) to give the title compound (3.2 g, 69%) as an oil.
$^1$H NMR (300 MHz, CHLOROFORM-d) δ ppm 0.85-1.31 (m, 5H) 1.59-1.60 (m, 5H) 2.04-2.12 (m, 1H) 2.20 (s, 3H) 3.80 (s, 2H) 4.37-4.44 (m, 1H) 6.73 (s, 1H) 7.54-7.66 (m, 2H) 7.66-7.79 (m, 2H)

(5) 3-[chloro(cyclohexyl)methyl]-2-[(methylsulfanyl)methyl]-5-[4-(trifluoromethyl)phenyl]furan To a solution of cyclohexyl{2-[(methylsulfanyl)methyl]-5-[4-(trifluoromethyl)phenyl]furan-3-yl}methanol (3.1 g) obtained by the above-mentioned reaction in toluene (20 mL) were added thionyl chloride (0.9 mL) and pyridine (1.0 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (3.3 g, 100%) as an oil.
$^1$H NMR (300 MHz, CHLOROFORM-d) δ ppm 0.99-1.33 (m, 5H) 1.54-1.94 (m, 5H) 2.12-2.20 (m, 4H) 3.76 (s, 2H) 4.65 (d, J=8.71 Hz, 1H) 6.78 (s, 1H) 7.52-7.66 (m, 2H) 7.66-7.79 (m, 2H)

(6) 4-[(cyclohexyl{2-[(methylsulfanyl)methyl]-5-[4-(trifluoromethyl)phenyl]furan-3-yl}methyl)amino]benzoic acid A mixture of 3-[chloro(cyclohexyl)methyl]-2-[(methylsulfanyl)methyl]-5-[4-(trifluoromethyl)phenyl]furan (3.3 g) obtained by the above-mentioned reaction, methyl 4-aminobenzoate (1.8 g), sodium carbonate (1.3 g) and sodium iodide (2.4 g) in N,N-dimethylacetamide (30 mL) was stirred at 80° C. for 10 hr. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (10 mL) and tetrahydrofuran (10 mL), 2N lithium hydroxide (10 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (2.0 g, 50%) as an amorphous compound.

$^1$H NMR (300 MHz, CHLOROFORM-d) δ ppm 0.91-1.39 (m, 7H) 1.64-1.83 (m, 5H) 2.20 (s, 3H) 3.80 (s, 2H) 4.26 (d, J=6.59 Hz, 1H) 6.44-6.54 (m, 1H) 6.54-6.64 (m, 2H) 7.49-7.62 (m, 2H) 7.65-7.69 (m, 2H) 7.85 (dd, J=8.85, 2.07 Hz, 2H)

(7) ethyl 3-[({4-[(cyclohexyl{2-[(methylsulfanyl)methyl]-5-[4-(trifluoromethyl)phenyl]furan-3-yl}methyl)amino]phenyl}carbonyl)amino]propanoate A solution of 4-[(cyclohexyl{2-[(methylsulfanyl)methyl]-5-[4-(trifluoromethyl)phenyl]furan-3-yl}methyl)amino]benzoic acid (1.0 g) obtained by the above-mentioned reaction, ethyl β-alaninate hydrochloride (0.4 g), 1-ethyl-3-(3-dimethylaminopropyl)carbodiimide hydrochloride (0.5 g), hydroxybenzotriazole monohydrate (0.4 g) and triethylamine (0.3 mL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the residue was purified by silica gel chromatography (10% ethyl acetate/hexane to 60% ethyl acetate/hexane) to give the title compound (1.2 g, 100%) as an oil.

$^1$H NMR (300 MHz, CHLOROFORM-d) δ ppm 0.96-1.35 (m, 8H) 1.62-1.83 (m, 5H) 1.94-1.99 (m, 1H) 2.20 (s, 3H) 2.57-2.61 (m, 2H) 3.63-3.69 (m, 2H) 3.80 (s, 2H) 4.06-4.32 (m, 6H) 6.45-6.54 (m, 1H) 6.54-6.66 (m, 4H) 7.49-7.69 (m, 4H)

(8) ethyl 3-[({4-[(cyclohexyl{2-[(methylsulfonyl)methyl]-5-[4-(trifluoromethyl)phenyl]furan-3-yl}methyl)amino]phenyl}carbonyl)amino]propanoate Ethyl 3-[({4-[(cyclohexyl{2-[(methylsulfanyl)methyl]-5-[4-(trifluoromethyl)phenyl]furan-3-yl}methyl)amino]phenyl}carbonyl)amino]propanoate (603 mg) obtained by the above-mentioned reaction was dissolved in methanol (9 mL) and water (1 mL), OXONE (0.7 g) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane) to give the title compound (351 mg, 55%) as an amorphous compound.

$^1$H NMR (300 MHz, CHLOROFORM-d) δ ppm 0.99-1.35 (m, 5H) 1.60-1.98 (m, 5H) 2.60 (t, J=5.93 Hz, 2H) 2.94 (s, 3H) 3.67 (q, J=5.97 Hz, 2H) 4.15 (q, J=7.16 Hz, 2H) 4.34 (t, J=6.69 Hz, 1H) 4.41 (d, J=5.09 Hz, 2H) 4.55 (d, J=7.35 Hz, 1H) 6.52-6.66 (m, 3H) 6.72 (s, 1H) 7.58 (d, J=8.67 Hz, 2H) 7.60-7.67 (m, 2H) 7.67-7.80 (m, 2H)

(9) 3-[({4-[(cyclohexyl{2-[(methylsulfonyl)methyl]-5-[4-(trifluoromethyl)phenyl]furan-3-yl}methyl)amino]phenyl}carbonyl)amino]propanoic acid Ethyl 3-[({4-[(cyclohexyl{2-[(methylsulfonyl)methyl]-5-[4-(trifluoromethyl)phenyl]furan-3-yl}methyl)amino]phenyl}carbonyl)amino]propanoate (349 mg) obtained by the above-mentioned reaction was dissolved in ethanol (2 mL) and tetrahydrofuran (2 mL), 1N lithium hydroxide (1.1 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (287 mg, 48%).

$^1$H NMR (300 MHz, DMSO-$d_6$) δ ppm 0.90-1.25 (m, 5H) 1.44-1.84 (m, 5H) 2.00 (d, J=8.85 Hz, 1H) 2.43 (t, J=7.06 Hz, 2H) 3.11 (s, 3H) 3.34-3.44 (m, 2H) 4.38 (t, J=7.82 Hz, 1H) 4.74-4.97 (m, 2H) 6.35 (d, J=8.29 Hz, 1H) 6.68 (d, J=8.85 Hz, 2H) 7.13 (s, 1H) 7.52 (d, J=8.67 Hz, 2H) 7.77 (m, 2H) 7.82 (m, 2H) 8.01 (t, J=5.46 Hz, 1H) 12.16 (brs, 1H)

Example 251

3-[({4-[(cyclohexyl{2-[(methylsulfonyl)methyl]-5-[4-(trifluoromethyl)phenyl]furan-3-yl}methyl)amino]phenyl}carbonyl)(methyl)amino]propanoic acid

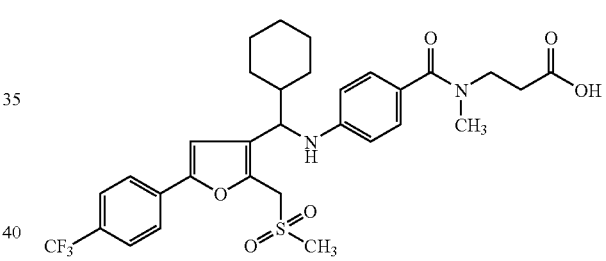

(1) ethyl 3-[({4-[(cyclohexyl{2-[(methylsulfanyl)methyl]-5-[4-(trifluoromethyl)phenyl]furan-3-yl}methyl)amino]phenyl}carbonyl)(methyl)amino]propanoate A solution of 4-[(cyclohexyl{2-[(methylsulfanyl)methyl]-5-[4-(trifluoromethyl)phenyl]furan-3-yl}methyl)amino]benzoic acid (1.0 g), ethyl 3-(methylamino)propanoate (0.3 g), 1-ethyl-3-(3-dimethylaminopropyl)carbodiimide hydrochloride (0.5 g), hydroxybenzotriazole monohydrate (0.4 g) and triethylamine (0.3 mL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the residue was purified by silica gel chromatography (10% ethyl acetate/hexane to 40% ethyl acetate/hexane) to give the title compound (1.2 g, 100%) as an amorphous compound.

$^1$H NMR (300 MHz, CHLOROFORM-d) δ ppm 0.96-1.38 (m, 5H) 1.66-1.83 (m, 5H) 1.95-2.02 (m, 1H) 2.19 (s, 3H) 2.61 (t, J=6.82 Hz, 2H) 3.02 (s, 5H) 3.71 (t, J=7.19 Hz, 2H) 3.91-4.30 (m, 4H) 6.49 (d, J=8.71 Hz, 1H) 6.53-6.61 (m, 3H) 7.22 (d, J=8.33 Hz, 2H) 7.52-7.62 (m, 2H) 7.62-7.74 (m, 2H)

(2) ethyl 3-[({4-[(cyclohexyl{2-[(methylsulfonyl)methyl]-5-[4-(trifluoromethyl)phenyl]furan-3-yl}methyl)amino]phenyl}carbonyl)(methyl)amino]propanoate Ethyl 3-[({4-[(cyclohexyl{2-[(methylsulfanyl)methyl]-5-[4-(trifluoromethyl)phenyl]furan-3-yl}methyl)amino]phenyl}carbonyl)(methyl)amino]propanoate (493 mg) obtained by the above-mentioned reaction was dissolved in methanol (9 mL) and water (1 mL), OXONE (0.6 g) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 50% ethyl acetate/hexane) to give the title compound (251 mg, 48%) as an amorphous compound.
$^1$H NMR (300 MHz, CHLOROFORM-d) δ ppm 1.02-1.38 (m, 5H) 1.63-1.98 (m, 6H) 2.62 (t, J=8.10 Hz, 2H) 2.94 (s, 3H) 3.03 (s, 3H) 3.75 (t, J=6.31 Hz, 2H) 4.12 (q, J=6.97 Hz, 2H) 4.30 (s, 1H) 4.34-4.54 (m, 2H) 6.52-6.63 (m, 2H) 6.73 (s, 1H) 7.23-7.26 (m, 2H) 7.57-7.67 (m, 2H) 7.70-7.73 (m, 2H)

(3) 3-[({4-[(cyclohexyl{2-[(methylsulfonyl)methyl]-5-[4-(trifluoromethyl)phenyl]furan-3-yl}methyl)amino]phenyl}carbonyl)(methyl)amino]propanoic acid Ethyl 3-[({4-[(cyclohexyl{2-[(methylsulfonyl)methyl]-5-[4-(trifluoromethyl)phenyl]furan-3-yl}methyl)amino]phenyl}carbonyl)(methyl)amino]propanoate (247 mg) obtained by the above-mentioned reaction was dissolved in ethanol (2 mL) and tetrahydrofuran (2 mL), 1N lithium hydroxide (0.8 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (199 mg, 84%).
$^1$H NMR (300 MHz, DMSO-d$_6$) δ ppm 0.96-1.25 (m, 5H) 1.43-1.83 (m, 5H) 2.01 (d, J=11.30 Hz, 1H) 2.46-2.51 (m, 2H) 2.90 (s, 3H) 3.10 (s, 3H) 3.52 (t, J=7.54 Hz, 2H) 4.27-4.43 (m, 1H) 4.77-4.96 (m, 2H) 6.25 (d, J=8.10 Hz, 1H) 6.65-6.68 (m, 2H) 7.09 (d, J=8.48 Hz, 2H) 7.15 (s, 1H) 7.73-7.80 (m, 2H) 7.80-7.88 (m, 2H) 12.28 (brs, 1H)

Example 252

3-[({4-[(cyclohexyl{2-[(methylsulfinyl)methyl]-5-[4-(trifluoromethyl)phenyl]furan-3-yl}methyl)amino]phenyl}carbonyl)amino]propanoic acid

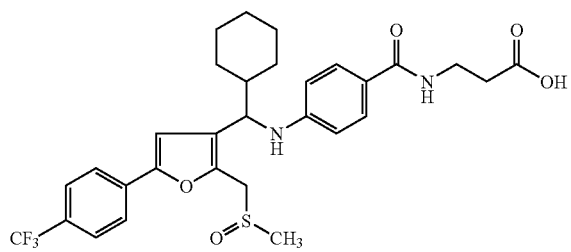

(1) ethyl 3-[({4-[(cyclohexyl{2-[(methylsulfinyl)methyl]-5-[4-(trifluoromethyl)phenyl]furan-3-yl}methyl)amino]phenyl}carbonyl)amino]propanoate Ethyl 3-[({4-[(cyclohexyl{2-[(methylsulfanyl)methyl]-5-[4-(trifluoromethyl)phenyl]furan-3-yl}methyl)amino]phenyl}carbonyl)amino]propanoate (482 mg) was dissolved in methanol (9 mL) and water (1 mL), OXONE (295 mg) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 100% ethyl acetate/hexane) to give the title compound (232 mg, 47%) as an oil.
$^1$H NMR (300 MHz, CHLOROFORM-d) δ ppm 1.02-1.34 (m, 8H) 1.61-2.00 (m, 6H) 2.49-2.68 (m, 5H) 3.67 (q, J=6.06 Hz, 2H) 3.93-4.08 (m, 1H) 4.08-4.26 (m, 3H) 4.26-4.39 (m, 1H) 4.90 (d, J=6.82 Hz, 1H) 6.58-6.62 (m, 3H) 6.70 (d, J=6.82 Hz, 1H) 7.58 (d, J=7.57 Hz, 2H) 7.62 (d, J=8.33 Hz, 2H) 7.70 (d, J=8.71 Hz, 2H)

(2) 3-[({4-[(cyclohexyl{2-[(methylsulfinyl)methyl]-5-[4-(trifluoromethyl)phenyl]furan-3-yl}methyl)amino]phenyl}carbonyl)amino]propanoic acid Ethyl 3-[({4-[(cyclohexyl{2-[(methylsulfinyl)methyl]-5-[4-(trifluoromethyl)phenyl]furan-3-yl}methyl)amino]phenyl}carbonyl)amino]propanoate (229 mg) obtained by the above-mentioned reaction was dissolved in ethanol (2 mL) and tetrahydrofuran (2 mL), 1N lithium hydroxide (0.8 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (174 mg, 80%).
$^1$H NMR (300 MHz, DMSO-d$_6$) δ ppm 0.93-1.30 (m, 5H) 1.44-1.83 (m, 5H) 1.92-2.09 (m, 1H) 2.42 (t, J=7.06 Hz, 2H) 2.69 (s, 3H) 3.26-3.47 (m, 2H) 4.22-4.51 (m, 3H) 6.36 (t, J=8.76 Hz, 1H) 6.66 (d, J=8.48 Hz, 2H) 7.10 (d, J=2.64 Hz, 1H) 7.52 (dd, J=8.76, 2.17 Hz, 2H) 7.70-7.85 (m, 4H) 8.02 (d, J=2.26 Hz, 1H)

Example 253

3-[({4-[(cyclohexyl{2-[(methylsulfinyl)methyl]-5-[4-(trifluoromethyl)phenyl]furan-3-yl}methyl)amino]phenyl}carbonyl)(methyl)amino]propanoic acid

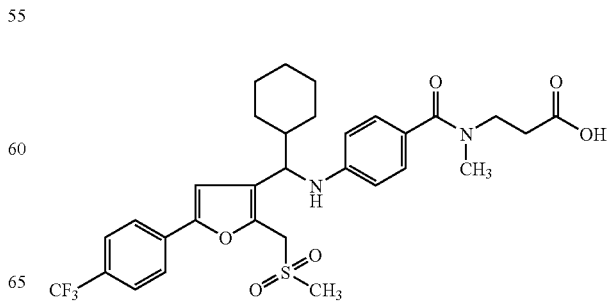

(1) ethyl 3-[({4-[(cyclohexyl{2-[(methylsulfinyl)methyl]-5-[4-(trifluoromethyl)phenyl]furan-3-yl}methyl)amino]phenyl}carbonyl)(methyl)amino]propanoate Ethyl 3-[({4-[(cyclohexyl{2-[(methylsulfanyl)methyl]-5-[4-(trifluoromethyl)phenyl]furan-3-yl}methyl)amino]phenyl}carbonyl)(methyl)amino]propanoate (0.37 g) obtained by the above-mentioned reaction was dissolved in methanol (9 mL) and water (1 mL), OXONE (221 mg) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 100% ethyl acetate/hexane) to give the title compound (143 mg, 38%) as an oil.

$^1$H NMR (300 MHz, CHLOROFORM-d) δ ppm 0.99-1.36 (m, 8H) 1.60-1.98 (m, 6H) 2.47-2.70 (m, 5H) 3.04 (s, 3H) 3.73 (q, J=7.32 Hz, 2H) 3.96-4.34 (m, 5H) 4.72 (brs, 1H) 6.58 (dd, J=8.90, 2.46 Hz, 2H) 6.70 (d, J=6.82 Hz, 1H) 7.18-7.25 (m, 2H) 7.62 (d, J=9.09 Hz, 2H) 7.70 (d, J=8.71 Hz, 2H)

(2) 3-[({4-[(cyclohexyl{2-[(methylsulfinyl)methyl]-5-[4-(trifluoromethyl)phenyl]furan-3-yl}methyl)amino]phenyl}carbonyl)(methyl)amino]propanoic acid Ethyl 3-[({4-[(cyclohexyl{2-[(methylsulfinyl)methyl]-5-[4-(trifluoromethyl)phenyl]furan-3-yl}methyl)amino]phenyl}carbonyl)(methyl)amino]propanoate (139 mg) obtained by the above-mentioned reaction was dissolved in ethanol (2 mL) and tetrahydrofuran (2 mL), 1N lithium hydroxide (0.5 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (97 mg, 73%).

$^1$H NMR (300 MHz, DMSO-d$_6$) δ ppm 0.92-1.28 (m, 5H) 1.46-1.85 (m, 5H) 2.03 (d, J=9.98 Hz, 1H) 2.46-2.51 (m, 2H) 2.68 (d, J=1.88 Hz, 3H) 2.90 (s, 3H) 3.51 (t, J=7.35 Hz, 2H) 4.20-4.49 (m, 3H) 6.26 (dd, J=10.64, 8.57 Hz, 1H) 6.65 (d, J=8.10 Hz, 2H) 7.02-7.16 (m, 3H) 7.72-7.78 (m, 2H) 7.78-7.86 (m, 2H)

Example 254

3-({[4-({1-[5-(6-methoxypyridin-3-yl)-2-methylfuran-3-yl]-3-methylbutyl}amino)phenyl]carbonyl}amino)propanoic acid

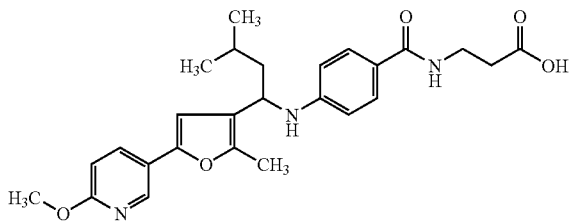

Ethyl 3-({[4-({1-[5-(6-methoxypyridin-3-yl)-2-methylfuran-3-yl]-3-methylbutyl}amino)phenyl]carbonyl}amino)propanoate (1000 mg) which is a synthetic intermediate in Example 148 was dissolved in ethanol-hexane (1:1, volume ratio), and the solution was subjected to HPLC using CHIRALPAK AD (50 mmID×500 mmL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 11.5 min were collected, and concentrated. The obtained amorphous compound (487 mg) was dissolved in ethanol (2 mL) and tetrahydrofuran (2 mL), 1N lithium hydroxide (2.0 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (454 mg, 89%).

$^1$H NMR (300 MHz, DMSO-d$_6$) δ ppm 0.92 (dd, J=18.17, 6.06 Hz, 6H) 1.46-1.80 (m, 3H) 2.38 (s, 3H) 2.42 (t, J=7.06 Hz, 2H) 3.30-3.45 (m, 2H) 3.85 (s, 3H) 4.36 (q, J=7.16 Hz, 1H) 6.37 (d, J=7.54 Hz, 1H) 6.55 (d, J=8.67 Hz, 2H) 6.73 (s, 1H) 6.83 (d, J=8.67 Hz, 1H) 7.54 (d, J=8.67 Hz, 2H) 7.87 (dd, J=8.67, 2.45 Hz, 1H) 8.02 (t, J=5.46 Hz, 1H) 8.38 (d, J=2.26 Hz, 1H) 12.21 (brs, 1H)

Example 255

3-({[4-({1-[5-(6-methoxypyridin-3-yl)-2-methylfuran-3-yl]-3-methylbutyl}amino)phenyl]carbonyl}amino)propanoic acid

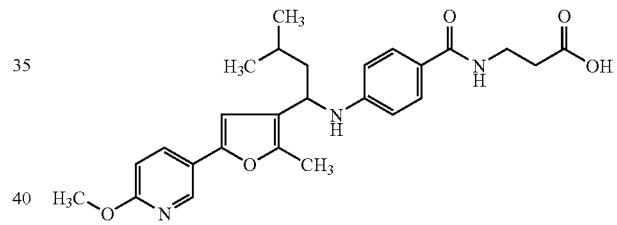

Ethyl 3-({[4-({1-[5-(6-methoxypyridin-3-yl)-2-methylfuran-3-yl]-3-methylbutyl}amino)phenyl]carbonyl}amino)propanoate (1000 mg) which is a synthetic intermediate in Example 148 was dissolved in ethanol-hexane (1:1, volume ratio), and the solution was subjected to HPLC using CHIRALPAK AD (50 mmID×500 mmL, manufactured by DAICEL CHEMICAL INDUSTRIES, LTD.) and eluted with ethanol-hexane (1:1, volume ratio) as mobile phase at 30° C., a flow rate 60 mL/min. The fractions showing a peak with retention time 16.9 min were collected, and concentrated. The obtained amorphous compound (488 mg) was dissolved in ethanol (2 mL) and tetrahydrofuran (2 mL), 1N lithium hydroxide (2.0 mL) was added, and the mixture was stirred at room temperature for 1 hr. The solvent was evaporated under reduced pressure, and water (20 mL) was added. The mixture was neutralized with 1N hydrochloric acid under ice-cooling, and stirred for 1 hr. The resulting precipitate was collected by filtration and dried to give the title compound (452 mg, 87%).

$^1$H NMR (300 MHz, DMSO-d$_6$) δ ppm 0.92 (dd, J=18.17, 6.06 Hz, 6H) 1.46-1.80 (m, 3H) 2.38 (s, 3H) 2.42 (t, J=7.06 Hz, 2H) 3.30-3.45 (m, 2H) 3.85 (s, 3H) 4.36 (q, J=7.16 Hz, 1H) 6.37 (d, J=7.54 Hz, 1H) 6.55 (d, J=8.67 Hz, 2H) 6.73 (s, 1H) 6.83 (d, J=8.67 Hz, 1H) 7.54 (d, J=8.67 Hz, 2H) 7.87 (dd, J=8.67, 2.45 Hz, 1H) 8.02 (t, J=5.46 Hz, 1H) 8.38 (d, J=2.26 Hz, 1H) 12.21 (brs, 1H)

Example 256

3-{[(4-{[cyclohexyl(2-methyl-5-{6-[2-(methylsulfanyl)ethoxy]pyridin-3-yl}furan-3-yl)methyl]amino}phenyl)carbonyl]amino}propanoic acid

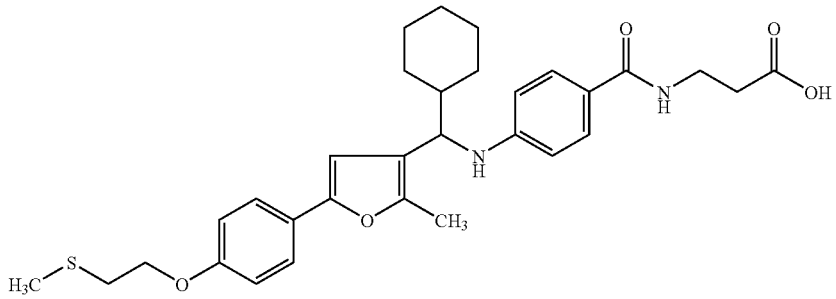

(1) 5-(4-hydroxyphenyl)-2-methylfuran-3-carbaldehyde

A mixture of 5-bromo-2-methylfuran-3-carbaldehyde (1.9 g), 4-hydroxyphenylboronic acid (1.7 g), tetrakis(triphenylphosphine)palladium(0) (0.6 g), 2N aqueous sodium carbonate solution (12 mL) and 1,2-dimethoxyethane (50 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 35% ethyl acetate/hexane) to give the title compound (1.6 g, 35%) as a yellow crystal.

$^1$H NMR (300 MHz, CHLOROFORM-d) δ ppm 2.65 (s, 3H) 6.76 (s, 1H) 6.87 (d, J=9.09 Hz, 2H) 7.54 (d, J=8.71 Hz, 2H) 9.95 (s, 1H)

(2) 2-methyl-5-{4-[(2-(methylsulfanyl)ethoxy]phenyl}furan-3-carbaldehyde

To a solution of 5-(4-hydroxyphenyl)-2-methylfuran-3-carbaldehyde (1.4 g) obtained by the above-mentioned reaction and 2-methylthioethanol (0.9 g) in tetrahydrofuran (20 mL) were added tributylphosphine (3.5 mL) and 1,1'-(azodicarbonyl)dipiperidine (3.5 g), and the mixture was stirred at room temperature overnight. The solvent was evaporated under reduced pressure, and the residue was purified by silica gel column (0% ethyl acetate/hexane to 25% ethyl acetate/hexane) to give the title compound (0.6 g, 30%) as a white crystal.

$^1$H NMR (300 MHz, CHLOROFORM-d) δ ppm 2.23 (s, 3H) 2.65 (s, 3H) 2.90 (t, J=6.82 Hz, 2H) 4.19 (t, J=6.82 Hz, 2H) 6.77 (s, 1H) 6.93 (d, J=8.71 Hz, 2H) 7.58 (d, J=9.09 Hz, 2H) 9.96 (s, 1H)

(3) cyclohexyl(2-methyl-5-{4-[2-(methylsulfanyl)ethoxy]phenyl}furan-3-yl)methanol To a solution of 2-methyl-5-{4-[2-(methylsulfanyl)ethoxy]phenyl}furan-3-carbaldehyde (0.6 g) obtained by the above-mentioned reaction in tetrahydrofuran (20 mL) was added dropwise 1N cyclohexylmagnesium bromide-tetrahydrofuran solution (3 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 25% ethyl acetate/hexane) to give the title compound (0.6 g, 86%) as an oil.

$^1$H NMR (300 MHz, CHLOROFORM-d) δ ppm 0.83-1.41 (m, 5H) 1.50-1.83 (m, 5H) 2.07 (d, J=14.77 Hz, 1H) 2.22 (s, 3H) 2.31 (s, 3H) 2.89 (t, J=6.82 Hz, 2H) 4.18 (t, J=6.82 Hz, 2H) 4.29 (d, J=7.57 Hz, 1H) 6.45 (s, 1H) 6.90 (d, J=8.71 Hz, 2H) 7.54 (d, J=8.71 Hz, 2H)

(4) 3-[chloro(cyclohexyl)methyl]-2-methyl-5-{4-[2-(methylsulfanyl)ethoxy]phenyl}furan To a solution of cyclohexyl(2-methyl-5-{4-[2-(methylsulfanyl)ethoxy]phenyl}furan-3-yl)methanol (1.1 g) obtained by the above-mentioned reaction in toluene (20 mL) were added thionyl chloride (0.3 mL) and pyridine (0.4 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.1 g, 100%) as an oil.

$^1$H NMR (300 MHz, CHLOROFORM-d) δ ppm 0.81-1.44 (m, 5H) 1.60-1.98 (m, 5H) 2.11-2.26 (m, 1H) 2.31 (s, 3H) 2.89 (t, J=6.82 Hz, 2H) 4.18 (t, J=6.82 Hz, 2H) 4.60 (d, J=8.71 Hz, 1H) 6.48 (s, 1H) 6.80-6.94 (m, 2H) 7.47-7.64 (m, 2H)

(6) 4-{[cyclohexyl(2-methyl-5-{4-[(methylsulfanyl)methoxy]phenyl}furan-3-yl)methyl]amino}benzoic acid A mixture of 3-[chloro(cyclohexyl)methyl]-2-methyl-5-{4-[2-(methylsulfanyl)ethoxy]phenyl}furan (1.1 g) obtained by the above-mentioned reaction, methyl 4-aminobenzoate (0.7 g), sodium carbonate (0.5 g) and sodium iodide (0.9 g) in N,N-dimethylacetamide (20 mL) was stirred at 80° C. for 10 hr. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL), 2N lithium hydroxide (3 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (0.8 g, 57%) as an amorphous compound.

¹H NMR (300 MHz, CHLOROFORM-d) δ ppm 0.91-1.39 (m, 5H) 1.52-1.85 (m, 5H) 1.96 (d, J=9.04 Hz, 1H) 2.21 (s, 3H) 2.36 (s, 3H) 2.87 (t, J=6.78 Hz, 2H) 4.16 (t, J=6.78 Hz, 2H) 4.01-4.21 (m, 1H) 6.31 (s, 1H) 6.51 (d, J=9.04 Hz, 2H) 6.87 (d, J=9.04 Hz, 2H) 7.50 (d, J=8.85 Hz, 2H) 7.84 (d, J=8.85 Hz, 2H)

(7) 3-{[(4-{[cyclohexyl(2-methyl-5-{6-[2-(methylsulfanyl)ethoxy]pyridin-3-yl}furan-3-yl)methyl]amino}phenyl)carbonyl]amino}propanoic acid A solution of 4-{[cyclohexyl(2-methyl-5-{4-[(methylsulfanyl)methoxy]phenyl}furan-3-yl)methyl]amino}benzoic acid (408 mg) obtained by the above-mentioned reaction, ethyl β-alaninate hydrochloride (157 mg), 1-ethyl-3-(3-dimethylaminopropyl)carbodiimide hydrochloride (196 mg), hydroxybenzotriazole monohydrate (156 mg) and triethylamine (142 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure to give ethyl 3-{[(4-{[cyclohexyl(2-methyl-5-{4-[(methylsulfanyl)methoxy]phenyl}furan-3-yl)methyl]amino}phenyl)carbonyl]amino}propanoate. To ethyl 3-{[(4-{[cyclohexyl(2-methyl-5-{4-[(methylsulfanyl)methoxy]phenyl}furan-3-yl)methyl]amino}phenyl)carbonyl]amino}propanoate (116 mg) were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (88 mg, 80%).

¹H NMR (300 MHz, DMSO-d₆) δ ppm 0.89-1.28 (m, 5H) 1.48-1.81 (m, 5H) 2.03 (d, J=11.36 Hz, 1H) 2.15 (s, 3H) 2.34 (s, 3H) 2.37-2.46 (m, 2H) 2.83 (t, J=6.63 Hz, 2H) 3.31-3.45 (m, 2H) 4.08 (t, J=7.76 Hz, 1H) 4.14 (t, J=6.63 Hz, 2H) 6.30 (d, J=7.95 Hz, 1H) 6.53-6.56 (m, 3H) 6.94 (d, J=9.09 Hz, 2H) 7.47 (d, J=8.71 Hz, 2H) 7.51 (d, J=8.71 Hz, 2H) 7.99 (t, J=5.49 Hz, 1H)

Example 257

3-{[(4-{[cyclohexyl(2-methyl-5-{6-[2-(methylsulfanyl)ethoxy]pyridin-3-yl}furan-3-yl)methyl]amino}phenyl)carbonyl](methyl)amino}propanoic acid

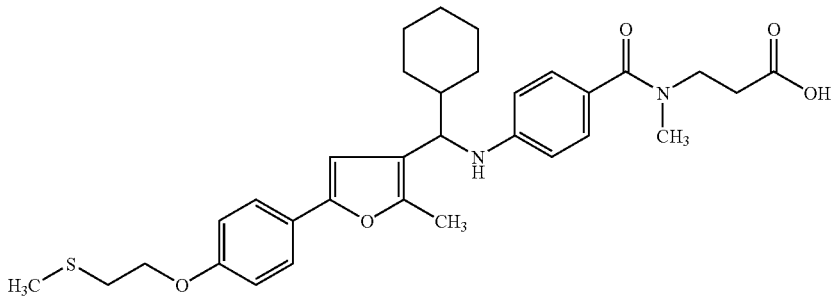

A solution of 4-{[cyclohexyl(2-methyl-5-{4-[(methylsulfanyl)methoxy]phenyl}furan-3-yl)methyl]amino}benzoic acid (408 mg), ethyl 3-(methylamino)propanoate (134 mg), 1-ethyl-3-(3-dimethylaminopropyl)carbodiimide hydrochloride (196 mg), hydroxybenzotriazole monohydrate (156 mg) and triethylamine (142 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure to give ethyl 3-{[(4-{[cyclohexyl(2-methyl-5-{4-[(methylsulfanyl)methoxy]phenyl}furan-3-yl)methyl]amino}phenyl)carbonyl](methyl)amino}propanoate. To ethyl 3-{[(4-{[cyclohexyl(2-methyl-5-{4-[(methylsulfanyl)methoxy]phenyl}furan-3-yl)methyl]amino}phenyl)carbonyl](methyl)amino}propanoate (119 mg) were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (82 mg, 72%).

¹H NMR (300 MHz, DMSO-d₆) δ ppm 0.86-1.31 (m, 5H) 1.50-1.82 (m, 5H) 1.96-2.09 (m, 1H) 2.15 (s, 3H) 2.34 (s, 3H) 2.46-2.51 (m, 2H) 2.83 (t, J=6.44 Hz, 2H) 2.90 (s, 3H) 3.51 (t, J=7.19 Hz, 2H) 4.04 (t, J=7.57 Hz, 1H) 4.14 (t, J=6.63 Hz, 2H) 6.20 (d, J=7.95 Hz, 1H) 6.54 (d, J=8.71 Hz, 2H) 6.58 (s, 1H) 6.94 (d, J=8.71 Hz, 2H) 7.10 (d, J=8.71 Hz, 2H) 7.48 (d, J=9.09 Hz, 2H)

Example 258

3-{[(4-{[cyclohexyl(2-methyl-5-{4-[3-(methylsulfonyl)propoxy]phenyl}furan-3-yl)methyl]amino}phenyl)carbonyl]amino}propanoic acid

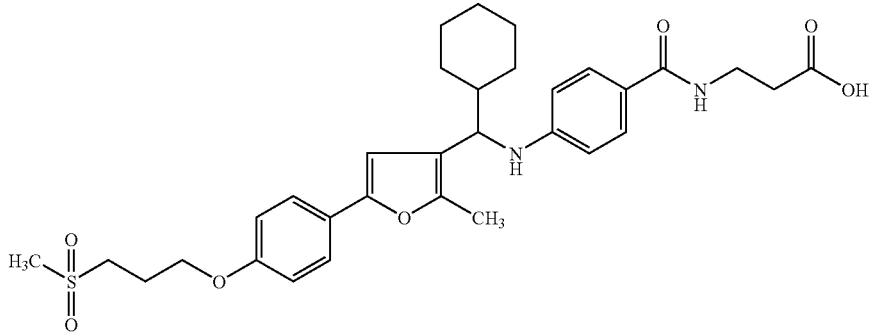

(1) 1-bromo-4-[3-(methylsulfanyl)propoxy]benzene

To a solution of 4-bromophenol (3.4 g) and 3-methylthio-1-propanol (2.6 g) in tetrahydrofuran (20 mL) were added tributylphosphine (7.5 mL) and 1,1'-(azodicarbonyl)dipiperidine (7.6 g), and the mixture was stirred at room temperature for 2 hr. The solvent was evaporated under reduced pressure, and the residue was purified by silica gel column (0% ethyl acetate/hexane to 20% ethyl acetate/hexane) to give the title compound (4.6 g, 83%) as a white crystal.
$^1$H NMR (300 MHz, CHLOROFORM-d) δ ppm 2.00-2.11 (m, 2H) 2.12 (s, 3H) 2.68 (t, J=7.00 Hz, 2H) 4.03 (t, J=6.06 Hz, 2H) 6.78 (m, 2H) 7.37 (m, 2H)

(2) (2-methyl-5-{4-[3-(methylsulfanyl)propoxy]phenyl}furan-3-yl)methanol

A mixture of tert-butyl({5-[(5,5-dimethyl-1,3,2-dioxaborinan-2-yl)methyl]-2-methylfuran-3-yl}methoxy)dimethylsilane (3.0 g), 1-bromo-4-[3-(methylsulfanyl)propoxy]benzene (2.8 g), tetrakis(triphenylphosphine)palladium(0) (0.5 g), 2N aqueous sodium carbonate solution (12 mL) and 1,2-dimethoxyethane (20 mL) was stirred overnight with refluxing under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was dissolved in tetrahydrofuran (20 mL), 1N tetrabutylammonium fluoride in tetrahydrofuran (10 mL) was added, and the mixture was stirred at room temperature for 2 hr. The reaction mixture was poured into water, and the mixture was extracted with ethyl acetate. The organic layer was washed with saturated brine, and dried over magnesium sulfate. The solvent was evaporated under reduced pressure, purified by silica gel chromatography (0% ethyl acetate/hexane to 40% ethyl acetate/hexane), and crystallized from ethyl acetate/hexane to give the title compound (2.2 g, 84%) as a white crystal.
$^1$H NMR (300 MHz, CHLOROFORM-d) δ ppm 1.34 (t, J=5.46 Hz, 1H) 1.99-2.11 (m, 2H) 2.13 (s, 3H) 2.35 (s, 3H) 2.70 (t, J=7.16 Hz, 2H) 4.09 (t, J=6.12 Hz, 2H) 4.50 (d, J=5.46 Hz, 2H) 6.49 (s, 1H) 6.87-6.92 (m, 2H) 7.51-7.56 (m, 2H)

(3) 2-methyl-5-{4-[3-(methylsulfanyl)propoxy]phenyl}furan-3-carbaldehyde

To a solution of (2-methyl-5-{4-[3-(methylsulfanyl)propoxy]phenyl}furan-3-yl)methanol (2.2 g) obtained by the above-mentioned reaction in acetonitrile (30 mL) was added Dess-Martin reagent (3.8 g) at 0° C., and the mixture was stirred at 0° C. for 2 hr. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 40% ethyl acetate/hexane) to give the title compound (0.4 g, 18%) as an oil.
$^1$H NMR (300 MHz, CHLOROFORM-d) δ ppm 2.09 (t, J=7.00 Hz, 2H) 2.13 (s, 3H) 2.65 (s, 3H) 2.70 (t, J=7.19 Hz, 2H) 4.02-4.18 (m, 2H) 6.76 (s, 1H) 6.90-6.95 (m, 2H) 7.55-7.60 (m, 2H) 9.95 (s, 1H)

(4) cyclohexyl(2-methyl-5-{4-[3-(methylsulfanyl)propoxy]phenyl}furan-3-yl)methanol To a solution of 2-methyl-5-{4-[3-(methylsulfanyl)propoxy]phenyl}furan-3-carbaldehyde (0.9 g) obtained by the above-mentioned reaction in tetrahydrofuran (20 mL) was added dropwise 1N cyclohexylmagnesium bromide-tetrahydrofuran solution (4.5 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.0 g, 85%) as a white crystal.
$^1$H NMR (300 MHz, CHLOROFORM-d) δ ppm 0.79-1.37 (m, 5H) 1.45-1.72 (m, 5H) 1.97-2.17 (m, 5H) 2.31 (s, 3H) 2.69 (t, J=7.19 Hz, 1H) 4.01-4.19 (m, 3H) 4.28 (d, J=7.95 Hz, 1H) 6.44 (s, 1H) 6.89 (d, J=8.71 Hz, 2H) 7.54 (d, J=8.71 Hz, 2H)

(5) 3-[chloro(cyclohexyl)methyl]-2-methyl-5-{4-[3-(methylsulfanyl)propoxy]phenyl}furan To a solution of cyclohexyl(2-methyl-5-{4-[3-(methylsulfanyl)propoxy]phenyl}furan-3-yl)methanol (0.9 g) obtained by the above-mentioned reaction in toluene (20 mL) were added thionyl chloride (0.3 mL) and pyridine (0.3 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.0 g, 100%) as an oil.

¹H NMR (300 MHz, CHLOROFORM-d) δ ppm 0.77-1.37 (m, 5H) 1.60-1.94 (m, 5H) 2.02-2.11 (m, 2H) 2.13 (s, 3H) 2.31 (s, 3H) 2.57-2.78 (m, 2H) 4.09 (t, J=6.06 Hz, 2H) 4.60 (d, J=8.71 Hz, 1H) 6.47 (s, 1H) 6.82-6.96 (m, 2H) 7.45-7.59 (m, 2H)

(6) 4-{[cyclohexyl(2-methyl-5-{4-[3-(methylsulfanyl)propoxy]phenyl}furan-3-yl)methyl]amino}benzoic acid A mixture of 3-[chloro(cyclohexyl)methyl]-2-methyl-5-{4-[3-(methylsulfanyl)propoxy]phenyl}furan (1.0 g) obtained by the above-mentioned reaction, methyl 4-aminobenzoate (0.6 g), sodium carbonate (0.4 g) and sodium iodide (0.8 g) in N,N-dimethylacetamide (20 mL) was stirred at 80° C. for 10 hr. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (2 mL) and tetrahydrofuran (2 mL), 2N lithium hydroxide (2.5 mL) was added, and the mixture was stirred at 80° C. for 5 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 50% ethyl acetate/hexane) to give the title compound (1.0 g, 81%) as an amorphous compound.
¹H NMR (300 MHz, CHLOROFORM-d) δ ppm 0.96-1.28 (m, 5H) 1.62-1.81 (m, 5H) 1.90-1.98 (m, 1H) 2.05-2.12 (m, 5H) 2.36 (s, 3H) 2.68 (t, J=7.06 Hz, 2H) 3.96-4.20 (m, 4H) 6.30 (s, 1H) 6.51 (d, J=8.85 Hz, 2H) 6.84-6.91 (m, 2H) 7.47-7.52 (m, 2H) 7.84 (d, J=8.85 Hz, 2H)

(7) ethyl 3-{[(4-{[cyclohexyl(2-methyl-5-{4-[3-(methylsulfanyl)propoxy]phenyl}furan-3-yl)methyl]amino}phenyl)carbonyl]amino}propanoate A solution of 4-{[cyclohexyl(2-methyl-5-{4-[3-(methylsulfanyl)propoxy]phenyl}furan-3-yl)methyl]amino}benzoic acid (494 mg) obtained by the above-mentioned reaction, ethyl β-alaninate hydrochloride (184 mg), 1-ethyl-3-(3-dimethylaminopropyl)carbodiimide hydrochloride (230 mg), hydroxybenzotriazole monohydrate (184 mg) and triethylamine (167 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure to give the title compound (593 g, 100%) as an oil.
¹H NMR (300 MHz, CHLOROFORM-d) δ ppm 0.96-1.35 (m, 8H) 1.62-1.83 (m, 5H) 1.94-1.99 (m, 1H) 2.20 (s, 3H) 2.57-2.61 (m, 2H) 3.63-3.69 (m, 2H) 3.80 (s, 2H) 4.06-4.32 (m, 6H) 6.45-6.54 (m, 1H) 6.54-6.66 (m, 4H) 7.49-7.69 (m, 4H)

(8) ethyl 3-{[(4-{[cyclohexyl(2-methyl-5-{4-[3-(methylsulfonyl)propoxy]phenyl}furan-3-yl)methyl]amino}phenyl)carbonyl]amino}propanoate Ethyl 3-{[(4-{[cyclohexyl(2-methyl-5-{4-[3-(methylsulfanyl)propoxy]phenyl}furan-3-yl)methyl]amino}phenyl)carbonyl]amino}propanoate (296 mg) obtained by the above-mentioned reaction was dissolved in methanol (9 mL) and water (1 mL), OXONE (0.6 g) was added, and the mixture was stirred at room temperature for 30 min. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 100% ethyl acetate/hexane) to give the title compound (209 mg, 67%) as an amorphous compound.
¹H NMR (300 MHz, CHLOROFORM-d) δ ppm 0.94-1.34 (m, 8H) 1.61-1.81 (m, 5H) 1.96 (d, J=10.22 Hz, 1H) 2.22-2.43 (m, 5H) 2.58 (t, J=5.87 Hz, 2H) 2.95 (s, 3H) 3.14-3.33 (m, 2H) 3.66 (q, J=6.06 Hz, 2H) 3.99-4.20 (m, 5H) 4.24 (d, J=6.82 Hz, 1H) 6.31 (s, 1H) 6.51 (d, J=9.09 Hz, 2H) 6.59 (t, J=6.06 Hz, 1H) 6.84 (d, J=9.09 Hz, 2H) 7.50 (d, J=8.71 Hz, 2H) 7.54 (d, J=8.71 Hz, 2H)

(9) 3-{[(4-{[cyclohexyl(2-methyl-5-{4-[3-(methylsulfonyl)propoxy]phenyl}furan-3-yl)methyl]amino}phenyl)carbonyl]amino}propanoic acid Ethyl 3-{[(4-{[cyclohexyl(2-methyl-5-{4-[3-(methylsulfonyl)propoxy]phenyl}furan-3-yl)methyl]amino}phenyl)carbonyl]amino}propanoate (156 mg) obtained by the above-mentioned reaction was dissolved in ethanol (2 mL) and tetrahydrofuran (2 mL), 1N lithium hydroxide (0.7 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (156 mg, 79%).
¹H NMR (300 MHz, DMSO-d₆) δ ppm 0.82-1.23 (m, 5H) 1.54-1.78 (m, 5H) 1.99-2.05 (m, 1H) 2.07-2.21 (m, 2H) 2.37 (s, 3H) 2.42 (t, J=7.00 Hz, 2H) 3.01 (s, 3H) 3.19-3.50 (m, 4H) 3.97-4.16 (m, 3H) 6.30 (d, J=8.33 Hz, 1H) 6.45-6.66 (m, 3H) 6.81-7.00 (m, 2H) 7.51 (d, J=8.71 Hz, 2H) 7.48 (d, J=8.71 Hz, 2H) 7.98 (t, J=5.49 Hz, 1H)

Example 259

3-{[(4-{[cyclohexyl(2-methyl-5-{4-[3-(methylsulfonyl)propoxy]phenyl}furan-3-yl)methyl]amino}phenyl)carbonyl](methyl)amino}propanoic acid

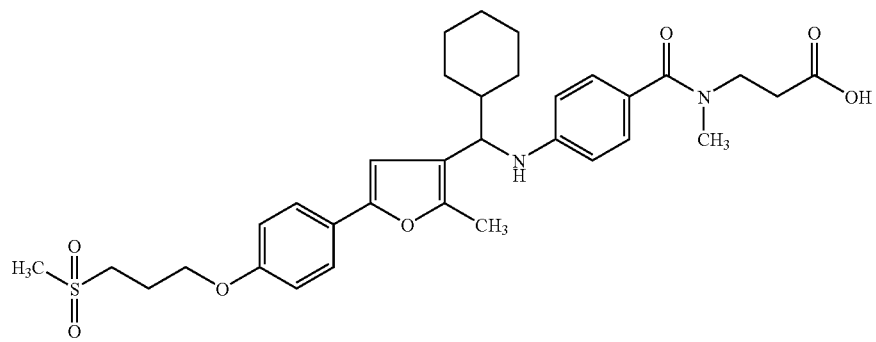

(1) ethyl 3-{[(4-{[cyclohexyl(2-methyl-5-{4-[3-(methylsulfanyl)propoxy]phenyl}furan-3-yl)methyl]amino}phenyl)carbonyl](methyl)amino}propanoate A solution of 4-{[cyclohexyl(2-methyl-5-{4-[3-(methylsulfanyl)propoxy]phenyl}furan-3-yl)methyl]amino}benzoic acid (494 mg), ethyl 3-(methylamino)propanoate (157 mg), 1-ethyl-3-(3-dimethylaminopropyl)carbodiimide hydrochloride (230 mg), hydroxybenzotriazole monohydrate (184 mg) and triethylamine (167 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure to give the title compound (607 mg, 100%) as an oil.

$^1$H NMR (300 MHz, CHLOROFORM-d) δ ppm 0.91-1.34 (m, 5H) 1.60-1.87 (m, 5H) 1.96 (d, J=12.87 Hz, 1H) 2.01-2.10 (m, 5H) 2.12 (s, 3H) 2.34 (s, 3H) 2.62 (t, J=7.00 Hz, 2H) 2.69 (t, J=7.00 Hz, 2H) 3.02 (s, 3H) 3.71 (t, J=7.00 Hz, 2H) 3.93-4.20 (m, 5H) 6.31 (s, 1H) 6.50 (d, J=8.71 Hz, 2H) 6.84-6.89 (m, 2H) 7.21 (d, J=8.71 Hz, 2H) 7.41-7.54 (m, 2H)

carbonyl](methyl)amino}propanoate (287 mg) obtained by the above-mentioned reaction was dissolved in ethanol (2 mL) and tetrahydrofuran (2 mL), and 1N lithium hydroxide (0.9 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (225 mg, 82%).

$^1$H NMR (300 MHz, DMSO-$d_6$) δ ppm 0.85-1.23 (m, 5H) 1.49-1.82 (m, 5H) 1.95-2.07 (m, 1H) 2.07-2.21 (m, 2H) 2.34 (s, 3H) 2.46-2.51 (m, 24H) 2.90 (s, 3H) 3.01 (s, 3H) 3.18-3.30 (m, 2H) 3.51 (t, J=7.38 Hz, 3H) 3.95-4.20 (m, 3H) 6.21 (d, J=7.95 Hz, 1H) 6.54 (d, J=8.71 Hz, 2H) 6.58 (s, 1H) 6.94 (d, J=8.71 Hz, 2H) 7.10 (d, J=8.33 Hz, 2H) 7.49 (d, J=9.09 Hz, 2H) 12.28 (brs, 1H)

Example 260

3-{[(4-{[cyclohexyl(2-methyl-5-{4-[3-(methylsulfinyl)propoxy]phenyl}furan-3-yl)methyl]amino}phenyl)carbonyl]amino}propanoic acid

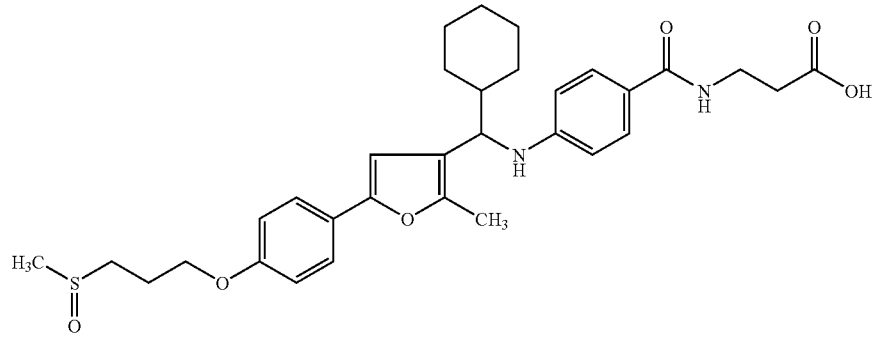

(2) ethyl 3-{[(4-{[cyclohexyl(2-methyl-5-{4-[3-(methylsulfonyl)propoxy]phenyl}furan-3-yl)methyl]amino}phenyl)carbonyl](methyl)amino}propanoate Ethyl 3-{[(4-{[cyclohexyl(2-methyl-5-{4-[3-(methylsulfanyl)propoxy]phenyl}furan-3-yl)methyl]amino}phenyl)carbonyl](methyl)amino}propanoate (303 mg) obtained by the above-mentioned reaction was dissolved in methanol (9 mL) and water (1 mL), OXONE (0.6 g) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (20% ethyl acetate/hexane to 100% ethyl acetate/hexane) to give the title compound (289 mg, 91%) as an oil.

$^1$H NMR (300 MHz, CHLOROFORM-d) δ ppm 0.92-1.32 (m, 8H) 1.60-1.81 (m, 5H) 1.96 (d, J=14.77 Hz, 1H) 2.29-2.42 (m, 5H) 2.62 (t, J=7.00 Hz, 2H) 2.95 (s, 3H) 3.02 (s, 3H) 3.18-3.35 (m, 2H) 3.65-3.72 (m, 2H) 3.95-4.07 (m, 1H) 4.07-4.18 (m, 5H) 6.32 (s, 1H) 6.49 (d, J=8.71 Hz, 2H) 6.85 (m, J=9.09 Hz, 2H) 7.20-7.23 (m, 2H) 7.43-7.55 (m, 2H)

(3) 3-{[(4-{[cyclohexyl(2-methyl-5-{4-[3-(methylsulfonyl)propoxy]phenyl}furan-3-yl)methyl]amino}phenyl)carbonyl](methyl)amino}propanoic acid Ethyl 3-{[(4-{[cyclohexyl(2-methyl-5-{4-[3-(methylsulfonyl)propoxy]phenyl}furan-3-yl)methyl]amino}phenyl)

(1) ethyl 3-{[(4-{[cyclohexyl(2-methyl-5-{4-[3-(methylsulfinyl)propoxy]phenyl}furan-3-yl)methyl]amino}phenyl)carbonyl]amino}propanoate Ethyl 3-{[(4-{[cyclohexyl(2-methyl-5-{4-[3-(methylsulfanyl)propoxy]phenyl}furan-3-yl)methyl]amino}phenyl)carbonyl]amino}propanoate (296 mg) was dissolved in methanol (9 mL) and water (1 mL), OXONE (277 mg) was added, and the mixture was stirred at room temperature for 30 min. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (0% methanol/ethyl acetate to 20% methanol/ethyl acetate) to give the title compound (278 mg, 91%) as an oil.

$^1$H NMR (300 MHz, CHLOROFORM-d) δ ppm 0.95-1.34 (m, 8H) 1.63-1.82 (m, 5H) 1.96 (d, J=12.87 Hz, 1H) 2.18-2.33 (m, 2H) 2.35 (s, 3H) 2.47-2.66 (m, 5H) 2.75-3.04 (m, 2H) 3.59-3.71 (m, 2H) 3.96-4.26 (m, 6H) 6.31 (s, 1H) 6.51 (d, J=8.71 Hz, 2H) 6.59 (t, J=5.87 Hz, 1H) 6.78-6.91 (m, 2H) 7.44-7.52 (m, 2H) 7.52-7.60 (m, 2H)

(2) 3-{[(4-{[cyclohexyl(2-methyl-5-{4-[3-(methylsulfinyl)propoxy]phenyl}furan-3-yl)methyl]amino}phenyl)carbonyl]amino}propanoic acid Ethyl 3-{[(4-{[cyclohexyl(2-methyl-5-{4-[3-(methylsulfinyl)propoxy]phenyl}furan-3-yl)methyl]amino}phenyl)

carbonyl]amino}propanoate (274 mg) obtained by the above-mentioned reaction was dissolved in ethanol (2 mL) and tetrahydrofuran (2 mL), and 1N lithium hydroxide (1.0 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (218 mg, 84%).

$^1$H NMR (300 MHz, DMSO-d$_6$) δ ppm 0.89-1.28 (m, 5H) 1.45-1.84 (m, 5H) 2.08 (dt, J=14.10, 6.77 Hz, 3H) 2.34 (s, 3H) 2.42 (t, J=7.00 Hz, 2H) 2.55 (s, 3H) 2.68-3.05 (m, 2H) 3.32-3.44 (m, 2H) 4.01-4.17 (m, 3H) 6.30 (d, J=7.95 Hz, 1H) 6.42-6.60 (m, 3H) 6.94 (d, J=8.71 Hz, 2H) 7.51 (d, J=8.71 Hz, 2H) 7.48 (d, J=8.71 Hz, 2H) 7.98 (t, J=5.49 Hz, 1H) 12.16 (brs, 1H)

Example 261

3-{[(4-{[cyclohexyl(2-methyl-5-{4-[3-(methylsulfinyl)propoxy]phenyl}furan-3-yl)methyl]amino}phenyl)carbonyl](methyl)amino}propanoic acid

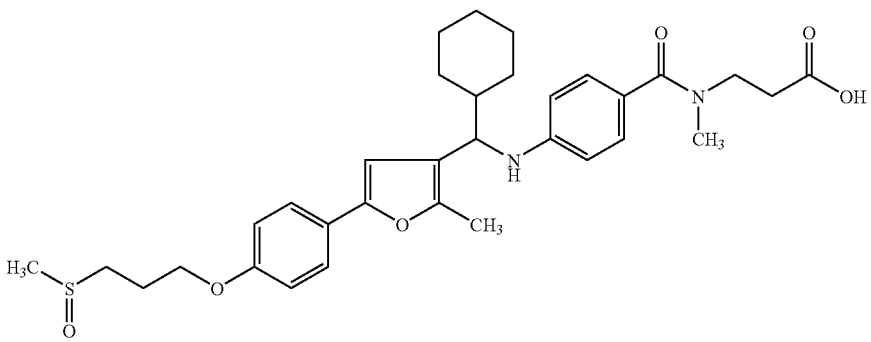

(1) ethyl 3-{[(4-{[cyclohexyl(2-methyl-5-{4-[3-(methylsulfinyl)propoxy]phenyl}furan-3-yl)methyl]amino}phenyl)carbonyl](methyl)amino}propanoate Ethyl 3-{[(4-{[cyclohexyl(2-methyl-5-{4-[3-(methylsulfanyl)propoxy]phenyl}furan-3-yl)methyl]amino}phenyl)carbonyl](methyl)amino}propanoate (0.37 g) synthesized in Example 259 (1) was dissolved in methanol (9 mL) and water (1 mL), OXONE (221 mg) was added, and the mixture was stirred at room temperature for 1 hr. The reaction mixture was poured into water, and the mixture was extracted with ethyl acetate. The organic layer was washed with saturated brine, and dried over magnesium sulfate. The solvent was evaporated under reduced pressure, and the residue was purified by silica gel chromatography (25% ethyl acetate/hexane to 100% ethyl acetate/hexane) to give the title compound (283 mg, 91%) as an oil.

$^1$H NMR (300 MHz, CHLOROFORM-d) δ ppm 0.95-1.34 (m, 8H) 1.60-1.81 (m, 5H) 1.90-2.01 (m, 1H) 2.19-2.33 (m, 2H) 2.35 (s, 3H) 2.51-2.68 (m, 5H) 2.73-2.99 (m, 2H) 3.02 (s, 3H) 3.61-3.73 (m, 2H) 3.95-4.24 (m, 6H) 6.32 (s, 1H) 6.49 (d, J=8.71 Hz, 2H) 6.83-6.87 (m, 2H) 7.21 (d, J=8.71 Hz, 2H) 7.44-7.57 (m, 2H)

(2) 3-{[(4-{[cyclohexyl(2-methyl-5-{4-[3-(methylsulfinyl)propoxy]phenyl}furan-3-yl)methyl]amino}phenyl)carbonyl](methyl)amino}propanoic acid Ethyl 3-{[(4-{[cyclohexyl(2-methyl-5-{4-[3-(methylsulfinyl)propoxy]phenyl}furan-3-yl)methyl]amino}phenyl)carbonyl](methyl)amino}propanoate (280 mg) obtained by the above-mentioned reaction was dissolved in ethanol (2 mL) and tetrahydrofuran (2 mL), and 1N lithium hydroxide (1.0 mL) was added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (201 mg, 75%).

$^1$H NMR (300 MHz, DMSO-d$_6$) δ ppm 1.05-1.27 (m, 5H) 1.54-1.77 (m, 5H) 1.95-2.17 (m, 3H) 2.34 (s, 3H) 2.42-2.49 (m, 2H) 2.56 (s, 3H) 2.68-2.99 (m, 5H) 3.51 (t, J=7.25 Hz, 2H) 3.94-4.17 (m, 3H) 6.21 (d, J=8.10 Hz, 1H) 6.54 (d, J=8.67 Hz, 2H) 6.57 (s, 1H) 6.92-6.96 (m, 2H) 7.10 (d, J=8.48 Hz, 2H) 7.49 (d, J=8.67 Hz, 2H)

Example 262

3-({[4-(3-methyl-1-{3-methyl-5-[4-(trifluoromethyl)phenyl]thiophen-2-yl}butoxy)phenyl]carbonyl}amino)propanoic acid

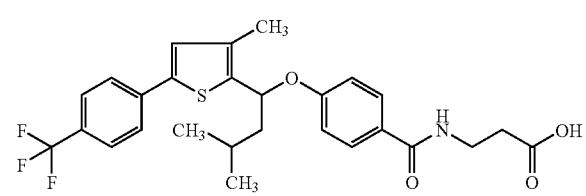

(1) 5-bromo-3-methylthiophene-2-carbaldehyde

To a solution of 3-methylthiophene-2-carbaldehyde (5.7 g) in chloroform (40 mL) was added dropwise bromine (2.5 mL) at 0° C. and, after the completion of the dropwise addition, the mixture was and stirred at 0° C. for 30 min, and then at room temperature for 1 hr, and then under reflux overnight. The reaction mixture was poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (8.1 g, 88%) as a brown solid.

$^1$H NMR (300 MHz, CHLOROFORM-d) δ ppm 2.54 (s, 3H) 6.96 (s, 1H) 9.91 (s, 1H)

(2) 3-methyl-5-[4-(trifluoromethyl)phenyl]thiophene-2-carbaldehyde

A mixture of 5-bromo-3-methylthiophene-2-carbaldehyde (2.1 g) obtained by the above-mentioned reaction, 4-(trifluoromethyl)phenylboronic acid (2.3 g), tetrakis(triphenylphosphine)palladium(0) (0.6 g), potassium carbonate (3.5 g), toluene (30 mL), ethanol (5 mL) and water (5 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 15% ethyl acetate/hexane), and crystallized from ethyl acetate/hexane to give the title compound (1.7 g, 63%) as a white crystal.

$^1$H NMR (300 MHz, CHLOROFORM-d) δ ppm 2.62 (s, 3H) 7.68 (d, J=8.33 Hz, 2H) 7.75 (d, J=8.33 Hz, 2H) 10.05 (s, 1H)

(3) 3-methyl-1-{3-methyl-5-[4-(trifluoromethyl)phenyl]thiophen-2-yl}butan-1-ol

To a solution of 3-methyl-5-[4-(trifluoromethyl)phenyl]thiophene-2-carbaldehyde (0.8 g) obtained by the above-mentioned reaction in tetrahydrofuran (20 mL) was added dropwise 1N isobutylmagnesium bromide-tetrahydrofuran solution (5 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (0.5 g, 54%) as an oil.

$^1$H NMR (300 MHz, CHLOROFORM-d) δ ppm 0.98 (dd, J=6.44, 1.89 Hz, 6H) 1.56-1.71 (m, 1H) 1.71-1.92 (m, 2H) 2.26 (s, 3H) 5.00-5.13 (m, 1H) 7.10 (s, 1H) 7.58-7.67 (m, 4H)

(4) 4-(3-methyl-1-{3-methyl-5-[4-(trifluoromethyl)phenyl]thiophen-2-yl}butoxy)benzoic acid To a solution of 3-methyl-1-{3-methyl-5-[4-(trifluoromethyl)phenyl]thiophen-2-yl}butan-1-ol (525 mg) obtained by the above-mentioned reaction and methyl 4-hydroxybenzoate (365 mg) in tetrahydrofuran (20 mL) were added tributylphosphine (0.8 mL) and 1,1'-(azodicarbonyl)dipiperidine (807 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-(3-methyl-1-{3-methyl-5-[4-(trifluoromethyl)phenyl]thiophen-2-yl}butoxy)benzoate as an amorphous compound. The obtained methyl 4-(3-methyl-1-{3-methyl-5-[4-(trifluoromethyl)phenyl]thiophen-2-yl}butoxy)benzoate was dissolved in methanol (3 mL) and tetrahydrofuran (3 mL), 2N sodium hydroxide (2.0 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (371 mg, 52%).

$^1$H NMR (300 MHz, CHLOROFORM-d) δ ppm 1.03 (d, J=6.82 Hz, 3H) 0.98 (d, J=6.44 Hz, 3H) 1.67-1.75 (m, 1H) 1.84-1.92 (m, 1H) 2.05-2.12 (m, 1H) 2.31 (s, 3H) 5.52 (dd, J=8.52, 5.11 Hz, 1H) 6.92 (d, J=8.71 Hz, 2H) 7.06 (s, 1H) 7.47-7.67 (m, 4H) 7.99 (d, J=9.09 Hz, 2H)

(5) 3-({[4-(3-methyl-1-{3-methyl-5-[4-(trifluoromethyl)phenyl]thiophen-2-yl}butoxy)phenyl]carbonyl}amino)propanoic acid A solution of 4-(3-methyl-1-{3-methyl-5-[4-(trifluoromethyl)phenyl]thiophen-2-yl}butoxy)benzoic acid (179 mg) obtained by the above-mentioned reaction, ethyl β-alaninate hydrochloride (74 mg), 1-ethyl-3-(3-dimethylaminopropyl)carbodiimide hydrochloride (92 mg), hydroxybenzotriazole monohydrate (74 mg) and triethylamine (67 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure. To the residue were added ethanol (2 mL), tetrahydrofuran (2 mL) and 1N sodium hydroxide (1.0 mL), and the mixture was stirred at room temperature for 1 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (185 mg, 89%) as a white solid.

$^1$H NMR (300 MHz, DMSO-$d_6$) δ ppm 0.97 (dd, J=10.74, 6.40 Hz, 6H) 1.59-1.86 (m, 2H) 1.92-2.09 (m, 1H) 2.30 (s, 3H) 2.37-2.48 (m, 2H) 3.34-3.48 (m, 3H) 5.72 (dd, J=8.10, 5.27 Hz, 1H) 6.99 (d, J=8.85 Hz, 2H) 7.40 (s, 1H) 7.68-7.78 (m, 6H) 8.24-8.39 (m, 1H) 12.21 (brs, 1H)

Example 263

3-[methyl({4-[(3-methyl-1-{3-methyl-5-[4-(trifluoromethyl)phenyl]thiophen-2-yl}butyl)amino]phenyl}carbonyl)amino]propanoic acid

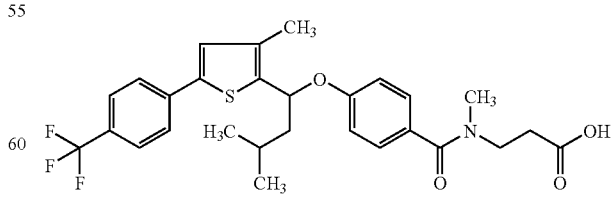

A solution of 4-(3-methyl-1-{3-methyl-5-[4-(trifluoromethyl)phenyl]thiophen-2-yl}butoxy)benzoic acid (179 mg), ethyl 3-(methylamino)propanoate (63 mg), 1-ethyl-3-(3-dimethylaminopropyl)carbodiimide hydrochloride (92 mg), hydroxybenzotriazole monohydrate (74 mg) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N sodium hydroxide (1.0 mL), and the mixture was stirred at room temperature for 1 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (165 mg, 78%) as an amorphous compound.

$^1$H NMR (300 MHz, DMSO-$d_6$) δ ppm 0.97 (dd, J=9.32, 6.50 Hz, 6H) 1.63-1.84 (m, 2H) 1.93-2.04 (m, 1H) 2.29 (s, 3H) 2.42-2.56 (m, 2H) 2.88 (s, 3H) 3.51 (brs, 2H) 5.65-5.69 (m, 1H) 6.97 (d, J=8.67 Hz, 2H) 7.29 (d, J=8.67 Hz, 2H) 7.41 (s, 1H) 7.70 (d, J=8.67 Hz, 2H) 7.77 (d, J=8.29 Hz, 2H)

Example 264

3-({[4-(cyclohexyl{3-methyl-5-[4-(trifluoromethyl)phenyl]thiophen-2-yl}methoxy)phenyl]carbonyl}amino)propanoic acid

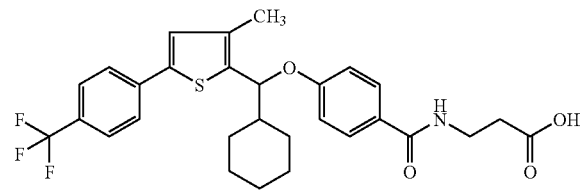

(1) cyclohexyl{3-methyl-5-[4-(trifluoromethyl)phenyl]thiophen-2-yl}methanol

To a solution of 3-methyl-5-[4-(trifluoromethyl)phenyl]thiophene-2-carbaldehyde (0.8 g) in tetrahydrofuran (20 mL) was added dropwise 1N cyclohexylmagnesium bromide-tetrahydrofuran solution (5 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (0.5 g, 51%) as a yellow crystal.

$^1$H NMR (300 MHz, CHLOROFORM-d) δ ppm 0.95-1.28 (m, 5H) 1.61-1.88 (m, 5H) 1.94 (d, J=3.20 Hz, 1H) 2.12-2.18 (m, 1H) 2.23 (s, 3H) 4.67 (dd, J=8.19, 3.30 Hz, 1H) 7.09 (s, 1H) 7.53-7.63 (m, 2H) 7.63-7.69 (m, 2H)

(2) 4-(cyclohexyl{3-methyl-5-[4-(trifluoromethyl)phenyl]thiophen-2-yl}methoxy)benzoic acid To a solution of cyclohexyl{3-methyl-5-[4-(trifluoromethyl)phenyl]thiophen-2-yl}methanol (532 mg) obtained by the above-mentioned reaction and methyl 4-hydroxybenzoate (350 mg) in tetrahydrofuran (20 mL) were added tributylphosphine (0.7 mL) and 1,1'-(azodicarbonyl)dipiperidine (807 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-(cyclohexyl{3-methyl-5-[4-(trifluoromethyl)phenyl]thiophen-2-yl}methoxy)benzoate as an oil. The obtained methyl 4-(cyclohexyl{3-methyl-5-[4-(trifluoromethyl)phenyl]thiophen-2-yl}methoxy)benzoate was dissolved in methanol (3 mL) and tetrahydrofuran (3 mL), 2N sodium hydroxide (2.5 mL) was added, and the mixture was stirred at 60° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and crystallized from ethyl acetate/hexane to give the title compound (371 mg, 66%) as a white solid.

$^1$H NMR (300 MHz, CHLOROFORM-d) δ ppm 1.08-1.33 (m, 5H) 1.56-1.99 (m, 5H) 2.16-2.25 (m, 1H) 2.31 (s, 3H) 5.13 (d, J=7.91 Hz, 1H) 6.87-6.92 (m, 2H) 7.06 (s, 1H) 7.47-7.64 (m, 4H) 7.94-7.98 (m, 2H)

(3) 3-({[4-(cyclohexyl{3-methyl-5-[4-(trifluoromethyl)phenyl]thiophen-2-yl}methoxy)phenyl]carbonyl}amino)propanoic acid A solution of 4-(cyclohexyl{3-methyl-5-[4-(trifluoromethyl)phenyl]thiophen-2-yl}methoxy)benzoic acid (214 mg) obtained by the above-mentioned reaction, ethyl β-alaninate hydrochloride (83 mg), 1-ethyl-3-(3-dimethylaminopropyl)carbodiimide hydrochloride (104 mg), hydroxybenzotriazole monohydrate (83 mg) and triethylamine (75 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N sodium hydroxide (1.0 mL), and the mixture was stirred at room temperature for 1 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was crystallized from ethyl acetate/hexane to give the title compound (242 mg, 98%) as a white solid.

$^1$H NMR (300 MHz, DMSO-$d_6$) δ ppm 1.03-1.33 (m, 5H) 1.46-1.49 (m, 1H) 1.59-1.91 (m, 4H) 2.05-2.12 (m, 1H) 2.30 (s, 3H) 2.45 (t, J=7.19 Hz, 2H) 3.34-3.48 (m, 2H) 5.44 (d, J=7.95 Hz, 1H) 6.95 (d, J=8.71 Hz, 2H) 7.40 (s, 1H) 7.59-7.82 (m, 6H) 8.30 (t, J=5.30 Hz, 1H)

Example 265

3-[{[4-(cyclohexyl{3-methyl-5-[4-(trifluoromethyl)phenyl]thiophen-2-yl}methoxy)phenyl]carbonyl}(methyl)amino]propanoic acid

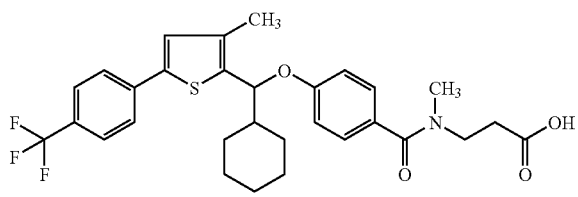

A solution of 4-{cyclohexyl[2-methyl-5-(pyridin-3-yl)furan-3-yl]methoxy}benzoic acid (214 mg), ethyl 3-(methylamino)propanoate (71 mg), 1-ethyl-3-(3-dimethylaminopropyl)carbodiimide hydrochloride (92 mg), hydroxybenzotriazole monohydrate (83 mg) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N sodium hydroxide (1.0 mL), and the mixture was stirred at room temperature for 1 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (218 mg, 86%) as an amorphous compound.

$^1$H NMR (300 MHz, DMSO-$d_6$) δ ppm 1.02-1.31 (m, 5H) 1.46-1.49 (m, 1H) 1.59-1.91 (m, 4H) 2.10 (d, J=11.74 Hz, 1H) 2.30 (s, 3H) 2.88 (s, 3H) 3.51 (brs, 2H) 5.38 (d, J=7.95 Hz, 1H) 6.93 (d, J=8.71 Hz, 2H) 7.27 (d, J=8.71 Hz, 2H) 7.40 (s, 1H) 7.70 (d, J=8.33 Hz, 2H) 7.77 (d, J=7.95 Hz, 2H)

Example 266

3-({[4-({cyclohexyl[5-(3,6-dihydro-2H-thiopyran-4-yl)-2-ethylthiophen-3-yl]methyl}amino)phenyl]carbonyl}amino)propanoic acid

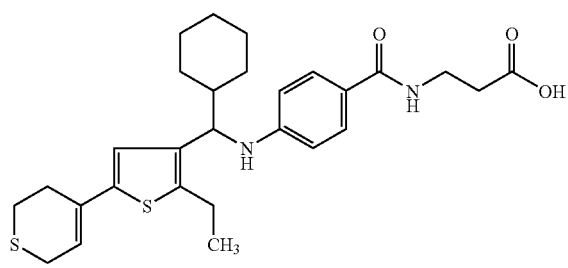

(1) 4-{4-[chloro(cyclohexyl)methyl]-5-ethylthiophen-2-yl}-3,6-dihydro-2H-thiopyran To a solution of 4-{4-[cyclohexyl(hydroxy)methyl]-5-ethylthiophen-2-yl}tetrahydro-2H-thiopyran-4-ol (532 mg) synthesized in Example 85 (3) in toluene (10 mL) was added thionyl chloride (137 µL), and the mixture was stirred at room temperature for 1 hr. The reaction mixture was poured into ice-cooled saturated aqueous sodium hydrogen carbonate solution, and the mixture was extracted with ethyl acetate. The extract was washed with saturated brine, dried over magnesium sulfate and concentrated under reduced pressure to give the title compound (491 mg, 92%) as a yellow oil.

$^1$H NMR (300 MHz, CDCl$_3$) δ ppm 0.74-0.90 (m, 1H), 0.95-1.22 (m, 4H), 1.26 (t, J=7.5 Hz, 3H), 1.43-1.53 (m, 1H), 1.58-1.70 (m, 2H), 1.75-1.87 (m, 2H), 2.23-2.32 (m, 1H), 2.65-2.89 (m, 6H), 3.28-3.33 (m, 2H), 4.64 (d, J=9.6 Hz, 1H), 6.20-6.26 (m, 1H), 6.86 (s, 1H).

(2) 4-({cyclohexyl[5-(3,6-dihydro-2H-thiopyran-4-yl)-2-ethylthiophen-3-yl]methyl}amino)benzoic acid To a mixture of 4-{4-[chloro(cyclohexyl)methyl]-5-ethylthiophen-2-yl}-3,6-dihydro-2H-thiopyran (1.37 g) synthesized above, methyl 4-aminobenzoate (1.15 g), sodium iodide (1.15 g) and N,N-dimethylacetamide (20 mL) was added sodium carbonate (810 mg), and the mixture was stirred overnight at 100° C. under an argon atmosphere. To the reaction mixture was added 1N hydrochloric acid to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=3:17, volume ratio) to give a pale-brown solid. To a mixture of the obtained solid, tetrahydrofuran (10 mL) and ethanol (10 mL) was added 1N aqueous sodium hydroxide solution (10 mL), and the mixture was stirred overnight at 50° C. To the reaction mixture was added 1N hydrochloric acid (10 mL), and the mixture was extracted with ethyl acetate. The extract was washed with saturated brine, dried over magnesium sulfate, and concentrated under reduced pressure. The residue was purified by silica gel column chromatography (ethyl acetate:hexane=1:3, volume ratio) to give the title compound (554 mg, 31%) as a brown solid.

$^1$H NMR (300 MHz, CDCl$_3$) δ ppm 0.93-1.39 (m, 8H), 1.48-1.86 (m, 5H), 1.92-2.03 (m, 1H), 2.57-2.68 (m, 2H), 2.72-2.94 (m, 4H), 3.23-3.32 (m, 2H), 4.20 (d, J=7.3 Hz, 1H), 6.16-6.23 (m, 1H), 6.47 (d, J=8.9 Hz, 2H), 6.67 (s, 1H), 7.82 (d, J=8.9 Hz, 2H).

(3) 3-({[4-({cyclohexyl[5-(3,6-dihydro-2H-thiopyran-4-yl)-2-ethylthiophen-3-yl]methyl}amino)phenyl]carbonyl}amino)propanoic acid To a mixture of 4-({cyclohexyl[5-(3,6-dihydro-2H-thiopyran-4-yl)-2-ethylthiophen-3-yl]methyl}amino)benzoic acid (246 mg) synthesized above, ethyl β-alaninate hydrochloride (98.8 mg), 1-hydroxybenzotriazole monohydrate (98.5 mg) and triethylamine (90 µL) in N,N-dimethylformamide (10 mL) was added 1-ethyl-3-(3-dimethylaminopropyl)carbodiimide hydrochloride (123 mg), and the mixture was stirred at room temperature for 8 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:1, volume ratio) to give a brown oil. To a mixture of the obtained oil, tetrahydrofuran (5 mL) and ethanol (5 mL) was added 1N aqueous sodium hydroxide solution (1 mL), and the mixture was stirred at room temperature for 2.5 hr, and concentrated under reduced pressure. The residue was dissolved in water (10 mL), and 1N hydrochloric acid (1 mL) was added at 0° C. The resulting precipitate was collected by filtration to give the title compound (145 mg, 47%) as a brown solid.

¹H NMR (300 MHz, CDCl₃) δ ppm 0.89-1.36 (m, 8H), 1.47-1.84 (m, 5H), 1.90-2.03 (m, 1H), 2.55-2.69 (m, 4H), 2.71-2.95 (m, 4H), 3.21-3.29 (m, 2H), 3.58-3.71 (m, 2H), 4.16 (d, J=7.3 Hz, 1H), 6.18 (t, J=4.3 Hz, 1H), 6.45 (d, J=8.8 Hz, 2H), 6.58-6.69 (m, 2H), 7.51 (d, J=8.8 Hz, 2H).

Example 267

3-[{[4-({cyclohexyl[5-(3,6-dihydro-2H-thiopyran-4-yl)-2-ethylthiophen-3-yl]methyl}amino)phenyl]carbonyl}(methyl)amino]propanoic acid

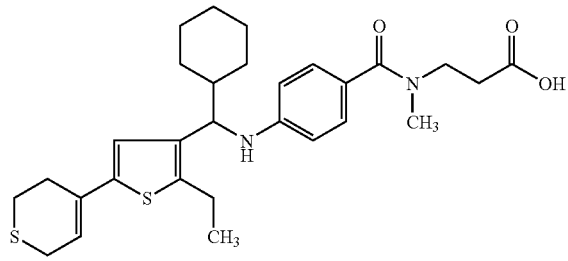

To a mixture of 4-({cyclohexyl[5-(3,6-dihydro-2H-thiopyran-4-yl)-2-ethylthiophen-3-yl]methyl}amino)benzoic acid (240 mg) synthesized in Example 266 (2), ethyl 3-(methylamino)propanoate (82.1 mg), 1-hydroxybenzotriazole monohydrate (95.9 mg) and triethylamine (87 μL) in N,N-dimethylformamide (10 mL) was added 1-ethyl-3-(3-dimethylaminopropyl)carbodiimide hydrochloride (120 mg), and the mixture was stirred at room temperature overnight. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:1, volume ratio) to give a brown oil. To a mixture of the obtained oil, tetrahydrofuran (5 mL) and ethanol (5 mL) was added 1N aqueous sodium hydroxide solution (1 mL), and the mixture was stirred at room temperature for 2 hr, and concentrated under reduced pressure. The residue was dissolved in water (10 mL), and 1N hydrochloric acid (1 mL) was added at 0° C. The resulting precipitate was collected by filtration to give the title compound (153 mg, 53%) as a brown solid.

¹H NMR (300 MHz, CDCl₃) δ ppm 0.90-1.35 (m, 8H), 1.48-1.85 (m, 5H), 1.92-2.03 (m, 1H), 2.57-2.96 (m, 8H), 3.06 (s, 3H), 3.24-3.31 (m, 2H), 3.71 (t, J=6.6 Hz, 2H), 4.14 (d, J=7.3 Hz, 1H), 6.15-6.23 (m, 1H), 6.45 (d, J=8.6 Hz, 2H), 6.68 (s, 1H), 7.22 (d, J=8.6 Hz, 2H).

Example 268

3-({[4-({cyclohexyl[2-ethyl-5-(tetrahydro-2H-pyran-4-yl)thiophen-3-yl]methyl}amino)phenyl]carbonyl}amino)propanoic acid

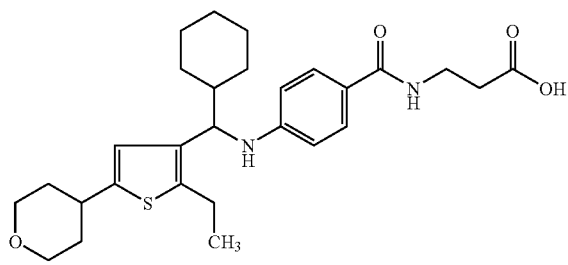

(1) ethyl 2-ethyl-5-(tetrahydro-2H-pyran-4-yl)thiophene-3-carboxylate

To a solution of ethyl 5-bromo-2-ethylthiophene-3-carboxylate (5.00 g) synthesized in Example 69 (4) in tetrahydrofuran (50 mL) was added dropwise 1.0M isopropylmagnesium bromide-tetrahydrofuran solution (22.8 mL) at −45° C., and the mixture was stirred for 1 hr under an argon atmosphere. Tetrahydro-4H-pyran-4-one (5.26 mL) was added dropwise, and the mixture was stirred at −45° C. for 1 hr, and then at room temperature for 2 hr. Saturated aqueous ammonium chloride solution was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (ethyl acetate:hexane=2:3, volume ratio) to give a colorless oil. To a solution of the obtained oil in trifluoroacetic acid (25 mL) was added triethylsilane (2.86 mL), and the mixture was stirred at room temperature for 1.5 hr, and concentrated under reduced pressure. The residue was purified by silica gel column chromatography (ethyl acetate:hexane=3:17, volume ratio) to give the title compound (1.35 g, 26%) as a colorless oil.

¹H NMR (300 MHz, CDCl₃) δ ppm 1.30 (t, J=7.5 Hz, 3H), 1.36 (t, J=6.9 Hz, 3H), 1.74-1.85 (m, 2H), 1.86-1.96 (m, 2H), 2.88-3.01 (m, 1H), 3.16 (q, J=7.5 Hz, 2H), 3.44-3.56 (m, 2H), 3.99-4.09 (m, 2H), 4.29 (q, J=6.9 Hz, 2H), 7.09 (s, 1H).

(2) 2-ethyl-5-(tetrahydro-2H-pyran-4-yl)thiophene-3-carbaldehyde

To a solution (20 mL) of ethyl 2-ethyl-5-(tetrahydro-2H-pyran-4-yl)thiophene-3-carboxylate (1.35 g) synthesized above in tetrahydrofuran was added 1.5M diisobutylaluminum hydride in toluene solution (15.1 mL) at 0° C., and the mixture was stirred for 1 hr. 1N Hydrochloric acid was added to quench the reaction, the organic solvent was evaporated using evaporator, and the mixture was extracted with ethyl acetate. The extract was washed with saturated brine, dried over magnesium sulfate and concentrated under reduced pressure to give a colorless oil. To a solution of the obtained oil in methylene chloride (20 mL) was added Dess-Martin reagent (2.47 g), and the mixture was stirred at room temperature for 1.5 hr. Saturated aqueous sodium sulfite solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (ethyl acetate:hexane=1:3, volume ratio) to give the title compound (692 mg, 61%) as a colorless oil.

¹H NMR (300 MHz, CDCl₃) δ ppm 1.37 (t, J=7.5 Hz, 3H), 1.70-1.85 (m, 2H), 1.86-1.96 (m, 2H), 2.90-3.02 (m, 1H), 3.17 (q, J=7.5 Hz, 2H), 3.44-3.56 (m, 2H), 3.99-4.08 (m, 2H), 7.08 (s, 1H), 9.96 (s, 1H).

(3) cyclohexyl[2-ethyl-5-(tetrahydro-2H-pyran-4-yl)thiophen-3-yl]methanol

To a solution of 2-ethyl-5-(tetrahydro-2H-pyran-4-yl)thiophene-3-carbaldehyde (692 mg) synthesized above in tetrahydrofuran (10 mL) was added dropwise 1.0M cyclohexylmagnesium bromide-tetrahydrofuran solution (4.64 mL) at 0° C., and the mixture was stirred for 2 hr. Saturated aqueous ammonium chloride solution was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (ethyl acetate:hexane=3:7, volume ratio) to give the title compound (737 mg, 77%) as a white solid.

$^1$H NMR (300 MHz, CDCl$_3$) δ ppm 0.76-0.92 (m, 1H), 0.96-1.41 (m, 8H), 1.52-1.96 (m, 9H), 2.06-2.16 (m, 1H), 2.64-2.86 (m, 2H), 2.88-3.01 (m, 1H), 3.43-3.55 (m, 2H), 3.98-4.08 (m, 2H), 4.36 (dd, J=8.3, 2.9 Hz, 1H), 6.66 (s, 1H).

(4) 4-{4-[chloro(cyclohexyl)methyl]-5-ethylthiophen-2-yl}tetrahydro-2H-pyran

To a solution of cyclohexyl[2-ethyl-5-(tetrahydro-2H-pyran-4-yl)thiophen-3-yl]methanol (737 mg) synthesized above in toluene (10 mL) was added thionyl chloride (209 μL), and the mixture was stirred at room temperature for 2 hr. The reaction mixture was poured into ice-cooled saturated aqueous sodium hydrogen carbonate solution, and the mixture was extracted with ethyl acetate. The extract was washed with saturated brine, dried over magnesium sulfate and concentrated under reduced pressure to give the title compound (725 mg, 93%) as a pale-yellow oil.

$^1$H NMR (300 MHz, CDCl$_3$) δ ppm 0.75-0.91 (m, 1H), 0.96-1.32 (m, 7H), 1.42-1.52 (m, 1H), 1.60-1.91 (m, 8H), 2.23-2.33 (m, 1H), 2.63-2.85 (m, 2H), 2.89-3.01 (m, 1H), 3.44-3.55 (m, 2H), 3.99-4.08 (m, 2H), 4.66 (d, J=9.0 Hz, 1H), 6.69 (s, 1H).

(5) 4-({cyclohexyl[2-ethyl-5-(tetrahydro-2H-pyran-4-yl)thiophen-3-yl]methyl}amino)benzoic acid To a mixture of 4-{4-[chloro(cyclohexyl)methyl]-5-ethylthiophen-2-yl}tetrahydro-2H-pyran (725 mg) synthesized above, methyl 4-aminobenzoate (671 mg), sodium iodide (666 mg) and N,N-dimethylacetamide (15 mL) was added sodium carbonate (471 mg), and the mixture was stirred overnight at 100° C. under an argon atmosphere. To the reaction mixture was added 1N hydrochloric acid to quench the reaction, and the mixture was extracted with ethyl acetate. The extract was washed with 1N hydrochloric acid and saturated brine, dried over magnesium sulfate, and concentrated under reduced pressure. The residue was purified by silica gel column chromatography (ethyl acetate:hexane=3:7, volume ratio) to give a white solid. To a mixture of the obtained solid, tetrahydrofuran (10 mL) and ethanol (10 mL) was added 1N aqueous sodium hydroxide solution (10 mL), and the mixture was stirred at 50° C. for 5 hr, and concentrated under reduced pressure. The residue was dissolved in water (20 mL), and 1N hydrochloric acid (10 mL) was added at 0° C. The resulting precipitate was collected by filtration to give the title compound (710 mg, 75%) as a white solid.

$^1$H NMR (300 MHz, CDCl$_3$) δ ppm 0.89-1.33 (m, 8H), 1.46-1.91 (m, 9H), 1.92-2.02 (m, 1H), 2.70-2.96 (m, 3H), 3.40-3.53 (m, 2H), 3.96-4.04 (m, 2H), 4.21 (d, J=7.5 Hz, 1H), 6.43-6.52 (m, 3H), 7.83 (d, J=8.9 Hz, 2H).

(6) 3-({[4-({cyclohexyl[2-ethyl-5-(tetrahydro-2H-pyran-4-yl)thiophen-3-yl]methyl}amino)phenyl]carbonyl}amino)propanoic acid To a mixture of 4-({cyclohexyl[2-ethyl-5-(tetrahydro-2H-pyran-4-yl)thiophen-3-yl]methyl}amino)benzoic acid (250 mg) synthesized above, ethyl β-alaninate hydrochloride (108 mg), 1-hydroxybenzotriazole monohydrate (108 mg) and triethylamine (98 μL) in N,N-dimethylformamide (10 mL) was added 1-ethyl-3-(3-dimethylaminopropyl)carbodiimide hydrochloride (135 mg), and the mixture was stirred at room temperature for 2 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by NH-silica gel column chromatography (ethyl acetate) to give a pale-yellow oil. To a mixture of the obtained oil, tetrahydrofuran (5 mL) and ethanol (5 mL) was added 1N aqueous sodium hydroxide solution (1 mL), and the mixture was stirred at room temperature for 3 hr, and concentrated under reduced pressure. The residue was dissolved in water (10 mL), and 1N hydrochloric acid (1 mL) was added at 0° C. The resulting precipitate was collected by filtration to give the title compound (158 mg, 54%) as a white solid.

$^1$H NMR (300 MHz, CDCl$_3$) δ ppm 0.79-1.33 (m, 8H), 1.46-1.90 (m, 9H), 1.91-2.02 (m, 1H), 2.66 (t, J=5.7 Hz, 2H), 2.70-2.96 (m, 3H), 3.40-3.52 (m, 2H), 3.61-3.72 (m, 2H), 3.94-4.07 (m, 2H), 4.17 (d, J=7.5 Hz, 1H), 6.43-6.50 (m, 3H), 6.61 (t, J=6.0 Hz, 1H), 7.52 (d, J=8.9 Hz, 2H).

Example 269

3-[{[4-({cyclohexyl[2-ethyl-5-(tetrahydro-2H-pyran-4-yl)thiophen-3-yl]methyl}amino)phenyl]carbonyl}(methyl)amino]propanoic acid

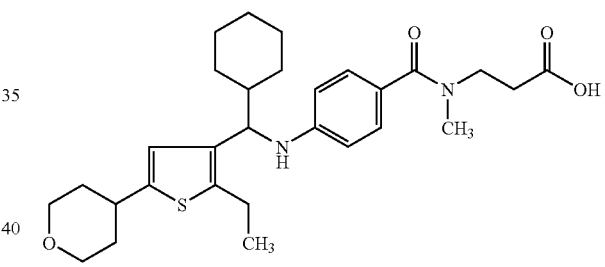

To a mixture of 4-({cyclohexyl[2-ethyl-5-(tetrahydro-2H-pyran-4-yl)thiophen-3-yl]methyl}amino)benzoic acid (250 mg) synthesized in Example 268 (5), ethyl 3-(methylamino)propanoate (92.1 mg), 1-hydroxybenzotriazole monohydrate (108 mg) and triethylamine (98 μL) in N,N-dimethylformamide (10 mL) was added 1-ethyl-3-(3-dimethylaminopropyl)carbodiimide hydrochloride (135 mg), and the mixture was stirred at room temperature for 3 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by NH-silica gel column chromatography (ethyl acetate) to give a colorless oil. To a mixture of the obtained oil, tetrahydrofuran (5 mL) and ethanol (5 mL) was added 1N aqueous sodium hydroxide solution (1 mL), and the mixture was stirred at room temperature for 4 hr, and concentrated under reduced pressure. The residue was dissolved in water (10 mL), and 1N hydrochloric acid (1 mL) was added at 0° C. The resulting precipitate was collected by filtration to give the title compound (160 mg, 53%) as a white solid.

$^1$H NMR (300 MHz, CDCl$_3$) δ ppm 0.94-1.33 (m, 8H), 1.47-1.91 (m, 9H), 1.92-2.02 (m, 1H), 2.63-2.72 (m, 2H), 2.72-2.97 (m, 3H), 3.07 (s, 3H), 3.41-3.53 (m, 2H), 3.71 (t, J=6.5 Hz, 2H), 3.96-4.05 (m, 2H), 4.16 (d, J=7.3 Hz, 1H), 6.42-6.50 (m, 3H), 7.23 (d, J=8.5 Hz, 2H).

Example 270

3-{[(4-{[cyclohexyl(2,5-dimethylthiophen-3-yl)methyl]amino}phenyl)carbonyl]amino}propanoic acid

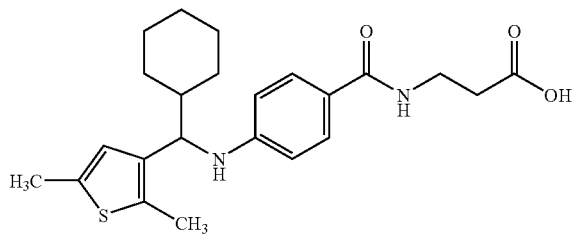

(1) 2,5-dimethylthiophene-3-carbaldehyde

To a solution (20 mL) of 2,5-dimethylthiophene-3-carboxylic acid (920 mg) in tetrahydrofuran was added 1.0M borane-tetrahydrofuran complex in tetrahydrofuran solution (7.07 mL) at 0° C., and the mixture was stirred at room temperature overnight. 1.0M Borane-tetrahydrofuran complex in tetrahydrofuran solution (14.1 mL) was added, and the mixture was further stirred at room temperature for 3 hr. 1N Hydrochloric acid was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by NH-silica gel column chromatography (ethyl acetate:hexane=2:3, volume ratio) to give a yellow oil. To a solution of the obtained oil in tetrahydrofuran (10 mL) was added activated manganese dioxide (3.32 g), and the mixture was stirred at room temperature overnight. Manganese dioxide was filtered off, and the filtrate was concentrated under reduced pressure to give the title compound (562 mg, 68%) as a yellow oil.

$^1$H NMR (300 MHz, CDCl$_3$) δ ppm 2.40 (s, 3H), 2.70 (s, 3H), 6.99 (s, 1H), 9.92 (s, 1H).

(2) cyclohexyl(2,5-dimethylthiophen-3-yl)methanol

To a solution of 2,5-dimethylthiophene-3-carbaldehyde (562 mg) synthesized above in tetrahydrofuran (10 mL) was added dropwise 1.0M cyclohexylmagnesium bromide-tetrahydrofuran solution (6.02 mL) at 0° C., and the mixture was stirred for 1 hr. Saturated aqueous ammonium chloride solution was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title compound (643 mg, 72%) as a white solid.

$^1$H NMR (300 MHz, CDCl$_3$) δ ppm 0.77-0.92 (m, 1H), 0.95-1.43 (m, 5H), 1.52-1.71 (m, 4H), 1.73-1.84 (m, 1H), 2.04-2.15 (m, 1H), 2.32 (s, 3H), 2.39 (s, 3H), 4.34 (dd, J=8.4, 2.4 Hz, 1H), 6.60 (s, 1H).

(3) 3-[chloro(cyclohexyl)methyl]-2,5-dimethylthiophene

To a solution of cyclohexyl(2,5-dimethylthiophen-3-yl)methanol (643 mg) synthesized above in toluene (10 mL) was added thionyl chloride (314 µL), and the mixture was stirred at room temperature for 6 hr. The reaction mixture was poured into ice-cooled saturated aqueous sodium hydrogen carbonate solution, and the mixture was extracted with ethyl acetate. The extract was washed with saturated brine, dried over magnesium sulfate and concentrated under reduced pressure to give the title compound (653 mg, 94%) as a brown oil.

$^1$H NMR (300 MHz, CDCl$_3$) δ ppm 0.75-0.90 (m, 1H) 0.95-1.35 (m, 4H) 1.45-1.57 (m, 1H) 1.60-1.72 (m, 2H), 1.75-1.87 (m, 2H) 2.20-2.34 (m, 4H) 2.39 (s, 3H) 4.63 (d, J=9.3 Hz, 1H), 6.63 (s, 1H).

(4) 4-{[cyclohexyl(2,5-dimethylthiophen-3-yl)methyl]amino}benzoic acid

To a mixture of 3-[chloro(cyclohexyl)methyl]-2,5-dimethylthiophene (653 mg) synthesized above, methyl 4-aminobenzoate (813 mg), sodium iodide (806 mg) and N,N-dimethylacetamide (15 mL) was added sodium carbonate (570 mg), and the mixture was stirred overnight at 100° C. under an argon atmosphere. 1N Hydrochloric acid was added to quench the reaction, and the mixture was extracted with ethyl acetate. The extract was washed with 1N hydrochloric acid and saturated brine, dried over magnesium sulfate, and concentrated under reduced pressure. The residue was purified by silica gel column chromatography (ethyl acetate:hexane=1:4, volume ratio) to give a white solid. To a mixture of the obtained solid, tetrahydrofuran (10 mL) and ethanol (10 mL) was added 1N aqueous sodium hydroxide solution (10 mL), and the mixture was stirred with heating under reflux overnight, and concentrated under reduced pressure. The residue was dissolved in water (20 mL), 1N hydrochloric acid (10 mL) was added at 0° C. The resulting precipitate was collected by filtration to give the title compound (815 mg, 88%) as a white solid.

$^1$H NMR (300 MHz, CDCl$_3$) δ ppm 0.83-1.30 (m, 5H), 1.43-1.82 (m, 5H), 1.90-2.02 (m, 1H), 2.20 (s, 3H), 2.26 (s, 3H), 3.98 (d, J=7.2 Hz, 1H), 6.11 (d, J=8.5 Hz, 2H), 6.37 (s, 1H), 7.53 (d, J=8.7 Hz, 2H).

(5) 3-{[(4-{[cyclohexyl(2,5-dimethylthiophen-3-yl)methyl]amino}phenyl)carbonyl]amino}propanoic acid To a mixture of 4-{[cyclohexyl(2,5-dimethylthiophen-3-yl)methyl]amino}benzoic acid (250 mg) synthesized above, ethyl β-alaninate hydrochloride (134 mg), 1-hydroxybenzotriazole monohydrate (134 mg) and triethylamine (122 µL) in N,N-dimethylformamide (10 mL) was added 1-ethyl-3-(3-dimethylaminopropyl)carbodiimide hydrochloride (168 mg), and the mixture was stirred at room temperature overnight. 1N Hydrochloric acid was added to quench the reaction, and the mixture was extracted with ethyl acetate. The extract was washed with saturated brine, dried over magnesium sulfate, and concentrated under reduced pressure. The residue was purified by NH-silica gel column chromatography (ethyl acetate) to give a colorless oil. To a mixture of the obtained oil, tetrahydrofuran (5 mL) and ethanol (5 mL) was added 1N aqueous sodium hydroxide solution (1 mL), and the mixture was stirred at room temperature for 2 hr, and concentrated under reduced pressure. The residue was dissolved in water (10 mL), and 1N hydrochloric acid (10 mL) was added at 0° C. The resulting precipitate was collected by filtration to give the title compound (250 mg, 83%) as a white solid.

$^1$H NMR (300 MHz, CDCl$_3$) δ ppm 0.94-1.28 (m, 5H), 1.49-1.84 (m, 5H), 1.93-2.03 (m, 1H), 2.32 (s, 3H), 2.38 (s, 3H), 2.66 (t, J=5.7 Hz, 2H), 3.61-3.70 (m, 2H), 4.11 (d, J=7.3 Hz, 1H), 6.40 (s, 1H), 6.44 (d, J=8.7 Hz, 2H), 6.52-6.60 (m, 1H), 7.51 (d, J=8.7 Hz, 2H).

Example 271

3-{[(4-{[cyclohexyl(2,5-dimethylthiophen-3-yl)methyl]amino}phenyl)carbonyl](methyl)amino}propanoic acid

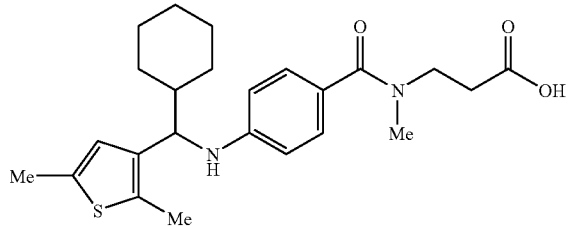

To a mixture of 4-{[cyclohexyl(2,5-dimethylthiophen-3-yl)methyl]amino}benzoic acid (250 mg) synthesized in Example 270 (4), ethyl 3-(methylamino)propanoate (115 mg), 1-hydroxybenzotriazole monohydrate (134 mg) and triethylamine (122 μL) in N,N-dimethylformamide (10 mL) was added 1-ethyl-3-(3-dimethylaminopropyl)carbodiimide hydrochloride (168 mg), and the mixture was stirred at room temperature for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by NH-silica gel column chromatography (ethyl acetate) to give a colorless oil. To a mixture of the obtained oil, tetrahydrofuran (5 mL) and ethanol (5 mL) was added 1N aqueous sodium hydroxide solution (1 mL), and the mixture was stirred at room temperature for 2.5 hr, and concentrated under reduced pressure. The residue was dissolved in water (10 mL), and 1N hydrochloric acid (1 mL) was added at 0° C. The resulting precipitate was collected by filtration to give a white solid. The obtained solid was purified by silica gel column chromatography (60% ethyl acetate/hexane) to give colorless oil. The obtained oil was crystallized from hexane to give the title compound (15.4 mg, 5%) as a white solid.

$^1$H NMR (300 MHz, CDCl$_3$) δ ppm 0.93-1.37 (m, 5H), 1.48-1.84 (m, 5H), 1.92-2.04 (m, 1H), 2.33 (s, 3H), 2.38 (s, 3H), 2.69 (t, J=6.3 Hz, 2H), 3.07 (s, 3H), 3.72 (t, J=6.3 Hz, 2H), 4.09 (d, J=7.2 Hz, 1H), 6.39-6.48 (m, 3H), 7.23 (d, J=8.5 Hz, 2H).

Example 272

3-({[4-({cyclohexyl[2-ethyl-5-(tetrahydro-2H-thiopyran-4-yl)thiophen-3-yl]methyl}amino)phenyl]carbonyl}amino)propanoic acid

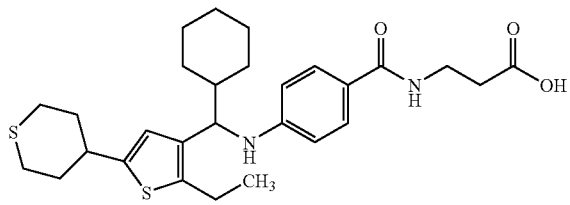

(1) [2-ethyl-5-(tetrahydro-2H-thiopyran-4-yl)thiophen-3-yl]methanol

To a solution of ethyl 5-bromo-2-ethylthiophene-3-carboxylate (5.28 g) synthesized in Example 69 (4) in tetrahydrofuran (60 mL) was added dropwise 1.0M isopropylmagnesium bromide-tetrahydrofuran solution (24.1 mL) at −45° C., and the mixture was stirred for 1 hr under an argon atmosphere. A solution of tetrahydro-4H-thiopyran-4-one (7.01 g) in tetrahydrofuran (15 mL) was added dropwise, and the mixture was stirred at −45° C. for 2 hr, and then at room temperature for 1.5 hr. Saturated aqueous ammonium chloride solution was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give a pale-yellow oil. A mixture of the obtained oil, triethylsilane (4.82 mL), methylene chloride (25 mL) and chloroform (50 mL) was cooled to −78° C., trifluoroacetic acid (10 mL) was added, and, under a nitrogen atmosphere, the mixture was stirred −78° C. for 1 hr, and then at room temperature for 3 hr. The reaction mixture was concentrated under reduced pressure, and the residue was purified by silica gel column chromatography (10% ethyl acetate/hexane) to give colorless oil. The obtained oil in tetrahydrofuran solution (60 was added 1.5M diisobutylaluminum hydride-toluene solution (23.2 mL) at 0° C., and the mixture was stirred for 1 hr. 1.5M Diisobutylaluminum hydride in toluene solution (15.5 mL) was added again, and the mixture was further stirred at 0° C. for 1 hr. 1N Hydrochloric acid was added to quench the reaction, the organic solvent was evaporated using evaporator, and the mixture was extracted with ethyl acetate. The extract was washed with saturated brine, dried over magnesium sulfate and concentrated under reduced pressure to give the title compound (2.76 g, 57%) as a colorless oil.

$^1$H NMR (300 MHz, CDCl$_3$) δ ppm 1.26 (t, J=7.5 Hz, 3H), 1.75-1.90 (m, 2H), 2.24-2.34 (m, 2H), 2.64-2.85 (m, 7H), 4.54 (d, J=5.4 Hz, 2H), 6.69 (s, 1H).

(2) 2-ethyl-5-(tetrahydro-2H-thiopyran-4-yl)thiophene-3-carbaldehyde

To a solution of [2-ethyl-5-(tetrahydro-2H-thiopyran-4-yl)thiophen-3-yl]methanol (2.76 g) synthesized above in tetrahydrofuran (50 mL) was added activated manganese dioxide (15.0 g), and the mixture was stirred at room temperature overnight. Activated manganese dioxide (8.00 g) was added again, and the mixture was further stirred at room temperature for 5 hr. Manganese dioxide was filtered off, and the filtrate was concentrated under reduced pressure. The residue was purified by silica gel column chromatography (15% ethyl acetate/hexane) to give the title compound (1.85 g, 68%) as a colorless oil.

$^1$H NMR (300 MHz, CDCl$_3$) δ ppm 1.36 (t, J=7.5 Hz, 3H), 1.75-1.91 (m, 2H), 2.24-2.36 (m, 2H), 2.65-2.87 (m, 5H), 3.17 (q, J=7.5 Hz, 2H), 7.07 (s, 1H), 9.97 (s, 1H).

(3) cyclohexyl[2-ethyl-5-(tetrahydro-2H-thiopyran-4-yl)thiophen-3-yl]methanol

To a solution of 2-ethyl-5-(tetrahydro-2H-thiopyran-4-yl)thiophene-3-carbaldehyde (1.85 g) synthesized above in tetrahydrofuran (20 mL) was added dropwise 1.0M cyclohexylmagnesium bromide-tetrahydrofuran solution (11.6 mL) at 0° C., and the mixture was stirred for 1 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give the title compound (1.91 g, 76%) as a pale-yellow oil.

$^1$H NMR (300 MHz, CDCl$_3$) δ ppm 0.76-0.91 (m, 1H), 0.96-1.28 (m, 8H), 1.30-1.40 (m, 1H), 1.59-1.69 (m, 3H), 1.74-1.90 (m, 3H), 2.05-2.15 (m, 1H), 2.24-2.34 (m, 2H), 2.63-2.85 (m, 7H), 4.33-4.39 (m, 1H), 6.65 (s 1H).

(4) 4-{4-[chloro(cyclohexyl)methyl]-5-ethylthiophen-2-yl}tetrahydro-2H-thiopyran To a solution of cyclohexyl[2-ethyl-5-(tetrahydro-2H-thiopyran-4-yl)thiophen-3-yl]methanol (1.91 g) synthesized above in toluene (20 mL) was added thionyl chloride (516 μL), and the mixture was stirred at room temperature for 1.5 hr. The reaction mixture was poured into ice-cooled saturated aqueous sodium hydrogen carbonate solution, and the mixture was extracted with ethyl acetate. The extract was washed with saturated brine, dried over magnesium sulfate and concentrated under reduced pressure to give the title compound (1.91 g, 95%) as a pale-yellow oil.

$^1$H NMR (300 MHz, CDCl$_3$) δ ppm 0.74-0.89 (m, 1H), 0.95-1.31 (m, 8H), 1.41-1.51 (m, 1H), 1.62-1.71 (m, 2H), 1.74-1.91 (m, 3H), 2.22-2.35 (m, 3H), 2.63-2.84 (m, 7H), 4.65 (d, J=9.0 Hz, 1H), 6.67 (s, 1H).

(5) 4-({cyclohexyl[2-ethyl-5-(tetrahydro-2H-thiopyran-4-yl)thiophen-3-yl]methyl}amino)benzoic acid To a mixture of 4-{4-[chloro(cyclohexyl)methyl]-5-ethylthiophen-2-yl}tetrahydro-2H-thiopyran (1.91 g) synthesized above, methyl 4-aminobenzoate (1.68 g), sodium iodide (1.66 g) and N,N-dimethylacetamide (20 mL) was added sodium carbonate (1.18 g), and the mixture was stirred overnight at 100° C. under an argon atmosphere. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give a white solid. To a mixture of the obtained solid, tetrahydrofuran (20 mL) and ethanol (20 mL) was added 1N aqueous sodium hydroxide solution (20 mL), and the mixture was stirred with heating under reflux overnight, and concentrated under reduced pressure. The residue was dissolved in water (60 mL), and 1N hydrochloric acid (20 mL) was added at 0° C. The resulting precipitate was collected by filtration to give the title compound (2.07 g, 84%) as a yellow solid.

$^1$H NMR (300 MHz, CDCl$_3$) δ ppm 0.93-1.34 (m, 8H), 1.46-1.86 (m, 7H), 1.91-2.01 (m, 1H), 2.18-2.30 (m, 2H), 2.60-3.93 (m, 7H), 4.20 (d, J=7.2 Hz, 1H) 6.43-6.50 (m, 3H) 7.82 (d, J=8.7 Hz, 2H).

(6) ethyl 3-({[4-({cyclohexyl[2-ethyl-5-(tetrahydro-2H-thiopyran-4-yl)thiophen-3-yl]methyl}amino)phenyl]carbonyl}amino)propanoate To a mixture of 4-({cyclohexyl[2-ethyl-5-(tetrahydro-2H-thiopyran-4-yl)thiophen-3-yl]methyl}amino)benzoic acid (1.00 g) synthesized above, ethyl β-alaninate hydrochloride (415 mg), 1-hydroxybenzotriazole monohydrate (414 mg) and triethylamine (376 μL) in N,N-dimethylformamide (20 mL) was added 1-ethyl-3-(3-dimethylaminopropyl)carbodiimide hydrochloride (518 mg), and the mixture was stirred at room temperature overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give the title compound (1.06 g, 87%) as a white solid.

$^1$H NMR (300 MHz, CDCl$_3$) δ ppm 0.93-1.32 (m, 11H), 1.46-1.84 (m, 6H), 1.90-2.00 (m, 1H), 2.18-2.28 (m, 2H), 2.56-2.89 (m, 9H), 3.62-3.70 (m, 2H), 4.10-4.19 (m, 3H), 4.20-4.32 (m, 1H), 6.42-6.48 (m, 3H), 6.59 (t, J=6.3 Hz, 1H), 7.51 (d, J=9.0 Hz, 2H)

(7) 3-({[4-({cyclohexyl[2-ethyl-5-(tetrahydro-2H-thiopyran-4-yl)thiophen-3-yl]methyl}amino)phenyl]carbonyl}amino)propanoic acid To a mixture of ethyl 3-({[4-({cyclohexyl[2-ethyl-5-(tetrahydro-2H-thiopyran-4-yl)thiophen-3-yl]methyl}amino)phenyl]carbonyl}amino)propanoate (338 mg) synthesized above, tetrahydrofuran (5 mL) and ethanol (5 mL) was added 1N aqueous sodium hydroxide solution (1 mL), and the mixture was stirred at room temperature for 3 hr, and concentrated under reduced pressure. The residue was dissolved in water (10 mL), and 1N hydrochloric acid (1 mL) was added at 0° C. The resulting precipitate was collected by filtration to give the title compound (296 mg, 93%) as a white solid.

$^1$H NMR (300 MHz, CDCl$_3$) δ ppm 0.87-1.34 (m, 8H), 1.44-1.87 (m, 7H), 1.89-2.02 (m, 1H), 2.17-2.30 (m, 2H), 2.57-2.92 (m, 9H), 3.58-3.72 (m, 2H), 4.16 (d, J=7.3 Hz, 1H), 6.40-6.50 (m, 3H), 6.59-6.69 (m, 1H), 7.51 (d, J=8.5 Hz, 2H).

Example 273

3-({[4-({cyclohexyl[2-ethyl-5-(1-oxidetetrahydro-2H-thiopyran-4-yl)thiophen-3-yl]methyl}amino)phenyl]carbonyl}amino)propanoic acid

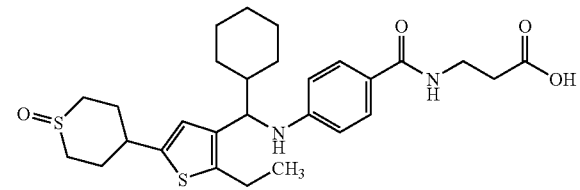

To a solution of ethyl 3-({[4-({cyclohexyl[2-ethyl-5-(tetrahydro-2H-thiopyran-4-yl)thiophen-3-yl]methyl}amino)phenyl]carbonyl}amino)propanoate (300 mg) synthesized in Example 272 (6) in methylene chloride (10 mL) was added m-chloroperbenzoic acid (containing water, purity 69-75%) (143 mg) at 0° C., and the mixture was stirred for 1 hr. Saturated aqueous sodium sulfite solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (15% methanol/ethyl acetate) to give a white solid. To a mixture of the obtained solid, tetrahydrofuran (5 mL) and ethanol (5 mL) was added 1N aqueous sodium hydroxide solution (1 mL), and the mixture was stirred at room temperature for 2 hr, and concentrated under reduced pressure. The residue was dissolved in water (10 mL), and 1N hydrochloric acid (1 mL) was added at 0° C. The resulting precipitate was collected by filtration to give the title compound (163 mg, 56%) as a white solid.

¹H NMR (300 MHz, CDCl₃) δ ppm 0.90-1.36 (m, 8H), 1.45-2.05 (m, 8H), 2.24-2.66 (m, 5H), 2.69-3.27 (m, 6H), 3.57-3.68 (m, 2H), 4.16 (d, J=7.2 Hz, 1H), 6.36-6.54 (m, 3H), 6.74-6.88 (m, 1H), 7.51 (d, J=8.5 Hz, 2H).

Example 274

3-({[4-({cyclohexyl[5-(1,1-dioxidetetrahydro-2H-thiopyran-4-yl)-2-ethylthiophen-3-yl]methyl}amino)phenyl]carbonyl}amino)propanoic acid

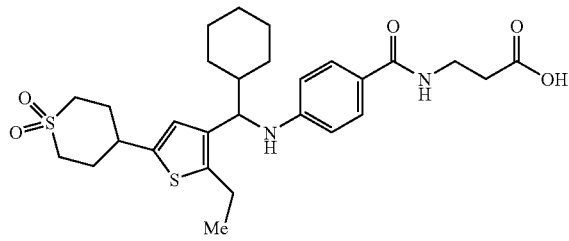

To a solution of ethyl 3-({[4-({cyclohexyl[2-ethyl-5-(tetrahydro-2H-thiopyran-4-yl)thiophen-3-yl]methyl}amino)phenyl]carbonyl}amino)propanoate (300 mg) synthesized in Example 272 (6) in methylene chloride (10 mL) was added m-chloroperbenzoic acid (containing water, purity 69-75%) (287 mg) at 0° C., and the mixture was stirred at 0° C. for 1 hr, and then at room temperature for 7 hr. Saturated aqueous sodium sulfite solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (80% ethyl acetate/hexane) to give a pale-yellow oil. To a mixture of the obtained oil, tetrahydrofuran (5 mL) and ethanol (5 mL) was added 1N aqueous sodium hydroxide solution (1 mL), and the mixture was stirred at room temperature for 5 hr, and concentrated under reduced pressure. The residue was dissolved in water (10 mL), and 1N hydrochloric acid (1 mL) was added at 0° C. The resulting precipitate was collected by filtration to give the title compound (191 mg, 63%) as a white solid.

¹H NMR (300 MHz, CDCl₃) δ ppm 0.90-1.35 (m, 8H), 1.45-1.84 (m, 5H), 1.88-2.00 (m, 1H), 2.23-2.36 (m, 4H), 2.63 (t, J=5.6 Hz, 2H), 2.71-3.10 (m, 7H), 3.57-3.70 (m, 2H), 4.17 (d, J=7.0 Hz, 1H), 6.43 (d, J=8.5 Hz, 2H), 6.50 (s, 1H), 6.66-6.75 (m, 1H), 7.50 (d, J=8.5 Hz, 2H).

Example 275

3-[{[4-({cyclohexyl[2-ethyl-5-(tetrahydro-2H-thiopyran-4-yl)thiophen-3-yl]methyl}amino)phenyl]carbonyl}(methyl)amino]propanoic acid

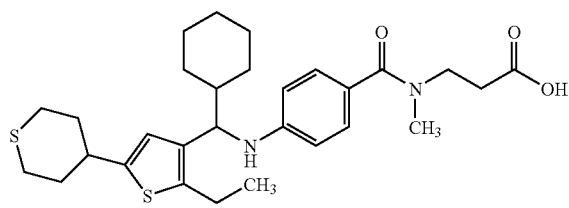

To a mixture of 4-({cyclohexyl[2-ethyl-5-(tetrahydro-2H-thiopyran-4-yl)thiophen-3-yl]methyl}amino)benzoic acid (250 mg) synthesized in Example 272-(5), ethyl 3-(methylamino)propanoate (88.7 mg), 1-hydroxybenzotriazole monohydrate (104 mg) and triethylamine (94 µL) in N,N-dimethylformamide (10 mL) was added 1-ethyl-3-(3-dimethylaminopropyl)carbodiimide hydrochloride (130 mg), and the mixture was stirred at room temperature overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 2 hr, and concentrated under reduced pressure. The residue was dissolved in water (10 mL), and 1N hydrochloric acid (1 mL) was added at 0° C. The resulting precipitate was collected by filtration to give the title compound (230 mg, 77%) as a white solid.

¹H NMR (300 MHz, CDCl₃) δ ppm 0.89-1.34 (m, 8H), 1.45-1.85 (m, 7H), 1.90-2.01 (m, 1H), 2.19-2.30 (m, 2H), 2.59-2.92 (m, 9H), 3.06 (s, 3H), 3.72 (t, J=6.4 Hz, 2H), 4.14 (d, J=7.3 Hz, 1H), 6.39-6.54 (m, 3H), 7.22 (d, J=8.3 Hz, 2H).

Example 276

3-[({4-[(cyclohexyl{3-methyl-5-[4-(trifluoromethyl)phenyl]thiophen-2-yl}methyl)amino]phenyl}carbonyl)amino]propanoic acid

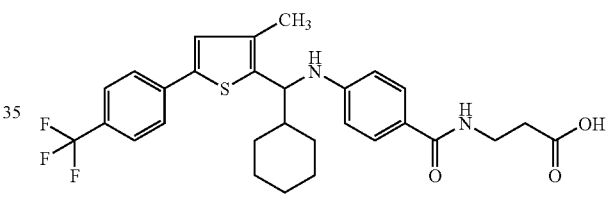

(1) 2-[chloro(cyclohexyl)methyl]-3-methyl-5-[4-(trifluoromethyl)phenyl]thiophene To a solution of cyclohexyl{3-methyl-5-[4-(trifluoromethyl)phenyl]thiophen-2-yl}methanol (1.3 g) in toluene (20 mL) was added thionyl chloride (0.4 mL), and the mixture was stirred at room temperature for 2 hr. The solvent was evaporated under reduced pressure to give the title compound (1.3 g, 100%) as an amorphous compound.

¹H NMR (300 MHz, CHLOROFORM-d) δ ppm 0.79-1.45 (m, 5H) 1.58-2.06 (m, 5H) 2.24 (s, 3H) 2.30 (d, J=11.74 Hz, 1H) 4.94 (d, J=9.47 Hz, 1H) 7.05 (s, 1H) 7.65 (d, J=8.71 Hz, 2H) 7.65 (d, J=8.71 Hz, 2H)

(2) 4-[(cyclohexyl{3-methyl-5-[4-(trifluoromethyl)phenyl]thiophen-2-yl}methyl)amino]benzoic acid A mixture of 2-[chloro(cyclohexyl)methyl]-3-methyl-5-[4-(trifluoromethyl)phenyl]thiophene (1.3 g) obtained by the above-mentioned reaction, methyl 4-aminobenzoate (1.1 g), sodium carbonate (0.8 g) and sodium iodide (2.2 g) in N,N-dimethylacetamide (20 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 40% ethyl acetate/hexane) to give methyl 4-[(cyclohexyl{3-methyl-5-[4-(trifluoromethyl)phenyl]thiophen-2-yl}methyl)amino]benzoate as an amorphous compound. The obtained methyl 4-[(cyclohexyl{3-methyl-5-[4-(trifluoromethyl)phenyl]thiophen-2-yl}methyl)amino]benzoate was dissolved in methanol (5 mL) and tetrahydrofuran (5 mL). 2N Lithium hydroxide (1.5 mL) was added, and the mixture was stirred at 70° C. for 3 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (0.7 g, 43%) as an amorphous compound.

$^1$H NMR (300 MHz, CHLOROFORM-d) δ ppm 1.07-1.30 (m, 5H) 1.56-1.92 (m, 5H) 2.05-2.10 (m, 1H) 2.31 (s, 3H) 4.45 (d, J=7.57 Hz, 1H) 6.52 (d, J=9.09 Hz, 2H) 7.08 (s, 1H) 7.46-7.67 (m, 4H) 7.85 (d, J=8.71 Hz, 2H)

(3) 3-[({4-[(cyclohexyl{3-methyl-5-[4-(trifluoromethyl)phenyl]thiophen-2-yl}methyl)amino]phenyl}carbonyl)amino]propanoic acid A solution of 4-[(cyclohexyl{3-methyl-5-[4-(trifluoromethyl)phenyl]thiophen-2-yl}methyl)amino]benzoic acid (355 mg) obtained by the above-mentioned reaction, ethyl β-alaninate hydrochloride (138 mg), 1-ethyl-3-(3-dimethylaminopropyl)carbodiimide hydrochloride (173 mg), hydroxybenzotriazole monohydrate (138 mg) and triethylamine (125 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (359 mg, 88%).

$^1$H NMR (300 MHz, DMSO-d$_6$) δ ppm 1.04-1.23 (m, 5H) 1.48-1.78 (m, 5H) 2.10 (d, J=7.57 Hz, 1H) 2.30 (s, 3H) 2.40 (t, J=7.00 Hz, 2H) 3.19-3.47 (m, 2H) 4.42 (t, J=7.19 Hz, 1H) 6.54 (d, J=8.71 Hz, 2H) 6.64 (d, J=6.82 Hz, 1H) 7.36 (s, 1H) 7.52 (d, J=8.71 Hz, 2H) 7.62-7.78 (m, 4H) 7.93-8.12 (m, 1H)

Example 277

3-[({4-[(cyclohexyl{3-methyl-5-[4-(trifluoromethyl)phenyl]thiophen-2-yl}methyl)amino]phenyl}carbonyl)(methyl)amino]propanoic acid

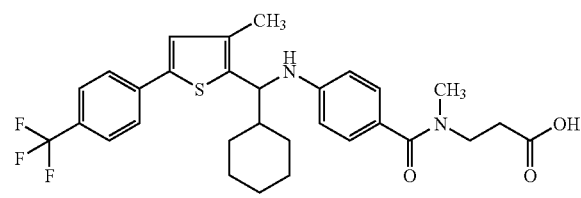

A solution of 4-[(cyclohexyl{3-methyl-5-[4-(trifluoromethyl)phenyl]thiophen-2-yl}methyl)amino]benzoic acid (355 mg) synthesized in Example 276 (2), ethyl 3-(methylamino)propanoate (118 mg), 1-ethyl-3-(3-dimethylaminopropyl)carbodiimide hydrochloride (173 mg), hydroxybenzotriazole monohydrate (138 mg) and triethylamine (125 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (384 mg, 92%).

$^1$H NMR (300 MHz, DMSO-d$_6$) δ ppm 1.00-1.32 (m, 5H) 1.46-1.81 (m, 5H) 2.04-2.19 (m, 1H) 2.30 (s, 3H) 2.45-2.50 (m, 2H) 2.89 (s, 3H) 3.50 (t, J=7.19 Hz, 2H) 4.38 (t, J=7.19 Hz, 1H) 6.51-6.55 (m, 3H) 7.10 (d, J=8.33 Hz, 2H) 7.37 (s, 1H) 7.67 (d, J=8.33 Hz, 2H) 7.73 (d, J=8.33 Hz, 2H)

Example 278

3-{[(4-{[cyclohexyl(2-methyl-5-phenylthiophen-3-yl)methyl]amino}phenyl)carbonyl]amino}propanoic acid

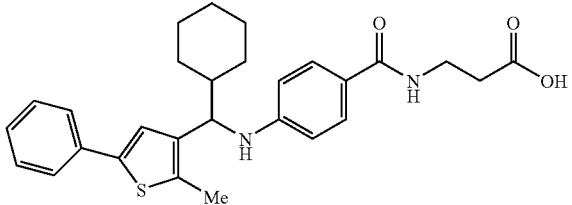

(1) 2-(thiophen-3-yl)-1,3-dioxolane

To a mixture of thiophene-3-carbaldehyde (25.0 g), ethylene glycol (18.7 mL) and toluene (250 mL) was added p-toluenesulfonic acid monohydrate (2.13 g), and the mixture was stirred with heated under reflux for 7 hr while dehydrating using Dean-Stark (Dean-Stark) apparatus. Triethylamine (3.11 mL) was added to quench the reaction, saturated aqueous sodium hydrogen carbonate solution was added, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give the title compound (33.6 g, 96%) as a dark brown oil.

$^1$H NMR (300 MHz, CDCl$_3$) δ ppm 3.95-4.16 (m, 4H), 5.90 (s, 1H), 7.13-7.17 (m, 1H), 7.28-7.33 (m, 1H), 7.39-7.43 (m, 1H).

(2) 2-(2-methylthiophen-3-yl)-1,3-dioxolane

A solution of 2-(thiophen-3-yl)-1,3-dioxolane (33.6 g) synthesized above in tetrahydrofuran (300 mL) was cooled to −10° C., 1.6M n-butyllithium in hexane solution (148 mL) was added dropwise, and the mixture was stirred for 1 hr under a nitrogen atmosphere. The reaction mixture was cooled to −78° C., methyl iodide (16.1 mL) was added, and the mixture was stirred at −78° C. for 30 min, and then at room temperature for 5 hr. Water was added to quench the reaction, the organic solvent was evaporated using evaporator, and the mixture was extracted with ethyl acetate. The extract was washed with saturated brine, dried over magnesium sulfate, and concentrated under reduced pressure. The residue was purified by silica gel column chromatography (5% ethyl acetate/hexane) to give the title compound (26.0 g, 71%) as a yellow oil.

$^1$H NMR (300 MHz, CDCl$_3$) δ ppm 2.50 (s, 3H), 3.94-4.18 (m, 4H), 5.85 (s, 1H), 6.98-7.05 (m, 2H).

(3) 2-(5-bromo-2-methylthiophen-3-yl)-1,3-dioxolane

To a solution of 2-(2-methylthiophen-3-yl)-1,3-dioxolane (2.30 g) synthesized above in acetonitrile (25 mL) was added N-bromosuccinimide (2.65 g), and the mixture was stirred at room temperature for 7 hr. The reaction mixture was concentrated under reduced pressure, and the residue was purified by silica gel column chromatography (5% ethyl acetate/hexane) to give the title compound (2.15 g, 64%) as a pale-yellow oil.

$^1$H NMR (300 MHz, CDCl$_3$) δ ppm 2.42 (s, 3H), 3.92-4.16 (m, 4H), 5.76 (s, 1H), 6.97 (s, 1H).

(4) 2-methyl-5-phenylthiophene-3-carbaldehyde

To a mixture of 2-(5-bromo-2-methylthiophen-3-yl)-1,3-dioxolane (3.50 g) synthesized above, phenylboronic acid (2.56 g), sodium carbonate (2.96 g), water (10 mL) and N,N-dimethylformamide (50 mL) was added [1,1'-bis(diphenylphosphino)ferrocene]dichloropalladium(II).dichloromethane adduct (1.14 g). The reaction mixture was deaerated, and the mixture was stirred at 80° C. for 3 hr under an argon atmosphere. Saturated aqueous ammonium chloride solution was added to quench the reaction, and the mixture was extracted with ethyl acetate. The extract was washed with saturated sodium hydrogen carbonate and saturated brine, dried over magnesium sulfate, and concentrated under reduced pressure. The residue was purified by silica gel column chromatography (20% ethyl acetate/hexane) to give a yellow oil. To a solution of the obtained oil in tetrahydrofuran (20 mL) was added 1N hydrochloric acid (10 mL), and the mixture was stirred at room temperature for 1 hr. Tetrahydrofuran was evaporated using evaporator, and the mixture was extracted with ethyl acetate. The extract was washed with saturated brine, dried over magnesium sulfate and concentrated under reduced pressure to give the title compound (1.72 g, 61%) as a pale-yellow solid.

$^1$H NMR (300 MHz, CDCl$_3$) δ ppm 2.80 (s, 3H), 7.26-7.33 (m, 1H), 7.34-7.42 (m, 2H), 7.51-7.58 (m, 3H), 10.02 (s, 1H).

(5) cyclohexyl (2-methyl-5-phenylthiophen-3-yl)methanol

To a solution of 2-methyl-5-phenylthiophene-3-carbaldehyde (1.72 g) synthesized above in tetrahydrofuran (40 mL) was added dropwise 1.0M cyclohexylmagnesium bromide-tetrahydrofuran solution (12.8 mL) at 0° C., and the mixture was stirred for 2 hr. 1.0M Cyclohexylmagnesium bromide-tetrahydrofuran solution (5 mL) was added dropwise again, and the mixture was further stirred at 0° C. for 1 hr. 1N Hydrochloric acid was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give the title compound (2.33 g, 96%) as a pale-yellow solid.

$^1$H NMR (300 MHz, CDCl$_3$) δ ppm 0.82-1.35 (m, 5H), 1.39-1.50 (m, 1H), 1.55-1.85 (m, 4H), 2.06-2.17 (m, 1H), 2.41 (s, 3H), 4.42 (d, J=8.4 Hz, 1H), 7.20 (s, 1H), 7.24 (d, J=7.2 Hz, 1H), 7.29-7.38 (m, 2H), 7.54 (d, J=7.5 Hz, 2H).

(6) 3-[chloro(cyclohexyl)methyl]-2-methyl-5-phenylthiophene

To a solution of cyclohexyl(2-methyl-5-phenylthiophen-3-yl)methanol (1.28 g) synthesized above in toluene (20 mL) was added thionyl chloride (391 μL), and the mixture was stirred at room temperature for 3 hr. The reaction mixture was poured into ice-cooled saturated aqueous sodium hydrogen carbonate solution, and the mixture was extracted with ethyl acetate. The extract was washed with saturated brine, dried over magnesium sulfate and concentrated under reduced pressure to give the title compound (1.08 g, 79%) as a yellow oil.

$^1$H NMR (300 MHz, CDCl$_3$) δ ppm 0.80-0.96 (m, 1H), 0.98-1.33 (m, 5H), 1.50-1.74 (m, 2H), 1.76-1.96 (m, 2H), 2.23-2.34 (m, 1H), 2.41 (s, 3H), 4.69 (d, J=8.7 Hz, 1H), 7.19-7.28 (m, 2H), 7.30-7.39 (m, 2H), 7.51-7.57 (m, 2H).

(7) 4-{[cyclohexyl(2-methyl-5-phenylthiophen-3-yl)methyl]amino}benzoic acid

To a mixture of 3-[chloro(cyclohexyl)methyl]-2-methyl-5-phenylthiophene (1.08 g) synthesized above, methyl 4-aminobenzoate (1.07 g), sodium iodide (1.06 g) and N,N-dimethylacetamide (20 mL) was added sodium carbonate (668 mg), and the mixture was stirred overnight at 100° C. under an argon atmosphere. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (30% ethyl acetate/hexane) to give a white solid. To a mixture of the obtained solid, tetrahydrofuran (10 mL) and ethanol (10 mL) 1N aqueous sodium hydroxide solution (10 mL) was added, and the mixture was stirred heated under reflux for 2.5 hr. 1N Aqueous sodium hydroxide solution (5 mL) was added again, and the mixture was further stirred with heated under reflux for 1 hr, and concentrated under reduced pressure. The residue was dissolved in water (50 mL), and 1N hydrochloric acid (15 mL) was added at 0° C. The resulting precipitate was collected by filtration, and the obtained white solid was dissolved in ethyl acetate. The solution was washed with saturated brine, dried over magnesium sulfate and concentrated under reduced pressure to give the title compound (1.21 g, 84%) as a pale-yellow solid.

$^1$H NMR (300 MHz, CDCl$_3$) δ ppm 0.94-1.33 (m, 5H), 1.53-1.86 (m, 5H), 1.94-2.06 (m, 1H), 2.48 (s, 3H), 4.22 (d, J=7.2 Hz, 1H), 6.47 (d, J=8.8 Hz, 2H), 7.01 (s, 1H), 7.16-7.36 (m, 3H), 7.45-7.52 (m, 2H), 7.82 (d, J=8.8 Hz, 2H).

(8) 3-{[(4-{[cyclohexyl(2-methyl-5-phenylthiophen-3-yl)methyl]amino}phenyl)carbonyl]amino}propanoic acid To a mixture of 4-{[cyclohexyl(2-methyl-5-phenylthiophen-3-yl)methyl]amino}benzoic acid (300 mg) synthesized above, ethyl β-alaninate hydrochloride (136 mg), 1-hydroxybenzotriazole monohydrate (136 mg) and triethylamine (124 μL) in N,N-dimethylformamide (10 mL) was added 1-ethyl-3-(3-dimethylaminopropyl)carbodiimide hydrochloride (170 mg), and the mixture was stirred at room temperature for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 1 hr, and concentrated under reduced pressure. The residue was dissolved in water (10 mL), and 1N hydrochloric acid (1 mL) was added at 0° C. The resulting precipitate was collected by filtration to give the title compound (232 mg, 66%) as a white solid.

$^1$H NMR (300 MHz, CDCl$_3$) δ ppm 0.95-1.33 (m, 5H), 1.54-1.84 (m, 5H), 1.95-2.05 (m, 1H), 2.46 (s, 3H), 2.60 (t, J=5.1 Hz, 2H), 3.55-3.67 (m, 2H), 4.17 (d, J=7.2 Hz, 1H), 6.46 (d, J=8.7 Hz, 2H), 6.52-6.63 (m, 1H), 7.00 (s, 1H), 7.15-7.23 (m, 1H), 7.26-7.34 (m, 2H), 7.45-7.53 (m, 4H).

Example 279

3-{[(4-{[cyclohexyl(2-methyl-5-phenylthiophen-3-yl)methyl]amino}phenyl)carbonyl](methyl)amino}propanoic acid

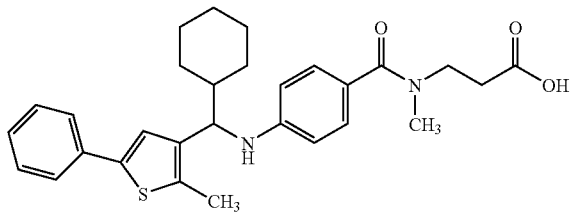

To a mixture of 4-{[cyclohexyl(2-methyl-5-phenylthiophen-3-yl)methyl]amino}benzoic acid (300 mg) synthesized in Example 278 (7), ethyl 3-(methylamino)propanoate (117 mg), 1-hydroxybenzotriazole monohydrate (136 mg) and triethylamine (124 μL) in N,N-dimethylformamide (10 mL) was added 1-ethyl-3-(3-dimethylaminopropyl)carbodiimide hydrochloride (170 mg), and the mixture was stirred at room temperature for 1.5 days. 1N Hydrochloric acid was added to quench the reaction, and the mixture was extracted with ethyl acetate. The extract was washed with saturated brine, dried over magnesium sulfate and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 2 hr, and concentrated under reduced pressure. The residue was dissolved in water (10 mL), and 1N hydrochloric acid (1 mL) was added at 0° C. The resulting precipitate was collected by filtration to give the title compound (281 mg, 77%) as a white solid.

$^1$H NMR (300 MHz, CDCl$_3$) δ ppm 0.94-1.33 (m, 5H), 1.55-1.85 (m, 5H), 1.95-2.06 (m, 1H), 2.47 (s, 3H), 2.62 (t, J=6.5 Hz, 2H), 3.01 (s, 3H), 3.68 (t, J=6.5 Hz, 2H), 4.16 (d, J=7.2 Hz, 1H), 6.46 (d, J=8.7 Hz, 2H), 7.03 (s, 1H), 7.16-7.25 (m, 3H), 7.27-7.35 (m, 2H), 7.46-7.52 (m, 2H).

Example 280

3-[({4-[(cyclohexyl{2-methyl-5-[4-(trifluoromethyl)phenyl]thiophen-3-yl}methyl)amino]phenyl}carbonyl)(methyl)amino]propanoic acid

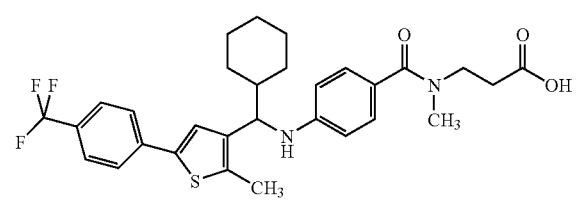

(1) 2-methyl-5-[4-(trifluoromethyl)phenyl]thiophene-3-carbaldehyde

To a mixture of 2-(5-bromo-2-methylthiophen-3-yl)-1,3-dioxolane (3.25 g) synthesized in Example 278 (3), 4-(trifluoromethyl)phenylboronic acid (3.70 g), sodium carbonate (2.76 g), water (10 mL) and N,N-dimethylformamide (50 mL) was added [1,1'-bis(diphenylphosphino)ferrocene]dichloropalladium(II).dichloromethane adduct (1.06 g). The reaction mixture was deaerated and stirred at 80° C. for 4 hr under an argon atmosphere. Phosphate buffer was added to quench the reaction, and the mixture was extracted with ethyl acetate. The extract was washed with saturated sodium hydrogen carbonate and saturated brine, dried over magnesium sulfate, and concentrated under reduced pressure. The residue was purified by silica gel column chromatography (20% ethyl acetate/hexane) to give a pale-yellow solid. To a solution of the obtained solid in tetrahydrofuran (25 mL) was added 1N hydrochloric acid (10 mL), and the mixture was stirred at room temperature for 1 hr. Tetrahydrofuran was evaporated using evaporator, and the mixture was extracted with ethyl acetate. The extract was washed with saturated brine, dried over magnesium sulfate and concentrated under reduced pressure to give the title compound (2.33 g, 66%) as a white solid.

$^1$H NMR (300 MHz, CDCl$_3$) δ ppm 2.82 (s, 3H), 7.60-7.69 (m, 5H), 10.03 (s, 1H).

(2) cyclohexyl{2-methyl-5-[4-(trifluoromethyl)phenyl]thiophen-3-yl}methanol

To a solution of 2-methyl-5-[4-(trifluoromethyl)phenyl]thiophene-3-carbaldehyde (2.33 g) synthesized above in tetrahydrofuran (50 mL) was added dropwise 1.0M cyclohexylmagnesium bromide-tetrahydrofuran solution (12.9 mL) at 0° C., and the mixture was stirred for 1 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (25% ethyl acetate/hexane), and then purified by NH-silica gel column chromatography (ethyl acetate) to give the title compound (1.98 g, 65%) as a white solid.

$^1$H NMR (300 MHz, CDCl$_3$) δ ppm 0.82-1.35 (m, 5H), 1.39-1.50 (m, 1H), 1.58-1.74 (m, 3H), 1.75-1.86 (m, 2H), 2.04-2.16 (m, 1H), 2.43 (s, 3H), 4.45 (dd, J=8.0, 2.7 Hz, 1H), 7.29 (s, 1H), 7.55-7.67 (m, 4H).

(3) 3-[chloro(cyclohexyl)methyl]-2-methyl-5-[4-(trifluoromethyl)phenyl]thiophene To a solution of cyclohexyl{2-methyl-5-[4-(trifluoromethyl)phenyl]thiophen-3-yl}methanol (1.20 g) synthesized above in toluene (20 mL) was added thionyl chloride (297 μL), and the mixture was stirred at room temperature for 3 hr. The reaction mixture was poured into ice-cooled saturated aqueous sodium hydrogen carbonate solution, and the mixture was extracted with ethyl acetate. The extract was washed with saturated brine, dried over magnesium sulfate and concentrated under reduced pressure to give the title compound (1.27 g, quantitative) as a pale-yellow solid.

$^1$H NMR (300 MHz, CDCl$_3$) δ ppm 0.82-1.36 (m, 5H), 1.50-1.74 (m, 3H), 1.77-1.96 (m, 2H), 2.23-2.33 (m, 1H), 2.43 (s, 3H), 4.69 (d, J=8.7 Hz, 1H), 7.29 (s, 1H), 7.58 (d, J=8.4 Hz, 2H), 7.63 (d, J=8.4 Hz, 2H).

(4) 4-[(cyclohexyl{2-methyl-5-[4-(trifluoromethyl) phenyl]thiophen-3-yl}methyl)amino]benzoic acid To a mixture of 3-[chloro(cyclohexyl)methyl]-2-methyl-5-[4-(trifluoromethyl)phenyl]thiophene (1.27 g) synthesized above, methyl 4-aminobenzoate (1.03 g), sodium iodide (1.02 g) and N,N-dimethylacetamide (25 mL) was added sodium carbonate (721 mg), and the mixture was stirred overnight at 100° C. under an argon atmosphere. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give a pale-yellow oil. To a mixture of the obtained oil, tetrahydrofuran (20 mL) and ethanol (20 mL) was added 1N aqueous sodium hydroxide solution (20 mL), and the mixture was stirred with heated under reflux for 4 hr, and concentrated under reduced pressure. The residue was dissolved in water (40 mL), 1N hydrochloric acid (20 mL) was added at 0° C. The resulting precipitate was collected by filtration to give the title compound (1.15 g, 71%) as a white solid.

$^1$H NMR (300 MHz, CDCl$_3$) δ ppm 0.92-1.35 (m, 5H), 1.50-1.86 (m, 5H), (m, 1H), 2.39-2.49 (m, 3H), 4.12-4.22 (m, 1H), 6.35-6.47 (m, 2H), 7.02-7.10 (m, 1H), 7.47-7.59 (m, 4H), 7.71-7.82 (m, 2H).

(5) 3-[({4-[(cyclohexyl{2-methyl-5-[4-(trifluoromethyl)phenyl]thiophen-3-yl}methyl)amino] phenyl}carbonyl)(methyl)amino]propanoic acid To a mixture of 4-[(cyclohexyl{2-methyl-5-[4-(trifluoromethyl)phenyl]thiophen-3-yl}methyl)amino]benzoic acid (326 mg) synthesized above, ethyl 3-(methylamino)propanoate (108 mg), 1-hydroxybenzotriazole monohydrate (126 mg) and triethylamine (115 μL) in N,N-dimethylformamide (10 mL) was added 1-ethyl-3-(3-dimethylaminopropyl)carbodiimide hydrochloride (158 mg), and the mixture was stirred at room temperature for 1.5 days. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 2.5 hr, and concentrated under reduced pressure. The residue was dissolved in water (10 mL), and 1N hydrochloric acid (1 mL) was added at 0° C. The resulting precipitate was collected by filtration to give the title compound (291 mg, 76%) as a white solid.

$^1$H NMR (300 MHz, CDCl$_3$) δ ppm 0.95-1.34 (m, 5H), 1.54-1.86 (m, 5H), 1.95-2.08 (m, 1H), 2.50 (s, 3H), 2.60-2.70 (m, 2H), 3.03 (s, 3H), 3.69 (t, J=6.5 Hz, 2H), 4.17 (d, J=7.2 Hz, 1H), 6.46 (d, J=8.8 Hz, 2H), 7.11 (s, 1H), 7.23 (d, J=8.8 Hz, 2H), 7.52-7.60 (m, 4H).

Example 281

3-[({4-[cyclohexyl(3-methyl-5-phenylthiophen-2-yl) methoxy]phenyl}carbonyl)amino]propanoic acid

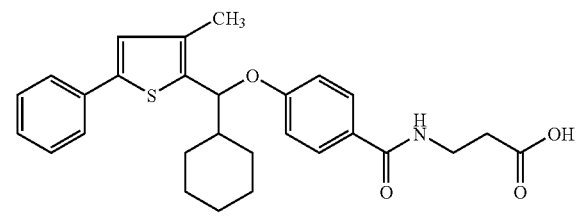

(1) 3-methyl-5-phenylthiophene-2-carbaldehyde

A mixture of 5-bromo-3-methylthiophene-2-carbaldehyde (2.1 g), phenylboronic acid (1.5 g), tetrakis(triphenylphosphine)palladium(0) (0.6 g), 2N aqueous sodium carbonate solution (12 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 20% ethyl acetate/hexane), and crystallized from ethyl acetate/hexane to give the title compound (1.3 g, 66%) as a yellow crystal.

$^1$H NMR (300 MHz, CHLOROFORM-d) δ ppm 2.60 (s, 3H) 7.19 (s, 1H) 7.33-7.51 (m, 3H) 7.65 (dd, J=8.14, 1.70 Hz, 2H) 10.02 (s, 1H)

(2) cyclohexyl (3-methyl-5-phenylthiophen-2-yl)methanol

To a solution of 3-methyl-5-phenylthiophene-2-carbaldehyde (1.3 g) obtained by the above-mentioned reaction in tetrahydrofuran (20 mL) was added dropwise 1N cyclohexylmagnesium bromide-tetrahydrofuran solution (10 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 20% ethyl acetate/hexane) to give the title compound (1.2 g, 67%) as an oil.

¹H NMR (300 MHz, CHLOROFORM-d) δ ppm 0.86-1.38 (m, 5H) 1.60-1.86 (m, 5H) 1.91 (d, J=3.41 Hz, 1H) 2.21 (s, 3H) 4.64 (dd, J=8.14, 3.22 Hz, 1H) 7.00 (s, 1H) 7.19-7.30 (m, 1H) 7.35 (t, J=7.38 Hz, 2H) 7.56 (d, J=7.19 Hz, 2H)

(3) 4-[cyclohexyl(3-methyl-5-phenylthiophen-2-yl) methoxy]benzoic acid

To a solution of cyclohexyl(3-methyl-5-phenylthiophen-2-yl)methanol (286 mg) obtained by the above-mentioned reaction and methyl 4-hydroxybenzoate (183 mg) in tetrahydrofuran (20 mL) were added tributylphosphine (0.4 mL) and 1,1'-(azodicarbonyl)dipiperidine (505 mg), and the mixture was stirred at room temperature overnight. The solvent was evaporated under reduced pressure, and the residue was purified by silica gel column (0% ethyl acetate/hexane to 15% ethyl acetate/hexane) to give methyl 4-[cyclohexyl(3-methyl-5-phenylthiophen-2-yl)methoxy]benzoate as an amorphous compound. The obtained methyl 4-[cyclohexyl(3-methyl-5-phenylthiophen-2-yl)methoxy]benzoate was dissolved in methanol (3 mL) and tetrahydrofuran (3 mL), 2N sodium hydroxide (2.0 mL) was added, and the mixture was stirred at 60° C. for 1 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (251 mg, 62%) as a white crystal.

¹H NMR (300 MHz, CHLOROFORM-d) δ ppm 1.06-1.28 (m, 5H) 1.46-1.73 (m, 6H) 2.29 (s, 3H) 5.11 (d, J=7.91 Hz, 1H) 6.90 (d, J=8.85 Hz, 2H) 6.98 (s, 1H) 7.19-7.33 (m, 1H) 7.50 (d, J=6.97 Hz, 2H) 7.94 (d, J=9.04 Hz, 2H)

(4) 3-[({4-[cyclohexyl(3-methyl-5-phenylthiophen-2-yl)methoxy]phenyl}carbonyl)amino]propanoic acid A solution of 4-[cyclohexyl(3-methyl-5-phenylthiophen-2-yl)methoxy]benzoic acid (122 mg) obtained by the above-mentioned reaction, ethyl β-alaninate hydrochloride (55 mg), 1-ethyl-3-(3-dimethylaminopropyl)carbodiimide hydrochloride (69 mg), hydroxybenzotriazole monohydrate (55 mg) and triethylamine (50 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (123 mg, 86%).

¹H NMR (300 MHz, DMSO-d₆) δ ppm 1.01-1.33 (m, 5H) 1.44-1.49 (m, 1H) 1.59-1.87 (m, 4H) 2.06-2.14 (m, 1H) 2.28 (s, 3H) 2.43 (t, J=7.16 Hz, 2H) 3.31-3.54 (m, 2H) 5.39 (d, J=7.91 Hz, 1H) 6.95 (d, J=8.85 Hz, 2H) 7.20 (s, 1H) 7.23-7.27 (m, 1H) 7.35 (t, J=7.44 Hz, 2H) 7.54 (d, J=7.16 Hz, 2H) 7.71 (d, J=8.85 Hz, 2H) 8.31 (brs, 1H)

Example 282

3-[({4-[cyclohexyl(3-methyl-5-phenylthiophen-2-yl)methoxy]phenyl}carbonyl)(methyl)amino]propanoic acid

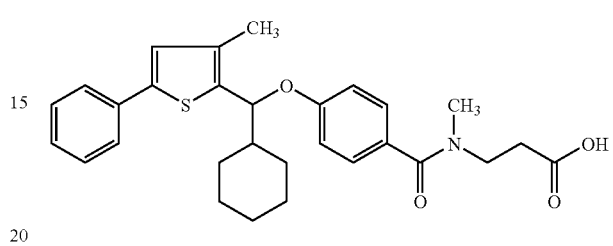

A solution of 4-[cyclohexyl(3-methyl-5-phenylthiophen-2-yl)methoxy]benzoic acid (122 mg), ethyl 3-(methylamino)propanoate (47 mg), 1-ethyl-3-(3-dimethylaminopropyl)carbodiimide hydrochloride (69 mg), hydroxybenzotriazole monohydrate (55 mg) and triethylamine (50 μL) in N,N-dimethylformamide (10 mL) was stirred at room temperature for 4 hr. Ethyl acetate was added, the mixture was washed with saturated aqueous sodium hydrogen carbonate solution and 1N hydrochloric acid, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (105 mg, 71%).

¹H NMR (300 MHz, DMSO-d₆) δ ppm 1.07-1.29 (m, 5H) 1.42-1.50 (m, 1H) 1.57-1.89 (m, 4H) 2.09-2.14 (m, 1H) 2.27 (s, 3H) 2.47-2.50 (m, 2H) 2.88 (s, 3H) 3.52 (brs, 2H) 5.33 (d, J=7.91 Hz, 1H) 6.92 (d, J=8.67 Hz, 2H) 7.21-7.28 (m, 4H) 7.36 (t, J=7.54 Hz, 2H) 7.55 (d, J=7.35 Hz, 2H)

Example 283

3-{[(4-{[cyclohexyl(3-methyl-5-phenylthiophen-2-yl)methyl]amino}phenyl)carbonyl]amino}propanoic acid

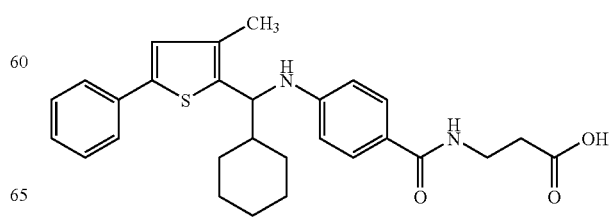

(1) 2-[chloro(cyclohexyl)methyl]-3-methyl-5-phenylthiophene

To a solution of cyclohexyl(3-methyl-5-phenylthiophen-2-yl)methanol (0.8 g) in toluene (20 mL) was added thionyl chloride (0.3 mL), and the mixture was stirred at room temperature for 2 hr. The solvent was evaporated under reduced pressure to give the title compound (0.9 g, 100%).

(2) 4-{[cyclohexyl(3-methyl-5-phenylthiophen-2-yl)methyl]amino}benzoic acid

A mixture of 2-[chloro(cyclohexyl)methyl]-3-methyl-5-[4-(trifluoromethyl)phenyl]thiophene (0.9 g) obtained by the above-mentioned reaction, methyl 4-aminobenzoate (0.9 g), sodium carbonate (0.6 g) and sodium iodide (1.8 g) in N,N-dimethylacetamide (20 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was purified by silica gel column (0% ethyl acetate/hexane to 30% ethyl acetate/hexane) to give methyl 4-{[cyclohexyl(3-methyl-5-phenylthiophen-2-yl)methyl]amino}benzoate as an amorphous compound. The obtained methyl 4-{[cyclohexyl(3-methyl-5-phenylthiophen-2-yl)methyl]amino}benzoate was dissolved in methanol (5 mL) and tetrahydrofuran (5 mL). 2N Lithium hydroxide (2 mL) was added, and the mixture was stirred at 70° C. overnight. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give the title compound (0.2 g, 20%) as an amorphous compound.

$^1$H NMR (300 MHz, CHLOROFORM-d) δ ppm 1.10-1.30 (m, 5H) 1.38-1.95 (m, 5H) 2.03-2.10 (m, 1H) 2.29 (s, 3H) 4.43-4.45 (m, 1H) 6.53 (d, J=9.09 Hz, 2H) 7.00 (s, 1H) 7.13-7.40 (m, 1H) 7.49 (d, J=7.19 Hz, 2H) 7.84 (d, J=9.09 Hz, 2H)

(3) 3-{[(4-{[cyclohexyl(3-methyl-5-phenylthiophen-2-yl)methyl]amino}phenyl)carbonyl]amino}propanoic acid A solution of 4-{[cyclohexyl(3-methyl-5-phenylthiophen-2-yl)methyl]amino}benzoic acid (122 mg) obtained by the above-mentioned reaction, ethyl β-alaninate hydrochloride (55 mg), 1-ethyl-3-(3-dimethylaminopropyl)carbodiimide hydrochloride (69 mg), hydroxybenzotriazole monohydrate (55 mg) and triethylamine (50 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (114 mg, 80%).

$^1$H NMR (300 MHz, DMSO-d$_6$) δ ppm 1.04-1.27 (m, 5H) 1.46-1.78 (m, 5H) 2.13 (d, J=5.27 Hz, 1H) 2.28 (s, 3H) 2.41 (t, J=7.06 Hz, 2H) 3.33 (q, J=6.78 Hz, 2H) 4.25-4.48 (m, 1H) 6.53 (d, J=8.67 Hz, 2H) 6.60 (d, J=6.40 Hz, 1H) 7.17 (s, 1H) 7.20-7.25 (m, 1H) 7.34 (t, J=7.63 Hz, 2H) 7.45-7.58 (m, 3H) 8.00 (brs, 1H)

Example 284

3-{[(4-{[cyclohexyl(3-methyl-5-phenylthiophen-2-yl)methyl]amino}phenyl)carbonyl](methyl)amino}propanoic acid

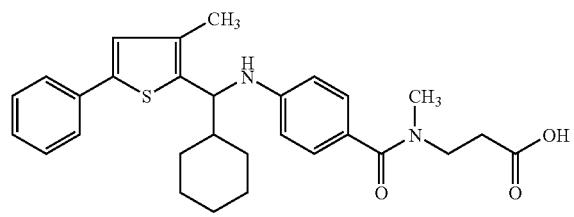

A solution of 4-{[cyclohexyl(3-methyl-5-phenylthiophen-2-yl)methyl]amino}benzoic acid (122 mg), ethyl 3-(methylamino)propanoate (47 mg), 1-ethyl-3-(3-dimethylaminopropyl)carbodiimide hydrochloride (69 mg), hydroxybenzotriazole monohydrate (55 mg) and triethylamine (50 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.6 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (121 mg, 82%).

$^1$H NMR (300 MHz, DMSO-d$_6$) δ ppm 1.03-1.28 (m, 5H) 1.45-1.79 (m, 5H) 2.11 (d, J=6.22 Hz, 1H) 2.28 (s, 3H) 2.46-2.51 (m, 2H) 2.89 (s, 3H) 3.51 (t, J=7.25 Hz, 2H) 4.34 (t, J=7.25 Hz, 1H) 6.41-6.66 (m, 3H) 7.10 (d, J=8.48 Hz, 2H) 7.15-7.29 (m, 2H) 7.34 (t, J=7.63 Hz, 2H) 7.52 (d, J=7.35 Hz, 2H)

Example 285

3-[({4-[(cyclohexyl{2-methyl-5-[4-(trifluoromethyl)phenyl]thiophen-3-yl}methyl)amino]phenyl}carbonyl)amino]propanoic acid

To a mixture of 4-[(cyclohexyl{2-methyl-5-[4-(trifluoromethyl)phenyl]thiophen-3-yl}methyl)amino]benzoic acid (300 mg) synthesized in Example 280-(4), ethyl β-alaninate hydrochloride (117 mg), 1-hydroxybenzotriazole monohydrate (117 mg) and triethylamine (106 μL) in N,N-dimethylformamide (10 mL) was added 1-ethyl-3-(3-dimethylaminopropyl)carbodiimide hydrochloride (146 mg), and the mixture was stirred at room temperature for 5 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 5 hr, and concentrated under reduced pressure. The residue was dissolved in water (10 mL), and 1N hydrochloric acid (1 mL) was added at 0° C. The resulting precipitate was collected by filtration to give the title compound (212 mg, 61%) as a white solid.

$^1$H NMR (300 MHz, CDCl$_3$) δ ppm 0.95-1.34 (m, 5H), 1.53-1.85 (m, 5H), 1.94-2.05 (m, 1H), 2.49 (s, 3H), 2.61 (t, J=5.7 Hz, 2H), 3.56-3.67 (m, 2H), 4.18 (d, J=7.2 Hz, 1H), 6.46 (d, J=8.9 Hz, 2H), 6.59 (t, J=5.8 Hz, 1H), 7.09 (s, 1H), 7.48-7.59 (m, 6H).

Example 286

3-{[(4-{[cyclohexyl(2-methyl-5-phenylthiophen-3-yl)methyl]amino}phenyl)carbonyl]amino}-2-hydroxypropanoic acid

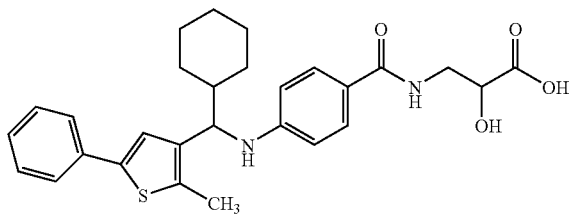

To a mixture of 4-{[cyclohexyl(2-methyl-5-phenylthiophen-3-yl)methyl]amino}benzoic acid (300 mg) synthesized in Example 278-(7), methyl 3-amino-2-hydroxypropanoate hydrochloride (138 mg), 1-hydroxybenzotriazole monohydrate (136 mg) and triethylamine (124 μL) in N,N-dimethylformamide (10 mL) was added 1-ethyl-3-(3-dimethylaminopropyl)carbodiimide hydrochloride (170 mg), and the mixture was stirred at room temperature for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (80% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 4 hr, and concentrated under reduced pressure. The residue was dissolved in water (10 mL), and 1N hydrochloric acid (1 mL) was added at 0° C. The resulting precipitate was collected by filtration to give the title compound (169 mg, 46%) as a white solid.

$^1$H NMR (300 MHz, CDCl$_3$) δ ppm 0.86-1.31 (m, 5H), 1.49-1.83 (m, 5H), 1.87-2.03 (m, 1H), 2.41 (s, 3H), 3.50-3.67 (m, 1H), 3.69-3.86 (m, 1H), 4.06-4.17 (m, 1H), 4.20-4.33 (m, 1H), 6.33-6.48 (m, 2H), 6.77-6.96 (m, 1H), 6.99 (s, 1H), 7.12-7.21 (m, 1H), 7.23-7.33 (m, 2H), 7.42-7.54 (m, 4H).

Example 287

3-({[4-({cyclohexyl[2-ethyl-5-(2-methylpropanoyl)thiophen-3-yl]methyl}amino)phenyl]carbonyl}amino)propanoic acid

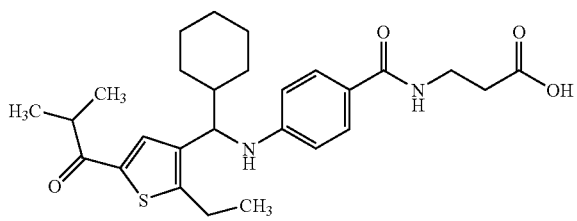

(1) ethyl 2-ethyl-5-formylthiophene-3-carboxylate

To a solution of ethyl 5-bromo-2-ethylthiophene-3-carboxylate (10.0 g) synthesized in Example 69 (4) in tetrahydrofuran (100 was added dropwise 1.0M isopropylmagnesium bromide-tetrahydrofuran solution (45.6 mL) at −45° C., and the mixture was stirred for 2 hr under an argon atmosphere. N,N-Dimethylformamide (8.80 mL) was added, and the mixture was stirred at −45° C. for 1 hr, and then at room temperature for 2 hr. 1N Hydrochloric acid was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (10% ethyl acetate/hexane) to give the title compound (7.82 g, 97%) as a yellow oil.

$^1$H NMR (300 MHz, CDCl$_3$) δ ppm 1.37 (t, J=7.4 Hz, 3H), 1.39 (t, J=7.1 Hz, 3H), 3.29 (q, J=7.4 Hz, 2H), 4.34 (q, J=7.1 Hz, 2H), 8.07 (s, 1H), 9.81 (s, 1H).

(2) ethyl 5-(1,3-dioxolan-2-yl)-2-ethylthiophene-3-carboxylate

To a mixture of ethyl 2-ethyl-5-formylthiophene-3-carboxylate (7.82 g) synthesized above, 1,2-bis(trimethylsiloxy)ethane (9.93 mL) and methylene chloride (80 mL) was added trimethylsilyl trifluoromethanesulfonate (661 μL) at −78° C., and the mixture was stirred for 2 hr under a nitrogen atmosphere. Pyridine (890 μL) was added to quench the reaction, and saturated aqueous sodium hydrogen carbonate solution was added. Methylene chloride was evaporated using evaporator, and the mixture was extracted with ethyl acetate. The extract was washed with saturated aqueous sodium hydrogen carbonate solution and saturated brine, dried over magnesium sulfate and concentrated under reduced pressure to give the title compound (9.71 g, quantitative) as a yellow oil.

$^1$H NMR (300 MHz, CDCl$_3$) δ ppm 1.31 (t, J=7.5 Hz, 3H), 1.35 (t, J=7.2 Hz, 3H), 3.20 (q, J=7.5 Hz, 2H), 3.95-4.18 (m, 4H), 4.29 (q, J=7.2 Hz, 2H), 5.99 (s, 1H), 7.45 (s, 1H)

(3) 5-(1,3-dioxolan-2-yl)-2-ethylthiophene-3-carbaldehyde

To a solution of ethyl 5-(1,3-dioxolan-2-yl)-2-ethylthiophene-3-carboxylate (8.71 g) synthesized above in tetrahydrofuran (170 mL) was added lithium aluminum hydride (2.58 g) at 0° C., and the mixture was stirred for 1 hr. Water (5.20 mL) was added to quench the reaction, 1N aqueous sodium hydroxide solution (5.20 mL) was added, and the mixture was stirred at room temperature for 1 hr. The resulting insoluble material was filtered off, and the filtrate was concentrated under reduced pressure to give a colorless oil. To a solution of the obtained oil in tetrahydrofuran (150 mL) was added activated manganese dioxide (36.0 g), and the mixture was stirred at room temperature for 4.5 hr. Manganese dioxide was filtered off, and the filtrate was concentrated under reduced pressure to give the title compound (6.36 g, 88%) as a yellow oil.

$^1$H NMR (300 MHz, CDCl$_3$) δ ppm 1.37 (t, J=7.5 Hz, 3H), 3.21 (q, J=7.5 Hz, 2H), 3.96-4.18 (m, 4H), 6.00 (s, 1H), 7.43 (s, 1H), 9.97 (s, 1H).

(4) cyclohexyl[5-(1,3-dioxolan-2-yl)-2-ethylthiophen-3-yl]methanol

To a solution of 5-(1,3-dioxolan-2-yl)-2-ethylthiophene-3-carbaldehyde (6.36 g) synthesized above in tetrahydrofuran (130 mL) was added dropwise 1.0M cyclohexylmagnesium bromide-tetrahydrofuran solution (40 mL) at 0° C., and the mixture was stirred for 1.5 hr under an argon atmosphere. Water was added to quench the reaction, tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (30% ethyl acetate/hexane) to give the title compound (6.30 g, 71%) as a pale-yellow oil.

$^1$H NMR (300 MHz, CDCl$_3$) δ ppm 0.76-0.92 (m, 1H), 0.95-1.30 (m, 7H), 1.32-1.42 (m, 1H), 1.53-1.68 (m, 3H), 1.73-1.82 (m, 1H), 2.05-2.14 (m, 1H), 2.68-2.90 (m, 2H), 3.94-4.19 (m, 4H), 4.38 (dd, J=8.1, 3.0 Hz, 1H), 5.99 (s, 1H), 7.05 (s, 1H).

(5) 2-{4-[chloro(cyclohexyl)methyl]-5-ethylthiophen-2-yl}-1,3-dioxolane

To a solution of cyclohexyl[5-(1,3-dioxolan-2-yl)-2-ethylthiophen-3-yl]methanol (3.00 g) synthesized above in toluene (60 mL) were added pyridine (979 μL) and thionyl chloride (883 μL) at 0° C., and the mixture was stirred at 0° C. for 1.5 hr, and then at room temperature for 30 min. Saturated aqueous sodium hydrogen carbonate solution was added to quench the reaction, and the mixture was extracted with ethyl acetate. The extract was washed with saturated brine, dried over magnesium sulfate and concentrated under reduced pressure to give the title compound (3.28 g, quantitative) as a pale-yellow oil.

$^1$H NMR (300 MHz, CDCl$_3$) δ 0.74-0.90 (m, 1H), 0.95-1.38 (m, 7H), 1.44-1.54 (m, 1H), 1.59-1.72 (m, 2H), 1.74-1.90 (m, 2H), 2.21-2.32 (m, 1H), 2.66-2.86 (m, 2H), 3.95-4.18 (m, 4H), 4.65 (d, J=9.3 Hz, 1H), 5.99 (s, 1H), 7.06 (s, 1H).

(6) methyl 4-{[cyclohexyl(2-ethyl-5-formylthiophen-3-yl)methyl]amino}benzoate To a mixture of 2-{4-[chloro(cyclohexyl)methyl]-5-ethylthiophen-2-yl}-1,3-dioxolane (3.08 g) synthesized above, methyl 4-aminobenzoate (2.96 g), sodium iodide (2.98 g) and N,N-dimethylacetamide (60 mL) sodium carbonate (2.08 g) was added, and the mixture was stirred overnight at 100° C. under an argon atmosphere. Water was added to quench the reaction, and the mixture was extracted with ethyl acetate. The extract was washed with saturated brine, dried over magnesium sulfate, and concentrated under reduced pressure. The residue was purified by silica gel column chromatography (30% ethyl acetate/hexane) to give a yellow oil. To a solution of the obtained oil in tetrahydrofuran (40 mL) was added 1N hydrochloric acid (10 mL), and the mixture was stirred at room temperature for 1 hr. Tetrahydrofuran was evaporated using evaporator, and the mixture was extracted with ethyl acetate. The extract was washed with saturated brine, dried over magnesium sulfate, and concentrated under reduced pressure. The residue was purified by silica gel column chromatography (40% ethyl acetate/hexane) to give the title compound (2.05 g, 54%) as a yellow solid.

$^1$H NMR (300 MHz, CDCl$_3$) δ ppm 0.97-1.30 (m, 5H), 1.41 (t, J=7.5 Hz, 3H), 1.51-1.86 (m, 5H), 1.90-2.00 (m, 1H), 2.81-3.03 (m, 2H), 3.81 (s, 3H), 4.25-4.30 (m, 1H), 4.45 (d, J=6.6 Hz, 1H), 6.42 (d, J=8.9 Hz, 2H), 7.50 (s, 1H), 7.77 (d, J=8.9 Hz, 2H), 9.71 (s, 1H).

(7) methyl 4-({cyclohexyl[2-ethyl-5-(2-methylpropanoyl)thiophen-3-yl]methyl}amino)benzoate To a solution of methyl 4-{[cyclohexyl(2-ethyl-5-formylthiophen-3-yl)methyl]amino}benzoate (400 mg) synthesized above in tetrahydrofuran (10 mL) was added dropwise 1.0M isopropylmagnesium bromide-tetrahydrofuran solution (1.25 mL) at 0° C., and the mixture was stirred for 1 hr under a nitrogen atmosphere. 1.0M Isopropylmagnesium bromide-tetrahydrofuran solution (1.25 mL) was added dropwise again, and the mixture was further stirred at 0° C. for 1 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by NH-silica gel column chromatography (ethyl acetate) to give a yellow oil. To a solution of the obtained oil in methylene chloride (10 mL) was added Dess-Martin reagent (662 mg) at 0° C., and the mixture was stirred for 1 hr. Saturated aqueous sodium sulfite solution was added to quench the reaction, methylene chloride was evaporated using evaporator, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (15% ethyl acetate/hexane) to give the title compound (268 mg, 60%) as a pale-yellow oil.

$^1$H NMR (300 MHz, CDCl$_3$) δ ppm 0.95-1.32 (m, 11H), 1.38 (t, J=7.5 Hz, 3H), 1.50-1.84 (m, 5H), 1.91-2.02 (m, 1H), 2.80-3.04 (m, 2H), 3.17-3.33 (m, 1H), 3.81 (s, 3H), 4.20-4.29 (m, 1H), 4.48 (d, J=6.0 Hz, 1H), 6.44 (d, J=8.7 Hz, 2H), 7.46 (s, 1H), 7.77 (d, J=8.7 Hz, 2H).

(8) 4-({cyclohexyl[2-ethyl-5-(2-methylpropanoyl)thiophen-3-yl]methyl}amino)benzoic acid To a mixture of methyl 4-({cyclohexyl[2-ethyl-5-(2-methylpropanoyl)thiophen-3-yl]methyl}amino)benzoate (268 mg) synthesized above, tetrahydrofuran (5 mL) and ethanol (5 mL) was added 1N aqueous sodium hydroxide solution (5 mL), and the mixture was stirred with heated under reflux for 2 hr. To the reaction mixture was added 1N hydrochloric acid (10 mL), and the mixture was extracted with ethyl acetate. The extract was washed with saturated brine, dried over magnesium sulfate and concentrated under reduced pressure to give the title compound (280 mg, quantitative) as a pale-brown solid.

$^1$H NMR (300 MHz, CDCl$_3$) δ ppm 0.93-1.29 (m, 11H), 1.38 (t, J=7.5 Hz, 3H), 1.50-1.85 (m, 5H), 1.91-2.01 (m, 1H), 2.80-3.04 (m, 2H), 3.18-3.33 (m, 1H), 4.27 (d, J=7.2 Hz, 1H), 6.45 (d, J=9.2 Hz, 2H), 7.46 (s, 1H), 7.82 (d, J=9.2 Hz, 2H).

(9) 3-({[4-({cyclohexyl[2-ethyl-5-(2-methylpropanoyl)thiophen-3-yl]methyl}amino)phenyl]carbonyl}amino)propanoic acid To a mixture of 4-({cyclohexyl[2-ethyl-5-(2-methylpropanoyl)thiophen-3-yl]methyl}amino)benzoic acid (140 mg) synthesized above, ethyl β-alaninate hydrochloride (62.5 mg), 1-hydroxybenzotriazole monohydrate (62.3 mg) and triethylamine (57 µL) in N,N-dimethylformamide (10 mL) was added 1-ethyl-3-(3-dimethylaminopropyl)carbodiimide hydrochloride (78.0 mg), and the mixture was stirred at room temperature for 2.5 days. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (40% ethyl acetate/hexane), and then purified by NH-silica gel column chromatography (ethyl acetate) to give a colorless oil. To a mixture of the obtained oil, tetrahydrofuran (5 mL) and ethanol (5 mL) was added 1N aqueous sodium hydroxide solution (1 mL), and the mixture was stirred at room temperature for 1 hr, and concentrated under reduced pressure. The residue was dissolved in water (10 mL), and 1N hydrochloric acid (1 mL) was added at 0° C. The resulting precipitate was collected by filtration to give the title compound (116 mg, 70%) as a white solid.

$^1$H NMR (300 MHz, CDCl$_3$) δ ppm 0.92-1.29 (m, 11H), 1.37 (t, J=7.4 Hz, 3H), 1.48-1.85 (m, 5H), 1.90-2.04 (m, 1H), 2.58-2.67 (m, 2H), 2.79-3.04 (m, 2H), 3.17-3.34 (m, 1H), 3.57-3.70 (m, 2H), 4.23 (d, J=7.2 Hz, 1H), 6.44 (d, J=8.7 Hz, 2H), 6.63-6.75 (m, 1H), 7.45-7.57 (m, 3H).

Example 288

3-[{[4-({cyclohexyl[2-ethyl-5-(2-methylpropanoyl)thiophen-3-yl]methyl}amino)phenyl]carbonyl}(methyl)amino]propanoic acid

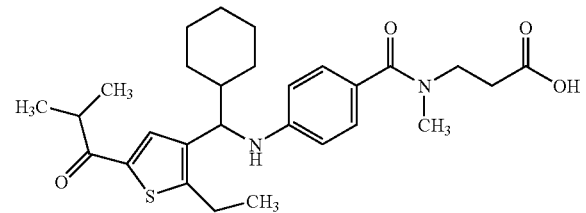

To a mixture of 4-({cyclohexyl[2-ethyl-5-(2-methylpropanoyl)thiophen-3-yl]methyl}amino)benzoic acid (139 mg) synthesized in Example 287 (8), ethyl 3-(methylamino)propanoate (53.0 mg), 1-hydroxybenzotriazole monohydrate (61.9 mg) and triethylamine (56 µL) in N,N-dimethylformamide (10 mL) 1-ethyl-3-(3-dimethylaminopropyl)carbodiimide hydrochloride (77.4 mg) was added, and the mixture was stirred at room temperature for 2.5 days. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (40% ethyl acetate/hexane), and then purified by NH-silica gel column chromatography (ethyl acetate) to give a colorless oil. To a mixture of the obtained oil, tetrahydrofuran (5 mL) and ethanol (5 mL) was added 1N aqueous sodium hydroxide solution (1 mL), and the mixture was stirred at room temperature for 1 hr, and concentrated under reduced pressure. The residue was dissolved in water (10 mL), and 1N hydrochloric acid (1 mL) was added at 0° C. The resulting precipitate was collected by filtration to give the title compound (101 mg, 60%) as a white solid.

$^1$H NMR (300 MHz, CDCl$_3$) δ ppm 0.92-1.31 (m, 11H), 1.37 (t, J=7.6 Hz, 3H), 1.48-1.85 (m, 5H), 1.89-2.03 (m, 1H), 2.60-2.70 (m, 2H), 2.79-3.08 (m, 5H), 3.19-3.35 (m, 1H), 3.70 (t, J=6.2 Hz, 2H), 4.21 (d, J=6.8 Hz, 1H), 6.43 (d, J=8.3 Hz, 2H), 7.21 (d, J=8.3 Hz, 2H), 7.49 (s, 1H).

Example 289

3-1{[(4-{[(5-butanoyl-2-ethylthiophen-3-yl)(cyclohexyl)methyl]amino}phenyl)carbonyl]amino}propanoic acid

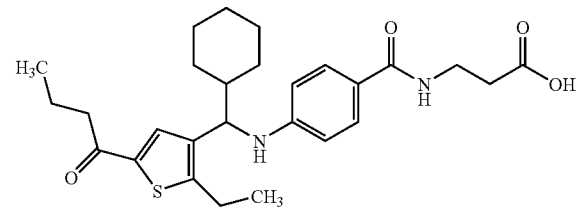

(1) methyl 4-{[(5-butanoyl-2-ethylthiophen-3-yl)(cyclohexyl)methyl]amino}benzoate To a solution of methyl 4-{[cyclohexyl(2-ethyl-5-formylthiophen-3-yl)methyl]amino}benzoate (500 mg) synthesized in Example 287 (6) in tetrahydrofuran (10 mL) was added dropwise 2.0M n-propylmagnesium chloride-diethyl ether solution (1.63 mL) at −45° C., and the mixture was stirred for 2 hr under a nitrogen atmosphere. Saturated aqueous ammonium chloride solution was added to quench the reaction, and the mixture was extracted with ethyl acetate. The extract was washed with saturated brine, dried over magnesium sulfate and concentrated under reduced pressure to give a yellow oil. To a solution of the obtained oil in methylene chloride (10 mL) was added Dess-Martin reagent (827 mg) at 0° C., and the mixture was stirred for 1 hr. Saturated aqueous sodium sulfite solution was added to quench the reaction, methylene chloride was evaporated using evaporator, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (25% ethyl acetate/hexane) to give the title compound (316 mg, 57%) as a colorless oil.

$^1$H NMR (300 MHz, CDCl$_3$) δ ppm 0.92-1.32 (m, 8H), 1.38 (t, J=7.5 Hz, 3H), 1.49-1.85 (m, 7H), 1.92-2.02 (m, 1H), 2.72-2.79 (m, 2H), 2.80-3.04 (m, 2H), 3.81 (s, 3H), 4.21-4.28 (m, 1H), 4.42 (d, J=6.3 Hz, 1H), 6.43 (d, J=8.7 Hz, 2H), 7.42 (s, 1H), 7.77 (d, J=8.7 Hz, 2H).

(2) 4-{[(5-butanoyl-2-ethylthiophen-3-yl)(cyclohexyl)methyl]amino}benzoic acid To a mixture of methyl 4-{[(5-butanoyl-2-ethylthiophen-3-yl)(cyclohexyl)methyl]amino}benzoate (316 mg) synthesized above, tetrahydrofuran (5 mL) and ethanol (5 mL) was added 1N aqueous sodium hydroxide solution (5 and the mixture was stirred with heating under reflux for 3 hr, and concentrated under reduced pressure. The residue was dissolved in water (10 mL), and 1N hydrochloric acid (5 mL) was added at 0° C. The resulting precipitate was collected by filtration to give the title compound (290 mg, 95%) as a white solid.

$^1$H NMR (300 MHz, CDCl$_3$) δ ppm 0.91-1.33 (m, 8H), 1.38 (t, J=7.4 Hz, 3H), 1.48-1.85 (m, 7H), 1.91-2.02 (m, 1H), 2.77 (t, J=7.2 Hz, 2H), 2.80-3.05 (m, 2H), 4.26 (d, J=7.2 Hz, 1H), 6.44 (d, J=8.7 Hz, 2H), 7.44 (s, 1H), 7.82 (d, J=8.7 Hz, 2H).

(3) 3-{[(4-{[(5-butanoyl-2-ethylthiophen-3-yl)(cyclohexyl)methyl]amino}phenyl)carbonyl]amino}propanoic acid To a mixture of 4-{[(5-butanoyl-2-ethylthiophen-3-yl)(cyclohexyl)methyl]amino}benzoic acid (125 mg) synthesized above, ethyl β-alaninate hydrochloride (69.6 mg), 1-hydroxybenzotriazole monohydrate (69.4 mg) and triethylamine (63 μL) in N,N-dimethylformamide (10 mL) was added 1-ethyl-3-(3-dimethylaminopropyl)carbodiimide hydrochloride (86.8 mg), and the mixture was stirred at room temperature for 5 hr. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 3 hr, and concentrated under reduced pressure. The residue was dissolved in water (10 mL), and 1N hydrochloric acid (1 mL) was added at 0° C. The resulting precipitate was collected by filtration to give the title compound (93.1 mg, 64%) as a white solid.

$^1$H NMR (300 MHz, CDCl$_3$) δ ppm 0.90-1.30 (m, 8H), 1.36 (t, J=7.6 Hz, 3H), 1.46-1.85 (m, 7H), 1.90-2.02 (m, 1H), 2.50-2.63 (m, 2H), 2.70-2.79 (m, 2H), 2.79-3.03 (m, 2H), 3.53-3.67 (m, 2H), 4.21 (d, J=7.2 Hz, 1H), 6.42 (d, J=8.3 Hz, 2H), 6.71-6.83 (m, 1H), 7.48 (s, 1H), 7.51 (d, J=8.3 Hz, 2H).

Example 290

3-{[(4-{[(5-butanoyl-2-ethylthiophen-3-yl)(cyclohexyl)methyl]amino}phenyl)carbonyl](methyl)amino}propanoic acid

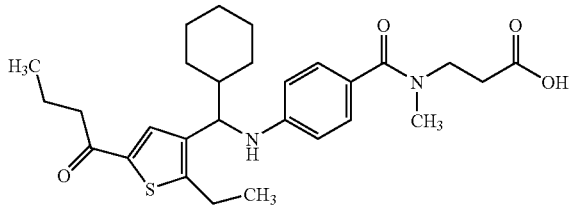

To a mixture of 4-{[(5-butanoyl-2-ethylthiophen-3-yl)(cyclohexyl)methyl]amino}benzoic acid (125 mg) synthesized in Example 289 (2), ethyl 3-(methylamino)propanoate (59.4 mg), 1-hydroxybenzotriazole monohydrate (69.4 mg) and triethylamine (63 μL) in N,N-dimethylformamide (10 mL) was added 1-ethyl-3-(3-dimethylaminopropyl)carbodiimide hydrochloride (86.8 mg), and the mixture was stirred at room temperature for 8 hr. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 4 hr, and concentrated under reduced pressure. The residue was dissolved in water (1 mL), and 1N hydrochloric acid (10 mL) was added at 0° C. The resulting precipitate was collected by filtration to give the title compound (93.4 mg, 62%) as a white solid.

$^1$H NMR (300 MHz, CDCl$_3$) δ ppm 0.91-1.32 (m, 8H), 1.37 (t, J=7.6 Hz, 3H), 1.47-1.84 (m, 7H), 1.90-2.03 (m, 1H), 2.57-2.66 (m, 2H), 2.77 (t, J=7.2 Hz, 2H), 2.82-3.01 (m, 2H), 3.02 (s, 3H), 3.69 (t, J=6.4 Hz, 2H), 4.20 (d, J=7.2 Hz, 1H), 6.43 (d, J=8.7 Hz, 2H), 7.20 (d, J=8.3 Hz, 2H), 7.47 (s, 1H).

Example 291

3-({[4-({cyclohexyl[5-(cyclohexylcarbonyl)-2-ethylthiophen-3-yl]methyl}amino)phenyl]carbonyl}amino)propanoic acid

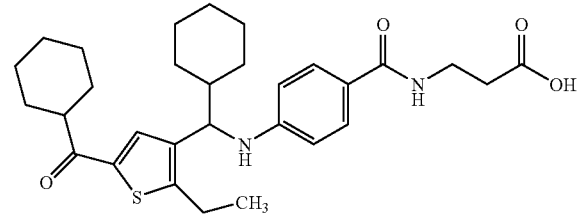

(1) methyl 4-({cyclohexyl[5-(cyclohexylcarbonyl)-2-ethylthiophen-3-yl]methyl}amino)benzoate To a solution of methyl 4-{[cyclohexyl(2-ethyl-5-formylthiophen-3-yl)methyl]amino}benzoate (500 mg) synthesized in Example 287 (6) in tetrahydrofuran (10 mL) was added dropwise 1.0M cyclohexylmagnesium bromide-tetrahydrofuran solution (3.25 mL) at −45° C., and the mixture was stirred for 1 hr. Saturated aqueous ammonium chloride solution was added to quench the reaction, and the mixture was extracted with ethyl acetate. The extract was washed with saturated brine, dried over magnesium sulfate and concentrated under reduced pressure to give a yellow oil. To a solution of the obtained oil in methylene chloride (10 mL) was added Dess-Martin reagent (827 mg) at 0° C., and the mixture was stirred for 1 hr. Saturated aqueous sodium sulfite solution was added to quench the reaction, methylene chloride was evaporated using evaporator, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (20% ethyl acetate/hexane) to give the title compound (347 mg, 57%) as a pale-brown oil.

$^1$H NMR (300 MHz, CDCl$_3$) δ ppm 0.94-1.41 (m, 12H), 1.43-1.59 (m, 3H), 1.60-1.90 (m, 8H), 1.92-2.02 (m, 1H), 2.80-3.03 (m, 3H), 3.81 (s, 3H), 4.20-4.28 (m, 1H), 4.41 (d, J=6.6 Hz, 1H), 6.44 (d, J=8.9 Hz, 2H), 7.43 (s, 1H), 7.77 (d, J=8.9 Hz, 2H).

(2) 4-({cyclohexyl[5-(cyclohexylcarbonyl)-2-ethylthiophen-3-yl]methyl}amino)benzoic acid To a mixture of methyl 4-({cyclohexyl[5-(cyclohexylcarbonyl)-2-ethylthiophen-3-yl]methyl}amino)benzoate (347 mg) synthesized above, tetrahydrofuran (5 mL) and ethanol (5 mL) was added 1N aqueous sodium hydroxide solution (5 mL), and the mixture was stirred with heating under reflux overnight, and concentrated under reduced pressure. The residue was dissolved in water (30 mL), and 1N hydrochloric acid (5 mL) was added at 0° C. The resulting precipitate was collected by filtration to give the title compound (296 mg, 88%) as a white solid.

$^1$H NMR (300 MHz, CDCl$_3$) δ ppm 0.92-1.43 (m, 10H), 1.44-1.59 (m, 3H), 1.59-1.91 (m, 10H), 1.92-2.03 (m, 1H), 2.80-3.05 (m, 3H), 4.26 (d, J=7.2 Hz, 1H), 6.46 (d, J=8.9 Hz, 2H), 7.44 (s, 1H), 7.83 (d, J=8.9 Hz, 2H).

(3) 3-({[4-({cyclohexyl[5-(cyclohexylcarbonyl)-2-ethylthiophen-3-yl]methyl}amino)phenyl]carbonyl}amino)propanoic acid To a mixture of 4-({cyclohexyl[5-(cyclohexylcarbonyl)-2-ethylthiophen-3-yl]methyl}amino)benzoic acid (130 mg) synthesized above, ethyl β-alaninate hydrochloride (66.2 mg), 1-hydroxybenzotriazole monohydrate (66.0 mg) and triethylamine (60 μL) in N,N-dimethylformamide (10 mL) was added 1-ethyl-3-(3-dimethylaminopropyl)carbodiimide hydrochloride (82.6 mg), and the mixture was stirred at room temperature overnight. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 5 hr, and concentrated under reduced pressure. The residue was dissolved in water (10 mL), and 1N hydrochloric acid (1 mL) was added at 0° C. The resulting precipitate was collected by filtration to give the title compound (125 mg, 83%) as a white solid.

$^1$H NMR (300 MHz, CDCl$_3$) δ ppm 0.91-1.42 (m, 11H), 1.42-1.58 (m, 3H), 1.58-1.91 (m, 9H), 1.93-2.04 (m, 1H), 2.51-2.64 (m, 2H), 2.79-3.04 (m, 3H), 3.55-3.68 (m, 2H), 4.21 (d, J=7.6 Hz, 1H), 6.43 (d, J=8.7 Hz, 2H), 6.71-6.82 (m, 1H), 7.47-7.57 (m, 3H).

Example 292

3-[{[4-({cyclohexyl[5-(cyclohexylcarbonyl)-2-ethylthiophen-3-yl]methyl}amino)phenyl]carbonyl}(methyl)amino]propanoic acid

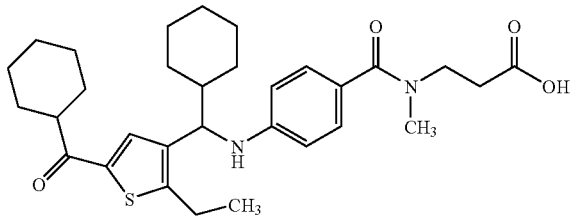

To a mixture of 4-({cyclohexyl[5-(cyclohexylcarbonyl)-2-ethylthiophen-3-yl]methyl}amino)benzoic acid (130 mg) synthesized in Example 291 (2), ethyl 3-(methylamino)propanoate (56.5 mg), 1-hydroxybenzotriazole monohydrate (66.0 mg) and triethylamine (60 μL) in N,N-dimethylformamide (10 mL) was added 1-ethyl-3-(3-dimethylaminopropyl)carbodiimide hydrochloride (82.6 mg), and the mixture was stirred at room temperature overnight. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 3 hr, and concentrated under reduced pressure. The residue was dissolved in water (10 mL), and 1N hydrochloric acid (1 mL) was added at 0° C. The resulting precipitate was collected by filtration to give the title compound (118 mg, 77%) as a pale-yellow solid.

$^1$H NMR (300 MHz, CDCl$_3$) δ ppm 0.92-1.44 (m, 11H), 1.44-1.58 (m, 3H), 1.59-1.91 (m, 9H), 1.92-2.03 (m, 1H), 2.58-2.70 (m, 2H), 2.80-3.07 (m, 6H), 3.70 (t, J=6.4 Hz, 2H), 4.20 (d, J=7.2 Hz, 1H), 6.43 (d, J=8.6 Hz, 2H), 7.21 (d, J=8.6 Hz, 2H), 7.47 (s, 1H).

Example 293

3-({[4-({cyclohexyl[2-ethyl-5-(1-hydroxy-2-methylpropyl)thiophen-3-yl]methyl}amino)phenyl]carbonyl}amino)propanoic acid

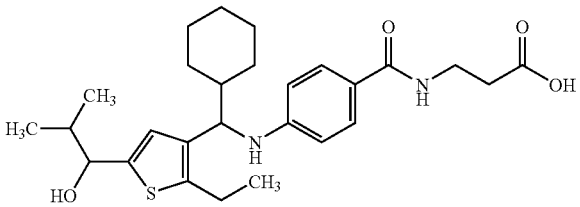

(1) 4-({cyclohexyl[2-ethyl-5-(1-hydroxy-2-methylpropyl)thiophen-3-yl]methyl}amino)benzoic acid To a solution of methyl 4-{[cyclohexyl(2-ethyl-5-formylthiophen-3-yl)methyl]amino}benzoate (540 mg) synthesized in Example 287 (6) in tetrahydrofuran (10 mL) was added dropwise 1.0M isopropylmagnesium bromide-tetrahydrofuran solution (3.50 mL) at −45° C., and the mixture was stirred for 3 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (25% ethyl acetate/hexane) to give a yellow oil. To a mixture of the obtained oil, tetrahydrofuran (5 mL) and ethanol (5 mL) was added 1N aqueous sodium hydroxide solution (5 mL), and the mixture was stirred with heated under reflux for 5 hr, and concentrated under reduced pressure. The residue was dissolved in water (10 mL), and 1N hydrochloric acid (5 mL) was added at 0° C. The resulting precipitate was collected by filtration to give the title compound (350 mg, 60%) as a pale-yellow solid. The obtained resultant product was a mixture of two diastereomers (about 2:3).

$^1$H NMR (300 MHz, CDCl$_3$) δ ppm 0.74 (d, J=6.8 Hz, 1.2H), 0.80 (d, J=6.8 Hz, 1.8H), 0.91-1.37 (m, 11H), 1.46-2.03 (m, 7H), 2.72-3.06 (m, 2H), 4.22 (d, J=7.3 Hz, 1H), 4.44 (d, J=7.0 Hz, 1H), 6.41-6.51 (m, 2H), 6.60-6.64 (m, 1H), 7.78-7.87 (m, 2H).

(2) 3-({[4-({cyclohexyl[2-ethyl-5-(1-hydroxy-2-methylpropyl)thiophen-3-yl]methyl}amino)phenyl]carbonyl}amino)propanoic acid To a mixture of 4-({cyclohexyl[2-ethyl-5-(1-hydroxy-2-methylpropyl)thiophen-3-yl]methyl}amino)benzoic acid (150 mg) synthesized above, ethyl β-alaninate hydrochloride (83.3 mg), 1-hydroxybenzotriazole monohydrate (83.0 mg) and triethylamine (76 μL) in N,N-dimethylformamide (10 mL) was added 1-ethyl-3-(3-dimethylaminopropyl)carbodiimide hydrochloride (104 mg), and the mixture was stirred at room temperature overnight. Saturated aqueous ammonium chloride solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 2.5 hr, and concentrated under reduced pressure. The residue was dissolved in water (10 mL), and 1N hydrochloric acid (1 mL) was added at 0° C. The resulting precipitate was collected by filtration to give the title compound (135 mg, 77%) as a white solid. The obtained resultant product was a mixture of two diastereomers.

$^1$H NMR (300 MHz, CDCl$_3$) δ ppm 0.74-0.83 (m, 3H), 0.91-1.27 (m, 8H), 1.30 (t, J=7.5 Hz, 3H), 1.45-2.04 (m, 7H), 2.58 (t, J=5.6 Hz, 2H), 2.72-2.95 (m, 2H), 3.52-3.63 (m, 2H), 4.17 (d, J=7.3 Hz, 1H), 4.39-4.47 (m, 1H), 6.37-6.46 (m, 2H), 6.57-6.69 (m, 2H), 7.40-7.49 (m, 2H).

Example 294

3-[{[4-({cyclohexyl[2-ethyl-5-(1-hydroxy-2-methylpropyl)thiophen-3-yl]methyl}amino)phenyl]carbonyl}(methyl)amino]propanoic acid

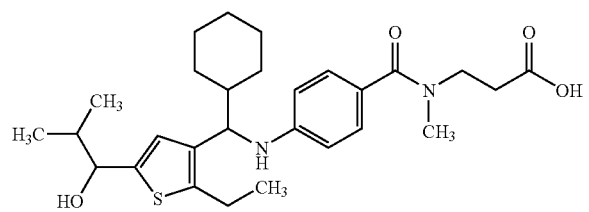

To a mixture of 4-({cyclohexyl[2-ethyl-5-(1-hydroxy-2-methylpropyl)thiophen-3-yl]methyl}amino)benzoic acid (150 mg) synthesized in Example 293 (1), ethyl 3-(methylamino)propanoate (71.1 mg), 1-hydroxybenzotriazole monohydrate (83.0 mg) and triethylamine (76 μL) in N,N-dimethylformamide (10 mL) was added 1-ethyl-3-(3-dimethylaminopropyl)carbodiimide hydrochloride (104 mg), and the mixture was stirred at room temperature overnight. Saturated aqueous ammonium chloride solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature for 2 hr, and concentrated under reduced pressure. The residue was dissolved in water (10 mL), and 1N hydrochloric acid (1 mL) was added at 0° C. The resulting precipitate was collected by filtration to give the title compound (132 mg, 73%) as a white solid. The obtained resultant product was a mixture of two diastereomers (about 2:3).

$^1$H NMR (300 MHz, CDCl$_3$) δ ppm 0.74 (d, J=6.4 Hz, 1.2H), 0.79 (d, J=6.8 Hz, 1.8H), 0.90-1.36 (m, 11H), 1.46-2.03 (m, 7H), 2.56-2.69 (m, 2H), 2.73-2.95 (m, 2H), 3.04 (s, 3H), 3.63-3.74 (m, 2H), 4.17 (d, J=7.2 Hz, 1H), 4.39-4.47 (m, 1H), 6.44 (d, J=8.3 Hz, 2H), 6.59 (s, 0.6H), 6.63 (s, 0.4H), 7.19 (d, J=8.3 Hz, 2H).

Example 295

3-[({4-[(cyclohexyl{2-methyl-5-[4-(trifluoromethyl)phenyl]thiophen-3-yl}methyl)amino]phenyl}carbonyl)amino]-2-hydroxypropanoic acid

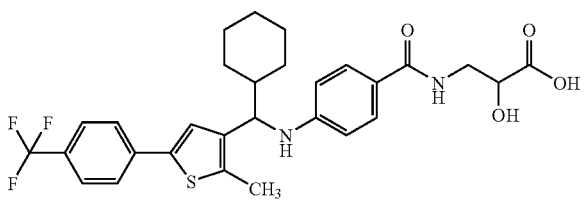

To a mixture of 4-[(cyclohexyl{2-methyl-5-[4-(trifluoromethyl)phenyl]thiophen-3-yl}methyl)amino]benzoic acid (300 mg) synthesized in Example 280 (4), methyl 3-amino-2-hydroxypropanoate hydrochloride (118 mg), 1-hydroxybenzotriazole monohydrate (117 mg) and triethylamine (106 μL) in N,N-dimethylformamide (10 mL) was added 1-ethyl-3-(3-dimethylaminopropyl)carbodiimide hydrochloride (146 mg), and the mixture was stirred at 50° C. for 1 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (70% ethyl acetate/hexane) to give colorless oil. To a mixture of the obtained oil, tetrahydrofuran (5 mL) and ethanol (5 mL) was added 1N aqueous sodium hydroxide solution (1 mL), and the mixture was stirred at room temperature overnight, and concentrated under reduced pressure. The residue was dissolved in water (10 mL), 1N hydrochloric acid (1 mL) was added at 0° C., and the resulting precipitate was collected by filtration to give a white solid. The obtained solid was dissolved in ethyl acetate, dried over magnesium sulfate, and concentrated under reduced pressure to give the title compound (190 mg, 53%) as a white solid.

$^1$H NMR (300 MHz, CDCl$_3$) δ ppm 0.96-1.31 (m, 5H), 1.55-1.87 (m, 5H), 1.95-2.06 (m, 1H), 2.50 (s, 3H), 3.65-3.78

(m, 1H), 3.83-3.95 (m, 1H), 4.20 (d, J=7.3 Hz, 1H), 4.29-4.36 (m, 1H), 6.47 (d, J=8.7 Hz, 2H), 6.69-6.77 (m, 1H), 7.08 (s, 1H), 7.49-7.59 (m, 6H).

Example 296

3-({[4-({1-[5-(6-methoxypyridin-3-yl)-2-methylthiophen-3-yl]-3-methylbutyl}amino)phenyl]carbonyl}amino)propanoic acid

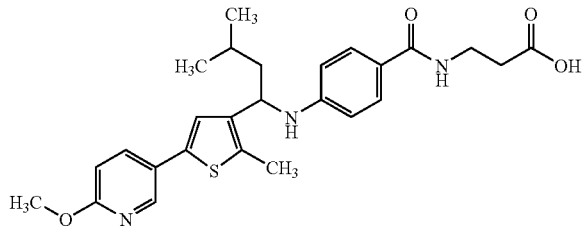

(1) 5-(6-methoxypyridin-3-yl)-2-methylthiophene-3-carbaldehyde

A mixture of 2-(5-bromo-2-methylthiophen-3-yl)-1,3-dioxolane (1.7 g), 2-methoxy-5-pyridineboronic acid (1.3 g), tetrakis(triphenylphosphine)palladium(0) (0.4 g), 2N aqueous sodium carbonate solution (10 mL) and 1,2-dimethoxyethane (20 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 30% ethyl acetate/hexane) to give 5-[4-(1,3-dioxolan-2-yl)-5-methylthiophen-2-yl]-2-methoxypyridine as an oil. The obtained 5-[4-(1,3-dioxolan-2-yl)-5-methylthiophen-2-yl]-2-methoxypyridine was dissolved in tetrahydrofuran (10 mL), 1N hydrochloric acid (10 mL) was added, and the mixture was stirred at room temperature for 1 hr. The reaction mixture was poured into water, and the mixture was extracted with ethyl acetate. The organic layer was washed with saturated brine, and dried over magnesium sulfate, the solvent was evaporated under reduced pressure, and the residue was crystallized from ethyl acetate/hexane to give the title compound (1.2 g, 75%) as a white solid.

$^1$H NMR (300 MHz, CHLOROFORM-d) δ ppm 2.80 (s, 3H) 3.97 (s, 3H) 6.80 (d, J=0.75 Hz, 1H) 7.46 (s, 1H) 7.74 (dd, J=8.57, 2.54 Hz, 1H) 8.37 (d, J=1.88 Hz, 1H) 10.03 (s, 1H)

(2) 1-[5-(6-methoxypyridin-3-yl)-2-methylthiophen-3-yl]-3-methylbutan-1-ol

To a solution of 5-(6-methoxypyridin-3-yl)-2-methylthiophene-3-carbaldehyde (1.2 g) obtained by the above-mentioned reaction in tetrahydrofuran (20 mL) was added 1N isobutylmagnesium bromide-tetrahydrofuran solution (7.5 mL) at 0° C. and, after the completion of the dropwise addition, the mixture was stirred at 0° C. for 30 min. The reaction mixture was treated with 1N hydrochloric acid and poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 30% ethyl acetate/hexane) to give the title compound (1.2 g, 82%) as an oil.

$^1$H NMR (300 MHz, CHLOROFORM-d) δ ppm 0.96 (dd, J=6.44, 1.89 Hz, 6H) 1.45-1.61 (m, 1H) 1.66 (d, J=3.41 Hz, 1H) 1.67-1.88 (m, 2H) 2.44 (s, 3H) 3.95 (s, 3H) 4.85 (td, J=5.40, 2.84 Hz, 1H) 6.74 (d, J=8.71 Hz, 1H) 7.13 (s, 1H) 7.72 (dd, J=8.71, 2.65 Hz, 1H) 8.34 (d, J=1.89 Hz, 1H)

(3) 5-[4-(1-chloro-3-methylbutyl)-5-methylthiophen-2-yl]-2-methoxypyridine

To a solution of 1-[5-(6-methoxypyridin-3-yl)-2-methylthiophen-3-yl]-3-methylbutan-1-ol (1.2 g) obtained by the above-mentioned reaction in toluene (20 mL) were added thionyl chloride (0.4 mL) and pyridine (0.5 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (1.2 g, 100%) as an oil.

$^1$H NMR (300 MHz, CHLOROFORM-d) δ ppm 0.95 (d, J=6.82 Hz, 6H) 1.72-1.92 (m, 2H) 2.04-2.15 (m, 1H) 2.46 (s, 3H) 3.96 (s, 3H) 5.05 (dd, J=8.33, 6.82 Hz, 1H) 6.75 (d, J=8.71 Hz, 1H) 7.13 (s, 1H) 7.73 (dd, J=8.71, 2.65 Hz, 1H) 8.35 (d, J=2.65 Hz, 1H)

(4) 4-({1-[5-(6-methoxypyridin-3-yl)-2-methylthiophen-3-yl]-3-methylbutyl}amino)benzoic acid A mixture of 5-[4-(1-chloro-3-methylbutyl)-5-methylthiophen-2-yl]-2-methoxypyridine (1.2 g) obtained by the above-mentioned reaction, methyl 4-aminobenzoate (0.9 g), sodium carbonate (0.6 g) and sodium iodide (1.2 g) in N,N-dimethylacetamide (10 mL) was stirred overnight at 100° C. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (4 mL) was added, and the mixture was stirred at 80° C. for 2 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (5% ethyl acetate/hexane to 40% ethyl acetate/hexane) to give the title compound (0.7 g, 40%) as an amorphous compound.

$^1$H NMR (300 MHz, CHLOROFORM-d) δ ppm 0.98 (dd, J=16.09, 6.25 Hz, 6H) 1.52-1.74 (m, 3H) 2.50 (s, 3H) 3.93 (s, 3H) 4.53 (t, J=6.82 Hz, 1H) 6.51 (d, J=9.09 Hz, 2H) 6.71 (d, J=7.95 Hz, 1H) 6.96 (s, 1H) 7.66 (dd, J=8.52, 2.46 Hz, 1H) 7.85 (d, J=9.09 Hz, 2H) 8.29 (d, J=2.65 Hz, 1H)

(5) 3-({[4-({1-[5-(6-methoxypyridin-3-yl)-2-methylthiophen-3-yl]-3-methylbutyl}amino)phenyl]carbonyl}amino)propanoic acid A solution of 4-({1-[5-(6-methoxypyridin-3-yl)-2-methylthiophen-3-yl]-3-methylbutyl}amino)benzoic acid (328 mg) obtained by the above-mentioned reaction, ethyl β-alaninate hydrochloride (154 mg), 1-ethyl-3-(3-dimethylaminopropyl)carbodiimide hydrochloride (192 mg), hydroxybenzotriazole monohydrate (154 mg) and triethylamine (139 μL)

in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (243 mg, 63%).

$^1$H NMR (300 MHz, DMSO-d$_6$) δ ppm 0.93 (dd, J=16.95, 6.40 Hz, 6H) 1.41-1.89 (m, 3H) 2.37-2.46 (m, 5H) 3.36-3.40 (m, 2H) 3.85 (s, 3H) 4.40-4.66 (m, 1H) 6.46 (d, J=7.91 Hz, 1H) 6.54 (d, J=8.85 Hz, 2H) 6.84 (d, J=8.67 Hz, 1H) 7.24 (s, 1H) 7.53 (d, J=8.67 Hz, 2H) 7.80 (dd, J=8.67, 2.64 Hz, 1H) 7.99 (t, J=5.65 Hz, 1H) 8.28 (d, J=2.45 Hz, 1H) 12.14 (s, 1H)

Example 297

3-[{[4-({1-[5-(6-methoxypyridin-3-yl)-2-methylthiophen-3-yl]-3-methylbutyl}amino)phenyl]carbonyl}(methyl)amino]propanoic acid

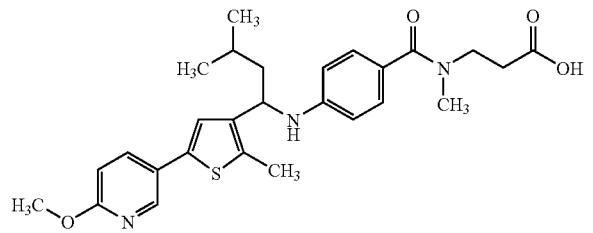

A solution of 4-({1-[5-(6-methoxypyridin-3-yl)-2-methylthiophen-3-yl]-3-methylbutyl}amino)benzoic acid (328 mg), ethyl 3-(methylamino)propanoate (131 mg), 1-ethyl-3-(3-dimethylaminopropyl)carbodiimide hydrochloride (192 mg), hydroxybenzotriazole monohydrate (154 mg) and triethylamine (139 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.5 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (329 mg, 83%).

$^1$H NMR (300 MHz, DMSO-d$_6$) δ ppm 0.93 (d, J=9.98 Hz, 6H) 1.40-1.57 (m, 1H) 1.57-1.88 (m, 2H) 2.47-2.51 (m, 5H) 2.90 (s, 3H) 3.52 (t, J=7.35 Hz, 2H) 3.85 (s, 3H) 4.34-4.57 (m, 1H) 6.35 (d, J=7.72 Hz, 1H) 6.54 (d, J=8.67 Hz, 2H) 6.84 (d, J=8.48 Hz, 1H) 7.11 (d, J=8.48 Hz, 2H) 7.25 (s, 1H) 7.81 (dd, J=8.67, 2.64 Hz, 1H) 8.28 (d, J=2.64 Hz, 1H) 12.24 (s, 1H)

Example 298

3-[({4-[(cyclohexyl{4-methyl-1-[3-(trifluoromethyl)phenyl]-1H-pyrrol-3-yl}methyl)amino]phenyl}carbonyl)(methyl)amino]propanoic acid

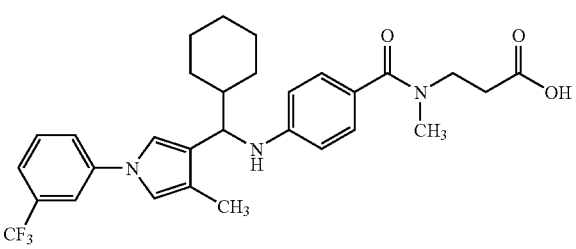

(1) ethyl 3-[methyl(4-nitrobenzoyl)amino]propanoate

To a mixture of 4-nitrobenzoic acid (16.7 g), ethyl 3-(methylamino)propanoate (13.1 g), 1-hydroxybenzotriazole monohydrate (18.4 g), and N,N-dimethylformamide (200 mL) was added 1-ethyl-3-(3-dimethylaminopropyl)carbodiimide hydrochloride (23.0 g), and the mixture was stirred at room temperature for 8 hr. The reaction mixture was poured into water, and the mixture was extracted with ethyl acetate. The extract was washed with 1N hydrochloric acid and saturated aqueous sodium hydrogen carbonate, dried over magnesium sulfate and concentrated under reduced pressure to give the title compound (28.0 g, 100%) as an oil.

$^1$H NMR (300 MHz, CDCl$_3$) δ ppm 1.26 (t, J=7.1 Hz, 3H), 2.51-2.78 (m, 2H), 2.99-3.10 (m, 3H), 3.46-3.86 (m, 2H), 4.03-4.28 (m, 2H), 7.50-7.65 (m, 2H), 8.28 (d, J=8.7 Hz, 2H)

(2) ethyl 3-{[(4-aminophenyl)carbonyl](methyl)amino}propanoate

A mixture of ethyl 3-[methyl(4-nitrobenzoyl)amino]propanoate (26.6 g) synthesized above, 5% palladium-carbon (8.9 g), tetrahydrofuran (150 mL) and ethanol (150 mL) was stirred at room temperature overnight under a hydrogen atmosphere. 5% palladium-carbon was filtered off, and the filtrate was concentrated under reduced pressure. The residue was purified by silica gel column chromatography (ethyl acetate:hexane=1:2, volume ratio) to give the title compound (26.6 g, 90%) as an oil.

$^1$H NMR (300 MHz, CDCl$_3$) δ ppm 1.26 (t, J=7.2 Hz, 3H), 2.64 (t, J=6.4 Hz, 2H), 3.05 (s, 3H), 3.74 (t, J=7.0 Hz, 2H), 3.85 (br. s., 2H), 4.14 (q, J=7.2 Hz, 2H), 6.59-6.72 (m, 2H), 7.23-7.28 (m, 2H)

(3) methyl 4-methyl-1H-pyrrole-3-carboxylate

To a solution (100 mL) of potassium t-butoxide (23.0 g) in tetrahydrofuran was added dropwise a solution (50 mL) of p-toluenesulfonylmethyl isocyanide (25.0 g) and methyl crotonate (12.3 mL) in tetrahydrofuran with stirring under ice-cooling. After the completion of the dropwise addition, the ice bath was removed, and the reaction mixture was stirred at room temperature for 1 hr. The reaction mixture was filtered through celite, and the filtrate was concentrated under reduced pressure. The residue was purified by silica gel chromatography (ethyl acetate:hexane=1:4, volume ratio) to give the title compound (7.6 g, 42%) as an oil.

$^1$H NMR (300 MHz, CDCl$_3$) δ ppm 2.29 (s, 3H), 3.80 (s, 3H), 6.54 (s, 1H), 7.34-7.40 (m, 1H)

(4) methyl 4-methyl-1-[3-(trifluoromethyl)phenyl]-1H-pyrrole-3-carboxylate

To a solution of methyl 4-methyl-1H-pyrrole-3-carboxylate (3.4 g) synthesized above in N-methyl-2-pyrrolidone (30 mL) were added 3-trifluoromethyliodobenzene (6.7 g), cuprous bromide (0.53 g) and potassium carbonate (4.4 g) at room temperature, and stirred for 1 hr with heating to 170° C. After cooling to room temperature, the reaction mixture was filtered through celite. Water was added to the filtrate and the mixture was extracted with diethyl ether. The extract was washed with brine, dried over magnesium sulfate, and concentrated under reduced pressure. The residue was purified by silica gel chromatography (ethyl acetate:hexane=1:4, volume ratio) to give the title compound (3.0 g, 42%) as a slightly yellow solid.

$^1$H NMR (300 MHz, CDCl$_3$) δ ppm 2.34 (s, 3H), 3.84 (s, 3H), 6.85-6.88 (m, 1H), 7.45-7.80 (m, 5H)

(5) 4-methyl-1-[3-(trifluoromethyl)phenyl]-1H-pyrrole-3-carbaldehyde

Methyl 4-methyl-1-[3-(trifluoromethyl)phenyl]-1H-pyrrole-3-carboxylate (3.0 g) synthesized above was dissolved in tetrahydrofuran (10 mL) and added dropwise to a solution (15 mL) of lithium aluminum hydride (0.40 g) in tetrahydrofuran at 0° C. The reaction mixture was stirred at 0° C. for 30 min, water (0.40 mL) was carefully added dropwise, 1N aqueous sodium hydroxide solution (2.0 mL) was added, and the mixture was stirred at room temperature for 30 min. The reaction mixture was filtered through celite, and the residue was washed with tetrahydrofuran (30 mL). The extracts were combined, dried over magnesium sulfate, and concentrated under reduced pressure. The residue was dissolved in toluene (50 mL), manganese dioxide (6.0 g) was added, and the mixture was heated under reflux under dehydrating conditions for 1 hr. After cooling, manganese dioxide was filtered off, and the residue was evaporated under reduced pressure to give the title compound (2.3 g, 86%) as a slightly yellow solid.

$^1$H NMR (300 MHz, CDCl$_3$) δ ppm 2.36 (s, 3H), 6.90 (s, 1H), 7.50-7.80 (m, 5H), 9.94 (s, 1H)

(6) cyclohexyl{4-methyl-1-[3-(trifluoromethyl)phenyl]-1H-pyrrol-3-yl}methanol To a solution of 4-methyl-1-[3-(trifluoromethyl)phenyl]-1H-pyrrole-3-carbaldehyde (2.3 g) synthesized above in tetrahydrofuran (20 mL) was added dropwise 1M cyclohexylmagnesium bromide-tetrahydrofuran solution (12 mL) at 0° C. After stirring at 0° C. for 1 hr, an aqueous ammonium chloride solution was added, and the mixture was extracted with ethyl acetate. The extract was concentrated under reduced pressure, and the residue was purified by silica gel column chromatography (ethyl acetate:hexane=1:4, volume ratio) to give the title compound (1.8 g, 52%) as a colorless solid.

$^1$H NMR (300 MHz, CDCl$_3$) δ ppm 0.88-1.89 (m, 12H), 2.13 (s, 3H), 4.40 (d, J=7.7 Hz, 1H), 6.86 (dd, J=2.4, 0.9 Hz, 1H), 7.00 (d, J=2.4 Hz, 1H), 7.37-7.64 (m, 4H)

(7) 3-[({4-[(cyclohexyl{4-methyl-1-[3-(trifluoromethyl)phenyl]-1H-pyrrol-3-yl}methyl)amino]phenyl}carbonyl)(methyl)amino]propanoic acid To a mixture of cyclohexyl{4-methyl-1-[3-(trifluoromethyl)phenyl]-1H-pyrrol-3-yl}methanol (0.50 g) synthesized above in tetrahydrofuran solution (10 mL) were added pyridine (0.22 mL) and thionyl chloride (0.20 mL) at room temperature, and the mixture was stirred for 30 min. The reaction mixture was poured into ice water, and the mixture was extracted with ethyl acetate. The extract was washed with saturated brine, dried over magnesium sulfate, and concentrated under reduced pressure. The residue was dissolved in dimethylacetamide (10 mL), sodium iodide (0.40 g), sodium carbonate (0.27 g) and ethyl 3-{[(4-aminophenyl)carbonyl](methyl)amino}propanoate (0.35 g) synthesized in Example 298 (2) were added, and the mixture was stirred at 80° C. for 2 hr. After cooling, water was added to the reaction mixture and the mixture was extracted with ethyl acetate. The extract was concentrated under reduced pressure, and the residue was purified by silica gel column chromatography (ethyl acetate:hexane=1:1, volume ratio) to give an ethyl ester form (0.17 g) of the title compound. This was dissolved in ethanol (1 mL), 1N sodium hydroxide (1 mL) was added at room temperature and the mixture was stirred for 1 hr. Ethanol was evaporated under reduced pressure, and 1N hydrochloric acid (1 mL) was added to the residue. The precipitate was washed with water to give the title compound (0.16 g, 20%) as a white solid.

$^1$H NMR (300 MHz, DMSO-d$_6$) δ ppm 0.81-2.01 (m, 11H), 2.07 (s, 3H), 2.50 (m, 3H), 2.90 (s, 3H), 3.52 (t, J=7.2 Hz, 2H), 4.09 (t, J=7.4 Hz, 1H), 6.13 (d, J=7.6 Hz, 1H), 6.60 (d, J=8.7 Hz, 2H), 7.06-7.90 (m, 8H), 12.22 (s, 1H)

Example 299

3-[({4-[(cyclohexyl{4-methyl-1-[3-(trifluoromethyl)phenyl]-1H-pyrrol-3-yl}methyl)amino]phenyl}carbonyl)amino]propanoic acid

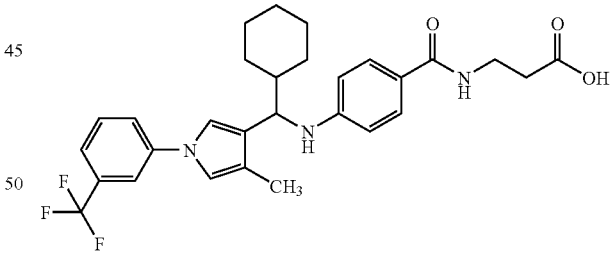

(1) ethyl 3-[(4-nitrobenzoyl)amino]propanoate

To a mixture of 4-nitrobenzoic acid (16.7 g), ethyl 13-alaninate hydrochloride (18.4 g), 1-hydroxybenzotriazole monohydrate (18.4 g), triethylamine (16.7 mL) and N,N-dimethylformamide (200 mL) was added 1-ethyl-3-(3-dimethylaminopropyl)carbodiimide hydrochloride (23.0 g), and the mixture was stirred at room temperature for 8 hr. The reaction mixture was poured into water, and the mixture was extracted with ethyl acetate. The extract was washed with 1N hydrochloric acid and saturated aqueous sodium hydrogen carbonate, dried over magnesium sulfate and concentrated under reduced pressure to give a white solid. Recrystallization from ethyl acetate-hexane gave the title compound (26.6 g, 100%) as a white crystal.
$^1$H NMR (300 MHz, CDCl$_3$) δ ppm 1.29 (t, J=7.2 Hz, 3H), 2.68 (t, J=6.1 Hz, 2H), 3.76 (q, J=6.1 Hz, 2H), 4.19 (q, J=7.1 Hz, 2H), 7.03 (br. s., 1H), 7.93 (d, J=9.1 Hz, 2H), 8.29 (d, J=8.7 Hz, 2H)

(2) ethyl 3-{[(4-aminophenyl)carbonyl]amino}propanoate

A mixture of ethyl 3-[(4-nitrobenzoyl)amino]propanoate (26.6 g) synthesized above, 5% palladium-carbon (8.9 g), tetrahydrofuran (150 mL) and ethanol (150 mL) was stirred under a hydrogen atmosphere at room temperature overnight. 5% Palladium-carbon was filtered off, and the filtrate was concentrated under reduced pressure to give a white solid. Recrystallization from ethyl acetate-diisopropyl ether gave the title compound (22.6 g, 95%) as a white crystal.
$^1$H NMR (300 MHz, CDCl$_3$) δ ppm 1.27 (t, J=7.2 Hz, 3H), 2.63 (t, J=6.0 Hz, 2H), 3.70 (q, J=6.0 Hz, 2H), 3.94 (br. s., 2H), 4.17 (q, J=7.2 Hz, 2H), 6.66 (d, J=8.7 Hz, 2H), 7.60 (d, J=8.7 Hz, 2H)

(3) 3-[({4-[(cyclohexyl{4-methyl-1-[3-(trifluoromethyl)phenyl]-1H-pyrrol-3-yl}methyl)amino]phenyl}carbonyl)amino]propanoic acid Using cyclohexyl{4-methyl-1-[3-(trifluoromethyl)phenyl]-1H-pyrrol-3-yl}methanol (0.50 g) synthesized in Example 298

(6) and ethyl 3-{[(4-aminophenyl)carbonyl]amino}propanoate (0.35 g) synthesized above and according to the method of Example 298 (7), the title compound (0.20 g, 20%) was obtained as a white solid.

$^1$H NMR (300 MHz, DMSO-d$_6$) δ ppm 0.80-2.02 (m, 11H), 2.06 (s, 3H), 2.41 (t, J=7.0 Hz, 2H), 3.36 (t, J=7.0 Hz, 2H), 4.13 (t, J=8.0 Hz, 1H), 6.23 (d, J=8.0 Hz, 1H), 6.60 (d, J=9.1 Hz, 2H), 7.22 (s, 1H), 7.38 (d, J=2.7 Hz, 1H), 7.44-7.56 (m, 3H), 7.62 (t, J=8.1 Hz, 1H), 7.77 (d, J=2.3 Hz, 2H), 7.98 (t, 1H)

Example 300

3-[{[4-(cyclohexyl{4-methyl-1-[3-(trifluoromethyl)phenyl]-1H-pyrrol-3-yl}methoxy)phenyl]carbonyl}(methyl)amino]propanoic acid

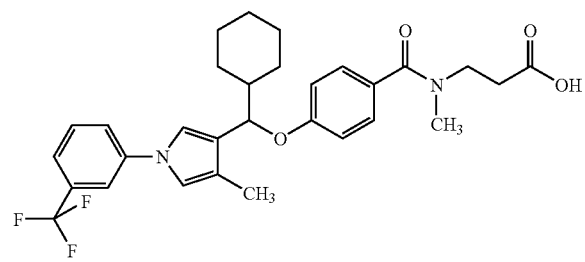

(1) 4-(cyclohexyl{4-methyl-1-[3-(trifluoromethyl)phenyl]-1H-pyrrol-3-yl}methoxy)benzoic acid To a solution (15 mL) of cyclohexyl{4-methyl-1-[3-(trifluoromethyl)phenyl]-1H-pyrrol-3-yl}methanol (0.81 g) synthesized in Example 298 (6) in tetrahydrofuran were added methyl 4-hydroxybenzoate (0.4 g), tributylphosphine (1.2 mL) and dipiperidide azodicarboxylate (1.2 g) with stirring under ice-cooling. The ice bath was removed, and the reaction mixture was stirred at room temperature overnight. Hexane was added to the reaction mixture, and the precipitate was filtered through celite. Water was added to the filtrate and the mixture was extracted with ethyl acetate. The extract was purified by silica gel chromatography (ethyl acetate:hexane=1:1, volume ratio) to give a methyl ester form of the title compound (0.96 g). This was dissolved in ethanol (5 mL), 1N sodium hydroxide (4 mL) was added at 60° C. and the mixture was stirred for 1 hr. Ethanol was evaporated under reduced pressure, and 1N hydrochloric acid (4 mL) was added to the residue to give the title compound (0.88 g, 80%) as an amorphous form.
$^1$H NMR (300 MHz, CDCl$_3$) δ ppm 0.91-1.91 (m, 11H), 2.16 (s, 3H), 4.79-5.01 (d, J=2.4 Hz, 1H), 6.76-8.09 (m, 10H)

(2) 3-[{[4-(cyclohexyl{4-methyl-1-[3-(trifluoromethyl)phenyl]-1H-pyrrol-3-yl}methoxy)phenyl]carbonyl}(methyl)amino]propanoic acid To a solution (10 mL) of 4-(cyclohexyl{4-methyl-1-[3-(trifluoromethyl)phenyl]-1H-pyrrol-3-yl}methoxy)benzoic acid (0.43 g) synthesized above in dimethylacetamide were added ethyl 3-(methylamino)propanoate (0.14 g), 1-ethyl-3-(3-dimethylaminopropyl)carbodiimide hydrochloride (0.29 g) and 1-hydroxybenzotriazole monohydrate (0.23 g) at room temperature, and the mixture was stirred at 60° C. for 1 hr. Water was added to the reaction mixture and the mixture was extracted with ethyl acetate. The extract was purified by silica gel chromatography (ethyl acetate:hexane=1:1, volume ratio) to give a methyl ester form of the title compound (0.44 g). This was dissolved in ethanol (2 mL), 1N sodium hydroxide (1.5 mL) was added and the mixture was stirred at room temperature for 1 hr. Ethanol was evaporated under reduced pressure, and 1N hydrochloric acid (1.5 mL) was added to the residue to give the title compound (0.40 g, 78%) as an amorphous form.
$^1$H NMR (300 MHz, CDCl$_3$) δ ppm 0.97-1.98 (m, 11H), 2.15 (s, 3H), 2.50 (br. s., 2H), 3.00 (s, 3H), 3.70 (br. s., 2H), 4.85 (d, J=6.8 Hz, 1H), 6.75-7.64 (m, 10H)

Example 301

3-({[4-(cyclohexyl{4-methyl-1-[3-(trifluoromethyl)phenyl]-1H-pyrrol-3-yl}methoxy)phenyl]carbonyl}amino)propanoic acid

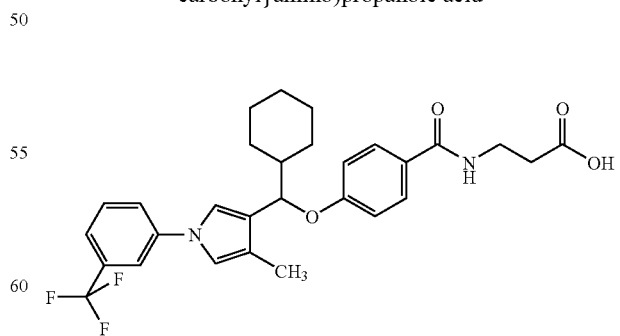

To a solution (10 mL) of 4-(cyclohexyl{4-methyl-1-[3-(trifluoromethyl)phenyl]-1H-pyrrol-3-yl}methoxy)benzoic acid (0.43 g) synthesized in Example 300 (1) in dimethylacetamide were added triethylamine (0.14 mL), ethyl 3-aminopropanoate hydrochloride (0.16 g), N-(3-dimethylaminopropyl)-ethylcarbodiimide hydrochloride (0.29 g) and 1-hydroxybenzotriazole monohydrate (0.23 g) at room temperature, and the mixture was stirred at 60° C. for 1 hr. Water was added to the reaction mixture and the mixture was extracted with ethyl acetate and purified by silica gel chromatography (ethyl acetate:hexane=1:1, volume ratio) to give a methyl ester form of the title compound (0.10 g). This was dissolved in ethanol (2 mL), 1N sodium hydroxide (1.5 mL) was added, and the mixture was stirred at room temperature for 1 hr. Ethanol was evaporated under reduced pressure, and 1N hydrochloric acid (1.5 mL) was added to the residue to give the title compound (25.4 mg, 5%) as an amorphous form.

$^1$H NMR (300 MHz, CDCl$_3$) δ ppm 0.89-2.09 (m, 12H), 2.13 (s, 3H), 2.58 (br. s., 2H), 3.62 (br. s., 2H), 4.87 (d, J=7.2 Hz, 1H), 6.55-7.77 (m, 11H)

Example 302

3-[{[4-({cyclohexyl[1-(3-fluorophenyl)-4-methyl-1H-pyrrol-3-yl]methyl}amino)phenyl]carbonyl}(methyl)amino]propanoic acid

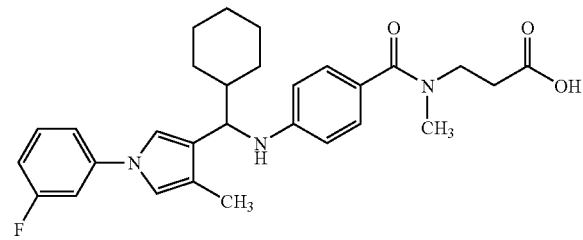

(1) cyclohexyl{4-methyl-1-(3-fluorophenyl)-1H-pyrrol-3-yl}methanol

An operation similar to that in Example 298 (6) was performed using 4-methyl-1-(3-fluorophenyl)-1H-pyrrole-3-carbaldehyde (0.87 g) to give the title compound (0.65 g, 52%) as an oil.

$^1$H NMR (300 MHz, CDCl$_3$) δ ppm 0.99-2.02 (m, 12H), 2.13 (s, 3H), 4.38 (d, J=6.2 Hz, 1H), 6.80-7.37 (m, 6H)

(2) 3-[{[4-({cyclohexyl[1-(3-fluorophenyl)-4-methyl-1H-pyrrol-3-yl]methyl}amino)phenyl]carbonyl}(methyl)amino]propanoic acid An operation similar to that in Example 298 (7) was performed using cyclohexyl{4-methyl-1-(3-fluorophenyl)-1H-pyrrol-3-yl}methanol (0.32 g) synthesized above to give the title compound (0.05 g, 9%) as an amorphous form.

$^1$H NMR (300 MHz, CDCl$_3$) δ ppm 0.99-2.02 (m, 11H), 2.12 (s, 3H), 2.73 (br. s., 2H), 3.09 (s, 3H), 3.72 (t, J=6.3 Hz, 2H), 4.18 (d, J=6.2 Hz, 1H), 6.52 (d, J=8.7 Hz, 2H), 6.78-7.37 (m, 8H)

Example 303

3-({[4-({cyclohexyl[1-(3-fluorophenyl)-4-methyl-1H-pyrrol-3-yl]methyl}amino)phenyl]carbonyl}amino)propanoic acid

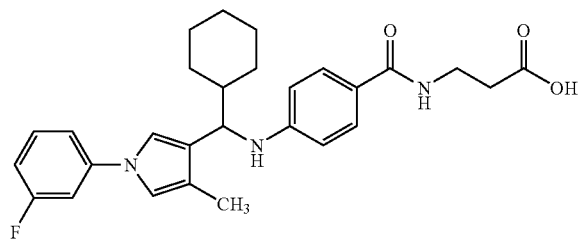

An operation similar to that in Example 299 (3) was performed using cyclohexyl{4-methyl-1-(3-fluorophenyl)-1H-pyrrol-3-yl}methanol (0.32 g) synthesized in Example 302 (1) to give the title compound (0.05 g, 10%) as an amorphous form.

$^1$H NMR (300 MHz, CDCl$_3$) δ ppm 0.95-1.97 (m, 12H), 2.11 (s, 3H), 2.67 (br. s., 2H), 3.67 (br. s., 2H), 4.20 (d, J=6.2 Hz, 1H), 6.43-6.60 (m, 3H), 6.76-7.60 (d, 8H)

Example 304

3-[{[4-({[1-(2-chloropyridin-4-yl)-4-methyl-1H-pyrrol-3-yl](cyclohexyl)methyl}amino)phenyl]carbonyl}(methyl)amino]propanoic acid

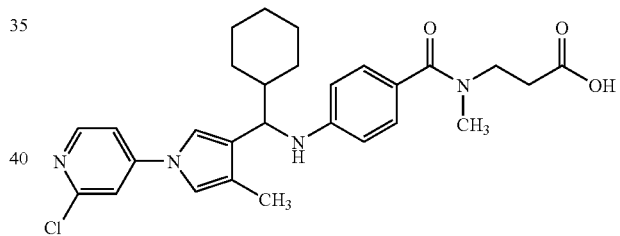

(1) cyclohexyl{1-(2-chloropyridin-4-yl)-4-methyl-1H-pyrrol-3-yl}methanol

An operation similar to that in Example 298 (6) was performed using 1-(2-chloropyridin-4-yl)-4-methyl-1H-pyrrole-3-carbaldehyde (1.13 g) to give the title compound (0.61 g, 39%) as an oil.

$^1$H NMR (300 MHz, CDCl$_3$) δ ppm 0.88-2.07 (m, 12H), 2.11 (s, 3H), 4.39 (d, J=7.3 Hz, 1H), 6.91 (dd, J=2.4, 1.1 Hz, 1H), 7.06 (d, J=2.4 Hz, 1H), 7.14 (dd, J=5.7, 2.1 Hz, 1H), 7.26 (m, 1H), 8.31 (d, J=5.7 Hz, 1H)

(2) 3-[{[4-({[1-(2-chloropyridin-4-yl)-4-methyl-1H-pyrrol-3-yl](cyclohexyl)methyl}amino)phenyl]carbonyl}(methyl)amino]propanoic acid An operation similar to that in Example 298 (7) was performed using cyclohexyl{1-(2-chloropyridin-4-yl)-4-methyl-1H-pyrrol-3-yl}methanol (0.30 g) synthesized above to give the title compound (0.10 g, 20%) as an amorphous form.

$^1$H NMR (300 MHz, CDCl$_3$) δ ppm 0.94-2.02 (m, 12H), 2.11 (s, 3H), 2.70 (t, J=6.0 Hz, 2H), 3.07 (s, 3H), 3.73 (t, J=6.0 Hz, 2H), 4.15 (d, J=6.4 Hz, 1H), 6.53 (br. s., 2H), 6.81-7.40 (m, 6H), 8.28 (d, J=5.7 Hz, 1H)

Example 305

3-({[4-({[1-(2-chloropyridin-4-yl)-4-methyl-1H-pyrrol-3-yl](cyclohexyl)methyl}amino)phenyl]carbonyl}amino)propanoic acid

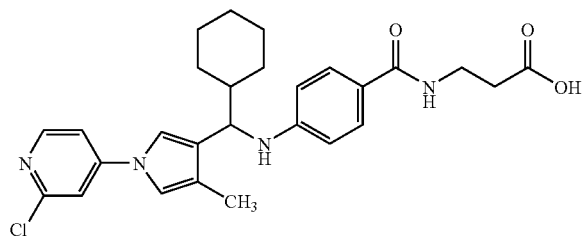

An operation similar to that in Example 299 (3) was performed using cyclohexyl{1-(2-chloropyridin-4-yl)-4-methyl-1H-pyrrol-3-yl}methanol (0.30 g) synthesized in Example 304 (1) to give the title compound (0.07 g, 13%) as an amorphous form.
$^1$H NMR (300 MHz, CDCl$_3$) δ ppm 0.95-2.03 (m, 12H), 2.12 (s, 3H), 2.68 (d, J=6.0 Hz, 2H), 3.67 (q, J=5.8 Hz, 2H), 4.17 (d, J=6.2 Hz, 1H), 6.48-6.70 (m, 3H), 6.92-7.20 (m, 4H), 7.54 (d, J=8.7 Hz, 2H), 8.28 (d, J=5.8 Hz, 1H)

Example 306

3-[{[4-({cyclohexyl[1-(4-fluorophenyl)-4-methyl-1H-pyrrol-3-yl]methyl}amino)phenyl]carbonyl}(methyl)amino]propanoic acid

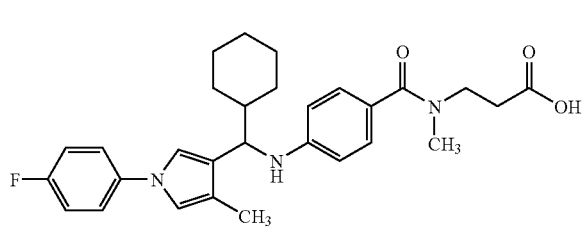

(1) cyclohexyl{4-methyl-1-(4-fluorophenyl)-1H-pyrrol-3-yl}methanol

An operation similar to that in Example 298 (6) was performed using 4-methyl-1-(4-fluorophenyl)-1H-pyrrole-3-carbaldehyde (1.19 g) to give the title compound (1.44 g, 85%) as an oil.
$^1$H NMR (300 MHz, CDCl$_3$) δ ppm 0.84-2.02 (m, 12H), 2.13 (s, 3H), 4.39 (d, J=7.7 Hz, 1H), 6.75 (d, J=0.9 Hz, 1H), 6.90 (d, J=2.4 Hz, 1H), 7.03-7.38 (m, 4H)

(2) 3-[{[4-({cyclohexyl[1-(4-fluorophenyl)-4-methyl-1H-pyrrol-3-yl]methyl}amino)phenyl]carbonyl}(methyl)amino]propanoic acid An operation similar to that in Example 298 (7) was performed using cyclohexyl{4-methyl-1-(4-fluorophenyl)-1H-pyrrol-3-yl}methanol (0.50 g) synthesized above to give the title compound (0.11 g, 13%) as an amorphous form.
$^1$H NMR (300 MHz, CDCl$_3$) δ ppm 0.92-2.06 (m, 12H), 2.11 (s, 3H), 2.73 (t, J=6.2 Hz, 2H), 3.09 (s, 3H), 3.72 (t, J=6.2 Hz, 2H), 4.18 (d, J=6.4 Hz, 1H), 6.53 (d, J=8.7 Hz, 2H), 6.76 (d, J=7.2 Hz, 2H), 6.98-7.37 (m, 6H)

Example 307

3-({[4-({cyclohexyl[1-(4-fluorophenyl)-4-methyl-1H-pyrrol-3-yl]methyl}amino)phenyl]carbonyl}amino)propanoic acid

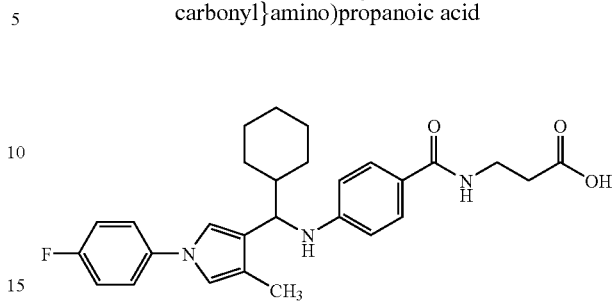

An operation similar to that in Example 299 (3) was performed using cyclohexyl{4-methyl-1-(4-fluorophenyl)-1H-pyrrol-3-yl}methanol (0.5 g) synthesized in Example 306 (1) to give the title compound (0.19 g, 23%) as an amorphous form.
$^1$H NMR (300 MHz, CDCl$_3$) δ ppm 0.89-2.00 (m, 12H), 2.09 (s, 3H), 2.57 (br. s., 2H), 3.60 (br. s., 2H), 4.18 (d, J=4.8 Hz, 1H), 6.51 (d, J=8.3 Hz, 2H), 6.58-6.66 (m, 1H), 6.75-7.40 (m, 6H), 7.52 (d, J=1.5 Hz, 2H)

Example 308

3-[{[4-({cyclohexyl[1-(2-fluorophenyl)-4-methyl-1H-pyrrol-3-yl]methyl}amino)phenyl]carbonyl}(methyl)amino]propanoic acid

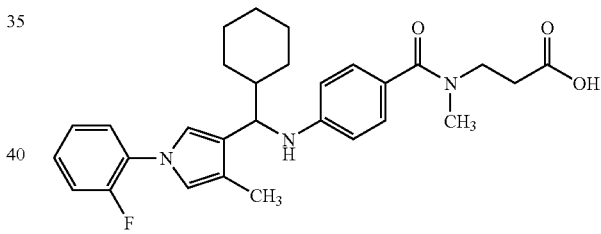

(1) cyclohexyl{4-methyl-1-(2-fluorophenyl)-1H-pyrrol-3-yl}methanol

An operation similar to that in Example 298 (6) was performed using 1-(2-fluorophenyl)-4-methyl-1H-pyrrole-3-carbaldehyde (1.68 g) to give the title compound (2.35 g, 98%) as an oil.
$^1$H NMR (300 MHz, CDCl$_3$) δ ppm 0.90-1.97 (m, 12H), 2.14 (s, 3H), 4.39 (d, J=5.7 Hz, 1H), 6.78 (s, 1H), 6.92 (t, J=2.1 Hz, 1H), 7.18-7.45 (m, 4H)

(2) 3-[{[4-({cyclohexyl[1-(2-fluorophenyl)-4-methyl-1H-pyrrol-3-yl]methyl}amino)phenyl]carbonyl}(methyl)amino]propanoic acid An operation similar to that in Example 298 (7) was performed using cyclohexyl{4-methyl-1-(2-fluorophenyl)-1H-pyrrol-3-yl}methanol (0.70 g) synthesized above to give the title compound (0.12 g, 10%) as an amorphous form.
$^1$H NMR (300 MHz, CDCl$_3$) δ ppm 1.10-2.00 (m, 12H), 2.11 (s, 3H), 2.72 (br. s., 2H), 3.08 (s, 3H), 3.72 (t, J=6.2 Hz, 2H), 4.20 (d, J=6.4 Hz, 1H), 6.53 (d, J=8.5 Hz, 2H), 6.73-7.22 (m, 8H)

Example 309

3-({[4-({cyclohexyl[1-(2-fluorophenyl)-4-methyl-1H-pyrrol-3-yl]methyl}amino)phenyl]carbonyl}amino)propanoic acid

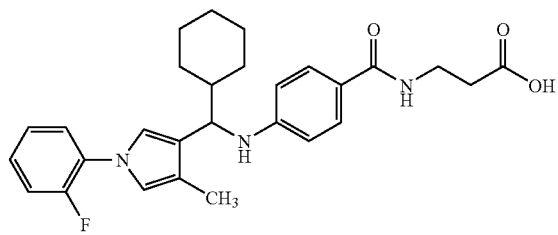

An operation similar to that in Example 299 (3) was performed using cyclohexyl{4-methyl-1-(2-fluorophenyl)-1H-pyrrol-3-yl}methanol (0.70 g) synthesized in Example 308 (1) to give the title compound (0.13 g, 11%) as an amorphous form.

$^1$H NMR (300 MHz, CDCl$_3$) δ ppm 0.98-2.00 (m, 11H), 2.11 (s, 3H), 2.54-2.79 (m, 2H), 3.67 (q, J=5.8 Hz, 2H), 4.21 (d, J=6.4 Hz, 1H), 6.52-6.55 (m, 3H), 6.60-7.54 (m, 8H)

Example 310

3-{[(5-{[cyclohexyl(2-methyl-5-phenylthiophen-3-yl)methyl]amino}pyridin-2-yl)carbonyl]amino}propanoic acid

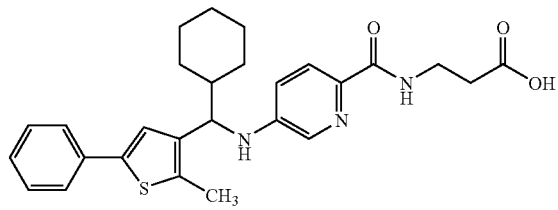

(1) 5-{[cyclohexyl(2-methyl-5-phenylthiophen-3-yl)methyl]amino}pyridine-2-carboxylic acid To a mixture of 3-[chloro(cyclohexyl)methyl]-2-methyl-5-phenylthiophene (909 mg) synthesized in Example 278 (6), methyl 5-amino-pyridine-2-carboxylate (438 mg), sodium iodide (863 mg) and N,N-dimethylformamide (10 mL) was added sodium carbonate (611 mg), and the mixture was stirred at 80° C. overnight. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel chromatography (30-70% ethyl acetate/hexane) to give a pale-brown oil. To a mixture of the obtained oil, tetrahydrofuran (10 mL) and ethanol (10 mL) was added 1N aqueous sodium hydroxide solution (10 mL), and the mixture was stirred with heating under reflux overnight. The reaction mixture was concentrated under reduced pressure. 1N Hydrochloric acid (10 mL) was added to the residue, and the mixture was extracted with ethyl acetate. The extract was washed with saturated brine, dried over magnesium sulfate, and concentrated under reduced pressure. The residue was washed with diisopropyl ether to give the title compound (342 mg, 29%) as a white solid.

$^1$H NMR (300 MHz, CDCl$_3$) δ ppm 0.96-1.40 (m, 5H), 1.56-1.88 (m, 5H), 1.98-2.12 (m, 1H), 2.50 (s, 3H), 4.19 (d, J=7.5 Hz, 1H), 6.78-6.88 (m, 1H), 7.02 (s, 1H), 7.17-7.36 (m, 3H), 7.49 (d, J=7.5 Hz, 2H), 7.88 (d, J=8.7 Hz, 1H), 7.99-8.09 (m, 1H).

(2) 3-{[(5-{[cyclohexyl(2-methyl-5-phenylthiophen-3-yl)methyl]amino}pyridin-2-yl)carbonyl]amino}propanoic acid To a mixture of 5-{[cyclohexyl(2-methyl-5-phenylthiophen-3-yl)methyl]amino}pyridine-2-carboxylic acid (386 mg) synthesized above, ethyl β-alaninate hydrochloride (218 mg), 1-hydroxybenzotriazole monohydrate (218 mg), triethylamine (397 μL) and N,N-dimethylformamide (10 mL) was added 1-ethyl-3-(3-dimethylaminopropyl)carbodiimide hydrochloride (272 mg), and the mixture was stirred at room temperature overnight. Saturated aqueous ammonium chloride solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel chromatography (30-50% ethyl acetate/hexane) to give a white solid. To a mixture of the obtained solid, tetrahydrofuran (5 mL) and ethanol (5 mL) was added 1N aqueous sodium hydroxide solution (2.00 mL), and the mixture was stirred at room temperature for 2 hr. The reaction mixture was concentrated under reduced pressure. The residue was dissolved in water (10 mL), and 1N hydrochloric acid (2.00 mL) was added at 0° C. The resulting precipitate was collected by filtration to give the title compound (311 mg, 69%) as a white solid.

$^1$H NMR (300 MHz, CDCl$_3$) δ ppm 0.94-1.35 (m, 5H), 1.55-1.86 (m, 5H), 1.94-2.07 (m, 1H), 2.48 (s, 3H), 2.65 (t, J=5.9 Hz, 2H), 3.63-3.74 (m, 2H), 4.17 (d, J=7.2 Hz, 1H), 6.77 (dd, J=8.7, 2.7 Hz, 1H), 6.99 (s, 1H), 7.17-7.35 (m, 3H), 7.47 (d, J=7.2 Hz, 2H), 7.82 (d, J=2.7 Hz, 1H), 7.88 (d, J=8.7 Hz, 1H), 8.12 (t, J=6.2 Hz, 1H).

Example 311

3-{[(5-{[cyclohexyl(2-methyl-5-phenylthiophen-3-yl)methyl]amino}pyridin-2-yl)carbonyl](methyl)amino}propanoic acid

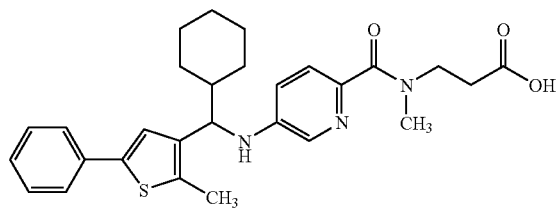

To a mixture of 5-{[cyclohexyl(2-methyl-5-phenylthiophen-3-yl)methyl]amino}pyridine-2-carboxylic acid (300 mg) synthesized in Example 310 (1), ethyl 3-(methylamino)propanoate (146 mg), 1-hydroxybenzotriazole monohydrate (170 mg), triethylamine (308 μL) and N,N-dimethylformamide (10 mL) was added 1-ethyl-3-(3-dimethylaminopropyl)carbodiimide hydrochloride (213 mg), and the mixture was stirred at room temperature overnight. Saturated aqueous ammonium chloride solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel chromatography (30-50% ethyl acetate/hexane) to give a colorless oil. To a mixture of the obtained oil, tetrahydrofuran (5 mL) and ethanol (5 mL) was added 1N aqueous sodium hydroxide solution (2.00 mL), and the mixture was stirred at room temperature for 2 hr. The reaction mixture was concentrated under reduced pressure. The residue was dissolved in water (10 mL), and 1N hydrochloric acid (2.00 mL) was added at 0° C. The resulting precipitate was collected by filtration to give the title compound (205 mg, 57%) as a white solid.

$^1$H NMR (300 MHz, CDCl$_3$) δ ppm 0.94-1.37 (m, 5H), 1.54-1.87 (m, 5H), 1.95-2.08 (m, 1H), 2.48 (s, 3H), 2.72-2.92 (m, 2H), 3.09 (br s, 3H), 3.77 (t, J=6.4 Hz, 2H), 4.16 (d, J=7.2 Hz, 1H), 6.76-6.86 (m, 1H), 7.01 (s, 1H), 7.18-7.25 (m, 1H), 7.28-7.36 (m, 2H), 7.45-7.52 (m, 2H), 7.53-7.64 (m, 1H), 7.83-7.91 (m, 1H).

Example 312

3-[methyl({4-[(2-methyl-5-phenylfuran-3-yl)(tetrahydro-2H-pyran-4-yl)methoxy]phenyl}carbonyl)amino]propanoic acid

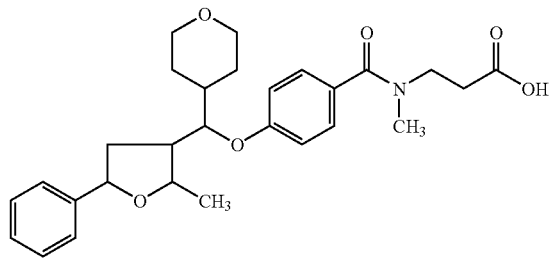

A solution of 4-[(2-methyl-5-phenylfuran-3-yl)(tetrahydro-2H-pyran-4-yl)methoxy]benzoic acid (177 mg), ethyl 3-(methylamino)propanoate (66 mg), 1-ethyl-3-(3-dimethylaminopropyl)carbodiimide hydrochloride (96 mg), hydroxybenzotriazole monohydrate (77 mg) and triethylamine (70 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (3 mL), tetrahydrofuran (3 mL) and 1N lithium hydroxide (1.0 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (61 mg, 29%).

$^1$H NMR (300 MHz, DMSO-d$_6$) δ ppm 1.31-1.48 (m, 3H) 1.89-1.93 (m, 1H) 2.04-2.13 (m, 1H) 2.39 (s, 3H) 2.46-2.51 (m, 2H) 2.88 (s, 3H) 3.51 (brs, 1H) 3.83-3.93 (m, 2H) 5.08 (d, J=7.91 Hz, 1H) 6.85 (s, 1H) 6.92 (d, J=8.67 Hz, 2H) 7.26 (t, J=8.76 Hz, 3H) 7.36 (t, J=7.63 Hz, 2H) 7.61 (d, J=7.35 Hz, 2H)

Example 313

3-({[4-({cyclohexyl[5-(4-fluorophenyl)-2-(methoxymethyl)furan-3-yl]methyl}amino)phenyl]carbonyl}amino)propanoic acid

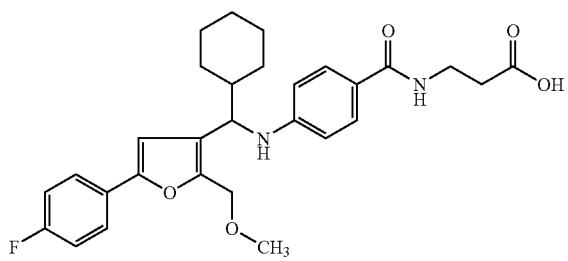

(1) methyl 5-(4-fluorophenyl)-2-(methoxymethyl)furan-3-carboxylate

A mixture of methyl 5-bromo-2-(methoxymethyl)furan-3-carboxylate (2.5 g), 4-fluorophenylboronic acid (1.7 g), tetrakis(triphenylphosphine)palladium(0) (0.6 g), 2N aqueous sodium carbonate solution (14 mL) and 1,2-dimethoxyethane (30 mL) was stirred under reflux overnight under an argon atmosphere. The reaction mixture was poured into water, and the mixture was extracted with ethyl acetate. The organic layer was washed with saturated brine, and dried over magnesium sulfate. The solvent was evaporated under reduced pressure. The residue was purified by silica gel chromatography (0% ethyl acetate/hexane to 25% ethyl acetate/hexane), and crystallized from ethyl acetate/hexane to give the title compound (2.4 g, 91%) as a white crystal.

$^1$H NMR (300 MHz, CHLOROFORM-d) δ ppm 3.45 (s, 3H) 3.88 (s, 3H) 4.79 (s, 2H) 6.87 (s, 1H) 7.02-7.17 (m, 2H) 7.62-7.72 (m, 2H)

(2) [5-(4-fluorophenyl)-2-(methoxymethyl)furan-3-yl]methanol

A solution of methyl 5-(4-fluorophenyl)-2-(methoxymethyl)furan-3-carboxylate (2.4 g) obtained by the above-mentioned reaction in tetrahydrofuran (20 mL) was added dropwise to a suspension of lithium aluminum hydride (0.3 g) in tetrahydrofuran (20 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was crystallized from ethyl acetate/hexane to give the title compound (2.1 g, 100%) as an oil.

$^1$H NMR (300 MHz, CHLOROFORM-d) δ ppm 1.90 (t, J=5.68 Hz, 1H) 3.42 (s, 3H) 4.51 (s, 2H) 4.60 (d, J=5.68 Hz, 2H) 6.61 (s, 1H) 7.07 (t, J=8.71 Hz, 2H) 7.47-7.79 (m, 2H)

(3) 5-(4-fluorophenyl)-2-(methoxymethyl)furan-3-carbaldehyde

To a solution of [5-(4-fluorophenyl)-2-(methoxymethyl)furan-3-yl]methanol (2.1 g) obtained by the above-mentioned reaction in acetonitrile (30 mL) was added a Dess-Martin reagent (4.6 g) at 0° C., and the mixture was stirred at 0° C. for 30 min. The reaction mixture was poured into water, and the mixture was extracted with ethyl acetate. The organic layer was washed with saturated aqueous sodium hydrogen carbonate, and dried over magnesium sulfate. The solvent was evaporated under reduced pressure, and the residue was purified by silica gel chromatography (0% ethyl acetate/hexane to 40% ethyl acetate/hexane) to give the title compound (1.7 g, 79%) as a white crystal.

$^1$H NMR (300 MHz, CHLOROFORM-d) δ ppm 3.48 (s, 3H) 4.76 (s, 2H) 6.92 (s, 1H) 7.11 (t, J=8.71 Hz, 2H) 7.67 (dd, J=9.09, 5.30 Hz, 2H) 10.10 (s, 1H)

(4) cyclohexyl[5-(4-fluorophenyl)-2-(methoxymethyl)furan-3-yl]methanol

To a solution of 5-(4-fluorophenyl)-2-(methoxymethyl)furan-3-carbaldehyde (1.6 g) obtained by the above-mentioned reaction in tetrahydrofuran (30 mL) was added 1N cyclohexylmagnesium bromide-tetrahydrofuran solution (10.5 mL) at 0° C. and, after the completion of the dropwise addition, the mixture was stirred at 0° C. for 30 min. The reaction mixture was treated with 1N hydrochloric acid, poured into water, and the mixture was extracted with ethyl acetate. The organic layer was washed with saturated brine, and dried over magnesium sulfate. The solvent was evaporated under reduced pressure, and the residue was purified by silica gel chromatography (0% ethyl acetate/hexane to 40% ethyl acetate/hexane) to give the title compound (2.0 g, 87%) as an oil.

$^1$H NMR (300 MHz, CHLOROFORM-d) δ ppm 0.95-1.35 (m, 5H) 1.58-1.95 (m, 5H) 1.95-2.14 (m, 1H) 3.41 (s, 3H) 4.41 (dd, J=7.00, 2.08 Hz, 1H) 4.47 (s, 2H) 6.55 (s, 1H) 7.02-7.10 (m, 2H) 7.60-7.66 (m, 2H)

(5) 3-[chloro(cyclohexyl)methyl]-5-(4-fluorophenyl)-2-(methoxymethyl)furan

To a solution of cyclohexyl[5-(4-fluorophenyl)-2-(methoxymethyl)furan-3-yl]methanol (1.9 g) obtained by the above-mentioned reaction in toluene (10 mL) were added thionyl chloride (0.7 mL) and pyridine (0.7 mL) at 0° C., and the mixture was stirred at 0° C. for 1 hr. The reaction mixture was poured into water, and the mixture was extracted with ethyl acetate. The organic layer was washed with saturated brine, and dried over magnesium sulfate. The solvent was evaporated under reduced pressure to give the title compound (2.0 g, 100%) as an oil.

$^1$H NMR (300 MHz, CHLOROFORM-d) δ ppm 0.85-1.38 (m, 5H) 1.58-1.95 (m, 5H) 2.23 (d, J=12.49 Hz, 1H) 3.39 (s, 3H) 4.36-4.58 (m, 2H) 4.70 (d, J=8.71 Hz, 1H) 6.62 (s, 1H) 6.99-7.12 (m, 2H) 7.57-7.76 (m, 2H)

(6) 4-({cyclohexyl[5-(4-fluorophenyl)-2-(methoxymethyl)furan-3-yl]methyl}amino)benzoic acid A mixture of 3-[chloro(cyclohexyl)methyl]-5-(4-fluorophenyl)-2-(methoxymethyl)furan (2.0 g) obtained by the above-mentioned reaction, methyl 4-aminobenzoate (1.4 g), sodium carbonate (1.0 g) and sodium iodide (1.8 g) in N,N-dimethylacetamide (20 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (6 mL) and tetrahydrofuran (6 mL). 2N Lithium hydroxide (6 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure, and the residue was purified by silica gel chromatography (10% ethyl acetate/hexane to 40% ethyl acetate/hexane) to give the title compound (1.3 g, 50%) as an amorphous compound.

$^1$H NMR (300 MHz, CHLOROFORM-d) δ ppm 0.98-1.34 (m, 5H) 1.44-1.83 (m, 5H) 1.97 (d, J=11.74 Hz, 1H) 3.41 (s, 3H) 4.28 (d, J=6.44 Hz, 1H) 4.48 (q, J=12.87 Hz, 2H) 6.45 (s, 1H) 6.58 (d, J=8.71 Hz, 2H) 6.96-7.11 (m, 2H) 7.51-7.64 (m, 2H) 7.84 (d, J=8.71 Hz, 2H)

(7) 3-({[4-({cyclohexyl[5-(4-fluorophenyl)-2-(methoxymethyl)furan-3-yl]methyl}amino)phenyl]carbonyl}amino)propanoic acid A solution of 4-({cyclohexyl[5-(4-fluorophenyl)-2-(methoxymethyl)furan-3-yl]methyl}amino)benzoic acid (219 mg) obtained by the above-mentioned reaction, ethyl β-alaninate hydrochloride (92 mg), 1-ethyl-3-(3-dimethylaminopropyl)carbodiimide hydrochloride (115 mg), hydroxybenzotriazole monohydrate (92 mg) and triethylamine (84 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.9 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (213 mg, 85%).

$^1$H NMR (300 MHz, DMSO-d$_6$) δ ppm 0.89-1.29 (m, 5H) 1.46-1.81 (m, 5H) 1.97-2.13 (m, 1H) 2.42 (t, J=7.19 Hz, 2H) 3.32 (s, 3H) 3.34-3.45 (m, 2H) 4.22 (t, J=7.76 Hz, 1H) 4.50 (q, J=12.87 Hz, 2H) 6.34 (d, J=7.95 Hz, 1H) 6.60 (d, J=8.71 Hz, 2H) 6.79 (s, 1H) 7.12-7.30 (m, 2H) 7.51 (d, J=8.71 Hz, 2H) 7.58-7.72 (m, 2H) 8.00 (t, J=5.30 Hz, 1H) 12.18 (brs, 1H)

Example 314

3-[{[4-({cyclohexyl[5-(4-fluorophenyl)-2-(methoxymethyl)furan-3-yl]methyl}amino)phenyl]carbonyl}(methyl)amino]propanoic acid

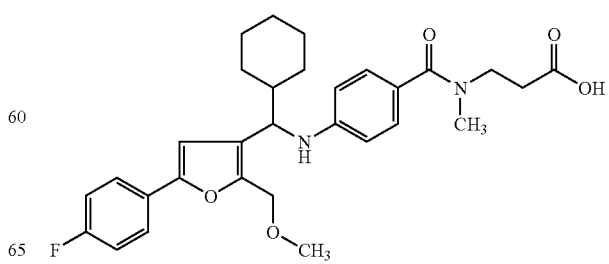

A solution of 4-({cyclohexyl[5-(4-fluorophenyl)-2-(methoxymethyl)furan-3-yl]methyl}amino)benzoic acid (219 mg), ethyl 3-(methylamino)propanoate (79 mg), 1-ethyl-3-(3-dimethylaminopropyl)carbodiimide hydrochloride (115 mg), hydroxybenzotriazole monohydrate (92 mg) and triethylamine (84 µL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. To the residue were added ethanol (2 mL), tetrahydrofuran (2 mL) and 1N lithium hydroxide (0.4 mL), and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (210 mg, 82%).

$^1$H NMR (300 MHz, DMSO-$d_6$) δ ppm 0.89-1.29 (m, 5H) 1.49-1.81 (m, 5H) 2.04 (d, J=12.12 Hz, 1H) 2.40-2.50 (m, 2H) 2.89 (s, 3H) 3.30 (s, 3H) 3.51 (t, J=7.38 Hz, 2H) 4.18 (t, J=7.76 Hz, 1H) 4.36-4.60 (m, 2H) 6.23 (d, J=8.33 Hz, 1H) 6.60 (d, J=8.71 Hz, 2H) 6.81 (s, 1H) 7.09 (d, J=8.71 Hz, 2H) 7.23 (t, J=8.90 Hz, 2H) 7.54-7.78 (m, 2H)

Example 315

3-({[5-({1-[5-(6-methoxypyridin-3-yl)-2-methylfuran-3-yl]-3-methylbutyl}amino)pyridin-2-yl]carbonyl}amino)propanoic acid

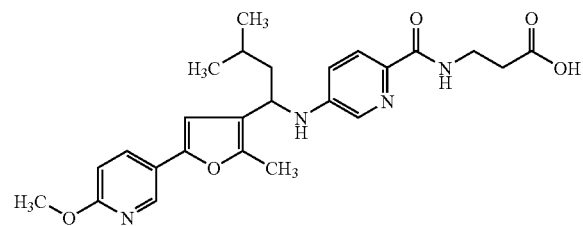

(1) ethyl 3-({[5-({1-[5-(6-methoxypyridin-3-yl)-2-methylfuran-3-yl]-3-methylbutyl}amino)pyridin-2-yl]carbonyl}amino)propanoate A mixture of 5-[4-(1-chloro-3-methylbutyl)-5-methylfuran-2-yl]-2-methoxypyridine (0.9 g), methyl 5-aminopyridine-2-carboxylate (0.5 g), sodium carbonate (0.5 g) and sodium iodide (0.9 g) in N,N-dimethylacetamide (20 mL) was stirred at 80° C. for 8 hr. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (6 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give 5-({1-[5-(6-methoxypyridin-3-yl)-2-methylfuran-3-yl]-3-methylbutyl}amino)pyridine-2-carboxylic acid. To the obtained 5-({1-[5-(6-methoxypyridin-3-yl)-2-methylfuran-3-yl]-3-methylbutyl}amino)pyridine-2-carboxylic acid (395 mg) were added ethyl β-alaninate hydrochloride (184 mg), 1-ethyl-3-(3-dimethylaminopropyl)carbodiimide hydrochloride (230 mg), hydroxybenzotriazole monohydrate (184 mg), triethylamine (168 µL) and N,N-dimethylformamide (10 mL) was added. The obtained mixture was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. The solvent was evaporated under reduced pressure, and the residue was purified by silica gel chromatography (10% ethyl acetate/hexane to 50% ethyl acetate/hexane) to give the title compound (171 mg, 35%) as an amorphous compound.

$^1$H NMR (300 MHz, CHLOROFORM-d) δ ppm 0.85-1.06 (m, 6H) 1.17-1.34 (m, 3H) 1.59-1.82 (m, 3H) 2.39 (s, 3H) 2.61 (t, J=6.25 Hz, 2H) 3.59-3.80 (m, 2H) 3.85-3.96 (m, 2H) 3.94 (s, 3H) 4.11-4.19 (m, 3H) 4.36 (q, J=6.82 Hz, 1H) 6.37 (s, 1H) 6.72 (d, J=8.71 Hz, 1H) 6.85 (dd, J=8.52, 2.84 Hz, 1H) 7.75 (dd, J=8.71, 2.65 Hz, 1H) 7.85 (d, J=2.65 Hz, 1H) 7.93 (d, J=8.33 Hz, 1H) 8.11 (t, J=6.25 Hz, 1H) 8.39 (d, J=1.89 Hz, 1H)

(2) 3-({[5-({1-[5-(6-methoxypyridin-3-yl)-2-methylfuran-3-yl]-3-methylbutyl}amino)pyridin-2-yl]carbonyl}amino)propanoic acid Ethyl 3-({[5-({1-[5-(6-methoxypyridin-3-yl)-2-methylfuran-3-yl]-3-methylbutyl}amino)pyridin-2-yl]carbonyl}amino)propanoate (148 mg) obtained by the above-mentioned reaction was dissolved in ethanol (2 mL) and tetrahydrofuran (2 mL) and 1N lithium hydroxide (0.9 mL) were added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (139 mg, 99%).

$^1$H NMR (300 MHz, DMSO-$d_6$) δ ppm 0.93 (dd, J=17.80, 6.06 Hz, 6H) 1.47-1.84 (m, 3H) 2.39 (s, 3H) 2.46 (t, J=7.00 Hz, 2H) 3.37-3.51 (m, 2H) 3.85 (s, 3H) 4.41 (q, J=6.82 Hz, 1H) 6.73 (s, 1H) 6.76 (d, J=7.57 Hz, 1H) 6.83 (d, J=8.71 Hz, 1H) 6.95 (dd, J=8.71, 2.65 Hz, 1H) 7.70 (d, J=8.71 Hz, 1H) 7.88 (dd, J=8.52, 2.46 Hz, 1H) 7.93 (d, J=2.65 Hz, 1H) 8.28 (t, J=6.06 Hz, 1H) 8.39 (d, J=2.27 Hz, 1H) 12.20 (brs, 1H)

Example 316

3-[{[5-({1-[5-(6-methoxypyridin-3-yl)-2-methylfuran-3-yl]-3-methylbutyl}amino)pyridin-2-yl]carbonyl}(methyl)amino]propanoic acid

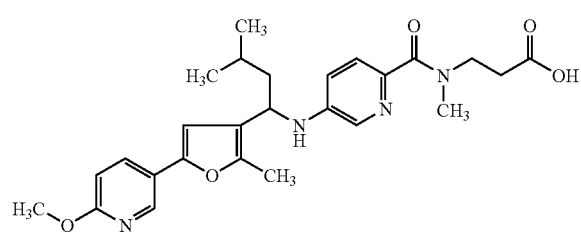

A solution of 5-({1-[5-(6-methoxypyridin-3-yl)-2-methylfuran-3-yl]-3-methylbutyl}amino)pyridine-2-carboxylic acid (395 mg), ethyl 3-(methylamino)propanoate (157 mg), 1-ethyl-3-(3-dimethylaminopropyl)carbodiimide hydrochloride (230 mg), hydroxybenzotriazole monohydrate (184 mg) and triethylamine (168 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. The residue was purified by silica gel chromatography (5% ethyl acetate/hexane to 50% ethyl acetate/hexane) to give ethyl 3-[{[5-({1-[5-(6-methoxypyridin-3-yl)-2-methylfuran-3-yl]-3-methylbutyl}amino)pyridin-2-yl]carbonyl}(methyl)amino]propanoate (155 mg). Ethyl 3-[{[5-({1-[5-(6-methoxypyridin-3-yl)-2-methylfuran-3-yl]-3-methylbutyl}amino)pyridin-2-yl]carbonyl}(methyl)amino]propanoate was dissolved in ethanol (2 mL), tetrahydrofuran (2 mL) and 1N lithium hydroxide (0.6 mL) were added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (100 mg, 70%).

$^1$H NMR (300 MHz, DMSO-$d_6$) δ ppm 0.96 (d, J=6.06 Hz, 3H) 0.90 (d, J=6.06 Hz, 3H) 1.45-1.85 (m, 3H) 2.39 (s, 3H) 2.50-2.62 (m, 1H) 2.90-3.06 (m, 3H) 3.55-3.65 (m, 2H) 3.86 (s, 3H) 4.39 (q, J=7.19 Hz, 1H) 6.57 (d, J=7.57 Hz, 1H) 6.74 (s, 1H) 6.83 (d, J=8.71 Hz, 1H) 6.92 (dd, J=8.71, 2.65 Hz, 1H) 7.36 (d, J=8.71 Hz, 1H) 7.81-7.95 (m, 2H) 8.39 (d, J=1.89 Hz, 1H) 12.23 (brs, 1H)

Example 317

3-({[5-({cyclohexyl[5-(4-fluorophenyl)-2-methylfuran-3-yl]methyl}amino)pyridin-2-yl]carbonyl}amino)propanoic acid

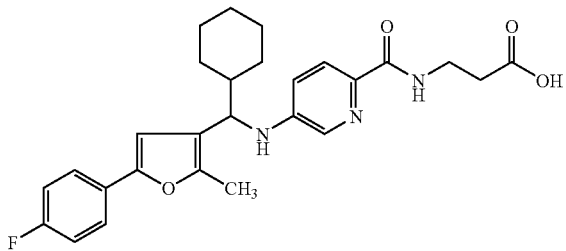

(1) ethyl 3-({[5-({cyclohexyl[5-(4-fluorophenyl)-2-methylfuran-3-yl]methyl}amino)pyridin-2-yl]carbonyl}amino)propanoate A mixture of 3-[chloro(cyclohexyl)methyl]-5-(4-fluorophenyl)-2-methylfuran (1.3 g), methy 5-aminopyridine-2-carboxylate (0.7 g), sodium carbonate (0.5 g) and sodium iodide (1.4 g) in N,N-dimethylacetamide (20 mL) was stirred at 80° C. for 10 hr. The reaction mixture was poured into water, and the mixture was extracted with ethyl acetate. The organic layer was washed with saturated brine, and dried over magnesium sulfate. The solvent was evaporated under reduced pressure, and the residue was dissolved in methanol (5 mL) and tetrahydrofuran (5 mL). 2N Lithium hydroxide (5 mL) was added, and the mixture was stirred at 80° C. for 4 hr. The reaction mixture was poured into water, and the mixture was acidified with 1N hydrochloric acid and extracted with ethyl acetate. The organic layer was washed with saturated brine, and dried over magnesium sulfate. The solvent was evaporated under reduced pressure to give 5-({cyclohexyl[5-(4-fluorophenyl)-2-methylfuran-3-yl]methyl}amino)pyridine-2-carboxylic acid. To the obtained 5-({cyclohexyl[5-(4-fluorophenyl)-2-methylfuran-3-yl]methyl}amino)pyridine-2-carboxylic acid (694 mg) were added ethyl β-alaninate hydrochloride (261 mg), 1-ethyl-3-(3-dimethylaminopropyl)carbodiimide hydrochloride (326 mg), hydroxybenzotriazole monohydrate (260 mg), triethylamine (237 μl) and N,N-dimethylformamide (10 mL), and the obtained mixture was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure, and the residue was purified by silica gel chromatography (5% ethyl acetate/hexane to 50% ethyl acetate/hexane) to give the title compound (521 mg, 60%) as an amorphous compound.

$^1$H NMR (300 MHz, CHLOROFORM-d) δ ppm 0.95-1.34 (m, 8H) 1.61-1.89 (m, 5H) 1.97 (d, J=11.68 Hz, 1H) 2.37 (s, 3H) 2.60 (t, J=6.22 Hz, 2H) 3.57-3.73 (m, 2H) 4.06 (t, J=6.59 Hz, 1H) 4.15 (q, J=6.91 Hz, 2H) 4.29 (d, J=6.41 Hz, 1H) 6.35 (s, 1H) 6.81 (dd, J=8.48, 2.83 Hz, 1H) 6.91-7.09 (m, 2H) 7.45-7.59 (m, 2H) 7.83 (d, J=2.26 Hz, 1H) 7.90 (d, J=8.67 Hz, 1H) 8.09 (t, J=6.22 Hz, 1H)

(2) 3-({[5-({cyclohexyl[5-(4-fluorophenyl)-2-methylfuran-3-yl]methyl}amino)pyridin-2-yl]carbonyl}amino)propanoic acid Ethyl 3-({[5-({cyclohexyl[5-(4-fluorophenyl)-2-methylfuran-3-yl]methyl}amino)pyridin-2-yl]carbonyl}amino)propanoate (508 mg) obtained by the above-mentioned reaction was dissolved in ethanol (2 mL) and tetrahydrofuran (2 mL) and 1N lithium hydroxide (2.0 mL) were added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (459 mg, 96%).

$^1$H NMR (300 MHz, DMSO-$d_6$) δ ppm 0.80-1.31 (m, 5H) 1.48-1.83 (m, 5H) 2.03 (d, J=12.81 Hz, 1H) 2.37 (s, 3H) 2.44 (t, J=6.97 Hz, 2H) 3.41 (q, J=6.53 Hz, 2H) 4.15 (t, J=7.54 Hz, 1H) 6.69 (s, 1H) 6.73 (d, J=7.54 Hz, 1H) 6.94 (dd, J=8.67, 2.64 Hz, 1H) 7.20 (t, J=8.85 Hz, 2H) 7.52-7.64 (m, 2H) 7.67 (d, J=8.67 Hz, 1H) 7.94 (d, J=2.64 Hz, 1H) 8.27 (t, J=6.03 Hz, 1H) 12.18 (brs, 1H)

Example 318

3-[{[5-({cyclohexyl[5-(4-fluorophenyl)-2-methylfuran-3-yl]methyl}amino)pyridin-2-yl]carbonyl}(methyl)amino]propanoic acid

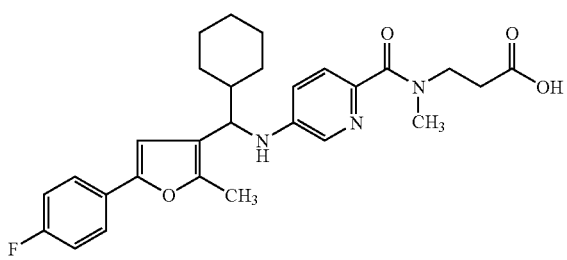

A solution of 5-({cyclohexyl[5-(4-fluorophenyl)-2-methylfuran-3-yl]methyl}amino)pyridine-2-carboxylic acid (694 mg), ethyl 3-(methylamino)propanoate (223 mg), 1-ethyl-3-(3-dimethylaminopropyl)carbodiimide hydrochloride (326 mg), hydroxybenzotriazole monohydrate (260 mg) and triethylamine (237 μL) in N,N-dimethylformamide (10 mL) was stirred at room temperature for 4 hr. Ethyl acetate was added, the mixture was washed with saturated aqueous sodium hydrogen carbonate solution and water, and the organic layer was dried over magnesium sulfate. The solvent was evaporated under reduced pressure, and the organic layer was dried over magnesium sulfate. The solvent was evaporated under reduced pressure. The residue was purified by silica gel chromatography (5% ethyl acetate/hexane to 50% ethyl acetate/hexane) to give ethyl 3-[{[5-({cyclohexyl[5-(4-fluorophenyl)-2-methylfuran-3-yl]methyl}amino)pyridin-2-yl]carbonyl}(methyl)amino]propanoate (263 mg) as an amorphous compound. Ethyl 3-[{[5-({cyclohexyl[5-(4-fluorophenyl)-2-methylfuran-3-yl]methyl}amino)pyridin-2-yl]carbonyl}(methyl)amino]propanoate was dissolved in ethanol (2 mL), tetrahydrofuran (2 mL) and 1N lithium hydroxide (1.0 mL) were added, and the mixture was stirred at room temperature for 1 hr. The solvent was evaporated under reduced pressure, and water (10 mL) was added. The mixture was neutralized with 1N hydrochloric acid under ice-cooling, and stirred for 1 hr. The resulting precipitate was collected by filtration and dried to give the title compound (246 mg, 30%).

$^1$H NMR (300 MHz, DMSO-d$_6$) δ ppm 0.89-1.31 (m, 5H) 1.49-1.84 (m, 5H) 2.03 (d, J=10.55 Hz, 1H) 2.37 (s, 3H) 2.54-2.67 (m, 2H) 2.89-3.05 (m, 3H) 3.41-3.74 (m, 2H) 4.12 (t, J=7.72 Hz, 1H) 6.55 (d, J=7.91 Hz, 1H) 6.70 (s, 1H) 6.90 (dd, J=8.67, 2.64 Hz, 1H) 7.08-7.28 (m, 2H) 7.34 (d, J=8.67 Hz, 1H) 7.48-7.68 (m, 2H) 7.90 (d, J=2.64 Hz, 1H) 12.19 (brs, 1H)

Example 319

3-[{[4-({1-[5-(6-methoxypyridin-3-yl)-2-methylfuran-3-yl]-3-methylbutyl}amino)phenyl]carbonyl}(methyl)amino]propanoic acid

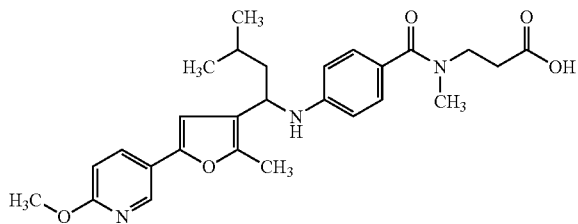

Ethyl 3-[{[4-({1-[5-(6-methoxypyridin-3-yl)-2-methylfuran-3-yl]-3-methylbutyl}amino)phenyl]carbonyl}(methyl)amino]propanoate (12.0 g) which is a synthetic intermediate in Example 149 was dissolved in 2-propanol-hexane (8:2, volume ratio), and the solution was subjected to HPLC using CHIRALPAK AD (50 mmID×500 mmL, manufactured by DAICEL CHEMICAL INDUSTRIES, LTD.) and eluted with 2-propanol-hexane (8:2, volume ratio) as mobile phase at 30° C., a flow rate 60 mL/min. The fractions showing a peak with retention time 23.7 min were collected, and concentrated. The obtained amorphous compound (5.58 g) was dissolved in ethanol (20 mL) and tetrahydrofuran (20 mL), 1N lithium hydroxide (20 mL) was added, and the mixture was stirred at room temperature for 1 hr. The solvent was evaporated under reduced pressure, and water (30 mL) was added. The mixture was neutralized with 1N hydrochloric acid under ice-cooling, and stirred for 1 hr. The resulting precipitate was collected by filtration and dried to give the title compound (5.2 g, 99%).

$^1$H NMR (300 MHz, DMSO-d$_6$) δ ppm 0.92 (dd, J=17.61, 6.25 Hz, 6H) 1.45-1.80 (m, 3H) 2.38 (s, 3H) 2.45-2.50 (m, 2H) 2.90 (s, 3H) 3.52 (t, J=7.57 Hz, 2H) 3.85 (s, 3H) 4.33 (q, J=6.44 Hz, 1H) 6.27 (d, J=6.82 Hz, 1H) 6.55 (d, J=8.71 Hz, 2H) 6.74 (s, 1H) 6.83 (d, J=8.71 Hz, 1H) 7.12 (d, J=8.33 Hz, 2H) 7.88 (dd, J=8.71, 2.65 Hz, 1H) 8.39 (d, J=1.89 Hz, 1H) 12.24 (brs, 1H)

Example 320

3-[{[4-({1-[5-(6-methoxypyridin-3-yl)-2-methylfuran-3-yl]-3-methylbutyl}amino)phenyl]carbonyl}(methyl)amino]propanoic acid

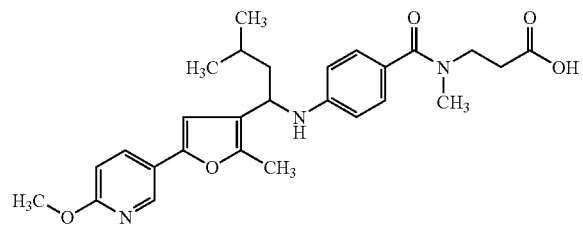

Ethyl 3-[{[4-({1-[5-(6-methoxypyridin-3-yl)-2-methylfuran-3-yl]-3-methylbutyl}amino)phenyl]carbonyl}(methyl)amino]propanoate (12.0 g) which is a synthetic intermediate in Example 149 was dissolved in 2-propanol-hexane (8:2, volume ratio), and the solution was subjected to HPLC using CHIRALPAK AD (50 mmID×500 mmL, manufactured by DAICEL CHEMICAL INDUSTRIES, LTD.) and eluted with 2-propanol-hexane (8:2, volume ratio) as mobile phase at 30° C., a flow rate 60 mL/min. The fractions showing a peak with retention time 44.7 min were collected, and concentrated. The obtained amorphous compound (5.58 g) was dissolved in ethanol (20 mL) and tetrahydrofuran (20 mL) and 1N lithium hydroxide (20 mL) was added, and the mixture was stirred at room temperature for 1 hr. The solvent was evaporated under reduced pressure, and water (30 mL) was added. The mixture was neutralized with 1N hydrochloric acid under ice-cooling, and stirred for 1 hr. The resulting precipitate was collected by filtration and dried to give the title compound (5.0 g, 94%).

$^1$H NMR (300 MHz, DMSO-d$_6$) δ ppm 0.92 (dd, J=17.61, 6.25 Hz, 6H) 1.45-1.80 (m, 3H) 2.38 (s, 3H) 2.45-2.50 (m, 2H) 2.90 (s, 3H) 3.52 (t, J=7.57 Hz, 2H) 3.85 (s, 3H) 4.33 (q, J=6.44 Hz, 1H) 6.27 (d, J=6.82 Hz, 1H) 6.55 (d, J=8.71 Hz, 2H) 6.74 (s, 1H) 6.83 (d, J=8.71 Hz, 1H) 7.12 (d, J=8.33 Hz, 2H) 7.88 (dd, J=8.71, 2.65 Hz, 1H) 8.39 (d, J=1.89 Hz, 1H) 12.24 (brs, 1H)

Experimental Example 1

The glucagon binding inhibitory action of the compound of the present invention was evaluated by the following method.
(1) Preparation of Glucagon Receptor Membrane Protein A human-type glucagon receptor was expressed using FreeStyle CHO Expression System (Invitrogen). A transient expression in FreeStyle CHO cell was performed using a human-type glucagon expression plasmid DNA and according to the manual attached to the FreeStyle CHO Expression System. The above-mentioned DNA was transfected and the cultured with shaking for 2 days (37° C., 8% CO$_2$, 125 rpm). 2400 ml of culture medium was centrifuged at 2,000 rpm for 10 min and the cells were collected. The collected cells were washed with PBS, suspended in homogenate buffer [10 mM NaHCO$_3$ (pH 7.4), 1 mM EDTA, Complete EDTA-free (Roche, 1 tablet/50 mL)] and disrupted by polytron cell disrupter (Kinematica AG). Disruption solution was centrifuged at 2,000 rpm for 10 min and the supernatant was collected. The supernatant was centrifuged at 35,000 rpm for 60 min and the precipitate was suspended in a buffer [20 mM Tris-HCl (pH 7.4), 5 mM EDTA, Complete EDTA-free (Roche, 1 tablet/50 mL)] to give a glucagon receptor membrane protein (452 mg).

(2) Measurement of Glucagon Binding Inhibitory Activity

To each well of 96 well plate (Corning Incorporated) were added 25 μl of test compound (containing 0.4% DMSO), 50 μl of glucagon receptor membrane protein diluted with reaction buffer [50 mM Tris-HCl (pH 7.4), 5 mM EGTA, 5 mM magnesium chloride, 0.1% BSA, 0.005% Tween20] to 100 μg/ml, and 25 μl of radioactive labeled glucagon ([$^{125}$I]-Receptor Grade Glucagon; Perkin Elmer Inc.) diluted with the reaction buffer to 200 pM, whereby the reaction was started. The plate was stood for 90 min at room temperature. The reaction solution was transferred from the reaction plate to a 96 well unifilter GF/C plate (Perkin Elmer Inc.) using a cell harvester (Perkin Elmer Inc.) and the membrane fraction was collected on the filter by suction. The filter was presoaked in 2 mg/ml of polyethyleneimine to prevent non-specific adsorption of labeled ligand. The filter was washed 4 times with a reaction buffer and dried for 2 hr at 42° C. To each well was added 25 μl of scintillator (MicroScint0; Perkin Elmer Inc.), and the fluorescence amount was measured using a microplate scintillation counter (TopCount NXT™; Perkin Elmer Inc.). The glucagon binding inhibitory activity (IC$_{50}$ value) of the well added with the test compound (containing 0.4% DMSO) was calculated, using the reaction rate of the well added only with 0.4% DMSO as 0% inhibitory rate, and the reaction rate of the well added with non-labeled glucagon (final concentration 1 μM) as 100% inhibitory rate. The results are shown in Table 1.

TABLE 1

| test compound | IC$_{50}$ value (nM) |
|---|---|
| Ex. 5 | 630 |
| Ex. 10 | 250 |
| Ex. 53 | 110 |
| Ex. 71 | 57 |
| Ex. 79 | 97 |
| Ex. 83 | 190 |
| Ex. 166 | 180 |
| Ex. 311 | 650 |
| Ex. 314 | 290 |
| Ex. 318 | 400 |
| Ex. 319 | 230 |

As mentioned above, it has been shown that the compound of the present invention has a superior glucagon binding inhibitory action.

Experimental Example 2

Test of Glucagon-Induced Blood Glucose Increase-Suppressive Action in Mouse

Full feeding ICR mouse (male, 7-week-old) was fasted, and 0.5% methylcellulose suspension (compound-administration group, 8 mice per group) containing a test compound (10 mg/kg body weight) or 0.5% methylcellulose suspension (compound-non-administration group, 8 mice per group) was orally administered. After 60 minutes, glucagon (10 μg/kg body weight, Novo Nordisk Pharma Ltd.) containing octreotide (100 μg/kg body weight, Novo Nordisk Pharma Ltd.) was subcutaneously administered. After 30 minutes from the glucagon administration, blood samples were collected from the tail vein of the mouse, and the blood glucose level was measured by a glucose self-test kit ACCU-CHEK (Roche Diagnostics K.K.). As a non-treatment group (8 mice per group), the blood glucose level of mouse of the compound-non-administration group, which was free of glucagon administration, was measured in the same manner as in the above.

The differences between the average blood glucose level of the compound-non-administration group, the average blood glucose level of the compound administration group, and the average blood glucose level of the non-treatment group were each calculated, and the percentage of the "difference between the blood glucose level of the compound administration group and that of the non-treatment group" relative to the "difference between the blood glucose level of the compound-non-administration group and that of the non-treatment group" as 100% was determined as an "increasing rate of blood glucose (% of control)". The results are shown in Table 2.

TABLE 2

| test compound | increasing rate of blood glucose (% of control) |
|---|---|
| Ex. 87 | 6.5 |
| Ex. 147 | 8.6 |
| Ex. 149 | 6.8 |

As mentioned above, it has been shown that the compound of the present invention has a superior blood glucose increase-suppressive action.

Formulation Example 1

Production of Capsule

| | |
|---|---|
| 1) compound of Example 1 | 30 mg |
| 2) finely powdered cellulose | 10 mg |
| 3) lactose | 19 mg |
| 4) magnesium stearate | 1 mg |
| Total | 60 mg |

1), 2), 3) and 4) are mixed and filled into a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

Total amount of 1), 2) and 3) and 30 g of 4) are kneaded with water, dried in vacuo and sieved. To this sieved powder are added 14 g of 4) and 1 g of 5), and the mixture is tableted by tableting machine. In this way, 1000 tablets containing 30 mg of Example 1 compound per tablet are obtained.

Industrial Applicability

The compound of the present invention has a glucagon antagonistic action, and is useful for the prophylaxis or treatment of diabetes and the like.

This application is based on a patent application No. 2007-285526 filed in Japan, the contents of which are incorporated in full herein by this reference.

The invention claimed is:

1. A compound represented by the formula (I):

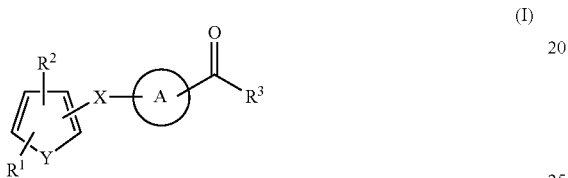

wherein ring A is a benzene ring or a pyridine ring, each of which is optionally further substituted;
Y is an oxygen atom, a sulfur atom or a nitrogen atom;
X is —O—, —S—, —SO—, —SO$_2$—, —CR$^4$R$^5$—O—, —O—CR$^4$R$^5$—, —CO—CR$^4$R$^5$, —CR$^4$R$^5$—CO— or —CR$^4$R$^5$—NR$^6$;
R$^4$ is a hydrogen atom or a C$_{1-6}$ alkyl group;
R$^5$ is an optionally substituted C$_{1-6}$ alkyl group, an optionally substituted C$_{3-10}$ cycloalkyl group, an optionally substituted C$_{6-14}$ aryl group or an optionally substituted 5- or 6-membered heterocyclic group;
R$^6$ is a hydrogen atom, an optionally substituted C$_{1-6}$ alkyl group, an optionally substituted C$_{3-10}$ cycloalkyl group, an optionally substituted C$_{6-14}$ aryl group or an optionally substituted 5- or 6-membered heterocyclic group;
R$^1$ is an optionally substituted hydrocarbon group, an optionally substituted heterocyclic group, an optionally substituted hydroxy group or an acyl group;
R$^2$ is a hydrogen atom, an optionally substituted hydrocarbon group, an optionally substituted heterocyclic group, an optionally substituted hydroxy group or an acyl group;
R$^3$ is —(CH$_2$)$_3$—COOH or —NR$^7$—CR$^8$R$^9$—CR$^{10}$R$^{11}$—COOH;
R$^7$ is a C$_{1-6}$ alkyl group;
R$^8$, R$^9$ and R$^{10}$ are each independently a hydrogen atom or a C$_{1-6}$ alkyl group;
R$^{11}$ is a hydrogen atom, a C$_{1-6}$ alkyl group or a hydroxy group, or a salt thereof.

2. The compound according to claim 1, wherein X is —CR$^4$R$^5$—O— or —CR$^4$R$^5$—NR$^6$—.

3. The compound according to claim 1, wherein R$^1$ is an optionally substituted C$_{1-6}$ alkyl group, an optionally substituted C$_{3-10}$ cycloalkyl group, an optionally substituted C$_{6-14}$ aryl group, an optionally substituted heterocyclic group, a C$_{1-6}$ alkyl-carbonyl group or a C$_{3-10}$ cycloalkyl-carbonyl group.

4. The compound according to claim 1, wherein R$^2$ is an optionally substituted C$_{1-6}$ alkyl group or an optionally substituted C$_{3-10}$ cycloalkyl group.

5. The compound according to claim 1, wherein R$^3$ is —NR$^7$—CR$^8$R$^9$—CR$^{10}$R$^{11}$—COOH.

6. The compound according to claim 1, wherein
X is —CR$^4$R$^5$—O— or —CR$^4$R$^5$—NR$^6$—;
R$^1$ is an optionally substituted C$_{1-6}$ alkyl group, an optionally substituted C$_{3-10}$ cycloalkyl group, an optionally substituted C$_{6-14}$ aryl group, an optionally substituted heterocyclic group, a C$_{1-6}$ alkyl-carbonyl group or a C$_{3-10}$ cycloalkyl-carbonyl group;
R$^2$ is an optionally substituted C$_{1-6}$ alkyl group or an optionally substituted C$_{3-10}$ cycloalkyl group; and
R$^3$ is —NR$^7$—CR$^8$R$^9$—CR$^{10}$R$^{11}$—COOH.

7. 3-[{[4-({1-[5-(6-Methoxypyridin-3-yl)-2-methylfuran-3-yl]-3-methylbutyl}amino)phenyl]carbonyl}(methyl)amino]propanoic acid or a salt thereof.

8. 3-[{[4-({Cyclohexyl[5-(4-fluorophenyl)-2-(methoxymethyl)furan-3-yl]methyl}amino)phenyl]carbonyl}(methyl)amino]propanoic acid or a salt thereof.

9. 3-[{[5-({Cyclohexyl[5-(4-fluorophenyl)-2-methylfuran-3-yl]methyl}amino)pyridin-2-yl]carbonyl}(methyl)amino]propanoic acid or a salt thereof.

10. 3-[{[4-({Cyclohexyl[5-(6-methoxypyridin-3-yl)-2-methylfuran-3-yl]methyl}amino)phenyl]carbonyl}(methyl)amino]propanoic acid or a salt thereof.

11. 3-{[(5-{[Cyclohexyl(2-methyl-5-phenylthiophen-3-yl)methyl]amino}pyridin-2-yl)carbonyl](methyl)amino}propanoic acid or a salt thereof.

12. A medicament comprising the compound according to claim 1.

13. A method of suppressing sugar production in a mammal, comprising administering the compound according to claim 1 to the mammal.

14. A method for the prophylaxis or treatment of diabetes in a mammal, comprising administering the compound according to claim 1 to the mammal.

15. A pharmaceutical composition comprising the compound according to claim 1 or a salt thereof and a pharmaceutically acceptable carrier.

* * * * *